United States Patent
Lin et al.

(10) Patent No.: US 9,512,136 B2
(45) Date of Patent: Dec. 6, 2016

(54) ORGANIC ELECTROLUMINESCENT MATERIALS AND DEVICES

(71) Applicant: Universal Display Corporation, Ewing, NJ (US)

(72) Inventors: Chun Lin, Yardley, PA (US); Chuanjun Xia, Lawrenceville, NJ (US); Raymond Kwong, Holland, PA (US)

(73) Assignee: UNIVERSAL DISPLAY CORPORATION, Ewing, NJ (US)

(*) Notice: Subject to any disclaimer, the term of this patent is extended or adjusted under 35 U.S.C. 154(b) by 395 days.

(21) Appl. No.: 13/685,458

(22) Filed: Nov. 26, 2012

(65) Prior Publication Data

US 2014/0145149 A1   May 29, 2014

(51) Int. Cl.
| | |
|---|---|
| *H01L 51/50* | (2006.01) |
| *C07D 491/048* | (2006.01) |
| *C07D 403/04* | (2006.01) |
| *C07D 403/14* | (2006.01) |
| *C07D 233/58* | (2006.01) |
| *H01L 51/00* | (2006.01) |
| *C09K 11/06* | (2006.01) |
| *H05B 33/14* | (2006.01) |

(52) U.S. Cl.
CPC ......... *C07D 491/048* (2013.01); *C07D 233/58* (2013.01); *C07D 403/04* (2013.01); *C07D 403/14* (2013.01); *C09K 11/06* (2013.01); *H01L 51/0061* (2013.01); *H01L 51/0067* (2013.01); *H01L 51/0072* (2013.01); *H05B 33/14* (2013.01); *C09K 2211/1007* (2013.01); *C09K 2211/1029* (2013.01); *C09K 2211/1033* (2013.01); *C09K 2211/1037* (2013.01); *C09K 2211/1044* (2013.01); *C09K 2211/1048* (2013.01); *C09K 2211/1059* (2013.01); *C09K 2211/1088* (2013.01); *C09K 2211/1092* (2013.01); *H01L 51/5012* (2013.01)

(58) Field of Classification Search
None
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Gregory Clark
(74) *Attorney, Agent, or Firm* — Duane Morris LLP

(57) ABSTRACT

Novel organic compounds containing an imidazole core and electron donor and acceptor fragments are provided. By selection of the disclosed donor and acceptor groups, compounds exhibiting small singlet-triplet gaps are obtained. These compounds are useful in OLED devices as host materials or as delayed fluorescent emitters.

22 Claims, 3 Drawing Sheets

(56) References Cited

U.S. PATENT DOCUMENTS

| | | | |
|---|---|---|---|
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,602,618 B2 * | 8/2003 | Watanabe et al. | 428/690 |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0151042 A1 | 8/2003 | Hueschen | |
| 2003/0152802 A1 | 8/2003 | Tsuboyama et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2013/0270541 A1 * | 10/2013 | Numata | 257/40 |

FOREIGN PATENT DOCUMENTS

| | | | |
|---|---|---|---|
| EP | 2034538 | 3/2009 | |
| JP | 200511610 | 1/2005 | |
| JP | 2007123392 | 5/2007 | |
| JP | 2007254297 | 10/2007 | |
| JP | 2008074939 | 4/2008 | |
| WO | 0139234 | 5/2001 | |
| WO | 0202714 | 1/2002 | |
| WO | 0215645 | 2/2002 | |
| WO | 03040257 | 5/2003 | |
| WO | 03060956 | 7/2003 | |
| WO | 2004093207 | 10/2004 | |
| WO | 2004107822 | 12/2004 | |
| WO | 2005014551 | 2/2005 | |
| WO | 2005019373 | 3/2005 | |
| WO | 2005030900 | 4/2005 | |
| WO | 2005089025 | 9/2005 | |
| WO | 2005123873 | 12/2005 | |
| WO | 2006009024 | 1/2006 | |
| WO | 2006056418 | 6/2006 | |
| WO | 2006072002 | 7/2006 | |
| WO | 2006082742 | 8/2006 | |
| WO | 2006098120 | 9/2006 | |
| WO | 2006100298 | 9/2006 | |
| WO | 2006103874 | 10/2006 | |
| WO | 2006114966 | 11/2006 | |
| WO | 2006132173 | 12/2006 | |
| WO | 2007002683 | 1/2007 | |
| WO | 2007004380 | 1/2007 | |
| WO | 2007063754 | 6/2007 | |
| WO | 2007063796 | 6/2007 | |
| WO | 2008056746 | 5/2008 | |
| WO | 2008101842 | 8/2008 | |
| WO | 2008132085 | 11/2008 | |
| WO | 2009000673 | 12/2008 | |
| WO | 2009003898 | 1/2009 | |
| WO | 2009008311 | 1/2009 | |
| WO | 2009018009 | 2/2009 | |
| WO | 2009050290 | 4/2009 | |
| WO | 2009021126 | 5/2009 | |
| WO | 2009062578 | 5/2009 | |
| WO | 2009063833 | 5/2009 | |
| WO | 2009066778 | 5/2009 | |
| WO | 2009066779 | 5/2009 | |
| WO | 2009086028 | 7/2009 | |
| WO | 2009100991 | 8/2009 | |
| WO | WO 2010051667 * | 4/2010 | H01L 51/54 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato)beryllium as an Emitter, " Chem. Lett., 905-906 (1993).

(56) References Cited

OTHER PUBLICATIONS

Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15)2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing $N^{\wedge}C^{\wedge}N$-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

Formula I

ORGANIC ELECTROLUMINESCENT MATERIALS AND DEVICES

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds containing imidazole cores bearing an electron acceptor and an electron donor fragment. The compounds exhibit delayed fluorescence behavior, and are useful materials in OLED devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

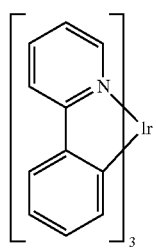

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A compound having the formula:

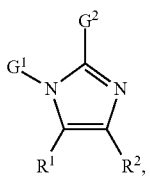

Formula I, is provided.

$G^1$ is an electron donor group or an electron acceptor group, and $G^2$ is also an electron donor group or an electron acceptor group. If $G^1$ is an electron donor group, then $G^2$ is an electron acceptor group, and if $G^1$ is an electron acceptor group, then $G^2$ is an electron donor group. The electron acceptor group is at least one chemical group selected from the group consisting of a six-membered aromatic ring system having at least two nitrogen atoms and a 5-membered aromatic ring system containing at least one nitrogen atom, one oxygen atom, one sulfur atom, or one selenium atom, where the electron acceptor group is optionally substituted.

$R^1$ and $R^2$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R^1$ and $R^2$ are optionally joined to form a ring, which may be further substituted.

In one aspect, the donor group comprises at least one chemical group selected from the group consisting of amino, indole, carbazole, benzothiophene, benzofuran, benzoselenophene, dibenzothiophene, dibenzofuran, dibenzoselenophene, and combinations thereof.

In one aspect, the donor group comprises at least one chemical group selected from the group consisting of:

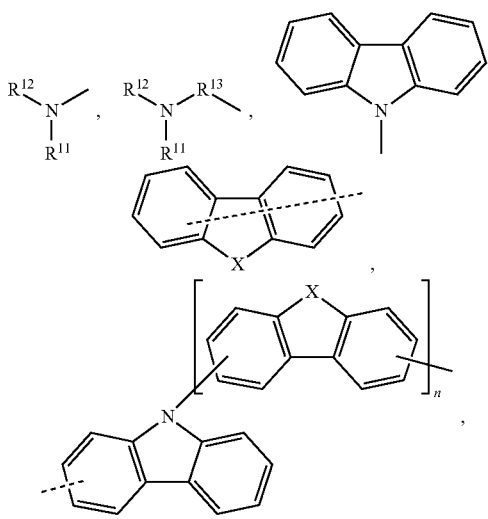

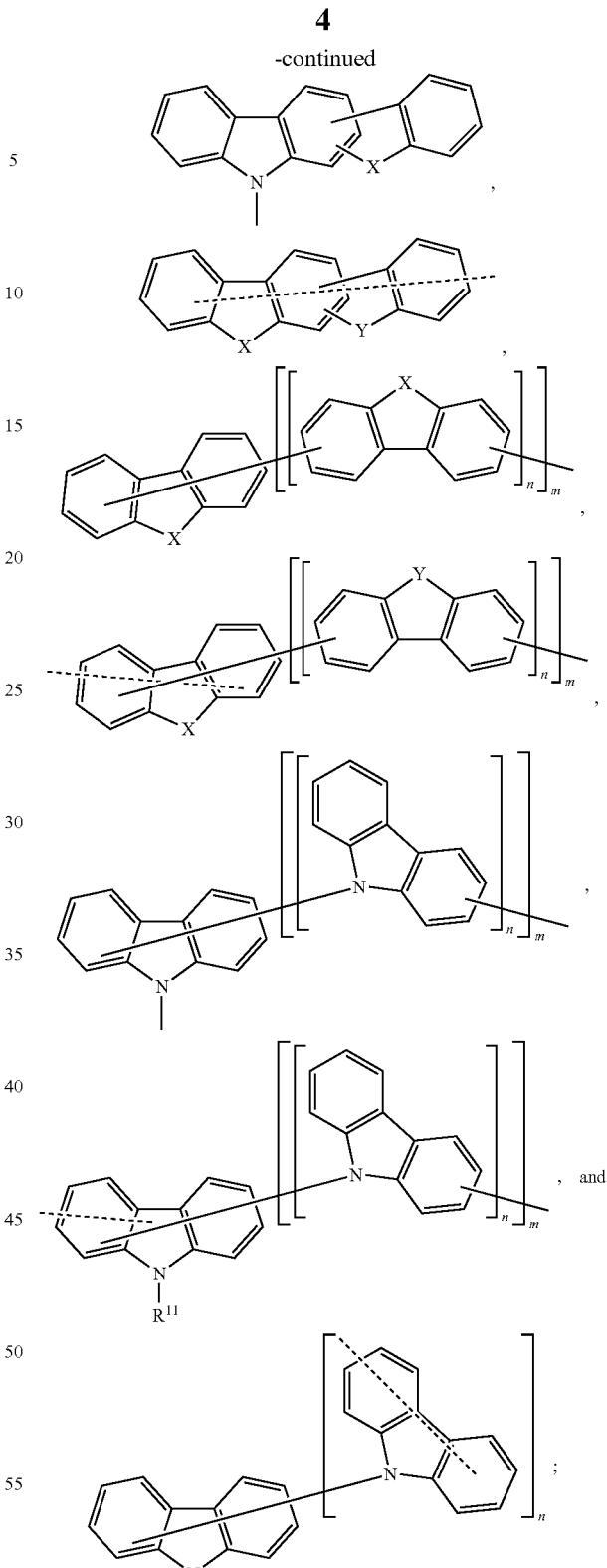

wherein n is an integer from 1 to 20, wherein m is an integer from 1 to 20, wherein X and Y are independently selected from the group consisting of O, S, and $NR^{14}$, and wherein $R^{11}$, $R^{12}$, $R^{13}$ and $R^{14}$ are selected from the group consisting of aryl and heteroaryl.

In one aspect, the electron acceptor group is selected from the group consisting of:

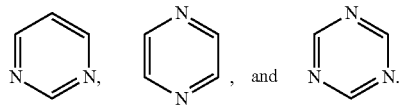

In one aspect, the electron acceptor group has the structure:

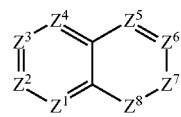

wherein $Z^1$ to $Z^8$ independently comprise C or N, and wherein at least two of $Z^1$ to $Z^8$ are N.

In one aspect, the electron acceptor group comprises at least one chemical group selected from the group consisting of:

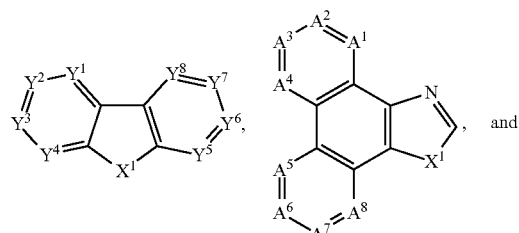

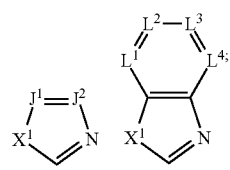

wherein $Y^1$ to $Y^8$ independently comprise C or N, wherein $A^1$ to $A^8$ independently comprise C or N, wherein $J^1$ and $J^2$ independently comprise C or N, wherein $L^1$ to $L^4$ independently comprise C or N, wherein $X^1$ is O, S, or $NR^{14}$, and wherein $R^{14}$ is aryl or heteroaryl.

In one aspect, the donor group is selected from the group consisting of:

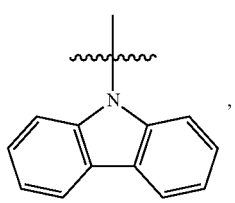
D<sup>101</sup>

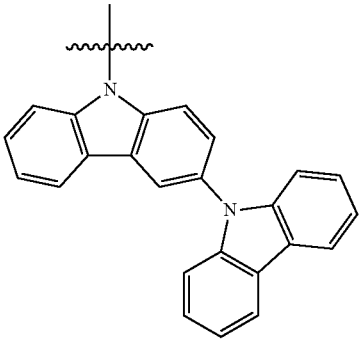
D<sup>102</sup>

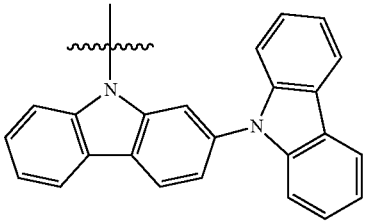
D<sup>103</sup>

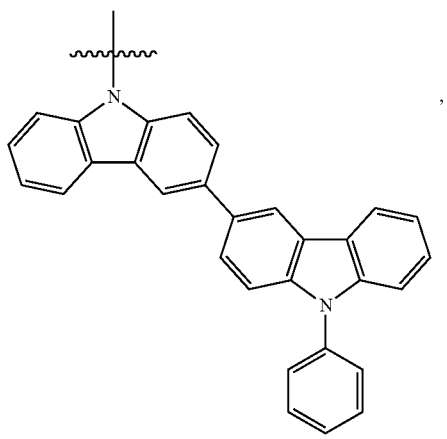
D<sup>104</sup>

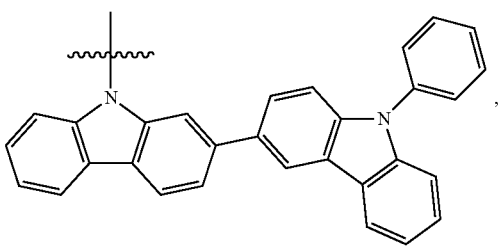
D<sup>105</sup>

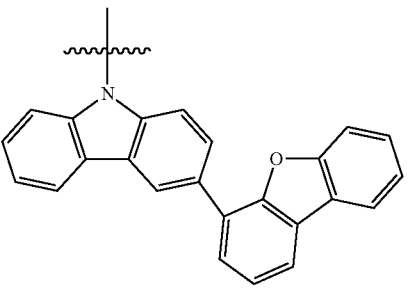
D<sup>106</sup>

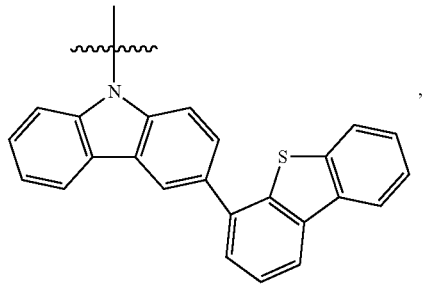
D107
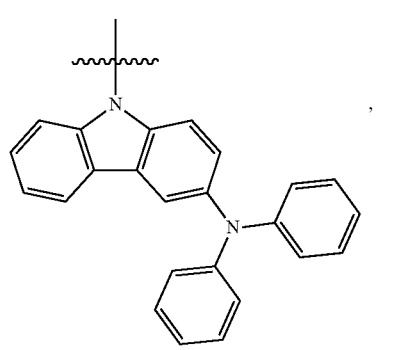
D108
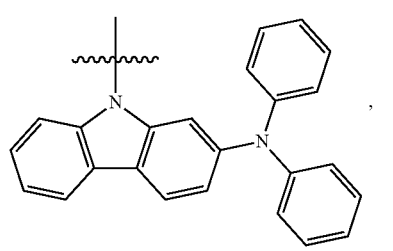
D109
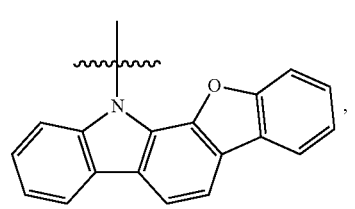
D110
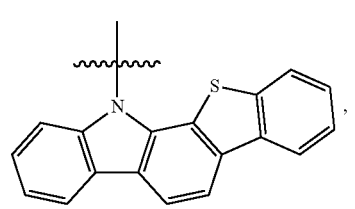
D111
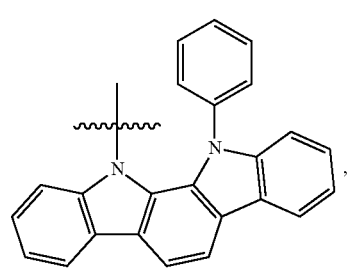
D112
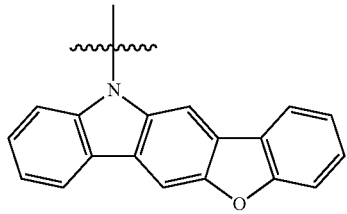
D113
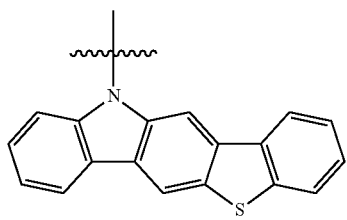
D114
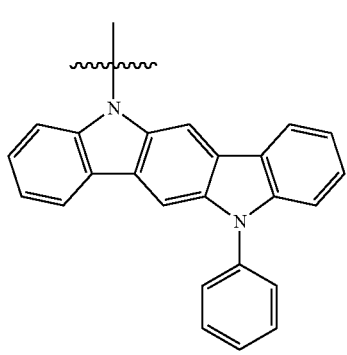
D115
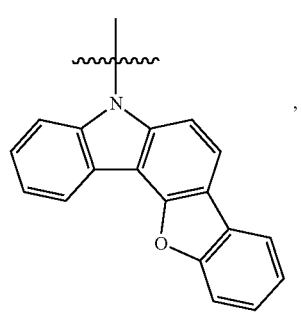
D116
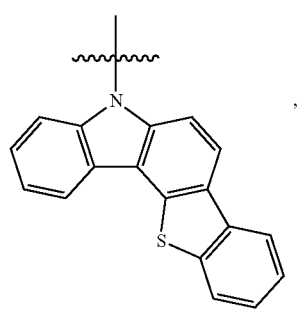
D117

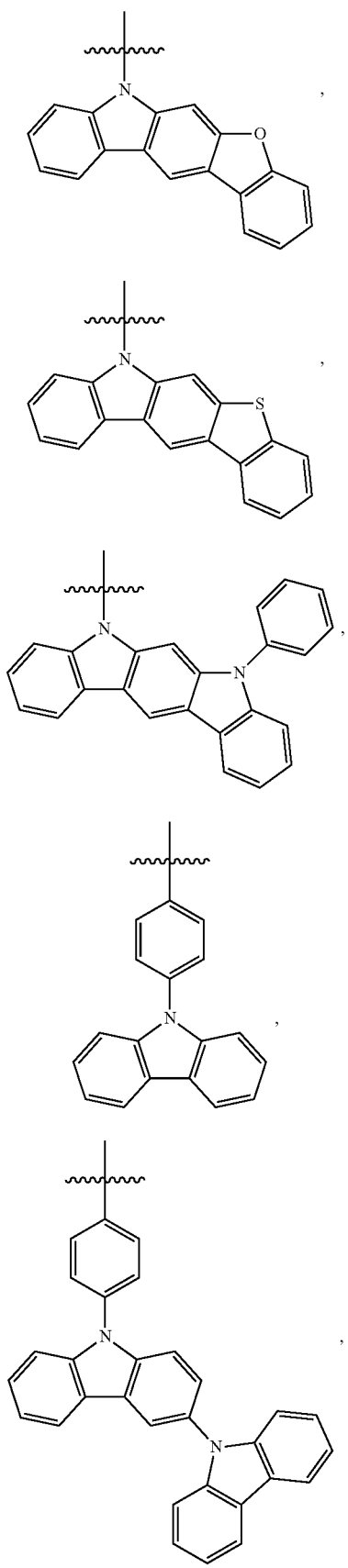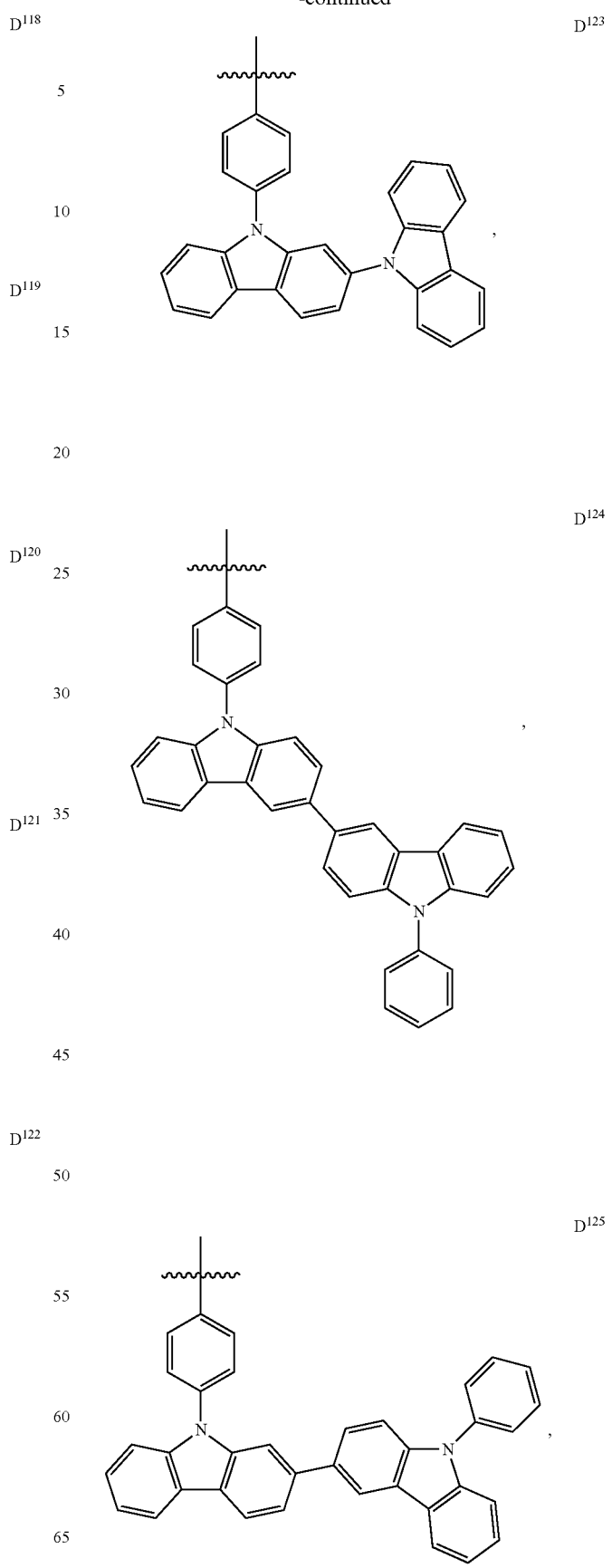

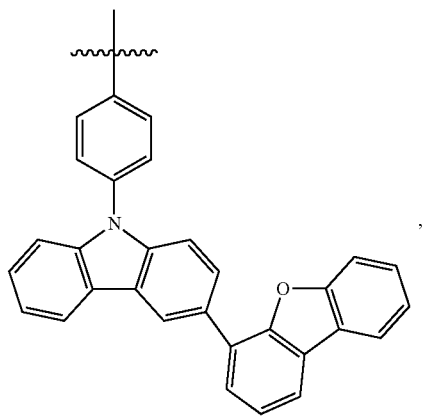 D¹²⁶
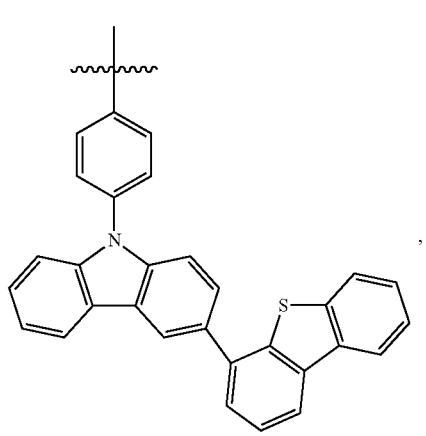 D¹²⁷
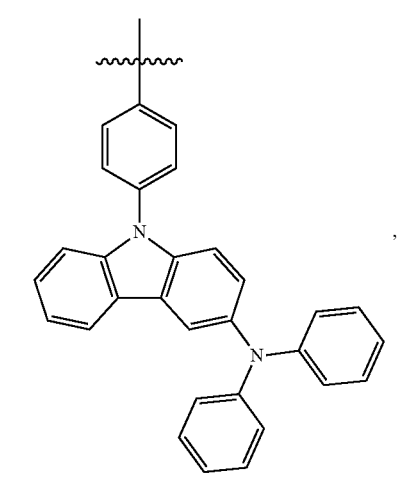 D¹²⁸
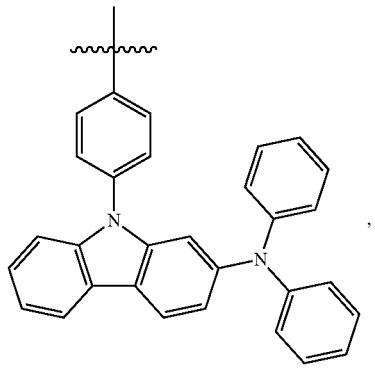 D¹²⁹
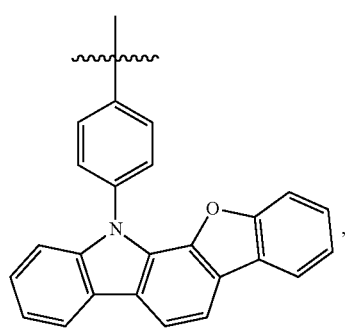 D¹³⁰
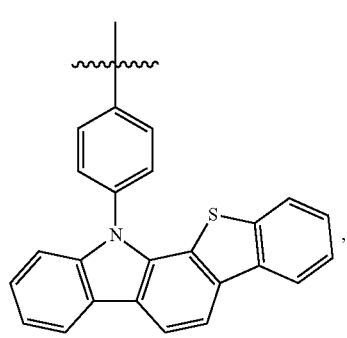 D¹³¹
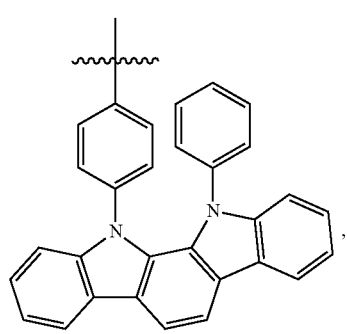 D¹³²

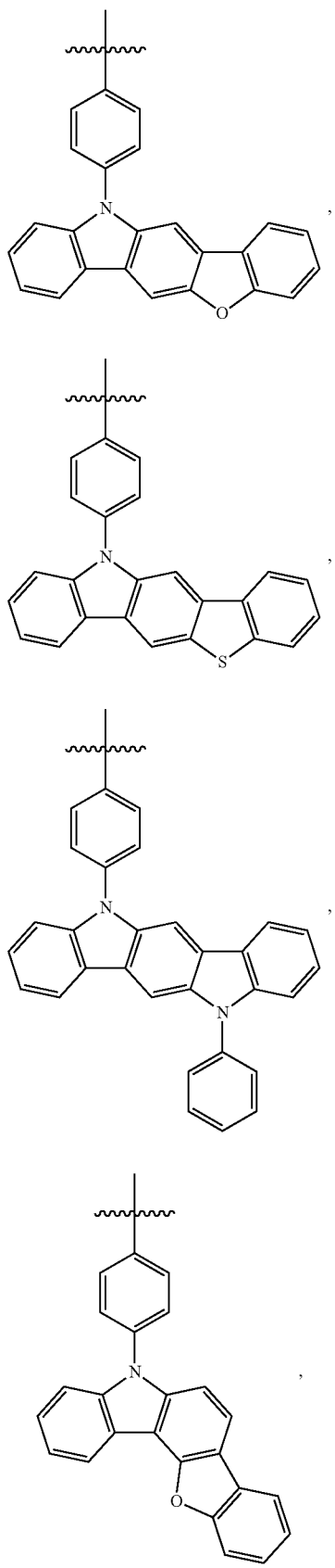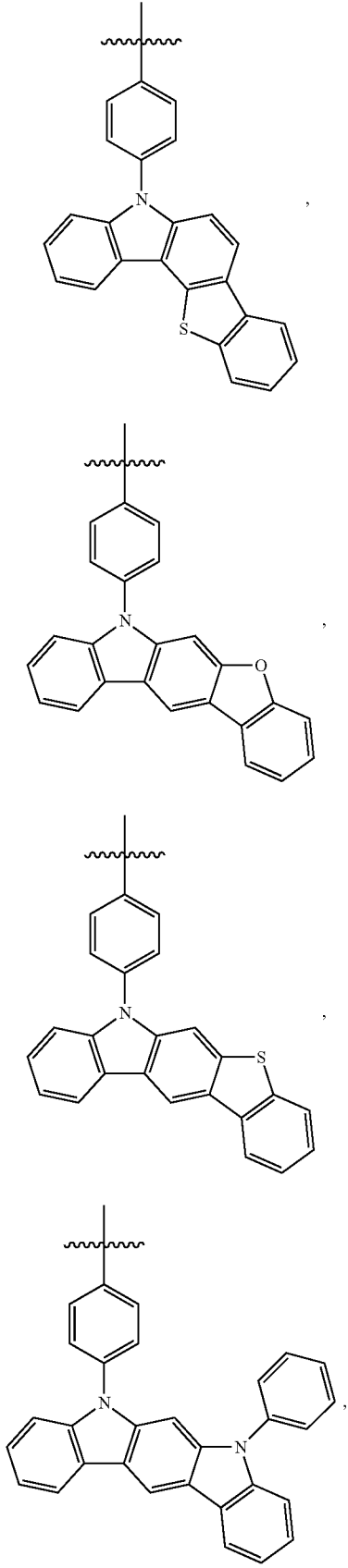

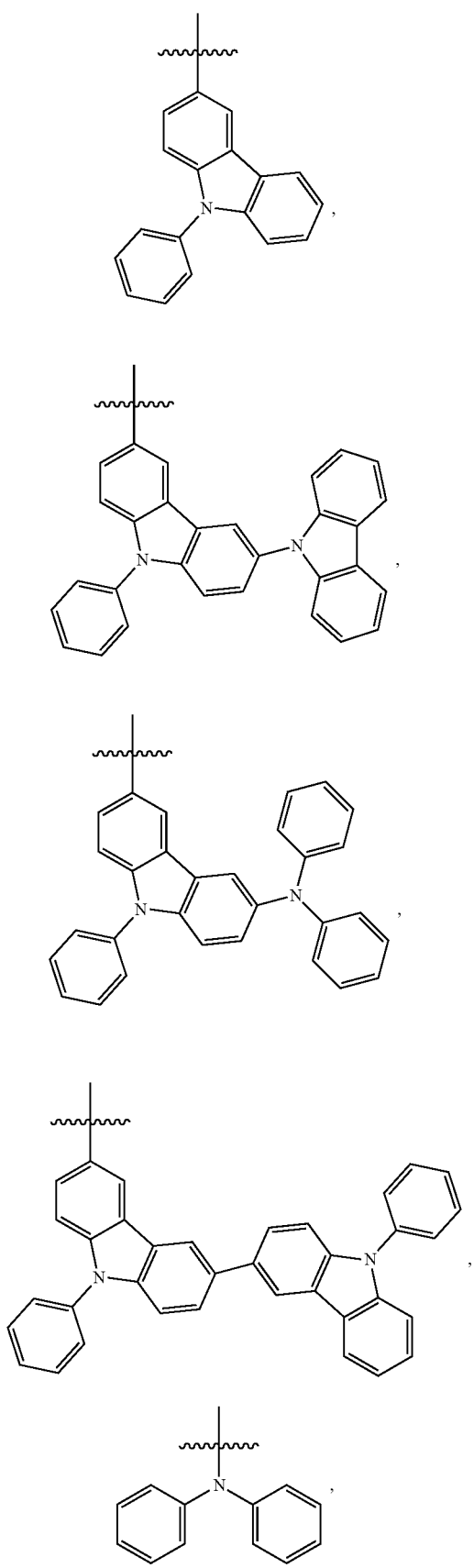
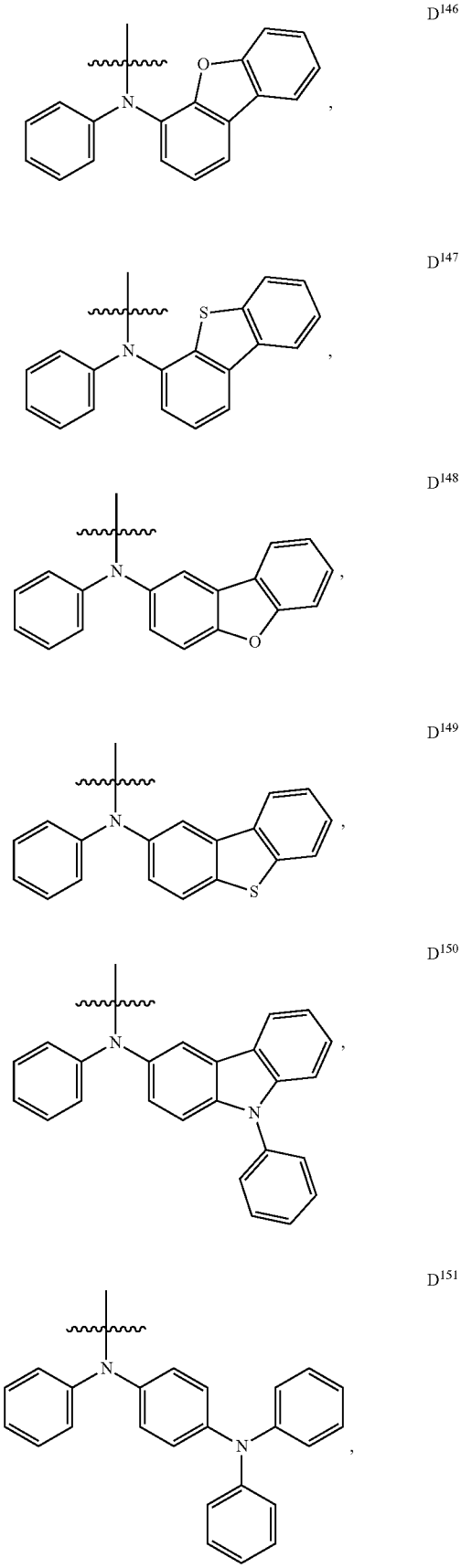

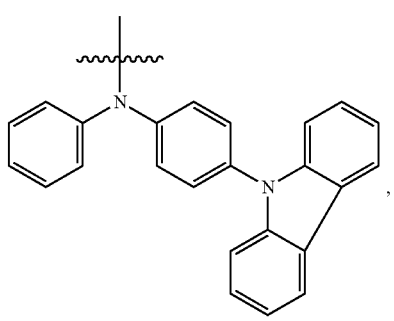
D¹⁵²
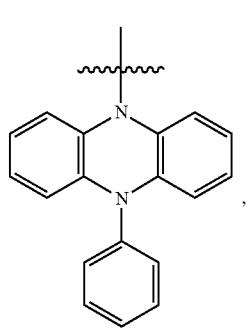
D¹⁵³
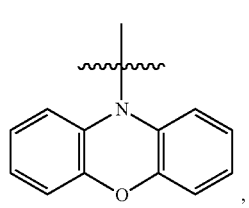
D¹⁵⁴
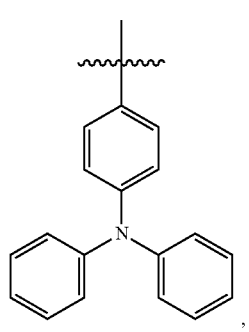
D¹⁵⁵
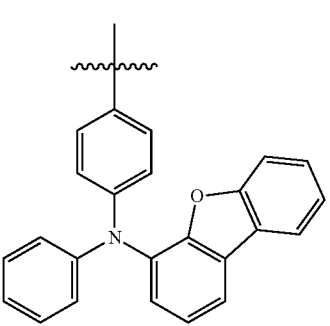
D¹⁵⁶
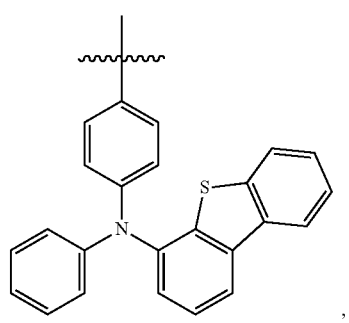
D¹⁵⁷
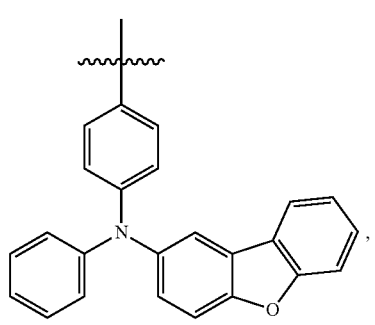
D¹⁵⁸
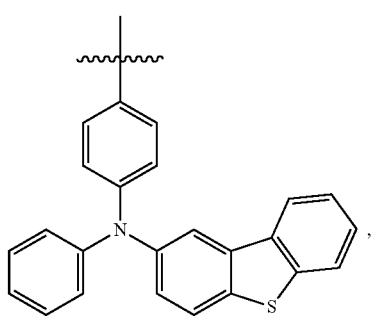
D¹⁵⁹
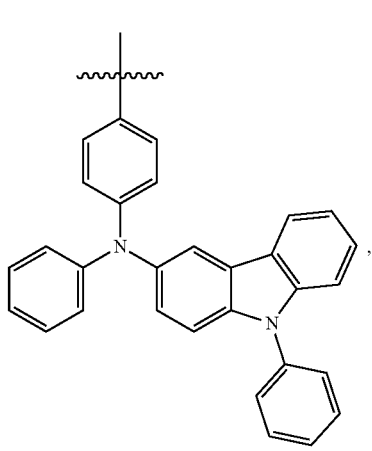
D¹⁶⁰

-continued
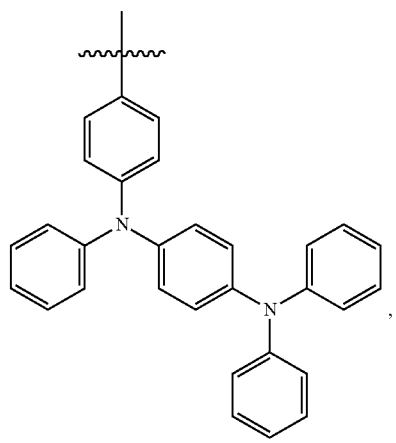
D¹⁶¹
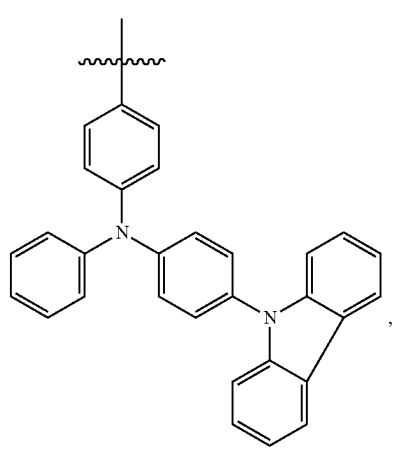
D¹⁶²
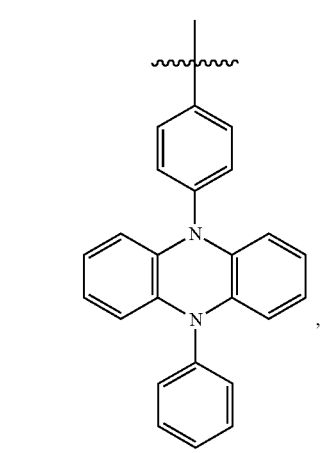
D¹⁶³
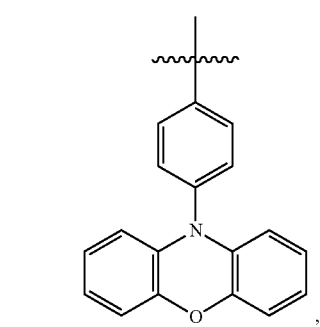
D¹⁶⁴
-continued
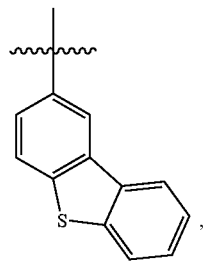
D¹⁶⁵
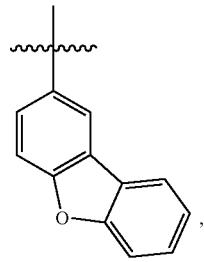
D¹⁶⁶
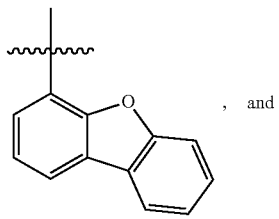
D¹⁶⁷
, and
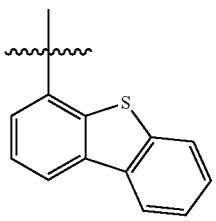
D¹⁶⁸
In one aspect, the acceptor group is selected from the group consisting of:
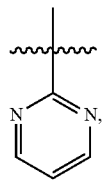
A¹⁰¹
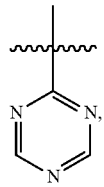
A¹⁰²

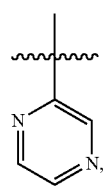 A103
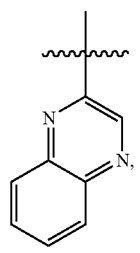 A104
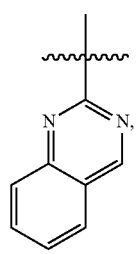 A105
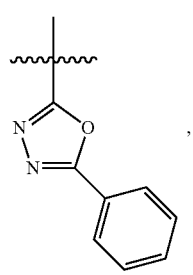 A106
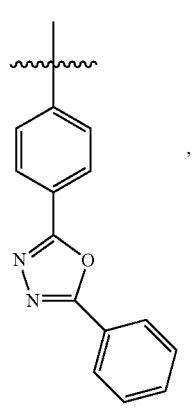 A107
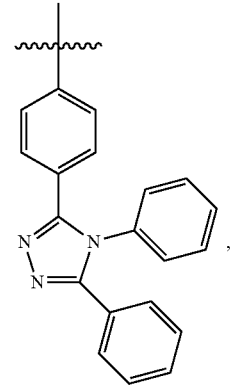 A108
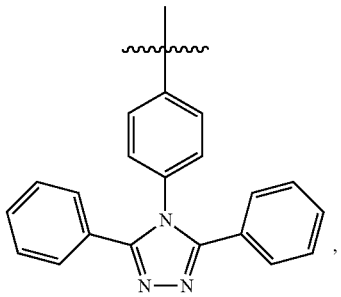 A109
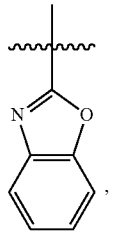 A110
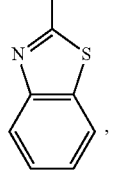 A111
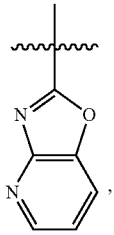 A112

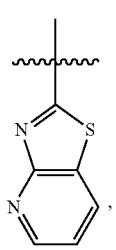 A¹¹³
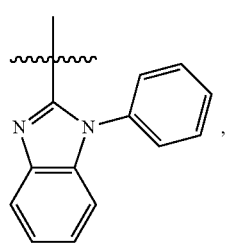 A¹¹⁴
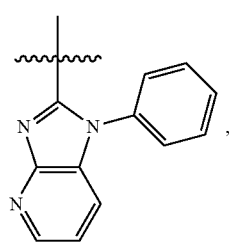 A¹¹⁵
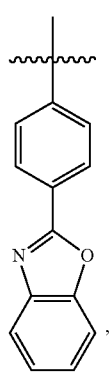 A¹¹⁶
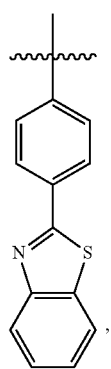 A¹¹⁷
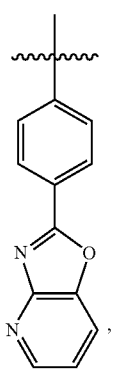 A¹¹⁸
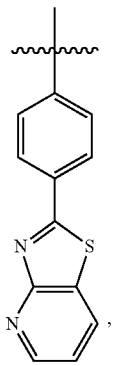 A¹¹⁹
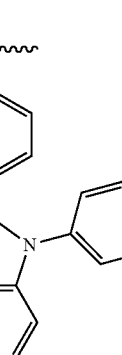 A¹²⁰
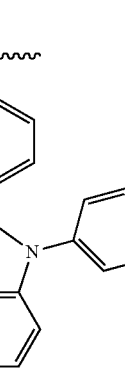 A¹²¹

-continued
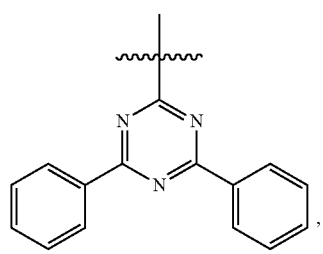
A¹²²,
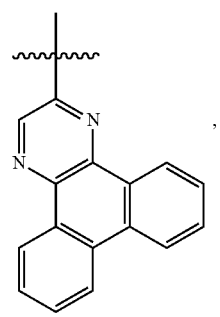
A¹²⁷,
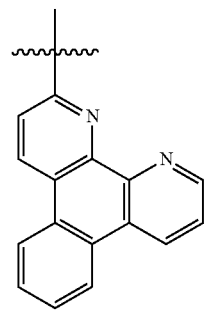
A¹²⁸,
A¹²³
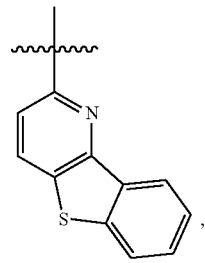
A¹²⁹,
A¹²⁴
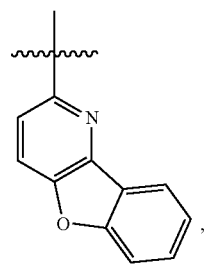
A¹³⁰,
A¹²⁵
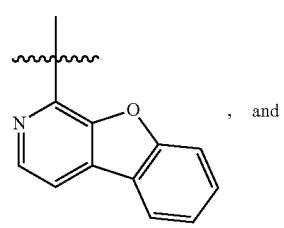
A¹³¹, and
A¹²⁶
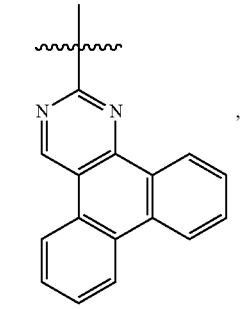

A[132]
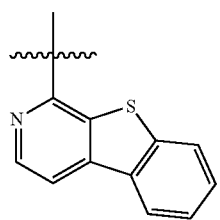
In one aspect, the compound is selected from the group consisting of:
Compound 22
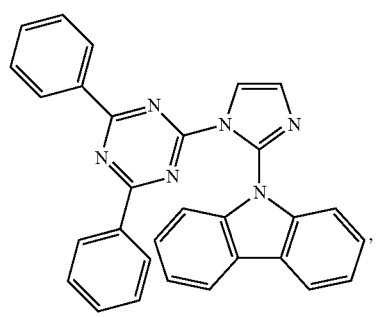
Compound 662
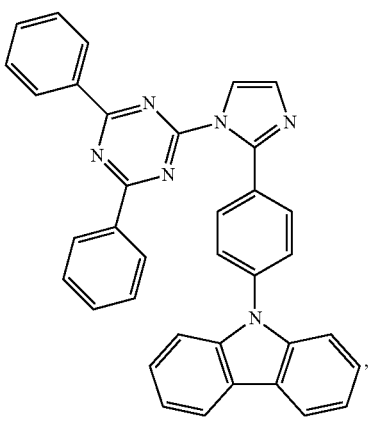
Compound 1430
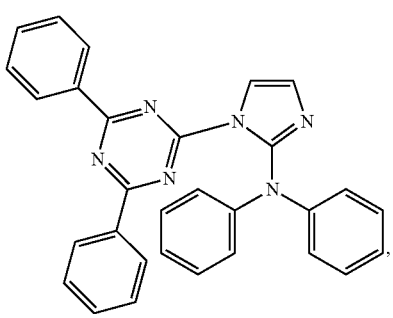
Compound 1750
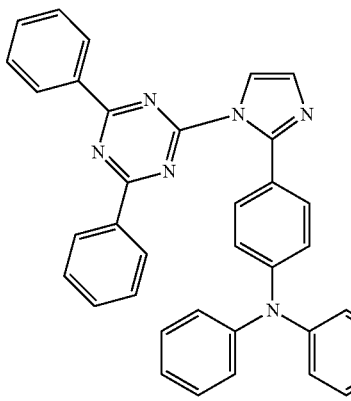
Compound 1654
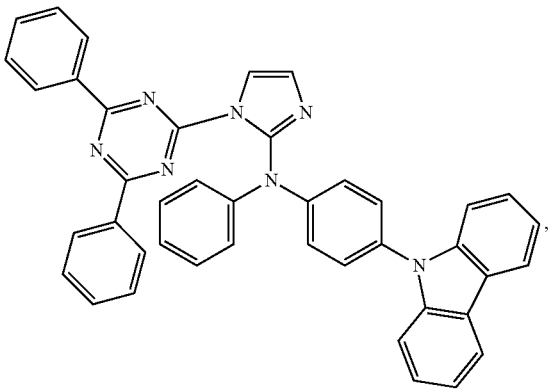
Compound 1974
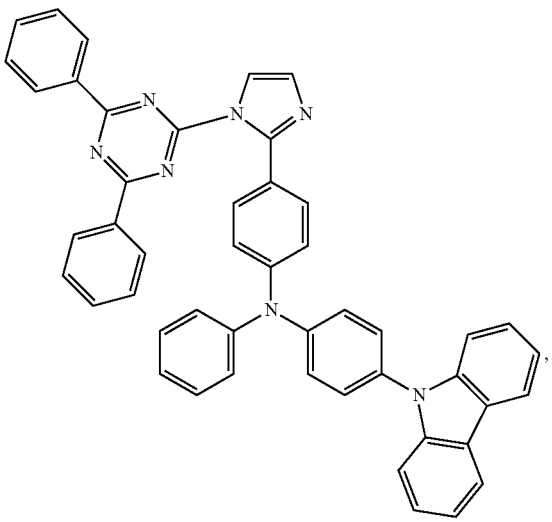

Compound 502
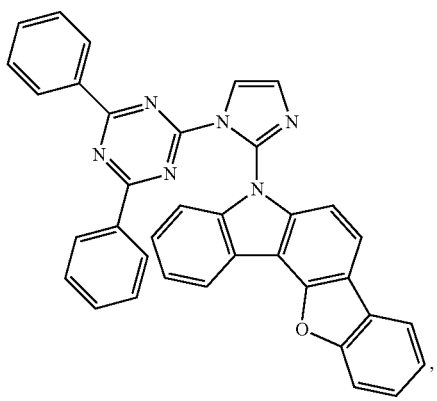
Compound 470
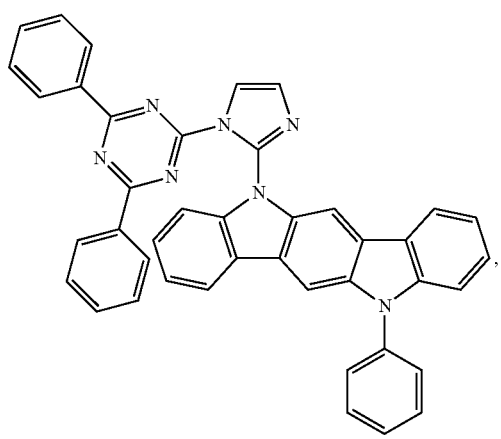
Compound 246
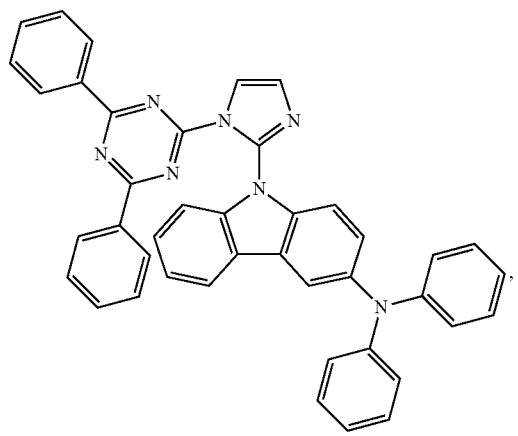
Compound 694
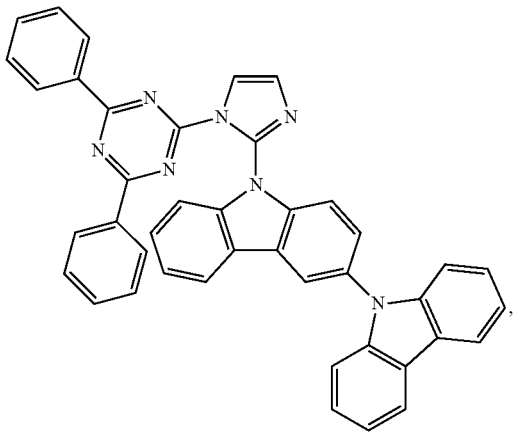
Compound 118
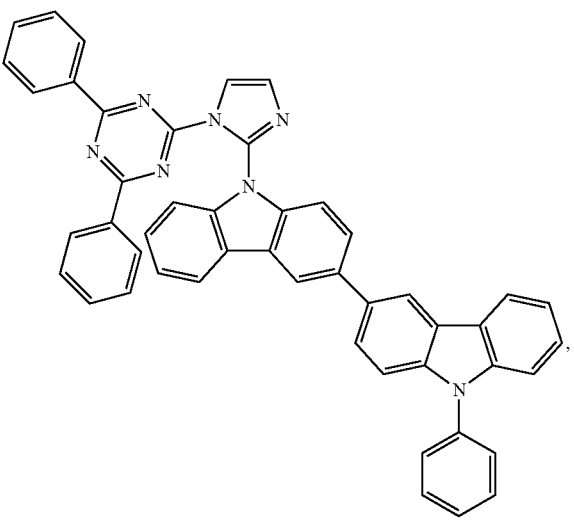
Compound 758
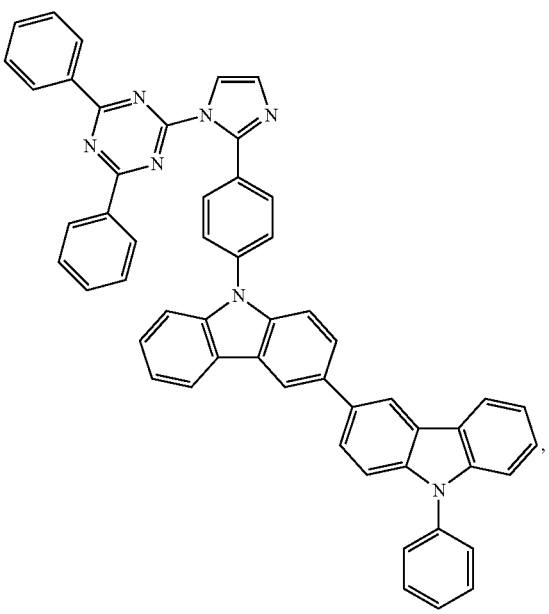

Compound 23
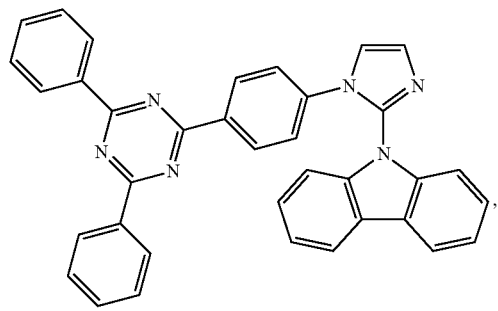
Compound 1975
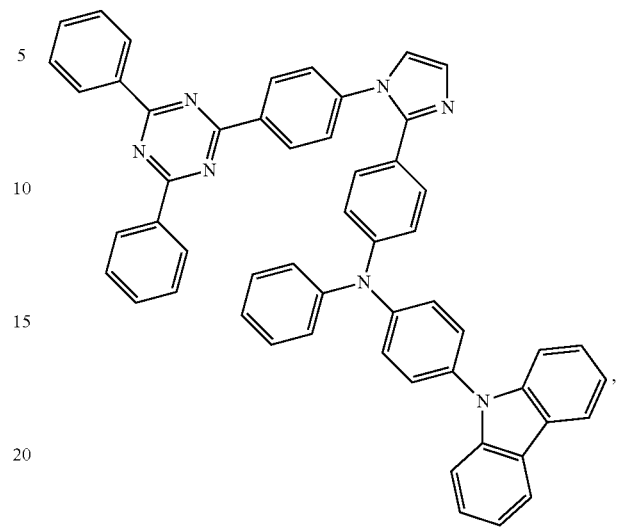
Compound 663
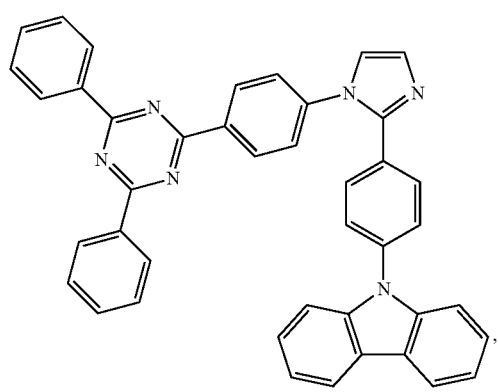
Compound 1431
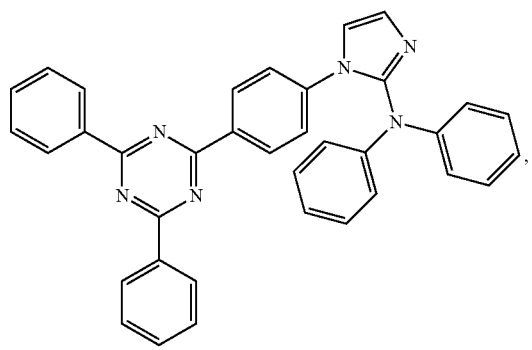
Compound 503
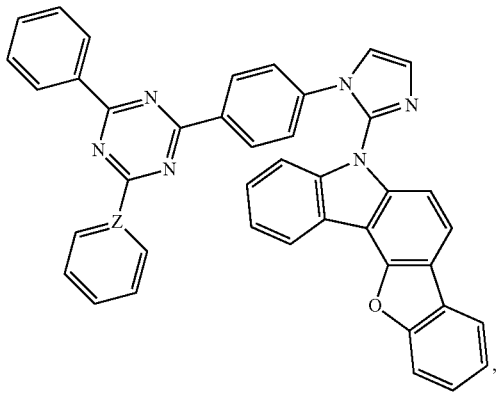
Compound 1655
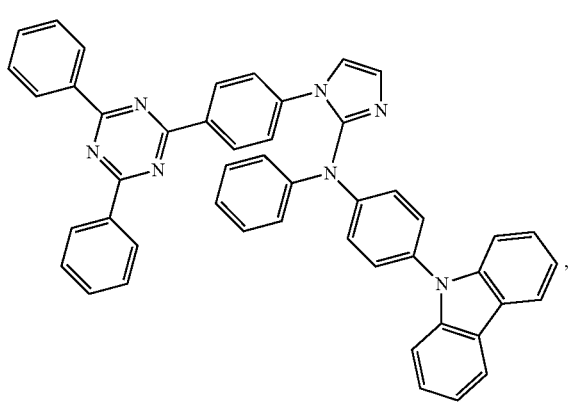
Compound 471
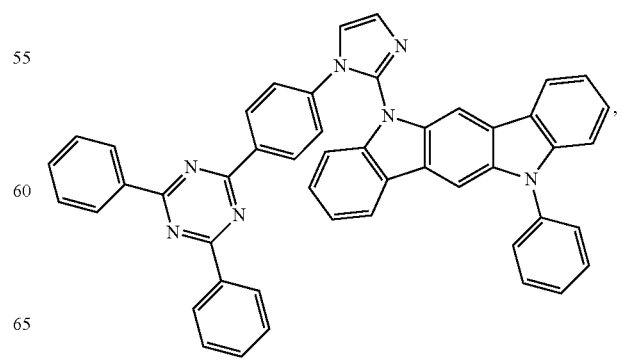

-continued
Compound 247
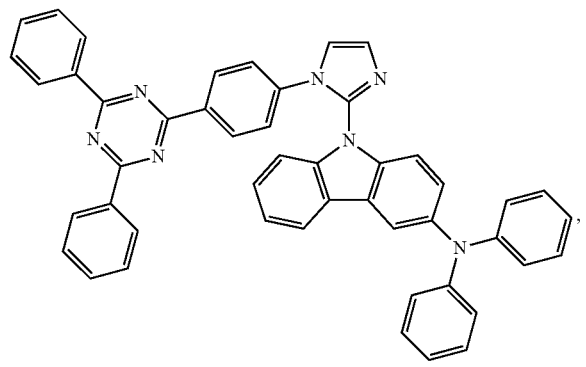
Compound 55
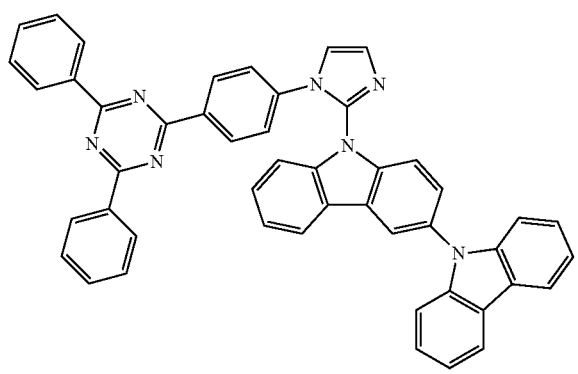
Compound 119
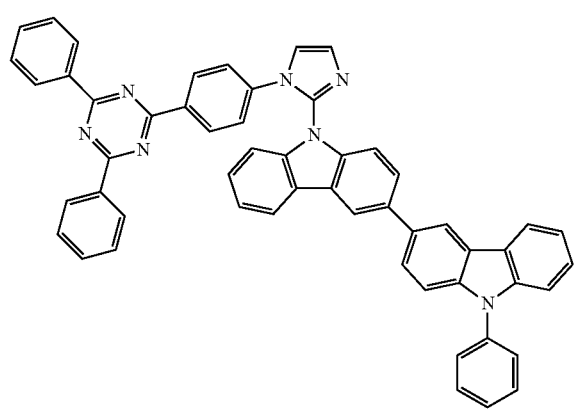
-continued
Compound 759
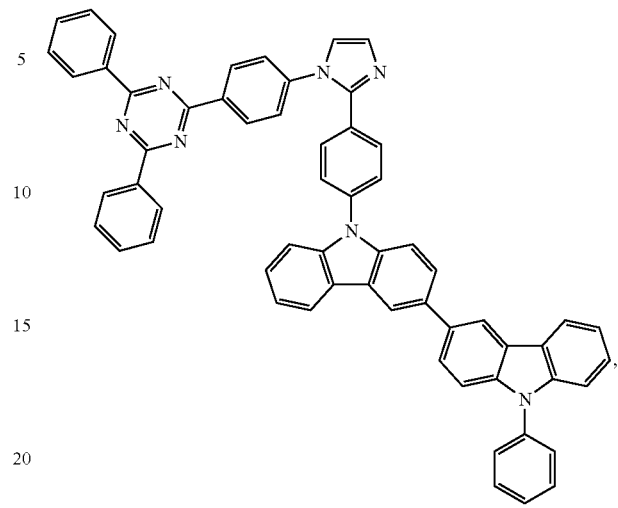
Compound 3414
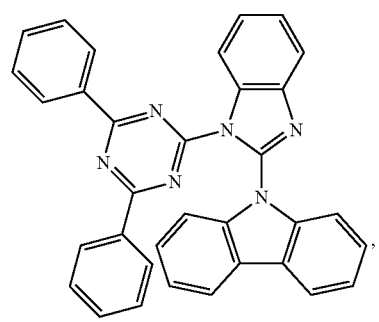
Compound 4822
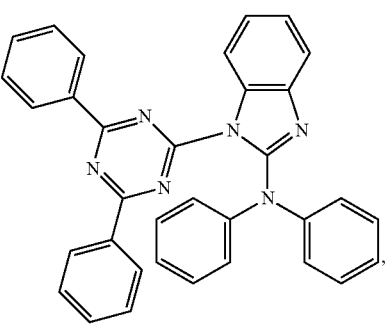
Compound 5142
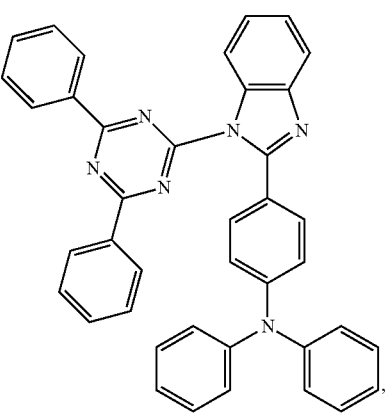

Compound 5046
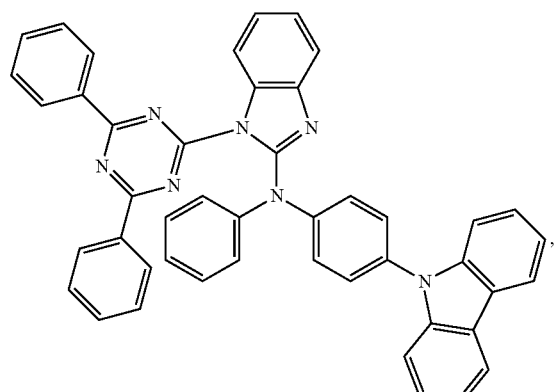
Compound 3862
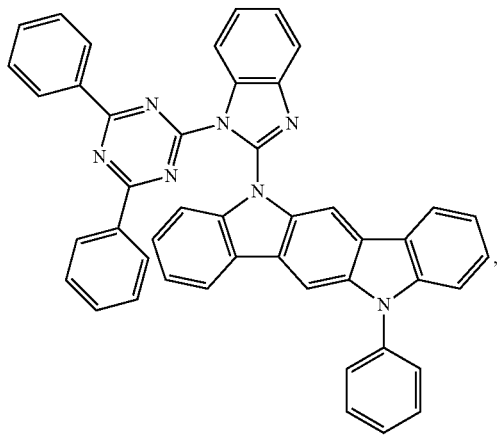
Compound 5366
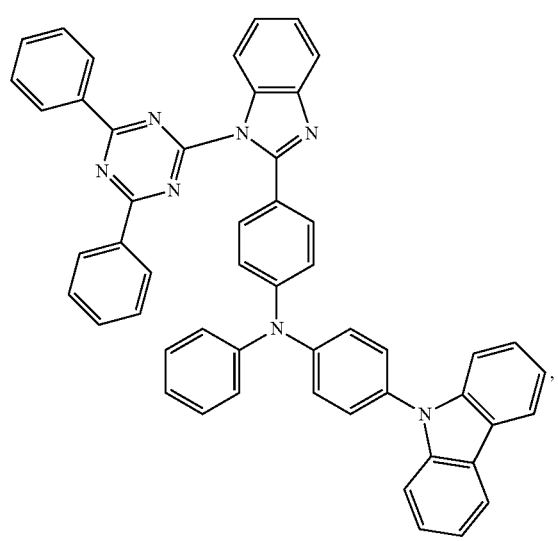
Compound 3638
Compound 3894
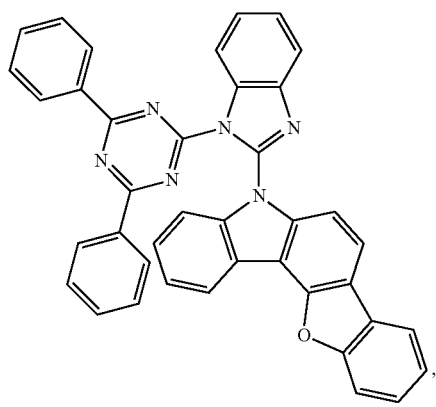
Compound 3446
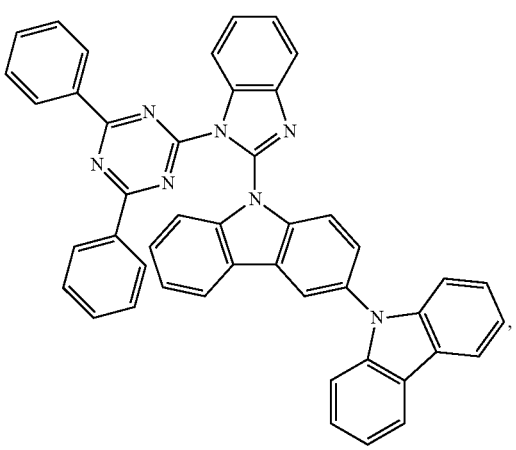

Compound 3510
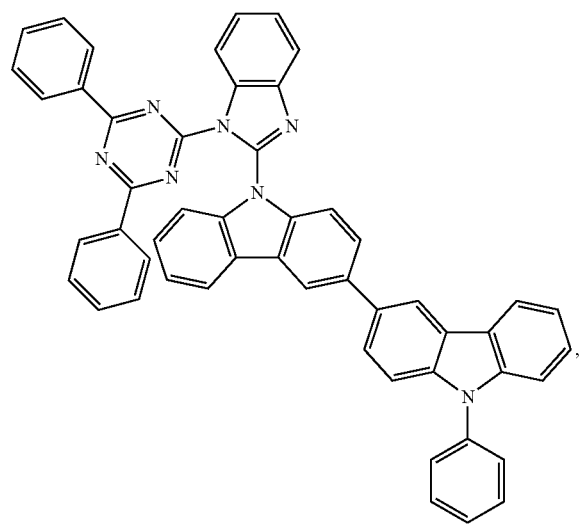
Compound 4150
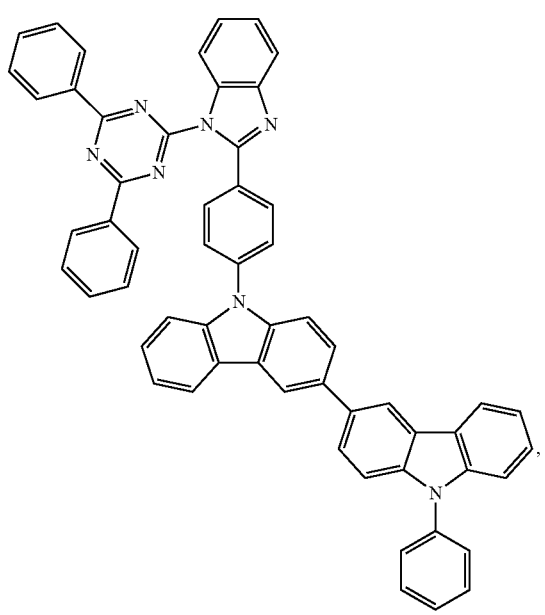
Compound 24
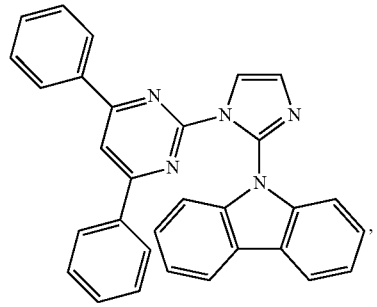
Compound 664
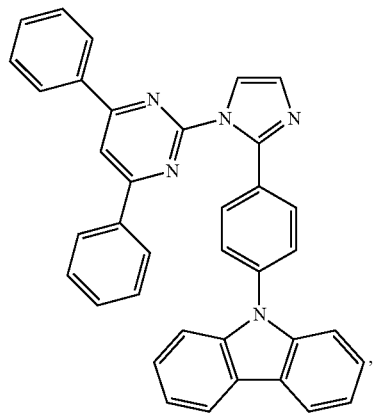
Compound 1432
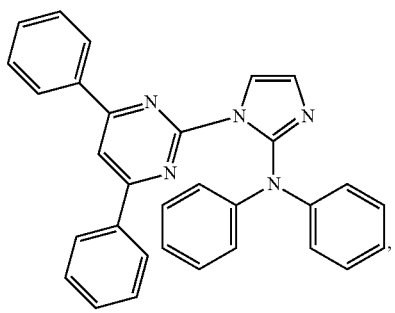
Compound 1752
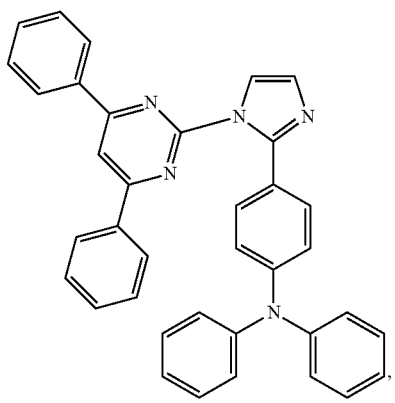
Compound 5110
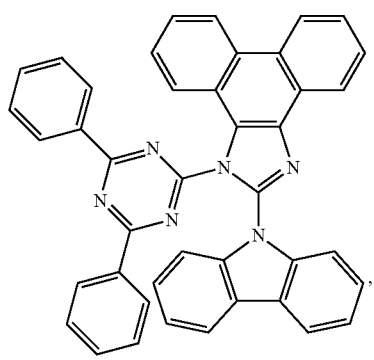

Compound 8534

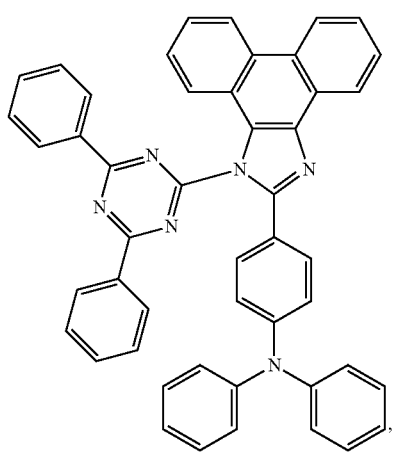

Compound 5

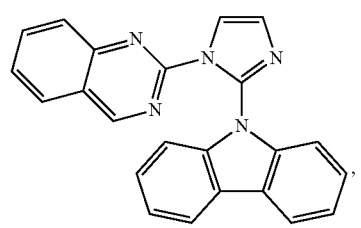

Compound 645

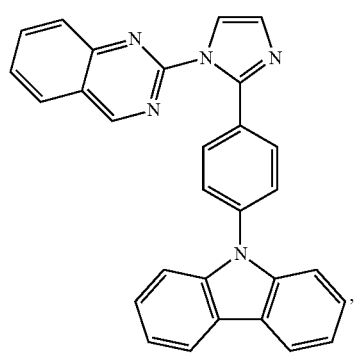

Compound 3397

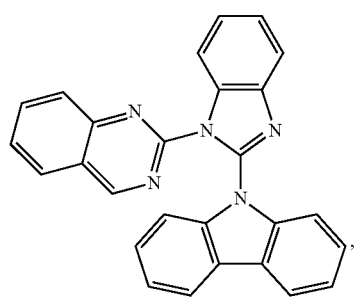

Compound 4805

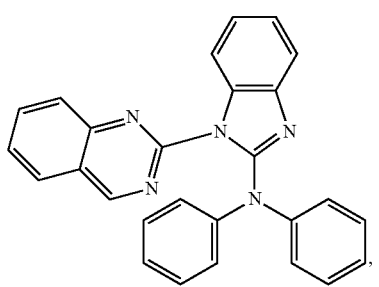

Compound 5125

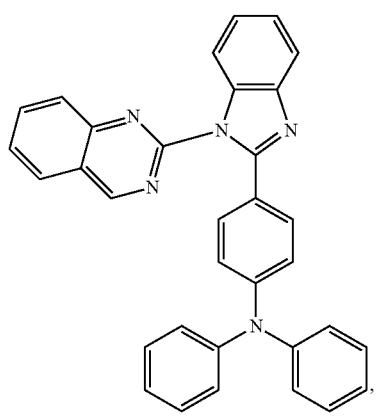

Compound 2966

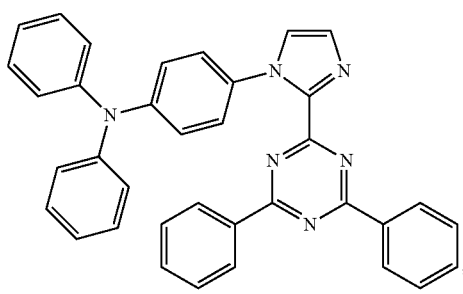

and

Compound 6358

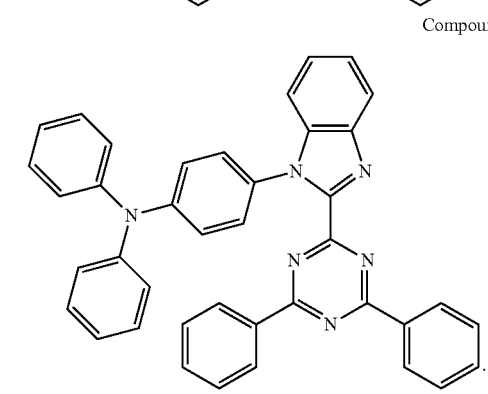

In one aspect, a first device is provided. The first device comprises a first organic light emitting device, further comprising an anode, a cathode; and an organic layer, disposed between the anode and the cathode, where the organic layer comprises a compound having the formula:
a compound of formula Formula I

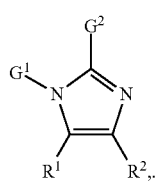

$G^1$ is an electron donor group or an electron acceptor group, and $G^2$ is also an electron donor group or an electron acceptor group. If $G^1$ is an electron donor group, then $G^2$ is an electron acceptor group, and if $G^1$ is an electron acceptor group, then $G^2$ is an electron donor group.

$R^1$ and $R^2$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R^1$ and $R^2$ are optionally joined to form a ring, which may be further substituted.

In one aspect, the organic layer is an emissive layer.

In one aspect, the electron acceptor group comprises at least one chemical group selected from the group consisting of a six-membered aromatic ring system having at least two nitrogen atoms and a 5-membered aromatic ring system containing at least one nitrogen atom, one oxygen atom, one sulfur atom, or one selenium atom.

In one aspect, the first device emits a luminescent radiation at room temperature when a voltage is applied across the first organic light emitting device, wherein the luminescent radiation comprises a delayed fluorescence process.

In one aspect, the emissive layer further comprises a first phosphorescent emitting material.

In one aspect, the emissive layer further comprises a second phosphorescent emitting material.

In one aspect, the emissive layer further comprises a host material.

In one aspect, the compound is a host.

In one aspect, the compound is an emissive dopant.

In one aspect, the first device emits a white light at room temperature when a voltage is applied across the organic light emitting device.

In one aspect, the compound emits a blue light having a peak wavelength between about 400 nm to about 500 nm.

In one aspect, the compound emits a yellow light having a peak wavelength between about 530 nm to about 580 nm.

In one aspect, the first device comprises a second organic light-emitting device, wherein the second organic light emitting device is stacked on the first organic light emitting device.

In one aspect, the first device is a consumer product.

In one aspect, the first device is an organic light-emitting device.

In one aspect, the first device comprises a lighting panel.

In one aspect, a method of making a first organic light emitting device is provided. The method comprises: depositing an anode on a substrate, depositing at least one organic layer comprising a compound of formula:

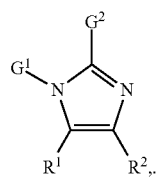

Formula I $G^1$ is an electron donor group or an electron acceptor group, and $G^2$ is also an electron donor group or an electron acceptor group. If $G^1$ is an electron donor group, then $G^2$ is an electron acceptor group, and if $G^1$ is an electron acceptor group, then $G^2$ is an electron donor group.

$R^1$ and $R^2$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R^1$ and $R^2$ are optionally joined to form a ring, which may be further substituted, and depositing a cathode, wherein the emissive layer is deposited between the anode and cathode.

In one aspect, the at least one organic layer is deposited using a solution process.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
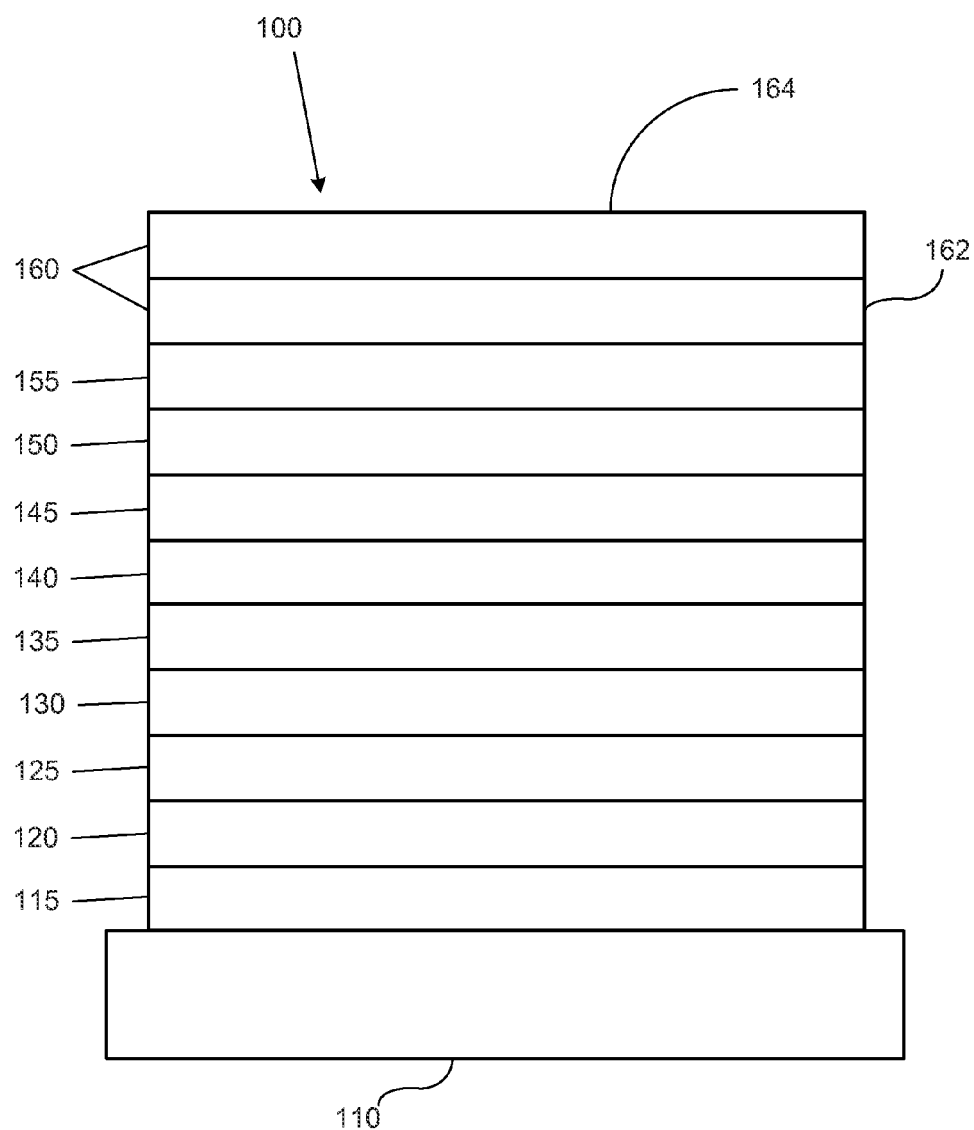
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
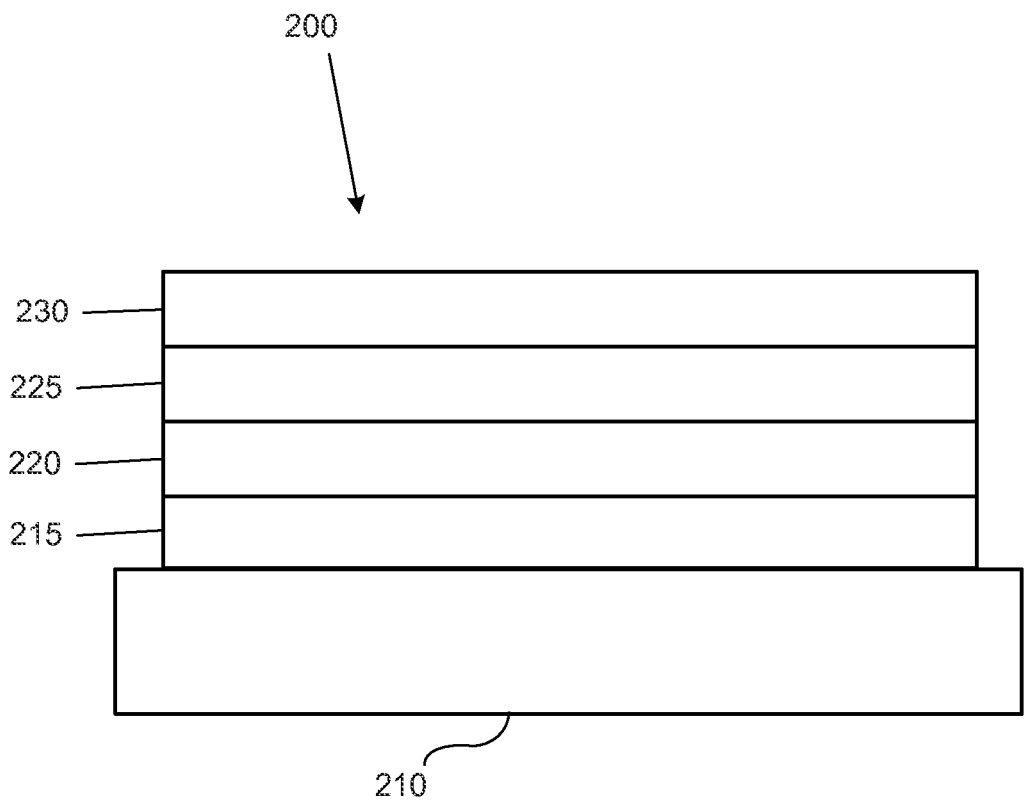
FIG. 2 shows an inverted organic light emitting device that does not have a separate electron transport layer.
Figure 3:
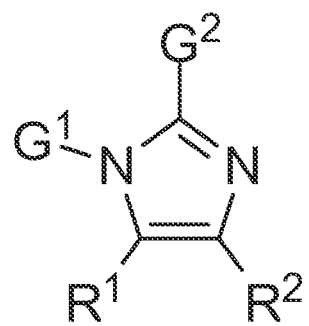
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

A compound having the formula:

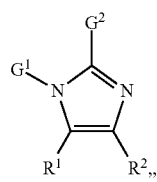

Formula I is provided.

$G^1$ is an electron donor group or an electron acceptor group, and $G^2$ is also an electron donor group or an electron acceptor group. If $G^1$ is an electron donor group, then $G^2$ is an electron acceptor group, and if $G^1$ is an electron acceptor group, then $G^2$ is an electron donor group.

As used herein, an "electron donor group" is a group that donates electron density to the aromatic system and an "electron acceptor group" is a group that accepts electron density from the aromatic system.

$R^1$ and $R^2$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R^1$ and $R^2$ are optionally joined to form a ring, which may be further substituted.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the thermal population between the triplet states and the singlet excited states. Compounds that are capable of generating E-type delayed fluorescence are required to have very small singlet-triplet gaps. Thermal energy can activate the transition from the triplet state back to the singlet state. This type of delayed fluorescence is also known as thermally activated delayed fluorescence (TADF). A distinctive feature of TADF is that the delayed component increases as temperature rises due to the increased thermal energy. If the reverse intersystem crossing rate is fast enough to minimize the non-radiative decay from the triplet state, the fraction of back populated singlet excited states can potentially reach 75%. The total singlet fraction can be 100%, far exceeding the spin statistics limit E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic rings.

The claimed compounds of Formula I, which are pure organic compounds lacking any metal, represent a different class of compounds that exhibit TADF characteristics. The compounds of Formula I are novel compounds with donor and acceptors substituted at the 1,2 positions of imidazole. This method of connecting donor and acceptor units into a single molecule can provide compounds exhibiting delayed fluorescence with high PLQY.

In one embodiment, the donor group comprises at least one chemical group selected from the group consisting of amino, indole, carbazole, benzothiophene, benzofuran, benzoselenophene, dibenzothiophene, dibenzofuran, dibenzoselenophene, and combinations thereof.

In one embodiment, the donor group comprises at least one chemical group selected from the group consisting of:

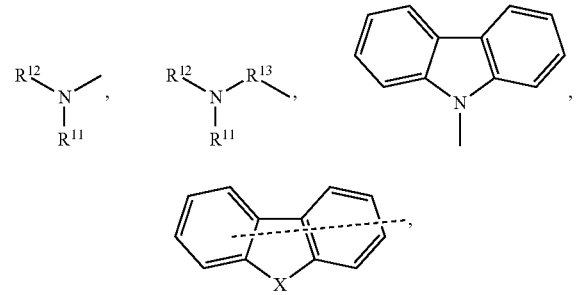

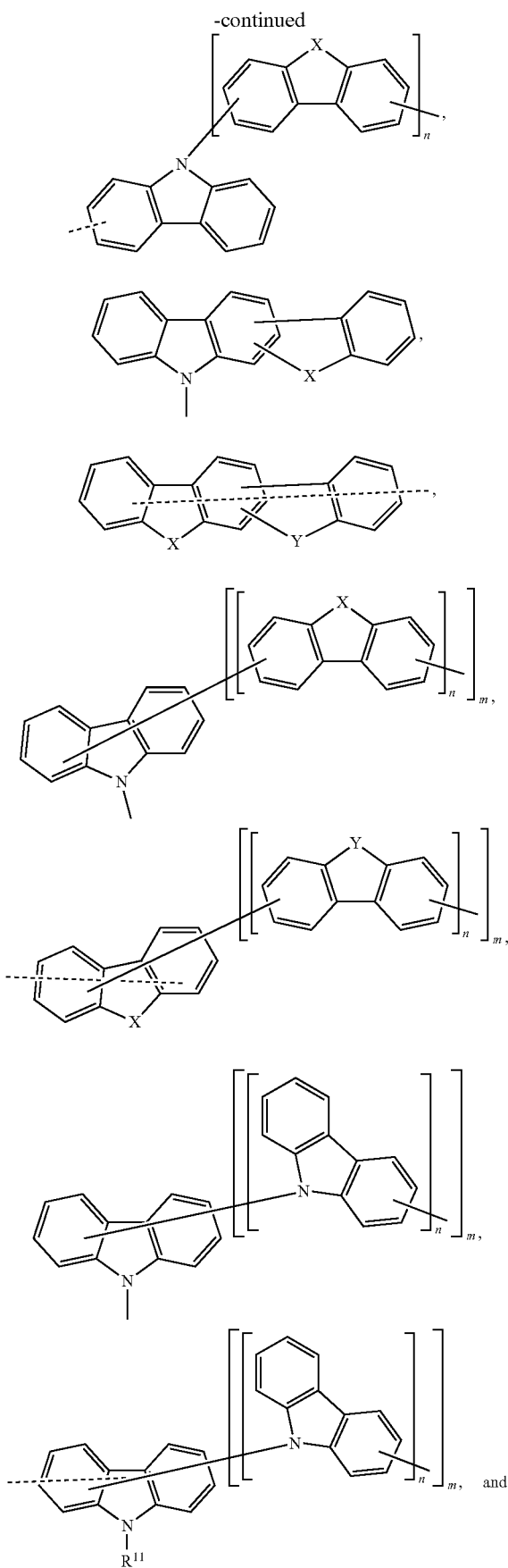

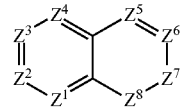

wherein n is an integer from 1 to 20, wherein m is an integer from 1 to 20, wherein X and Y are independently selected from the group consisting of O, S, and $NR^{14}$, and wherein $R^{11}$, $R^{12}$, $R^{13}$ and $R^{14}$ are selected from the group consisting of aryl and heteroaryl.

In one embodiment, the electron acceptor group is selected from the group consisting of:

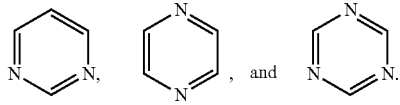

In one embodiment, the electron acceptor group has the structure:

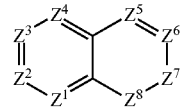

wherein $Z^1$ to $Z^8$ independently comprise C or N, and wherein at least two of $Z^1$ to $Z^8$ are N.

In one embodiment, the electron acceptor group comprises at least one chemical group selected from the group consisting of:

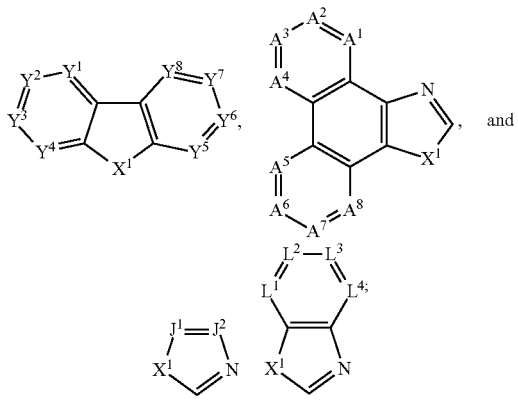

wherein $Y^1$ to $Y^8$ independently comprise C or N, wherein $A^1$ to $A^8$ independently comprise C or N, wherein $J^1$ and $J^2$ independently comprise C or N, wherein $L^1$ to $L^4$ independently comprise C or N, wherein $X^1$ is O, S, or $NR^{14}$, and wherein $R^{14}$ is aryl or heteroaryl.

In one embodiment, the donor group is selected from the group consisting of:
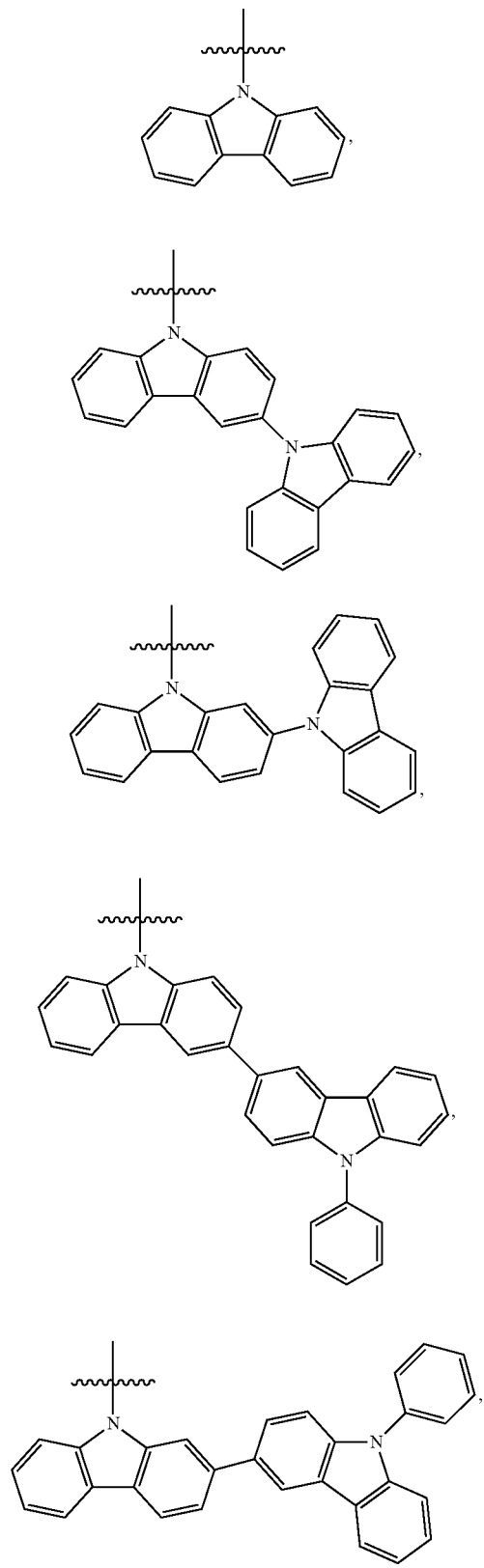
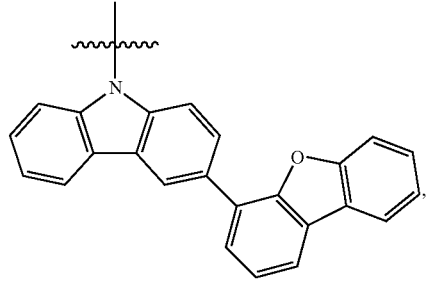
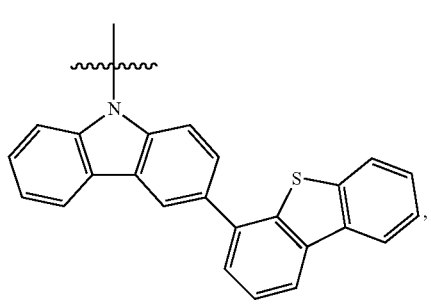
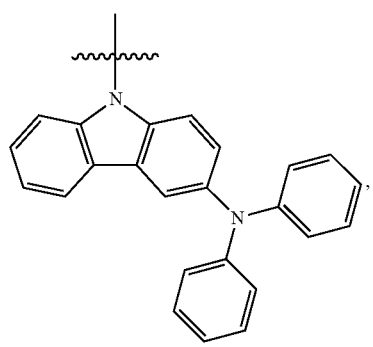
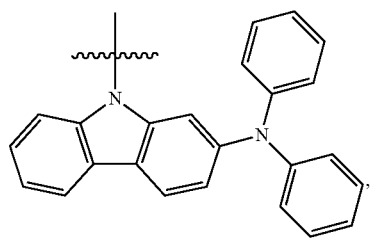
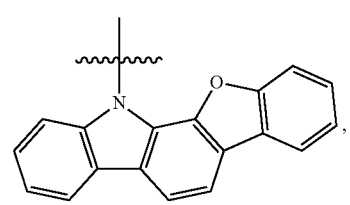
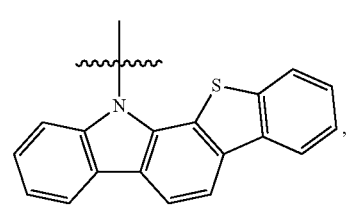

D112 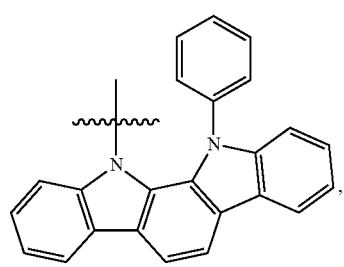
D113 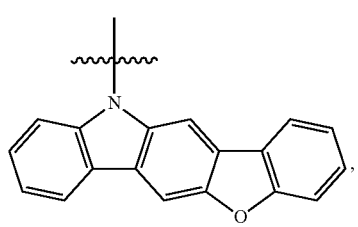
D114 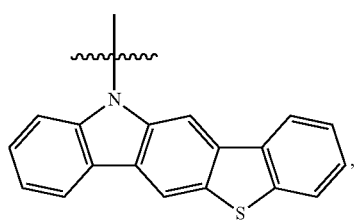
D115 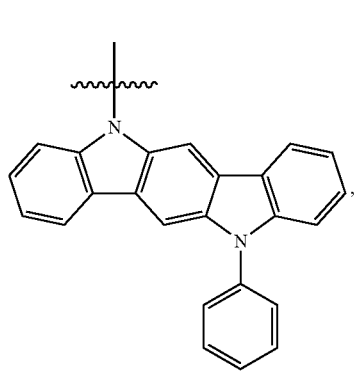
D116 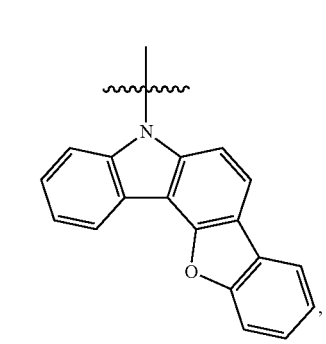
D117 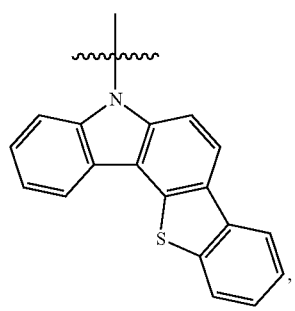
D118 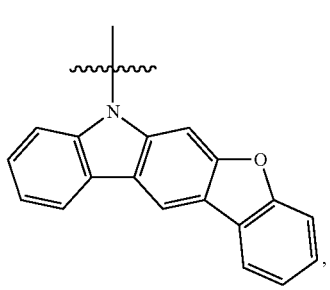
D119 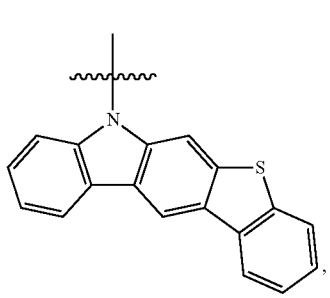
D120 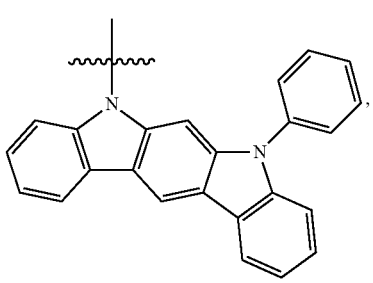
D121 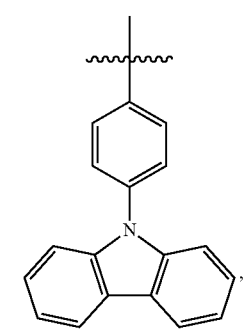

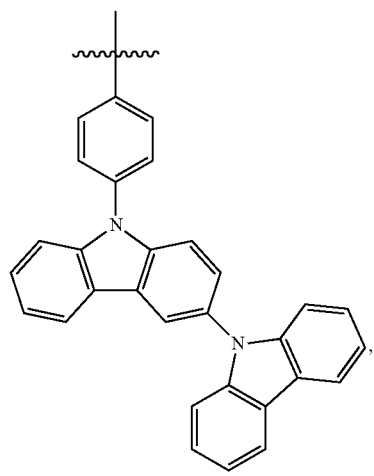
D¹²²
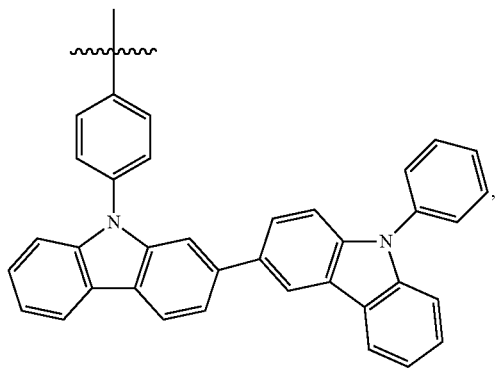
D¹²⁵
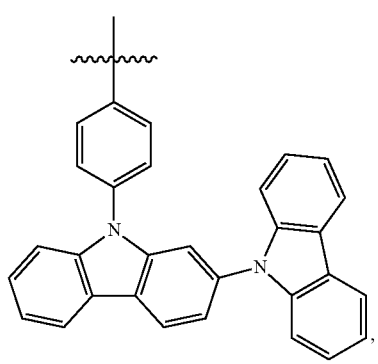
D¹²³
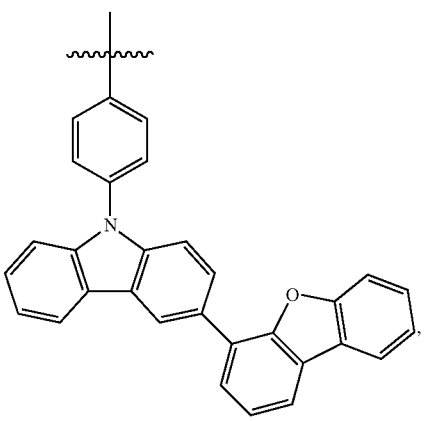
D¹²⁶
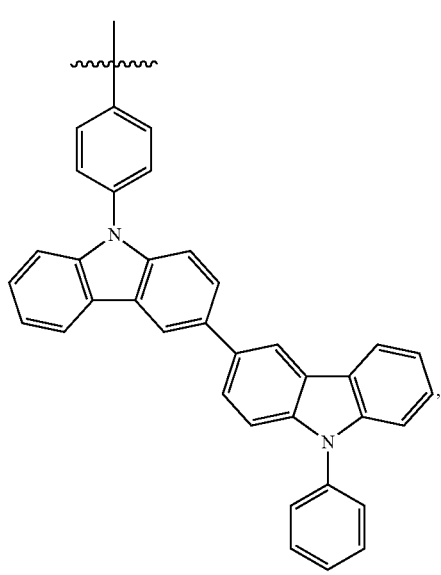
D¹²⁴
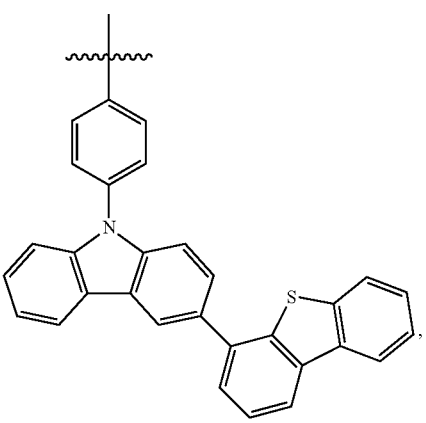
D¹²⁷

D[128]
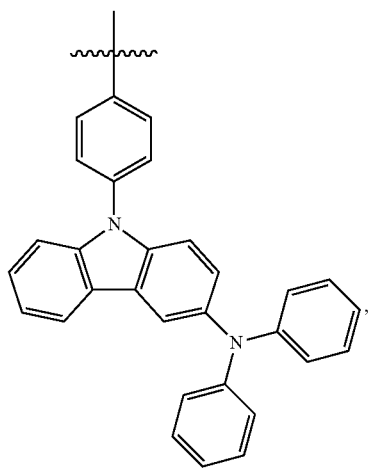
D[129]
D[130]
D[131]
D[132]
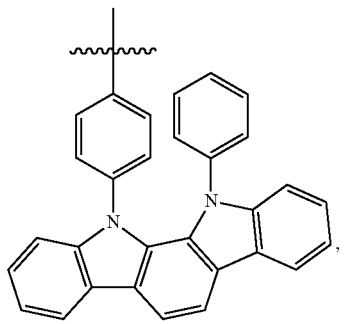
D[133]
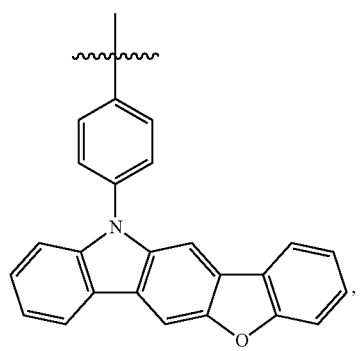
D[134]
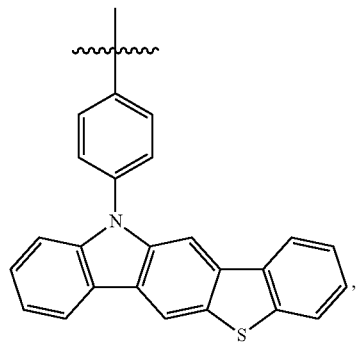
D[135]
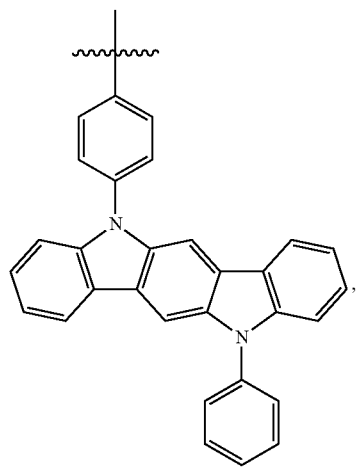

D[136]
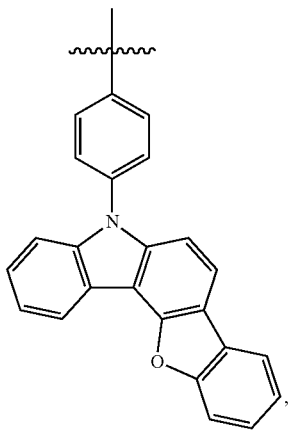
D[137]
D[138]
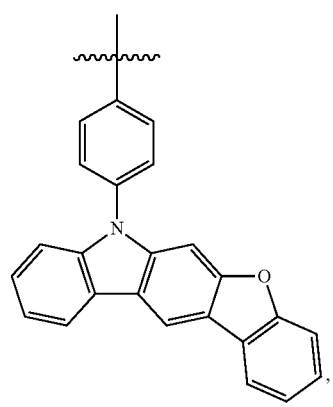
D[139]
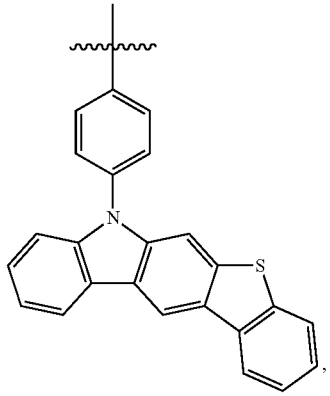
D[140]
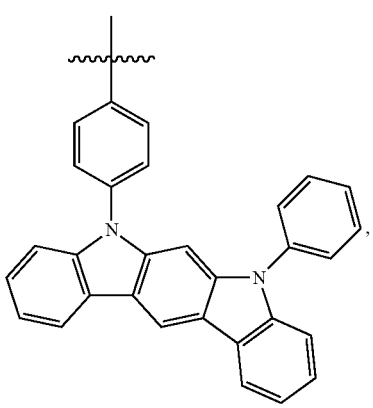
D[141]
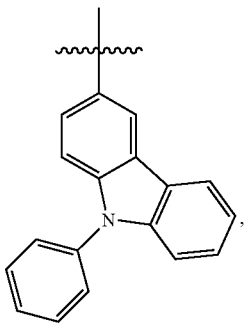
D[142]

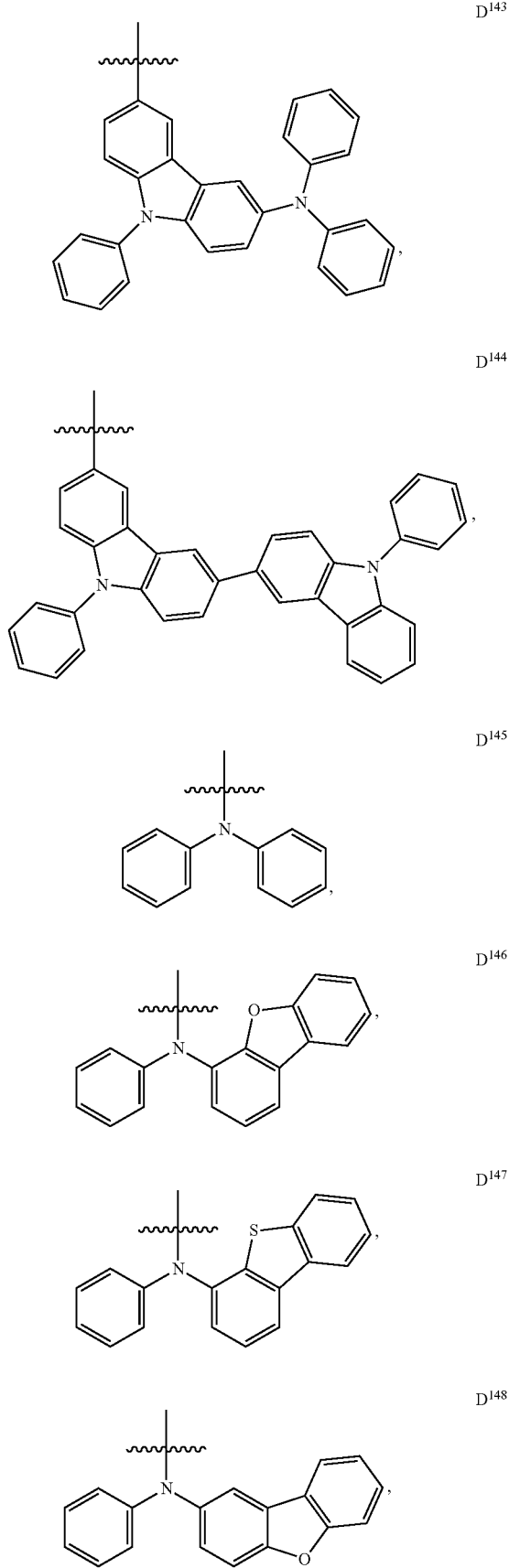
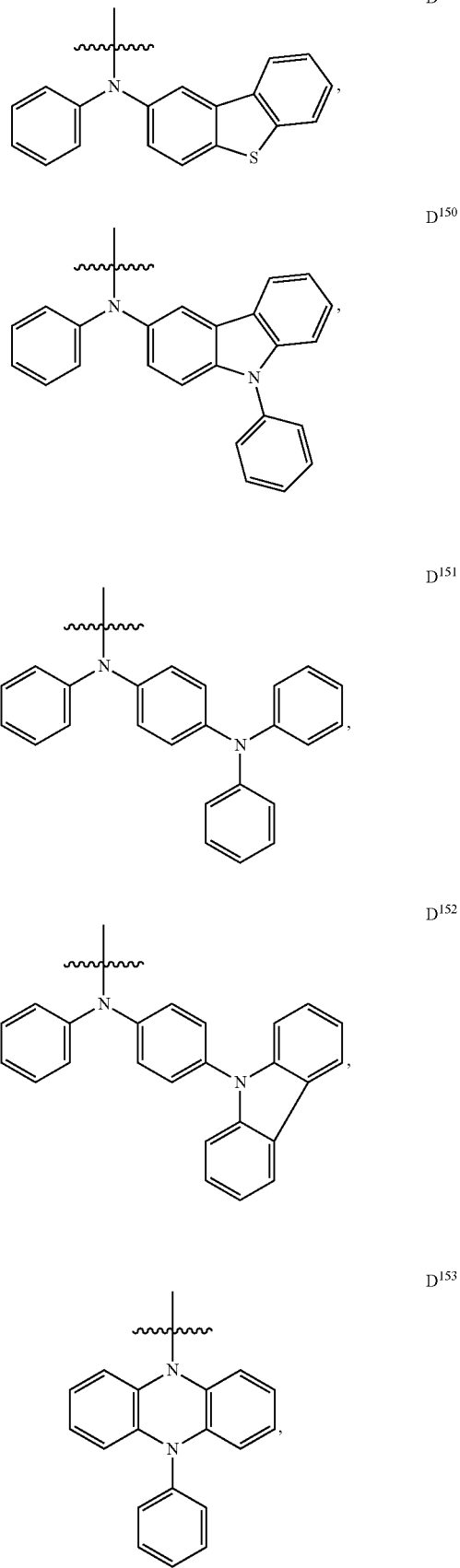

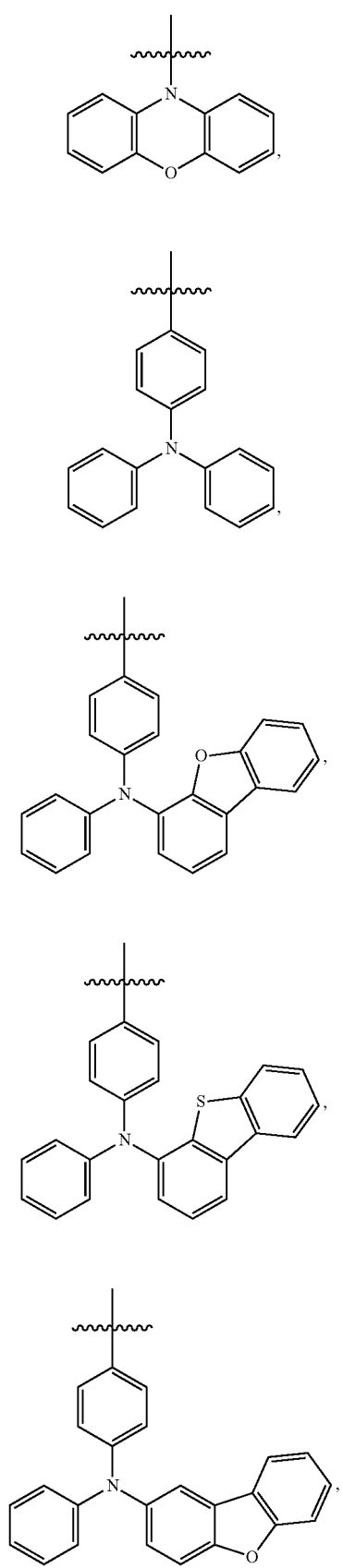
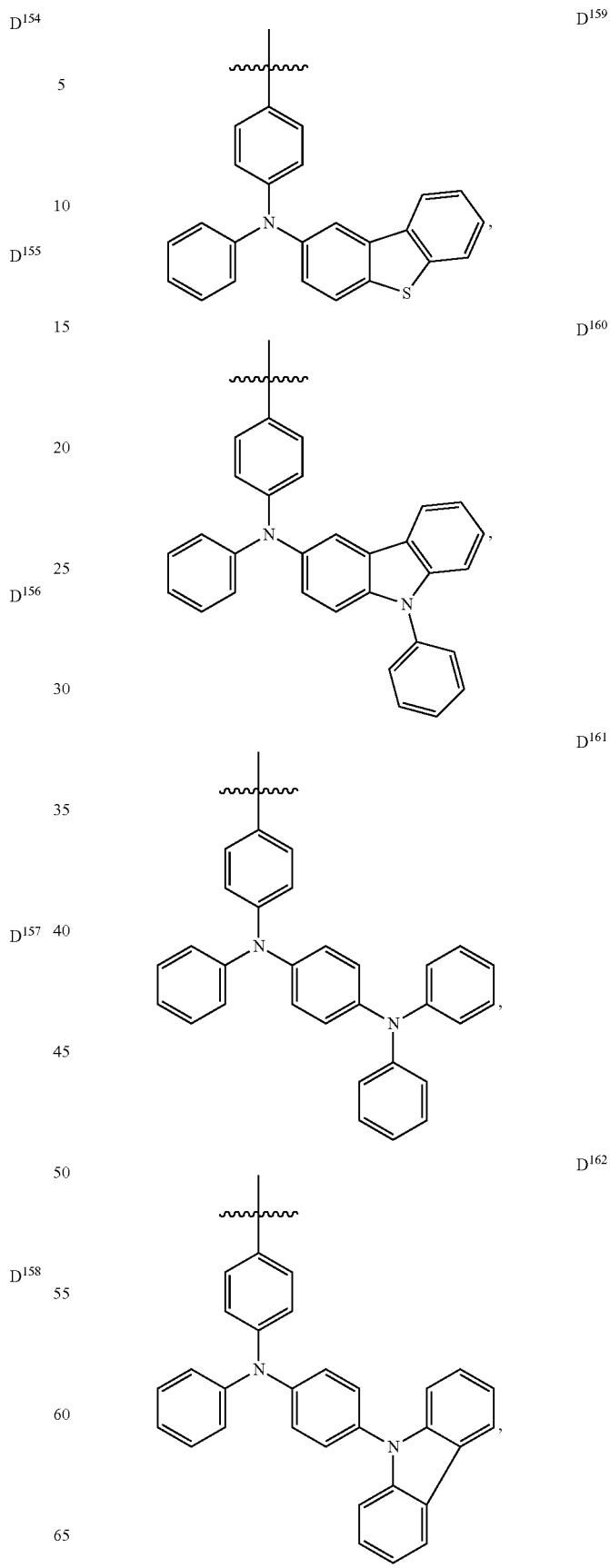

D¹⁶³
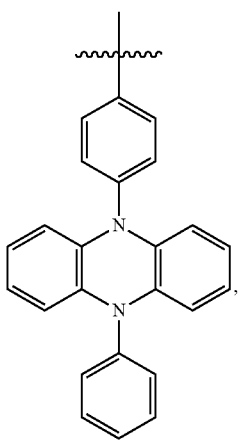
D¹⁶⁴
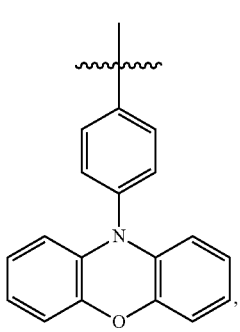
D¹⁶⁵
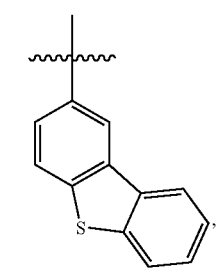
D¹⁶⁶
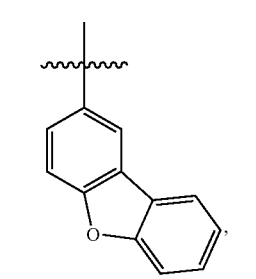
D¹⁶⁷
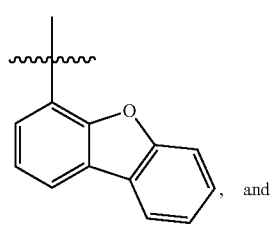, and
D¹⁶⁸
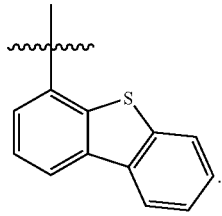
In one embodiment, the acceptor group is selected from the group consisting of:
A¹⁰¹
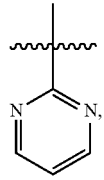
A¹⁰²
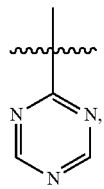
A¹⁰³
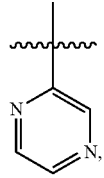
A¹⁰⁴
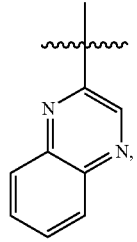
A¹⁰⁵
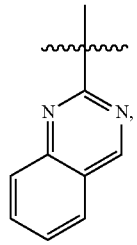

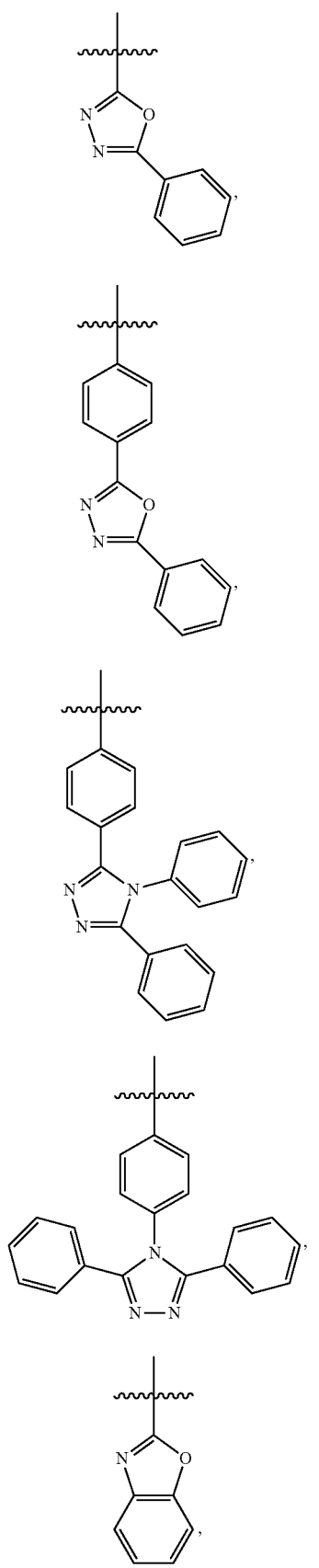

A117 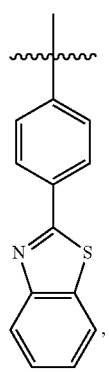
A118 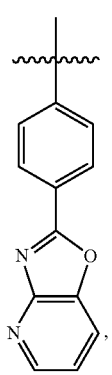
A119 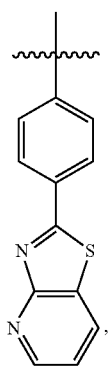
A120 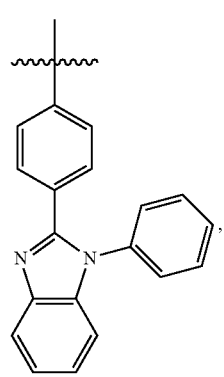
A121 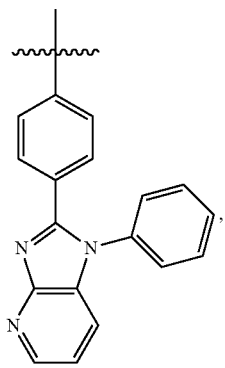
A122 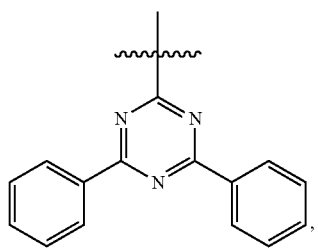
A123 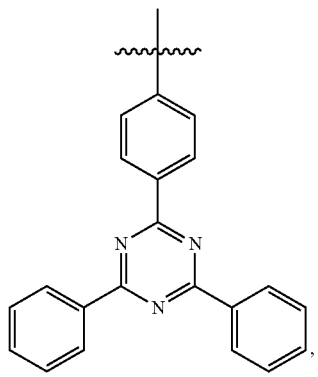
A124 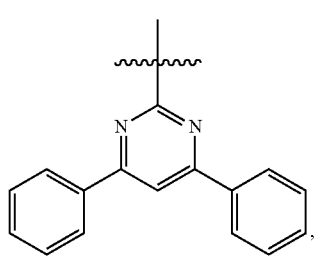
A125 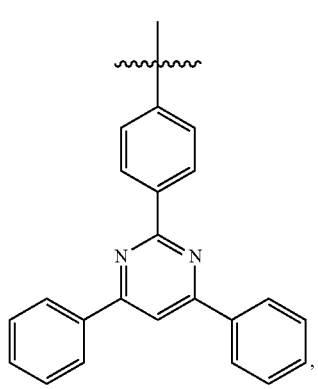

A[126]
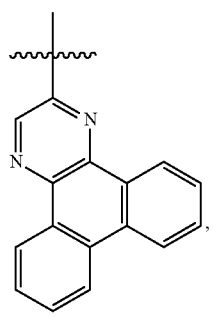
A[127]
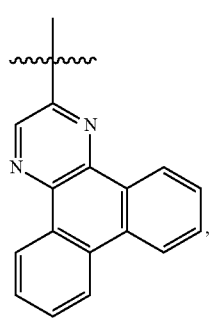
A[128]
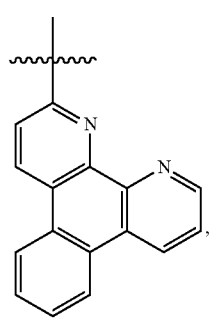
A[129]
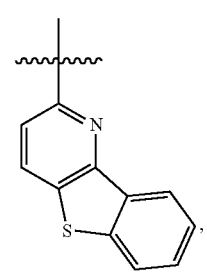
A[130]
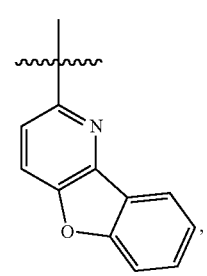
A[131]
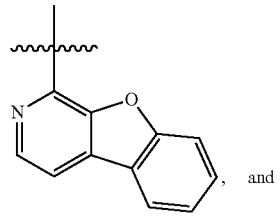, and
A[132]
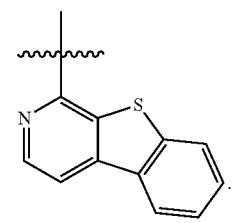.
In one embodiment, the compound is selected from the group consisting of:
Compound 22
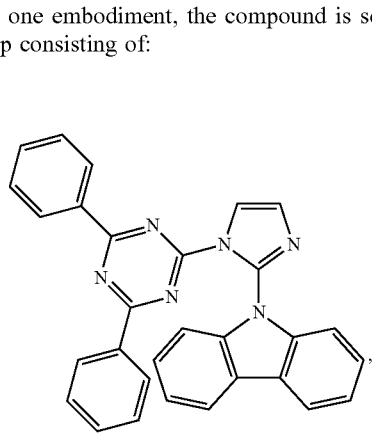
Compound 662
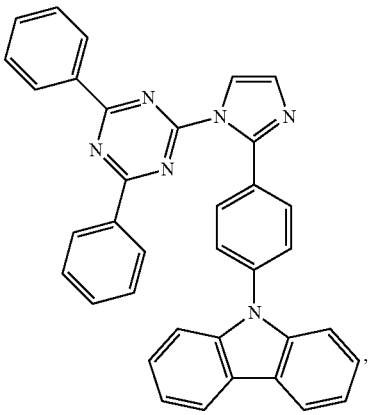
Compound 1430
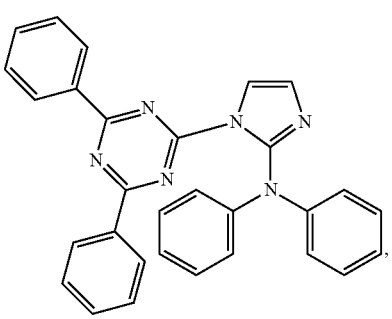

Compound 1750
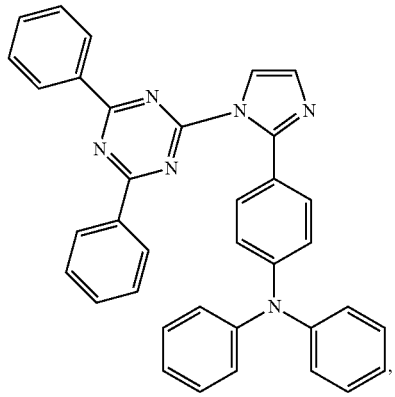
Compound 1654
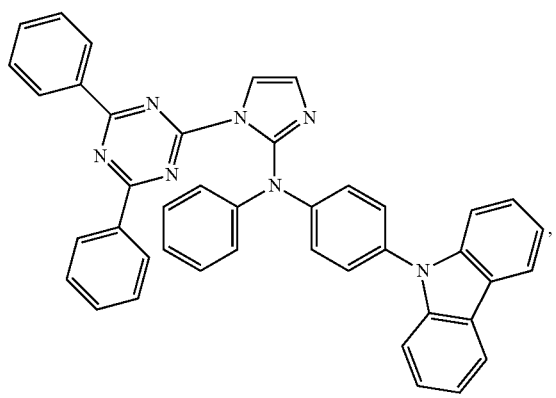
Compound 1974
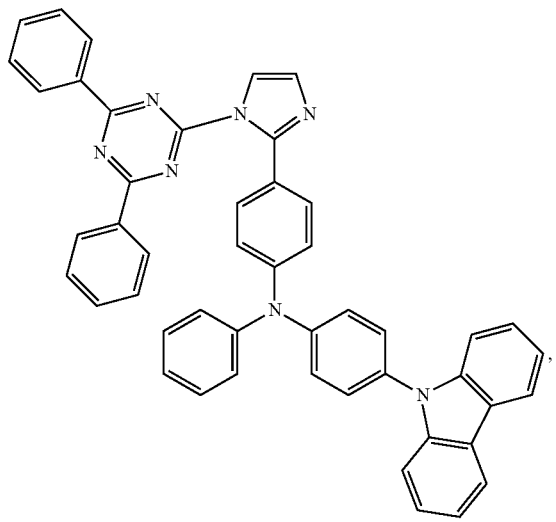
Compound 502
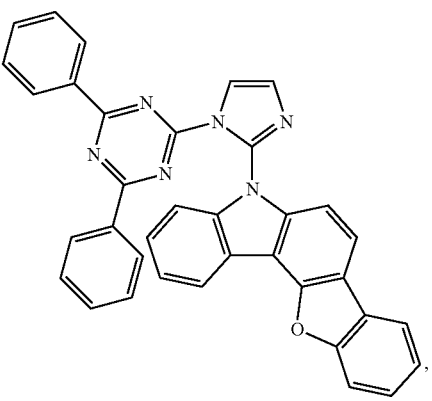
Compound 470
Compound 246
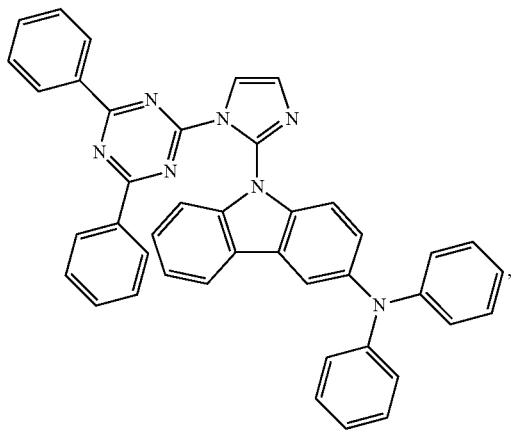

Compound 694
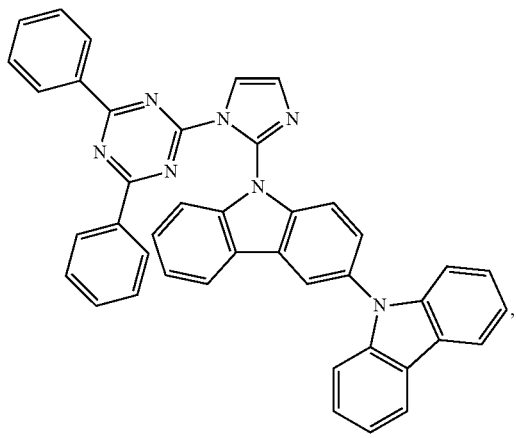
Compound 118
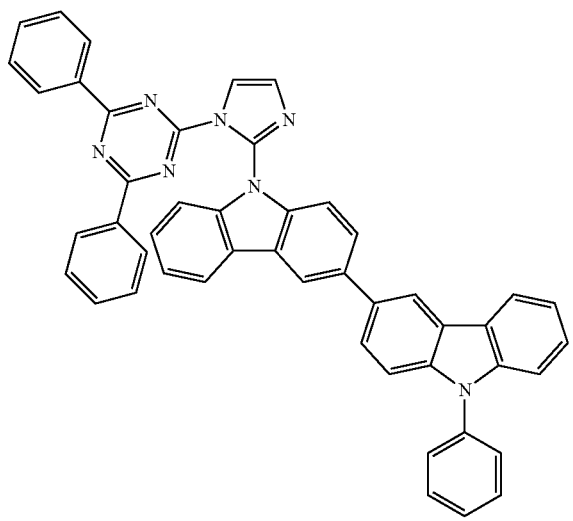
Compound 758
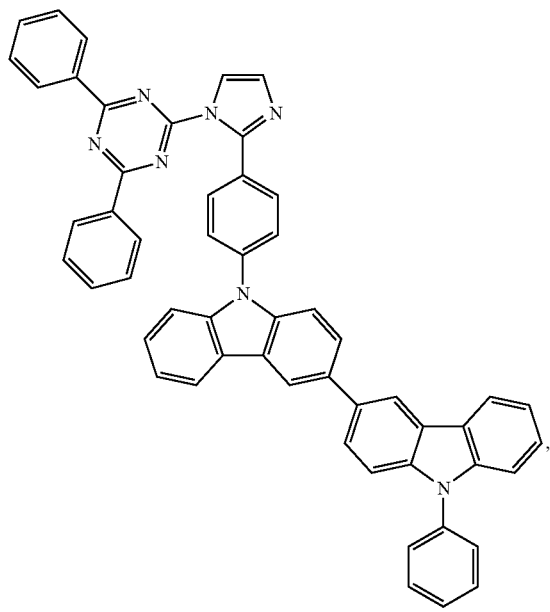
Compound 23
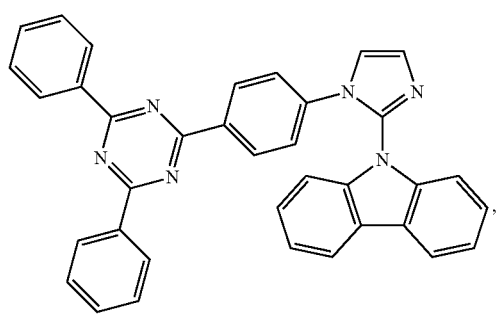
Compound 663
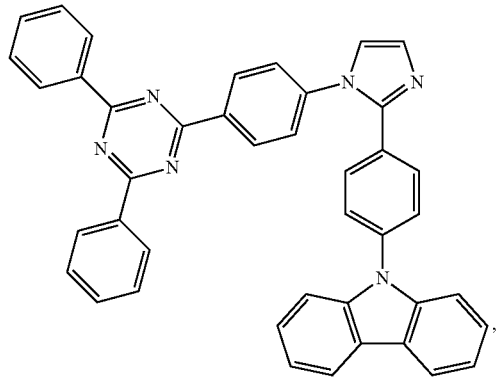
Compound 1431
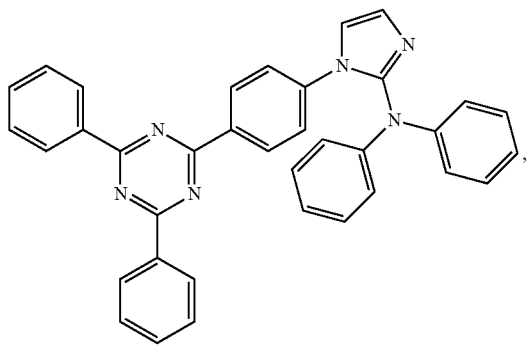
Compound 1655
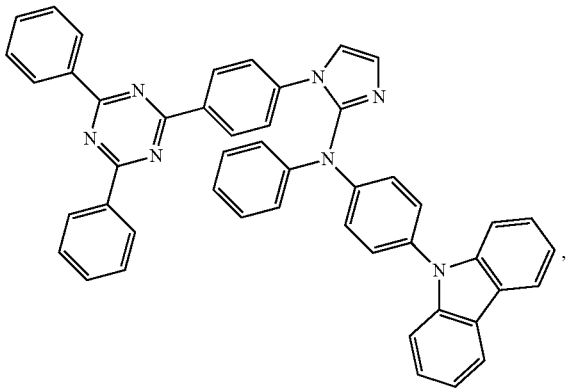

-continued
Compound 1975
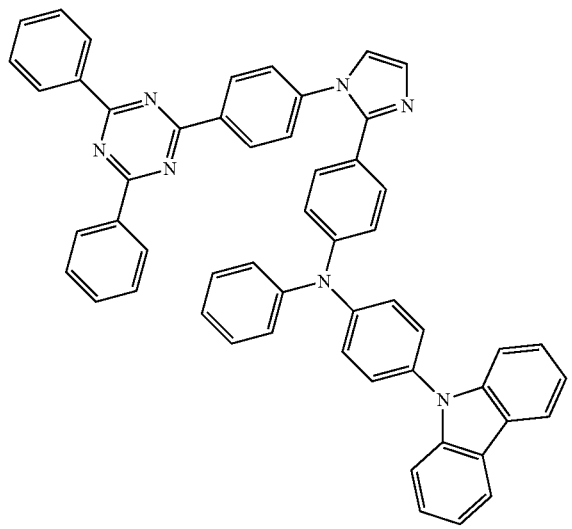
Compound 503
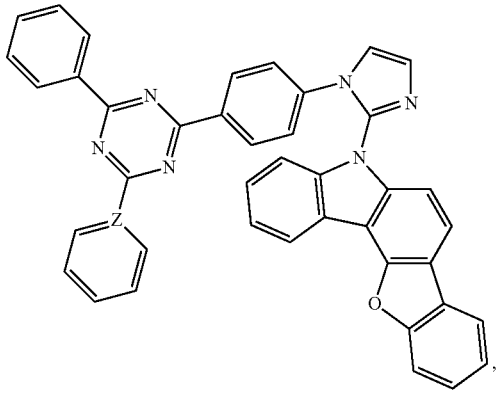
Compound 471
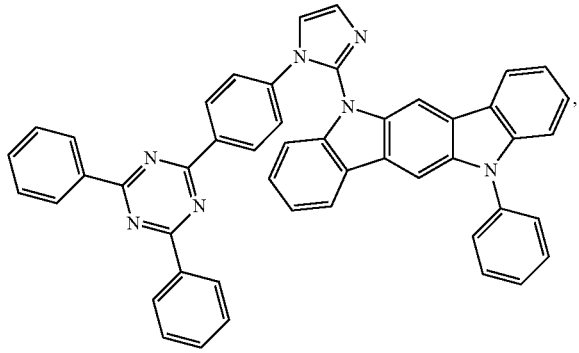
-continued
Compound 247
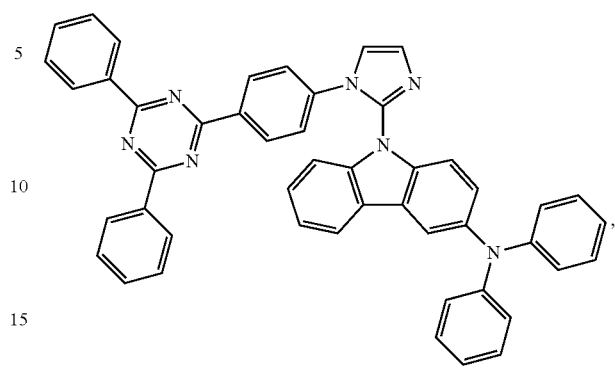
Compound 55
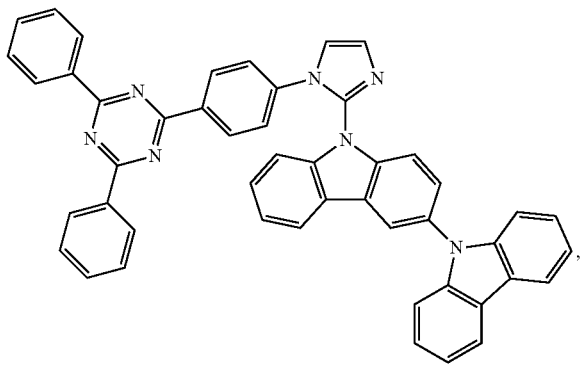
Compound 119
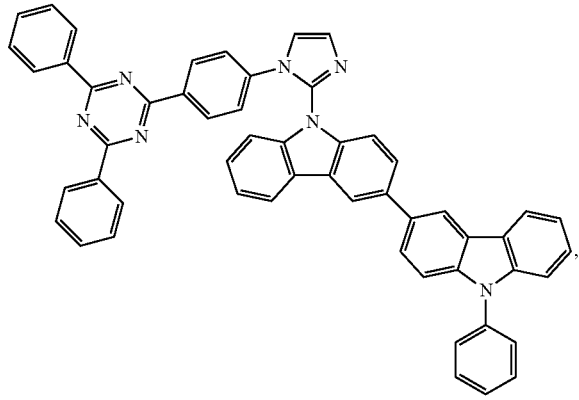

-continued
Compound 759
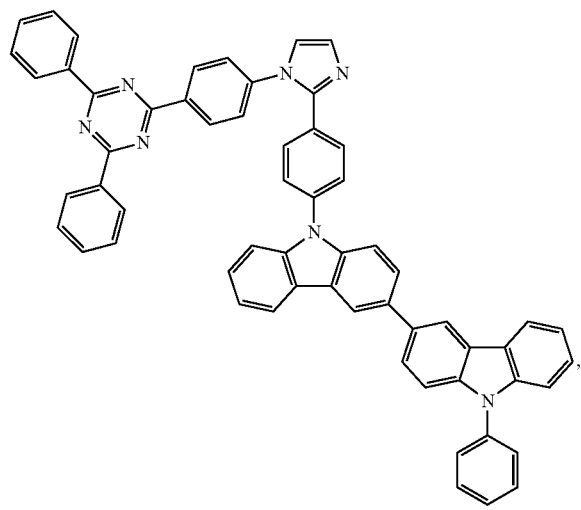
Compound 3414
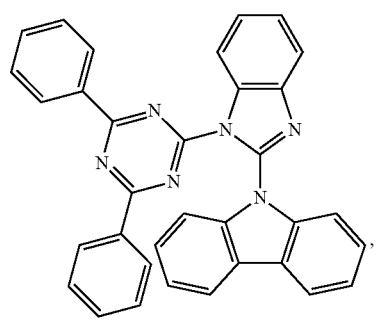
Compound 4822
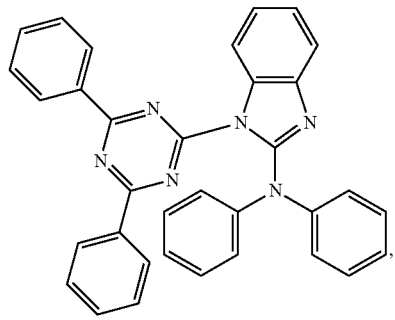
Compound 5142
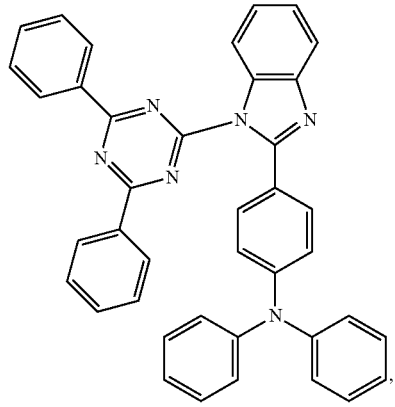
-continued
Compound 5046
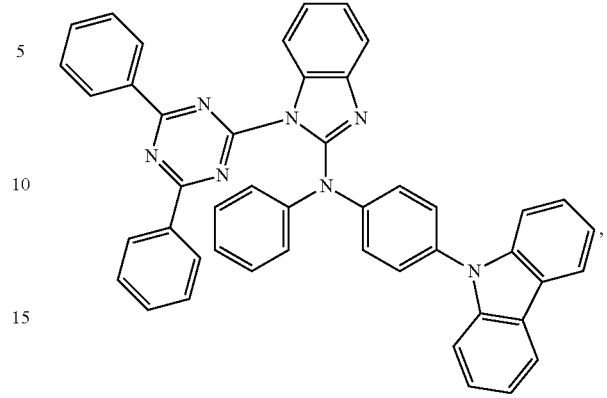
Compound 5366
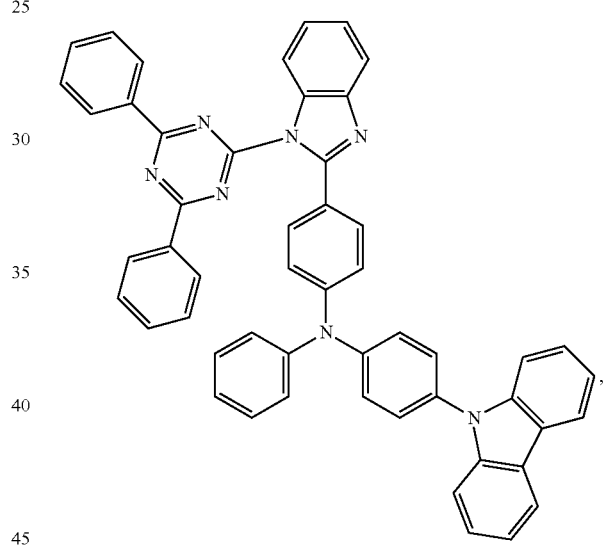
Compound 3894
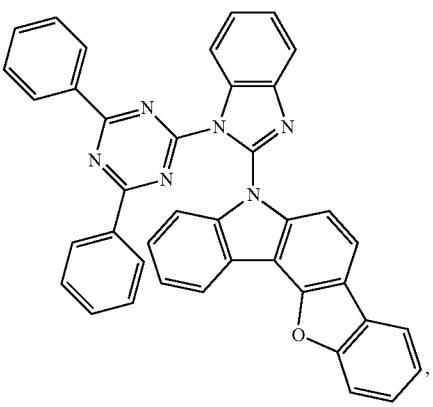

Compound 3862
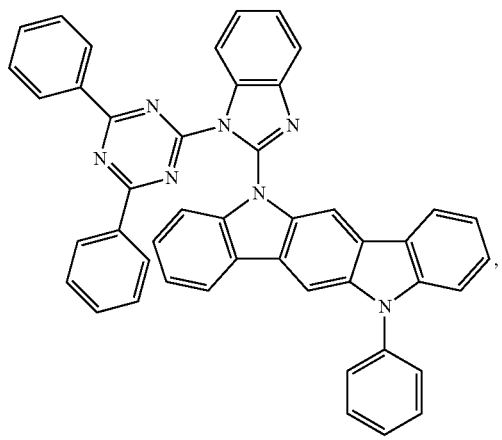
Compound 3638
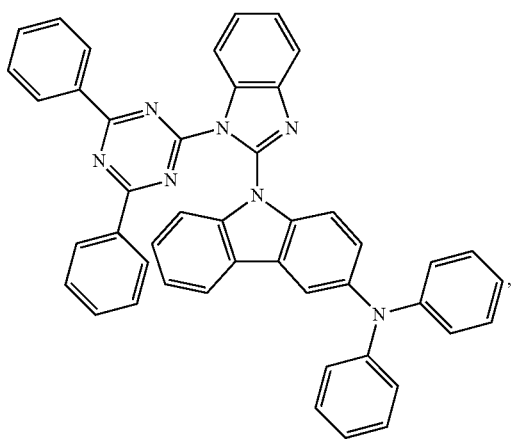
Compound 3446
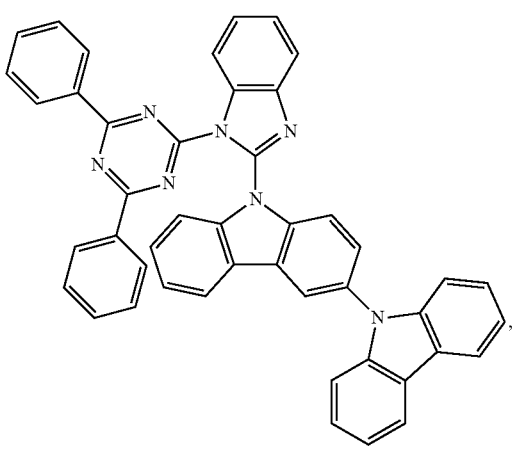
Compound 3510
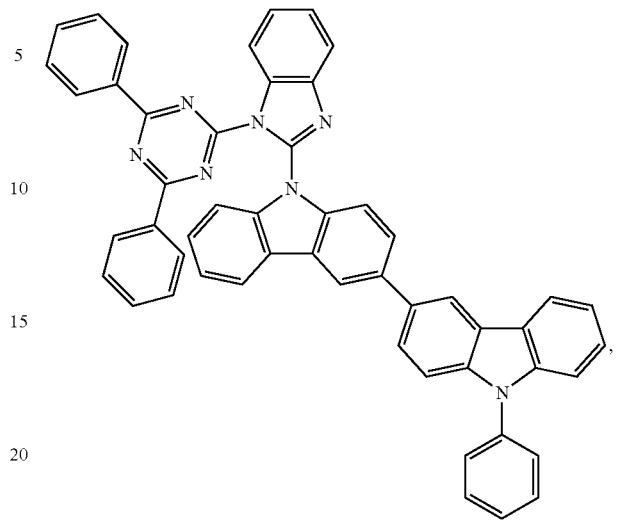
Compound 4150
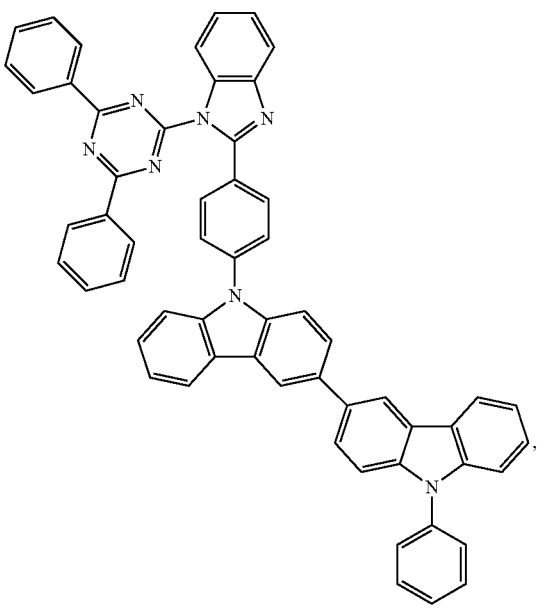
Compound 24
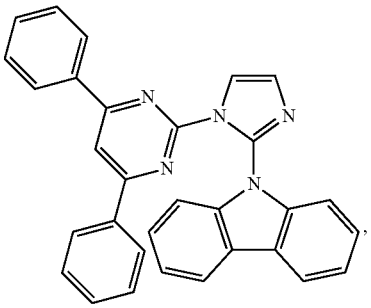

-continued
Compound 664
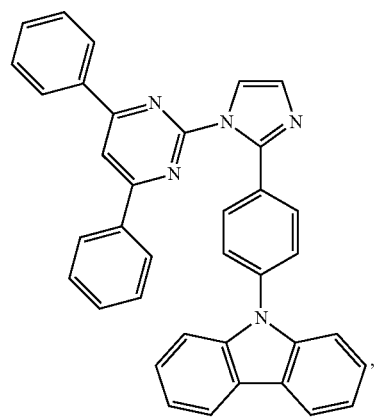
Compound 1432
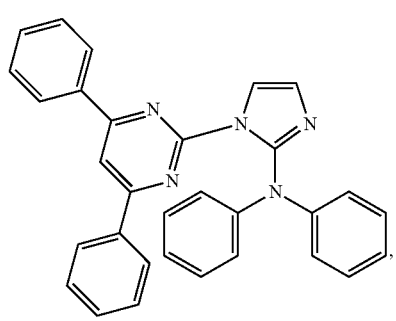
Compound 1752
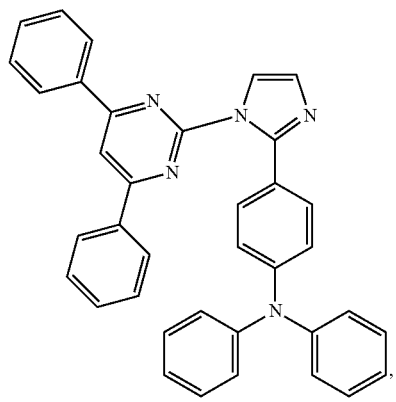
Compound 5110
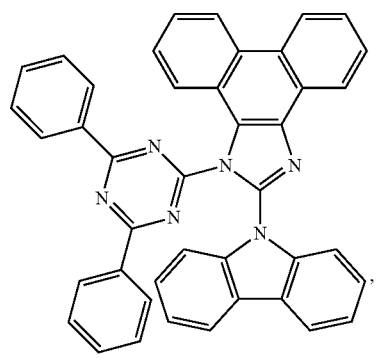
-continued
Compound 8534
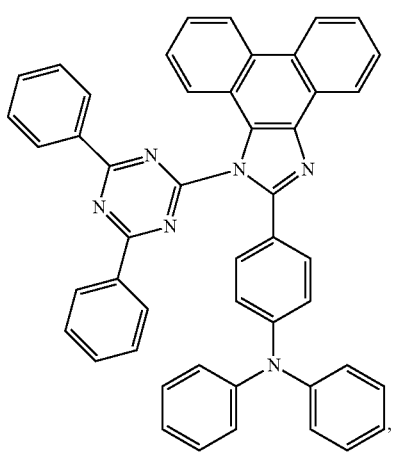
Compound 5
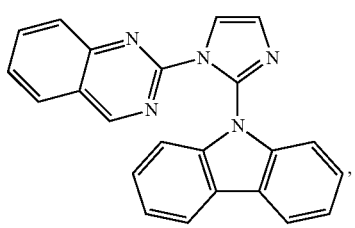
Compound 645
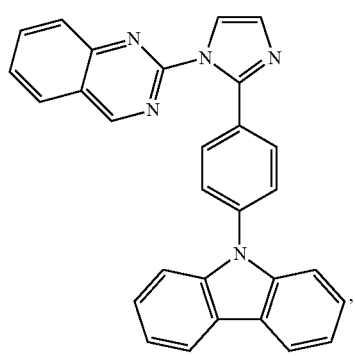
Compound 3397
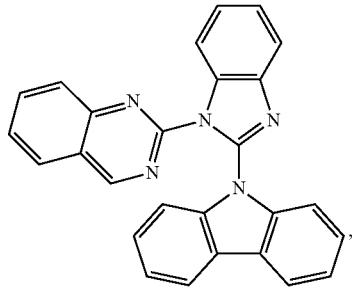
Compound 4805
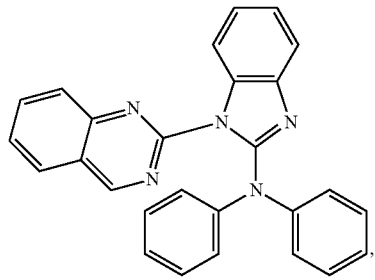

-continued

Compound 5125

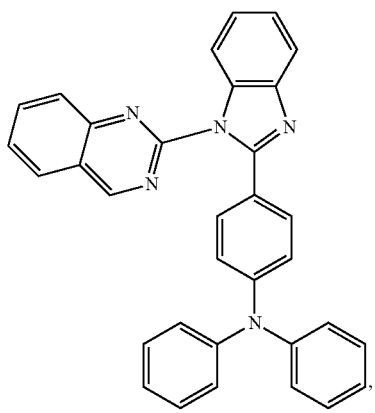

Compound 2966

Compound 6358

In one embodiment, the compound has the formula according to the table below. The respective compounds are generated by substituting $G^1$ and $G^2$ with the indicated electron donor and electron acceptor groups in the table.

Formula II

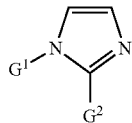

| Compound Number | G1 | G2 |
|---|---|---|
| 1. | A101 | D101 |
| 2. | A102 | D101 |
| 3. | A103 | D101 |
| 4. | A104 | D101 |
| 5. | A105 | D101 |
| 6. | A106 | D101 |
| 7. | A107 | D101 |
| 8. | A108 | D101 |

-continued

Formula II

| Compound Number | G1 | G2 |
|---|---|---|
| 9. | A109 | D101 |
| 10. | A110 | D101 |
| 11. | A111 | D101 |
| 12. | A112 | D101 |
| 13. | A113 | D101 |
| 14. | A114 | D101 |
| 15. | A115 | D101 |
| 16. | A116 | D101 |
| 17. | A117 | D101 |
| 18. | A118 | D101 |
| 19. | A119 | D101 |
| 20. | A120 | D101 |
| 21. | A121 | D101 |
| 22. | A122 | D101 |
| 23. | A123 | D101 |
| 24. | A124 | D101 |
| 25. | A125 | D101 |
| 26. | A126 | D101 |
| 27. | A127 | D101 |
| 28. | A128 | D101 |
| 29. | A129 | D101 |
| 30. | A130 | D101 |
| 31. | A131 | D101 |
| 32. | A132 | D101 |
| 33. | A101 | D102 |
| 34. | A102 | D102 |
| 35. | A103 | D102 |
| 36. | A104 | D102 |
| 37. | A105 | D102 |
| 38. | A106 | D102 |
| 39. | A107 | D102 |
| 40. | A108 | D102 |
| 41. | A109 | D102 |
| 42. | A110 | D102 |
| 43. | A111 | D102 |
| 44. | A112 | D102 |
| 45. | A113 | D102 |
| 46. | A114 | D102 |
| 47. | A115 | D102 |
| 48. | A116 | D102 |
| 49. | A117 | D102 |
| 50. | A118 | D102 |
| 51. | A119 | D102 |
| 52. | A120 | D102 |
| 53. | A121 | D102 |
| 54. | A122 | D102 |
| 55. | A123 | D102 |
| 56. | A124 | D102 |
| 57. | A125 | D102 |
| 58. | A126 | D102 |
| 59. | A127 | D102 |
| 60. | A128 | D102 |
| 61. | A129 | D102 |
| 62. | A130 | D102 |
| 63. | A131 | D102 |
| 64. | A132 | D102 |
| 65. | A101 | D103 |
| 66. | A102 | D103 |
| 67. | A103 | D103 |
| 68. | A104 | D103 |
| 69. | A105 | D103 |
| 70. | A106 | D103 |
| 71. | A107 | D103 |
| 72. | A108 | D103 |
| 73. | A109 | D103 |
| 74. | A110 | D103 |
| 75. | A111 | D103 |
| 76. | A112 | D103 |
| 77. | A113 | D103 |

-continued

Formula II

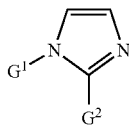

| Compound Number | G1 | G2 |
| --- | --- | --- |
| 78. | A114 | D103 |
| 79. | A115 | D103 |
| 80. | A116 | D103 |
| 81. | A117 | D103 |
| 82. | A118 | D103 |
| 83. | A119 | D103 |
| 84. | A120 | D103 |
| 85. | A121 | D103 |
| 86. | A122 | D103 |
| 87. | A123 | D103 |
| 88. | A124 | D103 |
| 89. | A125 | D103 |
| 90. | A126 | D103 |
| 91. | A127 | D103 |
| 92. | A128 | D103 |
| 93. | A129 | D103 |
| 94. | A130 | D103 |
| 95. | A131 | D103 |
| 96. | A132 | D103 |
| 97. | A133 | D103 |
| 98. | A134 | D103 |
| 99. | A135 | D103 |
| 100. | A136 | D103 |
| 101. | A137 | D103 |
| 102. | A138 | D103 |
| 103. | A139 | D103 |
| 104. | A140 | D103 |
| 105. | A141 | D103 |
| 106. | A142 | D103 |
| 107. | A143 | D103 |
| 108. | A144 | D103 |
| 109. | A145 | D103 |
| 110. | A146 | D103 |
| 111. | A147 | D103 |
| 112. | A148 | D103 |
| 113. | A149 | D103 |
| 114. | A150 | D103 |
| 115. | A160 | D103 |
| 116. | A120 | D104 |
| 117. | A121 | D104 |
| 118. | A122 | D104 |
| 119. | A123 | D104 |
| 120. | A124 | D104 |
| 121. | A125 | D104 |
| 122. | A126 | D104 |
| 123. | A127 | D104 |
| 124. | A128 | D104 |
| 125. | A129 | D104 |
| 126. | A130 | D104 |
| 127. | A131 | D104 |
| 128. | A132 | D104 |
| 129. | A101 | D105 |
| 130. | A102 | D105 |
| 131. | A103 | D105 |
| 132. | A104 | D105 |
| 133. | A105 | D105 |
| 134. | A106 | D105 |
| 135. | A107 | D105 |
| 136. | A108 | D105 |
| 137. | A109 | D105 |
| 138. | A110 | D105 |
| 139. | A111 | D105 |
| 140. | A112 | D105 |
| 141. | A113 | D105 |
| 142. | A114 | D105 |
| 143. | A115 | D105 |
| 144. | A116 | D105 |
| 145. | A117 | D105 |
| 146. | A118 | D105 |

-continued

Formula II

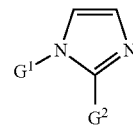

| Compound Number | G1 | G2 |
| --- | --- | --- |
| 147. | A119 | D105 |
| 148. | A120 | D105 |
| 149. | A121 | D105 |
| 150. | A122 | D105 |
| 151. | A123 | D105 |
| 152. | A124 | D105 |
| 153. | A125 | D105 |
| 154. | A126 | D105 |
| 155. | A127 | D105 |
| 156. | A128 | D105 |
| 157. | A129 | D105 |
| 158. | A130 | D105 |
| 159. | A131 | D105 |
| 160. | A132 | D105 |
| 161. | A101 | D106 |
| 162. | A102 | D106 |
| 163. | A103 | D106 |
| 164. | A104 | D106 |
| 165. | A105 | D106 |
| 166. | A106 | D106 |
| 167. | A107 | D106 |
| 168. | A108 | D106 |
| 169. | A109 | D106 |
| 170. | A110 | D106 |
| 171. | A111 | D106 |
| 172. | A112 | D106 |
| 173. | A113 | D106 |
| 174. | A114 | D106 |
| 175. | A115 | D106 |
| 176. | A116 | D106 |
| 177. | A117 | D106 |
| 178. | A118 | D106 |
| 179. | A119 | D106 |
| 180. | A120 | D106 |
| 181. | A121 | D106 |
| 182. | A122 | D106 |
| 183. | A123 | D106 |
| 184. | A124 | D106 |
| 185. | A125 | D106 |
| 186. | A126 | D106 |
| 187. | A127 | D106 |
| 188. | A128 | D106 |
| 189. | A129 | D106 |
| 190. | A130 | D106 |
| 191. | A131 | D106 |
| 192. | A132 | D106 |
| 193. | A101 | D107 |
| 194. | A102 | D107 |
| 195. | A103 | D107 |
| 196. | A104 | D107 |
| 197. | A105 | D107 |
| 198. | A106 | D107 |
| 199. | A107 | D107 |
| 200. | A108 | D107 |
| 201. | A109 | D107 |
| 202. | A110 | D107 |
| 203. | A111 | D107 |
| 204. | A112 | D107 |
| 205. | A113 | D107 |
| 206. | A114 | D107 |
| 207. | A115 | D107 |
| 208. | A116 | D107 |
| 209. | A117 | D107 |
| 210. | A118 | D107 |
| 211. | A119 | D107 |
| 212. | A120 | D107 |
| 213. | A121 | D107 |
| 214. | A122 | D107 |
| 215. | A123 | D107 |

87

-continued

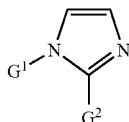

Formula II

| Compound Number | G1 | G2 |
|---|---|---|
| 216. | A124 | D107 |
| 217. | A125 | D107 |
| 218. | A126 | D107 |
| 219. | A127 | D107 |
| 220. | A128 | D107 |
| 221. | A129 | D107 |
| 222. | A130 | D107 |
| 223. | A131 | D107 |
| 224. | A132 | D107 |
| 225. | A101 | D108 |
| 226. | A102 | D108 |
| 227. | A103 | D108 |
| 228. | A104 | D108 |
| 229. | A105 | D108 |
| 230. | A106 | D108 |
| 231. | A107 | D108 |
| 232. | A108 | D108 |
| 233. | A109 | D108 |
| 234. | A110 | D108 |
| 235. | A111 | D108 |
| 236. | A112 | D108 |
| 237. | A113 | D108 |
| 238. | A114 | D108 |
| 239. | A115 | D108 |
| 240. | A116 | D108 |
| 241. | A117 | D108 |
| 242. | A118 | D108 |
| 243. | A119 | D108 |
| 244. | A120 | D108 |
| 245. | A121 | D108 |
| 246. | A122 | D108 |
| 247. | A123 | D108 |
| 248. | A124 | D108 |
| 249. | A125 | D108 |
| 250. | A126 | D108 |
| 251. | A127 | D108 |
| 252. | A128 | D108 |
| 253. | A129 | D108 |
| 254. | A130 | D108 |
| 255. | A131 | D108 |
| 256. | A132 | D108 |
| 257. | A101 | D109 |
| 258. | A102 | D109 |
| 259. | A103 | D109 |
| 260. | A104 | D109 |
| 261. | A105 | D109 |
| 262. | A106 | D109 |
| 263. | A107 | D109 |
| 264. | A108 | D109 |
| 265. | A109 | D109 |
| 266. | A110 | D109 |
| 267. | A111 | D109 |
| 268. | A112 | D109 |
| 269. | A113 | D109 |
| 270. | A114 | D109 |
| 271. | A115 | D109 |
| 272. | A116 | D109 |
| 273. | A117 | D109 |
| 274. | A118 | D109 |
| 275. | A119 | D109 |
| 276. | A120 | D109 |
| 277. | A121 | D109 |
| 278. | A122 | D109 |
| 279. | A123 | D109 |
| 280. | A124 | D109 |
| 281. | A125 | D109 |
| 282. | A126 | D109 |
| 283. | A127 | D109 |
| 284. | A128 | D109 |

88

-continued

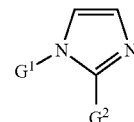

Formula II

| Compound Number | G1 | G2 |
|---|---|---|
| 285. | A129 | D109 |
| 286. | A130 | D109 |
| 287. | A131 | D109 |
| 288. | A132 | D109 |
| 289. | A101 | D110 |
| 290. | A102 | D110 |
| 291. | A103 | D110 |
| 292. | A104 | D110 |
| 293. | A105 | D110 |
| 294. | A106 | D110 |
| 295. | A107 | D110 |
| 296. | A108 | D110 |
| 297. | A109 | D110 |
| 298. | A110 | D110 |
| 299. | A111 | D110 |
| 300. | A112 | D110 |
| 301. | A113 | D110 |
| 302. | A114 | D110 |
| 303. | A115 | D110 |
| 304. | A116 | D110 |
| 305. | A117 | D110 |
| 306. | A118 | D110 |
| 307. | A119 | D110 |
| 308. | A120 | D110 |
| 309. | A121 | D110 |
| 310. | A122 | D110 |
| 311. | A123 | D110 |
| 312. | A124 | D110 |
| 313. | A125 | D110 |
| 314. | A126 | D110 |
| 315. | A127 | D110 |
| 316. | A128 | D110 |
| 317. | A129 | D110 |
| 318. | A130 | D110 |
| 319. | A131 | D110 |
| 320. | A132 | D110 |
| 321. | A101 | D111 |
| 322. | A102 | D111 |
| 323. | A103 | D111 |
| 324. | A104 | D111 |
| 325. | A105 | D111 |
| 326. | A106 | D111 |
| 327. | A107 | D111 |
| 328. | A108 | D111 |
| 329. | A109 | D111 |
| 330. | A110 | D111 |
| 331. | A111 | D111 |
| 332. | A112 | D111 |
| 333. | A113 | D111 |
| 334. | A114 | D111 |
| 335. | A115 | D111 |
| 336. | A116 | D111 |
| 337. | A117 | D111 |
| 338. | A118 | D111 |
| 339. | A119 | D111 |
| 340. | A120 | D111 |
| 341. | A121 | D111 |
| 342. | A122 | D111 |
| 343. | A123 | D111 |
| 344. | A124 | D111 |
| 345. | A125 | D111 |
| 346. | A126 | D111 |
| 347. | A127 | D111 |
| 348. | A128 | D111 |
| 349. | A129 | D111 |
| 350. | A130 | D111 |
| 351. | A131 | D111 |
| 352. | A132 | D111 |
| 353. | A101 | D112 |

Formula II

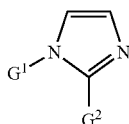

| Compound Number | G1 | G2 |
|---|---|---|
| 354. | A102 | D112 |
| 355. | A103 | D112 |
| 356. | A104 | D112 |
| 357. | A105 | D112 |
| 358. | A106 | D112 |
| 359. | A107 | D112 |
| 360. | A108 | D112 |
| 361. | A109 | D112 |
| 362. | A110 | D112 |
| 363. | A111 | D112 |
| 364. | A112 | D112 |
| 365. | A113 | D112 |
| 366. | A114 | D112 |
| 367. | A115 | D112 |
| 368. | A116 | D112 |
| 369. | A117 | D112 |
| 370. | A118 | D112 |
| 371. | A119 | D112 |
| 372. | A120 | D112 |
| 373. | A121 | D112 |
| 374. | A122 | D112 |
| 375. | A123 | D112 |
| 376. | A124 | D112 |
| 377. | A125 | D112 |
| 378. | A126 | D112 |
| 379. | A127 | D112 |
| 380. | A128 | D112 |
| 381. | A129 | D112 |
| 382. | A130 | D112 |
| 383. | A131 | D112 |
| 384. | A132 | D112 |
| 385. | A101 | D113 |
| 386. | A102 | D113 |
| 387. | A103 | D113 |
| 388. | A104 | D113 |
| 389. | A105 | D113 |
| 390. | A106 | D113 |
| 391. | A107 | D113 |
| 392. | A108 | D113 |
| 393. | A109 | D113 |
| 394. | A110 | D113 |
| 395. | A111 | D113 |
| 396. | A112 | D113 |
| 397. | A113 | D113 |
| 398. | A114 | D113 |
| 399. | A115 | D113 |
| 400. | A116 | D113 |
| 401. | A117 | D113 |
| 402. | A118 | D113 |
| 403. | A119 | D113 |
| 404. | A120 | D113 |
| 405. | A121 | D113 |
| 406. | A122 | D113 |
| 407. | A123 | D113 |
| 408. | A124 | D113 |
| 409. | A125 | D113 |
| 410. | A126 | D113 |
| 411. | A127 | D113 |
| 412. | A128 | D113 |
| 413. | A129 | D113 |
| 414. | A130 | D113 |
| 415. | A131 | D113 |
| 416. | A132 | D113 |
| 417. | A101 | D114 |
| 418. | A102 | D114 |
| 419. | A103 | D114 |
| 420. | A104 | D114 |
| 421. | A105 | D114 |
| 422. | A106 | D114 |

Formula II

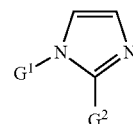

| Compound Number | G1 | G2 |
|---|---|---|
| 423. | A107 | D114 |
| 424. | A108 | D114 |
| 425. | A109 | D114 |
| 426. | A110 | D114 |
| 427. | A111 | D114 |
| 428. | A112 | D114 |
| 429. | A113 | D114 |
| 430. | A114 | D114 |
| 431. | A115 | D114 |
| 432. | A116 | D114 |
| 433. | A117 | D114 |
| 434. | A118 | D114 |
| 435. | A119 | D114 |
| 436. | A120 | D114 |
| 437. | A121 | D114 |
| 438. | A122 | D114 |
| 439. | A123 | D114 |
| 440. | A124 | D114 |
| 441. | A125 | D114 |
| 442. | A126 | D114 |
| 443. | A127 | D114 |
| 444. | A128 | D114 |
| 445. | A129 | D114 |
| 446. | A130 | D114 |
| 447. | A131 | D114 |
| 448. | A132 | D114 |
| 449. | A101 | D115 |
| 450. | A102 | D115 |
| 451. | A103 | D115 |
| 452. | A104 | D115 |
| 453. | A105 | D115 |
| 454. | A106 | D115 |
| 455. | A107 | D115 |
| 456. | A108 | D115 |
| 457. | A109 | D115 |
| 458. | A110 | D115 |
| 459. | A111 | D115 |
| 460. | A112 | D115 |
| 461. | A113 | D115 |
| 462. | A114 | D115 |
| 463. | A115 | D115 |
| 464. | A116 | D115 |
| 465. | A117 | D115 |
| 466. | A118 | D115 |
| 467. | A119 | D115 |
| 468. | A120 | D115 |
| 469. | A121 | D115 |
| 470. | A122 | D115 |
| 471. | A123 | D115 |
| 472. | A124 | D115 |
| 473. | A125 | D115 |
| 474. | A126 | D115 |
| 475. | A127 | D115 |
| 476. | A128 | D115 |
| 477. | A129 | D115 |
| 478. | A130 | D115 |
| 479. | A131 | D115 |
| 480. | A132 | D115 |
| 481. | A101 | D116 |
| 482. | A102 | D116 |
| 483. | A103 | D116 |
| 484. | A104 | D116 |
| 485. | A105 | D116 |
| 486. | A106 | D116 |
| 487. | A107 | D116 |
| 488. | A108 | D116 |
| 489. | A109 | D116 |
| 490. | A110 | D116 |
| 491. | A111 | D116 |

-continued

Formula II

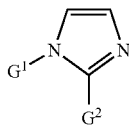

| Compound Number | G1 | G2 |
|---|---|---|
| 492. | A112 | D116 |
| 493. | A113 | D116 |
| 494. | A114 | D116 |
| 495. | A115 | D116 |
| 496. | A116 | D116 |
| 497. | A117 | D116 |
| 498. | A118 | D116 |
| 499. | A119 | D116 |
| 500. | A120 | D116 |
| 501. | A121 | D116 |
| 502. | A122 | D116 |
| 503. | A123 | D116 |
| 504. | A124 | D116 |
| 505. | A125 | D116 |
| 506. | A126 | D116 |
| 507. | A127 | D116 |
| 508. | A128 | D116 |
| 509. | A129 | D116 |
| 510. | A130 | D116 |
| 511. | A131 | D116 |
| 512. | A132 | D116 |
| 513. | A101 | D117 |
| 514. | A102 | D117 |
| 515. | A103 | D117 |
| 516. | A104 | D117 |
| 517. | A105 | D117 |
| 518. | A106 | D117 |
| 519. | A107 | D117 |
| 520. | A108 | D117 |
| 521. | A109 | D117 |
| 522. | A110 | D117 |
| 523. | A111 | D117 |
| 524. | A112 | D117 |
| 525. | A113 | D117 |
| 526. | A114 | D117 |
| 527. | A115 | D117 |
| 528. | A116 | D117 |
| 529. | A117 | D117 |
| 530. | A118 | D117 |
| 531. | A119 | D117 |
| 532. | A120 | D117 |
| 533. | A121 | D117 |
| 534. | A122 | D117 |
| 535. | A123 | D117 |
| 536. | A124 | D117 |
| 537. | A125 | D117 |
| 538. | A126 | D117 |
| 539. | A127 | D117 |
| 540. | A128 | D117 |
| 541. | A129 | D117 |
| 542. | A130 | D117 |
| 543. | A131 | D117 |
| 544. | A132 | D117 |
| 545. | A101 | D118 |
| 546. | A102 | D118 |
| 547. | A103 | D118 |
| 548. | A104 | D118 |
| 549. | A105 | D118 |
| 550. | A106 | D118 |
| 551. | A107 | D118 |
| 552. | A108 | D118 |
| 553. | A109 | D118 |
| 554. | A110 | D118 |
| 555. | A111 | D118 |
| 556. | A112 | D118 |
| 557. | A113 | D118 |
| 558. | A114 | D118 |
| 559. | A115 | D118 |
| 560. | A116 | D118 |

-continued

Formula II

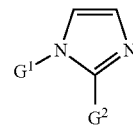

| Compound Number | G1 | G2 |
|---|---|---|
| 561. | A117 | D118 |
| 562. | A118 | D118 |
| 563. | A119 | D118 |
| 564. | A120 | D118 |
| 565. | A121 | D118 |
| 566. | A122 | D118 |
| 567. | A123 | D118 |
| 568. | A124 | D118 |
| 569. | A125 | D118 |
| 570. | A126 | D118 |
| 571. | A127 | D118 |
| 572. | A128 | D118 |
| 573. | A129 | D118 |
| 574. | A130 | D118 |
| 575. | A131 | D118 |
| 576. | A132 | D118 |
| 577. | A101 | D119 |
| 578. | A102 | D119 |
| 579. | A103 | D119 |
| 580. | A104 | D119 |
| 581. | A115 | D119 |
| 582. | A106 | D119 |
| 583. | A107 | D119 |
| 584. | A108 | D119 |
| 585. | A109 | D119 |
| 586. | A110 | D119 |
| 587. | A111 | D119 |
| 588. | A112 | D119 |
| 589. | A113 | D119 |
| 590. | A114 | D119 |
| 591. | A115 | D119 |
| 592. | A116 | D119 |
| 593. | A117 | D119 |
| 594. | A118 | D119 |
| 595. | A119 | D119 |
| 596. | A120 | D119 |
| 597. | A121 | D119 |
| 598. | A122 | D119 |
| 599. | A123 | D119 |
| 600. | A124 | D119 |
| 601. | A125 | D119 |
| 602. | A126 | D119 |
| 603. | A127 | D119 |
| 604. | A128 | D119 |
| 605. | A129 | D119 |
| 606. | A130 | D119 |
| 607. | A131 | D119 |
| 608. | A132 | D119 |
| 609. | A101 | D120 |
| 610. | A102 | D120 |
| 611. | A102 | D120 |
| 612. | A104 | D120 |
| 613. | A105 | D120 |
| 614. | A106 | D120 |
| 615. | A107 | D120 |
| 616. | A108 | D120 |
| 617. | A109 | D120 |
| 618. | A110 | D120 |
| 619. | A111 | D120 |
| 620. | A112 | D120 |
| 621. | A113 | D120 |
| 622. | A114 | D120 |
| 623. | A115 | D120 |
| 624. | A116 | D120 |
| 625. | A117 | D120 |
| 626. | A118 | D120 |
| 627. | A119 | D120 |
| 628. | A120 | D120 |
| 629. | A121 | D120 |

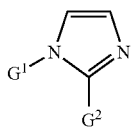

Formula II

| Compound Number | G1 | G2 |
|---|---|---|
| 630. | A122 | D120 |
| 631. | A123 | D120 |
| 632. | A124 | D120 |
| 633. | A125 | D120 |
| 634. | A126 | D120 |
| 635. | A127 | D120 |
| 636. | A128 | D120 |
| 637. | A129 | D121 |
| 638. | A130 | D120 |
| 639. | A131 | D120 |
| 640. | A132 | D120 |
| 641. | A101 | D121 |
| 642. | A102 | D121 |
| 643. | A103 | D121 |
| 644. | A104 | D121 |
| 645. | A105 | D121 |
| 646. | A106 | D121 |
| 647. | A107 | D121 |
| 648. | A108 | D121 |
| 649. | A109 | D121 |
| 650. | A110 | D121 |
| 651. | A111 | D121 |
| 652. | A112 | D121 |
| 653. | A113 | D121 |
| 654. | A114 | D121 |
| 655. | A115 | D121 |
| 656. | A116 | D121 |
| 657. | A117 | D121 |
| 658. | A118 | D121 |
| 659. | A119 | D121 |
| 660. | A120 | D121 |
| 661. | A121 | D121 |
| 662. | A122 | D121 |
| 663. | A123 | D121 |
| 664. | A124 | D121 |
| 665. | A125 | D121 |
| 666. | A126 | D121 |
| 667. | A127 | D121 |
| 668. | A128 | D121 |
| 669. | A129 | D121 |
| 670. | A130 | D121 |
| 671. | A131 | D121 |
| 672. | A132 | D121 |
| 673. | A101 | D122 |
| 674. | A102 | D122 |
| 675. | A193 | D122 |
| 676. | A104 | D122 |
| 677. | A195 | D122 |
| 678. | A106 | D122 |
| 679. | A197 | D122 |
| 680. | A108 | D122 |
| 681. | A109 | D122 |
| 682. | A110 | D122 |
| 683. | A111 | D122 |
| 684. | A112 | D122 |
| 685. | A113 | D122 |
| 686. | A114 | D122 |
| 687. | A115 | D122 |
| 688. | A116 | D122 |
| 689. | A117 | D122 |
| 690. | A118 | D122 |
| 691. | A119 | D122 |
| 692. | A120 | D122 |
| 693. | A121 | D122 |
| 694. | A122 | D122 |
| 695. | A123 | D122 |
| 696. | A124 | D122 |
| 697. | A125 | D122 |
| 698. | A126 | D122 |

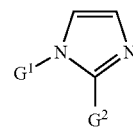

Formula II

| Compound Number | G1 | G2 |
|---|---|---|
| 699. | A127 | D122 |
| 700. | A128 | D122 |
| 701. | A129 | D122 |
| 702. | A130 | D122 |
| 703. | A131 | D122 |
| 704. | A132 | D122 |
| 705. | A101 | D123 |
| 706. | A102 | D123 |
| 707. | A103 | D123 |
| 708. | A104 | D123 |
| 709. | A105 | D123 |
| 710. | A106 | D123 |
| 711. | A107 | D123 |
| 712. | A108 | D123 |
| 713. | A109 | D123 |
| 714. | A110 | D123 |
| 715. | A111 | D123 |
| 716. | A112 | D123 |
| 717. | A113 | D123 |
| 718. | A114 | D123 |
| 719. | A115 | D123 |
| 720. | A116 | D123 |
| 721. | A117 | D123 |
| 722. | A118 | D123 |
| 723. | A119 | D123 |
| 724. | A120 | D123 |
| 725. | A121 | D123 |
| 726. | A122 | D123 |
| 727. | A123 | D123 |
| 728. | A124 | D123 |
| 729. | A125 | D123 |
| 730. | A126 | D123 |
| 731. | A127 | D123 |
| 732. | A128 | D123 |
| 733. | A129 | D123 |
| 734. | A130 | D123 |
| 735. | A131 | D123 |
| 736. | A132 | D123 |
| 737. | A101 | D124 |
| 738. | A102 | D124 |
| 739. | A103 | D124 |
| 740. | A104 | D124 |
| 741. | A105 | D124 |
| 742. | A106 | D124 |
| 743. | A107 | D124 |
| 744. | A108 | D124 |
| 745. | A109 | D124 |
| 746. | A110 | D124 |
| 747. | A111 | D124 |
| 748. | A112 | D124 |
| 749. | A113 | D124 |
| 750. | A114 | D124 |
| 751. | A115 | D124 |
| 752. | A116 | D124 |
| 753. | A117 | D124 |
| 754. | A118 | D124 |
| 755. | A119 | D124 |
| 756. | A120 | D124 |
| 757. | A121 | D124 |
| 758. | A122 | D124 |
| 759. | A123 | D124 |
| 760. | A124 | D124 |
| 761. | A125 | D124 |
| 762. | A126 | D124 |
| 763. | A127 | D124 |
| 764. | A128 | D124 |
| 765. | A129 | D124 |
| 766. | A130 | D124 |
| 767. | A131 | D124 |

Formula II

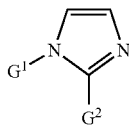

| Compound Number | G1 | G2 |
|---|---|---|
| 768. | A132 | D124 |
| 769. | A101 | D125 |
| 770. | A102 | D125 |
| 771. | A103 | D125 |
| 772. | A104 | D125 |
| 773. | A195 | D125 |
| 774. | A106 | D125 |
| 775. | A107 | D125 |
| 776. | A108 | D125 |
| 777. | A109 | D125 |
| 778. | A110 | D125 |
| 779. | A111 | D125 |
| 780. | A112 | D125 |
| 781. | A113 | D125 |
| 782. | A114 | D125 |
| 783. | A115 | D125 |
| 784. | A116 | D125 |
| 785. | A117 | D125 |
| 786. | A118 | D125 |
| 787. | A119 | D125 |
| 788. | A120 | D125 |
| 789. | A121 | D125 |
| 790. | A122 | D125 |
| 791. | A123 | D125 |
| 792. | A124 | D125 |
| 793. | A125 | D125 |
| 794. | A126 | D125 |
| 795. | A127 | D125 |
| 796. | A128 | D125 |
| 797. | A129 | D125 |
| 798. | A130 | D125 |
| 799. | A131 | D125 |
| 800. | A132 | D125 |
| 801. | A101 | D126 |
| 802. | A102 | D126 |
| 803. | A103 | D126 |
| 804. | A104 | D126 |
| 805. | A105 | D126 |
| 806. | A106 | D126 |
| 807. | A107 | D126 |
| 808. | A108 | D126 |
| 809. | A109 | D126 |
| 810. | A110 | D126 |
| 811. | A111 | D126 |
| 812. | A112 | D126 |
| 813. | A113 | D126 |
| 814. | A114 | D126 |
| 815. | A115 | D126 |
| 816. | A116 | D126 |
| 817. | A117 | D126 |
| 818. | A118 | D126 |
| 819. | A119 | D126 |
| 820. | A120 | D126 |
| 821. | A121 | D126 |
| 822. | A122 | D126 |
| 823. | A123 | D126 |
| 824. | A124 | D126 |
| 825. | A125 | D126 |
| 826. | A126 | D126 |
| 827. | A127 | D126 |
| 828. | A128 | D126 |
| 829. | A129 | D126 |
| 830. | A130 | D126 |
| 831. | A131 | D126 |
| 832. | A132 | D126 |
| 833. | A101 | D127 |
| 834. | A102 | D127 |
| 835. | A103 | D127 |
| 836. | A104 | D127 |

Formula II

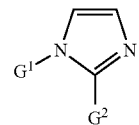

| Compound Number | G1 | G2 |
|---|---|---|
| 837. | A105 | D127 |
| 838. | A106 | D127 |
| 839. | A107 | D127 |
| 840. | A108 | D127 |
| 841. | A109 | D127 |
| 842. | A110 | D127 |
| 843. | A111 | D127 |
| 844. | A112 | D127 |
| 845. | A113 | D127 |
| 846. | A114 | D127 |
| 847. | A115 | D127 |
| 848. | A116 | D127 |
| 849. | A117 | D127 |
| 850. | A118 | D127 |
| 851. | A119 | D127 |
| 852. | A120 | D127 |
| 853. | A121 | D127 |
| 854. | A122 | D127 |
| 855. | A123 | D127 |
| 856. | A124 | D127 |
| 857. | A125 | D127 |
| 858. | A126 | D127 |
| 859. | A127 | D127 |
| 860. | A128 | D127 |
| 861. | A129 | D127 |
| 862. | A130 | D127 |
| 863. | A131 | D127 |
| 864. | A132 | D127 |
| 865. | A101 | D128 |
| 866. | A102 | D128 |
| 867. | A103 | D128 |
| 868. | A104 | D128 |
| 869. | A105 | D128 |
| 870. | A106 | D128 |
| 871. | A107 | D128 |
| 872. | A108 | D128 |
| 873. | A109 | D128 |
| 874. | A110 | D128 |
| 875. | A111 | D128 |
| 876. | A112 | D128 |
| 877. | A113 | D128 |
| 878. | A114 | D128 |
| 879. | A115 | D128 |
| 880. | A116 | D128 |
| 881. | A117 | D128 |
| 882. | A118 | D128 |
| 883. | A119 | D128 |
| 884. | A120 | D128 |
| 885. | A121 | D128 |
| 886. | A122 | D128 |
| 887. | A123 | D128 |
| 888. | A124 | D128 |
| 889. | A125 | D128 |
| 890. | A126 | D128 |
| 891. | A127 | D128 |
| 892. | A128 | D128 |
| 893. | A129 | D128 |
| 894. | A130 | D128 |
| 895. | A131 | D128 |
| 896. | A132 | D128 |
| 897. | A101 | D129 |
| 898. | A102 | D129 |
| 899. | A103 | D129 |
| 900. | A104 | D129 |
| 901. | A105 | D129 |
| 902. | A106 | D129 |
| 903. | A107 | D129 |
| 904. | A108 | D129 |
| 905. | A109 | D129 |

Formula II

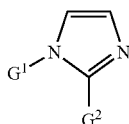

| Compound Number | G1 | G2 |
|---|---|---|
| 906. | A110 | D129 |
| 907. | A111 | D129 |
| 908. | A112 | D129 |
| 909. | A113 | D129 |
| 910. | A114 | D129 |
| 911. | A115 | D129 |
| 912. | A116 | D129 |
| 913. | A117 | D129 |
| 914. | A118 | D129 |
| 915. | A119 | D129 |
| 916. | A120 | D129 |
| 917. | A121 | D129 |
| 918. | A122 | D129 |
| 919. | A123 | D129 |
| 920. | A124 | D129 |
| 921. | A125 | D129 |
| 922. | A126 | D129 |
| 923. | A127 | D129 |
| 924. | A128 | D129 |
| 925. | A129 | D129 |
| 926. | A130 | D129 |
| 927. | A131 | D129 |
| 928. | A132 | D129 |
| 929. | A101 | D130 |
| 930. | A102 | D130 |
| 931. | A103 | D130 |
| 932. | A104 | D130 |
| 933. | A105 | D130 |
| 934. | A106 | D130 |
| 935. | A107 | D130 |
| 936. | A108 | D130 |
| 937. | A109 | D130 |
| 938. | A110 | D130 |
| 939. | A111 | D130 |
| 940. | A112 | D130 |
| 941. | A113 | D130 |
| 942. | A114 | D130 |
| 943. | A115 | D130 |
| 944. | A116 | D130 |
| 945. | A117 | D130 |
| 946. | A118 | D130 |
| 947. | A119 | D130 |
| 948. | A120 | D130 |
| 949. | A121 | D130 |
| 950. | A122 | D130 |
| 951. | A123 | D130 |
| 952. | A124 | D130 |
| 953. | A125 | D130 |
| 954. | A126 | D130 |
| 955. | A127 | D130 |
| 956. | A128 | D130 |
| 957. | A129 | D130 |
| 958. | A130 | D130 |
| 959. | A131 | D130 |
| 960. | A132 | D130 |
| 961. | A101 | D131 |
| 962. | A102 | D131 |
| 963. | A103 | D131 |
| 964. | A104 | D131 |
| 965. | A105 | D131 |
| 966. | A106 | D131 |
| 967. | A107 | D131 |
| 968. | A108 | D131 |
| 969. | A199 | D131 |
| 970. | A110 | D131 |
| 971. | A111 | D131 |
| 972. | A112 | D131 |
| 973. | A113 | D131 |
| 974. | A114 | D131 |

Formula II

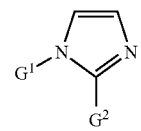

| Compound Number | G1 | G2 |
|---|---|---|
| 975. | A115 | D131 |
| 976. | A116 | D131 |
| 977. | A117 | D131 |
| 978. | A118 | D131 |
| 979. | A119 | D131 |
| 980. | A120 | D131 |
| 981. | A121 | D131 |
| 982. | A122 | D131 |
| 983. | A123 | D131 |
| 984. | A124 | D131 |
| 985. | A125 | D131 |
| 986. | A126 | D131 |
| 987. | A127 | D131 |
| 988. | A128 | D131 |
| 989. | A129 | D131 |
| 990. | A130 | D131 |
| 991. | A131 | D131 |
| 992. | A132 | D131 |
| 993. | A101 | D132 |
| 994. | A102 | D132 |
| 995. | A103 | D132 |
| 996. | A104 | D132 |
| 997. | A105 | D132 |
| 998. | A106 | D132 |
| 999. | A107 | D132 |
| 1000. | A108 | D132 |
| 1001. | A109 | D132 |
| 1002. | A110 | D132 |
| 1003. | A111 | D132 |
| 1004. | A112 | D132 |
| 1005. | A113 | D132 |
| 1006. | A114 | D132 |
| 1007. | A115 | D132 |
| 1008. | A116 | D132 |
| 1009. | A117 | D132 |
| 1010. | A118 | D132 |
| 1011. | A119 | D132 |
| 1012. | A120 | D132 |
| 1013. | A121 | D132 |
| 1014. | A122 | D132 |
| 1015. | A123 | D132 |
| 1016. | A124 | D132 |
| 1017. | A125 | D132 |
| 1018. | A126 | D132 |
| 1019. | A127 | D132 |
| 1020. | A128 | D132 |
| 1021. | A129 | D132 |
| 1022. | A130 | D132 |
| 1023. | A131 | D132 |
| 1024. | A132 | D132 |
| 1025. | A101 | D133 |
| 1026. | A102 | D133 |
| 1027. | A103 | D133 |
| 1028. | A104 | D133 |
| 1029. | A105 | D133 |
| 1030. | A106 | D133 |
| 1031. | A107 | D133 |
| 1032. | A108 | D133 |
| 1033. | A109 | D133 |
| 1034. | A110 | D133 |
| 1035. | A111 | D133 |
| 1036. | A112 | D133 |
| 1037. | A113 | D133 |
| 1038. | A114 | D133 |
| 1039. | A115 | D133 |
| 1040. | A116 | D133 |
| 1041. | A117 | D133 |
| 1042. | A118 | D133 |
| 1043. | A119 | D133 |

Formula II

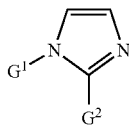

| Compound Number | G1 | G2 |
| --- | --- | --- |
| 1044. | A120 | D133 |
| 1045. | A121 | D133 |
| 1046. | A122 | D133 |
| 1047. | A123 | D133 |
| 1048. | A124 | D133 |
| 1049. | A125 | D133 |
| 1050. | A126 | D133 |
| 1051. | A127 | D133 |
| 1052. | A128 | D133 |
| 1053. | A129 | D133 |
| 1054. | A130 | D133 |
| 1055. | A131 | D133 |
| 1056. | A132 | D133 |
| 1057. | A101 | D134 |
| 1058. | A102 | D134 |
| 1059. | A103 | D134 |
| 1060. | A104 | D134 |
| 1061. | A105 | D134 |
| 1062. | A106 | D134 |
| 1063. | A107 | D134 |
| 1064. | A108 | D134 |
| 1065. | A109 | D134 |
| 1066. | A110 | D134 |
| 1067. | A111 | D134 |
| 1068. | A112 | D134 |
| 1069. | A113 | D134 |
| 1070. | A114 | D134 |
| 1071. | A115 | D134 |
| 1072. | A116 | D134 |
| 1073. | A117 | D134 |
| 1074. | A118 | D134 |
| 1075. | A119 | D134 |
| 1076. | A120 | D134 |
| 1077. | A121 | D134 |
| 1078. | A122 | D134 |
| 1079. | A123 | D134 |
| 1080. | A124 | D134 |
| 1081. | A125 | D134 |
| 1082. | A126 | D134 |
| 1083. | A127 | D134 |
| 1084. | A128 | D134 |
| 1085. | A129 | D134 |
| 1086. | A130 | D134 |
| 1087. | A131 | D134 |
| 1088. | A132 | D134 |
| 1089. | A101 | D135 |
| 1090. | A102 | D135 |
| 1091. | A103 | D135 |
| 1092. | A104 | D135 |
| 1093. | A105 | D135 |
| 1094. | A106 | D135 |
| 1095. | A107 | D135 |
| 1096. | A108 | D135 |
| 1097. | A109 | D135 |
| 1098. | A110 | D135 |
| 1099. | A111 | D135 |
| 1100. | A112 | D135 |
| 1101. | A113 | D135 |
| 1102. | A114 | D135 |
| 1103. | A115 | D135 |
| 1104. | A116 | D135 |
| 1105. | A117 | D135 |
| 1106. | A118 | D135 |
| 1107. | A119 | D135 |
| 1108. | A120 | D135 |
| 1109. | A121 | D135 |
| 1110. | A122 | D135 |
| 1111. | A123 | D135 |
| 1112. | A124 | D135 |

Formula II

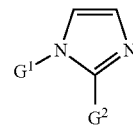

| Compound Number | G1 | G2 |
| --- | --- | --- |
| 1113. | A125 | D135 |
| 1114. | A126 | D135 |
| 1115. | A127 | D135 |
| 1116. | A128 | D135 |
| 1117. | A129 | D135 |
| 1118. | A130 | D135 |
| 1119. | A131 | D135 |
| 1120. | A132 | D135 |
| 1121. | A101 | D136 |
| 1122. | A102 | D136 |
| 1123. | A103 | D136 |
| 1124. | A104 | D136 |
| 1125. | A105 | D136 |
| 1126. | A106 | D136 |
| 1127. | A107 | D136 |
| 1128. | A108 | D136 |
| 1129. | A109 | D136 |
| 1130. | A110 | D136 |
| 1131. | A111 | D136 |
| 1132. | A112 | D136 |
| 1133. | A113 | D136 |
| 1134. | A114 | D136 |
| 1135. | A115 | D136 |
| 1136. | A116 | D136 |
| 1137. | A117 | D136 |
| 1138. | A118 | D136 |
| 1139. | A119 | D136 |
| 1140. | A120 | D136 |
| 1141. | A121 | D136 |
| 1142. | A122 | D136 |
| 1143. | A123 | D136 |
| 1144. | A124 | D136 |
| 1145. | A125 | D136 |
| 1146. | A126 | D136 |
| 1147. | A127 | D136 |
| 1148. | A128 | D136 |
| 1149. | A129 | D136 |
| 1150. | A130 | D136 |
| 1151. | A131 | D136 |
| 1152. | A132 | D136 |
| 1153. | A101 | D137 |
| 1154. | A102 | D137 |
| 1155. | A103 | D137 |
| 1156. | A104 | D137 |
| 1157. | A105 | D137 |
| 1158. | A106 | D137 |
| 1159. | A107 | D137 |
| 1160. | A108 | D137 |
| 1161. | A109 | D137 |
| 1162. | A110 | D137 |
| 1163. | A111 | D137 |
| 1164. | A112 | D137 |
| 1165. | A113 | D137 |
| 1166. | A114 | D137 |
| 1167. | A115 | D137 |
| 1168. | A116 | D137 |
| 1169. | A117 | D137 |
| 1170. | A118 | D137 |
| 1171. | A119 | D137 |
| 1172. | A120 | D137 |
| 1173. | A121 | D137 |
| 1174. | A122 | D137 |
| 1175. | A123 | D137 |
| 1176. | A124 | D137 |
| 1177. | A125 | D137 |
| 1178. | A126 | D137 |
| 1179. | A127 | D137 |
| 1180. | A128 | D137 |
| 1181. | A129 | D137 |

Formula II

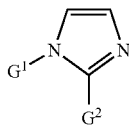

| Compound Number | G1 | G2 |
|---|---|---|
| 1182. | A130 | D137 |
| 1183. | A131 | D137 |
| 1184. | A132 | D137 |
| 1185. | A101 | D138 |
| 1186. | A102 | D138 |
| 1187. | A103 | D138 |
| 1188. | A104 | D138 |
| 1189. | A105 | D138 |
| 1190. | A106 | D138 |
| 1191. | A107 | D138 |
| 1192. | A108 | D138 |
| 1193. | A109 | D138 |
| 1194. | A110 | D138 |
| 1195. | A111 | D138 |
| 1196. | A112 | D138 |
| 1197. | A113 | D138 |
| 1198. | A114 | D138 |
| 1199. | A115 | D138 |
| 1200. | A116 | D138 |
| 1201. | A117 | D138 |
| 1202. | A118 | D138 |
| 1203. | A119 | D138 |
| 1204. | A120 | D138 |
| 1205. | A121 | D138 |
| 1206. | A122 | D138 |
| 1207. | A123 | D138 |
| 1208. | A124 | D138 |
| 1209. | A125 | D138 |
| 1210. | A126 | D138 |
| 1211. | A127 | D138 |
| 1212. | A128 | D138 |
| 1213. | A129 | D138 |
| 1214. | A130 | D138 |
| 1215. | A131 | D138 |
| 1216. | A132 | D138 |
| 1217. | A101 | D139 |
| 1218. | A102 | D139 |
| 1219. | A193 | D139 |
| 1220. | A104 | D139 |
| 1221. | A105 | D139 |
| 1222. | A106 | D139 |
| 1223. | A107 | D139 |
| 1224. | A108 | D139 |
| 1225. | A109 | D139 |
| 1226. | A110 | D139 |
| 1227. | A111 | D139 |
| 1228. | A112 | D139 |
| 1229. | A113 | D139 |
| 1230. | A114 | D139 |
| 1231. | A115 | D139 |
| 1232. | A116 | D139 |
| 1233. | A117 | D139 |
| 1234. | A118 | D139 |
| 1235. | A119 | D139 |
| 1236. | A120 | D139 |
| 1237. | A121 | D139 |
| 1238. | A122 | D139 |
| 1239. | A123 | D139 |
| 1240. | A124 | D139 |
| 1241. | A125 | D139 |
| 1242. | A126 | D139 |
| 1243. | A127 | D139 |
| 1244. | A128 | D139 |
| 1245. | A129 | D139 |
| 1246. | A130 | D139 |
| 1247. | A131 | D139 |
| 1248. | A132 | D139 |
| 1249. | A101 | D140 |
| 1250. | A102 | D140 |

Formula II

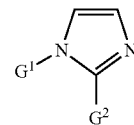

| Compound Number | G1 | G2 |
|---|---|---|
| 1251. | A103 | D140 |
| 1252. | A104 | D140 |
| 1253. | A105 | D140 |
| 1254. | A106 | D140 |
| 1255. | A107 | D140 |
| 1256. | A108 | D140 |
| 1257. | A109 | D140 |
| 1258. | A110 | D140 |
| 1259. | A111 | D140 |
| 1260. | A112 | D140 |
| 1261. | A113 | D140 |
| 1262. | A114 | D140 |
| 1263. | A115 | D140 |
| 1264. | A116 | D140 |
| 1265. | A117 | D140 |
| 1266. | A118 | D140 |
| 1267. | A119 | D140 |
| 1268. | A120 | D140 |
| 1269. | A121 | D140 |
| 1270. | A122 | D140 |
| 1271. | A123 | D140 |
| 1272. | A124 | D140 |
| 1273. | A125 | D140 |
| 1274. | A126 | D140 |
| 1275. | A127 | D140 |
| 1276. | A128 | D140 |
| 1277. | A129 | D140 |
| 1278. | A130 | D140 |
| 1279. | A131 | D140 |
| 1280. | A132 | D140 |
| 1281. | A101 | D141 |
| 1282. | A102 | D141 |
| 1283. | A103 | D141 |
| 1284. | A104 | D141 |
| 1285. | A105 | D141 |
| 1286. | A106 | D141 |
| 1287. | A107 | D141 |
| 1288. | A108 | D141 |
| 1289. | A109 | D141 |
| 1290. | A110 | D141 |
| 1291. | A111 | D141 |
| 1292. | A112 | D141 |
| 1293. | A113 | D141 |
| 1294. | A114 | D141 |
| 1295. | A115 | D141 |
| 1296. | A116 | D141 |
| 1297. | A117 | D141 |
| 1298. | A118 | D141 |
| 1299. | A119 | D141 |
| 1300. | A120 | D141 |
| 1301. | A121 | D141 |
| 1302. | A122 | D141 |
| 1303. | A123 | D141 |
| 1304. | A124 | D141 |
| 1305. | A125 | D141 |
| 1306. | A126 | D141 |
| 1307. | A127 | D141 |
| 1308. | A128 | D141 |
| 1309. | A129 | D141 |
| 1310. | A130 | D141 |
| 1311. | A131 | D141 |
| 1312. | A132 | D141 |
| 1313. | A101 | D142 |
| 1314. | A102 | D142 |
| 1315. | A103 | D142 |
| 1316. | A104 | D142 |
| 1317. | A105 | D142 |
| 1318. | A106 | D142 |
| 1319. | A107 | D142 |

Formula II

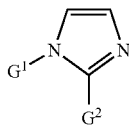

| Compound Number | G1 | G2 |
|---|---|---|
| 1320. | A108 | D142 |
| 1321. | A109 | D142 |
| 1322. | A110 | D142 |
| 1323. | A111 | D142 |
| 1324. | A112 | D142 |
| 1325. | A113 | D142 |
| 1326. | A114 | D142 |
| 1327. | A115 | D142 |
| 1328. | A116 | D142 |
| 1329. | A117 | D142 |
| 1330. | A118 | D142 |
| 1331. | A119 | D142 |
| 1332. | A120 | D142 |
| 1333. | A121 | D142 |
| 1334. | A122 | D142 |
| 1335. | A123 | D142 |
| 1336. | A124 | D142 |
| 1337. | A125 | D142 |
| 1338. | A126 | D142 |
| 1339. | A127 | D142 |
| 1340. | A128 | D142 |
| 1341. | A129 | D142 |
| 1342. | A130 | D142 |
| 1343. | A131 | D142 |
| 1344. | A132 | D142 |
| 1345. | A101 | D143 |
| 1346. | A102 | D143 |
| 1347. | A103 | D143 |
| 1348. | A104 | D143 |
| 1349. | A105 | D143 |
| 1350. | A106 | D143 |
| 1351. | A107 | D143 |
| 1352. | A108 | D143 |
| 1353. | A109 | D143 |
| 1354. | A110 | D143 |
| 1355. | A111 | D143 |
| 1356. | A112 | D143 |
| 1357. | A113 | D143 |
| 1358. | A114 | D143 |
| 1359. | A115 | D143 |
| 1360. | A116 | D143 |
| 1361. | A117 | D143 |
| 1362. | A118 | D143 |
| 1363. | A119 | D143 |
| 1364. | A120 | D143 |
| 1365. | A121 | D143 |
| 1366. | A122 | D143 |
| 1367. | A123 | D143 |
| 1368. | A124 | D143 |
| 1369. | A125 | D143 |
| 1370. | A126 | D143 |
| 1371. | A127 | D143 |
| 1372. | A128 | D143 |
| 1373. | A129 | D143 |
| 1374. | A130 | D143 |
| 1375. | A131 | D143 |
| 1376. | A132 | D143 |
| 1377. | A101 | D144 |
| 1378. | A102 | D144 |
| 1379. | A103 | D144 |
| 1380. | A104 | D144 |
| 1381. | A105 | D144 |
| 1382. | A106 | D144 |
| 1383. | A107 | D144 |
| 1384. | A108 | D144 |
| 1385. | A109 | D144 |
| 1386. | A110 | D144 |
| 1387. | A111 | D144 |
| 1388. | A112 | D144 |

Formula II

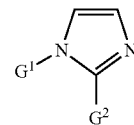

| Compound Number | G1 | G2 |
|---|---|---|
| 1389. | A113 | D144 |
| 1390. | A114 | D144 |
| 1391. | A115 | D144 |
| 1392. | A116 | D144 |
| 1393. | A117 | D144 |
| 1394. | A118 | D144 |
| 1395. | A119 | D144 |
| 1396. | A120 | D144 |
| 1397. | A121 | D144 |
| 1398. | A122 | D144 |
| 1399. | A123 | D144 |
| 1400. | A124 | D144 |
| 1401. | A125 | D144 |
| 1402. | A126 | D144 |
| 1403. | A127 | D144 |
| 1404. | A128 | D144 |
| 1405. | A129 | D144 |
| 1406. | A130 | D144 |
| 1407. | A131 | D144 |
| 1408. | A132 | D144 |
| 1409. | A101 | D145 |
| 1410. | A102 | D145 |
| 1411. | A103 | D145 |
| 1412. | A104 | D145 |
| 1413. | A105 | D145 |
| 1414. | A106 | D145 |
| 1415. | A107 | D145 |
| 1416. | A108 | D145 |
| 1417. | A109 | D145 |
| 1418. | A110 | D145 |
| 1419. | A111 | D145 |
| 1420. | A112 | D145 |
| 1421. | A113 | D145 |
| 1422. | A114 | D145 |
| 1423. | A115 | D145 |
| 1424. | A116 | D145 |
| 1425. | A117 | D145 |
| 1426. | A118 | D145 |
| 1427. | A119 | D145 |
| 1428. | A120 | D145 |
| 1429. | A121 | D145 |
| 1430. | A122 | D145 |
| 1431. | A123 | D145 |
| 1432. | A124 | D145 |
| 1433. | A125 | D145 |
| 1434. | A126 | D145 |
| 1435. | A127 | D145 |
| 1436. | A128 | D145 |
| 1437. | A129 | D145 |
| 1438. | A130 | D145 |
| 1439. | A131 | D145 |
| 1440. | A132 | D145 |
| 1441. | A101 | D146 |
| 1442. | A102 | D146 |
| 1443. | A103 | D146 |
| 1444. | A104 | D146 |
| 1445. | A105 | D146 |
| 1446. | A106 | D146 |
| 1447. | A107 | D146 |
| 1448. | A108 | D146 |
| 1449. | A109 | D146 |
| 1450. | A110 | D146 |
| 1451. | A111 | D146 |
| 1452. | A112 | D146 |
| 1453. | A113 | D146 |
| 1454. | A114 | D146 |
| 1455. | A115 | D146 |
| 1456. | A116 | D146 |
| 1457. | A117 | D146 |

Formula II

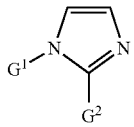

| Compound Number | G1 | G2 |
|---|---|---|
| 1458. | A118 | D146 |
| 1459. | A119 | D146 |
| 1460. | A120 | D146 |
| 1461. | A121 | D146 |
| 1462. | A122 | D146 |
| 1463. | A123 | D146 |
| 1464. | A124 | D146 |
| 1465. | A125 | D146 |
| 1466. | A126 | D146 |
| 1467. | A127 | D146 |
| 1468. | A128 | D146 |
| 1469. | A129 | D146 |
| 1470. | A130 | D146 |
| 1471. | A131 | D146 |
| 1472. | A132 | D146 |
| 1473. | A101 | D147 |
| 1474. | A102 | D147 |
| 1475. | A103 | D147 |
| 1476. | A104 | D147 |
| 1477. | A105 | D147 |
| 1478. | A106 | D147 |
| 1479. | A107 | D147 |
| 1480. | A108 | D147 |
| 1481. | A109 | D147 |
| 1482. | A110 | D147 |
| 1483. | A111 | D147 |
| 1484. | A112 | D147 |
| 1485. | A113 | D147 |
| 1486. | A114 | D147 |
| 1487. | A115 | D147 |
| 1488. | A116 | D147 |
| 1489. | A117 | D147 |
| 1490. | A118 | D147 |
| 1491. | A119 | D147 |
| 1492. | A120 | D147 |
| 1493. | A121 | D147 |
| 1494. | A122 | D147 |
| 1495. | A123 | D147 |
| 1496. | A124 | D147 |
| 1497. | A125 | D147 |
| 1498. | A126 | D147 |
| 1499. | A127 | D147 |
| 1500. | A128 | D147 |
| 1501. | A129 | D147 |
| 1502. | A130 | D147 |
| 1503. | A131 | D147 |
| 1504. | A132 | D147 |
| 1505. | A101 | D148 |
| 1506. | A102 | D148 |
| 1507. | A103 | D148 |
| 1508. | A104 | D148 |
| 1509. | A105 | D148 |
| 1510. | A106 | D148 |
| 1511. | A107 | D148 |
| 1512. | A108 | D148 |
| 1513. | A109 | D148 |
| 1514. | A110 | D148 |
| 1515. | A111 | D148 |
| 1516. | A112 | D148 |
| 1517. | A113 | D148 |
| 1518. | A114 | D148 |
| 1519. | A115 | D148 |
| 1520. | A116 | D148 |
| 1521. | A117 | D148 |
| 1522. | A118 | D148 |
| 1523. | A119 | D148 |
| 1524. | A120 | D148 |
| 1525. | A121 | D148 |
| 1526. | A122 | D148 |

Formula II

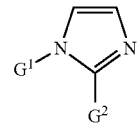

| Compound Number | G1 | G2 |
|---|---|---|
| 1527. | A123 | D148 |
| 1528. | A124 | D148 |
| 1529. | A125 | D148 |
| 1530. | A126 | D148 |
| 1531. | A127 | D148 |
| 1532. | A128 | D148 |
| 1533. | A129 | D148 |
| 1534. | A130 | D148 |
| 1535. | A131 | D148 |
| 1536. | A132 | D148 |
| 1537. | A101 | D149 |
| 1538. | A102 | D149 |
| 1539. | A103 | D149 |
| 1540. | A104 | D149 |
| 1541. | A105 | D149 |
| 1542. | A106 | D149 |
| 1543. | A107 | D149 |
| 1544. | A108 | D149 |
| 1545. | A109 | D149 |
| 1546. | A110 | D149 |
| 1547. | A111 | D149 |
| 1548. | A112 | D149 |
| 1549. | A113 | D149 |
| 1550. | A114 | D149 |
| 1551. | A115 | D149 |
| 1552. | A116 | D149 |
| 1553. | A117 | D149 |
| 1554. | A118 | D149 |
| 1555. | A119 | D149 |
| 1556. | A120 | D149 |
| 1557. | A121 | D149 |
| 1558. | A122 | D149 |
| 1559. | A123 | D149 |
| 1560. | A124 | D149 |
| 1561. | A125 | D149 |
| 1562. | A126 | D149 |
| 1563. | A127 | D149 |
| 1564. | A128 | D149 |
| 1565. | A129 | D149 |
| 1566. | A130 | D149 |
| 1567. | A131 | D149 |
| 1568. | A132 | D149 |
| 1569. | A101 | D150 |
| 1570. | A102 | D150 |
| 1571. | A103 | D150 |
| 1572. | A104 | D150 |
| 1573. | A105 | D150 |
| 1574. | A106 | D150 |
| 1575. | A107 | D150 |
| 1576. | A108 | D150 |
| 1577. | A109 | D150 |
| 1578. | A110 | D150 |
| 1579. | A111 | D150 |
| 1580. | A112 | D150 |
| 1581. | A113 | D150 |
| 1582. | A114 | D150 |
| 1583. | A115 | D150 |
| 1584. | A116 | D150 |
| 1585. | A117 | D150 |
| 1586. | A118 | D150 |
| 1587. | A119 | D150 |
| 1588. | A120 | D150 |
| 1589. | A121 | D150 |
| 1590. | A122 | D150 |
| 1591. | A123 | D150 |
| 1592. | A124 | D150 |
| 1593. | A125 | D150 |
| 1594. | A126 | D150 |
| 1595. | A127 | D150 |

Formula II

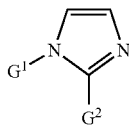

| Compound Number | G1 | G2 |
|---|---|---|
| 1596. | A128 | D150 |
| 1597. | A129 | D150 |
| 1598. | A130 | D150 |
| 1599. | A131 | D150 |
| 1600. | A132 | D150 |
| 1601. | A101 | D151 |
| 1602. | A102 | D151 |
| 1603. | A103 | D151 |
| 1604. | A104 | D151 |
| 1605. | A105 | D151 |
| 1606. | A106 | D151 |
| 1607. | A107 | D151 |
| 1608. | A108 | D151 |
| 1609. | A109 | D151 |
| 1610. | A110 | D151 |
| 1611. | A111 | D151 |
| 1612. | A112 | D151 |
| 1613. | A113 | D151 |
| 1614. | A114 | D151 |
| 1615. | A115 | D151 |
| 1616. | A116 | D151 |
| 1617. | A117 | D151 |
| 1618. | A118 | D151 |
| 1619. | A119 | D151 |
| 1620. | A120 | D151 |
| 1621. | A121 | D151 |
| 1622. | A122 | D151 |
| 1623. | A123 | D151 |
| 1624. | A124 | D151 |
| 1625. | A125 | D151 |
| 1626. | A126 | D151 |
| 1627. | A127 | D151 |
| 1628. | A128 | D151 |
| 1629. | A129 | D151 |
| 1630. | A130 | D151 |
| 1631. | A131 | D151 |
| 1632. | A132 | D151 |
| 1633. | A101 | D152 |
| 1634. | A102 | D152 |
| 1635. | A103 | D152 |
| 1636. | A104 | D152 |
| 1637. | A105 | D152 |
| 1638. | A106 | D152 |
| 1639. | A107 | D152 |
| 1640. | A108 | D152 |
| 1641. | A109 | D152 |
| 1642. | A110 | D152 |
| 1643. | A111 | D152 |
| 1644. | A112 | D152 |
| 1645. | A113 | D152 |
| 1646. | A114 | D152 |
| 1647. | A115 | D152 |
| 1648. | A116 | D152 |
| 1649. | A117 | D152 |
| 1650. | A118 | D152 |
| 1651. | A119 | D152 |
| 1652. | A120 | D152 |
| 1653. | A121 | D152 |
| 1654. | A122 | D152 |
| 1655. | A123 | D152 |
| 1656. | A124 | D152 |
| 1657. | A125 | D152 |
| 1658. | A126 | D152 |
| 1659. | A127 | D152 |
| 1660. | A128 | D152 |
| 1661. | A129 | D152 |
| 1662. | A130 | D152 |
| 1663. | A131 | D152 |
| 1664. | A132 | D152 |

Formula II

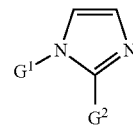

| Compound Number | G1 | G2 |
|---|---|---|
| 1665. | A101 | D153 |
| 1666. | A102 | D153 |
| 1667. | A103 | D153 |
| 1668. | A104 | D153 |
| 1669. | A105 | D153 |
| 1670. | A106 | D153 |
| 1671. | A107 | D153 |
| 1672. | A108 | D153 |
| 1673. | A109 | D153 |
| 1674. | A110 | D153 |
| 1675. | A111 | D153 |
| 1676. | A112 | D153 |
| 1677. | A113 | D153 |
| 1678. | A114 | D153 |
| 1679. | A115 | D153 |
| 1680. | A116 | D153 |
| 1681. | A117 | D153 |
| 1682. | A118 | D153 |
| 1683. | A119 | D153 |
| 1684. | A120 | D153 |
| 1685. | A121 | D153 |
| 1686. | A122 | D153 |
| 1687. | A123 | D153 |
| 1688. | A124 | D153 |
| 1689. | A125 | D153 |
| 1690. | A126 | D153 |
| 1691. | A127 | D153 |
| 1692. | A128 | D153 |
| 1693. | A129 | D153 |
| 1694. | A130 | D153 |
| 1695. | A131 | D153 |
| 1696. | A132 | D153 |
| 1697. | A101 | D154 |
| 1698. | A102 | D154 |
| 1699. | A103 | D154 |
| 1700. | A104 | D154 |
| 1701. | A105 | D154 |
| 1702. | A106 | D154 |
| 1703. | A107 | D154 |
| 1704. | A108 | D154 |
| 1705. | A109 | D154 |
| 1706. | A110 | D154 |
| 1707. | A111 | D154 |
| 1708. | A112 | D154 |
| 1709. | A113 | D154 |
| 1710. | A114 | D154 |
| 1711. | A115 | D154 |
| 1712. | A116 | D154 |
| 1713. | A117 | D154 |
| 1714. | A118 | D154 |
| 1715. | A119 | D154 |
| 1716. | A120 | D154 |
| 1717. | A121 | D154 |
| 1718. | A122 | D154 |
| 1719. | A123 | D154 |
| 1720. | A124 | D154 |
| 1721. | A125 | D154 |
| 1722. | A126 | D154 |
| 1723. | A127 | D154 |
| 1724. | A128 | D154 |
| 1725. | A129 | D154 |
| 1726. | A130 | D154 |
| 1727. | A131 | D154 |
| 1728. | A132 | D154 |
| 1729. | A101 | D155 |
| 1730. | A102 | D155 |
| 1731. | A103 | D155 |
| 1732. | A104 | D155 |
| 1733. | A105 | D155 |

Formula II

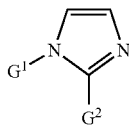

| Compound Number | G1 | G2 |
|---|---|---|
| 1734. | A106 | D155 |
| 1735. | A107 | D155 |
| 1736. | A108 | D155 |
| 1737. | A109 | D155 |
| 1738. | A110 | D155 |
| 1739. | A111 | D155 |
| 1740. | A112 | D155 |
| 1741. | A113 | D155 |
| 1742. | A114 | D155 |
| 1743. | A115 | D155 |
| 1744. | A116 | D155 |
| 1745. | A117 | D155 |
| 1746. | A118 | D155 |
| 1747. | A119 | D155 |
| 1748. | A120 | D155 |
| 1749. | A121 | D155 |
| 1750. | A122 | D155 |
| 1751. | A123 | D155 |
| 1752. | A124 | D155 |
| 1753. | A125 | D155 |
| 1754. | A126 | D155 |
| 1755. | A127 | D155 |
| 1756. | A128 | D155 |
| 1757. | A129 | D155 |
| 1758. | A130 | D155 |
| 1759. | A131 | D155 |
| 1760. | A132 | D155 |
| 1761. | A101 | D156 |
| 1762. | A102 | D156 |
| 1763. | A103 | D156 |
| 1764. | A104 | D156 |
| 1765. | A105 | D156 |
| 1766. | A106 | D156 |
| 1767. | A107 | D156 |
| 1768. | A108 | D156 |
| 1769. | A109 | D156 |
| 1770. | A110 | D156 |
| 1771. | A111 | D156 |
| 1772. | A112 | D156 |
| 1773. | A113 | D156 |
| 1774 | A114 | D156 |
| 1775. | A115 | D156 |
| 1776. | A116 | D156 |
| 1777. | A117 | D156 |
| 1778. | A118 | D156 |
| 1779. | A119 | D156 |
| 1780. | A120 | D156 |
| 1781. | A121 | D156 |
| 1782. | A122 | D156 |
| 1783. | A123 | D156 |
| 1784. | A124 | D156 |
| 1785. | A125 | D156 |
| 1786. | A126 | D156 |
| 1787. | A127 | D156 |
| 1788. | A128 | D156 |
| 1789. | A129 | D156 |
| 1790. | A130 | D156 |
| 1791. | A131 | D156 |
| 1792. | A132 | D156 |
| 1793. | A101 | D157 |
| 1794. | A102 | D157 |
| 1795. | A103 | D157 |
| 1796. | A104 | D157 |
| 1797. | A105 | D157 |
| 1798. | A106 | D157 |
| 1799. | A107 | D157 |
| 1800. | A108 | D157 |
| 1801. | A109 | D157 |
| 1802. | A110 | D157 |

Formula II

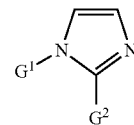

| Compound Number | G1 | G2 |
|---|---|---|
| 1803. | A111 | D157 |
| 1804. | A112 | D157 |
| 1805. | A113 | D157 |
| 1806. | A114 | D157 |
| 1807. | A115 | D157 |
| 1808. | A116 | D157 |
| 1809. | A117 | D157 |
| 1810. | A118 | D157 |
| 1811. | A119 | D157 |
| 1812. | A120 | D157 |
| 1813. | A121 | D157 |
| 1814. | A122 | D157 |
| 1815. | A123 | D157 |
| 1816. | A124 | D157 |
| 1817. | A125 | D157 |
| 1818. | A126 | D157 |
| 1819. | A127 | D157 |
| 1820. | A128 | D157 |
| 1821. | A129 | D157 |
| 1822. | A130 | D157 |
| 1823. | A131 | D157 |
| 1824. | A132 | D157 |
| 1825. | A101 | D158 |
| 1826. | A102 | D158 |
| 1827. | A103 | D158 |
| 1828. | A104 | D158 |
| 1829. | A105 | D158 |
| 1830. | A106 | D158 |
| 1831 | A107 | D158 |
| 1832 | A108 | D158 |
| 1833 | A109 | D158 |
| 1834 | A110 | D158 |
| 1835 | A111 | D158 |
| 1836 | A112 | D158 |
| 1837 | A113 | D158 |
| 1838 | A114 | D158 |
| 1839 | A115 | D158 |
| 1840 | A116 | D158 |
| 1841 | A117 | D158 |
| 1842 | A118 | D158 |
| 1843 | A119 | D158 |
| 1844 | A120 | D158 |
| 1845 | A121 | D158 |
| 1846 | A122 | D158 |
| 1847 | A123 | D158 |
| 1848 | A124 | D158 |
| 1849 | A125 | D158 |
| 1850 | A126 | D158 |
| 1851 | A127 | D158 |
| 1852 | A128 | D158 |
| 1853 | A129 | D158 |
| 1854 | A130 | D158 |
| 1855. | A131 | D158 |
| 1856. | A132 | D158 |
| 1857. | A101 | D159 |
| 1858. | A102 | D159 |
| 1859. | A103 | D159 |
| 1860. | A104 | D159 |
| 1861. | A105 | D159 |
| 1862. | A106 | D159 |
| 1863. | A107 | D159 |
| 1864. | A108 | D159 |
| 1865. | A109 | D159 |
| 1866. | A110 | D159 |
| 1867. | A111 | D159 |
| 1868. | A112 | D159 |
| 1869. | A113 | D159 |
| 1870. | A114 | D159 |
| 1871. | A115 | D159 |

111
-continued

Formula II

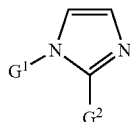

| Compound Number | G1 | G2 |
|---|---|---|
| 1872. | A116 | D159 |
| 1873. | A117 | D159 |
| 1874. | A118 | D159 |
| 1875. | A119 | D159 |
| 1876 | A120 | D159 |
| 1877. | A121 | D159 |
| 1878. | A122 | D159 |
| 1879. | A123 | D159 |
| 1880. | A124 | D159 |
| 1881. | A125 | D159 |
| 1882. | A126 | D159 |
| 1883. | A127 | D159 |
| 1884. | A128 | D159 |
| 1885. | A129 | D159 |
| 1886. | A130 | D159 |
| 1887. | A131 | D159 |
| 1888. | A132 | D159 |
| 1889. | A101 | D160 |
| 1890. | A102 | D160 |
| 1891. | A103 | D160 |
| 1892. | A104 | D160 |
| 1893. | A105 | D160 |
| 1894. | A106 | D160 |
| 1895. | A107 | D160 |
| 1896. | A108 | D160 |
| 1897. | A109 | D160 |
| 1898. | A110 | D160 |
| 1899. | A111 | D160 |
| 1900. | A112 | D160 |
| 1901. | A113 | D160 |
| 1902. | A114 | D160 |
| 1903. | A115 | D160 |
| 1904. | A116 | D160 |
| 1905. | A117 | D160 |
| 1906. | A118 | D160 |
| 1907. | A119 | D160 |
| 1908. | A120 | D160 |
| 1909. | A121 | D160 |
| 1910. | A122 | D160 |
| 1911. | A123 | D160 |
| 1912. | A124 | D160 |
| 1913. | A125 | D160 |
| 1914. | A126 | D160 |
| 1915. | A127 | D160 |
| 1916. | A128 | D160 |
| 1917. | A129 | D160 |
| 1918. | A130 | D160 |
| 1919. | A131 | D160 |
| 1920. | A132 | D160 |
| 1921. | A101 | D161 |
| 1922. | A102 | D161 |
| 1923. | A103 | D161 |
| 1924. | A104 | D161 |
| 1925. | A105 | D161 |
| 1926. | A106 | D161 |
| 1927. | A107 | D161 |
| 1928. | A108 | D161 |
| 1929. | A109 | D161 |
| 1930. | A110 | D161 |
| 1931. | A111 | D161 |
| 1932. | A112 | D161 |
| 1933. | A113 | D161 |
| 1934. | A114 | D161 |
| 1935. | A115 | D161 |
| 1936. | A116 | D161 |
| 1937. | A117 | D161 |
| 1938. | A118 | D161 |
| 1939. | A119 | D161 |
| 1940. | A120 | D161 |

112
-continued

Formula II

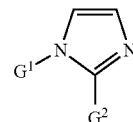

| Compound Number | G1 | G2 |
|---|---|---|
| 1941. | A121 | D161 |
| 1942. | A122 | D161 |
| 1943. | A123 | D161 |
| 1944. | A124 | D161 |
| 1945. | A125 | D161 |
| 1946. | A126 | D161 |
| 1947. | A127 | D161 |
| 1948. | A128 | D161 |
| 1949. | A129 | D161 |
| 1950. | A130 | D161 |
| 1951. | A131 | D161 |
| 1952. | A132 | D161 |
| 1953. | A101 | D162 |
| 1954. | A102 | D162 |
| 1955. | A103 | D162 |
| 1956. | A104 | D162 |
| 1957. | A105 | D162 |
| 1958. | A106 | D162 |
| 1959. | A107 | D162 |
| 1960. | A108 | D162 |
| 1961. | A109 | D162 |
| 1962. | A110 | D162 |
| 1963. | A111 | D162 |
| 1964. | A112 | D162 |
| 1965. | A113 | D162 |
| 1966. | A114 | D162 |
| 1967. | A115 | D162 |
| 1968. | A116 | D162 |
| 1969. | A117 | D162 |
| 1970. | A118 | D162 |
| 1971. | A119 | D162 |
| 1972. | A120 | D162 |
| 1973. | A121 | D162 |
| 1974. | A122 | D162 |
| 1975. | A123 | D162 |
| 1976. | A124 | D162 |
| 1977. | A125 | D162 |
| 1978. | A126 | D162 |
| 1979. | A127 | D162 |
| 1980. | A128 | D162 |
| 1981. | A129 | D162 |
| 1982. | A130 | D162 |
| 1983. | A131 | D162 |
| 1984. | A132 | D162 |
| 1985. | A101 | D163 |
| 1986. | A102 | D163 |
| 1987. | A103 | D163 |
| 1988. | A104 | D163 |
| 1989. | A105 | D163 |
| 1990. | A106 | D163 |
| 1991. | A107 | D163 |
| 1992. | A108 | D163 |
| 1993. | A109 | D163 |
| 1994. | A110 | D163 |
| 1995. | A111 | D163 |
| 1996. | A112 | D163 |
| 1997. | A113 | D163 |
| 1998. | A114 | D163 |
| 1999. | A115 | D163 |
| 2000. | A116 | D163 |
| 2001. | A117 | D163 |
| 2002. | A118 | D163 |
| 2003. | A119 | D163 |
| 2004. | A120 | D163 |
| 2005. | A121 | D163 |
| 2006. | A122 | D163 |
| 2007. | A123 | D163 |
| 2008. | A124 | D163 |
| 2009. | A125 | D163 |

113
-continued

Formula II

G¹—N⟨imidazole⟩—G²

| Compound Number | G1 | G2 |
|---|---|---|
| 2010. | A126 | D163 |
| 2011. | A127 | D163 |
| 2012. | A128 | D163 |
| 2013. | A129 | D163 |
| 2014. | A130 | D163 |
| 2015. | A131 | D163 |
| 2016. | A132 | D163 |
| 2017. | A101 | D164 |
| 2018. | A102 | D164 |
| 2019. | A103 | D164 |
| 2020. | A104 | D164 |
| 2021. | A105 | D164 |
| 2022. | A106 | D164 |
| 2023. | A107 | D164 |
| 2024. | A108 | D164 |
| 2025. | A109 | D164 |
| 2026. | A110 | D164 |
| 2027. | A111 | D164 |
| 2028. | A112 | D164 |
| 2029. | A113 | D164 |
| 2030. | A114 | D164 |
| 2031. | A115 | D164 |
| 2032. | A116 | D164 |
| 2033. | A117 | D164 |
| 2034. | A118 | D164 |
| 2035. | A119 | D164 |
| 2036. | A120 | D164 |
| 2037. | A121 | D164 |
| 2038. | A122 | D164 |
| 2039. | A123 | D164 |
| 2040. | A124 | D164 |
| 2041. | A125 | D164 |
| 2042. | A126 | D164 |
| 2043. | A127 | D164 |
| 2044. | A128 | D164 |
| 2045. | A129 | D164 |
| 2046. | A130 | D164 |
| 2047. | A131 | D164 |
| 2048. | A132 | D164 |
| 2049. | A101 | D165 |
| 2050. | A102 | D165 |
| 2051. | A103 | D165 |
| 2052. | A104 | D165 |
| 2053. | A105 | D165 |
| 2054. | A106 | D165 |
| 2055. | A107 | D165 |
| 2056. | A108 | D165 |
| 2057. | A109 | D165 |
| 2058. | A110 | D165 |
| 2059. | A111 | D165 |
| 2060. | A112 | D165 |
| 2061. | A113 | D165 |
| 2062. | A114 | D165 |
| 2063. | A115 | D165 |
| 2064. | A116 | D165 |
| 2065. | A117 | D165 |
| 2066. | A118 | D165 |
| 2067. | A119 | D165 |
| 2068. | A120 | D165 |
| 2069. | A121 | D165 |
| 2070. | A122 | D165 |
| 2071. | A123 | D165 |
| 2072. | A124 | D165 |
| 2073. | A125 | D165 |
| 2074. | A126 | D165 |
| 2075. | A127 | D165 |
| 2076. | A128 | D165 |
| 2077. | A129 | D165 |
| 2078. | A130 | D165 |

114
-continued

Formula II

G¹—N⟨imidazole⟩—G²

| Compound Number | G1 | G2 |
|---|---|---|
| 2079. | A131 | D165 |
| 2080. | A132 | D165 |
| 2081. | A101 | D166 |
| 2082. | A102 | D166 |
| 2083. | A103 | D166 |
| 2084. | A104 | D166 |
| 2085. | A105 | D166 |
| 2086. | A106 | D166 |
| 2087. | A107 | D166 |
| 2088. | A108 | D166 |
| 2089. | A109 | D166 |
| 2090. | A110 | D166 |
| 2091. | A111 | D166 |
| 2092. | A112 | D166 |
| 2093. | A113 | D166 |
| 2094. | A114 | D166 |
| 2095. | A115 | D166 |
| 2096. | A116 | D166 |
| 2097. | A117 | D166 |
| 2098. | A118 | D166 |
| 2099. | A119 | D166 |
| 2100. | A120 | D166 |
| 2101. | A121 | D166 |
| 2102. | A122 | D166 |
| 2103. | A123 | D166 |
| 2104. | A124 | D166 |
| 2105. | A125 | D166 |
| 2106. | A126 | D166 |
| 2107. | A127 | D166 |
| 2108. | A128 | D166 |
| 2109. | A129 | D166 |
| 2110. | A130 | D166 |
| 2111. | A131 | D166 |
| 2112. | A132 | D166 |
| 2113. | A101 | D167 |
| 2114. | A102 | D167 |
| 2115. | A103 | D167 |
| 2116. | A104 | D167 |
| 2117. | A105 | D167 |
| 2118. | A106 | D167 |
| 2119. | A107 | D167 |
| 2120. | A108 | D167 |
| 2121. | A109 | D167 |
| 2122. | A110 | D167 |
| 2123. | A111 | D167 |
| 2124. | A112 | D167 |
| 2125. | A113 | D167 |
| 2126. | A114 | D167 |
| 2127. | A115 | D167 |
| 2128. | A116 | D167 |
| 2129. | A117 | D167 |
| 2130. | A118 | D167 |
| 2131. | A119 | D167 |
| 2132. | A120 | D167 |
| 2133. | A121 | D167 |
| 2134. | A122 | D167 |
| 2135. | A123 | D167 |
| 2136. | A124 | D167 |
| 2137. | A125 | D167 |
| 2138. | A126 | D167 |
| 2139. | A127 | D167 |
| 2140. | A128 | D167 |
| 2141. | A129 | D167 |
| 2142. | A130 | D167 |
| 2143. | A131 | D167 |
| 2144. | A132 | D167 |
| 2145. | A101 | D168 |
| 2146. | A102 | D168 |
| 2147. | A103 | D168 |

Formula II

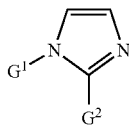

| Compound Number | G1 | G2 |
|---|---|---|
| 2148. | A104 | D168 |
| 2149. | A105 | D168 |
| 2150. | A106 | D168 |
| 2151. | A107 | D168 |
| 2152. | A108 | D168 |
| 2153. | A109 | D168 |
| 2154. | A110 | D168 |
| 2155. | A111 | D168 |
| 2156. | A112 | D168 |
| 2157. | A113 | D168 |
| 2158. | A114 | D168 |
| 2159. | A115 | D168 |
| 2160. | A116 | D168 |
| 2161. | A117 | D168 |
| 2162. | A118 | D168 |
| 2163. | A119 | D168 |
| 2164. | A120 | D168 |
| 2165. | A121 | D168 |
| 2166. | A122 | D168 |
| 2167. | A123 | D168 |
| 2168. | A124 | D168 |
| 2169. | A125 | D168 |
| 2170. | A126 | D168 |
| 2171. | A127 | D168 |
| 2172. | A128 | D168 |
| 2173. | A129 | D168 |
| 2174. | A130 | D168 |
| 2175. | A131 | D168 |
| 2176. | A132 | D168 |
| 2177. | D121 | A101 |
| 2178. | D121 | A102 |
| 2179. | D121 | A103 |
| 2180. | D121 | A104 |
| 2181. | D121 | A105 |
| 2182. | D121 | A106 |
| 2183. | D121 | A107 |
| 2184. | D121 | A108 |
| 2185. | D121 | A109 |
| 2186. | D121 | A110 |
| 2187. | D121 | A111 |
| 2188. | D121 | A112 |
| 2189. | D121 | A113 |
| 2190. | D121 | A114 |
| 2191. | D121 | A115 |
| 2192. | D121 | A116 |
| 2193. | D121 | A117 |
| 2194. | D121 | A118 |
| 2195. | D121 | A119 |
| 2196. | D121 | A120 |
| 2197. | D121 | A121 |
| 2198. | D121 | A122 |
| 2199. | D121 | A123 |
| 2200. | D121 | A124 |
| 2201. | D121 | A125 |
| 2202. | D121 | A126 |
| 2203. | D121 | A127 |
| 2204. | D121 | A128 |
| 2205. | D121 | A129 |
| 2206. | D121 | A130 |
| 2207. | D121 | A131 |
| 2208. | D121 | A132 |
| 2209. | D122 | A101 |
| 2210. | D122 | A102 |
| 2211. | D122 | A103 |
| 2212. | D122 | A104 |
| 2213. | D122 | A105 |
| 2214. | D122 | A106 |
| 2215. | D122 | A107 |
| 2216. | D122 | A108 |

Formula II

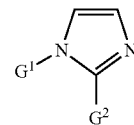

| Compound Number | G1 | G2 |
|---|---|---|
| 2217. | D122 | A109 |
| 2218. | D122 | A110 |
| 2219. | D122 | A111 |
| 2220. | D122 | A112 |
| 2221. | D122 | A112 |
| 2222. | D122 | A113 |
| 2223. | D122 | A114 |
| 2224. | D122 | A115 |
| 2225. | D122 | A117 |
| 2226. | D122 | A118 |
| 2227. | D122 | A119 |
| 2228. | D122 | A120 |
| 2229. | D122 | A121 |
| 2230. | D122 | A122 |
| 2231 | D122 | A123 |
| 2232 | D122 | A124 |
| 2233. | D122 | A125 |
| 2234. | D122 | A126 |
| 2235. | D122 | A127 |
| 2236. | D122 | A128 |
| 2237. | D122 | A129 |
| 2238. | D122 | A130 |
| 2239. | D122 | A131 |
| 2240. | D122 | A132 |
| 2241. | D123 | A101 |
| 2242. | D123 | A102 |
| 2243. | D123 | A103 |
| 2244. | D123 | A104 |
| 2245. | D123 | A105 |
| 2246. | D123 | A106 |
| 2247. | D123 | A107 |
| 2248. | D123 | A108 |
| 2249. | D123 | A109 |
| 2250. | D123 | A110 |
| 2251. | D123 | A111 |
| 2252. | D123 | A112 |
| 2253. | D123 | A113 |
| 2254. | D123 | A114 |
| 2255. | D123 | A115 |
| 2256. | D123 | A116 |
| 2257. | D123 | A117 |
| 2258. | D123 | A118 |
| 2259. | D123 | A119 |
| 2260. | D123 | A120 |
| 2261. | D123 | A121 |
| 2262. | D123 | A122 |
| 2263. | D123 | A123 |
| 2264. | D123 | A124 |
| 2265. | D123 | A125 |
| 2266. | D123 | A126 |
| 2267. | D123 | A127 |
| 2268. | D123 | A128 |
| 2269. | D123 | A129 |
| 2270. | D123 | A130 |
| 2271. | D123 | A131 |
| 2272. | D123 | A132 |
| 2273. | D124 | A101 |
| 2274. | D124 | A102 |
| 2275. | D124 | A103 |
| 2276. | D124 | A104 |
| 2277. | D124 | A105 |
| 2278. | D124 | A106 |
| 2279. | D124 | A107 |
| 2280. | D124 | A108 |
| 2281. | D124 | A109 |
| 2282. | D124 | A110 |
| 2283. | D124 | A111 |
| 2284. | D124 | A112 |
| 2285. | D124 | A113 |

117
-continued

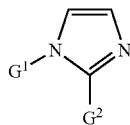

Formula II

| Compound Number | G1 | G2 |
|---|---|---|
| 2286. | D124 | A114 |
| 2287. | D124 | A115 |
| 2288. | D124 | A116 |
| 2289. | D124 | A117 |
| 2290. | D124 | A118 |
| 2291. | D124 | A119 |
| 2292. | D124 | A120 |
| 2293. | D124 | A121 |
| 2294. | D124 | A122 |
| 2295. | D124 | A123 |
| 2296. | D124 | A124 |
| 2297. | D124 | A125 |
| 2298. | D124 | A126 |
| 2299. | D124 | A127 |
| 2300. | D124 | A128 |
| 2301. | D124 | A129 |
| 2302. | D124 | A130 |
| 2303. | D124 | A131 |
| 2304. | D124 | A132 |
| 2305. | D125 | A101 |
| 2306. | D125 | A102 |
| 2307. | D125 | A103 |
| 2308. | D125 | A104 |
| 2309. | D125 | A105 |
| 2310. | D125 | A106 |
| 2311. | D125 | A107 |
| 2312. | D125 | A108 |
| 2313. | D125 | A109 |
| 2314. | D125 | A110 |
| 2315. | D125 | A111 |
| 2316. | D125 | A112 |
| 2317. | D125 | A113 |
| 2318. | D125 | A114 |
| 2319. | D125 | A115 |
| 2320. | D125 | A116 |
| 2321. | D125 | A117 |
| 2322. | D125 | A118 |
| 2323. | D125 | A119 |
| 2324. | D125 | A120 |
| 2325. | D125 | A121 |
| 2326. | D125 | A122 |
| 2327. | D125 | A123 |
| 2328. | D125 | A124 |
| 2329. | D125 | A125 |
| 2330. | D125 | A126 |
| 2331. | D125 | A127 |
| 2332. | D125 | A128 |
| 2333. | D125 | A129 |
| 2334. | D125 | A130 |
| 2335. | D125 | A131 |
| 2336. | D125 | A132 |
| 2337. | D126 | A101 |
| 2338. | D126 | A102 |
| 2339. | D126 | A103 |
| 2340. | D126 | A104 |
| 2341. | D126 | A105 |
| 2342. | D126 | A106 |
| 2343. | D126 | A107 |
| 2344. | D126 | A108 |
| 2345. | D126 | A109 |
| 2346. | D126 | A110 |
| 2347. | D126 | A111 |
| 2348. | D126 | A112 |
| 2349. | D126 | A113 |
| 2350. | D126 | A114 |
| 2351. | D126 | A115 |
| 2352. | D126 | A116 |
| 2353. | D126 | A117 |
| 2354. | D126 | A118 |

118
-continued

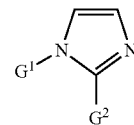

Formula II

| Compound Number | G1 | G2 |
|---|---|---|
| 2355. | D126 | A119 |
| 2356. | D126 | A120 |
| 2357. | D126 | A121 |
| 2358. | D126 | A122 |
| 2359. | D126 | A123 |
| 2360. | D126 | A124 |
| 2361. | D126 | A125 |
| 2362. | D126 | A126 |
| 2363. | D126 | A127 |
| 2364. | D126 | A128 |
| 2365. | D126 | A129 |
| 2366. | D126 | A130 |
| 2367. | D126 | A131 |
| 2368. | D126 | A132 |
| 2369. | D127 | A101 |
| 2370. | D127 | A102 |
| 2371. | D127 | A103 |
| 2372. | D127 | A104 |
| 2373. | D127 | A105 |
| 2374. | D127 | A106 |
| 2375. | D127 | A107 |
| 2376. | D127 | A108 |
| 2377. | D127 | A109 |
| 2378. | D127 | A110 |
| 2379. | D127 | A111 |
| 2380. | D127 | A112 |
| 2381. | D127 | A113 |
| 2382. | D127 | A114 |
| 2383. | D127 | A115 |
| 2384. | D127 | A116 |
| 2385. | D127 | A117 |
| 2386. | D127 | A118 |
| 2387. | D127 | A119 |
| 2388. | D127 | A120 |
| 2389. | D127 | A121 |
| 2390. | D127 | A122 |
| 2391. | D127 | A123 |
| 2392. | D127 | A124 |
| 2393. | D127 | A125 |
| 2394. | D127 | A126 |
| 2395. | D127 | A127 |
| 2396. | D127 | A128 |
| 2397. | D127 | A129 |
| 2398. | D127 | A130 |
| 2399. | D127 | A131 |
| 2400. | D127 | A132 |
| 2401. | D128 | A101 |
| 2402. | D128 | A102 |
| 2403. | D128 | A103 |
| 2404. | D128 | A104 |
| 2405. | D128 | A105 |
| 2406. | D128 | A106 |
| 2407. | D128 | A107 |
| 2408. | D128 | A108 |
| 2409. | D128 | A109 |
| 2410. | D128 | A110 |
| 2411. | D128 | A111 |
| 2412. | D128 | A112 |
| 2413. | D128 | A113 |
| 2414. | D128 | A114 |
| 2415. | D128 | A115 |
| 2416. | D128 | A116 |
| 2417. | D128 | A117 |
| 2418. | D128 | A118 |
| 2419. | D128 | A119 |
| 2420. | D128 | A120 |
| 2421. | D128 | A121 |
| 2422. | D128 | A122 |
| 2423. | D128 | A123 |

Formula II

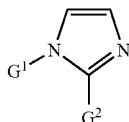

| Compound Number | G1 | G2 |
|---|---|---|
| 2424. | D128 | A124 |
| 2425. | D128 | A125 |
| 2426. | D128 | A126 |
| 2427. | D128 | A127 |
| 2428. | D128 | A128 |
| 2429. | D128 | A129 |
| 2430. | D128 | A130 |
| 2431. | D128 | A131 |
| 2432. | D128 | A132 |
| 2433. | D129 | A101 |
| 2434. | D129 | A102 |
| 2435. | D129 | A103 |
| 2436. | D129 | A104 |
| 2437. | D129 | A105 |
| 2438. | D129 | A106 |
| 2439. | D129 | A107 |
| 2440. | D129 | A108 |
| 2441. | D129 | A109 |
| 2442. | D129 | A110 |
| 2443. | D129 | A111 |
| 2444. | D129 | A112 |
| 2445. | D129 | A113 |
| 2446. | D129 | A114 |
| 2447. | D129 | A115 |
| 2448. | D129 | A116 |
| 2449. | D129 | A117 |
| 2450. | D129 | A118 |
| 2451. | D129 | A119 |
| 2452. | D129 | A120 |
| 2453. | D129 | A121 |
| 2454. | D129 | A122 |
| 2455. | D129 | A123 |
| 2456. | D129 | A124 |
| 2457. | D129 | A125 |
| 2458. | D129 | A126 |
| 2459. | D129 | A127 |
| 2460. | D129 | A128 |
| 2461. | D129 | A129 |
| 2462. | D129 | A130 |
| 2463. | D129 | A131 |
| 2464. | D129 | A132 |
| 2465. | D130 | A101 |
| 2466. | D130 | A102 |
| 2467. | D130 | A103 |
| 2468. | D130 | A104 |
| 2469. | D130 | A105 |
| 2470. | D130 | A106 |
| 2471. | D130 | A107 |
| 2472. | D130 | A108 |
| 2473. | D130 | A109 |
| 2474. | D130 | A110 |
| 2475. | D130 | A111 |
| 2476. | D130 | A112 |
| 2477. | D130 | A113 |
| 2478. | D130 | A114 |
| 2479. | D130 | A115 |
| 2480. | D130 | A116 |
| 2481. | D130 | A117 |
| 2482. | D130 | A118 |
| 2483. | D130 | A119 |
| 2484. | D130 | A120 |
| 2485. | D130 | A121 |
| 2486. | D130 | A122 |
| 2487. | D130 | A123 |
| 2488. | D130 | A124 |
| 2489. | D130 | A125 |
| 2490. | D130 | A126 |
| 2491. | D130 | A127 |
| 2492. | D130 | A128 |

Formula II

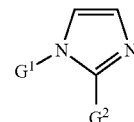

| Compound Number | G1 | G2 |
|---|---|---|
| 2493. | D130 | A129 |
| 2494. | D130 | A130 |
| 2495. | D130 | A131 |
| 2496. | D130 | A132 |
| 2497. | D131 | A101 |
| 2498. | D131 | A102 |
| 2499. | D131 | A103 |
| 2500. | D131 | A104 |
| 2501. | D131 | A105 |
| 2502. | D131 | A106 |
| 2503. | D131 | A107 |
| 2504. | D131 | A108 |
| 2505. | D131 | A109 |
| 2506. | D131 | A110 |
| 2507. | D131 | A111 |
| 2508. | D131 | A112 |
| 2509. | D131 | A113 |
| 2510. | D131 | A114 |
| 2511. | D131 | A115 |
| 2512. | D131 | A116 |
| 2513. | D131 | A117 |
| 2514. | D131 | A118 |
| 2515. | D131 | A119 |
| 2516. | D131 | A120 |
| 2517. | D131 | A121 |
| 2518. | D131 | A122 |
| 2519. | D131 | A123 |
| 2520. | D131 | A124 |
| 2521. | D131 | A125 |
| 2522. | D131 | A126 |
| 2523. | D131 | A127 |
| 2524. | D131 | A128 |
| 2525. | D131 | A129 |
| 2526. | D131 | A130 |
| 2527. | D131 | A131 |
| 2528. | D131 | A132 |
| 2529. | D132 | A101 |
| 2530. | D132 | A102 |
| 2531. | D132 | A103 |
| 2532. | D132 | A104 |
| 2533. | D132 | A105 |
| 2534. | D132 | A106 |
| 2535. | D132 | A107 |
| 2536. | D132 | A108 |
| 2537. | D132 | A109 |
| 2538. | D132 | A110 |
| 2539. | D132 | A111 |
| 2540. | D132 | A112 |
| 2541. | D132 | A113 |
| 2542. | D132 | A114 |
| 2543. | D132 | A115 |
| 2544. | D132 | A116 |
| 2545. | D132 | A117 |
| 2546. | D132 | A118 |
| 2547. | D132 | A119 |
| 2548. | D132 | A120 |
| 2549. | D132 | A121 |
| 2550. | D132 | A122 |
| 2551. | D132 | A123 |
| 2552. | D132 | A124 |
| 2553. | D132 | A125 |
| 2554. | D132 | A126 |
| 2555. | D132 | A127 |
| 2556. | D132 | A128 |
| 2557. | D132 | A129 |
| 2558. | D132 | A130 |
| 2559. | D132 | A131 |
| 2560. | D132 | A132 |
| 2561. | D133 | A101 |

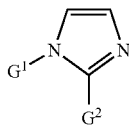

Formula II

| Compound Number | G1 | G2 |
|---|---|---|
| 2562. | D133 | A102 |
| 2563. | D133 | A103 |
| 2564. | D133 | A104 |
| 2565. | D133 | A105 |
| 2566. | D133 | A106 |
| 2567. | D133 | A107 |
| 2568. | D133 | A108 |
| 2569. | D133 | A109 |
| 2570. | D133 | A110 |
| 2571. | D133 | A111 |
| 2572. | D133 | A112 |
| 2573. | D133 | A113 |
| 2574. | D133 | A114 |
| 2575. | D133 | A115 |
| 2576. | D133 | A116 |
| 2577. | D133 | A117 |
| 2578. | D133 | A118 |
| 2579. | D133 | A119 |
| 2580. | D133 | A120 |
| 2581. | D133 | A121 |
| 2582. | D133 | A122 |
| 2583. | D133 | A123 |
| 2584. | D133 | A124 |
| 2585. | D133 | A125 |
| 2586. | D133 | A126 |
| 2587. | D133 | A127 |
| 2588. | D133 | A128 |
| 2589. | D133 | A129 |
| 2590. | D133 | A130 |
| 2591. | D133 | A131 |
| 2592. | D133 | A132 |
| 2593. | D134 | A101 |
| 2594. | D134 | A102 |
| 2595. | D134 | A103 |
| 2596. | D134 | A104 |
| 2597. | D134 | A105 |
| 2598. | D134 | A106 |
| 2599. | D134 | A107 |
| 2600. | D134 | A108 |
| 2601. | D134 | A109 |
| 2602. | D134 | A110 |
| 2603. | D134 | A111 |
| 2604. | D134 | A112 |
| 2605. | D134 | A113 |
| 2606. | D134 | A114 |
| 2607. | D134 | A115 |
| 2608. | D134 | A116 |
| 2609. | D134 | A117 |
| 2610. | D134 | A118 |
| 2611. | D134 | A119 |
| 2612. | D134 | A120 |
| 2613. | D134 | A121 |
| 2614. | D134 | A122 |
| 2615. | D134 | A123 |
| 2616. | D134 | A124 |
| 2617. | D134 | A125 |
| 2618. | D134 | A126 |
| 2619. | D134 | A127 |
| 2620. | D134 | A128 |
| 2621. | D134 | A129 |
| 2622. | D134 | A130 |
| 2623. | D134 | A131 |
| 2624. | D134 | A132 |
| 2625. | D135 | A101 |
| 2626. | D135 | A102 |
| 2627. | D135 | A103 |
| 2628. | D135 | A104 |
| 2629. | D135 | A105 |
| 2630. | D135 | A106 |

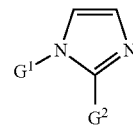

Formula II

| Compound Number | G1 | G2 |
|---|---|---|
| 2631. | D135 | A197 |
| 2632. | D135 | A198 |
| 2633. | D135 | A199 |
| 2634. | D135 | A110 |
| 2635. | D135 | A111 |
| 2636. | D135 | A112 |
| 2637. | D135 | A113 |
| 2638. | D135 | A114 |
| 2639. | D135 | A115 |
| 2640. | D135 | A116 |
| 2641. | D135 | A117 |
| 2642. | D135 | A118 |
| 2643. | D135 | A119 |
| 2644. | D135 | A120 |
| 2645. | D135 | A121 |
| 2646. | D135 | A122 |
| 2647. | D135 | A123 |
| 2648. | D135 | A124 |
| 2649. | D135 | A125 |
| 2650. | D135 | A126 |
| 2651. | D135 | A127 |
| 2652. | D135 | A128 |
| 2653. | D135 | A129 |
| 2654. | D135 | A130 |
| 2655. | D135 | A131 |
| 2656. | D135 | A132 |
| 2657. | D136 | A101 |
| 2658. | D136 | A102 |
| 2659. | D136 | A103 |
| 2660. | D136 | A104 |
| 2661. | D136 | A105 |
| 2662. | D136 | A106 |
| 2663. | D136 | A107 |
| 2664. | D136 | A108 |
| 2665. | D136 | A199 |
| 2666. | D136 | A110 |
| 2667. | D136 | A111 |
| 2668. | D136 | A112 |
| 2669. | D136 | A113 |
| 2670. | D136 | A114 |
| 2671. | D136 | A115 |
| 2672. | D136 | A116 |
| 2673. | D136 | A117 |
| 2674. | D136 | A118 |
| 2675. | D136 | A119 |
| 2676. | D136 | A120 |
| 2677. | D136 | A121 |
| 2678. | D136 | A122 |
| 2679. | D136 | A123 |
| 2680. | D136 | A124 |
| 2681. | D136 | A125 |
| 2682. | D136 | A126 |
| 2683. | D136 | A127 |
| 2684. | D136 | A128 |
| 2685. | D136 | A129 |
| 2686. | D136 | A130 |
| 2687. | D136 | A131 |
| 2688. | D136 | A132 |
| 2689. | D137 | A101 |
| 2690. | D137 | A102 |
| 2691. | D137 | A103 |
| 2692. | D137 | A104 |
| 2693. | D137 | A105 |
| 2694. | D137 | A106 |
| 2695. | D137 | A107 |
| 2696. | D137 | A108 |
| 2697. | D137 | A109 |
| 2698. | D137 | A110 |
| 2699. | D137 | A111 |

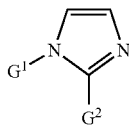

Formula II

| Compound Number | G1 | G2 |
|---|---|---|
| 2700. | D137 | A112 |
| 2701. | D137 | A113 |
| 2702. | D137 | A114 |
| 2703. | D137 | A115 |
| 2704. | D137 | A116 |
| 2705. | D137 | A117 |
| 2706. | D137 | A118 |
| 2707. | D137 | A119 |
| 2708. | D137 | A120 |
| 2709. | D137 | A121 |
| 2710. | D137 | A122 |
| 2711. | D137 | A123 |
| 2712. | D137 | A124 |
| 2713. | D137 | A125 |
| 2714. | D137 | A126 |
| 2715. | D137 | A127 |
| 2716. | D137 | A128 |
| 2717. | D137 | A129 |
| 2718. | D137 | A130 |
| 2719. | D137 | A131 |
| 2720. | D137 | A132 |
| 2721. | D138 | A101 |
| 2722. | D138 | A102 |
| 2723. | D138 | A103 |
| 2724. | D138 | A104 |
| 2725. | D138 | A105 |
| 2726. | D138 | A106 |
| 2727. | D138 | A107 |
| 2728. | D138 | A108 |
| 2729. | D138 | A109 |
| 2730. | D138 | A110 |
| 2731. | D138 | A111 |
| 2732. | D138 | A112 |
| 2733. | D138 | A113 |
| 2734. | D138 | A114 |
| 2735. | D138 | A115 |
| 2736. | D138 | A116 |
| 2737. | D138 | A117 |
| 2738. | D138 | A118 |
| 2739. | D138 | A119 |
| 2740. | D138 | A120 |
| 2741. | D138 | A121 |
| 2742. | D138 | A122 |
| 2743. | D138 | A123 |
| 2744. | D138 | A124 |
| 2745. | D138 | A125 |
| 2746. | D138 | A126 |
| 2747. | D138 | A127 |
| 2748. | D138 | A128 |
| 2749. | D138 | A129 |
| 2750. | D138 | A130 |
| 2751. | D138 | A131 |
| 2752. | D138 | A132 |
| 2753. | D139 | A101 |
| 2754. | D139 | A102 |
| 2755. | D139 | A103 |
| 2756. | D139 | A104 |
| 2757. | D139 | A105 |
| 2758. | D139 | A106 |
| 2759. | D139 | A107 |
| 2760. | D139 | A108 |
| 2761. | D139 | A109 |
| 2762. | D139 | A110 |
| 2763. | D139 | A111 |
| 2764. | D139 | A112 |
| 2765. | D139 | A113 |
| 2766. | D139 | A114 |
| 2767. | D139 | A115 |
| 2768. | D139 | A116 |

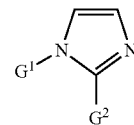

Formula II

| Compound Number | G1 | G2 |
|---|---|---|
| 2769. | D139 | A117 |
| 2770. | D139 | A118 |
| 2771. | D139 | A119 |
| 2772. | D139 | A120 |
| 2773. | D139 | A121 |
| 2774. | D139 | A122 |
| 2775. | D139 | A123 |
| 2776. | D139 | A124 |
| 2777. | D139 | A125 |
| 2778. | D139 | A126 |
| 2779. | D139 | A127 |
| 2780. | D139 | A128 |
| 2781. | D139 | A129 |
| 2782. | D139 | A130 |
| 2783. | D139 | A131 |
| 2784. | D139 | A132 |
| 2785. | D140 | A101 |
| 2786. | .D140 | A102 |
| 2787. | D140 | A103 |
| 2788. | D140 | A104 |
| 2789. | D140 | A105 |
| 2790. | D140 | A106 |
| 2791. | D140 | A107 |
| 2792. | D140 | A108 |
| 2793. | D140 | A109 |
| 2794. | D140 | A110 |
| 2795. | D140 | A111 |
| 2796. | D140 | A112 |
| 2797. | D140 | A113 |
| 2798. | D140 | A114 |
| 2799. | D140 | A115 |
| 2800. | D140 | A116 |
| 2801. | D140 | A117 |
| 2802. | D140 | A118 |
| 2803. | D140 | A119 |
| 2804. | D140 | A120 |
| 2805. | D140 | A121 |
| 2806. | D140 | A122 |
| 2807. | D140 | A123 |
| 2808. | D140 | A124 |
| 2809. | D140 | A125 |
| 2810. | D140 | A126 |
| 2811. | D140 | A127 |
| 2812. | D140 | A128 |
| 2813. | D140 | A129 |
| 2814. | D140 | A130 |
| 2815. | D140 | A131 |
| 2816. | D140 | A132 |
| 2817. | D141 | A101 |
| 2818. | D141 | A102 |
| 2819. | D141 | A103 |
| 2820. | D141 | A104 |
| 2821. | D141 | A105 |
| 2822. | D141 | A106 |
| 2823. | D141 | A107 |
| 2824. | D141 | A108 |
| 2825. | D141 | A109 |
| 2826. | D141 | A110 |
| 2827. | D141 | A111 |
| 2828. | D141 | A112 |
| 2829. | D141 | A113 |
| 2830. | D141 | A114 |
| 2831. | D141 | A115 |
| 2832. | D141 | A116 |
| 2833. | D141 | A117 |
| 2834. | D141 | A118 |
| 2835. | D141 | A119 |
| 2836. | D141 | A120 |
| 2837. | D141 | A121 |

125
-continued

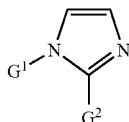

Formula II

| Compound Number | G1 | G2 |
|---|---|---|
| 2838. | D141 | A122 |
| 2839. | D141 | A123 |
| 2840. | D141 | A124 |
| 2841. | D141 | A125 |
| 2842. | D141 | A126 |
| 2843. | D141 | A127 |
| 2844. | D141 | A128 |
| 2845. | D141 | A129 |
| 2846. | D141 | A130 |
| 2847. | D141 | A131 |
| 2848. | D141 | A132 |
| 2849. | D142 | A101 |
| 2850. | D142 | A102 |
| 2851. | D142 | A103 |
| 2852. | D142 | A104 |
| 2853. | D142 | A105 |
| 2854. | D142 | A106 |
| 2855. | D142 | A107 |
| 2856. | D142 | A108 |
| 2857. | D142 | A109 |
| 2858. | D142 | A110 |
| 2859. | D142 | A111 |
| 2860. | D142 | A112 |
| 2861. | D142 | A113 |
| 2862. | D142 | A114 |
| 2863. | D142 | A115 |
| 2864. | D142 | A116 |
| 2865. | D142 | A117 |
| 2866. | D142 | A118 |
| 2867. | D142 | A119 |
| 2868. | D142 | A120 |
| 2869. | D142 | A121 |
| 2870. | D142 | A122 |
| 2871. | D142 | A123 |
| 2872. | D142 | A124 |
| 2873. | D142 | A125 |
| 2874. | D142 | A126 |
| 2875. | D142 | A127 |
| 2876. | D142 | A128 |
| 2877. | D142 | A129 |
| 2878. | D142 | A130 |
| 2879. | D142 | A131 |
| 2880. | D142 | A132 |
| 2881. | D143 | A101 |
| 2882. | D143 | A102 |
| 2883. | D143 | A103 |
| 2884. | D143 | A104 |
| 2885. | D143 | A105 |
| 2886. | D143 | A106 |
| 2887. | D143 | A107 |
| 2888. | D143 | A108 |
| 2889. | D143 | A109 |
| 2890. | D143 | A110 |
| 2891. | D143 | A111 |
| 2892. | D143 | A112 |
| 2893. | D143 | A113 |
| 2894. | D143 | A114 |
| 2895. | D143 | A115 |
| 2896. | D143 | A116 |
| 2897. | D143 | A117 |
| 2898. | D143 | A118 |
| 2899. | D143 | A119 |
| 2900. | D143 | A120 |
| 2901. | D143 | A121 |
| 2902. | D143 | A122 |
| 2903. | D143 | A123 |
| 2904. | D143 | A124 |
| 2905. | D143 | A125 |
| 2906. | D143 | A126 |

126
-continued

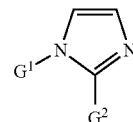

Formula II

| Compound Number | G1 | G2 |
|---|---|---|
| 2907. | D143 | A127 |
| 2908. | D143 | A128 |
| 2909. | D143 | A129 |
| 2910. | D143 | A130 |
| 2911. | D143 | A131 |
| 2912. | D143 | A132 |
| 2913. | D144 | A101 |
| 2914. | D144 | A102 |
| 2915. | D144 | A103 |
| 2916. | D144 | A104 |
| 2917. | D144 | A105 |
| 2918. | D144 | A106 |
| 2919. | D144 | A107 |
| 2920. | D144 | A108 |
| 2921. | D144 | A109 |
| 2922. | D144 | A110 |
| 2923. | D144 | A111 |
| 2924. | D144 | A112 |
| 2925. | D144 | A113 |
| 2926. | D144 | A114 |
| 2927. | D144 | A115 |
| 2928. | D144 | A116 |
| 2929. | D144 | A117 |
| 2930. | D144 | A118 |
| 2931. | D144 | A119 |
| 2932. | D144 | A120 |
| 2933. | D144 | A121 |
| 2934. | D144 | A122 |
| 2935. | D144 | A123 |
| 2936. | D144 | A124 |
| 2937. | D144 | A125 |
| 2938. | D144 | A126 |
| 2939. | D144 | A127 |
| 2940. | D144 | A128 |
| 2941. | D144 | A129 |
| 2942. | D144 | A130 |
| 2943. | D144 | A131 |
| 2944. | D144 | A132 |
| 2945. | D155 | A101 |
| 2946. | D155 | A102 |
| 2947. | D155 | A103 |
| 2948. | D155 | A104 |
| 2949. | D155 | A105 |
| 2950. | D155 | A106 |
| 2951. | D155 | A107 |
| 2952. | D155 | A108 |
| 2953. | D155 | A109 |
| 2954. | D155 | A110 |
| 2955. | D155 | A111 |
| 2956. | D155 | A112 |
| 2957. | D155 | A113 |
| 2958. | D155 | A114 |
| 2959. | D155 | A115 |
| 2960. | D155 | A116 |
| 2961. | D155 | A117 |
| 2962. | D155 | A118 |
| 2963. | D155 | A119 |
| 2964. | D155 | A126 |
| 2965. | D155 | A121 |
| 2966. | D155 | A122 |
| 2967. | D155 | A123 |
| 2968. | D155 | A124 |
| 2969. | D155 | A125 |
| 2970. | D155 | A126 |
| 2971. | D155 | A127 |
| 2972. | D155 | A128 |
| 2973. | D155 | A129 |
| 2974. | D155 | A130 |
| 2975. | D155 | A131 |

127
-continued

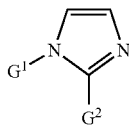

Formula II

| Compound Number | G1 | G2 |
|---|---|---|
| 2976. | D155 | A132 |
| 2977. | D156 | A101 |
| 2978. | D156 | A102 |
| 2979. | D156 | A103 |
| 2980. | D156 | A104 |
| 2981. | D156 | A105 |
| 2982. | D156 | A106 |
| 2983. | D156 | A107 |
| 2984. | D156 | A108 |
| 2985. | D156 | A109 |
| 2986. | D156 | A110 |
| 2987. | D156 | A111 |
| 2988. | D156 | A112 |
| 2989. | D156 | A113 |
| 2990. | D156 | A114 |
| 2991. | D156 | A115 |
| 2992. | D156 | A116 |
| 2993. | D156 | A117 |
| 2994. | D156 | A118 |
| 2995. | D156 | A119 |
| 2996. | D156 | A120 |
| 2997. | D156 | A121 |
| 2998. | D156 | A122 |
| 2999. | D156 | A123 |
| 3000. | D156 | A124 |
| 3001. | D156 | A125 |
| 3002. | D156 | A126 |
| 3003. | D156 | A127 |
| 3004. | D156 | A128 |
| 3005. | D156 | A129 |
| 3006. | D156 | A130 |
| 3007. | D156 | A131 |
| 3008. | D156 | A132 |
| 3009. | D157 | A101 |
| 3010. | D157 | A102 |
| 3011. | D157 | A103 |
| 3012. | D157 | A104 |
| 3013. | D157 | A105 |
| 3014. | D157 | A106 |
| 3015. | D157 | A107 |
| 3016. | D157 | A108 |
| 3017. | D157 | A109 |
| 3018. | D157 | A110 |
| 3019. | D157 | A111 |
| 3020. | D157 | A112 |
| 3021. | D157 | A113 |
| 3022. | D157 | A114 |
| 3023. | D157 | A115 |
| 3024. | D157 | A116 |
| 3025. | D157 | A117 |
| 3026. | D157 | A118 |
| 3027. | D157 | A119 |
| 3028. | D157 | A120 |
| 3029. | D157 | A121 |
| 3030. | D157 | A122 |
| 3031. | D157 | A123 |
| 3032. | D157 | A124 |
| 3033. | D157 | A125 |
| 3034. | D157 | A126 |
| 3035. | D157 | A127 |
| 3036. | D157 | A128 |
| 3037. | D157 | A129 |
| 3038. | D157 | A130 |
| 3039. | D157 | A131 |
| 3040. | D157 | A132 |
| 3041. | D158 | A101 |
| 3042. | D158 | A102 |
| 3043. | D158 | A103 |
| 3044. | D158 | A104 |

128
-continued

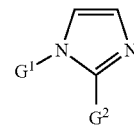

Formula II

| Compound Number | G1 | G2 |
|---|---|---|
| 3045. | D158 | A105 |
| 3046. | D158 | A106 |
| 3047. | D158 | A107 |
| 3048. | D158 | A108 |
| 3049. | D158 | A109 |
| 3050. | D158 | A110 |
| 3051. | D158 | A111 |
| 3052. | D158 | A112 |
| 3053. | D158 | A113 |
| 3054. | D158 | A114 |
| 3055. | D158 | A115 |
| 3056. | D158 | A116 |
| 3057. | D158 | A117 |
| 3058. | D158 | A118 |
| 3059. | D158 | A119 |
| 3060. | D158 | A120 |
| 3061. | D158 | A121 |
| 3062. | D158 | A122 |
| 3063. | D158 | A123 |
| 3064. | D158 | A124 |
| 3065. | D158 | A125 |
| 3066. | D158 | A126 |
| 3067. | D158 | A127 |
| 3068. | D158 | A128 |
| 3069. | D158 | A129 |
| 3070. | D158 | A130 |
| 3071. | D158 | A131 |
| 3072. | D158 | A132 |
| 3073. | D159 | A101 |
| 3074. | D159 | A102 |
| 3075. | D159 | A103 |
| 3076. | D159 | A104 |
| 3077. | D159 | A105 |
| 3078. | D159 | A106 |
| 3079. | D159 | A107 |
| 3080. | D159 | A108 |
| 3081. | D159 | A109 |
| 3082. | D159 | A110 |
| 3083. | D159 | A111 |
| 3084. | D159 | A112 |
| 3085. | D159 | A113 |
| 3086. | D159 | A114 |
| 3087. | D159 | A115 |
| 3088. | D159 | A116 |
| 3089. | D159 | A117 |
| 3090. | D159 | A118 |
| 3091. | D159 | A119 |
| 3092. | D159 | A120 |
| 3093. | D159 | A121 |
| 3094. | D159 | A122 |
| 3095. | D159 | A123 |
| 3096. | D159 | A124 |
| 3097. | D159 | A125 |
| 3098. | D159 | A126 |
| 3099. | D159 | A127 |
| 3100. | D159 | A128 |
| 3101. | D159 | A129 |
| 3102. | D159 | A130 |
| 3103. | D159 | A131 |
| 3104. | D159 | A132 |
| 3105. | D160 | A101 |
| 3106. | D160 | A102 |
| 3107. | D160 | A103 |
| 3108. | D160 | A104 |
| 3109. | D160 | A105 |
| 3110. | D160 | A106 |
| 3111. | D160 | A107 |
| 3112. | D160 | A108 |
| 3113. | D160 | A119 |

Formula II

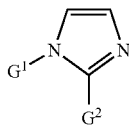

| Compound Number | G1 | G2 |
|---|---|---|
| 3114. | D160 | A110 |
| 3115. | D160 | A111 |
| 3116. | D160 | A112 |
| 3117. | D160 | A113 |
| 3118. | D160 | A114 |
| 3119. | D160 | A115 |
| 3120. | D160 | A116 |
| 3121. | D160 | A117 |
| 3122. | D160 | A118 |
| 3123. | D160 | A119 |
| 3124. | D160 | A120 |
| 3125. | D160 | A121 |
| 3126. | D160 | A122 |
| 3127. | D160 | A123 |
| 3128. | D160 | A124 |
| 3129. | D160 | A125 |
| 3130. | D160 | A126 |
| 3131. | D160 | A127 |
| 3132. | D160 | A128 |
| 3133. | D160 | A129 |
| 3134. | D160 | A130 |
| 3135. | D160 | A131 |
| 3136. | D160 | A132 |
| 3137. | D161 | A101 |
| 3138. | D161 | A102 |
| 3139. | D161 | A103 |
| 3140. | D161 | A104 |
| 3141. | D161 | A105 |
| 3142. | D161 | A106 |
| 3143. | D161 | A107 |
| 3144. | D161 | A108 |
| 3145. | D161 | A109 |
| 3146. | D161 | A110 |
| 3147. | D161 | A111 |
| 3148. | D161 | A112 |
| 3149. | D161 | A113 |
| 3150. | D161 | A114 |
| 3151. | D161 | A115 |
| 3152. | D161 | A116 |
| 3153. | D161 | A117 |
| 3154. | D161 | A118 |
| 3155. | D161 | A119 |
| 3156. | D161 | A120 |
| 3157. | D161 | A121 |
| 3158. | D161 | A122 |
| 3159. | D161 | A123 |
| 3160. | D161 | A124 |
| 3161. | D161 | A125 |
| 3162. | D161 | A126 |
| 3163. | D161 | A127 |
| 3164. | D161 | A128 |
| 3165. | D161 | A129 |
| 3166. | D161 | A130 |
| 3167. | D161 | A131 |
| 3168. | D161 | A132 |
| 3169. | D162 | A101 |
| 3170. | D162 | A102 |
| 3171. | D162 | A103 |
| 3172. | D162 | A104 |
| 3173. | D162 | A105 |
| 3174. | D162 | A106 |
| 3175. | D162 | A107 |
| 3176. | D162 | A108 |
| 3177. | D162 | A109 |
| 3178. | D162 | A110 |
| 3179. | D162 | A111 |
| 3180. | D162 | A112 |
| 3181. | D162 | A113 |
| 3182. | D162 | A114 |

Formula II

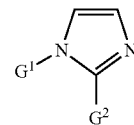

| Compound Number | G1 | G2 |
|---|---|---|
| 3183. | D162 | A115 |
| 3184. | D162 | A116 |
| 3185. | D162 | A117 |
| 3186. | D162 | A118 |
| 3187. | D162 | A119 |
| 3188. | D162 | A120 |
| 3189. | D162 | A121 |
| 3190. | D162 | A122 |
| 3191. | D162 | A123 |
| 3192. | D162 | A124 |
| 3193. | D162 | A125 |
| 3194. | D162 | A126 |
| 3195. | D162 | A127 |
| 3196. | D162 | A128 |
| 3197. | D162 | A129 |
| 3198. | D162 | A130 |
| 3199. | D162 | A131 |
| 3200. | D162 | A132 |
| 3201. | D163 | A101 |
| 3202. | D163 | A102 |
| 3203. | D163 | A103 |
| 3204. | D163 | A104 |
| 3205. | D163 | A105 |
| 3206. | D163 | A106 |
| 3207. | D163 | A107 |
| 3208. | D163 | A108 |
| 3209. | D163 | A109 |
| 3210. | D163 | A110 |
| 3211. | D163 | A111 |
| 3212. | D163 | A112 |
| 3213. | D163 | A113 |
| 3214. | D163 | A114 |
| 3215. | D163 | A115 |
| 3216. | D163 | A116 |
| 3217. | D163 | A117 |
| 3218. | D163 | A118 |
| 3219. | D163 | A119 |
| 3220. | D163 | A120 |
| 3221. | D163 | A121 |
| 3222. | D163 | A122 |
| 3223. | D163 | A123 |
| 3224. | D163 | A124 |
| 3225. | D163 | A125 |
| 3226. | D163 | A126 |
| 3227. | D163 | A127 |
| 3228. | D163 | A128 |
| 3229. | D163 | A129 |
| 3230. | D163 | A130 |
| 3231. | D163 | A131 |
| 3232. | D163 | A132 |
| 3233. | D164 | A101 |
| 3234. | D164 | A102 |
| 3235. | D164 | A103 |
| 3236. | D164 | A104 |
| 3237. | D164 | A105 |
| 3238. | D164 | A106 |
| 3239. | D164 | A107 |
| 3240. | D164 | A108 |
| 3241. | D164 | A109 |
| 3242. | D164 | A110 |
| 3243. | D164 | A111 |
| 3244. | D164 | A112 |
| 3245. | D164 | A113 |
| 3246. | D164 | A114 |
| 3247. | D164 | A115 |
| 3248. | D164 | A116 |
| 3249. | D164 | A117 |
| 3250. | D164 | A118 |
| 3251. | D164 | A119 |

131
-continued

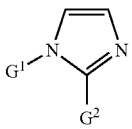

Formula II

| Compound Number | G1 | G2 |
|---|---|---|
| 3252. | D164 | A120 |
| 3253. | D164 | A121 |
| 3254. | D164 | A122 |
| 3255. | D164 | A123 |
| 3256. | D164 | A124 |
| 3257. | D164 | A125 |
| 3258. | D164 | A126 |
| 3259. | D164 | A127 |
| 3260. | D164 | A128 |
| 3261. | D164 | A129 |
| 3262. | D164 | A130 |
| 3263. | D164 | A131 |
| 3264. | D164 | A132 |
| 3265. | D165 | A101 |
| 3266. | D165 | A102 |
| 3267. | D165 | A103 |
| 3268. | D165 | A104 |
| 3269. | D165 | A105 |
| 3270. | D165 | A106 |
| 3271. | D165 | A107 |
| 3272. | D165 | A108 |
| 3273. | D165 | A109 |
| 3274. | D165 | A110 |
| 3275. | D165 | A111 |
| 3276. | D165 | A112 |
| 3277. | D165 | A113 |
| 3278. | D165 | A114 |
| 3279. | D165 | A115 |
| 3280. | D165 | A116 |
| 3281. | D165 | A117 |
| 3282. | D165 | A118 |
| 3283. | D165 | A119 |
| 3284. | D165 | A120 |
| 3285. | D165 | A121 |
| 3286. | D165 | A122 |
| 3287. | D165 | A123 |
| 3288. | D165 | A124 |
| 3289. | D165 | A125 |
| 3290. | D165 | A126 |
| 3291. | D165 | A127 |
| 3292. | D165 | A128 |
| 3293. | D165 | A129 |
| 3294. | D165 | A130 |
| 3295. | D165 | A110 |
| 3296. | D165 | A132 |
| 3297. | D166 | A101 |
| 3298. | D166 | A102 |
| 3299. | D166 | A103 |
| 3300. | D166 | A104 |
| 3301. | D166 | A105 |
| 3302. | D166 | A106 |
| 3303. | D166 | A107 |
| 3304. | D166 | A108 |
| 3305. | D166 | A109 |
| 3306. | D166 | A110 |
| 3307. | D166 | A111 |
| 3308. | D166 | A112 |
| 3309. | D166 | A113 |
| 3310. | D166 | A114 |
| 3311. | D166 | A115 |
| 3312. | D166 | A116 |
| 3313. | D166 | A117 |
| 3314. | D166 | A118 |
| 3315. | D166 | A119 |
| 3316. | D166 | A120 |
| 3317. | D166 | A121 |
| 3318. | D166 | A122 |
| 3319. | D166 | A123 |
| 3320. | D166 | A124 |

132
-continued

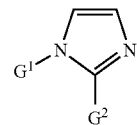

Formula II

| Compound Number | G1 | G2 |
|---|---|---|
| 3321. | D166 | A125 |
| 3322. | D166 | A126 |
| 3323. | D166 | A127 |
| 3324. | D166 | A128 |
| 3325. | D166 | A129 |
| 3326. | D166 | A130 |
| 3327. | D166 | A131 |
| 3328. | D166 | A132 |
| 3329. | D167 | A101 |
| 3330. | D167 | A102 |
| 3331. | D167 | A103 |
| 3332. | D167 | A104 |
| 3333. | D167 | A105 |
| 3334. | D167 | A106 |
| 3335. | D167 | A107 |
| 3336. | D167 | A108 |
| 3337. | D167 | A109 |
| 3338. | D167 | A110 |
| 3339. | D167 | A111 |
| 3340. | D167 | A112 |
| 3341. | D167 | A113 |
| 3342. | D167 | A114 |
| 3343. | D167 | A115 |
| 3344. | D167 | A116 |
| 3345. | D167 | A117 |
| 3346. | D167 | A118 |
| 3347. | D167 | A119 |
| 3348. | D167 | A120 |
| 3349. | D167 | A121 |
| 3350. | D167 | A122 |
| 3351. | D167 | A123 |
| 3352. | D167 | A124 |
| 3353. | D167 | A125 |
| 3354. | D167 | A126 |
| 3355. | D167 | A127 |
| 3356. | D167 | A128 |
| 3357. | D167 | A129 |
| 3358. | D167 | A130 |
| 3359. | D167 | A131 |
| 3360. | D167 | A132 |
| 3361. | D168 | A101 |
| 3362. | D168 | A102 |
| 3363. | D168 | A103 |
| 3364. | D168 | A104 |
| 3365. | D168 | A105 |
| 3366. | D168 | A106 |
| 3367. | D168 | A107 |
| 3368. | D168 | A108 |
| 3369. | D168 | A109 |
| 3370. | D168 | A110 |
| 3371. | D168 | A111 |
| 3372. | D168 | A112 |
| 3373. | D168 | A113 |
| 3374. | D168 | A114 |
| 3375. | D168 | A115 |
| 3376. | D168 | A116 |
| 3377. | D168 | A117 |
| 3378. | D168 | A118 |
| 3379. | D168 | A119 |
| 3380. | D168 | A120 |
| 3381. | D168 | A121 |
| 3382. | D168 | A122 |
| 3383. | D168 | A123 |
| 3384. | D168 | A124 |
| 3385. | D168 | A125 |
| 3386. | D168 | A126 |
| 3387. | D168 | A127 |
| 3388. | D168 | A128 |
| 3389. | D168 | A129 |

-continued

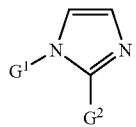

Formula II

| Compound Number | G1 | G2 |
|---|---|---|
| 3390. | D168 | A130 |
| 3391. | D168 | A131 |
| 3392. | D168 | A132 |

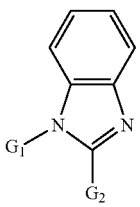

Formula III

| Compound Number | $G^1$ | $G^2$ |
|---|---|---|
| 3393. | $A^{101}$ | $D^{101}$ |
| 3394. | $A^{102}$ | $D^{101}$ |
| 3395. | $A^{103}$ | $D^{101}$ |
| 3396. | $A^{104}$ | $D^{101}$ |
| 3397. | $A^{105}$ | $D^{101}$ |
| 3398. | $A^{106}$ | $D^{101}$ |
| 3399. | $A^{107}$ | $D^{101}$ |
| 3400. | $A^{108}$ | $D^{101}$ |
| 3401. | $A^{109}$ | $D^{101}$ |
| 3402. | $A^{110}$ | $D^{101}$ |
| 3403. | $A^{111}$ | $D^{101}$ |
| 3404. | $A^{112}$ | $D^{101}$ |
| 3405. | $A^{113}$ | $D^{101}$ |
| 3406. | $A^{114}$ | $D^{101}$ |
| 3407. | $A^{115}$ | $D^{101}$ |
| 3408. | $A^{116}$ | $D^{101}$ |
| 3409. | $A^{117}$ | $D^{101}$ |
| 3410. | $A^{118}$ | $D^{101}$ |
| 3411. | $A^{119}$ | $D^{101}$ |
| 3412. | $A^{120}$ | $D^{101}$ |
| 3413. | $A^{121}$ | $D^{101}$ |
| 3414. | $A^{122}$ | $D^{101}$ |
| 3415. | $A^{123}$ | $D^{101}$ |
| 3416. | $A^{124}$ | $D^{101}$ |
| 3417. | $A^{125}$ | $D^{101}$ |
| 3418. | $A^{126}$ | $D^{101}$ |
| 3419. | $A^{127}$ | $D^{101}$ |
| 3420. | $A^{128}$ | $D^{101}$ |
| 3421. | $A^{129}$ | $D^{101}$ |
| 3422. | $A^{130}$ | $D^{101}$ |
| 3423. | $A^{131}$ | $D^{101}$ |
| 3424. | $A^{132}$ | $D^{101}$ |
| 3425. | $A^{101}$ | $D^{102}$ |
| 3426. | $A^{102}$ | $D^{102}$ |
| 3427. | $A^{103}$ | $D^{102}$ |
| 3428. | $A^{104}$ | $D^{102}$ |
| 3429. | $A^{105}$ | $D^{102}$ |
| 3430. | $A^{106}$ | $D^{102}$ |
| 3431. | $A^{107}$ | $D^{102}$ |
| 3432. | $A^{108}$ | $D^{102}$ |
| 3433. | $A^{109}$ | $D^{102}$ |
| 3434. | $A^{110}$ | $D^{102}$ |
| 3435. | $A^{111}$ | $D^{102}$ |
| 3436. | $A^{112}$ | $D^{102}$ |
| 3437. | $A^{113}$ | $D^{102}$ |
| 3438. | $A^{114}$ | $D^{102}$ |
| 3439. | $A^{115}$ | $D^{102}$ |

-continued

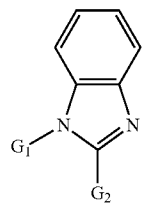

Formula III

| Compound Number | $G^1$ | $G^2$ |
|---|---|---|
| 3440. | $A^{116}$ | $D^{102}$ |
| 3441. | $A^{117}$ | $D^{102}$ |
| 3442. | $A^{118}$ | $D^{102}$ |
| 3443. | $A^{119}$ | $D^{102}$ |
| 3444. | $A^{120}$ | $D^{102}$ |
| 3445. | $A^{121}$ | $D^{102}$ |
| 3446. | $A^{122}$ | $D^{102}$ |
| 3447. | $A^{123}$ | $D^{102}$ |
| 3448. | $A^{124}$ | $D^{102}$ |
| 3449. | $A^{125}$ | $D^{102}$ |
| 3450. | $A^{126}$ | $D^{102}$ |
| 3451. | $A^{127}$ | $D^{102}$ |
| 3452. | $A^{128}$ | $D^{102}$ |
| 3453. | $A^{129}$ | $D^{102}$ |
| 3454. | $A^{130}$ | $D^{102}$ |
| 3455. | $A^{131}$ | $D^{102}$ |
| 3456. | $A^{132}$ | $D^{102}$ |
| 3457. | $A^{101}$ | $D^{103}$ |
| 3458. | $A^{102}$ | $D^{103}$ |
| 3459. | $A^{103}$ | $D^{103}$ |
| 3460. | $A^{104}$ | $D^{103}$ |
| 3461. | $A^{105}$ | $D^{103}$ |
| 3462. | $A^{106}$ | $D^{103}$ |
| 3463. | $A^{107}$ | $D^{103}$ |
| 3464. | $A^{108}$ | $D^{103}$ |
| 3465. | $A^{109}$ | $D^{103}$ |
| 3466. | $A^{110}$ | $D^{103}$ |
| 3467. | $A^{111}$ | $D^{103}$ |
| 3468. | $A^{112}$ | $D^{103}$ |
| 3469. | $A^{113}$ | $D^{103}$ |
| 3470. | $A^{114}$ | $D^{103}$ |
| 3471. | $A^{115}$ | $D^{103}$ |
| 3472. | $A^{116}$ | $D^{103}$ |
| 3473. | $A^{117}$ | $D^{103}$ |
| 3474. | $A^{118}$ | $D^{103}$ |
| 3475. | $A^{119}$ | $D^{103}$ |
| 3476. | $A^{120}$ | $D^{103}$ |
| 3477. | $A^{121}$ | $D^{103}$ |
| 3478. | $A^{122}$ | $D^{103}$ |
| 3479. | $A^{123}$ | $D^{103}$ |
| 3480. | $A^{124}$ | $D^{103}$ |
| 3481. | $A^{125}$ | $D^{103}$ |
| 3482. | $A^{126}$ | $D^{103}$ |
| 3483. | $A^{127}$ | $D^{103}$ |
| 3484. | $A^{128}$ | $D^{103}$ |
| 3485. | $A^{129}$ | $D^{103}$ |
| 3486. | $A^{130}$ | $D^{103}$ |
| 3487. | $A^{131}$ | $D^{103}$ |
| 3488. | $A^{132}$ | $D^{103}$ |
| 3489. | $A^{101}$ | $D^{104}$ |
| 3490. | $A^{102}$ | $D^{104}$ |
| 3491. | $A^{103}$ | $D^{104}$ |
| 3492. | $A^{104}$ | $D^{104}$ |
| 3493. | $A^{105}$ | $D^{104}$ |
| 3494. | $A^{106}$ | $D^{104}$ |
| 3495. | $A^{107}$ | $D^{104}$ |
| 3496. | $A^{108}$ | $D^{104}$ |
| 3497. | $A^{109}$ | $D^{104}$ |
| 3498. | $A^{110}$ | $D^{104}$ |
| 3499. | $A^{111}$ | $D^{104}$ |
| 3500. | $A^{112}$ | $D^{104}$ |
| 3501. | $A^{113}$ | $D^{104}$ |
| 3502. | $A^{114}$ | $D^{104}$ |
| 3503. | $A^{115}$ | $D^{104}$ |
| 3504. | $A^{116}$ | $D^{104}$ |

135
-continued

Formula III

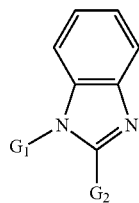

| Compound Number | $G^1$ | $G^2$ |
|---|---|---|
| 3505. | $A^{117}$ | $D^{104}$ |
| 3506. | $A^{118}$ | $D^{104}$ |
| 3507. | $A^{119}$ | $D^{104}$ |
| 3508. | $A^{120}$ | $D^{104}$ |
| 3509. | $A^{121}$ | $D^{104}$ |
| 3510. | $A^{122}$ | $D^{104}$ |
| 3511. | $A^{123}$ | $D^{104}$ |
| 3512. | $A^{124}$ | $D^{104}$ |
| 3513. | $A^{125}$ | $D^{104}$ |
| 3514. | $A^{126}$ | $D^{104}$ |
| 3515. | $A^{127}$ | $D^{104}$ |
| 3516. | $A^{128}$ | $D^{104}$ |
| 3517. | $A^{129}$ | $D^{104}$ |
| 3518. | $A^{130}$ | $D^{104}$ |
| 3519. | $A^{131}$ | $D^{104}$ |
| 3520. | $A^{132}$ | $D^{104}$ |
| 3521. | $A^{101}$ | $D^{105}$ |
| 3522. | $A^{102}$ | $D^{105}$ |
| 3523. | $A^{103}$ | $D^{105}$ |
| 3524. | $A^{104}$ | $D^{105}$ |
| 3525. | $A^{105}$ | $D^{105}$ |
| 3526. | $A^{106}$ | $D^{105}$ |
| 3527. | $A^{107}$ | $D^{105}$ |
| 3528. | $A^{108}$ | $D^{105}$ |
| 3529. | $A^{109}$ | $D^{105}$ |
| 3530. | $A^{110}$ | $D^{105}$ |
| 3531. | $A^{111}$ | $D^{105}$ |
| 3532. | $A^{112}$ | $D^{105}$ |
| 3533. | $A^{113}$ | $D^{105}$ |
| 3534. | $A^{114}$ | $D^{105}$ |
| 3535. | $A^{115}$ | $D^{105}$ |
| 3536. | $A^{116}$ | $D^{105}$ |
| 3537. | $A^{117}$ | $D^{105}$ |
| 3538. | $A^{118}$ | $D^{105}$ |
| 3539. | $A^{119}$ | $D^{105}$ |
| 3540. | $A^{120}$ | $D^{105}$ |
| 3541. | $A^{121}$ | $D^{105}$ |
| 3542. | $A^{122}$ | $D^{105}$ |
| 3543. | $A^{123}$ | $D^{105}$ |
| 3544. | $A^{124}$ | $D^{105}$ |
| 3545. | $A^{125}$ | $D^{105}$ |
| 3546. | $A^{126}$ | $D^{105}$ |
| 3547. | $A^{127}$ | $D^{105}$ |
| 3548. | $A^{128}$ | $D^{105}$ |
| 3549. | $A^{129}$ | $D^{105}$ |
| 3550. | $A^{130}$ | $D^{105}$ |
| 3551. | $A^{131}$ | $D^{105}$ |
| 3552. | $A^{132}$ | $D^{105}$ |
| 3553. | $A^{101}$ | $D^{106}$ |
| 3554. | $A^{102}$ | $D^{106}$ |
| 3555. | $A^{103}$ | $D^{106}$ |
| 3556. | $A^{104}$ | $D^{106}$ |
| 3557. | $A^{105}$ | $D^{106}$ |
| 3558. | $A^{106}$ | $D^{106}$ |
| 3559. | $A^{107}$ | $D^{106}$ |
| 3560. | $A^{108}$ | $D^{106}$ |
| 3561. | $A^{109}$ | $D^{106}$ |
| 3562. | $A^{110}$ | $D^{106}$ |
| 3563. | $A^{111}$ | $D^{106}$ |
| 3564. | $A^{112}$ | $D^{106}$ |
| 3565. | $A^{113}$ | $D^{106}$ |
| 3566. | $A^{114}$ | $D^{106}$ |
| 3567. | $A^{115}$ | $D^{106}$ |
| 3568. | $A^{116}$ | $D^{106}$ |
| 3569. | $A^{117}$ | $D^{106}$ |

136
-continued

Formula III

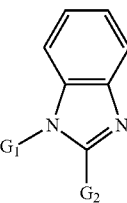

| Compound Number | $G^1$ | $G^2$ |
|---|---|---|
| 3570. | $A^{118}$ | $D^{106}$ |
| 3571. | $A^{119}$ | $D^{106}$ |
| 3572. | $A^{120}$ | $D^{106}$ |
| 3573. | $A^{121}$ | $D^{106}$ |
| 3574. | $A^{122}$ | $D^{106}$ |
| 3575. | $A^{123}$ | $D^{106}$ |
| 3576. | $A^{124}$ | $D^{106}$ |
| 3577. | $A^{125}$ | $D^{106}$ |
| 3578. | $A^{126}$ | $D^{106}$ |
| 3579. | $A^{127}$ | $D^{106}$ |
| 3580. | $A^{128}$ | $D^{106}$ |
| 3581. | $A^{129}$ | $D^{106}$ |
| 3582. | $A^{130}$ | $D^{106}$ |
| 3583. | $A^{131}$ | $D^{106}$ |
| 3584. | $A^{132}$ | $D^{106}$ |
| 3585. | $A^{101}$ | $D^{107}$ |
| 3586. | $A^{102}$ | $D^{107}$ |
| 3587. | $A^{103}$ | $D^{107}$ |
| 3588. | $A^{104}$ | $D^{107}$ |
| 3589. | $A^{105}$ | $D^{107}$ |
| 3590. | $A^{106}$ | $D^{107}$ |
| 3591. | $A^{107}$ | $D^{107}$ |
| 3592. | $A^{108}$ | $D^{107}$ |
| 3593. | $A^{109}$ | $D^{107}$ |
| 3594. | $A^{110}$ | $D^{107}$ |
| 3595. | $A^{111}$ | $D^{107}$ |
| 3596. | $A^{112}$ | $D^{107}$ |
| 3597. | $A^{113}$ | $D^{107}$ |
| 3598. | $A^{114}$ | $D^{107}$ |
| 3599. | $A^{115}$ | $D^{107}$ |
| 3600. | $A^{116}$ | $D^{107}$ |
| 3601. | $A^{117}$ | $D^{107}$ |
| 3602. | $A^{118}$ | $D^{107}$ |
| 3603. | $A^{119}$ | $D^{107}$ |
| 3604. | $A^{120}$ | $D^{107}$ |
| 3605. | $A^{121}$ | $D^{107}$ |
| 3606. | $A^{122}$ | $D^{107}$ |
| 3607. | $A^{123}$ | $D^{107}$ |
| 3608. | $A^{124}$ | $D^{107}$ |
| 3609. | $A^{125}$ | $D^{107}$ |
| 3610. | $A^{126}$ | $D^{107}$ |
| 3611. | $A^{127}$ | $D^{107}$ |
| 3612. | $A^{128}$ | $D^{107}$ |
| 3613. | $A^{129}$ | $D^{107}$ |
| 3614. | $A^{130}$ | $D^{107}$ |
| 3615. | $A^{131}$ | $D^{107}$ |
| 3616. | $A^{132}$ | $D^{107}$ |
| 3617. | $A^{101}$ | $D^{108}$ |
| 3618. | $A^{102}$ | $D^{108}$ |
| 3619. | $A^{103}$ | $D^{108}$ |
| 3620. | $A^{104}$ | $D^{108}$ |
| 3621. | $A^{105}$ | $D^{108}$ |
| 3622. | $A^{106}$ | $D^{108}$ |
| 3623. | $A^{107}$ | $D^{108}$ |
| 3624. | $A^{108}$ | $D^{108}$ |
| 3625. | $A^{109}$ | $D^{108}$ |
| 3626. | $A^{110}$ | $D^{108}$ |
| 3627. | $A^{111}$ | $D^{108}$ |
| 3628. | $A^{112}$ | $D^{108}$ |
| 3629. | $A^{113}$ | $D^{108}$ |
| 3630. | $A^{114}$ | $D^{108}$ |
| 3631. | $A^{115}$ | $D^{108}$ |
| 3632. | $A^{116}$ | $D^{108}$ |
| 3633. | $A^{117}$ | $D^{108}$ |
| 3634. | $A^{118}$ | $D^{108}$ |

137
-continued

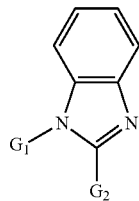

Formula III

| Compound Number | $G^1$ | $G^2$ |
|---|---|---|
| 3635. | $A^{119}$ | $D^{108}$ |
| 3636. | $A^{120}$ | $D^{108}$ |
| 3637. | $A^{121}$ | $D^{108}$ |
| 3638. | $A^{122}$ | $D^{108}$ |
| 3639. | $A^{123}$ | $D^{108}$ |
| 3640. | $A^{124}$ | $D^{108}$ |
| 3641. | $A^{125}$ | $D^{108}$ |
| 3642. | $A^{126}$ | $D^{108}$ |
| 3643. | $A^{127}$ | $D^{108}$ |
| 3644. | $A^{128}$ | $D^{108}$ |
| 3645. | $A^{129}$ | $D^{108}$ |
| 3646. | $A^{130}$ | $D^{108}$ |
| 3647. | $A^{131}$ | $D^{108}$ |
| 3648. | $A^{132}$ | $D^{108}$ |
| 3649. | $A^{101}$ | $D^{109}$ |
| 3650. | $A^{102}$ | $D^{109}$ |
| 3651. | $A^{103}$ | $D^{109}$ |
| 3652. | $A^{104}$ | $D^{109}$ |
| 3653. | $A^{105}$ | $D^{109}$ |
| 3654. | $A^{106}$ | $D^{109}$ |
| 3655. | $A^{107}$ | $D^{109}$ |
| 3656. | $A^{108}$ | $D^{109}$ |
| 3657. | $A^{109}$ | $D^{109}$ |
| 3658. | $A^{110}$ | $D^{109}$ |
| 3659. | $A^{111}$ | $D^{109}$ |
| 3660. | $A^{112}$ | $D^{109}$ |
| 3661. | $A^{113}$ | $D^{109}$ |
| 3662. | $A^{114}$ | $D^{109}$ |
| 3663. | $A^{115}$ | $D^{109}$ |
| 3664. | $A^{116}$ | $D^{109}$ |
| 3665. | $A^{117}$ | $D^{109}$ |
| 3666. | $A^{118}$ | $D^{109}$ |
| 3667. | $A^{119}$ | $D^{109}$ |
| 3668. | $A^{120}$ | $D^{109}$ |
| 3669. | $A^{121}$ | $D^{109}$ |
| 3670. | $A^{122}$ | $D^{109}$ |
| 3671. | $A^{123}$ | $D^{109}$ |
| 3672. | $A^{124}$ | $D^{109}$ |
| 3673. | $A^{125}$ | $D^{109}$ |
| 3674. | $A^{126}$ | $D^{109}$ |
| 3675. | $A^{127}$ | $D^{109}$ |
| 3676. | $A^{128}$ | $D^{109}$ |
| 3677. | $A^{129}$ | $D^{109}$ |
| 3678. | $A^{130}$ | $D^{109}$ |
| 3679. | $A^{131}$ | $D^{109}$ |
| 3680. | $A^{132}$ | $D^{109}$ |
| 3681. | $A^{101}$ | $D^{110}$ |
| 3682. | $A^{102}$ | $D^{110}$ |
| 3683. | $A^{103}$ | $D^{110}$ |
| 3684. | $A^{104}$ | $D^{110}$ |
| 3685. | $A^{105}$ | $D^{110}$ |
| 3686. | $A^{106}$ | $D^{110}$ |
| 3687. | $A^{107}$ | $D^{110}$ |
| 3688. | $A^{108}$ | $D^{110}$ |
| 3689. | $A^{109}$ | $D^{110}$ |
| 3690. | $A^{110}$ | $D^{110}$ |
| 3691. | $A^{111}$ | $D^{110}$ |
| 3692. | $A^{112}$ | $D^{110}$ |
| 3693. | $A^{113}$ | $D^{110}$ |
| 3694. | $A^{114}$ | $D^{110}$ |
| 3695. | $A^{115}$ | $D^{110}$ |
| 3696. | $A^{116}$ | $D^{110}$ |
| 3697. | $A^{117}$ | $D^{110}$ |
| 3698. | $A^{118}$ | $D^{110}$ |
| 3699. | $A^{119}$ | $D^{110}$ |

138
-continued

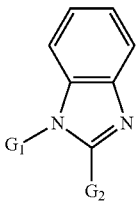

Formula III

| Compound Number | $G^1$ | $G^2$ |
|---|---|---|
| 3700. | $A^{120}$ | $D^{110}$ |
| 3701. | $A^{121}$ | $D^{110}$ |
| 3702. | $A^{122}$ | $D^{110}$ |
| 3703. | $A^{123}$ | $D^{110}$ |
| 3704. | $A^{124}$ | $D^{110}$ |
| 3705. | $A^{125}$ | $D^{110}$ |
| 3706. | $A^{126}$ | $D^{110}$ |
| 3707. | $A^{127}$ | $D^{110}$ |
| 3708. | $A^{128}$ | $D^{110}$ |
| 3709. | $A^{129}$ | $D^{110}$ |
| 3710. | $A^{130}$ | $D^{110}$ |
| 3711. | $A^{131}$ | $D^{110}$ |
| 3712. | $A^{132}$ | $D^{110}$ |
| 3713. | $A^{101}$ | $D^{111}$ |
| 3714. | $A^{102}$ | $D^{111}$ |
| 3715. | $A^{103}$ | $D^{111}$ |
| 3716. | $A^{104}$ | $D^{111}$ |
| 3717. | $A^{105}$ | $D^{111}$ |
| 3718. | $A^{106}$ | $D^{111}$ |
| 3719. | $A^{107}$ | $D^{111}$ |
| 3720. | $A^{108}$ | $D^{111}$ |
| 3721. | $A^{109}$ | $D^{111}$ |
| 3722. | $A^{110}$ | $D^{111}$ |
| 3723. | $A^{111}$ | $D^{111}$ |
| 3724. | $A^{112}$ | $D^{111}$ |
| 3725. | $A^{113}$ | $D^{111}$ |
| 3726. | $A^{114}$ | $D^{111}$ |
| 3727. | $A^{115}$ | $D^{111}$ |
| 3728. | $A^{116}$ | $D^{111}$ |
| 3729. | $A^{117}$ | $D^{111}$ |
| 3730. | $A^{118}$ | $D^{111}$ |
| 3731. | $A^{119}$ | $D^{111}$ |
| 3732. | $A^{120}$ | $D^{111}$ |
| 3733. | $A^{121}$ | $D^{111}$ |
| 3734. | $A^{122}$ | $D^{111}$ |
| 3735. | $A^{123}$ | $D^{111}$ |
| 3736. | $A^{124}$ | $D^{111}$ |
| 3737. | $A^{125}$ | $D^{111}$ |
| 3738. | $A^{126}$ | $D^{111}$ |
| 3739. | $A^{127}$ | $D^{111}$ |
| 3740. | $A^{128}$ | $D^{111}$ |
| 3741. | $A^{129}$ | $D^{111}$ |
| 3742. | $A^{130}$ | $D^{111}$ |
| 3743. | $A^{131}$ | $D^{111}$ |
| 3744. | $A^{132}$ | $D^{111}$ |
| 3745. | $A^{101}$ | $D^{112}$ |
| 3746. | $A^{102}$ | $D^{112}$ |
| 3747. | $A^{103}$ | $D^{112}$ |
| 3748. | $A^{104}$ | $D^{112}$ |
| 3749. | $A^{105}$ | $D^{112}$ |
| 3750. | $A^{106}$ | $D^{112}$ |
| 3751. | $A^{107}$ | $D^{112}$ |
| 3752. | $A^{108}$ | $D^{112}$ |
| 3753. | $A^{109}$ | $D^{112}$ |
| 3754. | $A^{110}$ | $D^{112}$ |
| 3755. | $A^{111}$ | $D^{112}$ |
| 3756. | $A^{112}$ | $D^{112}$ |
| 3757. | $A^{113}$ | $D^{112}$ |
| 3758. | $A^{114}$ | $D^{112}$ |
| 3759. | $A^{115}$ | $D^{112}$ |
| 3760. | $A^{116}$ | $D^{112}$ |
| 3761. | $A^{117}$ | $D^{112}$ |
| 3762. | $A^{118}$ | $D^{112}$ |
| 3763. | $A^{119}$ | $D^{112}$ |
| 3764. | $A^{120}$ | $D^{112}$ |

139
-continued

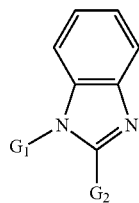

Formula III

| Compound Number | $G^1$ | $G^2$ |
|---|---|---|
| 3765. | $A^{121}$ | $D^{112}$ |
| 3766. | $A^{122}$ | $D^{112}$ |
| 3767. | $A^{123}$ | $D^{112}$ |
| 3768. | $A^{124}$ | $D^{112}$ |
| 3769. | $A^{125}$ | $D^{112}$ |
| 3770. | $A^{126}$ | $D^{112}$ |
| 3771. | $A^{127}$ | $D^{112}$ |
| 3772. | $A^{128}$ | $D^{112}$ |
| 3773. | $A^{129}$ | $D^{112}$ |
| 3774. | $A^{130}$ | $D^{112}$ |
| 3775. | $A^{131}$ | $D^{112}$ |
| 3776. | $A^{132}$ | $D^{112}$ |
| 3777. | $A^{101}$ | $D^{113}$ |
| 3778. | $A^{102}$ | $D^{113}$ |
| 3779. | $A^{103}$ | $D^{113}$ |
| 3780. | $A^{104}$ | $D^{113}$ |
| 3781. | $A^{105}$ | $D^{113}$ |
| 3782. | $A^{106}$ | $D^{113}$ |
| 3783. | $A^{107}$ | $D^{113}$ |
| 3784. | $A^{108}$ | $D^{113}$ |
| 3785. | $A^{109}$ | $D^{113}$ |
| 3786. | $A^{110}$ | $D^{113}$ |
| 3787. | $A^{111}$ | $D^{113}$ |
| 3788. | $A^{112}$ | $D^{113}$ |
| 3789. | $A^{113}$ | $D^{113}$ |
| 3790. | $A^{114}$ | $D^{113}$ |
| 3791. | $A^{115}$ | $D^{113}$ |
| 3792. | $A^{116}$ | $D^{113}$ |
| 3793. | $A^{117}$ | $D^{113}$ |
| 3794. | $A^{118}$ | $D^{113}$ |
| 3795. | $A^{119}$ | $D^{113}$ |
| 3796. | $A^{120}$ | $D^{113}$ |
| 3797. | $A^{121}$ | $D^{113}$ |
| 3798. | $A^{122}$ | $D^{113}$ |
| 3799. | $A^{123}$ | $D^{113}$ |
| 3800. | $A^{124}$ | $D^{113}$ |
| 3801. | $A^{125}$ | $D^{113}$ |
| 3802. | $A^{126}$ | $D^{113}$ |
| 3803. | $A^{127}$ | $D^{113}$ |
| 3804. | $A^{128}$ | $D^{113}$ |
| 3805. | $A^{129}$ | $D^{113}$ |
| 3806. | $A^{130}$ | $D^{113}$ |
| 3807. | $A^{131}$ | $D^{113}$ |
| 3808. | $A^{132}$ | $D^{113}$ |
| 3809. | $A^{101}$ | $D^{114}$ |
| 3810. | $A^{102}$ | $D^{114}$ |
| 3811. | $A^{103}$ | $D^{114}$ |
| 3812. | $A^{104}$ | $D^{114}$ |
| 3813. | $A^{105}$ | $D^{114}$ |
| 3814. | $A^{106}$ | $D^{114}$ |
| 3815. | $A^{107}$ | $D^{114}$ |
| 3816. | $A^{108}$ | $D^{114}$ |
| 3817. | $A^{109}$ | $D^{114}$ |
| 3818. | $A^{110}$ | $D^{114}$ |
| 3819. | $A^{111}$ | $D^{114}$ |
| 3820. | $A^{112}$ | $D^{114}$ |
| 3821. | $A^{113}$ | $D^{114}$ |
| 3822. | $A^{114}$ | $D^{114}$ |
| 3823. | $A^{115}$ | $D^{114}$ |
| 3824. | $A^{116}$ | $D^{114}$ |
| 3825. | $A^{117}$ | $D^{114}$ |
| 3826. | $A^{118}$ | $D^{114}$ |
| 3827. | $A^{119}$ | $D^{114}$ |
| 3828. | $A^{120}$ | $D^{114}$ |
| 3829. | $A^{121}$ | $D^{114}$ |

140
-continued

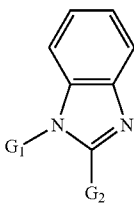

Formula III

| Compound Number | $G^1$ | $G^2$ |
|---|---|---|
| 3830. | $A^{122}$ | $D^{114}$ |
| 3831. | $A^{123}$ | $D^{114}$ |
| 3832. | $A^{124}$ | $D^{114}$ |
| 3833. | $A^{125}$ | $D^{114}$ |
| 3834. | $A^{126}$ | $D^{114}$ |
| 3835. | $A^{127}$ | $D^{114}$ |
| 3836. | $A^{128}$ | $D^{114}$ |
| 3837. | $A^{129}$ | $D^{114}$ |
| 3838. | $A^{130}$ | $D^{114}$ |
| 3839. | $A^{131}$ | $D^{114}$ |
| 3840. | $A^{132}$ | $D^{114}$ |
| 3841. | $A^{101}$ | $D^{115}$ |
| 3842. | $A^{102}$ | $D^{115}$ |
| 3843. | $A^{103}$ | $D^{115}$ |
| 3844. | $A^{104}$ | $D^{115}$ |
| 3845. | $A^{105}$ | $D^{115}$ |
| 3846. | $A^{106}$ | $D^{115}$ |
| 3847. | $A^{107}$ | $D^{115}$ |
| 3848. | $A^{108}$ | $D^{115}$ |
| 3849. | $A^{109}$ | $D^{115}$ |
| 3850. | $A^{110}$ | $D^{115}$ |
| 3851. | $A^{111}$ | $D^{115}$ |
| 3852. | $A^{112}$ | $D^{115}$ |
| 3853. | $A^{113}$ | $D^{115}$ |
| 3854. | $A^{114}$ | $D^{115}$ |
| 3855. | $A^{115}$ | $D^{115}$ |
| 3856. | $A^{116}$ | $D^{115}$ |
| 3857. | $A^{117}$ | $D^{115}$ |
| 3858. | $A^{118}$ | $D^{115}$ |
| 3859. | $A^{119}$ | $D^{115}$ |
| 3860. | $A^{120}$ | $D^{115}$ |
| 3861. | $A^{121}$ | $D^{115}$ |
| 3862. | $A^{122}$ | $D^{115}$ |
| 3863. | $A^{123}$ | $D^{115}$ |
| 3864. | $A^{124}$ | $D^{115}$ |
| 3865. | $A^{125}$ | $D^{115}$ |
| 3866. | $A^{126}$ | $D^{115}$ |
| 3867. | $A^{127}$ | $D^{115}$ |
| 3868. | $A^{128}$ | $D^{115}$ |
| 3869. | $A^{129}$ | $D^{115}$ |
| 3870. | $A^{130}$ | $D^{115}$ |
| 3871. | $A^{131}$ | $D^{115}$ |
| 3872. | $A^{132}$ | $D^{115}$ |
| 3873. | $A^{101}$ | $D^{116}$ |
| 3874. | $A^{102}$ | $D^{116}$ |
| 3875. | $A^{103}$ | $D^{116}$ |
| 3876. | $A^{104}$ | $D^{116}$ |
| 3877. | $A^{105}$ | $D^{116}$ |
| 3878. | $A^{106}$ | $D^{116}$ |
| 3879. | $A^{107}$ | $D^{116}$ |
| 3880. | $A^{108}$ | $D^{116}$ |
| 3881. | $A^{109}$ | $D^{116}$ |
| 3882. | $A^{110}$ | $D^{116}$ |
| 3883. | $A^{111}$ | $D^{116}$ |
| 3884. | $A^{112}$ | $D^{116}$ |
| 3885. | $A^{113}$ | $D^{116}$ |
| 3886. | $A^{114}$ | $D^{116}$ |
| 3887. | $A^{115}$ | $D^{116}$ |
| 3888. | $A^{116}$ | $D^{116}$ |
| 3889. | $A^{117}$ | $D^{116}$ |
| 3890. | $A^{118}$ | $D^{116}$ |
| 3891. | $A^{119}$ | $D^{116}$ |
| 3892. | $A^{120}$ | $D^{116}$ |
| 3893. | $A^{121}$ | $D^{116}$ |
| 3894. | $A^{122}$ | $D^{116}$ |

141

-continued

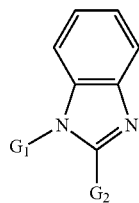

Formula III

| Compound Number | $G^1$ | $G^2$ |
|---|---|---|
| 3895. | $A^{123}$ | $D^{116}$ |
| 3896. | $A^{124}$ | $D^{116}$ |
| 3897. | $A^{125}$ | $D^{116}$ |
| 3898. | $A^{126}$ | $D^{116}$ |
| 3899. | $A^{127}$ | $D^{116}$ |
| 3900. | $A^{128}$ | $D^{116}$ |
| 3901. | $A^{129}$ | $D^{116}$ |
| 3902. | $A^{130}$ | $D^{116}$ |
| 3903. | $A^{131}$ | $D^{116}$ |
| 3904. | $A^{132}$ | $D^{116}$ |
| 3905. | $A^{101}$ | $D^{117}$ |
| 3906. | $A^{102}$ | $D^{117}$ |
| 3907. | $A^{103}$ | $D^{117}$ |
| 3908. | $A^{104}$ | $D^{117}$ |
| 3909. | $A^{105}$ | $D^{117}$ |
| 3910. | $A^{106}$ | $D^{117}$ |
| 3911. | $A^{107}$ | $D^{117}$ |
| 3912. | $A^{108}$ | $D^{117}$ |
| 3913. | $A^{109}$ | $D^{117}$ |
| 3914. | $A^{110}$ | $D^{117}$ |
| 3915. | $A^{111}$ | $D^{117}$ |
| 3916. | $A^{112}$ | $D^{117}$ |
| 3917. | $A^{113}$ | $D^{117}$ |
| 3918. | $A^{114}$ | $D^{117}$ |
| 3919. | $A^{115}$ | $D^{117}$ |
| 3920. | $A^{116}$ | $D^{117}$ |
| 3921. | $A^{117}$ | $D^{117}$ |
| 3922. | $A^{118}$ | $D^{117}$ |
| 3923. | $A^{119}$ | $D^{117}$ |
| 3924. | $A^{120}$ | $D^{117}$ |
| 3925. | $A^{121}$ | $D^{117}$ |
| 3926. | $A^{122}$ | $D^{117}$ |
| 3927. | $A^{123}$ | $D^{117}$ |
| 3928. | $A^{124}$ | $D^{117}$ |
| 3929. | $A^{125}$ | $D^{117}$ |
| 3930. | $A^{126}$ | $D^{117}$ |
| 3931. | $A^{127}$ | $D^{117}$ |
| 3932. | $A^{128}$ | $D^{117}$ |
| 3933. | $A^{129}$ | $D^{117}$ |
| 3934. | $A^{130}$ | $D^{117}$ |
| 3935. | $A^{131}$ | $D^{117}$ |
| 3936. | $A^{132}$ | $D^{117}$ |
| 3937. | $A^{101}$ | $D^{118}$ |
| 3938. | $A^{102}$ | $D^{118}$ |
| 3939. | $A^{103}$ | $D^{118}$ |
| 3940. | $A^{104}$ | $D^{118}$ |
| 3941. | $A^{105}$ | $D^{118}$ |
| 3942. | $A^{106}$ | $D^{118}$ |
| 3943. | $A^{107}$ | $D^{118}$ |
| 3944. | $A^{108}$ | $D^{118}$ |
| 3945. | $A^{109}$ | $D^{118}$ |
| 3946. | $A^{110}$ | $D^{118}$ |
| 3947. | $A^{111}$ | $D^{118}$ |
| 3948. | $A^{112}$ | $D^{118}$ |
| 3949. | $A^{113}$ | $D^{118}$ |
| 3950. | $A^{114}$ | $D^{118}$ |
| 3951. | $A^{115}$ | $D^{118}$ |
| 3952. | $A^{116}$ | $D^{118}$ |
| 3953. | $A^{117}$ | $D^{118}$ |
| 3954. | $A^{118}$ | $D^{118}$ |
| 3955. | $A^{119}$ | $D^{118}$ |
| 3956. | $A^{120}$ | $D^{118}$ |
| 3957. | $A^{121}$ | $D^{118}$ |
| 3958. | $A^{122}$ | $D^{118}$ |
| 3959. | $A^{123}$ | $D^{118}$ |

142

-continued

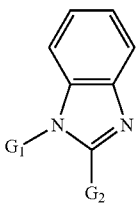

Formula III

| Compound Number | $G^1$ | $G^2$ |
|---|---|---|
| 3960. | $A^{124}$ | $D^{118}$ |
| 3961. | $A^{125}$ | $D^{118}$ |
| 3962. | $A^{126}$ | $D^{118}$ |
| 3963. | $A^{127}$ | $D^{118}$ |
| 3964. | $A^{128}$ | $D^{118}$ |
| 3965. | $A^{129}$ | $D^{118}$ |
| 3966. | $A^{130}$ | $D^{118}$ |
| 3967. | $A^{131}$ | $D^{118}$ |
| 3968. | $A^{132}$ | $D^{118}$ |
| 3969. | $A^{101}$ | $D^{119}$ |
| 3970. | $A^{102}$ | $D^{119}$ |
| 3971. | $A^{103}$ | $D^{119}$ |
| 3972. | $A^{104}$ | $D^{119}$ |
| 3973. | $A^{105}$ | $D^{119}$ |
| 3974. | $A^{106}$ | $D^{119}$ |
| 3975. | $A^{107}$ | $D^{119}$ |
| 3976. | $A^{108}$ | $D^{119}$ |
| 3977. | $A^{109}$ | $D^{119}$ |
| 3978. | $A^{110}$ | $D^{119}$ |
| 3979. | $A^{111}$ | $D^{119}$ |
| 3980. | $A^{112}$ | $D^{119}$ |
| 3981. | $A^{113}$ | $D^{119}$ |
| 3982. | $A^{114}$ | $D^{119}$ |
| 3983. | $A^{115}$ | $D^{119}$ |
| 3984. | $A^{116}$ | $D^{119}$ |
| 3985. | $A^{117}$ | $D^{119}$ |
| 3986. | $A^{118}$ | $D^{119}$ |
| 3987. | $A^{119}$ | $D^{119}$ |
| 3988. | $A^{120}$ | $D^{119}$ |
| 3989. | $A^{121}$ | $D^{119}$ |
| 3990. | $A^{122}$ | $D^{119}$ |
| 3991. | $A^{123}$ | $D^{119}$ |
| 3992. | $A^{124}$ | $D^{119}$ |
| 3993. | $A^{125}$ | $D^{119}$ |
| 3994. | $A^{126}$ | $D^{119}$ |
| 3995. | $A^{127}$ | $D^{119}$ |
| 3996. | $A^{128}$ | $D^{119}$ |
| 3997. | $A^{129}$ | $D^{119}$ |
| 3998. | $A^{130}$ | $D^{119}$ |
| 3999. | $A^{131}$ | $D^{119}$ |
| 4000. | $A^{132}$ | $D^{119}$ |
| 4001. | $A^{101}$ | $D^{120}$ |
| 4002. | $A^{102}$ | $D^{120}$ |
| 4003. | $A^{103}$ | $D^{120}$ |
| 4004. | $A^{104}$ | $D^{120}$ |
| 4005. | $A^{105}$ | $D^{120}$ |
| 4006. | $A^{106}$ | $D^{120}$ |
| 4007. | $A^{107}$ | $D^{120}$ |
| 4008. | $A^{108}$ | $D^{120}$ |
| 4009. | $A^{109}$ | $D^{120}$ |
| 4010. | $A^{110}$ | $D^{120}$ |
| 4011. | $A^{111}$ | $D^{120}$ |
| 4012. | $A^{112}$ | $D^{120}$ |
| 4013. | $A^{113}$ | $D^{120}$ |
| 4014. | $A^{114}$ | $D^{120}$ |
| 4015. | $A^{115}$ | $D^{120}$ |
| 4016. | $A^{116}$ | $D^{120}$ |
| 4017. | $A^{117}$ | $D^{120}$ |
| 4018. | $A^{118}$ | $D^{120}$ |
| 4019. | $A^{119}$ | $D^{120}$ |
| 4020. | $A^{120}$ | $D^{120}$ |
| 4021. | $A^{121}$ | $D^{120}$ |
| 4022. | $A^{122}$ | $D^{120}$ |
| 4023. | $A^{123}$ | $D^{120}$ |
| 4024. | $A^{124}$ | $D^{120}$ |

Formula III

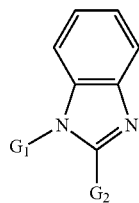

| Compound Number | $G^1$ | $G^2$ |
|---|---|---|
| 4025. | $A^{125}$ | $D^{120}$ |
| 4026. | $A^{126}$ | $D^{120}$ |
| 4027. | $A^{127}$ | $D^{120}$ |
| 4028. | $A^{128}$ | $D^{120}$ |
| 4029. | $A^{129}$ | $D^{120}$ |
| 4030. | $A^{130}$ | $D^{120}$ |
| 4031. | $A^{131}$ | $D^{120}$ |
| 4032. | $A^{132}$ | $D^{120}$ |
| 4033. | $A^{101}$ | $D^{121}$ |
| 4034. | $A^{102}$ | $D^{121}$ |
| 4035. | $A^{103}$ | $D^{121}$ |
| 4036. | $A^{104}$ | $D^{121}$ |
| 4037. | $A^{105}$ | $D^{121}$ |
| 4038. | $A^{106}$ | $D^{121}$ |
| 4039. | $A^{107}$ | $D^{121}$ |
| 4040. | $A^{108}$ | $D^{121}$ |
| 4041. | $A^{109}$ | $D^{121}$ |
| 4042. | $A^{110}$ | $D^{121}$ |
| 4043. | $A^{111}$ | $D^{121}$ |
| 4044. | $A^{112}$ | $D^{121}$ |
| 4045. | $A^{113}$ | $D^{121}$ |
| 4046. | $A^{114}$ | $D^{121}$ |
| 4047. | $A^{115}$ | $D^{121}$ |
| 4048. | $A^{116}$ | $D^{121}$ |
| 4049. | $A^{117}$ | $D^{121}$ |
| 4050. | $A^{118}$ | $D^{121}$ |
| 4051. | $A^{119}$ | $D^{121}$ |
| 4052. | $A^{120}$ | $D^{121}$ |
| 4053. | $A^{121}$ | $D^{121}$ |
| 4054. | $A^{122}$ | $D^{121}$ |
| 4055. | $A^{123}$ | $D^{121}$ |
| 4056. | $A^{124}$ | $D^{121}$ |
| 4057. | $A^{125}$ | $D^{121}$ |
| 4058. | $A^{126}$ | $D^{121}$ |
| 4059. | $A^{127}$ | $D^{121}$ |
| 4060. | $A^{128}$ | $D^{121}$ |
| 4061. | $A^{129}$ | $D^{121}$ |
| 4062. | $A^{130}$ | $D^{121}$ |
| 4063. | $A^{131}$ | $D^{121}$ |
| 4064. | $A^{132}$ | $D^{121}$ |
| 4065. | $A^{101}$ | $D^{122}$ |
| 4066. | $A^{102}$ | $D^{122}$ |
| 4067. | $A^{103}$ | $D^{122}$ |
| 4068. | $A^{104}$ | $D^{122}$ |
| 4069. | $A^{105}$ | $D^{122}$ |
| 4070. | $A^{106}$ | $D^{122}$ |
| 4071. | $A^{107}$ | $D^{122}$ |
| 4072. | $A^{108}$ | $D^{122}$ |
| 4073. | $A^{109}$ | $D^{122}$ |
| 4074. | $A^{110}$ | $D^{122}$ |
| 4075. | $A^{111}$ | $D^{122}$ |
| 4076. | $A^{112}$ | $D^{122}$ |
| 4077. | $A^{113}$ | $D^{122}$ |
| 4078. | $A^{114}$ | $D^{122}$ |
| 4079. | $A^{115}$ | $D^{122}$ |
| 4080. | $A^{116}$ | $D^{122}$ |
| 4081. | $A^{117}$ | $D^{122}$ |
| 4082. | $A^{118}$ | $D^{122}$ |
| 4083. | $A^{119}$ | $D^{122}$ |
| 4084. | $A^{120}$ | $D^{122}$ |
| 4085. | $A^{121}$ | $D^{122}$ |
| 4086. | $A^{122}$ | $D^{122}$ |
| 4087. | $A^{123}$ | $D^{122}$ |
| 4088. | $A^{124}$ | $D^{122}$ |
| 4089. | $A^{125}$ | $D^{122}$ |

Formula III

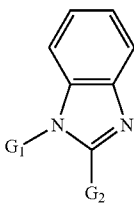

| Compound Number | $G^1$ | $G^2$ |
|---|---|---|
| 4090. | $A^{126}$ | $D^{122}$ |
| 4091. | $A^{127}$ | $D^{122}$ |
| 4092. | $A^{128}$ | $D^{122}$ |
| 4093. | $A^{129}$ | $D^{122}$ |
| 4094. | $A^{130}$ | $D^{122}$ |
| 4095. | $A^{131}$ | $D^{122}$ |
| 4096. | $A^{132}$ | $D^{122}$ |
| 4097. | $A^{101}$ | $D^{123}$ |
| 4098. | $A^{102}$ | $D^{123}$ |
| 4099. | $A^{103}$ | $D^{123}$ |
| 4100. | $A^{104}$ | $D^{123}$ |
| 4101. | $A^{105}$ | $D^{123}$ |
| 4102. | $A^{106}$ | $D^{123}$ |
| 4103. | $A^{107}$ | $D^{123}$ |
| 4104. | $A^{108}$ | $D^{123}$ |
| 4105. | $A^{109}$ | $D^{123}$ |
| 4106. | $A^{110}$ | $D^{123}$ |
| 4107. | $A^{111}$ | $D^{123}$ |
| 4108. | $A^{112}$ | $D^{123}$ |
| 4109. | $A^{113}$ | $D^{123}$ |
| 4110. | $A^{114}$ | $D^{123}$ |
| 4111. | $A^{115}$ | $D^{123}$ |
| 4112. | $A^{116}$ | $D^{123}$ |
| 4113. | $A^{117}$ | $D^{123}$ |
| 4114. | $A^{118}$ | $D^{123}$ |
| 4115. | $A^{119}$ | $D^{123}$ |
| 4116. | $A^{120}$ | $D^{123}$ |
| 4117. | $A^{121}$ | $D^{123}$ |
| 4118. | $A^{122}$ | $D^{123}$ |
| 4119. | $A^{123}$ | $D^{123}$ |
| 4120. | $A^{124}$ | $D^{123}$ |
| 4121. | $A^{125}$ | $D^{123}$ |
| 4122. | $A^{126}$ | $D^{123}$ |
| 4123. | $A^{127}$ | $D^{123}$ |
| 4124. | $A^{128}$ | $D^{123}$ |
| 4125. | $A^{129}$ | $D^{123}$ |
| 4126. | $A^{130}$ | $D^{123}$ |
| 4127. | $A^{131}$ | $D^{123}$ |
| 4128. | $A^{132}$ | $D^{123}$ |
| 4129. | $A^{101}$ | $D^{124}$ |
| 4130. | $A^{102}$ | $D^{124}$ |
| 4131. | $A^{103}$ | $D^{124}$ |
| 4132. | $A^{104}$ | $D^{124}$ |
| 4133. | $A^{105}$ | $D^{124}$ |
| 4134. | $A^{106}$ | $D^{124}$ |
| 4135. | $A^{107}$ | $D^{124}$ |
| 4136. | $A^{108}$ | $D^{124}$ |
| 4137. | $A^{109}$ | $D^{124}$ |
| 4138. | $A^{110}$ | $D^{124}$ |
| 4139. | $A^{111}$ | $D^{124}$ |
| 4140. | $A^{112}$ | $D^{124}$ |
| 4141. | $A^{113}$ | $D^{124}$ |
| 4142. | $A^{114}$ | $D^{124}$ |
| 4143. | $A^{115}$ | $D^{124}$ |
| 4144. | $A^{116}$ | $D^{124}$ |
| 4145. | $A^{117}$ | $D^{124}$ |
| 4146. | $A^{118}$ | $D^{124}$ |
| 4147. | $A^{119}$ | $D^{124}$ |
| 4148. | $A^{120}$ | $D^{124}$ |
| 4149. | $A^{121}$ | $D^{124}$ |
| 4150. | $A^{122}$ | $D^{124}$ |
| 4151. | $A^{123}$ | $D^{124}$ |
| 4152. | $A^{124}$ | $D^{124}$ |
| 4153. | $A^{125}$ | $D^{124}$ |
| 4154. | $A^{126}$ | $D^{124}$ |

145

-continued

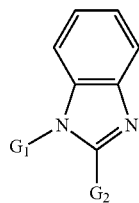

Formula III

| Compound Number | G¹ | G² |
|---|---|---|
| 4155. | $A^{127}$ | $D^{124}$ |
| 4156. | $A^{128}$ | $D^{124}$ |
| 4157. | $A^{129}$ | $D^{124}$ |
| 4158. | $A^{130}$ | $D^{124}$ |
| 4159. | $A^{131}$ | $D^{124}$ |
| 4160. | $A^{132}$ | $D^{124}$ |
| 4161. | $A^{101}$ | $D^{125}$ |
| 4162. | $A^{102}$ | $D^{125}$ |
| 4163. | $A^{103}$ | $D^{125}$ |
| 4164. | $A^{104}$ | $D^{125}$ |
| 4165. | $A^{105}$ | $D^{125}$ |
| 4166. | $A^{106}$ | $D^{125}$ |
| 4167. | $A^{107}$ | $D^{125}$ |
| 4168. | $A^{108}$ | $D^{125}$ |
| 4169. | $A^{109}$ | $D^{125}$ |
| 4170. | $A^{110}$ | $D^{125}$ |
| 4171. | $A^{111}$ | $D^{125}$ |
| 4172. | $A^{112}$ | $D^{125}$ |
| 4173. | $A^{113}$ | $D^{125}$ |
| 4174. | $A^{114}$ | $D^{125}$ |
| 4175. | $A^{115}$ | $D^{125}$ |
| 4176. | $A^{116}$ | $D^{125}$ |
| 4177. | $A^{117}$ | $D^{125}$ |
| 4178. | $A^{118}$ | $D^{125}$ |
| 4179. | $A^{119}$ | $D^{125}$ |
| 4180. | $A^{120}$ | $D^{125}$ |
| 4181. | $A^{121}$ | $D^{125}$ |
| 4182. | $A^{122}$ | $D^{125}$ |
| 4183. | $A^{123}$ | $D^{125}$ |
| 4184. | $A^{124}$ | $D^{125}$ |
| 4185. | $A^{125}$ | $D^{125}$ |
| 4186. | $A^{126}$ | $D^{125}$ |
| 4187. | $A^{127}$ | $D^{125}$ |
| 4188. | $A^{128}$ | $D^{125}$ |
| 4189. | $A^{129}$ | $D^{125}$ |
| 4190. | $A^{130}$ | $D^{125}$ |
| 4191. | $A^{131}$ | $D^{125}$ |
| 4192. | $A^{132}$ | $D^{125}$ |
| 4193. | $A^{101}$ | $D^{126}$ |
| 4194. | $A^{102}$ | $D^{126}$ |
| 4195. | $A^{103}$ | $D^{126}$ |
| 4196. | $A^{104}$ | $D^{126}$ |
| 4197. | $A^{105}$ | $D^{126}$ |
| 4198. | $A^{106}$ | $D^{126}$ |
| 4199. | $A^{107}$ | $D^{126}$ |
| 4200. | $A^{108}$ | $D^{126}$ |
| 4201. | $A^{109}$ | $D^{126}$ |
| 4202. | $A^{110}$ | $D^{126}$ |
| 4203. | $A^{111}$ | $D^{126}$ |
| 4204. | $A^{112}$ | $D^{126}$ |
| 4205. | $A^{113}$ | $D^{126}$ |
| 4206. | $A^{114}$ | $D^{126}$ |
| 4207. | $A^{115}$ | $D^{126}$ |
| 4208. | $A^{116}$ | $D^{126}$ |
| 4209. | $A^{117}$ | $D^{126}$ |
| 4210. | $A^{118}$ | $D^{126}$ |
| 4211. | $A^{119}$ | $D^{126}$ |
| 4212. | $A^{120}$ | $D^{126}$ |
| 4213. | $A^{121}$ | $D^{126}$ |
| 4214. | $A^{122}$ | $D^{126}$ |
| 4215. | $A^{123}$ | $D^{126}$ |
| 4216. | $A^{124}$ | $D^{126}$ |
| 4217. | $A^{125}$ | $D^{126}$ |
| 4218. | $A^{126}$ | $D^{126}$ |
| 4219. | $A^{127}$ | $D^{126}$ |

146

-continued

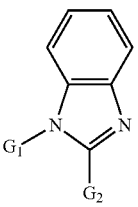

Formula III

| Compound Number | G¹ | G² |
|---|---|---|
| 4220. | $A^{128}$ | $D^{126}$ |
| 4221. | $A^{129}$ | $D^{126}$ |
| 4222. | $A^{130}$ | $D^{126}$ |
| 4223. | $A^{131}$ | $D^{126}$ |
| 4224. | $A^{132}$ | $D^{126}$ |
| 4225. | $A^{101}$ | $D^{127}$ |
| 4226. | $A^{102}$ | $D^{127}$ |
| 4227. | $A^{103}$ | $D^{127}$ |
| 4228. | $A^{104}$ | $D^{127}$ |
| 4229. | $A^{105}$ | $D^{127}$ |
| 4230. | $A^{106}$ | $D^{127}$ |
| 4231. | $A^{107}$ | $D^{127}$ |
| 4232. | $A^{108}$ | $D^{127}$ |
| 4233. | $A^{109}$ | $D^{127}$ |
| 4234. | $A^{110}$ | $D^{127}$ |
| 4235. | $A^{111}$ | $D^{127}$ |
| 4236. | $A^{112}$ | $D^{127}$ |
| 4237. | $A^{113}$ | $D^{127}$ |
| 4238. | $A^{114}$ | $D^{127}$ |
| 4239. | $A^{115}$ | $D^{127}$ |
| 4240. | $A^{116}$ | $D^{127}$ |
| 4241. | $A^{117}$ | $D^{127}$ |
| 4242. | $A^{118}$ | $D^{127}$ |
| 4243. | $A^{119}$ | $D^{127}$ |
| 4244. | $A^{120}$ | $D^{127}$ |
| 4245. | $A^{121}$ | $D^{127}$ |
| 4246. | $A^{122}$ | $D^{127}$ |
| 4247. | $A^{123}$ | $D^{127}$ |
| 4248. | $A^{124}$ | $D^{127}$ |
| 4249. | $A^{125}$ | $D^{127}$ |
| 4250. | $A^{126}$ | $D^{127}$ |
| 4251. | $A^{127}$ | $D^{127}$ |
| 4252. | $A^{128}$ | $D^{127}$ |
| 4253. | $A^{129}$ | $D^{127}$ |
| 4254. | $A^{130}$ | $D^{127}$ |
| 4255. | $A^{131}$ | $D^{127}$ |
| 4256. | $A^{132}$ | $D^{127}$ |
| 4257. | $A^{101}$ | $D^{128}$ |
| 4258. | $A^{102}$ | $D^{128}$ |
| 4259. | $A^{103}$ | $D^{128}$ |
| 4260. | $A^{104}$ | $D^{128}$ |
| 4261. | $A^{105}$ | $D^{128}$ |
| 4262. | $A^{106}$ | $D^{128}$ |
| 4263. | $A^{107}$ | $D^{128}$ |
| 4264. | $A^{108}$ | $D^{128}$ |
| 4265. | $A^{109}$ | $D^{128}$ |
| 4266. | $A^{110}$ | $D^{128}$ |
| 4267. | $A^{111}$ | $D^{128}$ |
| 4268. | $A^{112}$ | $D^{128}$ |
| 4269. | $A^{113}$ | $D^{128}$ |
| 4270. | $A^{114}$ | $D^{128}$ |
| 4271. | $A^{115}$ | $D^{128}$ |
| 4272. | $A^{116}$ | $D^{128}$ |
| 4273. | $A^{117}$ | $D^{128}$ |
| 4274. | $A^{118}$ | $D^{128}$ |
| 4275. | $A^{119}$ | $D^{128}$ |
| 4276. | $A^{120}$ | $D^{128}$ |
| 4277. | $A^{121}$ | $D^{128}$ |
| 4278. | $A^{122}$ | $D^{128}$ |
| 4279. | $A^{123}$ | $D^{128}$ |
| 4280. | $A^{124}$ | $D^{128}$ |
| 4281. | $A^{125}$ | $D^{128}$ |
| 4282. | $A^{126}$ | $D^{128}$ |
| 4283. | $A^{127}$ | $D^{128}$ |
| 4284. | $A^{128}$ | $D^{128}$ |

Formula III

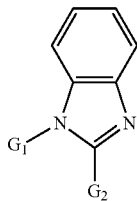

| Compound Number | $G^1$ | $G^2$ |
|---|---|---|
| 4285. | $A^{129}$ | $D^{128}$ |
| 4286. | $A^{130}$ | $D^{128}$ |
| 4287. | $A^{131}$ | $D^{128}$ |
| 4288. | $A^{132}$ | $D^{128}$ |
| 4289. | $A^{101}$ | $D^{129}$ |
| 4290. | $A^{102}$ | $D^{129}$ |
| 4291. | $A^{103}$ | $D^{129}$ |
| 4292. | $A^{104}$ | $D^{129}$ |
| 4293. | $A^{105}$ | $D^{129}$ |
| 4294. | $A^{106}$ | $D^{129}$ |
| 4295. | $A^{107}$ | $D^{129}$ |
| 4296. | $A^{108}$ | $D^{129}$ |
| 4297. | $A^{109}$ | $D^{129}$ |
| 4298. | $A^{110}$ | $D^{129}$ |
| 4299. | $A^{111}$ | $D^{129}$ |
| 4300. | $A^{112}$ | $D^{129}$ |
| 4301. | $A^{113}$ | $D^{129}$ |
| 4302. | $A^{114}$ | $D^{129}$ |
| 4303. | $A^{115}$ | $D^{129}$ |
| 4304. | $A^{116}$ | $D^{129}$ |
| 4305. | $A^{117}$ | $D^{129}$ |
| 4306. | $A^{118}$ | $D^{129}$ |
| 4307. | $A^{119}$ | $D^{129}$ |
| 4308. | $A^{120}$ | $D^{129}$ |
| 4309. | $A^{121}$ | $D^{129}$ |
| 4310. | $A^{122}$ | $D^{129}$ |
| 4311. | $A^{123}$ | $D^{129}$ |
| 4312. | $A^{124}$ | $D^{129}$ |
| 4313. | $A^{125}$ | $D^{129}$ |
| 4314. | $A^{126}$ | $D^{129}$ |
| 4315. | $A^{127}$ | $D^{129}$ |
| 4316. | $A^{128}$ | $D^{129}$ |
| 4317. | $A^{129}$ | $D^{129}$ |
| 4318. | $A^{130}$ | $D^{129}$ |
| 4319. | $A^{131}$ | $D^{129}$ |
| 4320. | $A^{132}$ | $D^{129}$ |
| 4321. | $A^{101}$ | $D^{130}$ |
| 4322. | $A^{102}$ | $D^{130}$ |
| 4323. | $A^{103}$ | $D^{130}$ |
| 4324. | $A^{104}$ | $D^{130}$ |
| 4325. | $A^{105}$ | $D^{130}$ |
| 4326. | $A^{106}$ | $D^{130}$ |
| 4327. | $A^{107}$ | $D^{130}$ |
| 4328. | $A^{108}$ | $D^{130}$ |
| 4329. | $A^{109}$ | $D^{130}$ |
| 4330. | $A^{110}$ | $D^{130}$ |
| 4331. | $A^{111}$ | $D^{130}$ |
| 4332. | $A^{112}$ | $D^{130}$ |
| 4333. | $A^{113}$ | $D^{130}$ |
| 4334. | $A^{114}$ | $D^{130}$ |
| 4335. | $A^{115}$ | $D^{130}$ |
| 4336. | $A^{116}$ | $D^{130}$ |
| 4337. | $A^{117}$ | $D^{130}$ |
| 4338. | $A^{118}$ | $D^{130}$ |
| 4339. | $A^{119}$ | $D^{130}$ |
| 4340. | $A^{120}$ | $D^{130}$ |
| 4341. | $A^{121}$ | $D^{130}$ |
| 4342. | $A^{122}$ | $D^{130}$ |
| 4343. | $A^{123}$ | $D^{130}$ |
| 4344. | $A^{124}$ | $D^{130}$ |
| 4345. | $A^{125}$ | $D^{130}$ |
| 4346. | $A^{126}$ | $D^{130}$ |
| 4347. | $A^{127}$ | $D^{130}$ |
| 4348. | $A^{128}$ | $D^{130}$ |
| 4349. | $A^{129}$ | $D^{130}$ |

Formula III

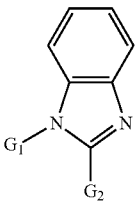

| Compound Number | $G^1$ | $G^2$ |
|---|---|---|
| 4350. | $A^{130}$ | $D^{130}$ |
| 4351. | $A^{131}$ | $D^{130}$ |
| 4352. | $A^{132}$ | $D^{130}$ |
| 4353. | $A^{101}$ | $D^{131}$ |
| 4354. | $A^{102}$ | $D^{131}$ |
| 4355. | $A^{103}$ | $D^{131}$ |
| 4356. | $A^{104}$ | $D^{131}$ |
| 4357. | $A^{105}$ | $D^{131}$ |
| 4358. | $A^{106}$ | $D^{131}$ |
| 4359. | $A^{107}$ | $D^{131}$ |
| 4360. | $A^{108}$ | $D^{131}$ |
| 4361. | $A^{109}$ | $D^{131}$ |
| 4362. | $A^{110}$ | $D^{131}$ |
| 4363. | $A^{111}$ | $D^{131}$ |
| 4364. | $A^{112}$ | $D^{131}$ |
| 4365. | $A^{113}$ | $D^{131}$ |
| 4366. | $A^{114}$ | $D^{131}$ |
| 4367. | $A^{115}$ | $D^{131}$ |
| 4368. | $A^{116}$ | $D^{131}$ |
| 4369. | $A^{117}$ | $D^{131}$ |
| 4370. | $A^{118}$ | $D^{131}$ |
| 4371. | $A^{119}$ | $D^{131}$ |
| 4372. | $A^{120}$ | $D^{131}$ |
| 4373. | $A^{121}$ | $D^{131}$ |
| 4374. | $A^{122}$ | $D^{131}$ |
| 4375. | $A^{123}$ | $D^{131}$ |
| 4376. | $A^{124}$ | $D^{131}$ |
| 4377. | $A^{125}$ | $D^{131}$ |
| 4378. | $A^{126}$ | $D^{131}$ |
| 4379. | $A^{127}$ | $D^{131}$ |
| 4380. | $A^{128}$ | $D^{131}$ |
| 4381. | $A^{129}$ | $D^{131}$ |
| 4382. | $A^{130}$ | $D^{131}$ |
| 4383. | $A^{131}$ | $D^{131}$ |
| 4384. | $A^{132}$ | $D^{131}$ |
| 4385. | $A^{101}$ | $D^{132}$ |
| 4386. | $A^{102}$ | $D^{132}$ |
| 4387. | $A^{103}$ | $D^{132}$ |
| 4388. | $A^{104}$ | $D^{132}$ |
| 4389. | $A^{105}$ | $D^{132}$ |
| 4390. | $A^{106}$ | $D^{132}$ |
| 4391. | $A^{107}$ | $D^{132}$ |
| 4392. | $A^{108}$ | $D^{132}$ |
| 4393. | $A^{109}$ | $D^{132}$ |
| 4394. | $A^{110}$ | $D^{132}$ |
| 4395. | $A^{111}$ | $D^{132}$ |
| 4396. | $A^{112}$ | $D^{132}$ |
| 4397. | $A^{113}$ | $D^{132}$ |
| 4398. | $A^{114}$ | $D^{132}$ |
| 4399. | $A^{115}$ | $D^{132}$ |
| 4400. | $A^{116}$ | $D^{132}$ |
| 4401. | $A^{117}$ | $D^{132}$ |
| 4402. | $A^{118}$ | $D^{132}$ |
| 4403. | $A^{119}$ | $D^{132}$ |
| 4404. | $A^{120}$ | $D^{132}$ |
| 4405. | $A^{121}$ | $D^{132}$ |
| 4406. | $A^{122}$ | $D^{132}$ |
| 4407. | $A^{123}$ | $D^{132}$ |
| 4408. | $A^{124}$ | $D^{132}$ |
| 4409. | $A^{125}$ | $D^{132}$ |
| 4410. | $A^{126}$ | $D^{132}$ |
| 4411. | $A^{127}$ | $D^{132}$ |
| 4412. | $A^{128}$ | $D^{132}$ |
| 4413. | $A^{129}$ | $D^{132}$ |
| 4414. | $A^{130}$ | $D^{132}$ |

Formula III

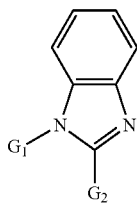

| Compound Number | G¹ | G² |
|---|---|---|
| 4415. | $A^{131}$ | $D^{132}$ |
| 4416. | $A^{132}$ | $D^{132}$ |
| 4417. | $A^{101}$ | $D^{133}$ |
| 4418. | $A^{102}$ | $D^{133}$ |
| 4419. | $A^{103}$ | $D^{133}$ |
| 4420. | $A^{104}$ | $D^{133}$ |
| 4421. | $A^{105}$ | $D^{133}$ |
| 4422. | $A^{106}$ | $D^{133}$ |
| 4423. | $A^{107}$ | $D^{133}$ |
| 4424. | $A^{108}$ | $D^{133}$ |
| 4425. | $A^{109}$ | $D^{133}$ |
| 4426. | $A^{110}$ | $D^{133}$ |
| 4427. | $A^{111}$ | $D^{133}$ |
| 4428. | $A^{112}$ | $D^{133}$ |
| 4429. | $A^{113}$ | $D^{133}$ |
| 4430. | $A^{114}$ | $D^{133}$ |
| 4431. | $A^{115}$ | $D^{133}$ |
| 4432. | $A^{116}$ | $D^{133}$ |
| 4433. | $A^{117}$ | $D^{133}$ |
| 4434. | $A^{118}$ | $D^{133}$ |
| 4435. | $A^{119}$ | $D^{133}$ |
| 4436. | $A^{120}$ | $D^{133}$ |
| 4437. | $A^{121}$ | $D^{133}$ |
| 4438. | $A^{122}$ | $D^{133}$ |
| 4439. | $A^{123}$ | $D^{133}$ |
| 4440. | $A^{124}$ | $D^{133}$ |
| 4441. | $A^{125}$ | $D^{133}$ |
| 4442. | $A^{126}$ | $D^{133}$ |
| 4443. | $A^{127}$ | $D^{133}$ |
| 4444. | $A^{128}$ | $D^{133}$ |
| 4445. | $A^{129}$ | $D^{133}$ |
| 4446. | $A^{130}$ | $D^{133}$ |
| 4447. | $A^{131}$ | $D^{133}$ |
| 4448. | $A^{132}$ | $D^{133}$ |
| 4449. | $A^{101}$ | $D^{134}$ |
| 4450. | $A^{102}$ | $D^{134}$ |
| 4451. | $A^{103}$ | $D^{134}$ |
| 4452. | $A^{104}$ | $D^{134}$ |
| 4453. | $A^{105}$ | $D^{134}$ |
| 4454. | $A^{106}$ | $D^{134}$ |
| 4455. | $A^{107}$ | $D^{134}$ |
| 4456. | $A^{108}$ | $D^{134}$ |
| 4457. | $A^{109}$ | $D^{134}$ |
| 4458. | $A^{110}$ | $D^{134}$ |
| 4459. | $A^{111}$ | $D^{134}$ |
| 4460. | $A^{112}$ | $D^{134}$ |
| 4461. | $A^{113}$ | $D^{134}$ |
| 4462. | $A^{114}$ | $D^{134}$ |
| 4463. | $A^{115}$ | $D^{134}$ |
| 4464. | $A^{116}$ | $D^{134}$ |
| 4465. | $A^{117}$ | $D^{134}$ |
| 4466. | $A^{118}$ | $D^{134}$ |
| 4467. | $A^{119}$ | $D^{134}$ |
| 4468. | $A^{120}$ | $D^{134}$ |
| 4469. | $A^{121}$ | $D^{134}$ |
| 4470. | $A^{122}$ | $D^{134}$ |
| 4471. | $A^{123}$ | $D^{134}$ |
| 4472. | $A^{124}$ | $D^{134}$ |
| 4473. | $A^{125}$ | $D^{134}$ |
| 4474. | $A^{126}$ | $D^{134}$ |
| 4475. | $A^{127}$ | $D^{134}$ |
| 4476. | $A^{128}$ | $D^{134}$ |
| 4477. | $A^{129}$ | $D^{134}$ |
| 4478. | $A^{130}$ | $D^{134}$ |
| 4479. | $A^{131}$ | $D^{134}$ |

Formula III

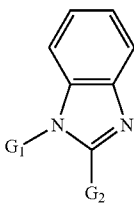

| Compound Number | G¹ | G² |
|---|---|---|
| 4480. | $A^{132}$ | $D^{134}$ |
| 4481. | $A^{101}$ | $D^{135}$ |
| 4482. | $A^{102}$ | $D^{135}$ |
| 4483. | $A^{103}$ | $D^{135}$ |
| 4484. | $A^{104}$ | $D^{135}$ |
| 4485. | $A^{105}$ | $D^{135}$ |
| 4486. | $A^{106}$ | $D^{135}$ |
| 4487. | $A^{107}$ | $D^{135}$ |
| 4488. | $A^{108}$ | $D^{135}$ |
| 4489. | $A^{109}$ | $D^{135}$ |
| 4490. | $A^{110}$ | $D^{135}$ |
| 4491. | $A^{111}$ | $D^{135}$ |
| 4492. | $A^{112}$ | $D^{135}$ |
| 4493. | $A^{113}$ | $D^{135}$ |
| 4494. | $A^{114}$ | $D^{135}$ |
| 4495. | $A^{115}$ | $D^{135}$ |
| 4496. | $A^{116}$ | $D^{135}$ |
| 4497. | $A^{117}$ | $D^{135}$ |
| 4498. | $A^{118}$ | $D^{135}$ |
| 4499. | $A^{119}$ | $D^{135}$ |
| 4500. | $A^{120}$ | $D^{135}$ |
| 4501. | $A^{121}$ | $D^{135}$ |
| 4502. | $A^{122}$ | $D^{135}$ |
| 4503. | $A^{123}$ | $D^{135}$ |
| 4504. | $A^{124}$ | $D^{135}$ |
| 4505. | $A^{125}$ | $D^{135}$ |
| 4506. | $A^{126}$ | $D^{135}$ |
| 4507. | $A^{127}$ | $D^{135}$ |
| 4508. | $A^{128}$ | $D^{135}$ |
| 4509. | $A^{129}$ | $D^{135}$ |
| 4510. | $A^{130}$ | $D^{135}$ |
| 4511. | $A^{131}$ | $D^{135}$ |
| 4512. | $A^{132}$ | $D^{135}$ |
| 4513. | $A^{101}$ | $D^{136}$ |
| 4514. | $A^{102}$ | $D^{136}$ |
| 4515. | $A^{103}$ | $D^{136}$ |
| 4516. | $A^{104}$ | $D^{136}$ |
| 4517. | $A^{105}$ | $D^{136}$ |
| 4518. | $A^{106}$ | $D^{136}$ |
| 4519. | $A^{107}$ | $D^{136}$ |
| 4520. | $A^{108}$ | $D^{136}$ |
| 4521. | $A^{109}$ | $D^{136}$ |
| 4522. | $A^{110}$ | $D^{136}$ |
| 4523. | $A^{111}$ | $D^{136}$ |
| 4524. | $A^{112}$ | $D^{136}$ |
| 4525. | $A^{113}$ | $D^{136}$ |
| 4526. | $A^{114}$ | $D^{136}$ |
| 4527. | $A^{115}$ | $D^{136}$ |
| 4528. | $A^{116}$ | $D^{136}$ |
| 4529. | $A^{117}$ | $D^{136}$ |
| 4530. | $A^{118}$ | $D^{136}$ |
| 4531. | $A^{119}$ | $D^{136}$ |
| 4532. | $A^{120}$ | $D^{136}$ |
| 4533. | $A^{121}$ | $D^{136}$ |
| 4534. | $A^{122}$ | $D^{136}$ |
| 4535. | $A^{123}$ | $D^{136}$ |
| 4536. | $A^{124}$ | $D^{136}$ |
| 4537. | $A^{125}$ | $D^{136}$ |
| 4538. | $A^{126}$ | $D^{136}$ |
| 4539. | $A^{127}$ | $D^{136}$ |
| 4540. | $A^{128}$ | $D^{136}$ |
| 4541. | $A^{129}$ | $D^{136}$ |
| 4542. | $A^{130}$ | $D^{136}$ |
| 4543. | $A^{131}$ | $D^{136}$ |
| 4544. | $A^{132}$ | $D^{136}$ |

Formula III

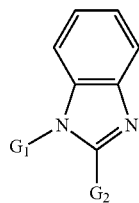

| Compound Number | G¹ | G² |
|---|---|---|
| 4545. | $A^{101}$ | $D^{137}$ |
| 4546. | $A^{102}$ | $D^{137}$ |
| 4547. | $A^{103}$ | $D^{137}$ |
| 4548. | $A^{104}$ | $D^{137}$ |
| 4549. | $A^{105}$ | $D^{137}$ |
| 4550. | $A^{106}$ | $D^{137}$ |
| 4551. | $A^{107}$ | $D^{137}$ |
| 4552. | $A^{108}$ | $D^{137}$ |
| 4553. | $A^{109}$ | $D^{137}$ |
| 4554. | $A^{110}$ | $D^{137}$ |
| 4555. | $A^{111}$ | $D^{137}$ |
| 4556. | $A^{112}$ | $D^{137}$ |
| 4557. | $A^{113}$ | $D^{137}$ |
| 4558. | $A^{114}$ | $D^{137}$ |
| 4559. | $A^{115}$ | $D^{137}$ |
| 4560. | $A^{116}$ | $D^{137}$ |
| 4561. | $A^{117}$ | $D^{137}$ |
| 4562. | $A^{118}$ | $D^{137}$ |
| 4563. | $A^{119}$ | $D^{137}$ |
| 4564. | $A^{120}$ | $D^{137}$ |
| 4565. | $A^{121}$ | $D^{137}$ |
| 4566. | $A^{122}$ | $D^{137}$ |
| 4567. | $A^{123}$ | $D^{137}$ |
| 4568. | $A^{124}$ | $D^{137}$ |
| 4569. | $A^{125}$ | $D^{137}$ |
| 4570. | $A^{126}$ | $D^{137}$ |
| 4571. | $A^{127}$ | $D^{137}$ |
| 4572. | $A^{128}$ | $D^{137}$ |
| 4573. | $A^{129}$ | $D^{137}$ |
| 4574. | $A^{130}$ | $D^{137}$ |
| 4575. | $A^{131}$ | $D^{137}$ |
| 4576. | $A^{132}$ | $D^{137}$ |
| 4577. | $A^{101}$ | $D^{138}$ |
| 4578. | $A^{102}$ | $D^{138}$ |
| 4579. | $A^{103}$ | $D^{138}$ |
| 4580. | $A^{104}$ | $D^{138}$ |
| 4581. | $A^{105}$ | $D^{138}$ |
| 4582. | $A^{106}$ | $D^{138}$ |
| 4583. | $A^{107}$ | $D^{138}$ |
| 4584. | $A^{108}$ | $D^{138}$ |
| 4585. | $A^{109}$ | $D^{138}$ |
| 4586. | $A^{110}$ | $D^{138}$ |
| 4587. | $A^{111}$ | $D^{138}$ |
| 4588. | $A^{112}$ | $D^{138}$ |
| 4589. | $A^{113}$ | $D^{138}$ |
| 4590. | $A^{114}$ | $D^{138}$ |
| 4591. | $A^{115}$ | $D^{138}$ |
| 4592. | $A^{116}$ | $D^{138}$ |
| 4593. | $A^{117}$ | $D^{138}$ |
| 4594. | $A^{118}$ | $D^{138}$ |
| 4595. | $A^{119}$ | $D^{138}$ |
| 4596. | $A^{120}$ | $D^{138}$ |
| 4597. | $A^{121}$ | $D^{138}$ |
| 4598. | $A^{122}$ | $D^{138}$ |
| 4599. | $A^{123}$ | $D^{138}$ |
| 4600. | $A^{124}$ | $D^{138}$ |
| 4601. | $A^{125}$ | $D^{138}$ |
| 4602. | $A^{126}$ | $D^{138}$ |
| 4603. | $A^{127}$ | $D^{138}$ |
| 4604. | $A^{128}$ | $D^{138}$ |
| 4605. | $A^{129}$ | $D^{138}$ |
| 4606. | $A^{130}$ | $D^{138}$ |
| 4607. | $A^{131}$ | $D^{138}$ |
| 4608. | $A^{132}$ | $D^{138}$ |
| 4609. | $A^{101}$ | $D^{139}$ |

Formula III

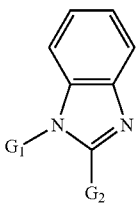

| Compound Number | G¹ | G² |
|---|---|---|
| 4610. | $A^{102}$ | $D^{139}$ |
| 4611. | $A^{103}$ | $D^{139}$ |
| 4612. | $A^{104}$ | $D^{139}$ |
| 4613. | $A^{105}$ | $D^{139}$ |
| 4614. | $A^{106}$ | $D^{139}$ |
| 4615. | $A^{107}$ | $D^{139}$ |
| 4616. | $A^{108}$ | $D^{139}$ |
| 4617. | $A^{109}$ | $D^{139}$ |
| 4618. | $A^{110}$ | $D^{139}$ |
| 4619. | $A^{111}$ | $D^{139}$ |
| 4620. | $A^{112}$ | $D^{139}$ |
| 4621. | $A^{113}$ | $D^{139}$ |
| 4622. | $A^{114}$ | $D^{139}$ |
| 4623. | $A^{115}$ | $D^{139}$ |
| 4624. | $A^{116}$ | $D^{139}$ |
| 4625. | $A^{117}$ | $D^{139}$ |
| 4626. | $A^{118}$ | $D^{139}$ |
| 4627. | $A^{119}$ | $D^{139}$ |
| 4628. | $A^{120}$ | $D^{139}$ |
| 4629. | $A^{121}$ | $D^{139}$ |
| 4630. | $A^{122}$ | $D^{139}$ |
| 4631. | $A^{123}$ | $D^{139}$ |
| 4632. | $A^{124}$ | $D^{139}$ |
| 4633. | $A^{125}$ | $D^{139}$ |
| 4634. | $A^{126}$ | $D^{139}$ |
| 4635. | $A^{127}$ | $D^{139}$ |
| 4636. | $A^{128}$ | $D^{139}$ |
| 4637. | $A^{129}$ | $D^{139}$ |
| 4638. | $A^{130}$ | $D^{139}$ |
| 4639. | $A^{131}$ | $D^{139}$ |
| 4640. | $A^{132}$ | $D^{139}$ |
| 4641. | $A^{101}$ | $D^{140}$ |
| 4642. | $A^{102}$ | $D^{140}$ |
| 4643. | $A^{103}$ | $D^{140}$ |
| 4644. | $A^{104}$ | $D^{140}$ |
| 4645. | $A^{105}$ | $D^{140}$ |
| 4646. | $A^{106}$ | $D^{140}$ |
| 4647. | $A^{107}$ | $D^{140}$ |
| 4648. | $A^{108}$ | $D^{140}$ |
| 4649. | $A^{109}$ | $D^{140}$ |
| 4650. | $A^{110}$ | $D^{140}$ |
| 4651. | $A^{111}$ | $D^{140}$ |
| 4652. | $A^{112}$ | $D^{140}$ |
| 4653. | $A^{113}$ | $D^{140}$ |
| 4654. | $A^{114}$ | $D^{140}$ |
| 4655. | $A^{115}$ | $D^{140}$ |
| 4656. | $A^{116}$ | $D^{140}$ |
| 4657. | $A^{117}$ | $D^{140}$ |
| 4658. | $A^{118}$ | $D^{140}$ |
| 4659. | $A^{119}$ | $D^{140}$ |
| 4660. | $A^{120}$ | $D^{140}$ |
| 4661. | $A^{121}$ | $D^{140}$ |
| 4662. | $A^{122}$ | $D^{140}$ |
| 4663. | $A^{123}$ | $D^{140}$ |
| 4664. | $A^{124}$ | $D^{140}$ |
| 4665. | $A^{125}$ | $D^{140}$ |
| 4666. | $A^{126}$ | $D^{140}$ |
| 4667. | $A^{127}$ | $D^{140}$ |
| 4668. | $A^{128}$ | $D^{140}$ |
| 4669. | $A^{129}$ | $D^{140}$ |
| 4670. | $A^{130}$ | $D^{140}$ |
| 4671. | $A^{131}$ | $D^{140}$ |
| 4672. | $A^{132}$ | $D^{140}$ |
| 4673. | $A^{101}$ | $D^{141}$ |
| 4674. | $A^{102}$ | $D^{141}$ |

Formula III

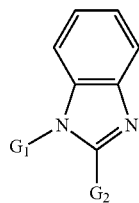

| Compound Number | G¹ | G² |
|---|---|---|
| 4675. | $A^{103}$ | $D^{141}$ |
| 4676. | $A^{104}$ | $D^{141}$ |
| 4677. | $A^{105}$ | $D^{141}$ |
| 4678. | $A^{106}$ | $D^{141}$ |
| 4679. | $A^{107}$ | $D^{141}$ |
| 4680. | $A^{108}$ | $D^{141}$ |
| 4681. | $A^{109}$ | $D^{141}$ |
| 4682. | $A^{110}$ | $D^{141}$ |
| 4683. | $A^{111}$ | $D^{141}$ |
| 4684. | $A^{112}$ | $D^{141}$ |
| 4685. | $A^{113}$ | $D^{141}$ |
| 4686. | $A^{114}$ | $D^{141}$ |
| 4687. | $A^{115}$ | $D^{141}$ |
| 4688. | $A^{116}$ | $D^{141}$ |
| 4689. | $A^{117}$ | $D^{141}$ |
| 4690. | $A^{118}$ | $D^{141}$ |
| 4691. | $A^{119}$ | $D^{141}$ |
| 4692. | $A^{120}$ | $D^{141}$ |
| 4693. | $A^{121}$ | $D^{141}$ |
| 4694. | $A^{122}$ | $D^{141}$ |
| 4695. | $A^{123}$ | $D^{141}$ |
| 4696. | $A^{124}$ | $D^{141}$ |
| 4697. | $A^{125}$ | $D^{141}$ |
| 4698. | $A^{126}$ | $D^{141}$ |
| 4699. | $A^{127}$ | $D^{141}$ |
| 4700. | $A^{128}$ | $D^{141}$ |
| 4701. | $A^{129}$ | $D^{141}$ |
| 4702. | $A^{130}$ | $D^{141}$ |
| 4703. | $A^{131}$ | $D^{141}$ |
| 4704. | $A^{132}$ | $D^{141}$ |
| 4705. | $A^{101}$ | $D^{142}$ |
| 4706. | $A^{102}$ | $D^{142}$ |
| 4707. | $A^{103}$ | $D^{142}$ |
| 4708. | $A^{104}$ | $D^{142}$ |
| 4709. | $A^{105}$ | $D^{142}$ |
| 4710. | $A^{106}$ | $D^{142}$ |
| 4711. | $A^{107}$ | $D^{142}$ |
| 4712. | $A^{108}$ | $D^{142}$ |
| 4713. | $A^{109}$ | $D^{142}$ |
| 4714. | $A^{110}$ | $D^{142}$ |
| 4715. | $A^{111}$ | $D^{142}$ |
| 4716. | $A^{112}$ | $D^{142}$ |
| 4717. | $A^{113}$ | $D^{142}$ |
| 4718. | $A^{114}$ | $D^{142}$ |
| 4719. | $A^{115}$ | $D^{142}$ |
| 4720. | $A^{116}$ | $D^{142}$ |
| 4721. | $A^{117}$ | $D^{142}$ |
| 4722. | $A^{118}$ | $D^{142}$ |
| 4723. | $A^{119}$ | $D^{142}$ |
| 4724. | $A^{120}$ | $D^{142}$ |
| 4725. | $A^{121}$ | $D^{142}$ |
| 4726. | $A^{122}$ | $D^{142}$ |
| 4727. | $A^{123}$ | $D^{142}$ |
| 4728. | $A^{124}$ | $D^{142}$ |
| 4729. | $A^{125}$ | $D^{142}$ |
| 4730. | $A^{126}$ | $D^{142}$ |
| 4731. | $A^{127}$ | $D^{142}$ |
| 4732. | $A^{128}$ | $D^{142}$ |
| 4733. | $A^{129}$ | $D^{142}$ |
| 4734. | $A^{130}$ | $D^{142}$ |
| 4735. | $A^{131}$ | $D^{142}$ |
| 4736. | $A^{132}$ | $D^{142}$ |
| 4737. | $A^{101}$ | $D^{143}$ |
| 4738. | $A^{102}$ | $D^{143}$ |
| 4739. | $A^{103}$ | $D^{143}$ |

Formula III

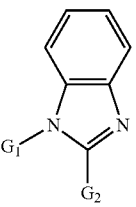

| Compound Number | G¹ | G² |
|---|---|---|
| 4740. | $A^{104}$ | $D^{143}$ |
| 4741. | $A^{105}$ | $D^{143}$ |
| 4742. | $A^{106}$ | $D^{143}$ |
| 4743. | $A^{107}$ | $D^{143}$ |
| 4744. | $A^{108}$ | $D^{143}$ |
| 4745. | $A^{109}$ | $D^{143}$ |
| 4746. | $A^{110}$ | $D^{143}$ |
| 4747. | $A^{111}$ | $D^{143}$ |
| 4748. | $A^{112}$ | $D^{143}$ |
| 4749. | $A^{113}$ | $D^{143}$ |
| 4750. | $A^{114}$ | $D^{143}$ |
| 4751. | $A^{115}$ | $D^{143}$ |
| 4752. | $A^{116}$ | $D^{143}$ |
| 4753. | $A^{117}$ | $D^{143}$ |
| 4754. | $A^{118}$ | $D^{143}$ |
| 4755. | $A^{119}$ | $D^{143}$ |
| 4756. | $A^{120}$ | $D^{143}$ |
| 4757. | $A^{121}$ | $D^{143}$ |
| 4758. | $A^{122}$ | $D^{143}$ |
| 4759. | $A^{123}$ | $D^{143}$ |
| 4760. | $A^{124}$ | $D^{143}$ |
| 4761. | $A^{125}$ | $D^{143}$ |
| 4762. | $A^{126}$ | $D^{143}$ |
| 4763. | $A^{127}$ | $D^{143}$ |
| 4764. | $A^{128}$ | $D^{143}$ |
| 4765. | $A^{129}$ | $D^{143}$ |
| 4766. | $A^{130}$ | $D^{143}$ |
| 4767. | $A^{131}$ | $D^{143}$ |
| 4768. | $A^{132}$ | $D^{143}$ |
| 4769. | $A^{101}$ | $D^{144}$ |
| 4770. | $A^{102}$ | $D^{144}$ |
| 4771. | $A^{103}$ | $D^{144}$ |
| 4772. | $A^{104}$ | $D^{144}$ |
| 4773. | $A^{105}$ | $D^{144}$ |
| 4774. | $A^{106}$ | $D^{144}$ |
| 4775. | $A^{107}$ | $D^{144}$ |
| 4776. | $A^{108}$ | $D^{144}$ |
| 4777. | $A^{109}$ | $D^{144}$ |
| 4778. | $A^{110}$ | $D^{144}$ |
| 4779. | $A^{111}$ | $D^{144}$ |
| 4780. | $A^{112}$ | $D^{144}$ |
| 4781. | $A^{113}$ | $D^{144}$ |
| 4782. | $A^{114}$ | $D^{144}$ |
| 4783. | $A^{115}$ | $D^{144}$ |
| 4784. | $A^{116}$ | $D^{144}$ |
| 4785. | $A^{117}$ | $D^{144}$ |
| 4786. | $A^{118}$ | $D^{144}$ |
| 4787. | $A^{119}$ | $D^{144}$ |
| 4788. | $A^{120}$ | $D^{144}$ |
| 4789. | $A^{121}$ | $D^{144}$ |
| 4790. | $A^{122}$ | $D^{144}$ |
| 4791. | $A^{123}$ | $D^{144}$ |
| 4792. | $A^{124}$ | $D^{144}$ |
| 4793. | $A^{125}$ | $D^{144}$ |
| 4794. | $A^{126}$ | $D^{144}$ |
| 4795. | $A^{127}$ | $D^{144}$ |
| 4796. | $A^{128}$ | $D^{144}$ |
| 4797. | $A^{129}$ | $D^{144}$ |
| 4798. | $A^{130}$ | $D^{144}$ |
| 4799. | $A^{131}$ | $D^{144}$ |
| 4800. | $A^{132}$ | $D^{144}$ |
| 4801. | $A^{101}$ | $D^{145}$ |
| 4802. | $A^{102}$ | $D^{145}$ |
| 4803. | $A^{103}$ | $D^{145}$ |
| 4804. | $A^{104}$ | $D^{145}$ |

-continued

Formula III

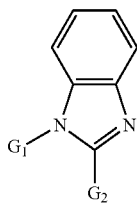

| Compound Number | $G^1$ | $G^2$ |
|---|---|---|
| 4805. | $A^{105}$ | $D^{145}$ |
| 4806. | $A^{106}$ | $D^{145}$ |
| 4807. | $A^{107}$ | $D^{145}$ |
| 4808. | $A^{108}$ | $D^{145}$ |
| 4809. | $A^{109}$ | $D^{145}$ |
| 4810. | $A^{110}$ | $D^{145}$ |
| 4811. | $A^{111}$ | $D^{145}$ |
| 4812. | $A^{112}$ | $D^{145}$ |
| 4813. | $A^{113}$ | $D^{145}$ |
| 4814. | $A^{114}$ | $D^{145}$ |
| 4815. | $A^{115}$ | $D^{145}$ |
| 4816. | $A^{116}$ | $D^{145}$ |
| 4817. | $A^{117}$ | $D^{145}$ |
| 4818. | $A^{118}$ | $D^{145}$ |
| 4819. | $A^{119}$ | $D^{145}$ |
| 4820. | $A^{120}$ | $D^{145}$ |
| 4821. | $A^{121}$ | $D^{145}$ |
| 4822. | $A^{122}$ | $D^{145}$ |
| 4823. | $A^{123}$ | $D^{145}$ |
| 4824. | $A^{124}$ | $D^{145}$ |
| 4825. | $A^{125}$ | $D^{145}$ |
| 4826. | $A^{126}$ | $D^{145}$ |
| 4827. | $A^{127}$ | $D^{145}$ |
| 4828. | $A^{128}$ | $D^{145}$ |
| 4829. | $A^{129}$ | $D^{145}$ |
| 4830. | $A^{130}$ | $D^{145}$ |
| 4831. | $A^{131}$ | $D^{145}$ |
| 4832. | $A^{132}$ | $D^{145}$ |
| 4833. | $A^{101}$ | $D^{146}$ |
| 4834. | $A^{102}$ | $D^{146}$ |
| 4835. | $A^{103}$ | $D^{146}$ |
| 4836. | $A^{104}$ | $D^{146}$ |
| 4837. | $A^{105}$ | $D^{146}$ |
| 4838. | $A^{106}$ | $D^{146}$ |
| 4839. | $A^{107}$ | $D^{146}$ |
| 4840. | $A^{108}$ | $D^{146}$ |
| 4841. | $A^{109}$ | $D^{146}$ |
| 4842. | $A^{110}$ | $D^{146}$ |
| 4843. | $A^{111}$ | $D^{146}$ |
| 4844. | $A^{112}$ | $D^{146}$ |
| 4845. | $A^{113}$ | $D^{146}$ |
| 4846. | $A^{114}$ | $D^{146}$ |
| 4847. | $A^{115}$ | $D^{146}$ |
| 4848. | $A^{116}$ | $D^{146}$ |
| 4849. | $A^{117}$ | $D^{146}$ |
| 4850. | $A^{118}$ | $D^{146}$ |
| 4851. | $A^{119}$ | $D^{146}$ |
| 4852. | $A^{120}$ | $D^{146}$ |
| 4853. | $A^{121}$ | $D^{146}$ |
| 4854. | $A^{122}$ | $D^{146}$ |
| 4855. | $A^{123}$ | $D^{146}$ |
| 4856. | $A^{124}$ | $D^{146}$ |
| 4857. | $A^{125}$ | $D^{146}$ |
| 4858. | $A^{126}$ | $D^{146}$ |
| 4859. | $A^{127}$ | $D^{146}$ |
| 4860. | $A^{128}$ | $D^{146}$ |
| 4861. | $A^{129}$ | $D^{146}$ |
| 4862. | $A^{130}$ | $D^{146}$ |
| 4863. | $A^{131}$ | $D^{146}$ |
| 4864. | $A^{132}$ | $D^{146}$ |
| 4865. | $A^{101}$ | $D^{147}$ |
| 4866. | $A^{102}$ | $D^{147}$ |
| 4867. | $A^{103}$ | $D^{147}$ |
| 4868. | $A^{104}$ | $D^{147}$ |
| 4869. | $A^{105}$ | $D^{147}$ |

-continued

Formula III

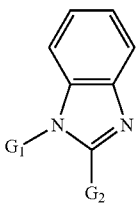

| Compound Number | $G^1$ | $G^2$ |
|---|---|---|
| 4870. | $A^{106}$ | $D^{147}$ |
| 4871. | $A^{107}$ | $D^{147}$ |
| 4872. | $A^{108}$ | $D^{147}$ |
| 4873. | $A^{109}$ | $D^{147}$ |
| 4874. | $A^{110}$ | $D^{147}$ |
| 4875. | $A^{111}$ | $D^{147}$ |
| 4876. | $A^{112}$ | $D^{147}$ |
| 4877. | $A^{113}$ | $D^{147}$ |
| 4878. | $A^{114}$ | $D^{147}$ |
| 4879. | $A^{115}$ | $D^{147}$ |
| 4880. | $A^{116}$ | $D^{147}$ |
| 4881. | $A^{117}$ | $D^{147}$ |
| 4882. | $A^{118}$ | $D^{147}$ |
| 4883. | $A^{119}$ | $D^{147}$ |
| 4884. | $A^{120}$ | $D^{147}$ |
| 4885. | $A^{121}$ | $D^{147}$ |
| 4886. | $A^{122}$ | $D^{147}$ |
| 4887. | $A^{123}$ | $D^{147}$ |
| 4888. | $A^{124}$ | $D^{147}$ |
| 4889. | $A^{125}$ | $D^{147}$ |
| 4890. | $A^{126}$ | $D^{147}$ |
| 4891. | $A^{127}$ | $D^{147}$ |
| 4892. | $A^{128}$ | $D^{147}$ |
| 4893. | $A^{129}$ | $D^{147}$ |
| 4894. | $A^{130}$ | $D^{147}$ |
| 4895. | $A^{131}$ | $D^{147}$ |
| 4896. | $A^{132}$ | $D^{147}$ |
| 4897. | $A^{101}$ | $D^{148}$ |
| 4898. | $A^{102}$ | $D^{148}$ |
| 4899. | $A^{103}$ | $D^{148}$ |
| 4900. | $A^{104}$ | $D^{148}$ |
| 4901. | $A^{105}$ | $D^{148}$ |
| 4902. | $A^{106}$ | $D^{148}$ |
| 4903. | $A^{107}$ | $D^{148}$ |
| 4904. | $A^{108}$ | $D^{148}$ |
| 4905. | $A^{109}$ | $D^{148}$ |
| 4906. | $A^{110}$ | $D^{148}$ |
| 4907. | $A^{111}$ | $D^{148}$ |
| 4908. | $A^{112}$ | $D^{148}$ |
| 4909. | $A^{113}$ | $D^{148}$ |
| 4910. | $A^{114}$ | $D^{148}$ |
| 4911. | $A^{115}$ | $D^{148}$ |
| 4912. | $A^{116}$ | $D^{148}$ |
| 4913. | $A^{117}$ | $D^{148}$ |
| 4914. | $A^{118}$ | $D^{148}$ |
| 4915. | $A^{119}$ | $D^{148}$ |
| 4916. | $A^{120}$ | $D^{148}$ |
| 4917. | $A^{121}$ | $D^{148}$ |
| 4918. | $A^{122}$ | $D^{148}$ |
| 4919. | $A^{123}$ | $D^{148}$ |
| 4920. | $A^{124}$ | $D^{148}$ |
| 4921. | $A^{125}$ | $D^{148}$ |
| 4922. | $A^{126}$ | $D^{148}$ |
| 4923. | $A^{127}$ | $D^{148}$ |
| 4924. | $A^{128}$ | $D^{148}$ |
| 4925. | $A^{129}$ | $D^{148}$ |
| 4926. | $A^{130}$ | $D^{148}$ |
| 4927. | $A^{131}$ | $D^{148}$ |
| 4928. | $A^{132}$ | $D^{148}$ |
| 4929. | $A^{101}$ | $D^{149}$ |
| 4930. | $A^{102}$ | $D^{149}$ |
| 4931. | $A^{103}$ | $D^{149}$ |
| 4932. | $A^{104}$ | $D^{149}$ |
| 4933. | $A^{105}$ | $D^{149}$ |
| 4934. | $A^{106}$ | $D^{149}$ |

157

-continued

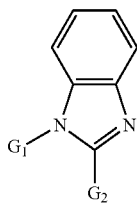

Formula III

| Compound Number | $G^1$ | $G^2$ |
|---|---|---|
| 4935. | $A^{107}$ | $D^{149}$ |
| 4936. | $A^{108}$ | $D^{149}$ |
| 4937. | $A^{109}$ | $D^{149}$ |
| 4938. | $A^{110}$ | $D^{149}$ |
| 4939. | $A^{111}$ | $D^{149}$ |
| 4940. | $A^{112}$ | $D^{149}$ |
| 4941. | $A^{113}$ | $D^{149}$ |
| 4942. | $A^{114}$ | $D^{149}$ |
| 4943. | $A^{115}$ | $D^{149}$ |
| 4944. | $A^{116}$ | $D^{149}$ |
| 4945. | $A^{117}$ | $D^{149}$ |
| 4946. | $A^{118}$ | $D^{149}$ |
| 4947. | $A^{119}$ | $D^{149}$ |
| 4948. | $A^{120}$ | $D^{149}$ |
| 4949. | $A^{121}$ | $D^{149}$ |
| 4950. | $A^{122}$ | $D^{149}$ |
| 4951. | $A^{123}$ | $D^{149}$ |
| 4952. | $A^{124}$ | $D^{149}$ |
| 4953. | $A^{125}$ | $D^{149}$ |
| 4954. | $A^{126}$ | $D^{149}$ |
| 4955. | $A^{127}$ | $D^{149}$ |
| 4956. | $A^{128}$ | $D^{149}$ |
| 4957. | $A^{129}$ | $D^{149}$ |
| 4958. | $A^{130}$ | $D^{149}$ |
| 4959. | $A^{131}$ | $D^{149}$ |
| 4960. | $A^{132}$ | $D^{149}$ |
| 4961. | $A^{101}$ | $D^{150}$ |
| 4962. | $A^{102}$ | $D^{150}$ |
| 4963. | $A^{103}$ | $D^{150}$ |
| 4964. | $A^{104}$ | $D^{150}$ |
| 4965. | $A^{105}$ | $D^{150}$ |
| 4966. | $A^{106}$ | $D^{150}$ |
| 4967. | $A^{107}$ | $D^{150}$ |
| 4968. | $A^{108}$ | $D^{150}$ |
| 4969. | $A^{109}$ | $D^{150}$ |
| 4970. | $A^{110}$ | $D^{150}$ |
| 4971. | $A^{111}$ | $D^{150}$ |
| 4972. | $A^{112}$ | $D^{150}$ |
| 4973. | $A^{113}$ | $D^{150}$ |
| 4974. | $A^{114}$ | $D^{150}$ |
| 4975. | $A^{115}$ | $D^{150}$ |
| 4976. | $A^{116}$ | $D^{150}$ |
| 4977. | $A^{117}$ | $D^{150}$ |
| 4978. | $A^{118}$ | $D^{150}$ |
| 4979. | $A^{119}$ | $D^{150}$ |
| 4980. | $A^{120}$ | $D^{150}$ |
| 4981. | $A^{121}$ | $D^{150}$ |
| 4982. | $A^{122}$ | $D^{150}$ |
| 4983. | $A^{123}$ | $D^{150}$ |
| 4984. | $A^{124}$ | $D^{150}$ |
| 4985. | $A^{125}$ | $D^{150}$ |
| 4986. | $A^{126}$ | $D^{150}$ |
| 4987. | $A^{127}$ | $D^{150}$ |
| 4988. | $A^{128}$ | $D^{150}$ |
| 4989. | $A^{129}$ | $D^{150}$ |
| 4990. | $A^{130}$ | $D^{150}$ |
| 4991. | $A^{131}$ | $D^{150}$ |
| 4992. | $A^{132}$ | $D^{150}$ |
| 4993. | $A^{101}$ | $D^{151}$ |
| 4994. | $A^{102}$ | $D^{151}$ |
| 4995. | $A^{103}$ | $D^{151}$ |
| 4996. | $A^{104}$ | $D^{151}$ |
| 4997. | $A^{105}$ | $D^{151}$ |
| 4998. | $A^{106}$ | $D^{151}$ |
| 4999. | $A^{107}$ | $D^{151}$ |

158

-continued

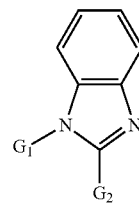

Formula III

| Compound Number | $G^1$ | $G^2$ |
|---|---|---|
| 5000. | $A^{108}$ | $D^{151}$ |
| 5001. | $A^{109}$ | $D^{151}$ |
| 5002. | $A^{110}$ | $D^{151}$ |
| 5003. | $A^{111}$ | $D^{151}$ |
| 5004. | $A^{112}$ | $D^{151}$ |
| 5005. | $A^{113}$ | $D^{151}$ |
| 5006. | $A^{114}$ | $D^{151}$ |
| 5007. | $A^{115}$ | $D^{151}$ |
| 5008. | $A^{116}$ | $D^{151}$ |
| 5009. | $A^{117}$ | $D^{151}$ |
| 5010. | $A^{118}$ | $D^{151}$ |
| 5011. | $A^{119}$ | $D^{151}$ |
| 5012. | $A^{120}$ | $D^{151}$ |
| 5013. | $A^{121}$ | $D^{151}$ |
| 5014. | $A^{122}$ | $D^{151}$ |
| 5015. | $A^{123}$ | $D^{151}$ |
| 5016. | $A^{124}$ | $D^{151}$ |
| 5017. | $A^{125}$ | $D^{151}$ |
| 5018. | $A^{126}$ | $D^{151}$ |
| 5019. | $A^{127}$ | $D^{151}$ |
| 5020. | $A^{128}$ | $D^{151}$ |
| 5021. | $A^{129}$ | $D^{151}$ |
| 5022. | $A^{130}$ | $D^{151}$ |
| 5023. | $A^{131}$ | $D^{151}$ |
| 5024. | $A^{132}$ | $D^{151}$ |
| 5025. | $A^{101}$ | $D^{152}$ |
| 5026. | $A^{102}$ | $D^{152}$ |
| 5027. | $A^{103}$ | $D^{152}$ |
| 5028. | $A^{104}$ | $D^{152}$ |
| 5029. | $A^{105}$ | $D^{152}$ |
| 5030. | $A^{106}$ | $D^{152}$ |
| 5031. | $A^{107}$ | $D^{152}$ |
| 5032. | $A^{108}$ | $D^{152}$ |
| 5033. | $A^{109}$ | $D^{152}$ |
| 5034. | $A^{110}$ | $D^{152}$ |
| 5035. | $A^{111}$ | $D^{152}$ |
| 5036. | $A^{112}$ | $D^{152}$ |
| 5037. | $A^{113}$ | $D^{152}$ |
| 5038. | $A^{114}$ | $D^{152}$ |
| 5039. | $A^{115}$ | $D^{152}$ |
| 5040. | $A^{116}$ | $D^{152}$ |
| 5041. | $A^{117}$ | $D^{152}$ |
| 5042. | $A^{118}$ | $D^{152}$ |
| 5043. | $A^{119}$ | $D^{152}$ |
| 5044. | $A^{120}$ | $D^{152}$ |
| 5045. | $A^{121}$ | $D^{152}$ |
| 5046. | $A^{122}$ | $D^{152}$ |
| 5047. | $A^{123}$ | $D^{152}$ |
| 5048. | $A^{124}$ | $D^{152}$ |
| 5049. | $A^{125}$ | $D^{152}$ |
| 5050. | $A^{126}$ | $D^{152}$ |
| 5051. | $A^{127}$ | $D^{152}$ |
| 5052. | $A^{128}$ | $D^{152}$ |
| 5053. | $A^{129}$ | $D^{152}$ |
| 5054. | $A^{130}$ | $D^{152}$ |
| 5055. | $A^{131}$ | $D^{152}$ |
| 5056. | $A^{132}$ | $D^{152}$ |
| 5057. | $A^{101}$ | $D^{153}$ |
| 5058. | $A^{102}$ | $D^{153}$ |
| 5059. | $A^{103}$ | $D^{153}$ |
| 5060. | $A^{104}$ | $D^{153}$ |
| 5061. | $A^{105}$ | $D^{153}$ |
| 5062. | $A^{106}$ | $D^{153}$ |
| 5063. | $A^{107}$ | $D^{153}$ |
| 5064. | $A^{108}$ | $D^{153}$ |

159
-continued

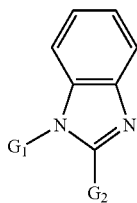

Formula III

| Compound Number | $G^1$ | $G^2$ |
|---|---|---|
| 5065. | $A^{109}$ | $D^{153}$ |
| 5066. | $A^{110}$ | $D^{153}$ |
| 5067. | $A^{111}$ | $D^{153}$ |
| 5068. | $A^{112}$ | $D^{153}$ |
| 5069. | $A^{113}$ | $D^{153}$ |
| 5070. | $A^{114}$ | $D^{153}$ |
| 5071. | $A^{115}$ | $D^{153}$ |
| 5072. | $A^{116}$ | $D^{153}$ |
| 5073. | $A^{117}$ | $D^{153}$ |
| 5074. | $A^{118}$ | $D^{153}$ |
| 5075. | $A^{119}$ | $D^{153}$ |
| 5076. | $A^{120}$ | $D^{153}$ |
| 5077. | $A^{121}$ | $D^{153}$ |
| 5078. | $A^{122}$ | $D^{153}$ |
| 5079. | $A^{123}$ | $D^{153}$ |
| 5080. | $A^{124}$ | $D^{153}$ |
| 5081. | $A^{125}$ | $D^{153}$ |
| 5082. | $A^{126}$ | $D^{153}$ |
| 5083. | $A^{127}$ | $D^{153}$ |
| 5084. | $A^{128}$ | $D^{153}$ |
| 5085. | $A^{129}$ | $D^{153}$ |
| 5086. | $A^{130}$ | $D^{153}$ |
| 5087. | $A^{131}$ | $D^{153}$ |
| 5088. | $A^{132}$ | $D^{153}$ |
| 5089. | $A^{101}$ | $D^{154}$ |
| 5090. | $A^{102}$ | $D^{154}$ |
| 5091. | $A^{103}$ | $D^{154}$ |
| 5092. | $A^{104}$ | $D^{154}$ |
| 5093. | $A^{105}$ | $D^{154}$ |
| 5094. | $A^{106}$ | $D^{154}$ |
| 5095. | $A^{107}$ | $D^{154}$ |
| 5096. | $A^{108}$ | $D^{154}$ |
| 5097. | $A^{109}$ | $D^{154}$ |
| 5098. | $A^{110}$ | $D^{154}$ |
| 5099. | $A^{111}$ | $D^{154}$ |
| 5100. | $A^{112}$ | $D^{154}$ |
| 5101. | $A^{113}$ | $D^{154}$ |
| 5102. | $A^{114}$ | $D^{154}$ |
| 5103. | $A^{115}$ | $D^{154}$ |
| 5104. | $A^{116}$ | $D^{154}$ |
| 5105. | $A^{117}$ | $D^{154}$ |
| 5106. | $A^{118}$ | $D^{154}$ |
| 5107. | $A^{119}$ | $D^{154}$ |
| 5108. | $A^{120}$ | $D^{154}$ |
| 5109. | $A^{121}$ | $D^{154}$ |
| 5110. | $A^{122}$ | $D^{154}$ |
| 5111. | $A^{123}$ | $D^{154}$ |
| 5112. | $A^{124}$ | $D^{154}$ |
| 5113. | $A^{125}$ | $D^{154}$ |
| 5114. | $A^{126}$ | $D^{154}$ |
| 5115. | $A^{127}$ | $D^{154}$ |
| 5116. | $A^{128}$ | $D^{154}$ |
| 5117. | $A^{129}$ | $D^{154}$ |
| 5118. | $A^{130}$ | $D^{154}$ |
| 5119. | $A^{131}$ | $D^{154}$ |
| 5120. | $A^{132}$ | $D^{154}$ |
| 5121. | $A^{101}$ | $D^{155}$ |
| 5122. | $A^{102}$ | $D^{155}$ |
| 5123. | $A^{103}$ | $D^{155}$ |
| 5124. | $A^{104}$ | $D^{155}$ |
| 5125. | $A^{105}$ | $D^{155}$ |
| 5126. | $A^{106}$ | $D^{155}$ |
| 5127. | $A^{107}$ | $D^{155}$ |
| 5128. | $A^{108}$ | $D^{155}$ |
| 5129. | $A^{109}$ | $D^{155}$ |

160
-continued

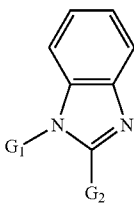

Formula III

| Compound Number | $G^1$ | $G^2$ |
|---|---|---|
| 5130. | $A^{110}$ | $D^{155}$ |
| 5131. | $A^{111}$ | $D^{155}$ |
| 5132. | $A^{112}$ | $D^{155}$ |
| 5133. | $A^{113}$ | $D^{155}$ |
| 5134. | $A^{114}$ | $D^{155}$ |
| 5135. | $A^{115}$ | $D^{155}$ |
| 5136. | $A^{116}$ | $D^{155}$ |
| 5137. | $A^{117}$ | $D^{155}$ |
| 5138. | $A^{118}$ | $D^{155}$ |
| 5139. | $A^{119}$ | $D^{155}$ |
| 5140. | $A^{120}$ | $D^{155}$ |
| 5141. | $A^{121}$ | $D^{155}$ |
| 5142. | $A^{122}$ | $D^{155}$ |
| 5143. | $A^{123}$ | $D^{155}$ |
| 5144. | $A^{124}$ | $D^{155}$ |
| 5145. | $A^{125}$ | $D^{155}$ |
| 5146. | $A^{126}$ | $D^{155}$ |
| 5147. | $A^{127}$ | $D^{155}$ |
| 5148. | $A^{128}$ | $D^{155}$ |
| 5149. | $A^{129}$ | $D^{155}$ |
| 5150. | $A^{130}$ | $D^{155}$ |
| 5151. | $A^{131}$ | $D^{155}$ |
| 5152. | $A^{132}$ | $D^{155}$ |
| 5153. | $A^{101}$ | $D^{156}$ |
| 5154. | $A^{102}$ | $D^{156}$ |
| 5155. | $A^{103}$ | $D^{156}$ |
| 5156. | $A^{104}$ | $D^{156}$ |
| 5157. | $A^{105}$ | $D^{156}$ |
| 5158. | $A^{106}$ | $D^{156}$ |
| 5159. | $A^{107}$ | $D^{156}$ |
| 5160. | $A^{108}$ | $D^{156}$ |
| 5161. | $A^{109}$ | $D^{156}$ |
| 5162. | $A^{110}$ | $D^{156}$ |
| 5163. | $A^{111}$ | $D^{156}$ |
| 5164. | $A^{112}$ | $D^{156}$ |
| 5165. | $A^{113}$ | $D^{156}$ |
| 5166. | $A^{114}$ | $D^{156}$ |
| 5167. | $A^{115}$ | $D^{156}$ |
| 5168. | $A^{116}$ | $D^{156}$ |
| 5169. | $A^{117}$ | $D^{156}$ |
| 5170. | $A^{118}$ | $D^{156}$ |
| 5171. | $A^{119}$ | $D^{156}$ |
| 5172. | $A^{120}$ | $D^{156}$ |
| 5173. | $A^{121}$ | $D^{156}$ |
| 5174. | $A^{122}$ | $D^{156}$ |
| 5175. | $A^{123}$ | $D^{156}$ |
| 5176. | $A^{124}$ | $D^{156}$ |
| 5177. | $A^{125}$ | $D^{156}$ |
| 5178. | $A^{126}$ | $D^{156}$ |
| 5179. | $A^{127}$ | $D^{156}$ |
| 5180. | $A^{128}$ | $D^{156}$ |
| 5181. | $A^{129}$ | $D^{156}$ |
| 5182. | $A^{130}$ | $D^{156}$ |
| 5183. | $A^{131}$ | $D^{156}$ |
| 5184. | $A^{132}$ | $D^{156}$ |
| 5185. | $A^{101}$ | $D^{157}$ |
| 5186. | $A^{102}$ | $D^{157}$ |
| 5187. | $A^{103}$ | $D^{157}$ |
| 5188. | $A^{104}$ | $D^{157}$ |
| 5189. | $A^{105}$ | $D^{157}$ |
| 5190. | $A^{106}$ | $D^{157}$ |
| 5191. | $A^{107}$ | $D^{157}$ |
| 5192. | $A^{108}$ | $D^{157}$ |
| 5193. | $A^{109}$ | $D^{157}$ |
| 5194. | $A^{110}$ | $D^{157}$ |

161
-continued

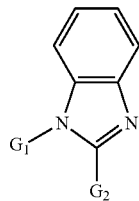

Formula III

| Compound Number | $G^1$ | $G^2$ |
|---|---|---|
| 5195. | $A^{111}$ | $D^{157}$ |
| 5196. | $A^{112}$ | $D^{157}$ |
| 5197. | $A^{113}$ | $D^{157}$ |
| 5198. | $A^{114}$ | $D^{157}$ |
| 5199. | $A^{115}$ | $D^{157}$ |
| 5200. | $A^{116}$ | $D^{157}$ |
| 5201. | $A^{117}$ | $D^{157}$ |
| 5202. | $A^{118}$ | $D^{157}$ |
| 5203. | $A^{119}$ | $D^{157}$ |
| 5204. | $A^{120}$ | $D^{157}$ |
| 5205. | $A^{121}$ | $D^{157}$ |
| 5206. | $A^{122}$ | $D^{157}$ |
| 5207. | $A^{123}$ | $D^{157}$ |
| 5208. | $A^{124}$ | $D^{157}$ |
| 5209. | $A^{125}$ | $D^{157}$ |
| 5210. | $A^{126}$ | $D^{157}$ |
| 5211. | $A^{127}$ | $D^{157}$ |
| 5212. | $A^{128}$ | $D^{157}$ |
| 5213. | $A^{129}$ | $D^{157}$ |
| 5214. | $A^{130}$ | $D^{157}$ |
| 5215. | $A^{131}$ | $D^{157}$ |
| 5216. | $A^{132}$ | $D^{157}$ |
| 5217. | $A^{101}$ | $D^{158}$ |
| 5218. | $A^{102}$ | $D^{158}$ |
| 5219. | $A^{103}$ | $D^{158}$ |
| 5220. | $A^{104}$ | $D^{158}$ |
| 5221. | $A^{105}$ | $D^{158}$ |
| 5222. | $A^{106}$ | $D^{158}$ |
| 5223. | $A^{107}$ | $D^{158}$ |
| 5224. | $A^{108}$ | $D^{158}$ |
| 5225. | $A^{109}$ | $D^{158}$ |
| 5226. | $A^{110}$ | $D^{158}$ |
| 5227. | $A^{111}$ | $D^{158}$ |
| 5228. | $A^{112}$ | $D^{158}$ |
| 5229. | $A^{113}$ | $D^{158}$ |
| 5230. | $A^{114}$ | $D^{158}$ |
| 5231. | $A^{115}$ | $D^{158}$ |
| 5232. | $A^{116}$ | $D^{158}$ |
| 5233. | $A^{117}$ | $D^{158}$ |
| 5234. | $A^{118}$ | $D^{158}$ |
| 5235. | $A^{119}$ | $D^{158}$ |
| 5236. | $A^{120}$ | $D^{158}$ |
| 5237. | $A^{121}$ | $D^{158}$ |
| 5238. | $A^{122}$ | $D^{158}$ |
| 5239. | $A^{123}$ | $D^{158}$ |
| 5240. | $A^{124}$ | $D^{158}$ |
| 5241. | $A^{125}$ | $D^{158}$ |
| 5242. | $A^{126}$ | $D^{158}$ |
| 5243. | $A^{127}$ | $D^{158}$ |
| 5244. | $A^{128}$ | $D^{158}$ |
| 5245. | $A^{129}$ | $D^{158}$ |
| 5246. | $A^{130}$ | $D^{158}$ |
| 5247. | $A^{131}$ | $D^{158}$ |
| 5248. | $A^{132}$ | $D^{158}$ |
| 5249. | $A^{101}$ | $D^{159}$ |
| 5250. | $A^{102}$ | $D^{159}$ |
| 5251. | $A^{103}$ | $D^{159}$ |
| 5252. | $A^{104}$ | $D^{159}$ |
| 5253. | $A^{105}$ | $D^{159}$ |
| 5254. | $A^{106}$ | $D^{159}$ |
| 5255. | $A^{107}$ | $D^{159}$ |
| 5256. | $A^{108}$ | $D^{159}$ |
| 5257. | $A^{109}$ | $D^{159}$ |
| 5258. | $A^{110}$ | $D^{159}$ |
| 5259. | $A^{111}$ | $D^{159}$ |

162
-continued

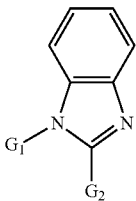

Formula III

| Compound Number | $G^1$ | $G^2$ |
|---|---|---|
| 5260. | $A^{112}$ | $D^{159}$ |
| 5261. | $A^{113}$ | $D^{159}$ |
| 5262. | $A^{114}$ | $D^{159}$ |
| 5263. | $A^{115}$ | $D^{159}$ |
| 5264. | $A^{116}$ | $D^{159}$ |
| 5265. | $A^{117}$ | $D^{159}$ |
| 5266. | $A^{118}$ | $D^{159}$ |
| 5267. | $A^{119}$ | $D^{159}$ |
| 5268. | $A^{120}$ | $D^{159}$ |
| 5269. | $A^{121}$ | $D^{159}$ |
| 5270. | $A^{122}$ | $D^{159}$ |
| 5271. | $A^{123}$ | $D^{159}$ |
| 5272. | $A^{124}$ | $D^{159}$ |
| 5273. | $A^{125}$ | $D^{159}$ |
| 5274. | $A^{126}$ | $D^{159}$ |
| 5275. | $A^{127}$ | $D^{159}$ |
| 5276. | $A^{128}$ | $D^{159}$ |
| 5277. | $A^{129}$ | $D^{159}$ |
| 5278. | $A^{130}$ | $D^{159}$ |
| 5279. | $A^{131}$ | $D^{159}$ |
| 5280. | $A^{132}$ | $D^{159}$ |
| 5281. | $A^{101}$ | $D^{160}$ |
| 5282. | $A^{102}$ | $D^{160}$ |
| 5283. | $A^{103}$ | $D^{160}$ |
| 5284. | $A^{104}$ | $D^{160}$ |
| 5285. | $A^{105}$ | $D^{160}$ |
| 5286. | $A^{106}$ | $D^{160}$ |
| 5287. | $A^{107}$ | $D^{160}$ |
| 5288. | $A^{108}$ | $D^{160}$ |
| 5289. | $A^{109}$ | $D^{160}$ |
| 5290. | $A^{110}$ | $D^{160}$ |
| 5291. | $A^{111}$ | $D^{160}$ |
| 5292. | $A^{112}$ | $D^{160}$ |
| 5293. | $A^{113}$ | $D^{160}$ |
| 5294. | $A^{114}$ | $D^{160}$ |
| 5295. | $A^{115}$ | $D^{160}$ |
| 5296. | $A^{116}$ | $D^{160}$ |
| 5297. | $A^{117}$ | $D^{160}$ |
| 5298. | $A^{118}$ | $D^{160}$ |
| 5299. | $A^{119}$ | $D^{160}$ |
| 5300. | $A^{120}$ | $D^{160}$ |
| 5301. | $A^{121}$ | $D^{160}$ |
| 5302. | $A^{122}$ | $D^{160}$ |
| 5303. | $A^{123}$ | $D^{160}$ |
| 5304. | $A^{124}$ | $D^{160}$ |
| 5305. | $A^{125}$ | $D^{160}$ |
| 5306. | $A^{126}$ | $D^{160}$ |
| 5307. | $A^{127}$ | $D^{160}$ |
| 5308. | $A^{128}$ | $D^{160}$ |
| 5309. | $A^{129}$ | $D^{160}$ |
| 5310. | $A^{130}$ | $D^{160}$ |
| 5311. | $A^{131}$ | $D^{160}$ |
| 5312. | $A^{132}$ | $D^{160}$ |
| 5313. | $A^{101}$ | $D^{161}$ |
| 5314. | $A^{102}$ | $D^{161}$ |
| 5315. | $A^{103}$ | $D^{161}$ |
| 5316. | $A^{104}$ | $D^{161}$ |
| 5317. | $A^{105}$ | $D^{161}$ |
| 5318. | $A^{106}$ | $D^{161}$ |
| 5319. | $A^{107}$ | $D^{161}$ |
| 5320. | $A^{108}$ | $D^{161}$ |
| 5321. | $A^{109}$ | $D^{161}$ |
| 5322. | $A^{110}$ | $D^{161}$ |
| 5323. | $A^{111}$ | $D^{161}$ |
| 5324. | $A^{112}$ | $D^{161}$ |

163
-continued

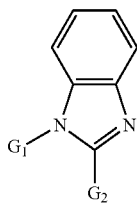

Formula III

| Compound Number | $G^1$ | $G^2$ |
|---|---|---|
| 5325. | $A^{113}$ | $D^{161}$ |
| 5326. | $A^{114}$ | $D^{161}$ |
| 5327. | $A^{115}$ | $D^{161}$ |
| 5328. | $A^{116}$ | $D^{161}$ |
| 5329. | $A^{117}$ | $D^{161}$ |
| 5330. | $A^{118}$ | $D^{161}$ |
| 5331. | $A^{119}$ | $D^{161}$ |
| 5332. | $A^{120}$ | $D^{161}$ |
| 5333. | $A^{121}$ | $D^{161}$ |
| 5334. | $A^{122}$ | $D^{161}$ |
| 5335. | $A^{123}$ | $D^{161}$ |
| 5336. | $A^{124}$ | $D^{161}$ |
| 5337. | $A^{125}$ | $D^{161}$ |
| 5338. | $A^{126}$ | $D^{161}$ |
| 5339. | $A^{127}$ | $D^{161}$ |
| 5340. | $A^{128}$ | $D^{161}$ |
| 5341. | $A^{129}$ | $D^{161}$ |
| 5342. | $A^{130}$ | $D^{161}$ |
| 5343. | $A^{131}$ | $D^{161}$ |
| 5344. | $A^{132}$ | $D^{161}$ |
| 5345. | $A^{101}$ | $D^{162}$ |
| 5346. | $A^{102}$ | $D^{162}$ |
| 5347. | $A^{103}$ | $D^{162}$ |
| 5348. | $A^{104}$ | $D^{162}$ |
| 5349. | $A^{105}$ | $D^{162}$ |
| 5350. | $A^{106}$ | $D^{162}$ |
| 5351. | $A^{107}$ | $D^{162}$ |
| 5352. | $A^{108}$ | $D^{162}$ |
| 5353. | $A^{109}$ | $D^{162}$ |
| 5354. | $A^{110}$ | $D^{162}$ |
| 5355. | $A^{111}$ | $D^{162}$ |
| 5356. | $A^{112}$ | $D^{162}$ |
| 5357. | $A^{113}$ | $D^{162}$ |
| 5358. | $A^{114}$ | $D^{162}$ |
| 5359. | $A^{115}$ | $D^{162}$ |
| 5360. | $A^{116}$ | $D^{162}$ |
| 5361. | $A^{117}$ | $D^{162}$ |
| 5362. | $A^{118}$ | $D^{162}$ |
| 5363. | $A^{119}$ | $D^{162}$ |
| 5364. | $A^{120}$ | $D^{162}$ |
| 5365. | $A^{121}$ | $D^{162}$ |
| 5366. | $A^{122}$ | $D^{162}$ |
| 5367. | $A^{123}$ | $D^{162}$ |
| 5368. | $A^{124}$ | $D^{162}$ |
| 5369. | $A^{125}$ | $D^{162}$ |
| 5370. | $A^{126}$ | $D^{162}$ |
| 5371. | $A^{127}$ | $D^{162}$ |
| 5372. | $A^{128}$ | $D^{162}$ |
| 5373. | $A^{129}$ | $D^{162}$ |
| 5374. | $A^{130}$ | $D^{162}$ |
| 5375. | $A^{131}$ | $D^{162}$ |
| 5376. | $A^{132}$ | $D^{162}$ |
| 5377. | $A^{101}$ | $D^{163}$ |
| 5378. | $A^{102}$ | $D^{163}$ |
| 5379. | $A^{103}$ | $D^{163}$ |
| 5380. | $A^{104}$ | $D^{163}$ |
| 5381. | $A^{105}$ | $D^{163}$ |
| 5382. | $A^{106}$ | $D^{163}$ |
| 5383. | $A^{107}$ | $D^{163}$ |
| 5384. | $A^{108}$ | $D^{163}$ |
| 5385. | $A^{109}$ | $D^{163}$ |
| 5386. | $A^{110}$ | $D^{163}$ |
| 5387. | $A^{111}$ | $D^{163}$ |
| 5388. | $A^{112}$ | $D^{163}$ |
| 5389. | $A^{113}$ | $D^{163}$ |

164
-continued

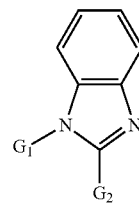

Formula III

| Compound Number | $G^1$ | $G^2$ |
|---|---|---|
| 5390. | $A^{114}$ | $D^{163}$ |
| 5391. | $A^{115}$ | $D^{163}$ |
| 5392. | $A^{116}$ | $D^{163}$ |
| 5393. | $A^{117}$ | $D^{163}$ |
| 5394. | $A^{118}$ | $D^{163}$ |
| 5395. | $A^{119}$ | $D^{163}$ |
| 5396. | $A^{120}$ | $D^{163}$ |
| 5397. | $A^{121}$ | $D^{163}$ |
| 5398. | $A^{122}$ | $D^{163}$ |
| 5399. | $A^{123}$ | $D^{163}$ |
| 5400. | $A^{124}$ | $D^{163}$ |
| 5401. | $A^{125}$ | $D^{163}$ |
| 5402. | $A^{126}$ | $D^{163}$ |
| 5403. | $A^{127}$ | $D^{163}$ |
| 5404. | $A^{128}$ | $D^{163}$ |
| 5405. | $A^{129}$ | $D^{163}$ |
| 5406. | $A^{130}$ | $D^{163}$ |
| 5407. | $A^{131}$ | $D^{163}$ |
| 5408. | $A^{132}$ | $D^{163}$ |
| 5409. | $A^{101}$ | $D^{164}$ |
| 5410. | $A^{102}$ | $D^{164}$ |
| 5411. | $A^{103}$ | $D^{164}$ |
| 5412. | $A^{104}$ | $D^{164}$ |
| 5413. | $A^{105}$ | $D^{164}$ |
| 5414. | $A^{106}$ | $D^{164}$ |
| 5415. | $A^{107}$ | $D^{164}$ |
| 5416. | $A^{108}$ | $D^{164}$ |
| 5417. | $A^{109}$ | $D^{164}$ |
| 5418. | $A^{110}$ | $D^{164}$ |
| 5419. | $A^{111}$ | $D^{164}$ |
| 5420. | $A^{112}$ | $D^{164}$ |
| 5421. | $A^{113}$ | $D^{164}$ |
| 5422. | $A^{114}$ | $D^{164}$ |
| 5423. | $A^{115}$ | $D^{164}$ |
| 5424. | $A^{116}$ | $D^{164}$ |
| 5425. | $A^{117}$ | $D^{164}$ |
| 5426. | $A^{118}$ | $D^{164}$ |
| 5427. | $A^{119}$ | $D^{164}$ |
| 5428. | $A^{120}$ | $D^{164}$ |
| 5429. | $A^{121}$ | $D^{164}$ |
| 5430. | $A^{122}$ | $D^{164}$ |
| 5431. | $A^{123}$ | $D^{164}$ |
| 5432. | $A^{124}$ | $D^{164}$ |
| 5433. | $A^{125}$ | $D^{164}$ |
| 5434. | $A^{126}$ | $D^{164}$ |
| 5435. | $A^{127}$ | $D^{164}$ |
| 5436. | $A^{128}$ | $D^{164}$ |
| 5437. | $A^{129}$ | $D^{164}$ |
| 5438. | $A^{130}$ | $D^{164}$ |
| 5439. | $A^{131}$ | $D^{164}$ |
| 5440. | $A^{132}$ | $D^{164}$ |
| 5441. | $A^{101}$ | $D^{165}$ |
| 5442. | $A^{102}$ | $D^{165}$ |
| 5443. | $A^{103}$ | $D^{165}$ |
| 5444. | $A^{104}$ | $D^{165}$ |
| 5445. | $A^{105}$ | $D^{165}$ |
| 5446. | $A^{106}$ | $D^{165}$ |
| 5447. | $A^{107}$ | $D^{165}$ |
| 5448. | $A^{108}$ | $D^{165}$ |
| 5449. | $A^{109}$ | $D^{165}$ |
| 5450. | $A^{110}$ | $D^{165}$ |
| 5451. | $A^{111}$ | $D^{165}$ |
| 5452. | $A^{112}$ | $D^{165}$ |
| 5453. | $A^{113}$ | $D^{165}$ |
| 5454. | $A^{114}$ | $D^{165}$ |

165
-continued

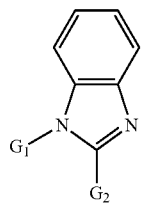

Formula III

| Compound Number | G¹ | G² |
|---|---|---|
| 5455. | $A^{115}$ | $D^{165}$ |
| 5456. | $A^{116}$ | $D^{165}$ |
| 5457. | $A^{117}$ | $D^{165}$ |
| 5458. | $A^{118}$ | $D^{165}$ |
| 5459. | $A^{119}$ | $D^{165}$ |
| 5460. | $A^{120}$ | $D^{165}$ |
| 5461. | $A^{121}$ | $D^{165}$ |
| 5462. | $A^{122}$ | $D^{165}$ |
| 5463. | $A^{123}$ | $D^{165}$ |
| 5464. | $A^{124}$ | $D^{165}$ |
| 5465. | $A^{125}$ | $D^{165}$ |
| 5466. | $A^{126}$ | $D^{165}$ |
| 5467. | $A^{127}$ | $D^{165}$ |
| 5468. | $A^{128}$ | $D^{165}$ |
| 5469. | $A^{129}$ | $D^{165}$ |
| 5470. | $A^{130}$ | $D^{165}$ |
| 5471. | $A^{131}$ | $D^{165}$ |
| 5472. | $A^{132}$ | $D^{165}$ |
| 5473. | $A^{101}$ | $D^{166}$ |
| 5474. | $A^{102}$ | $D^{166}$ |
| 5475. | $A^{103}$ | $D^{166}$ |
| 5476. | $A^{104}$ | $D^{166}$ |
| 5477. | $A^{105}$ | $D^{166}$ |
| 5478. | $A^{106}$ | $D^{166}$ |
| 5479. | $A^{107}$ | $D^{166}$ |
| 5480. | $A^{108}$ | $D^{166}$ |
| 5481. | $A^{109}$ | $D^{166}$ |
| 5482. | $A^{110}$ | $D^{166}$ |
| 5483. | $A^{111}$ | $D^{166}$ |
| 5484. | $A^{112}$ | $D^{166}$ |
| 5485. | $A^{113}$ | $D^{166}$ |
| 5486. | $A^{114}$ | $D^{166}$ |
| 5487. | $A^{115}$ | $D^{166}$ |
| 5488. | $A^{116}$ | $D^{166}$ |
| 5489. | $A^{117}$ | $D^{166}$ |
| 5490. | $A^{118}$ | $D^{166}$ |
| 5491. | $A^{119}$ | $D^{166}$ |
| 5492. | $A^{120}$ | $D^{166}$ |
| 5493. | $A^{121}$ | $D^{166}$ |
| 5494. | $A^{122}$ | $D^{166}$ |
| 5495. | $A^{123}$ | $D^{166}$ |
| 5496. | $A^{124}$ | $D^{166}$ |
| 5497. | $A^{125}$ | $D^{166}$ |
| 5498. | $A^{126}$ | $D^{166}$ |
| 5499. | $A^{127}$ | $D^{166}$ |
| 5500. | $A^{128}$ | $D^{166}$ |
| 5501. | $A^{129}$ | $D^{166}$ |
| 5502. | $A^{130}$ | $D^{166}$ |
| 5503. | $A^{131}$ | $D^{166}$ |
| 5504. | $A^{132}$ | $D^{166}$ |
| 5505. | $A^{101}$ | $D^{167}$ |
| 5506. | $A^{102}$ | $D^{167}$ |
| 5507. | $A^{103}$ | $D^{167}$ |
| 5508. | $A^{104}$ | $D^{167}$ |
| 5509. | $A^{105}$ | $D^{167}$ |
| 5510. | $A^{106}$ | $D^{167}$ |
| 5511. | $A^{107}$ | $D^{167}$ |
| 5512. | $A^{108}$ | $D^{167}$ |
| 5513. | $A^{109}$ | $D^{167}$ |
| 5514. | $A^{110}$ | $D^{167}$ |
| 5515. | $A^{111}$ | $D^{167}$ |
| 5516. | $A^{112}$ | $D^{167}$ |
| 5517. | $A^{113}$ | $D^{167}$ |
| 5518. | $A^{114}$ | $D^{167}$ |
| 5519. | $A^{115}$ | $D^{167}$ |

166
-continued

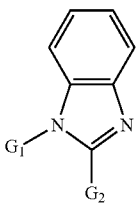

Formula III

| Compound Number | G¹ | G² |
|---|---|---|
| 5520. | $A^{116}$ | $D^{167}$ |
| 5521. | $A^{117}$ | $D^{167}$ |
| 5522. | $A^{118}$ | $D^{167}$ |
| 5523. | $A^{119}$ | $D^{167}$ |
| 5524. | $A^{120}$ | $D^{167}$ |
| 5525. | $A^{121}$ | $D^{167}$ |
| 5526. | $A^{122}$ | $D^{167}$ |
| 5527. | $A^{123}$ | $D^{167}$ |
| 5528. | $A^{124}$ | $D^{167}$ |
| 5529. | $A^{125}$ | $D^{167}$ |
| 5530. | $A^{126}$ | $D^{167}$ |
| 5531. | $A^{127}$ | $D^{167}$ |
| 5532. | $A^{128}$ | $D^{167}$ |
| 5533. | $A^{129}$ | $D^{167}$ |
| 5534. | $A^{130}$ | $D^{167}$ |
| 5535. | $A^{131}$ | $D^{167}$ |
| 5536. | $A^{132}$ | $D^{167}$ |
| 5537. | $A^{101}$ | $D^{168}$ |
| 5538. | $A^{102}$ | $D^{168}$ |
| 5539. | $A^{103}$ | $D^{168}$ |
| 5540. | $A^{104}$ | $D^{168}$ |
| 5541. | $A^{105}$ | $D^{168}$ |
| 5542. | $A^{106}$ | $D^{168}$ |
| 5543. | $A^{107}$ | $D^{168}$ |
| 5544. | $A^{108}$ | $D^{168}$ |
| 5545. | $A^{109}$ | $D^{168}$ |
| 5546. | $A^{110}$ | $D^{168}$ |
| 5547. | $A^{111}$ | $D^{168}$ |
| 5548. | $A^{112}$ | $D^{168}$ |
| 5549. | $A^{113}$ | $D^{168}$ |
| 5550. | $A^{114}$ | $D^{168}$ |
| 5551. | $A^{115}$ | $D^{168}$ |
| 5552. | $A^{116}$ | $D^{168}$ |
| 5553. | $A^{117}$ | $D^{168}$ |
| 5554. | $A^{118}$ | $D^{168}$ |
| 5555. | $A^{119}$ | $D^{168}$ |
| 5556. | $A^{120}$ | $D^{168}$ |
| 5557. | $A^{121}$ | $D^{168}$ |
| 5558. | $A^{122}$ | $D^{168}$ |
| 5559. | $A^{123}$ | $D^{168}$ |
| 5560. | $A^{124}$ | $D^{168}$ |
| 5561. | $A^{125}$ | $D^{168}$ |
| 5562. | $A^{126}$ | $D^{168}$ |
| 5563. | $A^{127}$ | $D^{168}$ |
| 5564. | $A^{128}$ | $D^{168}$ |
| 5565. | $A^{129}$ | $D^{168}$ |
| 5566. | $A^{130}$ | $D^{168}$ |
| 5567. | $A^{131}$ | $D^{168}$ |
| 5568. | $A^{132}$ | $D^{168}$ |
| 5569. | $D^{121}$ | $A^{101}$ |
| 5570. | $D^{121}$ | $A^{102}$ |
| 5571. | $D^{121}$ | $A^{103}$ |
| 5572. | $D^{121}$ | $A^{104}$ |
| 5573. | $D^{121}$ | $A^{105}$ |
| 5574. | $D^{121}$ | $A^{106}$ |
| 5575. | $D^{121}$ | $A^{107}$ |
| 5576. | $D^{121}$ | $A^{108}$ |
| 5577. | $D^{121}$ | $A^{109}$ |
| 5578. | $D^{121}$ | $A^{110}$ |
| 5579. | $D^{121}$ | $A^{111}$ |
| 5580. | $D^{121}$ | $A^{112}$ |
| 5581. | $D^{121}$ | $A^{113}$ |
| 5582. | $D^{121}$ | $A^{114}$ |
| 5583. | $D^{121}$ | $A^{115}$ |
| 5584. | $D^{121}$ | $A^{116}$ |

167

-continued

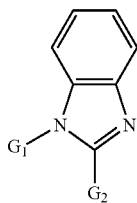

Formula III

| Compound Number | G¹ | G² |
|---|---|---|
| 5585. | $D^{121}$ | $A^{117}$ |
| 5586. | $D^{121}$ | $A^{118}$ |
| 5587. | $D^{121}$ | $A^{119}$ |
| 5588. | $D^{121}$ | $A^{120}$ |
| 5589. | $D^{121}$ | $A^{121}$ |
| 5590. | $D^{121}$ | $A^{122}$ |
| 5591. | $D^{121}$ | $A^{123}$ |
| 5592. | $D^{121}$ | $A^{124}$ |
| 5593. | $D^{121}$ | $A^{125}$ |
| 5594. | $D^{121}$ | $A^{126}$ |
| 5595. | $D^{121}$ | $A^{127}$ |
| 5596. | $D^{121}$ | $A^{128}$ |
| 5597. | $D^{121}$ | $A^{129}$ |
| 5598. | $D^{121}$ | $A^{130}$ |
| 5599. | $D^{121}$ | $A^{131}$ |
| 5600. | $D^{121}$ | $A^{132}$ |
| 5601. | $D^{122}$ | $A^{101}$ |
| 5602. | $D^{122}$ | $A^{102}$ |
| 5603. | $D^{122}$ | $A^{103}$ |
| 5604. | $D^{122}$ | $A^{104}$ |
| 5605. | $D^{122}$ | $A^{105}$ |
| 5606. | $D^{122}$ | $A^{106}$ |
| 5607. | $D^{122}$ | $A^{107}$ |
| 5608. | $D^{122}$ | $A^{108}$ |
| 5609. | $D^{122}$ | $A^{109}$ |
| 5610. | $D^{122}$ | $A^{110}$ |
| 5611. | $D^{122}$ | $A^{111}$ |
| 5612. | $D^{122}$ | $A^{112}$ |
| 5613. | $D^{122}$ | $A^{113}$ |
| 5614. | $D^{122}$ | $A^{114}$ |
| 5615. | $D^{122}$ | $A^{115}$ |
| 5616. | $D^{122}$ | $A^{116}$ |
| 5617. | $D^{122}$ | $A^{117}$ |
| 5618. | $D^{122}$ | $A^{118}$ |
| 5619. | $D^{122}$ | $A^{119}$ |
| 5620. | $D^{122}$ | $A^{120}$ |
| 5621. | $D^{122}$ | $A^{121}$ |
| 5622. | $D^{122}$ | $A^{122}$ |
| 5623. | $D^{122}$ | $A^{123}$ |
| 5624. | $D^{122}$ | $A^{124}$ |
| 5625. | $D^{122}$ | $A^{125}$ |
| 5626. | $D^{122}$ | $A^{126}$ |
| 5627. | $D^{122}$ | $A^{127}$ |
| 5628. | $D^{122}$ | $A^{128}$ |
| 5629. | $D^{122}$ | $A^{129}$ |
| 5630. | $D^{122}$ | $A^{130}$ |
| 5631. | $D^{122}$ | $A^{131}$ |
| 5632. | $D^{122}$ | $A^{132}$ |
| 5633. | $D^{123}$ | $A^{101}$ |
| 5634. | $D^{123}$ | $A^{102}$ |
| 5635. | $D^{123}$ | $A^{103}$ |
| 5636. | $D^{123}$ | $A^{104}$ |
| 5637. | $D^{123}$ | $A^{105}$ |
| 5638. | $D^{123}$ | $A^{106}$ |
| 5639. | $D^{123}$ | $A^{107}$ |
| 5640. | $D^{123}$ | $A^{108}$ |
| 5641. | $D^{123}$ | $A^{109}$ |
| 5642. | $D^{123}$ | $A^{110}$ |
| 5643. | $D^{123}$ | $A^{111}$ |
| 5644. | $D^{123}$ | $A^{112}$ |
| 5645. | $D^{123}$ | $A^{113}$ |
| 5646. | $D^{123}$ | $A^{114}$ |
| 5647. | $D^{123}$ | $A^{115}$ |
| 5648. | $D^{123}$ | $A^{116}$ |
| 5649. | $D^{123}$ | $A^{117}$ |

168

-continued

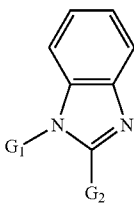

Formula III

| Compound Number | G¹ | G² |
|---|---|---|
| 5650. | $D^{123}$ | $A^{118}$ |
| 5651. | $D^{123}$ | $A^{119}$ |
| 5652. | $D^{123}$ | $A^{120}$ |
| 5653. | $D^{123}$ | $A^{121}$ |
| 5654. | $D^{123}$ | $A^{122}$ |
| 5655. | $D^{123}$ | $A^{123}$ |
| 5656. | $D^{123}$ | $A^{124}$ |
| 5657. | $D^{123}$ | $A^{125}$ |
| 5658. | $D^{123}$ | $A^{126}$ |
| 5659. | $D^{123}$ | $A^{127}$ |
| 5660. | $D^{123}$ | $A^{128}$ |
| 5661. | $D^{123}$ | $A^{129}$ |
| 5662. | $D^{123}$ | $A^{130}$ |
| 5663. | $D^{123}$ | $A^{131}$ |
| 5664. | $D^{123}$ | $A^{132}$ |
| 5665. | $D^{124}$ | $A^{101}$ |
| 5666. | $D^{124}$ | $A^{102}$ |
| 5667. | $D^{124}$ | $A^{103}$ |
| 5668. | $D^{124}$ | $A^{104}$ |
| 5669. | $D^{124}$ | $A^{105}$ |
| 5670. | $D^{124}$ | $A^{106}$ |
| 5671. | $D^{124}$ | $A^{107}$ |
| 5672. | $D^{124}$ | $A^{108}$ |
| 5673. | $D^{124}$ | $A^{109}$ |
| 5674. | $D^{124}$ | $A^{110}$ |
| 5675. | $D^{124}$ | $A^{111}$ |
| 5676. | $D^{124}$ | $A^{112}$ |
| 5677. | $D^{124}$ | $A^{113}$ |
| 5678. | $D^{124}$ | $A^{114}$ |
| 5679. | $D^{124}$ | $A^{115}$ |
| 5680. | $D^{124}$ | $A^{116}$ |
| 5681. | $D^{124}$ | $A^{117}$ |
| 5682. | $D^{124}$ | $A^{118}$ |
| 5683. | $D^{124}$ | $A^{119}$ |
| 5684. | $D^{124}$ | $A^{120}$ |
| 5685. | $D^{124}$ | $A^{121}$ |
| 5686. | $D^{124}$ | $A^{122}$ |
| 5687. | $D^{124}$ | $A^{123}$ |
| 5688. | $D^{124}$ | $A^{124}$ |
| 5689. | $D^{124}$ | $A^{125}$ |
| 5690. | $D^{124}$ | $A^{126}$ |
| 5691. | $D^{124}$ | $A^{127}$ |
| 5692. | $D^{124}$ | $A^{128}$ |
| 5693. | $D^{124}$ | $A^{129}$ |
| 5694. | $D^{124}$ | $A^{130}$ |
| 5695. | $D^{124}$ | $A^{131}$ |
| 5696. | $D^{124}$ | $A^{132}$ |
| 5697. | $D^{125}$ | $A^{101}$ |
| 5698. | $D^{125}$ | $A^{102}$ |
| 5699. | $D^{125}$ | $A^{103}$ |
| 5700. | $D^{125}$ | $A^{104}$ |
| 5701. | $D^{125}$ | $A^{105}$ |
| 5702. | $D^{125}$ | $A^{106}$ |
| 5703. | $D^{125}$ | $A^{107}$ |
| 5704. | $D^{125}$ | $A^{108}$ |
| 5705. | $D^{125}$ | $A^{109}$ |
| 5706. | $D^{125}$ | $A^{110}$ |
| 5707. | $D^{125}$ | $A^{111}$ |
| 5708. | $D^{125}$ | $A^{112}$ |
| 5709. | $D^{125}$ | $A^{113}$ |
| 5710. | $D^{125}$ | $A^{114}$ |
| 5711. | $D^{125}$ | $A^{115}$ |
| 5712. | $D^{125}$ | $A^{116}$ |
| 5713. | $D^{125}$ | $A^{117}$ |
| 5714. | $D^{125}$ | $A^{118}$ |

169
-continued

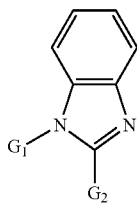

Formula III

| Compound Number | $G^1$ | $G^2$ |
|---|---|---|
| 5715. | $D^{125}$ | $A^{119}$ |
| 5716. | $D^{125}$ | $A^{120}$ |
| 5717. | $D^{125}$ | $A^{121}$ |
| 5718. | $D^{125}$ | $A^{122}$ |
| 5719. | $D^{125}$ | $A^{123}$ |
| 5720. | $D^{125}$ | $A^{124}$ |
| 5721. | $D^{125}$ | $A^{125}$ |
| 5722. | $D^{125}$ | $A^{126}$ |
| 5723. | $D^{125}$ | $A^{127}$ |
| 5724. | $D^{125}$ | $A^{128}$ |
| 5725. | $D^{125}$ | $A^{129}$ |
| 5726. | $D^{125}$ | $A^{130}$ |
| 5727. | $D^{125}$ | $A^{131}$ |
| 5728. | $D^{125}$ | $A^{132}$ |
| 5729. | $D^{126}$ | $A^{101}$ |
| 5730. | $D^{126}$ | $A^{102}$ |
| 5731. | $D^{126}$ | $A^{103}$ |
| 5732. | $D^{126}$ | $A^{104}$ |
| 5733. | $D^{126}$ | $A^{105}$ |
| 5734. | $D^{126}$ | $A^{106}$ |
| 5735. | $D^{126}$ | $A^{107}$ |
| 5736. | $D^{126}$ | $A^{108}$ |
| 5737. | $D^{126}$ | $A^{109}$ |
| 5738. | $D^{126}$ | $A^{110}$ |
| 5739. | $D^{126}$ | $A^{111}$ |
| 5740. | $D^{126}$ | $A^{112}$ |
| 5741. | $D^{126}$ | $A^{113}$ |
| 5742. | $D^{126}$ | $A^{114}$ |
| 5743. | $D^{126}$ | $A^{115}$ |
| 5744. | $D^{126}$ | $A^{116}$ |
| 5745. | $D^{126}$ | $A^{117}$ |
| 5746. | $D^{126}$ | $A^{118}$ |
| 5747. | $D^{126}$ | $A^{119}$ |
| 5748. | $D^{126}$ | $A^{120}$ |
| 5749. | $D^{126}$ | $A^{121}$ |
| 5750. | $D^{126}$ | $A^{122}$ |
| 5751. | $D^{126}$ | $A^{123}$ |
| 5752. | $D^{126}$ | $A^{124}$ |
| 5753. | $D^{126}$ | $A^{125}$ |
| 5754. | $D^{126}$ | $A^{126}$ |
| 5755. | $D^{126}$ | $A^{127}$ |
| 5756. | $D^{126}$ | $A^{128}$ |
| 5757. | $D^{126}$ | $A^{129}$ |
| 5758. | $D^{126}$ | $A^{130}$ |
| 5759. | $D^{126}$ | $A^{131}$ |
| 5760. | $D^{126}$ | $A^{132}$ |
| 5761. | $D^{127}$ | $A^{101}$ |
| 5762. | $D^{127}$ | $A^{102}$ |
| 5763. | $D^{127}$ | $A^{103}$ |
| 5764. | $D^{127}$ | $A^{104}$ |
| 5765. | $D^{127}$ | $A^{105}$ |
| 5766. | $D^{127}$ | $A^{106}$ |
| 5767. | $D^{127}$ | $A^{107}$ |
| 5768. | $D^{127}$ | $A^{108}$ |
| 5769. | $D^{127}$ | $A^{109}$ |
| 5770. | $D^{127}$ | $A^{110}$ |
| 5771. | $D^{127}$ | $A^{111}$ |
| 5772. | $D^{127}$ | $A^{112}$ |
| 5773. | $D^{127}$ | $A^{113}$ |
| 5774. | $D^{127}$ | $A^{114}$ |
| 5775. | $D^{127}$ | $A^{115}$ |
| 5776. | $D^{127}$ | $A^{116}$ |
| 5777. | $D^{127}$ | $A^{117}$ |
| 5778. | $D^{127}$ | $A^{118}$ |
| 5779. | $D^{127}$ | $A^{119}$ |

170
-continued

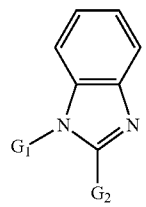

Formula III

| Compound Number | $G^1$ | $G^2$ |
|---|---|---|
| 5780. | $D^{127}$ | $A^{120}$ |
| 5781. | $D^{127}$ | $A^{121}$ |
| 5782. | $D^{127}$ | $A^{122}$ |
| 5783. | $D^{127}$ | $A^{123}$ |
| 5784. | $D^{127}$ | $A^{124}$ |
| 5785. | $D^{127}$ | $A^{125}$ |
| 5786. | $D^{127}$ | $A^{126}$ |
| 5787. | $D^{127}$ | $A^{127}$ |
| 5788. | $D^{127}$ | $A^{128}$ |
| 5789. | $D^{127}$ | $A^{129}$ |
| 5790. | $D^{127}$ | $A^{130}$ |
| 5791. | $D^{127}$ | $A^{131}$ |
| 5792. | $D^{127}$ | $A^{132}$ |
| 5793. | $D^{128}$ | $A^{101}$ |
| 5794. | $D^{128}$ | $A^{102}$ |
| 5795. | $D^{128}$ | $A^{103}$ |
| 5796. | $D^{128}$ | $A^{104}$ |
| 5797. | $D^{128}$ | $A^{105}$ |
| 5798. | $D^{128}$ | $A^{106}$ |
| 5799. | $D^{128}$ | $A^{107}$ |
| 5800. | $D^{128}$ | $A^{108}$ |
| 5801. | $D^{128}$ | $A^{109}$ |
| 5802. | $D^{128}$ | $A^{110}$ |
| 5803. | $D^{128}$ | $A^{111}$ |
| 5804. | $D^{128}$ | $A^{112}$ |
| 5805. | $D^{128}$ | $A^{113}$ |
| 5806. | $D^{128}$ | $A^{114}$ |
| 5807. | $D^{128}$ | $A^{115}$ |
| 5808. | $D^{128}$ | $A^{116}$ |
| 5809. | $D^{128}$ | $A^{117}$ |
| 5810. | $D^{128}$ | $A^{118}$ |
| 5811. | $D^{128}$ | $A^{119}$ |
| 5812. | $D^{128}$ | $A^{120}$ |
| 5813. | $D^{128}$ | $A^{121}$ |
| 5814. | $D^{128}$ | $A^{122}$ |
| 5815. | $D^{128}$ | $A^{123}$ |
| 5816. | $D^{128}$ | $A^{124}$ |
| 5817. | $D^{128}$ | $A^{125}$ |
| 5818. | $D^{128}$ | $A^{126}$ |
| 5819. | $D^{128}$ | $A^{127}$ |
| 5820. | $D^{128}$ | $A^{128}$ |
| 5821. | $D^{128}$ | $A^{129}$ |
| 5822. | $D^{128}$ | $A^{130}$ |
| 5823. | $D^{128}$ | $A^{131}$ |
| 5824. | $D^{128}$ | $A^{132}$ |
| 5825. | $D^{129}$ | $A^{101}$ |
| 5826. | $D^{129}$ | $A^{102}$ |
| 5827. | $D^{129}$ | $A^{103}$ |
| 5828. | $D^{129}$ | $A^{104}$ |
| 5829. | $D^{129}$ | $A^{105}$ |
| 5830. | $D^{129}$ | $A^{106}$ |
| 5831. | $D^{129}$ | $A^{107}$ |
| 5832. | $D^{129}$ | $A^{108}$ |
| 5833. | $D^{129}$ | $A^{109}$ |
| 5834. | $D^{129}$ | $A^{110}$ |
| 5835. | $D^{129}$ | $A^{111}$ |
| 5836. | $D^{129}$ | $A^{112}$ |
| 5837. | $D^{129}$ | $A^{113}$ |
| 5838. | $D^{129}$ | $A^{114}$ |
| 5839. | $D^{129}$ | $A^{115}$ |
| 5840. | $D^{129}$ | $A^{116}$ |
| 5841. | $D^{129}$ | $A^{117}$ |
| 5842. | $D^{129}$ | $A^{118}$ |
| 5843. | $D^{129}$ | $A^{119}$ |
| 5844. | $D^{129}$ | $A^{120}$ |

171
-continued

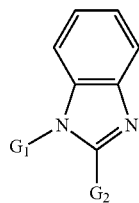

Formula III

| Compound Number | G¹ | G² |
|---|---|---|
| 5845. | $D^{129}$ | $A^{121}$ |
| 5846. | $D^{129}$ | $A^{122}$ |
| 5847. | $D^{129}$ | $A^{123}$ |
| 5848. | $D^{129}$ | $A^{124}$ |
| 5849. | $D^{129}$ | $A^{125}$ |
| 5850. | $D^{129}$ | $A^{126}$ |
| 5851. | $D^{129}$ | $A^{127}$ |
| 5852. | $D^{129}$ | $A^{128}$ |
| 5853. | $D^{129}$ | $A^{129}$ |
| 5854. | $D^{129}$ | $A^{130}$ |
| 5855. | $D^{129}$ | $A^{131}$ |
| 5856. | $D^{129}$ | $A^{132}$ |
| 5857. | $D^{130}$ | $A^{101}$ |
| 5858. | $D^{130}$ | $A^{102}$ |
| 5859. | $D^{130}$ | $A^{103}$ |
| 5860. | $D^{130}$ | $A^{104}$ |
| 5861. | $D^{130}$ | $A^{105}$ |
| 5862. | $D^{130}$ | $A^{106}$ |
| 5863. | $D^{130}$ | $A^{107}$ |
| 5864. | $D^{130}$ | $A^{108}$ |
| 5865. | $D^{130}$ | $A^{109}$ |
| 5866. | $D^{130}$ | $A^{110}$ |
| 5867. | $D^{130}$ | $A^{111}$ |
| 5868. | $D^{130}$ | $A^{112}$ |
| 5869. | $D^{130}$ | $A^{113}$ |
| 5870. | $D^{130}$ | $A^{114}$ |
| 5871. | $D^{130}$ | $A^{115}$ |
| 5872. | $D^{130}$ | $A^{116}$ |
| 5873. | $D^{130}$ | $A^{117}$ |
| 5874. | $D^{130}$ | $A^{118}$ |
| 5875. | $D^{130}$ | $A^{119}$ |
| 5876. | $D^{130}$ | $A^{120}$ |
| 5877. | $D^{130}$ | $A^{121}$ |
| 5878. | $D^{130}$ | $A^{122}$ |
| 5879. | $D^{130}$ | $A^{123}$ |
| 5880. | $D^{130}$ | $A^{124}$ |
| 5881. | $D^{130}$ | $A^{125}$ |
| 5882. | $D^{130}$ | $A^{126}$ |
| 5883. | $D^{130}$ | $A^{127}$ |
| 5884. | $D^{130}$ | $A^{128}$ |
| 5885. | $D^{130}$ | $A^{129}$ |
| 5886. | $D^{130}$ | $A^{130}$ |
| 5887. | $D^{130}$ | $A^{131}$ |
| 5888. | $D^{130}$ | $A^{132}$ |
| 5889. | $D^{131}$ | $A^{101}$ |
| 5890. | $D^{131}$ | $A^{102}$ |
| 5891. | $D^{131}$ | $A^{103}$ |
| 5892. | $D^{131}$ | $A^{104}$ |
| 5893. | $D^{131}$ | $A^{105}$ |
| 5894. | $D^{131}$ | $A^{106}$ |
| 5895. | $D^{131}$ | $A^{107}$ |
| 5896. | $D^{131}$ | $A^{108}$ |
| 5897. | $D^{131}$ | $A^{109}$ |
| 5898. | $D^{131}$ | $A^{110}$ |
| 5899. | $D^{131}$ | $A^{111}$ |
| 5900. | $D^{131}$ | $A^{112}$ |
| 5901. | $D^{131}$ | $A^{113}$ |
| 5902. | $D^{131}$ | $A^{114}$ |
| 5903. | $D^{131}$ | $A^{115}$ |
| 5904. | $D^{131}$ | $A^{116}$ |
| 5905. | $D^{131}$ | $A^{117}$ |
| 5906. | $D^{131}$ | $A^{118}$ |
| 5907. | $D^{131}$ | $A^{119}$ |
| 5908. | $D^{131}$ | $A^{120}$ |
| 5909. | $D^{131}$ | $A^{121}$ |

172
-continued

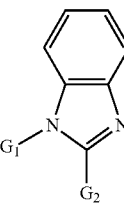

Formula III

| Compound Number | G¹ | G² |
|---|---|---|
| 5910. | $D^{131}$ | $A^{122}$ |
| 5911. | $D^{131}$ | $A^{123}$ |
| 5912. | $D^{131}$ | $A^{124}$ |
| 5913. | $D^{131}$ | $A^{125}$ |
| 5914. | $D^{131}$ | $A^{126}$ |
| 5915. | $D^{131}$ | $A^{127}$ |
| 5916. | $D^{131}$ | $A^{128}$ |
| 5917. | $D^{131}$ | $A^{129}$ |
| 5918. | $D^{131}$ | $A^{130}$ |
| 5919. | $D^{131}$ | $A^{131}$ |
| 5920. | $D^{131}$ | $A^{132}$ |
| 5921. | $D^{132}$ | $A^{101}$ |
| 5922. | $D^{132}$ | $A^{102}$ |
| 5923. | $D^{132}$ | $A^{103}$ |
| 5924. | $D^{132}$ | $A^{104}$ |
| 5925. | $D^{132}$ | $A^{105}$ |
| 5926. | $D^{132}$ | $A^{106}$ |
| 5927. | $D^{132}$ | $A^{107}$ |
| 5928. | $D^{132}$ | $A^{108}$ |
| 5929. | $D^{132}$ | $A^{109}$ |
| 5930. | $D^{132}$ | $A^{110}$ |
| 5931. | $D^{132}$ | $A^{111}$ |
| 5932. | $D^{132}$ | $A^{112}$ |
| 5933. | $D^{132}$ | $A^{113}$ |
| 5934. | $D^{132}$ | $A^{114}$ |
| 5935. | $D^{132}$ | $A^{115}$ |
| 5936. | $D^{132}$ | $A^{116}$ |
| 5937. | $D^{132}$ | $A^{117}$ |
| 5938. | $D^{132}$ | $A^{118}$ |
| 5939. | $D^{132}$ | $A^{119}$ |
| 5940. | $D^{132}$ | $A^{120}$ |
| 5941. | $D^{132}$ | $A^{121}$ |
| 5942. | $D^{132}$ | $A^{122}$ |
| 5943. | $D^{132}$ | $A^{123}$ |
| 5944. | $D^{132}$ | $A^{124}$ |
| 5945. | $D^{132}$ | $A^{125}$ |
| 5946. | $D^{132}$ | $A^{126}$ |
| 5947. | $D^{132}$ | $A^{127}$ |
| 5948. | $D^{132}$ | $A^{128}$ |
| 5949. | $D^{132}$ | $A^{129}$ |
| 5950. | $D^{132}$ | $A^{130}$ |
| 5951. | $D^{132}$ | $A^{131}$ |
| 5952. | $D^{132}$ | $A^{132}$ |
| 5953. | $D^{133}$ | $A^{101}$ |
| 5954. | $D^{133}$ | $A^{102}$ |
| 5955. | $D^{133}$ | $A^{103}$ |
| 5956. | $D^{133}$ | $A^{104}$ |
| 5957. | $D^{133}$ | $A^{105}$ |
| 5958. | $D^{133}$ | $A^{106}$ |
| 5959. | $D^{133}$ | $A^{107}$ |
| 5960. | $D^{133}$ | $A^{108}$ |
| 5961. | $D^{133}$ | $A^{109}$ |
| 5962. | $D^{133}$ | $A^{110}$ |
| 5963. | $D^{133}$ | $A^{111}$ |
| 5964. | $D^{133}$ | $A^{112}$ |
| 5965. | $D^{133}$ | $A^{113}$ |
| 5966. | $D^{133}$ | $A^{114}$ |
| 5967. | $D^{133}$ | $A^{115}$ |
| 5968. | $D^{133}$ | $A^{116}$ |
| 5969. | $D^{133}$ | $A^{117}$ |
| 5970. | $D^{133}$ | $A^{118}$ |
| 5971. | $D^{133}$ | $A^{119}$ |
| 5972. | $D^{133}$ | $A^{120}$ |
| 5973. | $D^{133}$ | $A^{121}$ |
| 5974. | $D^{133}$ | $A^{122}$ |

173
-continued

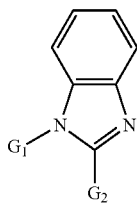

Formula III

| Compound Number | G¹ | G² |
|---|---|---|
| 5975. | $D^{133}$ | $A^{123}$ |
| 5976. | $D^{133}$ | $A^{124}$ |
| 5977. | $D^{133}$ | $A^{125}$ |
| 5978. | $D^{133}$ | $A^{126}$ |
| 5979. | $D^{133}$ | $A^{127}$ |
| 5980. | $D^{133}$ | $A^{128}$ |
| 5981. | $D^{133}$ | $A^{129}$ |
| 5982. | $D^{133}$ | $A^{130}$ |
| 5983. | $D^{133}$ | $A^{131}$ |
| 5984. | $D^{133}$ | $A^{132}$ |
| 5985. | $D^{134}$ | $A^{101}$ |
| 5986. | $D^{134}$ | $A^{102}$ |
| 5987. | $D^{134}$ | $A^{103}$ |
| 5988. | $D^{134}$ | $A^{104}$ |
| 5989. | $D^{134}$ | $A^{105}$ |
| 5990. | $D^{134}$ | $A^{106}$ |
| 5991. | $D^{134}$ | $A^{107}$ |
| 5992. | $D^{134}$ | $A^{108}$ |
| 5993. | $D^{134}$ | $A^{109}$ |
| 5994. | $D^{134}$ | $A^{110}$ |
| 5995. | $D^{134}$ | $A^{111}$ |
| 5996. | $D^{134}$ | $A^{112}$ |
| 5997. | $D^{134}$ | $A^{113}$ |
| 5998. | $D^{134}$ | $A^{114}$ |
| 5999. | $D^{134}$ | $A^{115}$ |
| 6000. | $D^{134}$ | $A^{116}$ |
| 6001. | $D^{134}$ | $A^{117}$ |
| 6002. | $D^{134}$ | $A^{118}$ |
| 6003. | $D^{134}$ | $A^{119}$ |
| 6004. | $D^{134}$ | $A^{120}$ |
| 6005. | $D^{134}$ | $A^{121}$ |
| 6006. | $D^{134}$ | $A^{122}$ |
| 6007. | $D^{134}$ | $A^{123}$ |
| 6008. | $D^{134}$ | $A^{124}$ |
| 6009. | $D^{134}$ | $A^{125}$ |
| 6010. | $D^{134}$ | $A^{126}$ |
| 6011. | $D^{134}$ | $A^{127}$ |
| 6012. | $D^{134}$ | $A^{128}$ |
| 6013. | $D^{134}$ | $A^{129}$ |
| 6014. | $D^{134}$ | $A^{130}$ |
| 6015. | $D^{134}$ | $A^{131}$ |
| 6016. | $D^{134}$ | $A^{132}$ |
| 6017. | $D^{135}$ | $A^{101}$ |
| 6018. | $D^{135}$ | $A^{102}$ |
| 6019. | $D^{135}$ | $A^{103}$ |
| 6020. | $D^{135}$ | $A^{104}$ |
| 6021. | $D^{135}$ | $A^{105}$ |
| 6022. | $D^{135}$ | $A^{106}$ |
| 6023. | $D^{135}$ | $A^{107}$ |
| 6024. | $D^{135}$ | $A^{108}$ |
| 6025. | $D^{135}$ | $A^{109}$ |
| 6026. | $D^{135}$ | $A^{110}$ |
| 6027. | $D^{135}$ | $A^{111}$ |
| 6028. | $D^{135}$ | $A^{112}$ |
| 6029. | $D^{135}$ | $A^{113}$ |
| 6030. | $D^{135}$ | $A^{114}$ |
| 6031. | $D^{135}$ | $A^{115}$ |
| 6032. | $D^{135}$ | $A^{116}$ |
| 6033. | $D^{135}$ | $A^{117}$ |
| 6034. | $D^{135}$ | $A^{118}$ |
| 6035. | $D^{135}$ | $A^{119}$ |
| 6036. | $D^{135}$ | $A^{120}$ |
| 6037. | $D^{135}$ | $A^{121}$ |
| 6038. | $D^{135}$ | $A^{122}$ |
| 6039. | $D^{135}$ | $A^{123}$ |

174
-continued

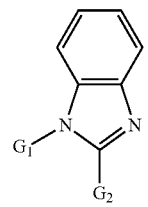

Formula III

| Compound Number | G¹ | G² |
|---|---|---|
| 6040. | $D^{135}$ | $A^{124}$ |
| 6041. | $D^{135}$ | $A^{125}$ |
| 6042. | $D^{135}$ | $A^{126}$ |
| 6043. | $D^{135}$ | $A^{127}$ |
| 6044. | $D^{135}$ | $A^{128}$ |
| 6045. | $D^{135}$ | $A^{129}$ |
| 6046. | $D^{135}$ | $A^{130}$ |
| 6047. | $D^{135}$ | $A^{131}$ |
| 6048. | $D^{135}$ | $A^{132}$ |
| 6049. | $D^{136}$ | $A^{101}$ |
| 6050. | $D^{136}$ | $A^{102}$ |
| 6051. | $D^{136}$ | $A^{103}$ |
| 6052. | $D^{136}$ | $A^{104}$ |
| 6053. | $D^{136}$ | $A^{105}$ |
| 6054. | $D^{136}$ | $A^{106}$ |
| 6055. | $D^{136}$ | $A^{107}$ |
| 6056. | $D^{136}$ | $A^{108}$ |
| 6057. | $D^{136}$ | $A^{109}$ |
| 6058. | $D^{136}$ | $A^{110}$ |
| 6059. | $D^{136}$ | $A^{111}$ |
| 6060. | $D^{136}$ | $A^{112}$ |
| 6061. | $D^{136}$ | $A^{113}$ |
| 6062. | $D^{136}$ | $A^{114}$ |
| 6063. | $D^{136}$ | $A^{115}$ |
| 6064. | $D^{136}$ | $A^{116}$ |
| 6065. | $D^{136}$ | $A^{117}$ |
| 6066. | $D^{136}$ | $A^{118}$ |
| 6067. | $D^{136}$ | $A^{119}$ |
| 6068. | $D^{136}$ | $A^{120}$ |
| 6069. | $D^{136}$ | $A^{121}$ |
| 6070. | $D^{136}$ | $A^{122}$ |
| 6071. | $D^{136}$ | $A^{123}$ |
| 6072. | $D^{136}$ | $A^{124}$ |
| 6073. | $D^{136}$ | $A^{125}$ |
| 6074. | $D^{136}$ | $A^{126}$ |
| 6075. | $D^{136}$ | $A^{127}$ |
| 6076. | $D^{136}$ | $A^{128}$ |
| 6077. | $D^{136}$ | $A^{129}$ |
| 6078. | $D^{136}$ | $A^{130}$ |
| 6079. | $D^{136}$ | $A^{131}$ |
| 6080. | $D^{136}$ | $A^{132}$ |
| 6081. | $D^{137}$ | $A^{101}$ |
| 6082. | $D^{137}$ | $A^{102}$ |
| 6083. | $D^{137}$ | $A^{103}$ |
| 6084. | $D^{137}$ | $A^{104}$ |
| 6085. | $D^{137}$ | $A^{105}$ |
| 6086. | $D^{137}$ | $A^{106}$ |
| 6087. | $D^{137}$ | $A^{107}$ |
| 6088. | $D^{137}$ | $A^{108}$ |
| 6089. | $D^{137}$ | $A^{109}$ |
| 6090. | $D^{137}$ | $A^{110}$ |
| 6091. | $D^{137}$ | $A^{111}$ |
| 6092. | $D^{137}$ | $A^{112}$ |
| 6093. | $D^{137}$ | $A^{113}$ |
| 6094. | $D^{137}$ | $A^{114}$ |
| 6095. | $D^{137}$ | $A^{115}$ |
| 6096. | $D^{137}$ | $A^{116}$ |
| 6097. | $D^{137}$ | $A^{117}$ |
| 6098. | $D^{137}$ | $A^{118}$ |
| 6099. | $D^{137}$ | $A^{119}$ |
| 6100. | $D^{137}$ | $A^{120}$ |
| 6101. | $D^{137}$ | $A^{121}$ |
| 6102. | $D^{137}$ | $A^{122}$ |
| 6103. | $D^{137}$ | $A^{123}$ |
| 6104. | $D^{137}$ | $A^{124}$ |

175
-continued

Formula III

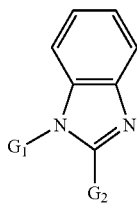

| Compound Number | G¹ | G² |
|---|---|---|
| 6105. | $D^{137}$ | $A^{125}$ |
| 6106. | $D^{137}$ | $A^{126}$ |
| 6107. | $D^{137}$ | $A^{127}$ |
| 6108. | $D^{137}$ | $A^{128}$ |
| 6109. | $D^{137}$ | $A^{129}$ |
| 6110. | $D^{137}$ | $A^{130}$ |
| 6111. | $D^{137}$ | $A^{131}$ |
| 6112. | $D^{137}$ | $A^{132}$ |
| 6113. | $D^{138}$ | $A^{101}$ |
| 6114. | $D^{138}$ | $A^{102}$ |
| 6115. | $D^{138}$ | $A^{103}$ |
| 6116. | $D^{138}$ | $A^{104}$ |
| 6117. | $D^{138}$ | $A^{105}$ |
| 6118. | $D^{138}$ | $A^{106}$ |
| 6119. | $D^{138}$ | $A^{107}$ |
| 6120. | $D^{138}$ | $A^{108}$ |
| 6121. | $D^{138}$ | $A^{109}$ |
| 6122. | $D^{138}$ | $A^{110}$ |
| 6123. | $D^{138}$ | $A^{111}$ |
| 6124. | $D^{138}$ | $A^{112}$ |
| 6125. | $D^{138}$ | $A^{113}$ |
| 6126. | $D^{138}$ | $A^{114}$ |
| 6127. | $D^{138}$ | $A^{115}$ |
| 6128. | $D^{138}$ | $A^{116}$ |
| 6129. | $D^{138}$ | $A^{117}$ |
| 6130. | $D^{138}$ | $A^{118}$ |
| 6131. | $D^{138}$ | $A^{119}$ |
| 6132. | $D^{138}$ | $A^{120}$ |
| 6133. | $D^{138}$ | $A^{121}$ |
| 6134. | $D^{138}$ | $A^{122}$ |
| 6135. | $D^{138}$ | $A^{123}$ |
| 6136. | $D^{138}$ | $A^{124}$ |
| 6137. | $D^{138}$ | $A^{125}$ |
| 6138. | $D^{138}$ | $A^{126}$ |
| 6139. | $D^{138}$ | $A^{127}$ |
| 6140. | $D^{138}$ | $A^{128}$ |
| 6141. | $D^{138}$ | $A^{129}$ |
| 6142. | $D^{138}$ | $A^{130}$ |
| 6143. | $D^{138}$ | $A^{131}$ |
| 6144. | $D^{138}$ | $A^{132}$ |
| 6145. | $D^{139}$ | $A^{101}$ |
| 6146. | $D^{139}$ | $A^{102}$ |
| 6147. | $D^{139}$ | $A^{103}$ |
| 6148. | $D^{139}$ | $A^{104}$ |
| 6149. | $D^{139}$ | $A^{105}$ |
| 6150. | $D^{139}$ | $A^{106}$ |
| 6151. | $D^{139}$ | $A^{107}$ |
| 6152. | $D^{139}$ | $A^{108}$ |
| 6153. | $D^{139}$ | $A^{109}$ |
| 6154. | $D^{139}$ | $A^{110}$ |
| 6155. | $D^{139}$ | $A^{111}$ |
| 6156. | $D^{139}$ | $A^{112}$ |
| 6157. | $D^{139}$ | $A^{113}$ |
| 6158. | $D^{139}$ | $A^{114}$ |
| 6159. | $D^{139}$ | $A^{115}$ |
| 6160. | $D^{139}$ | $A^{116}$ |
| 6161. | $D^{139}$ | $A^{117}$ |
| 6162. | $D^{139}$ | $A^{118}$ |
| 6163. | $D^{139}$ | $A^{119}$ |
| 6164. | $D^{139}$ | $A^{120}$ |
| 6165. | $D^{139}$ | $A^{121}$ |
| 6166. | $D^{139}$ | $A^{122}$ |
| 6167. | $D^{139}$ | $A^{123}$ |
| 6168. | $D^{139}$ | $A^{124}$ |
| 6169. | $D^{139}$ | $A^{125}$ |

176
-continued

Formula III

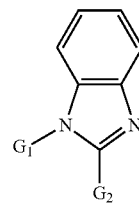

| Compound Number | G¹ | G² |
|---|---|---|
| 6170. | $D^{139}$ | $A^{126}$ |
| 6171. | $D^{139}$ | $A^{127}$ |
| 6172. | $D^{139}$ | $A^{128}$ |
| 6173. | $D^{139}$ | $A^{129}$ |
| 6174. | $D^{139}$ | $A^{130}$ |
| 6175. | $D^{139}$ | $A^{131}$ |
| 6176. | $D^{139}$ | $A^{132}$ |
| 6177. | $D^{140}$ | $A^{101}$ |
| 6178. | $D^{140}$ | $A^{102}$ |
| 6179. | $D^{140}$ | $A^{103}$ |
| 6180. | $D^{140}$ | $A^{104}$ |
| 6181. | $D^{140}$ | $A^{105}$ |
| 6182. | $D^{140}$ | $A^{106}$ |
| 6183. | $D^{140}$ | $A^{107}$ |
| 6184. | $D^{140}$ | $A^{108}$ |
| 6185. | $D^{140}$ | $A^{109}$ |
| 6186. | $D^{140}$ | $A^{110}$ |
| 6187. | $D^{140}$ | $A^{111}$ |
| 6188. | $D^{140}$ | $A^{112}$ |
| 6189. | $D^{140}$ | $A^{113}$ |
| 6190. | $D^{140}$ | $A^{114}$ |
| 6191. | $D^{140}$ | $A^{115}$ |
| 6192. | $D^{140}$ | $A^{116}$ |
| 6193. | $D^{140}$ | $A^{117}$ |
| 6194. | $D^{140}$ | $A^{118}$ |
| 6195. | $D^{140}$ | $A^{119}$ |
| 6196. | $D^{140}$ | $A^{120}$ |
| 6197. | $D^{140}$ | $A^{121}$ |
| 6198. | $D^{140}$ | $A^{122}$ |
| 6199. | $D^{140}$ | $A^{123}$ |
| 6200. | $D^{140}$ | $A^{124}$ |
| 6201. | $D^{140}$ | $A^{125}$ |
| 6202. | $D^{140}$ | $A^{126}$ |
| 6203. | $D^{140}$ | $A^{127}$ |
| 6204. | $D^{140}$ | $A^{128}$ |
| 6205. | $D^{140}$ | $A^{129}$ |
| 6206. | $D^{140}$ | $A^{130}$ |
| 6207. | $D^{140}$ | $A^{131}$ |
| 6208. | $D^{140}$ | $A^{132}$ |
| 6209. | $D^{141}$ | $A^{101}$ |
| 6210. | $D^{141}$ | $A^{102}$ |
| 6211. | $D^{141}$ | $A^{103}$ |
| 6212. | $D^{141}$ | $A^{104}$ |
| 6213. | $D^{141}$ | $A^{105}$ |
| 6214. | $D^{141}$ | $A^{106}$ |
| 6215. | $D^{141}$ | $A^{107}$ |
| 6216. | $D^{141}$ | $A^{108}$ |
| 6217. | $D^{141}$ | $A^{109}$ |
| 6218. | $D^{141}$ | $A^{110}$ |
| 6219. | $D^{141}$ | $A^{111}$ |
| 6220. | $D^{141}$ | $A^{112}$ |
| 6221. | $D^{141}$ | $A^{113}$ |
| 6222. | $D^{141}$ | $A^{114}$ |
| 6223. | $D^{141}$ | $A^{115}$ |
| 6224. | $D^{141}$ | $A^{116}$ |
| 6225. | $D^{141}$ | $A^{117}$ |
| 6226. | $D^{141}$ | $A^{118}$ |
| 6227. | $D^{141}$ | $A^{119}$ |
| 6228. | $D^{141}$ | $A^{120}$ |
| 6229. | $D^{141}$ | $A^{121}$ |
| 6230. | $D^{141}$ | $A^{122}$ |
| 6231. | $D^{141}$ | $A^{123}$ |
| 6232. | $D^{141}$ | $A^{124}$ |
| 6233. | $D^{141}$ | $A^{125}$ |
| 6234. | $D^{141}$ | $A^{126}$ |

177
-continued

Formula III

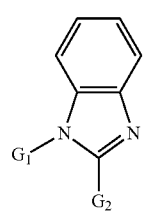

| Compound Number | G¹ | G² |
|---|---|---|
| 6235. | $D^{141}$ | $A^{127}$ |
| 6236. | $D^{141}$ | $A^{128}$ |
| 6237. | $D^{141}$ | $A^{129}$ |
| 6238. | $D^{141}$ | $A^{130}$ |
| 6239. | $D^{141}$ | $A^{131}$ |
| 6240. | $D^{141}$ | $A^{132}$ |
| 6241. | $D^{142}$ | $A^{101}$ |
| 6242. | $D^{142}$ | $A^{102}$ |
| 6243. | $D^{142}$ | $A^{103}$ |
| 6244. | $D^{142}$ | $A^{104}$ |
| 6245. | $D^{142}$ | $A^{105}$ |
| 6246. | $D^{142}$ | $A^{106}$ |
| 6247. | $D^{142}$ | $A^{107}$ |
| 6248. | $D^{142}$ | $A^{108}$ |
| 6249. | $D^{142}$ | $A^{109}$ |
| 6250. | $D^{142}$ | $A^{110}$ |
| 6251. | $D^{142}$ | $A^{111}$ |
| 6252. | $D^{142}$ | $A^{112}$ |
| 6253. | $D^{142}$ | $A^{113}$ |
| 6254. | $D^{142}$ | $A^{114}$ |
| 6255. | $D^{142}$ | $A^{115}$ |
| 6256. | $D^{142}$ | $A^{116}$ |
| 6257. | $D^{142}$ | $A^{117}$ |
| 6258. | $D^{142}$ | $A^{118}$ |
| 6259. | $D^{142}$ | $A^{119}$ |
| 6260. | $D^{142}$ | $A^{120}$ |
| 6261. | $D^{142}$ | $A^{121}$ |
| 6262. | $D^{142}$ | $A^{122}$ |
| 6263. | $D^{142}$ | $A^{123}$ |
| 6264. | $D^{142}$ | $A^{124}$ |
| 6265. | $D^{142}$ | $A^{125}$ |
| 6266. | $D^{142}$ | $A^{126}$ |
| 6267. | $D^{142}$ | $A^{127}$ |
| 6268. | $D^{142}$ | $A^{128}$ |
| 6269. | $D^{142}$ | $A^{129}$ |
| 6270. | $D^{142}$ | $A^{130}$ |
| 6271. | $D^{142}$ | $A^{131}$ |
| 6272. | $D^{142}$ | $A^{132}$ |
| 6273. | $D^{143}$ | $A^{101}$ |
| 6274. | $D^{143}$ | $A^{102}$ |
| 6275. | $D^{143}$ | $A^{103}$ |
| 6276. | $D^{143}$ | $A^{104}$ |
| 6277. | $D^{143}$ | $A^{105}$ |
| 6278. | $D^{143}$ | $A^{106}$ |
| 6279. | $D^{143}$ | $A^{107}$ |
| 6280. | $D^{143}$ | $A^{108}$ |
| 6281. | $D^{143}$ | $A^{109}$ |
| 6282. | $D^{143}$ | $A^{110}$ |
| 6283. | $D^{143}$ | $A^{111}$ |
| 6284. | $D^{143}$ | $A^{112}$ |
| 6285. | $D^{143}$ | $A^{113}$ |
| 6286. | $D^{143}$ | $A^{114}$ |
| 6287. | $D^{143}$ | $A^{115}$ |
| 6288. | $D^{143}$ | $A^{116}$ |
| 6289. | $D^{143}$ | $A^{117}$ |
| 6290. | $D^{143}$ | $A^{118}$ |
| 6291. | $D^{143}$ | $A^{119}$ |
| 6292. | $D^{143}$ | $A^{120}$ |
| 6293. | $D^{143}$ | $A^{121}$ |
| 6294. | $D^{143}$ | $A^{122}$ |
| 6295. | $D^{143}$ | $A^{123}$ |
| 6296. | $D^{143}$ | $A^{124}$ |
| 6297. | $D^{143}$ | $A^{125}$ |
| 6298. | $D^{143}$ | $A^{126}$ |
| 6299. | $D^{143}$ | $A^{127}$ |

178
-continued

Formula III

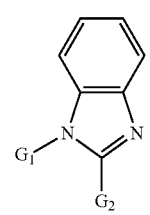

| Compound Number | G¹ | G² |
|---|---|---|
| 6300. | $D^{143}$ | $A^{128}$ |
| 6301. | $D^{143}$ | $A^{129}$ |
| 6302. | $D^{143}$ | $A^{130}$ |
| 6303. | $D^{143}$ | $A^{131}$ |
| 6304. | $D^{143}$ | $A^{132}$ |
| 6305. | $D^{144}$ | $A^{101}$ |
| 6306. | $D^{144}$ | $A^{102}$ |
| 6307. | $D^{144}$ | $A^{103}$ |
| 6308. | $D^{144}$ | $A^{104}$ |
| 6309. | $D^{144}$ | $A^{105}$ |
| 6310. | $D^{144}$ | $A^{106}$ |
| 6311. | $D^{144}$ | $A^{107}$ |
| 6312. | $D^{144}$ | $A^{108}$ |
| 6313. | $D^{144}$ | $A^{109}$ |
| 6314. | $D^{144}$ | $A^{110}$ |
| 6315. | $D^{144}$ | $A^{111}$ |
| 6316. | $D^{144}$ | $A^{112}$ |
| 6317. | $D^{144}$ | $A^{113}$ |
| 6318. | $D^{144}$ | $A^{114}$ |
| 6319. | $D^{144}$ | $A^{115}$ |
| 6320. | $D^{144}$ | $A^{116}$ |
| 6321. | $D^{144}$ | $A^{117}$ |
| 6322. | $D^{144}$ | $A^{118}$ |
| 6323. | $D^{144}$ | $A^{119}$ |
| 6324. | $D^{144}$ | $A^{120}$ |
| 6325. | $D^{144}$ | $A^{121}$ |
| 6326. | $D^{144}$ | $A^{122}$ |
| 6327. | $D^{144}$ | $A^{123}$ |
| 6328. | $D^{144}$ | $A^{124}$ |
| 6329. | $D^{144}$ | $A^{125}$ |
| 6330. | $D^{144}$ | $A^{126}$ |
| 6331. | $D^{144}$ | $A^{127}$ |
| 6332. | $D^{144}$ | $A^{128}$ |
| 6333. | $D^{144}$ | $A^{129}$ |
| 6334. | $D^{144}$ | $A^{130}$ |
| 6335. | $D^{144}$ | $A^{131}$ |
| 6336. | $D^{144}$ | $A^{132}$ |
| 6337. | $D^{155}$ | $A^{101}$ |
| 6338. | $D^{155}$ | $A^{102}$ |
| 6339. | $D^{155}$ | $A^{103}$ |
| 6340. | $D^{155}$ | $A^{104}$ |
| 6341. | $D^{155}$ | $A^{105}$ |
| 6342. | $D^{155}$ | $A^{106}$ |
| 6343. | $D^{155}$ | $A^{107}$ |
| 6344. | $D^{155}$ | $A^{108}$ |
| 6345. | $D^{155}$ | $A^{109}$ |
| 6346. | $D^{155}$ | $A^{110}$ |
| 6347. | $D^{155}$ | $A^{111}$ |
| 6348. | $D^{155}$ | $A^{112}$ |
| 6349. | $D^{155}$ | $A^{113}$ |
| 6350. | $D^{155}$ | $A^{114}$ |
| 6351. | $D^{155}$ | $A^{115}$ |
| 6352. | $D^{155}$ | $A^{116}$ |
| 6353. | $D^{155}$ | $A^{117}$ |
| 6354. | $D^{155}$ | $A^{118}$ |
| 6355. | $D^{155}$ | $A^{119}$ |
| 6356. | $D^{155}$ | $A^{120}$ |
| 6357. | $D^{155}$ | $A^{121}$ |
| 6358. | $D^{155}$ | $A^{122}$ |
| 6359. | $D^{155}$ | $A^{123}$ |
| 6360. | $D^{155}$ | $A^{124}$ |
| 6361. | $D^{155}$ | $A^{125}$ |
| 6362. | $D^{155}$ | $A^{126}$ |
| 6363. | $D^{155}$ | $A^{127}$ |
| 6364. | $D^{155}$ | $A^{128}$ |

Formula III

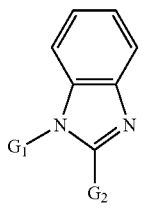

| Compound Number | $G^1$ | $G^2$ |
|---|---|---|
| 6365. | $D^{155}$ | $A^{129}$ |
| 6366. | $D^{155}$ | $A^{130}$ |
| 6367. | $D^{155}$ | $A^{131}$ |
| 6368. | $D^{155}$ | $A^{132}$ |
| 6369. | $D^{156}$ | $A^{101}$ |
| 6370. | $D^{156}$ | $A^{102}$ |
| 6371. | $D^{156}$ | $A^{103}$ |
| 6372. | $D^{156}$ | $A^{104}$ |
| 6373. | $D^{156}$ | $A^{105}$ |
| 6374. | $D^{156}$ | $A^{106}$ |
| 6375. | $D^{156}$ | $A^{107}$ |
| 6376. | $D^{156}$ | $A^{108}$ |
| 6377. | $D^{156}$ | $A^{109}$ |
| 6378. | $D^{156}$ | $A^{110}$ |
| 6379. | $D^{156}$ | $A^{111}$ |
| 6380. | $D^{156}$ | $A^{112}$ |
| 6381. | $D^{156}$ | $A^{113}$ |
| 6382. | $D^{156}$ | $A^{114}$ |
| 6383. | $D^{156}$ | $A^{115}$ |
| 6384. | $D^{156}$ | $A^{116}$ |
| 6385. | $D^{156}$ | $A^{117}$ |
| 6386. | $D^{156}$ | $A^{118}$ |
| 6387. | $D^{156}$ | $A^{119}$ |
| 6388. | $D^{156}$ | $A^{120}$ |
| 6389. | $D^{156}$ | $A^{121}$ |
| 6390. | $D^{156}$ | $A^{122}$ |
| 6391. | $D^{156}$ | $A^{123}$ |
| 6392. | $D^{156}$ | $A^{124}$ |
| 6393. | $D^{156}$ | $A^{125}$ |
| 6394. | $D^{156}$ | $A^{126}$ |
| 6395. | $D^{156}$ | $A^{127}$ |
| 6396. | $D^{156}$ | $A^{128}$ |
| 6397. | $D^{156}$ | $A^{129}$ |
| 6398. | $D^{156}$ | $A^{130}$ |
| 6399. | $D^{156}$ | $A^{131}$ |
| 6400. | $D^{156}$ | $A^{132}$ |
| 6401. | $D^{157}$ | $A^{101}$ |
| 6402. | $D^{157}$ | $A^{102}$ |
| 6403. | $D^{157}$ | $A^{103}$ |
| 6404. | $D^{157}$ | $A^{104}$ |
| 6405. | $D^{157}$ | $A^{105}$ |
| 6406. | $D^{157}$ | $A^{106}$ |
| 6407. | $D^{157}$ | $A^{107}$ |
| 6408. | $D^{157}$ | $A^{108}$ |
| 6409. | $D^{157}$ | $A^{109}$ |
| 6410. | $D^{157}$ | $A^{110}$ |
| 6411. | $D^{157}$ | $A^{111}$ |
| 6412. | $D^{157}$ | $A^{112}$ |
| 6413. | $D^{157}$ | $A^{113}$ |
| 6414. | $D^{157}$ | $A^{114}$ |
| 6415. | $D^{157}$ | $A^{115}$ |
| 6416. | $D^{157}$ | $A^{116}$ |
| 6417. | $D^{157}$ | $A^{117}$ |
| 6418. | $D^{157}$ | $A^{118}$ |
| 6419. | $D^{157}$ | $A^{119}$ |
| 6420. | $D^{157}$ | $A^{120}$ |
| 6421. | $D^{157}$ | $A^{121}$ |
| 6422. | $D^{157}$ | $A^{122}$ |
| 6423. | $D^{157}$ | $A^{123}$ |
| 6424. | $D^{157}$ | $A^{124}$ |
| 6425. | $D^{157}$ | $A^{125}$ |
| 6426. | $D^{157}$ | $A^{126}$ |
| 6427. | $D^{157}$ | $A^{127}$ |
| 6428. | $D^{157}$ | $A^{128}$ |
| 6429. | $D^{157}$ | $A^{129}$ |

Formula III

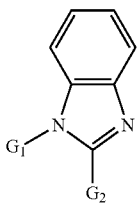

| Compound Number | $G^1$ | $G^2$ |
|---|---|---|
| 6430. | $D^{157}$ | $A^{130}$ |
| 6431. | $D^{157}$ | $A^{131}$ |
| 6432. | $D^{157}$ | $A^{132}$ |
| 6433. | $D^{158}$ | $A^{101}$ |
| 6434. | $D^{158}$ | $A^{102}$ |
| 6435. | $D^{158}$ | $A^{103}$ |
| 6436. | $D^{158}$ | $A^{104}$ |
| 6437. | $D^{158}$ | $A^{105}$ |
| 6438. | $D^{158}$ | $A^{106}$ |
| 6439. | $D^{158}$ | $A^{107}$ |
| 6440. | $D^{158}$ | $A^{108}$ |
| 6441. | $D^{158}$ | $A^{109}$ |
| 6442. | $D^{158}$ | $A^{110}$ |
| 6443. | $D^{158}$ | $A^{111}$ |
| 6444. | $D^{158}$ | $A^{112}$ |
| 6445. | $D^{158}$ | $A^{113}$ |
| 6446. | $D^{158}$ | $A^{114}$ |
| 6447. | $D^{158}$ | $A^{115}$ |
| 6448. | $D^{158}$ | $A^{116}$ |
| 6449. | $D^{158}$ | $A^{117}$ |
| 6450. | $D^{158}$ | $A^{118}$ |
| 6451. | $D^{158}$ | $A^{119}$ |
| 6452. | $D^{158}$ | $A^{120}$ |
| 6453. | $D^{158}$ | $A^{121}$ |
| 6454. | $D^{158}$ | $A^{122}$ |
| 6455. | $D^{158}$ | $A^{123}$ |
| 6456. | $D^{158}$ | $A^{124}$ |
| 6457. | $D^{158}$ | $A^{125}$ |
| 6458. | $D^{158}$ | $A^{126}$ |
| 6459. | $D^{158}$ | $A^{127}$ |
| 6460. | $D^{158}$ | $A^{128}$ |
| 6461. | $D^{158}$ | $A^{129}$ |
| 6462. | $D^{158}$ | $A^{130}$ |
| 6463. | $D^{158}$ | $A^{131}$ |
| 6464. | $D^{158}$ | $A^{132}$ |
| 6465. | $D^{159}$ | $A^{101}$ |
| 6466. | $D^{159}$ | $A^{102}$ |
| 6467. | $D^{159}$ | $A^{103}$ |
| 6468. | $D^{159}$ | $A^{104}$ |
| 6469. | $D^{159}$ | $A^{105}$ |
| 6470. | $D^{159}$ | $A^{106}$ |
| 6471. | $D^{159}$ | $A^{107}$ |
| 6472. | $D^{159}$ | $A^{108}$ |
| 6473. | $D^{159}$ | $A^{109}$ |
| 6474. | $D^{159}$ | $A^{110}$ |
| 6475. | $D^{159}$ | $A^{111}$ |
| 6476. | $D^{159}$ | $A^{112}$ |
| 6477. | $D^{159}$ | $A^{113}$ |
| 6478. | $D^{159}$ | $A^{114}$ |
| 6479. | $D^{159}$ | $A^{115}$ |
| 6480. | $D^{159}$ | $A^{116}$ |
| 6481. | $D^{159}$ | $A^{117}$ |
| 6482. | $D^{159}$ | $A^{118}$ |
| 6483. | $D^{159}$ | $A^{119}$ |
| 6484. | $D^{159}$ | $A^{120}$ |
| 6485. | $D^{159}$ | $A^{121}$ |
| 6486. | $D^{159}$ | $A^{122}$ |
| 6487. | $D^{159}$ | $A^{123}$ |
| 6488. | $D^{159}$ | $A^{124}$ |
| 6489. | $D^{159}$ | $A^{125}$ |
| 6490. | $D^{159}$ | $A^{126}$ |
| 6491. | $D^{159}$ | $A^{127}$ |
| 6492. | $D^{159}$ | $A^{128}$ |
| 6493. | $D^{159}$ | $A^{129}$ |
| 6494. | $D^{159}$ | $A^{130}$ |

Formula III

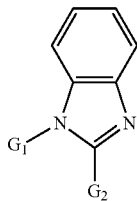

| Compound Number | $G^1$ | $G^2$ |
|---|---|---|
| 6495. | $D^{159}$ | $A^{131}$ |
| 6496. | $D^{159}$ | $A^{132}$ |
| 6497. | $D^{160}$ | $A^{101}$ |
| 6498. | $D^{160}$ | $A^{102}$ |
| 6499. | $D^{160}$ | $A^{103}$ |
| 6500. | $D^{160}$ | $A^{104}$ |
| 6501. | $D^{160}$ | $A^{105}$ |
| 6502. | $D^{160}$ | $A^{106}$ |
| 6503. | $D^{160}$ | $A^{107}$ |
| 6504. | $D^{160}$ | $A^{108}$ |
| 6505. | $D^{160}$ | $A^{109}$ |
| 6506. | $D^{160}$ | $A^{110}$ |
| 6507. | $D^{160}$ | $A^{111}$ |
| 6508. | $D^{160}$ | $A^{112}$ |
| 6509. | $D^{160}$ | $A^{113}$ |
| 6510. | $D^{160}$ | $A^{114}$ |
| 6511. | $D^{160}$ | $A^{115}$ |
| 6512. | $D^{160}$ | $A^{116}$ |
| 6513. | $D^{160}$ | $A^{117}$ |
| 6514. | $D^{160}$ | $A^{118}$ |
| 6515. | $D^{160}$ | $A^{119}$ |
| 6516. | $D^{160}$ | $A^{120}$ |
| 6517. | $D^{160}$ | $A^{121}$ |
| 6518. | $D^{160}$ | $A^{122}$ |
| 6519. | $D^{160}$ | $A^{123}$ |
| 6520. | $D^{160}$ | $A^{124}$ |
| 6521. | $D^{160}$ | $A^{125}$ |
| 6522. | $D^{160}$ | $A^{126}$ |
| 6523. | $D^{160}$ | $A^{127}$ |
| 6524. | $D^{160}$ | $A^{128}$ |
| 6525. | $D^{160}$ | $A^{129}$ |
| 6526. | $D^{160}$ | $A^{130}$ |
| 6527. | $D^{160}$ | $A^{131}$ |
| 6528. | $D^{160}$ | $A^{132}$ |
| 6529. | $D^{161}$ | $A^{101}$ |
| 6530. | $D^{161}$ | $A^{102}$ |
| 6531. | $D^{161}$ | $A^{103}$ |
| 6532. | $D^{161}$ | $A^{104}$ |
| 6533. | $D^{161}$ | $A^{105}$ |
| 6534. | $D^{161}$ | $A^{106}$ |
| 6535. | $D^{161}$ | $A^{107}$ |
| 6536. | $D^{161}$ | $A^{108}$ |
| 6537. | $D^{161}$ | $A^{109}$ |
| 6538. | $D^{161}$ | $A^{110}$ |
| 6539. | $D^{161}$ | $A^{111}$ |
| 6540. | $D^{161}$ | $A^{112}$ |
| 6541. | $D^{161}$ | $A^{113}$ |
| 6542. | $D^{161}$ | $A^{114}$ |
| 6543. | $D^{161}$ | $A^{115}$ |
| 6544. | $D^{161}$ | $A^{116}$ |
| 6545. | $D^{161}$ | $A^{117}$ |
| 6546. | $D^{161}$ | $A^{118}$ |
| 6547. | $D^{161}$ | $A^{119}$ |
| 6548. | $D^{161}$ | $A^{120}$ |
| 6549. | $D^{161}$ | $A^{121}$ |
| 6550. | $D^{161}$ | $A^{122}$ |
| 6551. | $D^{161}$ | $A^{123}$ |
| 6552. | $D^{161}$ | $A^{124}$ |
| 6553. | $D^{161}$ | $A^{125}$ |
| 6554. | $D^{161}$ | $A^{126}$ |
| 6555. | $D^{161}$ | $A^{127}$ |
| 6556. | $D^{161}$ | $A^{128}$ |
| 6557. | $D^{161}$ | $A^{129}$ |
| 6558. | $D^{161}$ | $A^{130}$ |
| 6559. | $D^{161}$ | $A^{131}$ |

Formula III

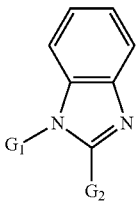

| Compound Number | $G^1$ | $G^2$ |
|---|---|---|
| 6560. | $D^{161}$ | $A^{132}$ |
| 6561. | $D^{162}$ | $A^{101}$ |
| 6562. | $D^{162}$ | $A^{102}$ |
| 6563. | $D^{162}$ | $A^{103}$ |
| 6564. | $D^{162}$ | $A^{104}$ |
| 6565. | $D^{162}$ | $A^{105}$ |
| 6566. | $D^{162}$ | $A^{106}$ |
| 6567. | $D^{162}$ | $A^{107}$ |
| 6568. | $D^{162}$ | $A^{108}$ |
| 6569. | $D^{162}$ | $A^{109}$ |
| 6570. | $D^{162}$ | $A^{110}$ |
| 6571. | $D^{162}$ | $A^{111}$ |
| 6572. | $D^{162}$ | $A^{112}$ |
| 6573. | $D^{162}$ | $A^{113}$ |
| 6574. | $D^{162}$ | $A^{114}$ |
| 6575. | $D^{162}$ | $A^{115}$ |
| 6576. | $D^{162}$ | $A^{116}$ |
| 6577. | $D^{162}$ | $A^{117}$ |
| 6578. | $D^{162}$ | $A^{118}$ |
| 6579. | $D^{162}$ | $A^{119}$ |
| 6580. | $D^{162}$ | $A^{120}$ |
| 6581. | $D^{162}$ | $A^{121}$ |
| 6582. | $D^{162}$ | $A^{122}$ |
| 6583. | $D^{162}$ | $A^{123}$ |
| 6584. | $D^{162}$ | $A^{124}$ |
| 6585. | $D^{162}$ | $A^{125}$ |
| 6586. | $D^{162}$ | $A^{126}$ |
| 6587. | $D^{162}$ | $A^{127}$ |
| 6588. | $D^{162}$ | $A^{128}$ |
| 6589. | $D^{162}$ | $A^{129}$ |
| 6590. | $D^{162}$ | $A^{130}$ |
| 6591. | $D^{162}$ | $A^{131}$ |
| 6592. | $D^{162}$ | $A^{132}$ |
| 6593. | $D^{163}$ | $A^{101}$ |
| 6594. | $D^{163}$ | $A^{102}$ |
| 6595. | $D^{163}$ | $A^{103}$ |
| 6596. | $D^{163}$ | $A^{104}$ |
| 6597. | $D^{163}$ | $A^{105}$ |
| 6598. | $D^{163}$ | $A^{106}$ |
| 6599. | $D^{163}$ | $A^{107}$ |
| 6600. | $D^{163}$ | $A^{108}$ |
| 6601. | $D^{163}$ | $A^{109}$ |
| 6602. | $D^{163}$ | $A^{110}$ |
| 6603. | $D^{163}$ | $A^{111}$ |
| 6604. | $D^{163}$ | $A^{112}$ |
| 6605. | $D^{163}$ | $A^{113}$ |
| 6606. | $D^{163}$ | $A^{114}$ |
| 6607. | $D^{163}$ | $A^{115}$ |
| 6608. | $D^{163}$ | $A^{116}$ |
| 6609. | $D^{163}$ | $A^{117}$ |
| 6610. | $D^{163}$ | $A^{118}$ |
| 6611. | $D^{163}$ | $A^{119}$ |
| 6612. | $D^{163}$ | $A^{120}$ |
| 6613. | $D^{163}$ | $A^{121}$ |
| 6614. | $D^{163}$ | $A^{122}$ |
| 6615. | $D^{163}$ | $A^{123}$ |
| 6616. | $D^{163}$ | $A^{124}$ |
| 6617. | $D^{163}$ | $A^{125}$ |
| 6618. | $D^{163}$ | $A^{126}$ |
| 6619. | $D^{163}$ | $A^{127}$ |
| 6620. | $D^{163}$ | $A^{128}$ |
| 6621. | $D^{163}$ | $A^{129}$ |
| 6622. | $D^{163}$ | $A^{130}$ |
| 6623. | $D^{163}$ | $A^{131}$ |
| 6624. | $D^{163}$ | $A^{132}$ |

-continued

Formula III

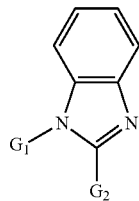

| Compound Number | G¹ | G² |
|---|---|---|
| 6625. | $D^{164}$ | $A^{101}$ |
| 6626. | $D^{164}$ | $A^{102}$ |
| 6627. | $D^{164}$ | $A^{103}$ |
| 6628. | $D^{164}$ | $A^{104}$ |
| 6629. | $D^{164}$ | $A^{105}$ |
| 6630. | $D^{164}$ | $A^{106}$ |
| 6631. | $D^{164}$ | $A^{107}$ |
| 6632. | $D^{164}$ | $A^{108}$ |
| 6633. | $D^{164}$ | $A^{109}$ |
| 6634. | $D^{164}$ | $A^{110}$ |
| 6635. | $D^{164}$ | $A^{111}$ |
| 6636. | $D^{164}$ | $A^{112}$ |
| 6637. | $D^{164}$ | $A^{113}$ |
| 6638. | $D^{164}$ | $A^{114}$ |
| 6639. | $D^{164}$ | $A^{115}$ |
| 6640. | $D^{164}$ | $A^{116}$ |
| 6641. | $D^{164}$ | $A^{117}$ |
| 6642. | $D^{164}$ | $A^{118}$ |
| 6643. | $D^{164}$ | $A^{119}$ |
| 6644. | $D^{164}$ | $A^{120}$ |
| 6645. | $D^{164}$ | $A^{121}$ |
| 6646. | $D^{164}$ | $A^{122}$ |
| 6647. | $D^{164}$ | $A^{123}$ |
| 6648. | $D^{164}$ | $A^{124}$ |
| 6649. | $D^{164}$ | $A^{125}$ |
| 6650. | $D^{164}$ | $A^{126}$ |
| 6651. | $D^{164}$ | $A^{127}$ |
| 6652. | $D^{164}$ | $A^{128}$ |
| 6653. | $D^{164}$ | $A^{129}$ |
| 6654. | $D^{164}$ | $A^{130}$ |
| 6655. | $D^{164}$ | $A^{131}$ |
| 6656. | $D^{164}$ | $A^{132}$ |
| 6657. | $D^{165}$ | $A^{101}$ |
| 6658. | $D^{165}$ | $A^{102}$ |
| 6659. | $D^{165}$ | $A^{103}$ |
| 6660. | $D^{165}$ | $A^{104}$ |
| 6661. | $D^{165}$ | $A^{105}$ |
| 6662. | $D^{165}$ | $A^{106}$ |
| 6663. | $D^{165}$ | $A^{107}$ |
| 6664. | $D^{165}$ | $A^{108}$ |
| 6665. | $D^{165}$ | $A^{109}$ |
| 6666. | $D^{165}$ | $A^{110}$ |
| 6667. | $D^{165}$ | $A^{111}$ |
| 6668. | $D^{165}$ | $A^{112}$ |
| 6669. | $D^{165}$ | $A^{113}$ |
| 6670. | $D^{165}$ | $A^{114}$ |
| 6671. | $D^{165}$ | $A^{115}$ |
| 6672. | $D^{165}$ | $A^{116}$ |
| 6673. | $D^{165}$ | $A^{117}$ |
| 6674. | $D^{165}$ | $A^{118}$ |
| 6675. | $D^{165}$ | $A^{119}$ |
| 6676. | $D^{165}$ | $A^{120}$ |
| 6677. | $D^{165}$ | $A^{121}$ |
| 6678. | $D^{165}$ | $A^{122}$ |
| 6679. | $D^{165}$ | $A^{123}$ |
| 6680. | $D^{165}$ | $A^{124}$ |
| 6681. | $D^{165}$ | $A^{125}$ |
| 6682. | $D^{165}$ | $A^{126}$ |
| 6683. | $D^{165}$ | $A^{127}$ |
| 6684. | $D^{165}$ | $A^{128}$ |
| 6685. | $D^{165}$ | $A^{129}$ |
| 6686. | $D^{165}$ | $A^{130}$ |
| 6687. | $D^{165}$ | $A^{131}$ |
| 6688. | $D^{165}$ | $A^{132}$ |
| 6689. | $D^{166}$ | $A^{101}$ |

-continued

Formula III

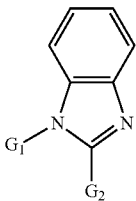

| Compound Number | G¹ | G² |
|---|---|---|
| 6690. | $D^{166}$ | $A^{102}$ |
| 6691. | $D^{166}$ | $A^{103}$ |
| 6692. | $D^{166}$ | $A^{104}$ |
| 6693. | $D^{166}$ | $A^{105}$ |
| 6694. | $D^{166}$ | $A^{106}$ |
| 6695. | $D^{166}$ | $A^{107}$ |
| 6696. | $D^{166}$ | $A^{108}$ |
| 6697. | $D^{166}$ | $A^{109}$ |
| 6698. | $D^{166}$ | $A^{110}$ |
| 6699. | $D^{166}$ | $A^{111}$ |
| 6700. | $D^{166}$ | $A^{112}$ |
| 6701. | $D^{166}$ | $A^{113}$ |
| 6702. | $D^{166}$ | $A^{114}$ |
| 6703. | $D^{166}$ | $A^{115}$ |
| 6704. | $D^{166}$ | $A^{116}$ |
| 6705. | $D^{166}$ | $A^{117}$ |
| 6706. | $D^{166}$ | $A^{118}$ |
| 6707. | $D^{166}$ | $A^{119}$ |
| 6708. | $D^{166}$ | $A^{120}$ |
| 6709. | $D^{166}$ | $A^{121}$ |
| 6710. | $D^{166}$ | $A^{122}$ |
| 6711. | $D^{166}$ | $A^{123}$ |
| 6712. | $D^{166}$ | $A^{124}$ |
| 6713. | $D^{166}$ | $A^{125}$ |
| 6714. | $D^{166}$ | $A^{126}$ |
| 6715. | $D^{166}$ | $A^{127}$ |
| 6716. | $D^{166}$ | $A^{128}$ |
| 6717. | $D^{166}$ | $A^{129}$ |
| 6718. | $D^{166}$ | $A^{130}$ |
| 6719. | $D^{166}$ | $A^{131}$ |
| 6720. | $D^{166}$ | $A^{132}$ |
| 6721. | $D^{167}$ | $A^{101}$ |
| 6722. | $D^{167}$ | $A^{102}$ |
| 6723. | $D^{167}$ | $A^{103}$ |
| 6724. | $D^{167}$ | $A^{104}$ |
| 6725. | $D^{167}$ | $A^{105}$ |
| 6726. | $D^{167}$ | $A^{106}$ |
| 6727. | $D^{167}$ | $A^{107}$ |
| 6728. | $D^{167}$ | $A^{108}$ |
| 6729. | $D^{167}$ | $A^{109}$ |
| 6730. | $D^{167}$ | $A^{110}$ |
| 6731. | $D^{167}$ | $A^{111}$ |
| 6732. | $D^{167}$ | $A^{112}$ |
| 6733. | $D^{167}$ | $A^{113}$ |
| 6734. | $D^{167}$ | $A^{114}$ |
| 6735. | $D^{167}$ | $A^{115}$ |
| 6736. | $D^{167}$ | $A^{116}$ |
| 6737. | $D^{167}$ | $A^{117}$ |
| 6738. | $D^{167}$ | $A^{118}$ |
| 6739. | $D^{167}$ | $A^{119}$ |
| 6740. | $D^{167}$ | $A^{120}$ |
| 6741. | $D^{167}$ | $A^{121}$ |
| 6742. | $D^{167}$ | $A^{122}$ |
| 6743. | $D^{167}$ | $A^{123}$ |
| 6744. | $D^{167}$ | $A^{124}$ |
| 6745. | $D^{167}$ | $A^{125}$ |
| 6746. | $D^{167}$ | $A^{126}$ |
| 6747. | $D^{167}$ | $A^{127}$ |
| 6748. | $D^{167}$ | $A^{128}$ |
| 6749. | $D^{167}$ | $A^{129}$ |
| 6750. | $D^{167}$ | $A^{130}$ |
| 6751. | $D^{167}$ | $A^{131}$ |
| 6752. | $D^{167}$ | $A^{132}$ |
| 6753. | $D^{168}$ | $A^{101}$ |
| 6754. | $D^{168}$ | $A^{102}$ |

-continued

Formula III

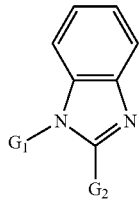

| Compound Number | $G^1$ | $G^2$ |
|---|---|---|
| 6755. | $D^{168}$ | $A^{103}$ |
| 6756. | $D^{168}$ | $A^{104}$ |
| 6757. | $D^{168}$ | $A^{105}$ |
| 6758. | $D^{168}$ | $A^{106}$ |
| 6759. | $D^{168}$ | $A^{107}$ |
| 6760. | $D^{168}$ | $A^{108}$ |
| 6761. | $D^{168}$ | $A^{109}$ |
| 6762. | $D^{168}$ | $A^{110}$ |
| 6763. | $D^{168}$ | $A^{111}$ |
| 6764. | $D^{168}$ | $A^{112}$ |
| 6765. | $D^{168}$ | $A^{113}$ |
| 6766. | $D^{168}$ | $A^{114}$ |
| 6767. | $D^{168}$ | $A^{115}$ |
| 6768. | $D^{168}$ | $A^{116}$ |
| 6769. | $D^{168}$ | $A^{117}$ |
| 6770. | $D^{168}$ | $A^{118}$ |
| 6771. | $D^{168}$ | $A^{119}$ |
| 6772. | $D^{168}$ | $A^{120}$ |
| 6773. | $D^{168}$ | $A^{121}$ |
| 6774. | $D^{168}$ | $A^{122}$ |
| 6775. | $D^{168}$ | $A^{123}$ |
| 6776. | $D^{168}$ | $A^{124}$ |
| 6777. | $D^{168}$ | $A^{125}$ |
| 6778. | $D^{168}$ | $A^{126}$ |
| 6779. | $D^{168}$ | $A^{127}$ |
| 6780. | $D^{168}$ | $A^{128}$ |
| 6781. | $D^{168}$ | $A^{129}$ |
| 6782. | $D^{168}$ | $A^{130}$ |
| 6783. | $D^{168}$ | $A^{131}$ |
| 6784. | $D^{168}$ | $A^{132}$ |

Formula IV

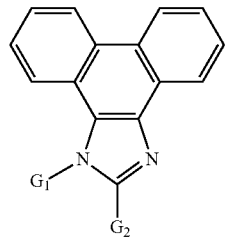

| Compound Number | $G^1$ | $G^2$ |
|---|---|---|
| 5089. | $A^{101}$ | $D^{101}$ |
| 5090. | $A^{102}$ | $D^{101}$ |
| 5091. | $A^{103}$ | $D^{101}$ |
| 5092. | $A^{104}$ | $D^{101}$ |
| 5093. | $A^{105}$ | $D^{101}$ |
| 5094. | $A^{106}$ | $D^{101}$ |
| 5095. | $A^{107}$ | $D^{101}$ |
| 5096. | $A^{108}$ | $D^{101}$ |
| 5097. | $A^{109}$ | $D^{101}$ |
| 5098. | $A^{110}$ | $D^{101}$ |
| 5099. | $A^{111}$ | $D^{101}$ |
| 5100. | $A^{112}$ | $D^{101}$ |
| 5101. | $A^{113}$ | $D^{101}$ |
| 5102. | $A^{114}$ | $D^{101}$ |

-continued

Formula IV

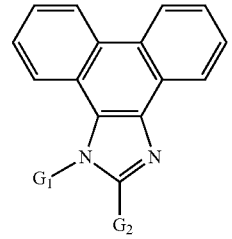

| Compound Number | $G^1$ | $G^2$ |
|---|---|---|
| 5103. | $A^{115}$ | $D^{101}$ |
| 5104. | $A^{116}$ | $D^{101}$ |
| 5105. | $A^{117}$ | $D^{101}$ |
| 5106. | $A^{118}$ | $D^{101}$ |
| 5107. | $A^{119}$ | $D^{101}$ |
| 5108. | $A^{120}$ | $D^{101}$ |
| 5109. | $A^{121}$ | $D^{101}$ |
| 5110. | $A^{122}$ | $D^{101}$ |
| 5111. | $A^{123}$ | $D^{101}$ |
| 5112. | $A^{124}$ | $D^{101}$ |
| 5113. | $A^{125}$ | $D^{101}$ |
| 5114. | $A^{126}$ | $D^{101}$ |
| 5115. | $A^{127}$ | $D^{101}$ |
| 5116. | $A^{128}$ | $D^{101}$ |
| 5117. | $A^{129}$ | $D^{101}$ |
| 5118. | $A^{130}$ | $D^{101}$ |
| 5119. | $A^{131}$ | $D^{101}$ |
| 5120. | $A^{132}$ | $D^{101}$ |
| 5121. | $A^{101}$ | $D^{102}$ |
| 5122. | $A^{102}$ | $D^{102}$ |
| 5123. | $A^{103}$ | $D^{102}$ |
| 5124. | $A^{104}$ | $D^{102}$ |
| 5125. | $A^{105}$ | $D^{102}$ |
| 5126. | $A^{106}$ | $D^{102}$ |
| 5127. | $A^{107}$ | $D^{102}$ |
| 5128. | $A^{108}$ | $D^{102}$ |
| 5129. | $A^{109}$ | $D^{102}$ |
| 5130. | $A^{110}$ | $D^{102}$ |
| 5131. | $A^{111}$ | $D^{102}$ |
| 5132. | $A^{112}$ | $D^{102}$ |
| 5133. | $A^{113}$ | $D^{102}$ |
| 5134. | $A^{114}$ | $D^{102}$ |
| 5135. | $A^{115}$ | $D^{102}$ |
| 5136. | $A^{116}$ | $D^{102}$ |
| 5137. | $A^{117}$ | $D^{102}$ |
| 5138. | $A^{118}$ | $D^{102}$ |
| 5139. | $A^{119}$ | $D^{102}$ |
| 5140. | $A^{120}$ | $D^{102}$ |
| 5141. | $A^{121}$ | $D^{102}$ |
| 5142. | $A^{122}$ | $D^{102}$ |
| 5143. | $A^{123}$ | $D^{102}$ |
| 5144. | $A^{124}$ | $D^{102}$ |
| 5145. | $A^{125}$ | $D^{102}$ |
| 5146. | $A^{126}$ | $D^{102}$ |
| 5147. | $A^{127}$ | $D^{102}$ |
| 5148. | $A^{128}$ | $D^{102}$ |
| 5149. | $A^{129}$ | $D^{102}$ |
| 5150. | $A^{130}$ | $D^{102}$ |
| 5151. | $A^{131}$ | $D^{102}$ |
| 5152. | $A^{132}$ | $D^{102}$ |
| 5153. | $A^{101}$ | $D^{103}$ |
| 5154. | $A^{102}$ | $D^{103}$ |
| 5155. | $A^{103}$ | $D^{103}$ |
| 5156. | $A^{104}$ | $D^{103}$ |
| 5157. | $A^{105}$ | $D^{103}$ |
| 5158. | $A^{106}$ | $D^{103}$ |
| 5159. | $A^{107}$ | $D^{103}$ |
| 5160. | $A^{108}$ | $D^{103}$ |
| 5161. | $A^{109}$ | $D^{103}$ |
| 5162. | $A^{110}$ | $D^{103}$ |
| 5163. | $A^{111}$ | $D^{103}$ |
| 5164. | $A^{112}$ | $D^{103}$ |
| 5165. | $A^{113}$ | $D^{103}$ |

Formula IV

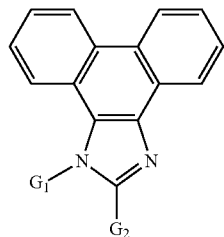

| Compound Number | $G^1$ | $G^2$ |
|---|---|---|
| 5166. | $A^{114}$ | $D^{103}$ |
| 5167. | $A^{115}$ | $D^{103}$ |
| 5168. | $A^{116}$ | $D^{103}$ |
| 5169. | $A^{117}$ | $D^{103}$ |
| 5170. | $A^{118}$ | $D^{103}$ |
| 5171. | $A^{119}$ | $D^{103}$ |
| 5172. | $A^{120}$ | $D^{103}$ |
| 5173. | $A^{121}$ | $D^{103}$ |
| 5174. | $A^{122}$ | $D^{103}$ |
| 5175. | $A^{123}$ | $D^{103}$ |
| 5176. | $A^{124}$ | $D^{103}$ |
| 5177. | $A^{125}$ | $D^{103}$ |
| 5178. | $A^{126}$ | $D^{103}$ |
| 5179. | $A^{127}$ | $D^{103}$ |
| 5180. | $A^{128}$ | $D^{103}$ |
| 5181. | $A^{129}$ | $D^{103}$ |
| 5182. | $A^{130}$ | $D^{103}$ |
| 5183. | $A^{131}$ | $D^{103}$ |
| 5184. | $A^{132}$ | $D^{103}$ |
| 5185. | $A^{101}$ | $D^{104}$ |
| 5186. | $A^{102}$ | $D^{104}$ |
| 5187. | $A^{103}$ | $D^{104}$ |
| 5188. | $A^{104}$ | $D^{104}$ |
| 5189. | $A^{105}$ | $D^{104}$ |
| 5190. | $A^{106}$ | $D^{104}$ |
| 5191. | $A^{107}$ | $D^{104}$ |
| 5192. | $A^{108}$ | $D^{104}$ |
| 5193. | $A^{109}$ | $D^{104}$ |
| 5194. | $A^{110}$ | $D^{104}$ |
| 5195. | $A^{111}$ | $D^{104}$ |
| 5196. | $A^{112}$ | $D^{104}$ |
| 5197. | $A^{113}$ | $D^{104}$ |
| 5198. | $A^{114}$ | $D^{104}$ |
| 5199. | $A^{115}$ | $D^{104}$ |
| 5200. | $A^{116}$ | $D^{104}$ |
| 5201. | $A^{117}$ | $D^{104}$ |
| 5202. | $A^{118}$ | $D^{104}$ |
| 5203. | $A^{119}$ | $D^{104}$ |
| 5204. | $A^{120}$ | $D^{104}$ |
| 5205. | $A^{121}$ | $D^{104}$ |
| 5206. | $A^{122}$ | $D^{104}$ |
| 5207. | $A^{123}$ | $D^{104}$ |
| 5208. | $A^{124}$ | $D^{104}$ |
| 5209. | $A^{125}$ | $D^{104}$ |
| 5210. | $A^{126}$ | $D^{104}$ |
| 5211. | $A^{127}$ | $D^{104}$ |
| 5212. | $A^{128}$ | $D^{104}$ |
| 5213. | $A^{129}$ | $D^{104}$ |
| 5214. | $A^{130}$ | $D^{104}$ |
| 5215. | $A^{131}$ | $D^{104}$ |
| 5216. | $A^{132}$ | $D^{104}$ |
| 5217. | $A^{101}$ | $D^{105}$ |
| 5218. | $A^{102}$ | $D^{105}$ |
| 5219. | $A^{103}$ | $D^{105}$ |
| 5220. | $A^{104}$ | $D^{105}$ |
| 5221. | $A^{105}$ | $D^{105}$ |
| 5222. | $A^{106}$ | $D^{105}$ |
| 5223. | $A^{107}$ | $D^{105}$ |
| 5224. | $A^{108}$ | $D^{105}$ |
| 5225. | $A^{109}$ | $D^{105}$ |
| 5226. | $A^{110}$ | $D^{105}$ |
| 5227. | $A^{111}$ | $D^{105}$ |
| 5228. | $A^{112}$ | $D^{105}$ |

Formula IV

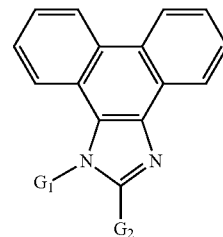

| Compound Number | $G^1$ | $G^2$ |
|---|---|---|
| 5229. | $A^{113}$ | $D^{105}$ |
| 5230. | $A^{114}$ | $D^{105}$ |
| 5231. | $A^{115}$ | $D^{105}$ |
| 5232. | $A^{116}$ | $D^{105}$ |
| 5233. | $A^{117}$ | $D^{105}$ |
| 5234. | $A^{118}$ | $D^{105}$ |
| 5235. | $A^{119}$ | $D^{105}$ |
| 5236. | $A^{120}$ | $D^{105}$ |
| 5237. | $A^{121}$ | $D^{105}$ |
| 5238. | $A^{122}$ | $D^{105}$ |
| 5239. | $A^{123}$ | $D^{105}$ |
| 5240. | $A^{124}$ | $D^{105}$ |
| 5241. | $A^{125}$ | $D^{105}$ |
| 5242. | $A^{126}$ | $D^{105}$ |
| 5243. | $A^{127}$ | $D^{105}$ |
| 5244. | $A^{128}$ | $D^{105}$ |
| 5245. | $A^{129}$ | $D^{105}$ |
| 5246. | $A^{130}$ | $D^{105}$ |
| 5247. | $A^{131}$ | $D^{105}$ |
| 5248. | $A^{132}$ | $D^{105}$ |
| 5249. | $A^{101}$ | $D^{106}$ |
| 5250. | $A^{102}$ | $D^{106}$ |
| 5251. | $A^{103}$ | $D^{106}$ |
| 5252. | $A^{104}$ | $D^{106}$ |
| 5253. | $A^{105}$ | $D^{106}$ |
| 5254. | $A^{106}$ | $D^{106}$ |
| 5255. | $A^{107}$ | $D^{106}$ |
| 5256. | $A^{108}$ | $D^{106}$ |
| 5257. | $A^{109}$ | $D^{106}$ |
| 5258. | $A^{110}$ | $D^{106}$ |
| 5259. | $A^{111}$ | $D^{106}$ |
| 5260. | $A^{112}$ | $D^{106}$ |
| 5261. | $A^{113}$ | $D^{106}$ |
| 5262. | $A^{114}$ | $D^{106}$ |
| 5263. | $A^{115}$ | $D^{106}$ |
| 5264. | $A^{116}$ | $D^{106}$ |
| 5265. | $A^{117}$ | $D^{106}$ |
| 5266. | $A^{118}$ | $D^{106}$ |
| 5267. | $A^{119}$ | $D^{106}$ |
| 5268. | $A^{120}$ | $D^{106}$ |
| 5269. | $A^{121}$ | $D^{106}$ |
| 5270. | $A^{122}$ | $D^{106}$ |
| 5271. | $A^{123}$ | $D^{106}$ |
| 5272. | $A^{124}$ | $D^{106}$ |
| 5273. | $A^{125}$ | $D^{106}$ |
| 5274. | $A^{126}$ | $D^{106}$ |
| 5275. | $A^{127}$ | $D^{106}$ |
| 5276. | $A^{128}$ | $D^{106}$ |
| 5277. | $A^{129}$ | $D^{106}$ |
| 5278. | $A^{130}$ | $D^{106}$ |
| 5279. | $A^{131}$ | $D^{106}$ |
| 5280. | $A^{132}$ | $D^{106}$ |
| 5281. | $A^{101}$ | $D^{107}$ |
| 5282. | $A^{102}$ | $D^{107}$ |
| 5283. | $A^{103}$ | $D^{107}$ |
| 5284. | $A^{104}$ | $D^{107}$ |
| 5285. | $A^{105}$ | $D^{107}$ |
| 5286. | $A^{106}$ | $D^{107}$ |
| 5287. | $A^{107}$ | $D^{107}$ |
| 5288. | $A^{108}$ | $D^{107}$ |
| 5289. | $A^{109}$ | $D^{107}$ |
| 5290. | $A^{110}$ | $D^{107}$ |
| 5291. | $A^{111}$ | $D^{107}$ |

Formula IV

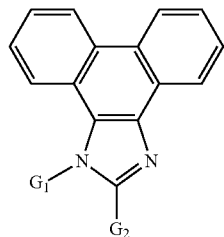

| Compound Number | G¹ | G² |
|---|---|---|
| 5292. | $A^{112}$ | $D^{107}$ |
| 5293. | $A^{113}$ | $D^{107}$ |
| 5294. | $A^{114}$ | $D^{107}$ |
| 5295. | $A^{115}$ | $D^{107}$ |
| 5296. | $A^{116}$ | $D^{107}$ |
| 5297. | $A^{117}$ | $D^{107}$ |
| 5298. | $A^{118}$ | $D^{107}$ |
| 5299. | $A^{119}$ | $D^{107}$ |
| 5300. | $A^{120}$ | $D^{107}$ |
| 5301. | $A^{121}$ | $D^{107}$ |
| 5302. | $A^{122}$ | $D^{107}$ |
| 5303. | $A^{123}$ | $D^{107}$ |
| 5304. | $A^{124}$ | $D^{107}$ |
| 5305. | $A^{125}$ | $D^{107}$ |
| 5306. | $A^{126}$ | $D^{107}$ |
| 5307. | $A^{127}$ | $D^{107}$ |
| 5308. | $A^{128}$ | $D^{107}$ |
| 5309. | $A^{129}$ | $D^{107}$ |
| 5310. | $A^{130}$ | $D^{107}$ |
| 5311. | $A^{131}$ | $D^{107}$ |
| 5312. | $A^{132}$ | $D^{107}$ |
| 5313. | $A^{101}$ | $D^{108}$ |
| 5314. | $A^{102}$ | $D^{108}$ |
| 5315. | $A^{103}$ | $D^{108}$ |
| 5316. | $A^{104}$ | $D^{108}$ |
| 5317. | $A^{105}$ | $D^{108}$ |
| 5318. | $A^{106}$ | $D^{108}$ |
| 5319. | $A^{107}$ | $D^{108}$ |
| 5320. | $A^{108}$ | $D^{108}$ |
| 5321. | $A^{109}$ | $D^{108}$ |
| 5322. | $A^{110}$ | $D^{108}$ |
| 5323. | $A^{111}$ | $D^{108}$ |
| 5324. | $A^{112}$ | $D^{108}$ |
| 5325. | $A^{113}$ | $D^{108}$ |
| 5326. | $A^{114}$ | $D^{108}$ |
| 5327. | $A^{115}$ | $D^{108}$ |
| 5328. | $A^{116}$ | $D^{108}$ |
| 5329. | $A^{117}$ | $D^{108}$ |
| 5330. | $A^{118}$ | $D^{108}$ |
| 5331. | $A^{119}$ | $D^{108}$ |
| 5332. | $A^{120}$ | $D^{108}$ |
| 5333. | $A^{121}$ | $D^{108}$ |
| 5334. | $A^{122}$ | $D^{108}$ |
| 5335. | $A^{123}$ | $D^{108}$ |
| 5336. | $A^{124}$ | $D^{108}$ |
| 5337. | $A^{125}$ | $D^{108}$ |
| 5338. | $A^{126}$ | $D^{108}$ |
| 5339. | $A^{127}$ | $D^{108}$ |
| 5340. | $A^{128}$ | $D^{108}$ |
| 5341. | $A^{129}$ | $D^{108}$ |
| 5342. | $A^{130}$ | $D^{108}$ |
| 5343. | $A^{131}$ | $D^{108}$ |
| 5344. | $A^{132}$ | $D^{108}$ |
| 5345. | $A^{101}$ | $D^{109}$ |
| 5346. | $A^{102}$ | $D^{109}$ |
| 5347. | $A^{103}$ | $D^{109}$ |
| 5348. | $A^{104}$ | $D^{109}$ |
| 5349. | $A^{105}$ | $D^{109}$ |
| 5350. | $A^{106}$ | $D^{109}$ |
| 5351. | $A^{107}$ | $D^{109}$ |
| 5352. | $A^{108}$ | $D^{109}$ |
| 5353. | $A^{109}$ | $D^{109}$ |
| 5354. | $A^{110}$ | $D^{109}$ |

Formula IV

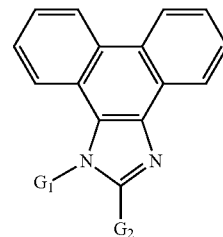

| Compound Number | G¹ | G² |
|---|---|---|
| 5355. | $A^{111}$ | $D^{109}$ |
| 5356. | $A^{112}$ | $D^{109}$ |
| 5357. | $A^{113}$ | $D^{109}$ |
| 5358. | $A^{114}$ | $D^{109}$ |
| 5359. | $A^{115}$ | $D^{109}$ |
| 5360. | $A^{116}$ | $D^{109}$ |
| 5361. | $A^{117}$ | $D^{109}$ |
| 5362. | $A^{118}$ | $D^{109}$ |
| 5363. | $A^{119}$ | $D^{109}$ |
| 5364. | $A^{120}$ | $D^{109}$ |
| 5365. | $A^{121}$ | $D^{109}$ |
| 5366. | $A^{122}$ | $D^{109}$ |
| 5367. | $A^{123}$ | $D^{109}$ |
| 5368. | $A^{124}$ | $D^{109}$ |
| 5369. | $A^{125}$ | $D^{109}$ |
| 5370. | $A^{126}$ | $D^{109}$ |
| 5371. | $A^{127}$ | $D^{109}$ |
| 5372. | $A^{128}$ | $D^{109}$ |
| 5373. | $A^{129}$ | $D^{109}$ |
| 5374. | $A^{130}$ | $D^{109}$ |
| 5375. | $A^{131}$ | $D^{109}$ |
| 5376. | $A^{132}$ | $D^{109}$ |
| 5377. | $A^{101}$ | $D^{110}$ |
| 5378. | $A^{102}$ | $D^{110}$ |
| 5379. | $A^{103}$ | $D^{110}$ |
| 5380. | $A^{104}$ | $D^{110}$ |
| 5381. | $A^{105}$ | $D^{110}$ |
| 5382. | $A^{106}$ | $D^{110}$ |
| 5383. | $A^{107}$ | $D^{110}$ |
| 5384. | $A^{108}$ | $D^{110}$ |
| 5385. | $A^{109}$ | $D^{110}$ |
| 5386. | $A^{110}$ | $D^{110}$ |
| 5387. | $A^{111}$ | $D^{110}$ |
| 5388. | $A^{112}$ | $D^{110}$ |
| 5389. | $A^{113}$ | $D^{110}$ |
| 5390. | $A^{114}$ | $D^{110}$ |
| 5391. | $A^{115}$ | $D^{110}$ |
| 5392. | $A^{116}$ | $D^{110}$ |
| 5393. | $A^{117}$ | $D^{110}$ |
| 5394. | $A^{118}$ | $D^{110}$ |
| 5395. | $A^{119}$ | $D^{110}$ |
| 5396. | $A^{120}$ | $D^{110}$ |
| 5397. | $A^{121}$ | $D^{110}$ |
| 5398. | $A^{122}$ | $D^{110}$ |
| 5399. | $A^{123}$ | $D^{110}$ |
| 5400. | $A^{124}$ | $D^{110}$ |
| 5401. | $A^{125}$ | $D^{110}$ |
| 5402. | $A^{126}$ | $D^{110}$ |
| 5403. | $A^{127}$ | $D^{110}$ |
| 5404. | $A^{128}$ | $D^{110}$ |
| 5405. | $A^{129}$ | $D^{110}$ |
| 5406. | $A^{130}$ | $D^{110}$ |
| 5407. | $A^{131}$ | $D^{110}$ |
| 5408. | $A^{132}$ | $D^{110}$ |
| 5409. | $A^{101}$ | $D^{111}$ |
| 5410. | $A^{102}$ | $D^{111}$ |
| 5411. | $A^{103}$ | $D^{111}$ |
| 5412. | $A^{104}$ | $D^{111}$ |
| 5413. | $A^{105}$ | $D^{111}$ |
| 5414. | $A^{106}$ | $D^{111}$ |
| 5415. | $A^{107}$ | $D^{111}$ |
| 5416. | $A^{108}$ | $D^{111}$ |
| 5417. | $A^{109}$ | $D^{111}$ |

Formula IV

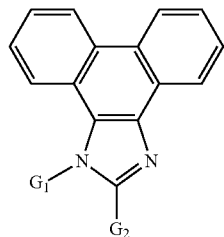

| Compound Number | G¹ | G² |
|---|---|---|
| 5418. | $A^{110}$ | $D^{111}$ |
| 5419. | $A^{111}$ | $D^{111}$ |
| 5420. | $A^{112}$ | $D^{111}$ |
| 5421. | $A^{113}$ | $D^{111}$ |
| 5422. | $A^{114}$ | $D^{111}$ |
| 5423. | $A^{115}$ | $D^{111}$ |
| 5424. | $A^{116}$ | $D^{111}$ |
| 5425. | $A^{117}$ | $D^{111}$ |
| 5426. | $A^{118}$ | $D^{111}$ |
| 5427. | $A^{119}$ | $D^{111}$ |
| 5428. | $A^{120}$ | $D^{111}$ |
| 5429. | $A^{121}$ | $D^{111}$ |
| 5430. | $A^{122}$ | $D^{111}$ |
| 5431. | $A^{123}$ | $D^{111}$ |
| 5432. | $A^{124}$ | $D^{111}$ |
| 5433. | $A^{125}$ | $D^{111}$ |
| 5434. | $A^{126}$ | $D^{111}$ |
| 5435. | $A^{127}$ | $D^{111}$ |
| 5436. | $A^{128}$ | $D^{111}$ |
| 5437. | $A^{129}$ | $D^{111}$ |
| 5438. | $A^{130}$ | $D^{111}$ |
| 5439. | $A^{131}$ | $D^{111}$ |
| 5440. | $A^{132}$ | $D^{111}$ |
| 5441. | $A^{101}$ | $D^{112}$ |
| 5442. | $A^{102}$ | $D^{112}$ |
| 5443. | $A^{103}$ | $D^{112}$ |
| 5444. | $A^{104}$ | $D^{112}$ |
| 5445. | $A^{105}$ | $D^{112}$ |
| 5446. | $A^{106}$ | $D^{112}$ |
| 5447. | $A^{107}$ | $D^{112}$ |
| 5448. | $A^{108}$ | $D^{112}$ |
| 5449. | $A^{109}$ | $D^{112}$ |
| 5450. | $A^{110}$ | $D^{112}$ |
| 5451. | $A^{111}$ | $D^{112}$ |
| 5452. | $A^{112}$ | $D^{112}$ |
| 5453. | $A^{113}$ | $D^{112}$ |
| 5454. | $A^{114}$ | $D^{112}$ |
| 5455. | $A^{115}$ | $D^{112}$ |
| 5456. | $A^{116}$ | $D^{112}$ |
| 5457. | $A^{117}$ | $D^{112}$ |
| 5458. | $A^{118}$ | $D^{112}$ |
| 5459. | $A^{119}$ | $D^{112}$ |
| 5460. | $A^{120}$ | $D^{112}$ |
| 5461. | $A^{121}$ | $D^{112}$ |
| 5462. | $A^{122}$ | $D^{112}$ |
| 5463. | $A^{123}$ | $D^{112}$ |
| 5464. | $A^{124}$ | $D^{112}$ |
| 5465. | $A^{125}$ | $D^{112}$ |
| 5466. | $A^{126}$ | $D^{112}$ |
| 5467. | $A^{127}$ | $D^{112}$ |
| 5468. | $A^{128}$ | $D^{112}$ |
| 5469. | $A^{129}$ | $D^{112}$ |
| 5470. | $A^{130}$ | $D^{112}$ |
| 5471. | $A^{131}$ | $D^{112}$ |
| 5472. | $A^{132}$ | $D^{112}$ |
| 5473. | $A^{101}$ | $D^{113}$ |
| 5474. | $A^{102}$ | $D^{113}$ |
| 5475. | $A^{103}$ | $D^{113}$ |
| 5476. | $A^{104}$ | $D^{113}$ |
| 5477. | $A^{105}$ | $D^{113}$ |
| 5478. | $A^{106}$ | $D^{113}$ |
| 5479. | $A^{107}$ | $D^{113}$ |
| 5480. | $A^{108}$ | $D^{113}$ |

Formula IV

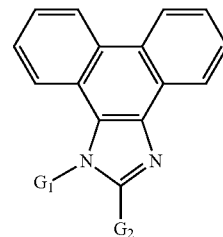

| Compound Number | G¹ | G² |
|---|---|---|
| 5481. | $A^{109}$ | $D^{113}$ |
| 5482. | $A^{110}$ | $D^{113}$ |
| 5483. | $A^{111}$ | $D^{113}$ |
| 5484. | $A^{112}$ | $D^{113}$ |
| 5485. | $A^{113}$ | $D^{113}$ |
| 5486. | $A^{114}$ | $D^{113}$ |
| 5487. | $A^{115}$ | $D^{113}$ |
| 5488. | $A^{116}$ | $D^{113}$ |
| 5489. | $A^{117}$ | $D^{113}$ |
| 5490. | $A^{118}$ | $D^{113}$ |
| 5491. | $A^{119}$ | $D^{113}$ |
| 5492. | $A^{120}$ | $D^{113}$ |
| 5493. | $A^{121}$ | $D^{113}$ |
| 5494. | $A^{122}$ | $D^{113}$ |
| 5495. | $A^{123}$ | $D^{113}$ |
| 5496. | $A^{124}$ | $D^{113}$ |
| 5497. | $A^{125}$ | $D^{113}$ |
| 5498. | $A^{126}$ | $D^{113}$ |
| 5499. | $A^{127}$ | $D^{113}$ |
| 5500. | $A^{128}$ | $D^{113}$ |
| 5501. | $A^{129}$ | $D^{113}$ |
| 5502. | $A^{130}$ | $D^{113}$ |
| 5503. | $A^{131}$ | $D^{113}$ |
| 5504. | $A^{132}$ | $D^{113}$ |
| 5505. | $A^{101}$ | $D^{114}$ |
| 5506. | $A^{102}$ | $D^{114}$ |
| 5507. | $A^{103}$ | $D^{114}$ |
| 5508. | $A^{104}$ | $D^{114}$ |
| 5509. | $A^{105}$ | $D^{114}$ |
| 5510. | $A^{106}$ | $D^{114}$ |
| 5511. | $A^{107}$ | $D^{114}$ |
| 5512. | $A^{108}$ | $D^{114}$ |
| 5513. | $A^{109}$ | $D^{114}$ |
| 5514. | $A^{110}$ | $D^{114}$ |
| 5515. | $A^{111}$ | $D^{114}$ |
| 5516. | $A^{112}$ | $D^{114}$ |
| 5517. | $A^{113}$ | $D^{114}$ |
| 5518. | $A^{114}$ | $D^{114}$ |
| 5519. | $A^{115}$ | $D^{114}$ |
| 5520. | $A^{116}$ | $D^{114}$ |
| 5521. | $A^{117}$ | $D^{114}$ |
| 5522. | $A^{118}$ | $D^{114}$ |
| 5523. | $A^{119}$ | $D^{114}$ |
| 5524. | $A^{120}$ | $D^{114}$ |
| 5525. | $A^{121}$ | $D^{114}$ |
| 5526. | $A^{122}$ | $D^{114}$ |
| 5527. | $A^{123}$ | $D^{114}$ |
| 5528. | $A^{124}$ | $D^{114}$ |
| 5529. | $A^{125}$ | $D^{114}$ |
| 5530. | $A^{126}$ | $D^{114}$ |
| 5531. | $A^{127}$ | $D^{114}$ |
| 5532. | $A^{128}$ | $D^{114}$ |
| 5533. | $A^{129}$ | $D^{114}$ |
| 5534. | $A^{130}$ | $D^{114}$ |
| 5535. | $A^{131}$ | $D^{114}$ |
| 5536. | $A^{132}$ | $D^{114}$ |
| 5537. | $A^{101}$ | $D^{115}$ |
| 5538. | $A^{102}$ | $D^{115}$ |
| 5539. | $A^{103}$ | $D^{115}$ |
| 5540. | $A^{104}$ | $D^{115}$ |
| 5541. | $A^{105}$ | $D^{115}$ |
| 5542. | $A^{106}$ | $D^{115}$ |
| 5543. | $A^{107}$ | $D^{115}$ |

-continued

Formula IV

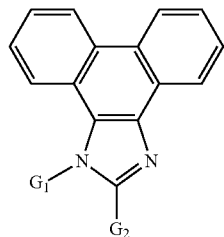

| Compound Number | G¹ | G² |
|---|---|---|
| 5544. | $A^{108}$ | $D^{115}$ |
| 5545. | $A^{109}$ | $D^{115}$ |
| 5546. | $A^{110}$ | $D^{115}$ |
| 5547. | $A^{111}$ | $D^{115}$ |
| 5548. | $A^{112}$ | $D^{115}$ |
| 5549. | $A^{113}$ | $D^{115}$ |
| 5550. | $A^{114}$ | $D^{115}$ |
| 5551. | $A^{115}$ | $D^{115}$ |
| 5552. | $A^{116}$ | $D^{115}$ |
| 5553. | $A^{117}$ | $D^{115}$ |
| 5554. | $A^{118}$ | $D^{115}$ |
| 5555. | $A^{119}$ | $D^{115}$ |
| 5556. | $A^{120}$ | $D^{115}$ |
| 5557. | $A^{121}$ | $D^{115}$ |
| 5558. | $A^{122}$ | $D^{115}$ |
| 5559. | $A^{123}$ | $D^{115}$ |
| 5560. | $A^{124}$ | $D^{115}$ |
| 5561. | $A^{125}$ | $D^{115}$ |
| 5562. | $A^{126}$ | $D^{115}$ |
| 5563. | $A^{127}$ | $D^{115}$ |
| 5564. | $A^{128}$ | $D^{115}$ |
| 5565. | $A^{129}$ | $D^{115}$ |
| 5566. | $A^{130}$ | $D^{115}$ |
| 5567. | $A^{131}$ | $D^{115}$ |
| 5568. | $A^{132}$ | $D^{115}$ |
| 5569. | $A^{101}$ | $D^{116}$ |
| 5570. | $A^{102}$ | $D^{116}$ |
| 5571. | $A^{103}$ | $D^{116}$ |
| 5572. | $A^{104}$ | $D^{116}$ |
| 5573. | $A^{105}$ | $D^{116}$ |
| 5574. | $A^{106}$ | $D^{116}$ |
| 5575. | $A^{107}$ | $D^{116}$ |
| 5576. | $A^{108}$ | $D^{116}$ |
| 5577. | $A^{109}$ | $D^{116}$ |
| 5578. | $A^{110}$ | $D^{116}$ |
| 5579. | $A^{111}$ | $D^{116}$ |
| 5580. | $A^{112}$ | $D^{116}$ |
| 5581. | $A^{113}$ | $D^{116}$ |
| 5582. | $A^{114}$ | $D^{116}$ |
| 5583. | $A^{115}$ | $D^{116}$ |
| 5584. | $A^{116}$ | $D^{116}$ |
| 5585. | $A^{117}$ | $D^{116}$ |
| 5586. | $A^{118}$ | $D^{116}$ |
| 5587. | $A^{119}$ | $D^{116}$ |
| 5588. | $A^{120}$ | $D^{116}$ |
| 5589. | $A^{121}$ | $D^{116}$ |
| 5590. | $A^{122}$ | $D^{116}$ |
| 5591. | $A^{123}$ | $D^{116}$ |
| 5592. | $A^{124}$ | $D^{116}$ |
| 5593. | $A^{125}$ | $D^{116}$ |
| 5594. | $A^{126}$ | $D^{116}$ |
| 5595. | $A^{127}$ | $D^{116}$ |
| 5596. | $A^{128}$ | $D^{116}$ |
| 5597. | $A^{129}$ | $D^{116}$ |
| 5598. | $A^{130}$ | $D^{116}$ |
| 5599. | $A^{131}$ | $D^{116}$ |
| 5600. | $A^{132}$ | $D^{116}$ |
| 5601. | $A^{101}$ | $D^{117}$ |
| 5602. | $A^{102}$ | $D^{117}$ |
| 5603. | $A^{103}$ | $D^{117}$ |
| 5604. | $A^{104}$ | $D^{117}$ |
| 5605. | $A^{105}$ | $D^{117}$ |
| 5606. | $A^{106}$ | $D^{117}$ |

-continued

Formula IV

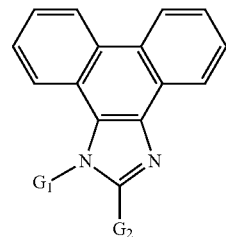

| Compound Number | G¹ | G² |
|---|---|---|
| 5607. | $A^{107}$ | $D^{117}$ |
| 5608. | $A^{108}$ | $D^{117}$ |
| 5609. | $A^{109}$ | $D^{117}$ |
| 5610. | $A^{110}$ | $D^{117}$ |
| 5611. | $A^{111}$ | $D^{117}$ |
| 5612. | $A^{112}$ | $D^{117}$ |
| 5613. | $A^{113}$ | $D^{117}$ |
| 5614. | $A^{114}$ | $D^{117}$ |
| 5615. | $A^{115}$ | $D^{117}$ |
| 5616. | $A^{116}$ | $D^{117}$ |
| 5617. | $A^{117}$ | $D^{117}$ |
| 5618. | $A^{118}$ | $D^{117}$ |
| 5619. | $A^{119}$ | $D^{117}$ |
| 5620. | $A^{120}$ | $D^{117}$ |
| 5621. | $A^{121}$ | $D^{117}$ |
| 5622. | $A^{122}$ | $D^{117}$ |
| 5623. | $A^{123}$ | $D^{117}$ |
| 5624. | $A^{124}$ | $D^{117}$ |
| 5625. | $A^{125}$ | $D^{117}$ |
| 5626. | $A^{126}$ | $D^{117}$ |
| 5627. | $A^{127}$ | $D^{117}$ |
| 5628. | $A^{128}$ | $D^{117}$ |
| 5629. | $A^{129}$ | $D^{117}$ |
| 5630. | $A^{130}$ | $D^{117}$ |
| 5631. | $A^{131}$ | $D^{117}$ |
| 5632. | $A^{132}$ | $D^{117}$ |
| 5633. | $A^{101}$ | $D^{118}$ |
| 5634. | $A^{102}$ | $D^{118}$ |
| 5635. | $A^{103}$ | $D^{118}$ |
| 5636. | $A^{104}$ | $D^{118}$ |
| 5637. | $A^{105}$ | $D^{118}$ |
| 5638. | $A^{106}$ | $D^{118}$ |
| 5639. | $A^{107}$ | $D^{118}$ |
| 5640. | $A^{108}$ | $D^{118}$ |
| 5641. | $A^{109}$ | $D^{118}$ |
| 5642. | $A^{110}$ | $D^{118}$ |
| 5643. | $A^{111}$ | $D^{118}$ |
| 5644. | $A^{112}$ | $D^{118}$ |
| 5645. | $A^{113}$ | $D^{118}$ |
| 5646. | $A^{114}$ | $D^{118}$ |
| 5647. | $A^{115}$ | $D^{118}$ |
| 5648. | $A^{116}$ | $D^{118}$ |
| 5649. | $A^{117}$ | $D^{118}$ |
| 5650. | $A^{118}$ | $D^{118}$ |
| 5651. | $A^{119}$ | $D^{118}$ |
| 5652. | $A^{120}$ | $D^{118}$ |
| 5653. | $A^{121}$ | $D^{118}$ |
| 5654. | $A^{122}$ | $D^{118}$ |
| 5655. | $A^{123}$ | $D^{118}$ |
| 5656. | $A^{124}$ | $D^{118}$ |
| 5657. | $A^{125}$ | $D^{118}$ |
| 5658. | $A^{126}$ | $D^{118}$ |
| 5659. | $A^{127}$ | $D^{118}$ |
| 5660. | $A^{128}$ | $D^{118}$ |
| 5661. | $A^{129}$ | $D^{118}$ |
| 5662. | $A^{130}$ | $D^{118}$ |
| 5663. | $A^{131}$ | $D^{118}$ |
| 5664. | $A^{132}$ | $D^{118}$ |
| 5665. | $A^{101}$ | $D^{119}$ |
| 5666. | $A^{102}$ | $D^{119}$ |
| 5667. | $A^{103}$ | $D^{119}$ |
| 5668. | $A^{104}$ | $D^{119}$ |
| 5669. | $A^{105}$ | $D^{119}$ |

Formula IV

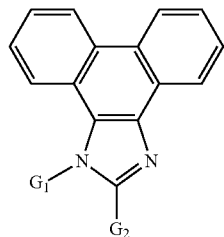

| Compound Number | $G^1$ | $G^2$ |
|---|---|---|
| 5670. | $A^{106}$ | $D^{119}$ |
| 5671. | $A^{107}$ | $D^{119}$ |
| 5672. | $A^{108}$ | $D^{119}$ |
| 5673. | $A^{109}$ | $D^{119}$ |
| 5674. | $A^{110}$ | $D^{119}$ |
| 5675. | $A^{111}$ | $D^{119}$ |
| 5676. | $A^{112}$ | $D^{119}$ |
| 5677. | $A^{113}$ | $D^{119}$ |
| 5678. | $A^{114}$ | $D^{119}$ |
| 5679. | $A^{115}$ | $D^{119}$ |
| 5680. | $A^{116}$ | $D^{119}$ |
| 5681. | $A^{117}$ | $D^{119}$ |
| 5682. | $A^{118}$ | $D^{119}$ |
| 5683. | $A^{119}$ | $D^{119}$ |
| 5684. | $A^{120}$ | $D^{119}$ |
| 5685. | $A^{121}$ | $D^{119}$ |
| 5686. | $A^{122}$ | $D^{119}$ |
| 5687. | $A^{123}$ | $D^{119}$ |
| 5688. | $A^{124}$ | $D^{119}$ |
| 5689. | $A^{125}$ | $D^{119}$ |
| 5690. | $A^{126}$ | $D^{119}$ |
| 5691. | $A^{127}$ | $D^{119}$ |
| 5692. | $A^{128}$ | $D^{119}$ |
| 5693. | $A^{129}$ | $D^{119}$ |
| 5694. | $A^{130}$ | $D^{119}$ |
| 5695. | $A^{131}$ | $D^{119}$ |
| 5696. | $A^{132}$ | $D^{119}$ |
| 5697. | $A^{101}$ | $D^{120}$ |
| 5698. | $A^{102}$ | $D^{120}$ |
| 5699. | $A^{103}$ | $D^{120}$ |
| 5700. | $A^{104}$ | $D^{120}$ |
| 5701. | $A^{105}$ | $D^{120}$ |
| 5702. | $A^{106}$ | $D^{120}$ |
| 5703. | $A^{107}$ | $D^{120}$ |
| 5704. | $A^{108}$ | $D^{120}$ |
| 5705. | $A^{109}$ | $D^{120}$ |
| 5706. | $A^{110}$ | $D^{120}$ |
| 5707. | $A^{111}$ | $D^{120}$ |
| 5708. | $A^{112}$ | $D^{120}$ |
| 5709. | $A^{113}$ | $D^{120}$ |
| 5710. | $A^{114}$ | $D^{120}$ |
| 5711. | $A^{115}$ | $D^{120}$ |
| 5712. | $A^{116}$ | $D^{120}$ |
| 5713. | $A^{117}$ | $D^{120}$ |
| 5714. | $A^{118}$ | $D^{120}$ |
| 5715. | $A^{119}$ | $D^{120}$ |
| 5716. | $A^{120}$ | $D^{120}$ |
| 5717. | $A^{121}$ | $D^{120}$ |
| 5718. | $A^{122}$ | $D^{120}$ |
| 5719. | $A^{123}$ | $D^{120}$ |
| 5720. | $A^{124}$ | $D^{120}$ |
| 5721. | $A^{125}$ | $D^{120}$ |
| 5722. | $A^{126}$ | $D^{120}$ |
| 5723. | $A^{127}$ | $D^{120}$ |
| 5724. | $A^{128}$ | $D^{120}$ |
| 5725. | $A^{129}$ | $D^{120}$ |
| 5726. | $A^{130}$ | $D^{120}$ |
| 5727. | $A^{131}$ | $D^{120}$ |
| 5728. | $A^{132}$ | $D^{120}$ |
| 5729. | $A^{101}$ | $D^{121}$ |
| 5730. | $A^{102}$ | $D^{121}$ |
| 5731. | $A^{103}$ | $D^{121}$ |
| 5732. | $A^{104}$ | $D^{121}$ |

Formula IV

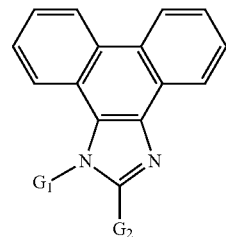

| Compound Number | $G^1$ | $G^2$ |
|---|---|---|
| 5733. | $A^{105}$ | $D^{121}$ |
| 5734. | $A^{106}$ | $D^{121}$ |
| 5735. | $A^{107}$ | $D^{121}$ |
| 5736. | $A^{108}$ | $D^{121}$ |
| 5737. | $A^{109}$ | $D^{121}$ |
| 5738. | $A^{110}$ | $D^{121}$ |
| 5739. | $A^{111}$ | $D^{121}$ |
| 5740. | $A^{112}$ | $D^{121}$ |
| 5741. | $A^{113}$ | $D^{121}$ |
| 5742. | $A^{114}$ | $D^{121}$ |
| 5743. | $A^{115}$ | $D^{121}$ |
| 5744. | $A^{116}$ | $D^{121}$ |
| 5745. | $A^{117}$ | $D^{121}$ |
| 5746. | $A^{118}$ | $D^{121}$ |
| 5747. | $A^{119}$ | $D^{121}$ |
| 5748. | $A^{120}$ | $D^{121}$ |
| 5749. | $A^{121}$ | $D^{121}$ |
| 5750. | $A^{122}$ | $D^{121}$ |
| 5751. | $A^{123}$ | $D^{121}$ |
| 5752. | $A^{124}$ | $D^{121}$ |
| 5753. | $A^{125}$ | $D^{121}$ |
| 5754. | $A^{126}$ | $D^{121}$ |
| 5755. | $A^{127}$ | $D^{121}$ |
| 5756. | $A^{128}$ | $D^{121}$ |
| 5757. | $A^{129}$ | $D^{121}$ |
| 5758. | $A^{130}$ | $D^{121}$ |
| 5759. | $A^{131}$ | $D^{121}$ |
| 5760. | $A^{132}$ | $D^{121}$ |
| 5761. | $A^{101}$ | $D^{122}$ |
| 5762. | $A^{102}$ | $D^{122}$ |
| 5763. | $A^{103}$ | $D^{122}$ |
| 5764. | $A^{104}$ | $D^{122}$ |
| 5765. | $A^{105}$ | $D^{122}$ |
| 5766. | $A^{106}$ | $D^{122}$ |
| 5767. | $A^{107}$ | $D^{122}$ |
| 5768. | $A^{108}$ | $D^{122}$ |
| 5769. | $A^{109}$ | $D^{122}$ |
| 5770. | $A^{110}$ | $D^{122}$ |
| 5771. | $A^{111}$ | $D^{122}$ |
| 5772. | $A^{112}$ | $D^{122}$ |
| 5773. | $A^{113}$ | $D^{122}$ |
| 5774. | $A^{114}$ | $D^{122}$ |
| 5775. | $A^{115}$ | $D^{122}$ |
| 5776. | $A^{116}$ | $D^{122}$ |
| 5777. | $A^{117}$ | $D^{122}$ |
| 5778. | $A^{118}$ | $D^{122}$ |
| 5779. | $A^{119}$ | $D^{122}$ |
| 5780. | $A^{120}$ | $D^{122}$ |
| 5781. | $A^{121}$ | $D^{122}$ |
| 5782. | $A^{122}$ | $D^{122}$ |
| 5783. | $A^{123}$ | $D^{122}$ |
| 5784. | $A^{124}$ | $D^{122}$ |
| 5785. | $A^{125}$ | $D^{122}$ |
| 5786. | $A^{126}$ | $D^{122}$ |
| 5787. | $A^{127}$ | $D^{122}$ |
| 5788. | $A^{128}$ | $D^{122}$ |
| 5789. | $A^{129}$ | $D^{122}$ |
| 5790. | $A^{130}$ | $D^{122}$ |
| 5791. | $A^{131}$ | $D^{122}$ |
| 5792. | $A^{132}$ | $D^{122}$ |
| 5793. | $A^{101}$ | $D^{123}$ |
| 5794. | $A^{102}$ | $D^{123}$ |
| 5795. | $A^{103}$ | $D^{123}$ |

Formula IV

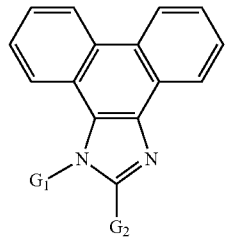

| Compound Number | G¹ | G² |
|---|---|---|
| 5796. | $A^{104}$ | $D^{123}$ |
| 5797. | $A^{105}$ | $D^{123}$ |
| 5798. | $A^{106}$ | $D^{123}$ |
| 5799. | $A^{107}$ | $D^{123}$ |
| 5800. | $A^{108}$ | $D^{123}$ |
| 5801. | $A^{109}$ | $D^{123}$ |
| 5802. | $A^{110}$ | $D^{123}$ |
| 5803. | $A^{111}$ | $D^{123}$ |
| 5804. | $A^{112}$ | $D^{123}$ |
| 5805. | $A^{113}$ | $D^{123}$ |
| 5806. | $A^{114}$ | $D^{123}$ |
| 5807. | $A^{115}$ | $D^{123}$ |
| 5808. | $A^{116}$ | $D^{123}$ |
| 5809. | $A^{117}$ | $D^{123}$ |
| 5810. | $A^{118}$ | $D^{123}$ |
| 5811. | $A^{119}$ | $D^{123}$ |
| 5812. | $A^{120}$ | $D^{123}$ |
| 5813. | $A^{121}$ | $D^{123}$ |
| 5814. | $A^{122}$ | $D^{123}$ |
| 5815. | $A^{123}$ | $D^{123}$ |
| 5816. | $A^{124}$ | $D^{123}$ |
| 5817. | $A^{125}$ | $D^{123}$ |
| 5818. | $A^{126}$ | $D^{123}$ |
| 5819. | $A^{127}$ | $D^{123}$ |
| 5820. | $A^{128}$ | $D^{123}$ |
| 5821. | $A^{129}$ | $D^{123}$ |
| 5822. | $A^{130}$ | $D^{123}$ |
| 5823. | $A^{131}$ | $D^{123}$ |
| 5824. | $A^{132}$ | $D^{123}$ |
| 5825. | $A^{101}$ | $D^{124}$ |
| 5826. | $A^{102}$ | $D^{124}$ |
| 5827. | $A^{103}$ | $D^{124}$ |
| 5828. | $A^{104}$ | $D^{124}$ |
| 5829. | $A^{105}$ | $D^{124}$ |
| 5830. | $A^{106}$ | $D^{124}$ |
| 5831. | $A^{107}$ | $D^{124}$ |
| 5832. | $A^{108}$ | $D^{124}$ |
| 5833. | $A^{109}$ | $D^{124}$ |
| 5834. | $A^{110}$ | $D^{124}$ |
| 5835. | $A^{111}$ | $D^{124}$ |
| 5836. | $A^{112}$ | $D^{124}$ |
| 5837. | $A^{113}$ | $D^{124}$ |
| 5838. | $A^{114}$ | $D^{124}$ |
| 5839. | $A^{115}$ | $D^{124}$ |
| 5840. | $A^{116}$ | $D^{124}$ |
| 5841. | $A^{117}$ | $D^{124}$ |
| 5842. | $A^{118}$ | $D^{124}$ |
| 5843. | $A^{119}$ | $D^{124}$ |
| 5844. | $A^{120}$ | $D^{124}$ |
| 5845. | $A^{121}$ | $D^{124}$ |
| 5846. | $A^{122}$ | $D^{124}$ |
| 5847. | $A^{123}$ | $D^{124}$ |
| 5848. | $A^{124}$ | $D^{124}$ |
| 5849. | $A^{125}$ | $D^{124}$ |
| 5850. | $A^{126}$ | $D^{124}$ |
| 5851. | $A^{127}$ | $D^{124}$ |
| 5852. | $A^{128}$ | $D^{124}$ |
| 5853. | $A^{129}$ | $D^{124}$ |
| 5854. | $A^{130}$ | $D^{124}$ |
| 5855. | $A^{131}$ | $D^{124}$ |
| 5856. | $A^{132}$ | $D^{124}$ |
| 5857. | $A^{101}$ | $D^{125}$ |
| 5858. | $A^{102}$ | $D^{125}$ |

Formula IV

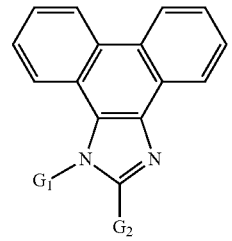

| Compound Number | G¹ | G² |
|---|---|---|
| 5859. | $A^{103}$ | $D^{125}$ |
| 5860. | $A^{104}$ | $D^{125}$ |
| 5861. | $A^{105}$ | $D^{125}$ |
| 5862. | $A^{106}$ | $D^{125}$ |
| 5863. | $A^{107}$ | $D^{125}$ |
| 5864. | $A^{108}$ | $D^{125}$ |
| 5865. | $A^{109}$ | $D^{125}$ |
| 5866. | $A^{110}$ | $D^{125}$ |
| 5867. | $A^{111}$ | $D^{125}$ |
| 5868. | $A^{112}$ | $D^{125}$ |
| 5869. | $A^{113}$ | $D^{125}$ |
| 5870. | $A^{114}$ | $D^{125}$ |
| 5871. | $A^{115}$ | $D^{125}$ |
| 5872. | $A^{116}$ | $D^{125}$ |
| 5873. | $A^{117}$ | $D^{125}$ |
| 5874. | $A^{118}$ | $D^{125}$ |
| 5875. | $A^{119}$ | $D^{125}$ |
| 5876. | $A^{120}$ | $D^{125}$ |
| 5877. | $A^{121}$ | $D^{125}$ |
| 5878. | $A^{122}$ | $D^{125}$ |
| 5879. | $A^{123}$ | $D^{125}$ |
| 5880. | $A^{124}$ | $D^{125}$ |
| 5881. | $A^{125}$ | $D^{125}$ |
| 5882. | $A^{126}$ | $D^{125}$ |
| 5883. | $A^{127}$ | $D^{125}$ |
| 5884. | $A^{128}$ | $D^{125}$ |
| 5885. | $A^{129}$ | $D^{125}$ |
| 5886. | $A^{130}$ | $D^{125}$ |
| 5887. | $A^{131}$ | $D^{125}$ |
| 5888. | $A^{132}$ | $D^{125}$ |
| 5889. | $A^{101}$ | $D^{126}$ |
| 5890. | $A^{102}$ | $D^{126}$ |
| 5891. | $A^{103}$ | $D^{126}$ |
| 5892. | $A^{104}$ | $D^{126}$ |
| 5893. | $A^{105}$ | $D^{126}$ |
| 5894. | $A^{106}$ | $D^{126}$ |
| 5895. | $A^{107}$ | $D^{126}$ |
| 5896. | $A^{108}$ | $D^{126}$ |
| 5897. | $A^{109}$ | $D^{126}$ |
| 5898. | $A^{110}$ | $D^{126}$ |
| 5899. | $A^{111}$ | $D^{126}$ |
| 5900. | $A^{112}$ | $D^{126}$ |
| 5901. | $A^{113}$ | $D^{126}$ |
| 5902. | $A^{114}$ | $D^{126}$ |
| 5903. | $A^{115}$ | $D^{126}$ |
| 5904. | $A^{116}$ | $D^{126}$ |
| 5905. | $A^{117}$ | $D^{126}$ |
| 5906. | $A^{118}$ | $D^{126}$ |
| 5907. | $A^{119}$ | $D^{126}$ |
| 5908. | $A^{120}$ | $D^{126}$ |
| 5909. | $A^{121}$ | $D^{126}$ |
| 5910. | $A^{122}$ | $D^{126}$ |
| 5911. | $A^{123}$ | $D^{126}$ |
| 5912. | $A^{124}$ | $D^{126}$ |
| 5913. | $A^{125}$ | $D^{126}$ |
| 5914. | $A^{126}$ | $D^{126}$ |
| 5915. | $A^{127}$ | $D^{126}$ |
| 5916. | $A^{128}$ | $D^{126}$ |
| 5917. | $A^{129}$ | $D^{126}$ |
| 5918. | $A^{130}$ | $D^{126}$ |
| 5919. | $A^{131}$ | $D^{126}$ |
| 5920. | $A^{132}$ | $D^{126}$ |
| 5921. | $A^{101}$ | $D^{127}$ |

199
-continued

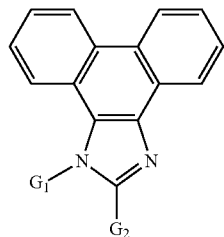

Formula IV

| Compound Number | G¹ | G² |
|---|---|---|
| 5922. | $A^{102}$ | $D^{127}$ |
| 5923. | $A^{103}$ | $D^{127}$ |
| 5924. | $A^{104}$ | $D^{127}$ |
| 5925. | $A^{105}$ | $D^{127}$ |
| 5926. | $A^{106}$ | $D^{127}$ |
| 5927. | $A^{107}$ | $D^{127}$ |
| 5928. | $A^{108}$ | $D^{127}$ |
| 5929. | $A^{109}$ | $D^{127}$ |
| 5930. | $A^{110}$ | $D^{127}$ |
| 5931. | $A^{111}$ | $D^{127}$ |
| 5932. | $A^{112}$ | $D^{127}$ |
| 5933. | $A^{113}$ | $D^{127}$ |
| 5934. | $A^{114}$ | $D^{127}$ |
| 5935. | $A^{115}$ | $D^{127}$ |
| 5936. | $A^{116}$ | $D^{127}$ |
| 5937. | $A^{117}$ | $D^{127}$ |
| 5938. | $A^{118}$ | $D^{127}$ |
| 5939. | $A^{119}$ | $D^{127}$ |
| 5940. | $A^{120}$ | $D^{127}$ |
| 5941. | $A^{121}$ | $D^{127}$ |
| 5942. | $A^{122}$ | $D^{127}$ |
| 5943. | $A^{123}$ | $D^{127}$ |
| 5944. | $A^{124}$ | $D^{127}$ |
| 5945. | $A^{125}$ | $D^{127}$ |
| 5946. | $A^{126}$ | $D^{127}$ |
| 5947. | $A^{127}$ | $D^{127}$ |
| 5948. | $A^{128}$ | $D^{127}$ |
| 5949. | $A^{129}$ | $D^{127}$ |
| 5950. | $A^{130}$ | $D^{127}$ |
| 5951. | $A^{131}$ | $D^{127}$ |
| 5952. | $A^{132}$ | $D^{127}$ |
| 5953. | $A^{101}$ | $D^{128}$ |
| 5954. | $A^{102}$ | $D^{128}$ |
| 5955. | $A^{103}$ | $D^{128}$ |
| 5956. | $A^{104}$ | $D^{128}$ |
| 5957. | $A^{105}$ | $D^{128}$ |
| 5958. | $A^{106}$ | $D^{128}$ |
| 5959. | $A^{107}$ | $D^{128}$ |
| 5960. | $A^{108}$ | $D^{128}$ |
| 5961. | $A^{109}$ | $D^{128}$ |
| 5962. | $A^{110}$ | $D^{128}$ |
| 5963. | $A^{111}$ | $D^{128}$ |
| 5964. | $A^{112}$ | $D^{128}$ |
| 5965. | $A^{113}$ | $D^{128}$ |
| 5966. | $A^{114}$ | $D^{128}$ |
| 5967. | $A^{115}$ | $D^{128}$ |
| 5968. | $A^{116}$ | $D^{128}$ |
| 5969. | $A^{117}$ | $D^{128}$ |
| 5970. | $A^{118}$ | $D^{128}$ |
| 5971. | $A^{119}$ | $D^{128}$ |
| 5972. | $A^{120}$ | $D^{128}$ |
| 5973. | $A^{121}$ | $D^{128}$ |
| 5974. | $A^{122}$ | $D^{128}$ |
| 5975. | $A^{123}$ | $D^{128}$ |
| 5976. | $A^{124}$ | $D^{128}$ |
| 5977. | $A^{125}$ | $D^{128}$ |
| 5978. | $A^{126}$ | $D^{128}$ |
| 5979. | $A^{127}$ | $D^{128}$ |
| 5980. | $A^{128}$ | $D^{128}$ |
| 5981. | $A^{129}$ | $D^{128}$ |
| 5982. | $A^{130}$ | $D^{128}$ |
| 5983. | $A^{131}$ | $D^{128}$ |
| 5984. | $A^{132}$ | $D^{128}$ |

200
-continued

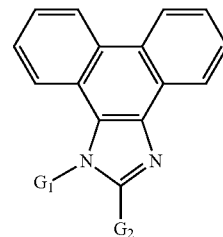

Formula IV

| Compound Number | G¹ | G² |
|---|---|---|
| 5985. | $A^{101}$ | $D^{129}$ |
| 5986. | $A^{102}$ | $D^{129}$ |
| 5987. | $A^{103}$ | $D^{129}$ |
| 5988. | $A^{104}$ | $D^{129}$ |
| 5989. | $A^{105}$ | $D^{129}$ |
| 5990. | $A^{106}$ | $D^{129}$ |
| 5991. | $A^{107}$ | $D^{129}$ |
| 5992. | $A^{108}$ | $D^{129}$ |
| 5993. | $A^{109}$ | $D^{129}$ |
| 5994. | $A^{110}$ | $D^{129}$ |
| 5995. | $A^{111}$ | $D^{129}$ |
| 5996. | $A^{112}$ | $D^{129}$ |
| 5997. | $A^{113}$ | $D^{129}$ |
| 5998. | $A^{114}$ | $D^{129}$ |
| 5999. | $A^{115}$ | $D^{129}$ |
| 6000. | $A^{116}$ | $D^{129}$ |
| 6001. | $A^{117}$ | $D^{129}$ |
| 6002. | $A^{118}$ | $D^{129}$ |
| 6003. | $A^{119}$ | $D^{129}$ |
| 6004. | $A^{120}$ | $D^{129}$ |
| 6005. | $A^{121}$ | $D^{129}$ |
| 6006. | $A^{122}$ | $D^{129}$ |
| 6007. | $A^{123}$ | $D^{129}$ |
| 6008. | $A^{124}$ | $D^{129}$ |
| 6009. | $A^{125}$ | $D^{129}$ |
| 6010. | $A^{126}$ | $D^{129}$ |
| 6011. | $A^{127}$ | $D^{129}$ |
| 6012. | $A^{128}$ | $D^{129}$ |
| 6013. | $A^{129}$ | $D^{129}$ |
| 6014. | $A^{130}$ | $D^{129}$ |
| 6015. | $A^{131}$ | $D^{129}$ |
| 6016. | $A^{132}$ | $D^{129}$ |
| 6017. | $A^{101}$ | $D^{130}$ |
| 6018. | $A^{102}$ | $D^{130}$ |
| 6019. | $A^{103}$ | $D^{130}$ |
| 6020. | $A^{104}$ | $D^{130}$ |
| 6021. | $A^{105}$ | $D^{130}$ |
| 6022. | $A^{106}$ | $D^{130}$ |
| 6023. | $A^{107}$ | $D^{130}$ |
| 6024. | $A^{108}$ | $D^{130}$ |
| 6025. | $A^{109}$ | $D^{130}$ |
| 6026. | $A^{110}$ | $D^{130}$ |
| 6027. | $A^{111}$ | $D^{130}$ |
| 6028. | $A^{112}$ | $D^{130}$ |
| 6029. | $A^{113}$ | $D^{130}$ |
| 6030. | $A^{114}$ | $D^{130}$ |
| 6031. | $A^{115}$ | $D^{130}$ |
| 6032. | $A^{116}$ | $D^{130}$ |
| 6033. | $A^{117}$ | $D^{130}$ |
| 6034. | $A^{118}$ | $D^{130}$ |
| 6035. | $A^{119}$ | $D^{130}$ |
| 6036. | $A^{120}$ | $D^{130}$ |
| 6037. | $A^{121}$ | $D^{130}$ |
| 6038. | $A^{122}$ | $D^{130}$ |
| 6039. | $A^{123}$ | $D^{130}$ |
| 6040. | $A^{124}$ | $D^{130}$ |
| 6041. | $A^{125}$ | $D^{130}$ |
| 6042. | $A^{126}$ | $D^{130}$ |
| 6043. | $A^{127}$ | $D^{130}$ |
| 6044. | $A^{128}$ | $D^{130}$ |
| 6045. | $A^{129}$ | $D^{130}$ |
| 6046. | $A^{130}$ | $D^{130}$ |
| 6047. | $A^{131}$ | $D^{130}$ |

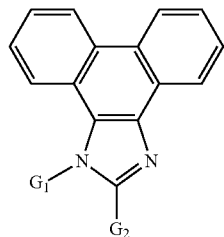

Formula IV

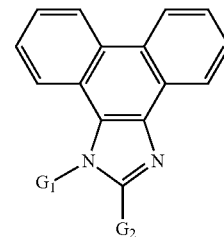

Formula IV

| Compound Number | $G^1$ | $G^2$ |
|---|---|---|
| 6048. | $A^{132}$ | $D^{130}$ |
| 6049. | $A^{101}$ | $D^{131}$ |
| 6050. | $A^{102}$ | $D^{131}$ |
| 6051. | $A^{103}$ | $D^{131}$ |
| 6052. | $A^{104}$ | $D^{131}$ |
| 6053. | $A^{105}$ | $D^{131}$ |
| 6054. | $A^{106}$ | $D^{131}$ |
| 6055. | $A^{107}$ | $D^{131}$ |
| 6056. | $A^{108}$ | $D^{131}$ |
| 6057. | $A^{109}$ | $D^{131}$ |
| 6058. | $A^{110}$ | $D^{131}$ |
| 6059. | $A^{111}$ | $D^{131}$ |
| 6060. | $A^{112}$ | $D^{131}$ |
| 6061. | $A^{113}$ | $D^{131}$ |
| 6062. | $A^{114}$ | $D^{131}$ |
| 6063. | $A^{115}$ | $D^{131}$ |
| 6064. | $A^{116}$ | $D^{131}$ |
| 6065. | $A^{117}$ | $D^{131}$ |
| 6066. | $A^{118}$ | $D^{131}$ |
| 6067. | $A^{119}$ | $D^{131}$ |
| 6068. | $A^{120}$ | $D^{131}$ |
| 6069. | $A^{121}$ | $D^{131}$ |
| 6070. | $A^{122}$ | $D^{131}$ |
| 6071. | $A^{123}$ | $D^{131}$ |
| 6072. | $A^{124}$ | $D^{131}$ |
| 6073. | $A^{125}$ | $D^{131}$ |
| 6074. | $A^{126}$ | $D^{131}$ |
| 6075. | $A^{127}$ | $D^{131}$ |
| 6076. | $A^{128}$ | $D^{131}$ |
| 6077. | $A^{129}$ | $D^{131}$ |
| 6078. | $A^{130}$ | $D^{131}$ |
| 6079. | $A^{131}$ | $D^{131}$ |
| 6080. | $A^{132}$ | $D^{131}$ |
| 6081. | $A^{101}$ | $D^{132}$ |
| 6082. | $A^{102}$ | $D^{132}$ |
| 6083. | $A^{103}$ | $D^{132}$ |
| 6084. | $A^{104}$ | $D^{132}$ |
| 6085. | $A^{105}$ | $D^{132}$ |
| 6086. | $A^{106}$ | $D^{132}$ |
| 6087. | $A^{107}$ | $D^{132}$ |
| 6088. | $A^{108}$ | $D^{132}$ |
| 6089. | $A^{109}$ | $D^{132}$ |
| 6090. | $A^{110}$ | $D^{132}$ |
| 6091. | $A^{111}$ | $D^{132}$ |
| 6092. | $A^{112}$ | $D^{132}$ |
| 6093. | $A^{113}$ | $D^{132}$ |
| 6094. | $A^{114}$ | $D^{132}$ |
| 6095. | $A^{115}$ | $D^{132}$ |
| 6096. | $A^{116}$ | $D^{132}$ |
| 6097. | $A^{117}$ | $D^{132}$ |
| 6098. | $A^{118}$ | $D^{132}$ |
| 6099. | $A^{119}$ | $D^{132}$ |
| 6100. | $A^{120}$ | $D^{132}$ |
| 6101. | $A^{121}$ | $D^{132}$ |
| 6102. | $A^{122}$ | $D^{132}$ |
| 6103. | $A^{123}$ | $D^{132}$ |
| 6104. | $A^{124}$ | $D^{132}$ |
| 6105. | $A^{125}$ | $D^{132}$ |
| 6106. | $A^{126}$ | $D^{132}$ |
| 6107. | $A^{127}$ | $D^{132}$ |
| 6108. | $A^{128}$ | $D^{132}$ |
| 6109. | $A^{129}$ | $D^{132}$ |
| 6110. | $A^{130}$ | $D^{132}$ |
| 6111. | $A^{131}$ | $D^{132}$ |
| 6112. | $A^{132}$ | $D^{132}$ |
| 6113. | $A^{101}$ | $D^{133}$ |
| 6114. | $A^{102}$ | $D^{133}$ |
| 6115. | $A^{103}$ | $D^{133}$ |
| 6116. | $A^{104}$ | $D^{133}$ |
| 6117. | $A^{105}$ | $D^{133}$ |
| 6118. | $A^{106}$ | $D^{133}$ |
| 6119. | $A^{107}$ | $D^{133}$ |
| 6120. | $A^{108}$ | $D^{133}$ |
| 6121. | $A^{109}$ | $D^{133}$ |
| 6122. | $A^{110}$ | $D^{133}$ |
| 6123. | $A^{111}$ | $D^{133}$ |
| 6124. | $A^{112}$ | $D^{133}$ |
| 6125. | $A^{113}$ | $D^{133}$ |
| 6126. | $A^{114}$ | $D^{133}$ |
| 6127. | $A^{115}$ | $D^{133}$ |
| 6128. | $A^{116}$ | $D^{133}$ |
| 6129. | $A^{117}$ | $D^{133}$ |
| 6130. | $A^{118}$ | $D^{133}$ |
| 6131. | $A^{119}$ | $D^{133}$ |
| 6132. | $A^{120}$ | $D^{133}$ |
| 6133. | $A^{121}$ | $D^{133}$ |
| 6134. | $A^{122}$ | $D^{133}$ |
| 6135. | $A^{123}$ | $D^{133}$ |
| 6136. | $A^{124}$ | $D^{133}$ |
| 6137. | $A^{125}$ | $D^{133}$ |
| 6138. | $A^{126}$ | $D^{133}$ |
| 6139. | $A^{127}$ | $D^{133}$ |
| 6140. | $A^{128}$ | $D^{133}$ |
| 6141. | $A^{129}$ | $D^{133}$ |
| 6142. | $A^{130}$ | $D^{133}$ |
| 6143. | $A^{131}$ | $D^{133}$ |
| 6144. | $A^{132}$ | $D^{133}$ |
| 6145. | $A^{101}$ | $D^{134}$ |
| 6146. | $A^{102}$ | $D^{134}$ |
| 6147. | $A^{103}$ | $D^{134}$ |
| 6148. | $A^{104}$ | $D^{134}$ |
| 6149. | $A^{105}$ | $D^{134}$ |
| 6150. | $A^{106}$ | $D^{134}$ |
| 6151. | $A^{107}$ | $D^{134}$ |
| 6152. | $A^{108}$ | $D^{134}$ |
| 6153. | $A^{109}$ | $D^{134}$ |
| 6154. | $A^{110}$ | $D^{134}$ |
| 6155. | $A^{111}$ | $D^{134}$ |
| 6156. | $A^{112}$ | $D^{134}$ |
| 6157. | $A^{113}$ | $D^{134}$ |
| 6158. | $A^{114}$ | $D^{134}$ |
| 6159. | $A^{115}$ | $D^{134}$ |
| 6160. | $A^{116}$ | $D^{134}$ |
| 6161. | $A^{117}$ | $D^{134}$ |
| 6162. | $A^{118}$ | $D^{134}$ |
| 6163. | $A^{119}$ | $D^{134}$ |
| 6164. | $A^{120}$ | $D^{134}$ |
| 6165. | $A^{121}$ | $D^{134}$ |
| 6166. | $A^{122}$ | $D^{134}$ |
| 6167. | $A^{123}$ | $D^{134}$ |
| 6168. | $A^{124}$ | $D^{134}$ |
| 6169. | $A^{125}$ | $D^{134}$ |
| 6170. | $A^{126}$ | $D^{134}$ |
| 6171. | $A^{127}$ | $D^{134}$ |
| 6172. | $A^{128}$ | $D^{134}$ |
| 6173. | $A^{129}$ | $D^{134}$ |

-continued

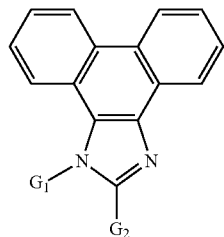

Formula IV

| Compound Number | $G^1$ | $G^2$ |
|---|---|---|
| 6174. | $A^{130}$ | $D^{134}$ |
| 6175. | $A^{131}$ | $D^{134}$ |
| 6176. | $A^{132}$ | $D^{134}$ |
| 6177. | $A^{101}$ | $D^{135}$ |
| 6178. | $A^{102}$ | $D^{135}$ |
| 6179. | $A^{103}$ | $D^{135}$ |
| 6180. | $A^{104}$ | $D^{135}$ |
| 6181. | $A^{105}$ | $D^{135}$ |
| 6182. | $A^{106}$ | $D^{135}$ |
| 6183. | $A^{107}$ | $D^{135}$ |
| 6184. | $A^{108}$ | $D^{135}$ |
| 6185. | $A^{109}$ | $D^{135}$ |
| 6186. | $A^{110}$ | $D^{135}$ |
| 6187. | $A^{111}$ | $D^{135}$ |
| 6188. | $A^{112}$ | $D^{135}$ |
| 6189. | $A^{113}$ | $D^{135}$ |
| 6190. | $A^{114}$ | $D^{135}$ |
| 6191. | $A^{115}$ | $D^{135}$ |
| 6192. | $A^{116}$ | $D^{135}$ |
| 6193. | $A^{117}$ | $D^{135}$ |
| 6194. | $A^{118}$ | $D^{135}$ |
| 6195. | $A^{119}$ | $D^{135}$ |
| 6196. | $A^{120}$ | $D^{135}$ |
| 6197. | $A^{121}$ | $D^{135}$ |
| 6198. | $A^{122}$ | $D^{135}$ |
| 6199. | $A^{123}$ | $D^{135}$ |
| 6200. | $A^{124}$ | $D^{135}$ |
| 6201. | $A^{125}$ | $D^{135}$ |
| 6202. | $A^{126}$ | $D^{135}$ |
| 6203. | $A^{127}$ | $D^{135}$ |
| 6204. | $A^{128}$ | $D^{135}$ |
| 6205. | $A^{129}$ | $D^{135}$ |
| 6206. | $A^{130}$ | $D^{135}$ |
| 6207. | $A^{131}$ | $D^{135}$ |
| 6208. | $A^{132}$ | $D^{135}$ |
| 6209. | $A^{101}$ | $D^{136}$ |
| 6210. | $A^{102}$ | $D^{136}$ |
| 6211. | $A^{103}$ | $D^{136}$ |
| 6212. | $A^{104}$ | $D^{136}$ |
| 6213. | $A^{105}$ | $D^{136}$ |
| 6214. | $A^{106}$ | $D^{136}$ |
| 6215. | $A^{107}$ | $D^{136}$ |
| 6216. | $A^{108}$ | $D^{136}$ |
| 6217. | $A^{109}$ | $D^{136}$ |
| 6218. | $A^{110}$ | $D^{136}$ |
| 6219. | $A^{111}$ | $D^{136}$ |
| 6220. | $A^{112}$ | $D^{136}$ |
| 6221. | $A^{113}$ | $D^{136}$ |
| 6222. | $A^{114}$ | $D^{136}$ |
| 6223. | $A^{115}$ | $D^{136}$ |
| 6224. | $A^{116}$ | $D^{136}$ |
| 6225. | $A^{117}$ | $D^{136}$ |
| 6226. | $A^{118}$ | $D^{136}$ |
| 6227. | $A^{119}$ | $D^{136}$ |
| 6228. | $A^{120}$ | $D^{136}$ |
| 6229. | $A^{121}$ | $D^{136}$ |
| 6230. | $A^{122}$ | $D^{136}$ |
| 6231. | $A^{123}$ | $D^{136}$ |
| 6232. | $A^{124}$ | $D^{136}$ |
| 6233. | $A^{125}$ | $D^{136}$ |
| 6234. | $A^{126}$ | $D^{136}$ |
| 6235. | $A^{127}$ | $D^{136}$ |
| 6236. | $A^{128}$ | $D^{136}$ |

-continued

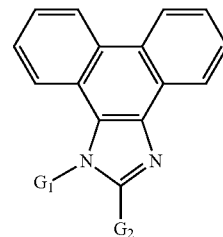

Formula IV

| Compound Number | $G^1$ | $G^2$ |
|---|---|---|
| 6237. | $A^{129}$ | $D^{136}$ |
| 6238. | $A^{130}$ | $D^{136}$ |
| 6239. | $A^{131}$ | $D^{136}$ |
| 6240. | $A^{132}$ | $D^{136}$ |
| 6241. | $A^{101}$ | $D^{137}$ |
| 6242. | $A^{102}$ | $D^{137}$ |
| 6243. | $A^{103}$ | $D^{137}$ |
| 6244. | $A^{104}$ | $D^{137}$ |
| 6245. | $A^{105}$ | $D^{137}$ |
| 6246. | $A^{106}$ | $D^{137}$ |
| 6247. | $A^{107}$ | $D^{137}$ |
| 6248. | $A^{108}$ | $D^{137}$ |
| 6249. | $A^{109}$ | $D^{137}$ |
| 6250. | $A^{110}$ | $D^{137}$ |
| 6251. | $A^{111}$ | $D^{137}$ |
| 6252. | $A^{112}$ | $D^{137}$ |
| 6253. | $A^{113}$ | $D^{137}$ |
| 6254. | $A^{114}$ | $D^{137}$ |
| 6255. | $A^{115}$ | $D^{137}$ |
| 6256. | $A^{116}$ | $D^{137}$ |
| 6257. | $A^{117}$ | $D^{137}$ |
| 6258. | $A^{118}$ | $D^{137}$ |
| 6259. | $A^{119}$ | $D^{137}$ |
| 6260. | $A^{120}$ | $D^{137}$ |
| 6261. | $A^{121}$ | $D^{137}$ |
| 6262. | $A^{122}$ | $D^{137}$ |
| 6263. | $A^{123}$ | $D^{137}$ |
| 6264. | $A^{124}$ | $D^{137}$ |
| 6265. | $A^{125}$ | $D^{137}$ |
| 6266. | $A^{126}$ | $D^{137}$ |
| 6267. | $A^{127}$ | $D^{137}$ |
| 6268. | $A^{128}$ | $D^{137}$ |
| 6269. | $A^{129}$ | $D^{137}$ |
| 6270. | $A^{130}$ | $D^{137}$ |
| 6271. | $A^{131}$ | $D^{137}$ |
| 6272. | $A^{132}$ | $D^{137}$ |
| 6273. | $A^{101}$ | $D^{138}$ |
| 6274. | $A^{102}$ | $D^{138}$ |
| 6275. | $A^{103}$ | $D^{138}$ |
| 6276. | $A^{104}$ | $D^{138}$ |
| 6277. | $A^{105}$ | $D^{138}$ |
| 6278. | $A^{106}$ | $D^{138}$ |
| 6279. | $A^{107}$ | $D^{138}$ |
| 6280. | $A^{108}$ | $D^{138}$ |
| 6281. | $A^{109}$ | $D^{138}$ |
| 6282. | $A^{110}$ | $D^{138}$ |
| 6283. | $A^{111}$ | $D^{138}$ |
| 6284. | $A^{112}$ | $D^{138}$ |
| 6285. | $A^{113}$ | $D^{138}$ |
| 6286. | $A^{114}$ | $D^{138}$ |
| 6287. | $A^{115}$ | $D^{138}$ |
| 6288. | $A^{116}$ | $D^{138}$ |
| 6289. | $A^{117}$ | $D^{138}$ |
| 6290. | $A^{118}$ | $D^{138}$ |
| 6291. | $A^{119}$ | $D^{138}$ |
| 6292. | $A^{120}$ | $D^{138}$ |
| 6293. | $A^{121}$ | $D^{138}$ |
| 6294. | $A^{122}$ | $D^{138}$ |
| 6295. | $A^{123}$ | $D^{138}$ |
| 6296. | $A^{124}$ | $D^{138}$ |
| 6297. | $A^{125}$ | $D^{138}$ |
| 6298. | $A^{126}$ | $D^{138}$ |
| 6299. | $A^{127}$ | $D^{138}$ |

Formula IV

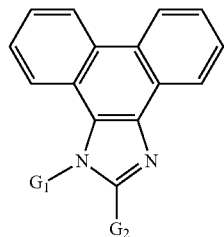

| Compound Number | $G^1$ | $G^2$ |
|---|---|---|
| 6300. | $A^{128}$ | $D^{138}$ |
| 6301. | $A^{129}$ | $D^{138}$ |
| 6302. | $A^{130}$ | $D^{138}$ |
| 6303. | $A^{131}$ | $D^{138}$ |
| 6304. | $A^{132}$ | $D^{138}$ |
| 6305. | $A^{101}$ | $D^{139}$ |
| 6306. | $A^{102}$ | $D^{139}$ |
| 6307. | $A^{103}$ | $D^{139}$ |
| 6308. | $A^{104}$ | $D^{139}$ |
| 6309. | $A^{105}$ | $D^{139}$ |
| 6310. | $A^{106}$ | $D^{139}$ |
| 6311. | $A^{107}$ | $D^{139}$ |
| 6312. | $A^{108}$ | $D^{139}$ |
| 6313. | $A^{109}$ | $D^{139}$ |
| 6314. | $A^{110}$ | $D^{139}$ |
| 6315. | $A^{111}$ | $D^{139}$ |
| 6316. | $A^{112}$ | $D^{139}$ |
| 6317. | $A^{113}$ | $D^{139}$ |
| 6318. | $A^{114}$ | $D^{139}$ |
| 6319. | $A^{115}$ | $D^{139}$ |
| 6320. | $A^{116}$ | $D^{139}$ |
| 6321. | $A^{117}$ | $D^{139}$ |
| 6322. | $A^{118}$ | $D^{139}$ |
| 6323. | $A^{119}$ | $D^{139}$ |
| 6324. | $A^{120}$ | $D^{139}$ |
| 6325. | $A^{121}$ | $D^{139}$ |
| 6326. | $A^{122}$ | $D^{139}$ |
| 6327. | $A^{123}$ | $D^{139}$ |
| 6328. | $A^{124}$ | $D^{139}$ |
| 6329. | $A^{125}$ | $D^{139}$ |
| 6330. | $A^{126}$ | $D^{139}$ |
| 6331. | $A^{127}$ | $D^{139}$ |
| 6332. | $A^{128}$ | $D^{139}$ |
| 6333. | $A^{129}$ | $D^{139}$ |
| 6334. | $A^{130}$ | $D^{139}$ |
| 6335. | $A^{131}$ | $D^{139}$ |
| 6336. | $A^{132}$ | $D^{139}$ |
| 6337. | $A^{101}$ | $D^{140}$ |
| 6338. | $A^{102}$ | $D^{140}$ |
| 6339. | $A^{103}$ | $D^{140}$ |
| 6340. | $A^{104}$ | $D^{140}$ |
| 6341. | $A^{105}$ | $D^{140}$ |
| 6342. | $A^{106}$ | $D^{140}$ |
| 6343. | $A^{107}$ | $D^{140}$ |
| 6344. | $A^{108}$ | $D^{140}$ |
| 6345. | $A^{109}$ | $D^{140}$ |
| 6346. | $A^{110}$ | $D^{140}$ |
| 6347. | $A^{111}$ | $D^{140}$ |
| 6348. | $A^{112}$ | $D^{140}$ |
| 6349. | $A^{113}$ | $D^{140}$ |
| 6350. | $A^{114}$ | $D^{140}$ |
| 6351. | $A^{115}$ | $D^{140}$ |
| 6352. | $A^{116}$ | $D^{140}$ |
| 6353. | $A^{117}$ | $D^{140}$ |
| 6354. | $A^{118}$ | $D^{140}$ |
| 6355. | $A^{119}$ | $D^{140}$ |
| 6356. | $A^{120}$ | $D^{140}$ |
| 6357. | $A^{121}$ | $D^{140}$ |
| 6358. | $A^{122}$ | $D^{140}$ |
| 6359. | $A^{123}$ | $D^{140}$ |
| 6360. | $A^{124}$ | $D^{140}$ |
| 6361. | $A^{125}$ | $D^{140}$ |
| 6362. | $A^{126}$ | $D^{140}$ |

Formula IV

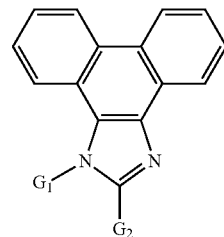

| Compound Number | $G^1$ | $G^2$ |
|---|---|---|
| 6363. | $A^{127}$ | $D^{140}$ |
| 6364. | $A^{128}$ | $D^{140}$ |
| 6365. | $A^{129}$ | $D^{140}$ |
| 6366. | $A^{130}$ | $D^{140}$ |
| 6367. | $A^{131}$ | $D^{140}$ |
| 6368. | $A^{132}$ | $D^{140}$ |
| 6369. | $A^{101}$ | $D^{141}$ |
| 6370. | $A^{102}$ | $D^{141}$ |
| 6371. | $A^{103}$ | $D^{141}$ |
| 6372. | $A^{104}$ | $D^{141}$ |
| 6373. | $A^{105}$ | $D^{141}$ |
| 6374. | $A^{106}$ | $D^{141}$ |
| 6375. | $A^{107}$ | $D^{141}$ |
| 6376. | $A^{108}$ | $D^{141}$ |
| 6377. | $A^{109}$ | $D^{141}$ |
| 6378. | $A^{110}$ | $D^{141}$ |
| 6379. | $A^{111}$ | $D^{141}$ |
| 6380. | $A^{112}$ | $D^{141}$ |
| 6381. | $A^{113}$ | $D^{141}$ |
| 6382. | $A^{114}$ | $D^{141}$ |
| 6383. | $A^{115}$ | $D^{141}$ |
| 6384. | $A^{116}$ | $D^{141}$ |
| 6385. | $A^{117}$ | $D^{141}$ |
| 6386. | $A^{118}$ | $D^{141}$ |
| 6387. | $A^{119}$ | $D^{141}$ |
| 6388. | $A^{120}$ | $D^{141}$ |
| 6389. | $A^{121}$ | $D^{141}$ |
| 6390. | $A^{122}$ | $D^{141}$ |
| 6391. | $A^{123}$ | $D^{141}$ |
| 6392. | $A^{124}$ | $D^{141}$ |
| 6393. | $A^{125}$ | $D^{141}$ |
| 6394. | $A^{126}$ | $D^{141}$ |
| 6395. | $A^{127}$ | $D^{141}$ |
| 6396. | $A^{128}$ | $D^{141}$ |
| 6397. | $A^{129}$ | $D^{141}$ |
| 6398. | $A^{130}$ | $D^{141}$ |
| 6399. | $A^{131}$ | $D^{141}$ |
| 6400. | $A^{132}$ | $D^{141}$ |
| 6401. | $A^{101}$ | $D^{142}$ |
| 6402. | $A^{102}$ | $D^{142}$ |
| 6403. | $A^{103}$ | $D^{142}$ |
| 6404. | $A^{104}$ | $D^{142}$ |
| 6405. | $A^{105}$ | $D^{142}$ |
| 6406. | $A^{106}$ | $D^{142}$ |
| 6407. | $A^{107}$ | $D^{142}$ |
| 6408. | $A^{108}$ | $D^{142}$ |
| 6409. | $A^{109}$ | $D^{142}$ |
| 6410. | $A^{110}$ | $D^{142}$ |
| 6411. | $A^{111}$ | $D^{142}$ |
| 6412. | $A^{112}$ | $D^{142}$ |
| 6413. | $A^{113}$ | $D^{142}$ |
| 6414. | $A^{114}$ | $D^{142}$ |
| 6415. | $A^{115}$ | $D^{142}$ |
| 6416. | $A^{116}$ | $D^{142}$ |
| 6417. | $A^{117}$ | $D^{142}$ |
| 6418. | $A^{118}$ | $D^{142}$ |
| 6419. | $A^{119}$ | $D^{142}$ |
| 6420. | $A^{120}$ | $D^{142}$ |
| 6421. | $A^{121}$ | $D^{142}$ |
| 6422. | $A^{122}$ | $D^{142}$ |
| 6423. | $A^{123}$ | $D^{142}$ |
| 6424. | $A^{124}$ | $D^{142}$ |
| 6425. | $A^{125}$ | $D^{142}$ |

207

-continued

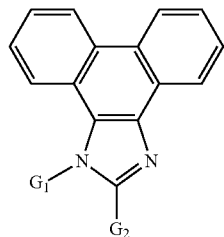

Formula IV

| Compound Number | $G^1$ | $G^2$ |
|---|---|---|
| 6426. | $A^{126}$ | $D^{142}$ |
| 6427. | $A^{127}$ | $D^{142}$ |
| 6428. | $A^{128}$ | $D^{142}$ |
| 6429. | $A^{129}$ | $D^{142}$ |
| 6430. | $A^{130}$ | $D^{142}$ |
| 6431. | $A^{131}$ | $D^{142}$ |
| 6432. | $A^{132}$ | $D^{142}$ |
| 6433. | $A^{101}$ | $D^{143}$ |
| 6434. | $A^{102}$ | $D^{143}$ |
| 6435. | $A^{103}$ | $D^{143}$ |
| 6436. | $A^{104}$ | $D^{143}$ |
| 6437. | $A^{105}$ | $D^{143}$ |
| 6438. | $A^{106}$ | $D^{143}$ |
| 6439. | $A^{107}$ | $D^{143}$ |
| 6440. | $A^{108}$ | $D^{143}$ |
| 6441. | $A^{109}$ | $D^{143}$ |
| 6442. | $A^{110}$ | $D^{143}$ |
| 6443. | $A^{111}$ | $D^{143}$ |
| 6444. | $A^{112}$ | $D^{143}$ |
| 6445. | $A^{113}$ | $D^{143}$ |
| 6446. | $A^{114}$ | $D^{143}$ |
| 6447. | $A^{115}$ | $D^{143}$ |
| 6448. | $A^{116}$ | $D^{143}$ |
| 6449. | $A^{117}$ | $D^{143}$ |
| 6450. | $A^{118}$ | $D^{143}$ |
| 6451. | $A^{119}$ | $D^{143}$ |
| 6452. | $A^{120}$ | $D^{143}$ |
| 6453. | $A^{121}$ | $D^{143}$ |
| 6454. | $A^{122}$ | $D^{143}$ |
| 6455. | $A^{123}$ | $D^{143}$ |
| 6456. | $A^{124}$ | $D^{143}$ |
| 6457. | $A^{125}$ | $D^{143}$ |
| 6458. | $A^{126}$ | $D^{143}$ |
| 6459. | $A^{127}$ | $D^{143}$ |
| 6460. | $A^{128}$ | $D^{143}$ |
| 6461. | $A^{129}$ | $D^{143}$ |
| 6462. | $A^{130}$ | $D^{143}$ |
| 6463. | $A^{131}$ | $D^{143}$ |
| 6464. | $A^{132}$ | $D^{143}$ |
| 6465. | $A^{101}$ | $D^{144}$ |
| 6466. | $A^{102}$ | $D^{144}$ |
| 6467. | $A^{103}$ | $D^{144}$ |
| 6468. | $A^{104}$ | $D^{144}$ |
| 6469. | $A^{105}$ | $D^{144}$ |
| 6470. | $A^{106}$ | $D^{144}$ |
| 6471. | $A^{107}$ | $D^{144}$ |
| 6472. | $A^{108}$ | $D^{144}$ |
| 6473. | $A^{109}$ | $D^{144}$ |
| 6474. | $A^{110}$ | $D^{144}$ |
| 6475. | $A^{111}$ | $D^{144}$ |
| 6476. | $A^{112}$ | $D^{144}$ |
| 6477. | $A^{113}$ | $D^{144}$ |
| 6478. | $A^{114}$ | $D^{144}$ |
| 6479. | $A^{115}$ | $D^{144}$ |
| 6480. | $A^{116}$ | $D^{144}$ |
| 6481. | $A^{117}$ | $D^{144}$ |
| 6482. | $A^{118}$ | $D^{144}$ |
| 6483. | $A^{119}$ | $D^{144}$ |
| 6484. | $A^{120}$ | $D^{144}$ |
| 6485. | $A^{121}$ | $D^{144}$ |
| 6486. | $A^{122}$ | $D^{144}$ |
| 6487. | $A^{123}$ | $D^{144}$ |
| 6488. | $A^{124}$ | $D^{144}$ |

208

-continued

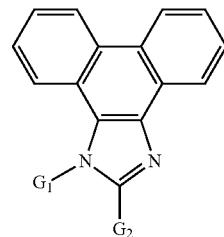

Formula IV

| Compound Number | $G^1$ | $G^2$ |
|---|---|---|
| 6489. | $A^{125}$ | $D^{144}$ |
| 6490. | $A^{126}$ | $D^{144}$ |
| 6491. | $A^{127}$ | $D^{144}$ |
| 6492. | $A^{128}$ | $D^{144}$ |
| 6493. | $A^{129}$ | $D^{144}$ |
| 6494. | $A^{130}$ | $D^{144}$ |
| 6495. | $A^{131}$ | $D^{144}$ |
| 6496. | $A^{132}$ | $D^{144}$ |
| 6497. | $A^{101}$ | $D^{145}$ |
| 6498. | $A^{102}$ | $D^{145}$ |
| 6499. | $A^{103}$ | $D^{145}$ |
| 6500. | $A^{104}$ | $D^{145}$ |
| 6501. | $A^{105}$ | $D^{145}$ |
| 6502. | $A^{106}$ | $D^{145}$ |
| 6503. | $A^{107}$ | $D^{145}$ |
| 6504. | $A^{108}$ | $D^{145}$ |
| 6505. | $A^{109}$ | $D^{145}$ |
| 6506. | $A^{110}$ | $D^{145}$ |
| 6507. | $A^{111}$ | $D^{145}$ |
| 6508. | $A^{112}$ | $D^{145}$ |
| 6509. | $A^{113}$ | $D^{145}$ |
| 6510. | $A^{114}$ | $D^{145}$ |
| 6511. | $A^{115}$ | $D^{145}$ |
| 6512. | $A^{116}$ | $D^{145}$ |
| 6513. | $A^{117}$ | $D^{145}$ |
| 6514. | $A^{118}$ | $D^{145}$ |
| 6515. | $A^{119}$ | $D^{145}$ |
| 6516. | $A^{120}$ | $D^{145}$ |
| 6517. | $A^{121}$ | $D^{145}$ |
| 6518. | $A^{122}$ | $D^{145}$ |
| 6519. | $A^{123}$ | $D^{145}$ |
| 6520. | $A^{124}$ | $D^{145}$ |
| 6521. | $A^{125}$ | $D^{145}$ |
| 6522. | $A^{126}$ | $D^{145}$ |
| 6523. | $A^{127}$ | $D^{145}$ |
| 6524. | $A^{128}$ | $D^{145}$ |
| 6525. | $A^{129}$ | $D^{145}$ |
| 6526. | $A^{130}$ | $D^{145}$ |
| 6527. | $A^{131}$ | $D^{145}$ |
| 6528. | $A^{132}$ | $D^{145}$ |
| 6529. | $A^{101}$ | $D^{146}$ |
| 6530. | $A^{102}$ | $D^{146}$ |
| 6531. | $A^{103}$ | $D^{146}$ |
| 6532. | $A^{104}$ | $D^{146}$ |
| 6533. | $A^{105}$ | $D^{146}$ |
| 6534. | $A^{106}$ | $D^{146}$ |
| 6535. | $A^{107}$ | $D^{146}$ |
| 6536. | $A^{108}$ | $D^{146}$ |
| 6537. | $A^{109}$ | $D^{146}$ |
| 6538. | $A^{110}$ | $D^{146}$ |
| 6539. | $A^{111}$ | $D^{146}$ |
| 6540. | $A^{112}$ | $D^{146}$ |
| 6541. | $A^{113}$ | $D^{146}$ |
| 6542. | $A^{114}$ | $D^{146}$ |
| 6543. | $A^{115}$ | $D^{146}$ |
| 6544. | $A^{116}$ | $D^{146}$ |
| 6545. | $A^{117}$ | $D^{146}$ |
| 6546. | $A^{118}$ | $D^{146}$ |
| 6547. | $A^{119}$ | $D^{146}$ |
| 6548. | $A^{120}$ | $D^{146}$ |
| 6549. | $A^{121}$ | $D^{146}$ |
| 6550. | $A^{122}$ | $D^{146}$ |
| 6551. | $A^{123}$ | $D^{146}$ |

Formula IV

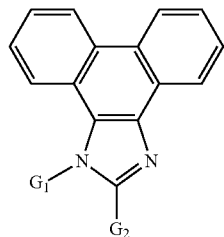

| Compound Number | G¹ | G² |
|---|---|---|
| 6552. | $A^{124}$ | $D^{146}$ |
| 6553. | $A^{125}$ | $D^{146}$ |
| 6554. | $A^{126}$ | $D^{146}$ |
| 6555. | $A^{127}$ | $D^{146}$ |
| 6556. | $A^{128}$ | $D^{146}$ |
| 6557. | $A^{129}$ | $D^{146}$ |
| 6558. | $A^{130}$ | $D^{146}$ |
| 6559. | $A^{131}$ | $D^{146}$ |
| 6560. | $A^{132}$ | $D^{146}$ |
| 6561. | $A^{101}$ | $D^{147}$ |
| 6562. | $A^{102}$ | $D^{147}$ |
| 6563. | $A^{103}$ | $D^{147}$ |
| 6564. | $A^{104}$ | $D^{147}$ |
| 6565. | $A^{105}$ | $D^{147}$ |
| 6566. | $A^{106}$ | $D^{147}$ |
| 6567. | $A^{107}$ | $D^{147}$ |
| 6568. | $A^{108}$ | $D^{147}$ |
| 6569. | $A^{109}$ | $D^{147}$ |
| 6570. | $A^{110}$ | $D^{147}$ |
| 6571. | $A^{111}$ | $D^{147}$ |
| 6572. | $A^{112}$ | $D^{147}$ |
| 6573. | $A^{113}$ | $D^{147}$ |
| 6574. | $A^{114}$ | $D^{147}$ |
| 6575. | $A^{115}$ | $D^{147}$ |
| 6576. | $A^{116}$ | $D^{147}$ |
| 6577. | $A^{117}$ | $D^{147}$ |
| 6578. | $A^{118}$ | $D^{147}$ |
| 6579. | $A^{119}$ | $D^{147}$ |
| 6580. | $A^{120}$ | $D^{147}$ |
| 6581. | $A^{121}$ | $D^{147}$ |
| 6582. | $A^{122}$ | $D^{147}$ |
| 6583. | $A^{123}$ | $D^{147}$ |
| 6584. | $A^{124}$ | $D^{147}$ |
| 6585. | $A^{125}$ | $D^{147}$ |
| 6586. | $A^{126}$ | $D^{147}$ |
| 6587. | $A^{127}$ | $D^{147}$ |
| 6588. | $A^{128}$ | $D^{147}$ |
| 6589. | $A^{129}$ | $D^{147}$ |
| 6590. | $A^{130}$ | $D^{147}$ |
| 6591. | $A^{131}$ | $D^{147}$ |
| 6592. | $A^{132}$ | $D^{147}$ |
| 6593. | $A^{101}$ | $D^{148}$ |
| 6594. | $A^{102}$ | $D^{148}$ |
| 6595. | $A^{103}$ | $D^{148}$ |
| 6596. | $A^{104}$ | $D^{148}$ |
| 6597. | $A^{105}$ | $D^{148}$ |
| 6598. | $A^{106}$ | $D^{148}$ |
| 6599. | $A^{107}$ | $D^{148}$ |
| 6600. | $A^{108}$ | $D^{148}$ |
| 6601. | $A^{109}$ | $D^{148}$ |
| 6602. | $A^{110}$ | $D^{148}$ |
| 6603. | $A^{111}$ | $D^{148}$ |
| 6604. | $A^{112}$ | $D^{148}$ |
| 6605. | $A^{113}$ | $D^{148}$ |
| 6606. | $A^{114}$ | $D^{148}$ |
| 6607. | $A^{115}$ | $D^{148}$ |
| 6608. | $A^{116}$ | $D^{148}$ |
| 6609. | $A^{117}$ | $D^{148}$ |
| 6610. | $A^{118}$ | $D^{148}$ |
| 6611. | $A^{119}$ | $D^{148}$ |
| 6612. | $A^{120}$ | $D^{148}$ |
| 6613. | $A^{121}$ | $D^{148}$ |
| 6614. | $A^{122}$ | $D^{148}$ |

Formula IV

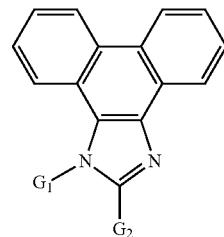

| Compound Number | G¹ | G² |
|---|---|---|
| 6615. | $A^{123}$ | $D^{148}$ |
| 6616. | $A^{124}$ | $D^{148}$ |
| 6617. | $A^{125}$ | $D^{148}$ |
| 6618. | $A^{126}$ | $D^{148}$ |
| 6619. | $A^{127}$ | $D^{148}$ |
| 6620. | $A^{128}$ | $D^{148}$ |
| 6621. | $A^{129}$ | $D^{148}$ |
| 6622. | $A^{130}$ | $D^{148}$ |
| 6623. | $A^{131}$ | $D^{148}$ |
| 6624. | $A^{132}$ | $D^{148}$ |
| 6625. | $A^{101}$ | $D^{149}$ |
| 6626. | $A^{102}$ | $D^{149}$ |
| 6627. | $A^{103}$ | $D^{149}$ |
| 6628. | $A^{104}$ | $D^{149}$ |
| 6629. | $A^{105}$ | $D^{149}$ |
| 6630. | $A^{106}$ | $D^{149}$ |
| 6631. | $A^{107}$ | $D^{149}$ |
| 6632. | $A^{108}$ | $D^{149}$ |
| 6633. | $A^{109}$ | $D^{149}$ |
| 6634. | $A^{110}$ | $D^{149}$ |
| 6635. | $A^{111}$ | $D^{149}$ |
| 6636. | $A^{112}$ | $D^{149}$ |
| 6637. | $A^{113}$ | $D^{149}$ |
| 6638. | $A^{114}$ | $D^{149}$ |
| 6639. | $A^{115}$ | $D^{149}$ |
| 6640. | $A^{116}$ | $D^{149}$ |
| 6641. | $A^{117}$ | $D^{149}$ |
| 6642. | $A^{118}$ | $D^{149}$ |
| 6643. | $A^{119}$ | $D^{149}$ |
| 6644. | $A^{120}$ | $D^{149}$ |
| 6645. | $A^{121}$ | $D^{149}$ |
| 6646. | $A^{122}$ | $D^{149}$ |
| 6647. | $A^{123}$ | $D^{149}$ |
| 6648. | $A^{124}$ | $D^{149}$ |
| 6649. | $A^{125}$ | $D^{149}$ |
| 6650. | $A^{126}$ | $D^{149}$ |
| 6651. | $A^{127}$ | $D^{149}$ |
| 6652. | $A^{128}$ | $D^{149}$ |
| 6653. | $A^{129}$ | $D^{149}$ |
| 6654. | $A^{130}$ | $D^{149}$ |
| 6655. | $A^{131}$ | $D^{149}$ |
| 6656. | $A^{132}$ | $D^{149}$ |
| 6657. | $A^{101}$ | $D^{150}$ |
| 6658. | $A^{102}$ | $D^{150}$ |
| 6659. | $A^{103}$ | $D^{150}$ |
| 6660. | $A^{104}$ | $D^{150}$ |
| 6661. | $A^{105}$ | $D^{150}$ |
| 6662. | $A^{106}$ | $D^{150}$ |
| 6663. | $A^{107}$ | $D^{150}$ |
| 6664. | $A^{108}$ | $D^{150}$ |
| 6665. | $A^{109}$ | $D^{150}$ |
| 6666. | $A^{110}$ | $D^{150}$ |
| 6667. | $A^{111}$ | $D^{150}$ |
| 6668. | $A^{112}$ | $D^{150}$ |
| 6669. | $A^{113}$ | $D^{150}$ |
| 6670. | $A^{114}$ | $D^{150}$ |
| 6671. | $A^{115}$ | $D^{150}$ |
| 6672. | $A^{116}$ | $D^{150}$ |
| 6673. | $A^{117}$ | $D^{150}$ |
| 6674. | $A^{118}$ | $D^{150}$ |
| 6675. | $A^{119}$ | $D^{150}$ |
| 6676. | $A^{120}$ | $D^{150}$ |
| 6677. | $A^{121}$ | $D^{150}$ |

211

-continued

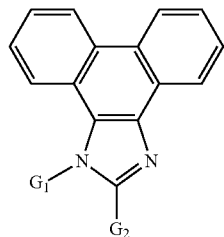

Formula IV

| Compound Number | $G^1$ | $G^2$ |
|---|---|---|
| 6678. | $A^{122}$ | $D^{150}$ |
| 6679. | $A^{123}$ | $D^{150}$ |
| 6680. | $A^{124}$ | $D^{150}$ |
| 6681. | $A^{125}$ | $D^{150}$ |
| 6682. | $A^{126}$ | $D^{150}$ |
| 6683. | $A^{127}$ | $D^{150}$ |
| 6684. | $A^{128}$ | $D^{150}$ |
| 6685. | $A^{129}$ | $D^{150}$ |
| 6686. | $A^{130}$ | $D^{150}$ |
| 6687. | $A^{131}$ | $D^{150}$ |
| 6688. | $A^{132}$ | $D^{150}$ |
| 6689. | $A^{101}$ | $D^{151}$ |
| 6690. | $A^{102}$ | $D^{151}$ |
| 6691. | $A^{103}$ | $D^{151}$ |
| 6692. | $A^{104}$ | $D^{151}$ |
| 6693. | $A^{105}$ | $D^{151}$ |
| 6694. | $A^{106}$ | $D^{151}$ |
| 6695. | $A^{107}$ | $D^{151}$ |
| 6696. | $A^{108}$ | $D^{151}$ |
| 6697. | $A^{109}$ | $D^{151}$ |
| 6698. | $A^{110}$ | $D^{151}$ |
| 6699. | $A^{111}$ | $D^{151}$ |
| 6700. | $A^{112}$ | $D^{151}$ |
| 6701. | $A^{113}$ | $D^{151}$ |
| 6702. | $A^{114}$ | $D^{151}$ |
| 6703. | $A^{115}$ | $D^{151}$ |
| 6704. | $A^{116}$ | $D^{151}$ |
| 6705. | $A^{117}$ | $D^{151}$ |
| 6706. | $A^{118}$ | $D^{151}$ |
| 6707. | $A^{119}$ | $D^{151}$ |
| 6708. | $A^{120}$ | $D^{151}$ |
| 6709. | $A^{121}$ | $D^{151}$ |
| 6710. | $A^{122}$ | $D^{151}$ |
| 6711. | $A^{123}$ | $D^{151}$ |
| 6712. | $A^{124}$ | $D^{151}$ |
| 6713. | $A^{125}$ | $D^{151}$ |
| 6714. | $A^{126}$ | $D^{151}$ |
| 6715. | $A^{127}$ | $D^{151}$ |
| 6716. | $A^{128}$ | $D^{151}$ |
| 6717. | $A^{129}$ | $D^{151}$ |
| 6718. | $A^{130}$ | $D^{151}$ |
| 6719. | $A^{131}$ | $D^{151}$ |
| 6720. | $A^{132}$ | $D^{151}$ |
| 6721. | $A^{101}$ | $D^{152}$ |
| 6722. | $A^{102}$ | $D^{152}$ |
| 6723. | $A^{103}$ | $D^{152}$ |
| 6724. | $A^{104}$ | $D^{152}$ |
| 6725. | $A^{105}$ | $D^{152}$ |
| 6726. | $A^{106}$ | $D^{152}$ |
| 6727. | $A^{107}$ | $D^{152}$ |
| 6728. | $A^{108}$ | $D^{152}$ |
| 6729. | $A^{109}$ | $D^{152}$ |
| 6730. | $A^{110}$ | $D^{152}$ |
| 6731. | $A^{111}$ | $D^{152}$ |
| 6732. | $A^{112}$ | $D^{152}$ |
| 6733. | $A^{113}$ | $D^{152}$ |
| 6734. | $A^{114}$ | $D^{152}$ |
| 6735. | $A^{115}$ | $D^{152}$ |
| 6736. | $A^{116}$ | $D^{152}$ |
| 6737. | $A^{117}$ | $D^{152}$ |
| 6738. | $A^{118}$ | $D^{152}$ |
| 6739. | $A^{119}$ | $D^{152}$ |
| 6740. | $A^{120}$ | $D^{152}$ |

212

-continued

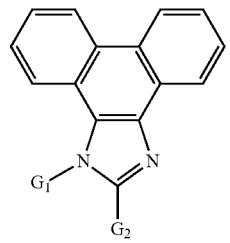

Formula IV

| Compound Number | $G^1$ | $G^2$ |
|---|---|---|
| 6741. | $A^{121}$ | $D^{152}$ |
| 6742. | $A^{122}$ | $D^{152}$ |
| 6743. | $A^{123}$ | $D^{152}$ |
| 6744. | $A^{124}$ | $D^{152}$ |
| 6745. | $A^{125}$ | $D^{152}$ |
| 6746. | $A^{126}$ | $D^{152}$ |
| 6747. | $A^{127}$ | $D^{152}$ |
| 6748. | $A^{128}$ | $D^{152}$ |
| 6749. | $A^{129}$ | $D^{152}$ |
| 6750. | $A^{130}$ | $D^{152}$ |
| 6751. | $A^{131}$ | $D^{152}$ |
| 6752. | $A^{132}$ | $D^{152}$ |
| 6753. | $A^{101}$ | $D^{153}$ |
| 6754. | $A^{102}$ | $D^{153}$ |
| 6755. | $A^{103}$ | $D^{153}$ |
| 6756. | $A^{104}$ | $D^{153}$ |
| 6757. | $A^{105}$ | $D^{153}$ |
| 6758. | $A^{106}$ | $D^{153}$ |
| 6759. | $A^{107}$ | $D^{153}$ |
| 6760. | $A^{108}$ | $D^{153}$ |
| 6761. | $A^{109}$ | $D^{153}$ |
| 6762. | $A^{110}$ | $D^{153}$ |
| 6763. | $A^{111}$ | $D^{153}$ |
| 6764. | $A^{112}$ | $D^{153}$ |
| 6765. | $A^{113}$ | $D^{153}$ |
| 6766. | $A^{114}$ | $D^{153}$ |
| 6767. | $A^{115}$ | $D^{153}$ |
| 6768. | $A^{116}$ | $D^{153}$ |
| 6769. | $A^{117}$ | $D^{153}$ |
| 6770. | $A^{118}$ | $D^{153}$ |
| 6771. | $A^{119}$ | $D^{153}$ |
| 6772. | $A^{120}$ | $D^{153}$ |
| 6773. | $A^{121}$ | $D^{153}$ |
| 6774. | $A^{122}$ | $D^{153}$ |
| 6775. | $A^{123}$ | $D^{153}$ |
| 6776. | $A^{124}$ | $D^{153}$ |
| 6777. | $A^{125}$ | $D^{153}$ |
| 6778. | $A^{126}$ | $D^{153}$ |
| 6779. | $A^{127}$ | $D^{153}$ |
| 6780. | $A^{128}$ | $D^{153}$ |
| 6781. | $A^{129}$ | $D^{153}$ |
| 6782. | $A^{130}$ | $D^{153}$ |
| 6783. | $A^{131}$ | $D^{153}$ |
| 6784. | $A^{132}$ | $D^{153}$ |
| 8481. | $A^{101}$ | $D^{154}$ |
| 8482. | $A^{102}$ | $D^{154}$ |
| 8483. | $A^{103}$ | $D^{154}$ |
| 8484. | $A^{104}$ | $D^{154}$ |
| 8485. | $A^{105}$ | $D^{154}$ |
| 8486. | $A^{106}$ | $D^{154}$ |
| 8487. | $A^{107}$ | $D^{154}$ |
| 8488. | $A^{108}$ | $D^{154}$ |
| 8489. | $A^{109}$ | $D^{154}$ |
| 8490. | $A^{110}$ | $D^{154}$ |
| 8491. | $A^{111}$ | $D^{154}$ |
| 8492. | $A^{112}$ | $D^{154}$ |
| 8493. | $A^{113}$ | $D^{154}$ |
| 8494. | $A^{114}$ | $D^{154}$ |
| 8495. | $A^{115}$ | $D^{154}$ |
| 8496. | $A^{116}$ | $D^{154}$ |
| 8497. | $A^{117}$ | $D^{154}$ |
| 8498. | $A^{118}$ | $D^{154}$ |
| 8499. | $A^{119}$ | $D^{154}$ |

Formula IV

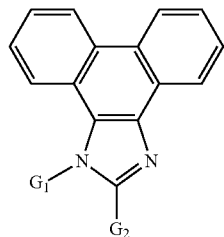

| Compound Number | G¹ | G² |
|---|---|---|
| 8500. | $A^{120}$ | $D^{154}$ |
| 8501. | $A^{121}$ | $D^{154}$ |
| 8502. | $A^{122}$ | $D^{154}$ |
| 8503. | $A^{123}$ | $D^{154}$ |
| 8504. | $A^{124}$ | $D^{154}$ |
| 8505. | $A^{125}$ | $D^{154}$ |
| 8506. | $A^{126}$ | $D^{154}$ |
| 8507. | $A^{127}$ | $D^{154}$ |
| 8508. | $A^{128}$ | $D^{154}$ |
| 8509. | $A^{129}$ | $D^{154}$ |
| 8510. | $A^{130}$ | $D^{154}$ |
| 8511. | $A^{131}$ | $D^{154}$ |
| 8512. | $A^{132}$ | $D^{154}$ |
| 8513. | $A^{101}$ | $D^{155}$ |
| 8514. | $A^{102}$ | $D^{155}$ |
| 8515. | $A^{103}$ | $D^{155}$ |
| 8516. | $A^{104}$ | $D^{155}$ |
| 8517. | $A^{105}$ | $D^{155}$ |
| 8518. | $A^{106}$ | $D^{155}$ |
| 8519. | $A^{107}$ | $D^{155}$ |
| 8520. | $A^{108}$ | $D^{155}$ |
| 8521. | $A^{109}$ | $D^{155}$ |
| 8522. | $A^{110}$ | $D^{155}$ |
| 8523. | $A^{111}$ | $D^{155}$ |
| 8524. | $A^{112}$ | $D^{155}$ |
| 8525. | $A^{113}$ | $D^{155}$ |
| 8526. | $A^{114}$ | $D^{155}$ |
| 8527. | $A^{115}$ | $D^{155}$ |
| 8528. | $A^{116}$ | $D^{155}$ |
| 8529. | $A^{117}$ | $D^{155}$ |
| 8530. | $A^{118}$ | $D^{155}$ |
| 8531. | $A^{119}$ | $D^{155}$ |
| 8532. | $A^{120}$ | $D^{155}$ |
| 8533. | $A^{121}$ | $D^{155}$ |
| 8534. | $A^{122}$ | $D^{155}$ |
| 8535. | $A^{123}$ | $D^{155}$ |
| 8536. | $A^{124}$ | $D^{155}$ |
| 8537. | $A^{125}$ | $D^{155}$ |
| 8538. | $A^{126}$ | $D^{155}$ |
| 8539. | $A^{127}$ | $D^{155}$ |
| 8540. | $A^{128}$ | $D^{155}$ |
| 8541. | $A^{129}$ | $D^{155}$ |
| 8542. | $A^{130}$ | $D^{155}$ |
| 8543. | $A^{131}$ | $D^{155}$ |
| 8544. | $A^{132}$ | $D^{155}$ |
| 8545. | $A^{101}$ | $D^{156}$ |
| 8546. | $A^{102}$ | $D^{156}$ |
| 8547. | $A^{103}$ | $D^{156}$ |
| 8548. | $A^{104}$ | $D^{156}$ |
| 8549. | $A^{105}$ | $D^{156}$ |
| 8550. | $A^{106}$ | $D^{156}$ |
| 8551. | $A^{107}$ | $D^{156}$ |
| 8552. | $A^{108}$ | $D^{156}$ |
| 8553. | $A^{109}$ | $D^{156}$ |
| 8554. | $A^{110}$ | $D^{156}$ |
| 8555. | $A^{111}$ | $D^{156}$ |
| 8556. | $A^{112}$ | $D^{156}$ |
| 8557. | $A^{113}$ | $D^{156}$ |
| 8558. | $A^{114}$ | $D^{156}$ |
| 8559. | $A^{115}$ | $D^{156}$ |
| 8560. | $A^{116}$ | $D^{156}$ |
| 8561. | $A^{117}$ | $D^{156}$ |
| 8562. | $A^{118}$ | $D^{156}$ |

Formula IV

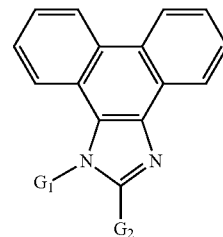

| Compound Number | G¹ | G² |
|---|---|---|
| 8563. | $A^{119}$ | $D^{156}$ |
| 8564. | $A^{120}$ | $D^{156}$ |
| 8565. | $A^{121}$ | $D^{156}$ |
| 8566. | $A^{122}$ | $D^{156}$ |
| 8567. | $A^{123}$ | $D^{156}$ |
| 8568. | $A^{124}$ | $D^{156}$ |
| 8569. | $A^{125}$ | $D^{156}$ |
| 8570. | $A^{126}$ | $D^{156}$ |
| 8571. | $A^{127}$ | $D^{156}$ |
| 8572. | $A^{128}$ | $D^{156}$ |
| 8573. | $A^{129}$ | $D^{156}$ |
| 8574. | $A^{130}$ | $D^{156}$ |
| 8575. | $A^{131}$ | $D^{156}$ |
| 8576. | $A^{132}$ | $D^{156}$ |
| 8577. | $A^{101}$ | $D^{157}$ |
| 8578. | $A^{102}$ | $D^{157}$ |
| 8579. | $A^{103}$ | $D^{157}$ |
| 8580. | $A^{104}$ | $D^{157}$ |
| 8581. | $A^{105}$ | $D^{157}$ |
| 8582. | $A^{106}$ | $D^{157}$ |
| 8583. | $A^{107}$ | $D^{157}$ |
| 8584. | $A^{108}$ | $D^{157}$ |
| 8585. | $A^{109}$ | $D^{157}$ |
| 8586. | $A^{110}$ | $D^{157}$ |
| 8587. | $A^{111}$ | $D^{157}$ |
| 8588. | $A^{112}$ | $D^{157}$ |
| 8589. | $A^{113}$ | $D^{157}$ |
| 8590. | $A^{114}$ | $D^{157}$ |
| 8591. | $A^{115}$ | $D^{157}$ |
| 8592. | $A^{116}$ | $D^{157}$ |
| 8593. | $A^{117}$ | $D^{157}$ |
| 8594. | $A^{118}$ | $D^{157}$ |
| 8595. | $A^{119}$ | $D^{157}$ |
| 8596. | $A^{120}$ | $D^{157}$ |
| 8597. | $A^{121}$ | $D^{157}$ |
| 8598. | $A^{122}$ | $D^{157}$ |
| 8599. | $A^{123}$ | $D^{157}$ |
| 8600. | $A^{124}$ | $D^{157}$ |
| 8601. | $A^{125}$ | $D^{157}$ |
| 8602. | $A^{126}$ | $D^{157}$ |
| 8603. | $A^{127}$ | $D^{157}$ |
| 8604. | $A^{128}$ | $D^{157}$ |
| 8605. | $A^{129}$ | $D^{157}$ |
| 8606. | $A^{130}$ | $D^{157}$ |
| 8607. | $A^{131}$ | $D^{157}$ |
| 8608. | $A^{132}$ | $D^{157}$ |
| 8609. | $A^{101}$ | $D^{158}$ |
| 8610. | $A^{102}$ | $D^{158}$ |
| 8611. | $A^{103}$ | $D^{158}$ |
| 8612. | $A^{104}$ | $D^{158}$ |
| 8613. | $A^{105}$ | $D^{158}$ |
| 8614. | $A^{106}$ | $D^{158}$ |
| 8615. | $A^{107}$ | $D^{158}$ |
| 8616. | $A^{108}$ | $D^{158}$ |
| 8617. | $A^{109}$ | $D^{158}$ |
| 8618. | $A^{110}$ | $D^{158}$ |
| 8619. | $A^{111}$ | $D^{158}$ |
| 8620. | $A^{112}$ | $D^{158}$ |
| 8621. | $A^{113}$ | $D^{158}$ |
| 8622. | $A^{114}$ | $D^{158}$ |
| 8623. | $A^{115}$ | $D^{158}$ |
| 8624. | $A^{116}$ | $D^{158}$ |
| 8625. | $A^{117}$ | $D^{158}$ |

-continued

Formula IV

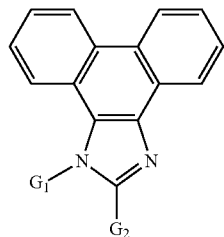

| Compound Number | G¹ | G² |
| --- | --- | --- |
| 8626. | $A^{118}$ | $D^{158}$ |
| 8627. | $A^{119}$ | $D^{158}$ |
| 8628. | $A^{120}$ | $D^{158}$ |
| 8629. | $A^{121}$ | $D^{158}$ |
| 8630. | $A^{122}$ | $D^{158}$ |
| 8631. | $A^{123}$ | $D^{158}$ |
| 8632. | $A^{124}$ | $D^{158}$ |
| 8633. | $A^{125}$ | $D^{158}$ |
| 8634. | $A^{126}$ | $D^{158}$ |
| 8635. | $A^{127}$ | $D^{158}$ |
| 8636. | $A^{128}$ | $D^{158}$ |
| 8637. | $A^{129}$ | $D^{158}$ |
| 8638. | $A^{130}$ | $D^{158}$ |
| 8639. | $A^{131}$ | $D^{158}$ |
| 8640. | $A^{132}$ | $D^{158}$ |
| 8641. | $A^{101}$ | $D^{159}$ |
| 8642. | $A^{102}$ | $D^{159}$ |
| 8643. | $A^{103}$ | $D^{159}$ |
| 8644. | $A^{104}$ | $D^{159}$ |
| 8645. | $A^{105}$ | $D^{159}$ |
| 8646. | $A^{106}$ | $D^{159}$ |
| 8647. | $A^{107}$ | $D^{159}$ |
| 8648. | $A^{108}$ | $D^{159}$ |
| 8649. | $A^{109}$ | $D^{159}$ |
| 8650. | $A^{110}$ | $D^{159}$ |
| 8651. | $A^{111}$ | $D^{159}$ |
| 8652. | $A^{112}$ | $D^{159}$ |
| 8653. | $A^{113}$ | $D^{159}$ |
| 8654. | $A^{114}$ | $D^{159}$ |
| 8655. | $A^{115}$ | $D^{159}$ |
| 8656. | $A^{116}$ | $D^{159}$ |
| 8657. | $A^{117}$ | $D^{159}$ |
| 8658. | $A^{118}$ | $D^{159}$ |
| 8659. | $A^{119}$ | $D^{159}$ |
| 8660. | $A^{120}$ | $D^{159}$ |
| 8661. | $A^{121}$ | $D^{159}$ |
| 8662. | $A^{122}$ | $D^{159}$ |
| 8663. | $A^{123}$ | $D^{159}$ |
| 8664. | $A^{124}$ | $D^{159}$ |
| 8665. | $A^{125}$ | $D^{159}$ |
| 8666. | $A^{126}$ | $D^{159}$ |
| 8667. | $A^{127}$ | $D^{159}$ |
| 8668. | $A^{128}$ | $D^{159}$ |
| 8669. | $A^{129}$ | $D^{159}$ |
| 8670. | $A^{130}$ | $D^{159}$ |
| 8671. | $A^{131}$ | $D^{159}$ |
| 8672. | $A^{132}$ | $D^{159}$ |
| 8673. | $A^{101}$ | $D^{160}$ |
| 8674. | $A^{102}$ | $D^{160}$ |
| 8675. | $A^{103}$ | $D^{160}$ |
| 8676. | $A^{104}$ | $D^{160}$ |
| 8677. | $A^{105}$ | $D^{160}$ |
| 8678. | $A^{106}$ | $D^{160}$ |
| 8679. | $A^{107}$ | $D^{160}$ |
| 8680. | $A^{108}$ | $D^{160}$ |
| 8681. | $A^{109}$ | $D^{160}$ |
| 8682. | $A^{110}$ | $D^{160}$ |
| 8683. | $A^{111}$ | $D^{160}$ |
| 8684. | $A^{112}$ | $D^{160}$ |
| 8685. | $A^{113}$ | $D^{160}$ |
| 8686. | $A^{114}$ | $D^{160}$ |
| 8687. | $A^{115}$ | $D^{160}$ |
| 8688. | $A^{116}$ | $D^{160}$ |

-continued

Formula IV

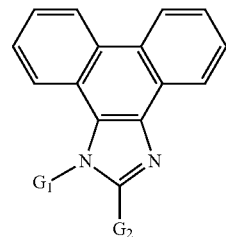

| Compound Number | G¹ | G² |
| --- | --- | --- |
| 8689. | $A^{117}$ | $D^{160}$ |
| 8690. | $A^{118}$ | $D^{160}$ |
| 8691. | $A^{119}$ | $D^{160}$ |
| 8692. | $A^{120}$ | $D^{160}$ |
| 8693. | $A^{121}$ | $D^{160}$ |
| 8694. | $A^{122}$ | $D^{160}$ |
| 8695. | $A^{123}$ | $D^{160}$ |
| 8696. | $A^{124}$ | $D^{160}$ |
| 8697. | $A^{125}$ | $D^{160}$ |
| 8698. | $A^{126}$ | $D^{160}$ |
| 8699. | $A^{127}$ | $D^{160}$ |
| 8700. | $A^{128}$ | $D^{160}$ |
| 8701. | $A^{129}$ | $D^{160}$ |
| 8702. | $A^{130}$ | $D^{160}$ |
| 8703. | $A^{131}$ | $D^{160}$ |
| 8704. | $A^{132}$ | $D^{160}$ |
| 8705. | $A^{101}$ | $D^{161}$ |
| 8706. | $A^{102}$ | $D^{161}$ |
| 8707. | $A^{103}$ | $D^{161}$ |
| 8708. | $A^{104}$ | $D^{161}$ |
| 8709. | $A^{105}$ | $D^{161}$ |
| 8710. | $A^{106}$ | $D^{161}$ |
| 8711. | $A^{107}$ | $D^{161}$ |
| 8712. | $A^{108}$ | $D^{161}$ |
| 8713. | $A^{109}$ | $D^{161}$ |
| 8714. | $A^{110}$ | $D^{161}$ |
| 8715. | $A^{111}$ | $D^{161}$ |
| 8716. | $A^{112}$ | $D^{161}$ |
| 8717. | $A^{113}$ | $D^{161}$ |
| 8718. | $A^{114}$ | $D^{161}$ |
| 8719. | $A^{115}$ | $D^{161}$ |
| 8720. | $A^{116}$ | $D^{161}$ |
| 8721. | $A^{117}$ | $D^{161}$ |
| 8722. | $A^{118}$ | $D^{161}$ |
| 8723. | $A^{119}$ | $D^{161}$ |
| 8724. | $A^{120}$ | $D^{161}$ |
| 8725. | $A^{121}$ | $D^{161}$ |
| 8726. | $A^{122}$ | $D^{161}$ |
| 8727. | $A^{123}$ | $D^{161}$ |
| 8728. | $A^{124}$ | $D^{161}$ |
| 8729. | $A^{125}$ | $D^{161}$ |
| 8730. | $A^{126}$ | $D^{161}$ |
| 8731. | $A^{127}$ | $D^{161}$ |
| 8732. | $A^{128}$ | $D^{161}$ |
| 8733. | $A^{129}$ | $D^{161}$ |
| 8734. | $A^{130}$ | $D^{161}$ |
| 8735. | $A^{131}$ | $D^{161}$ |
| 8736. | $A^{132}$ | $D^{161}$ |
| 8737. | $A^{101}$ | $D^{162}$ |
| 8738. | $A^{102}$ | $D^{162}$ |
| 8739. | $A^{103}$ | $D^{162}$ |
| 8740. | $A^{104}$ | $D^{162}$ |
| 8741. | $A^{105}$ | $D^{162}$ |
| 8742. | $A^{106}$ | $D^{162}$ |
| 8743. | $A^{107}$ | $D^{162}$ |
| 8744. | $A^{108}$ | $D^{162}$ |
| 8745. | $A^{109}$ | $D^{162}$ |
| 8746. | $A^{110}$ | $D^{162}$ |
| 8747. | $A^{111}$ | $D^{162}$ |
| 8748. | $A^{112}$ | $D^{162}$ |
| 8749. | $A^{113}$ | $D^{162}$ |
| 8750. | $A^{114}$ | $D^{162}$ |
| 8751. | $A^{115}$ | $D^{162}$ |

Formula IV

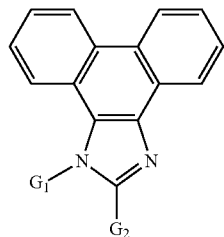

| Compound Number | $G^1$ | $G^2$ |
|---|---|---|
| 8752. | $A^{116}$ | $D^{162}$ |
| 8753. | $A^{117}$ | $D^{162}$ |
| 8754. | $A^{118}$ | $D^{162}$ |
| 8755. | $A^{119}$ | $D^{162}$ |
| 8756. | $A^{120}$ | $D^{162}$ |
| 8757. | $A^{121}$ | $D^{162}$ |
| 8758. | $A^{122}$ | $D^{162}$ |
| 8759. | $A^{123}$ | $D^{162}$ |
| 8760. | $A^{124}$ | $D^{162}$ |
| 8761. | $A^{125}$ | $D^{162}$ |
| 8762. | $A^{126}$ | $D^{162}$ |
| 8763. | $A^{127}$ | $D^{162}$ |
| 8764. | $A^{128}$ | $D^{162}$ |
| 8765. | $A^{129}$ | $D^{162}$ |
| 8766. | $A^{130}$ | $D^{162}$ |
| 8767. | $A^{131}$ | $D^{162}$ |
| 8768. | $A^{132}$ | $D^{162}$ |
| 8769. | $A^{101}$ | $D^{163}$ |
| 8770. | $A^{102}$ | $D^{163}$ |
| 8771. | $A^{103}$ | $D^{163}$ |
| 8772. | $A^{104}$ | $D^{163}$ |
| 8773. | $A^{105}$ | $D^{163}$ |
| 8774. | $A^{106}$ | $D^{163}$ |
| 8775. | $A^{107}$ | $D^{163}$ |
| 8776. | $A^{108}$ | $D^{163}$ |
| 8777. | $A^{109}$ | $D^{163}$ |
| 8778. | $A^{110}$ | $D^{163}$ |
| 8779. | $A^{111}$ | $D^{163}$ |
| 8780. | $A^{112}$ | $D^{163}$ |
| 8781. | $A^{113}$ | $D^{163}$ |
| 8782. | $A^{114}$ | $D^{163}$ |
| 8783. | $A^{115}$ | $D^{163}$ |
| 8784. | $A^{116}$ | $D^{163}$ |
| 8785. | $A^{117}$ | $D^{163}$ |
| 8786. | $A^{118}$ | $D^{163}$ |
| 8787. | $A^{119}$ | $D^{163}$ |
| 8788. | $A^{120}$ | $D^{163}$ |
| 8789. | $A^{121}$ | $D^{163}$ |
| 8790. | $A^{122}$ | $D^{163}$ |
| 8791. | $A^{123}$ | $D^{163}$ |
| 8792. | $A^{124}$ | $D^{163}$ |
| 8793. | $A^{125}$ | $D^{163}$ |
| 8794. | $A^{126}$ | $D^{163}$ |
| 8795. | $A^{127}$ | $D^{163}$ |
| 8796. | $A^{128}$ | $D^{163}$ |
| 8797. | $A^{129}$ | $D^{163}$ |
| 8798. | $A^{130}$ | $D^{163}$ |
| 8799. | $A^{131}$ | $D^{163}$ |
| 8800. | $A^{132}$ | $D^{163}$ |
| 8801. | $A^{101}$ | $D^{164}$ |
| 8802. | $A^{102}$ | $D^{164}$ |
| 8803. | $A^{103}$ | $D^{164}$ |
| 8804. | $A^{104}$ | $D^{164}$ |
| 8805. | $A^{105}$ | $D^{164}$ |
| 8806. | $A^{106}$ | $D^{164}$ |
| 8807. | $A^{107}$ | $D^{164}$ |
| 8808. | $A^{108}$ | $D^{164}$ |
| 8809. | $A^{109}$ | $D^{164}$ |
| 8810. | $A^{110}$ | $D^{164}$ |
| 8811. | $A^{111}$ | $D^{164}$ |
| 8812. | $A^{112}$ | $D^{164}$ |
| 8813. | $A^{113}$ | $D^{164}$ |
| 8814. | $A^{114}$ | $D^{164}$ |

Formula IV

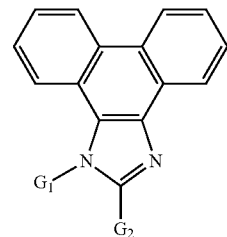

| Compound Number | $G^1$ | $G^2$ |
|---|---|---|
| 8815. | $A^{115}$ | $D^{164}$ |
| 8816. | $A^{116}$ | $D^{164}$ |
| 8817. | $A^{117}$ | $D^{164}$ |
| 8818. | $A^{118}$ | $D^{164}$ |
| 8819. | $A^{119}$ | $D^{164}$ |
| 8820. | $A^{120}$ | $D^{164}$ |
| 8821. | $A^{121}$ | $D^{164}$ |
| 8822. | $A^{122}$ | $D^{164}$ |
| 8823. | $A^{123}$ | $D^{164}$ |
| 8824. | $A^{124}$ | $D^{164}$ |
| 8825. | $A^{125}$ | $D^{164}$ |
| 8826. | $A^{126}$ | $D^{164}$ |
| 8827. | $A^{127}$ | $D^{164}$ |
| 8828. | $A^{128}$ | $D^{164}$ |
| 8829. | $A^{129}$ | $D^{164}$ |
| 8830. | $A^{130}$ | $D^{164}$ |
| 8831. | $A^{131}$ | $D^{164}$ |
| 8832. | $A^{132}$ | $D^{164}$ |
| 8833. | $A^{101}$ | $D^{165}$ |
| 8834. | $A^{102}$ | $D^{165}$ |
| 8835. | $A^{103}$ | $D^{165}$ |
| 8836. | $A^{104}$ | $D^{165}$ |
| 8837. | $A^{105}$ | $D^{165}$ |
| 8838. | $A^{106}$ | $D^{165}$ |
| 8839. | $A^{107}$ | $D^{165}$ |
| 8840. | $A^{108}$ | $D^{165}$ |
| 8841. | $A^{109}$ | $D^{165}$ |
| 8842. | $A^{110}$ | $D^{165}$ |
| 8843. | $A^{111}$ | $D^{165}$ |
| 8844. | $A^{112}$ | $D^{165}$ |
| 8845. | $A^{113}$ | $D^{165}$ |
| 8846. | $A^{114}$ | $D^{165}$ |
| 8847. | $A^{115}$ | $D^{165}$ |
| 8848. | $A^{116}$ | $D^{165}$ |
| 8849. | $A^{117}$ | $D^{165}$ |
| 8850. | $A^{118}$ | $D^{165}$ |
| 8851. | $A^{119}$ | $D^{165}$ |
| 8852. | $A^{120}$ | $D^{165}$ |
| 8853. | $A^{121}$ | $D^{165}$ |
| 8854. | $A^{122}$ | $D^{165}$ |
| 8855. | $A^{123}$ | $D^{165}$ |
| 8856. | $A^{124}$ | $D^{165}$ |
| 8857. | $A^{125}$ | $D^{165}$ |
| 8858. | $A^{126}$ | $D^{165}$ |
| 8859. | $A^{127}$ | $D^{165}$ |
| 8860. | $A^{128}$ | $D^{165}$ |
| 8861. | $A^{129}$ | $D^{165}$ |
| 8862. | $A^{130}$ | $D^{165}$ |
| 8863. | $A^{131}$ | $D^{165}$ |
| 8864. | $A^{132}$ | $D^{165}$ |
| 8865. | $A^{101}$ | $D^{166}$ |
| 8866. | $A^{102}$ | $D^{166}$ |
| 8867. | $A^{103}$ | $D^{166}$ |
| 8868. | $A^{104}$ | $D^{166}$ |
| 8869. | $A^{105}$ | $D^{166}$ |
| 8870. | $A^{106}$ | $D^{166}$ |
| 8871. | $A^{107}$ | $D^{166}$ |
| 8872. | $A^{108}$ | $D^{166}$ |
| 8873. | $A^{109}$ | $D^{166}$ |
| 8874. | $A^{110}$ | $D^{166}$ |
| 8875. | $A^{111}$ | $D^{166}$ |
| 8876. | $A^{112}$ | $D^{166}$ |
| 8877. | $A^{113}$ | $D^{166}$ |

-continued

Formula IV

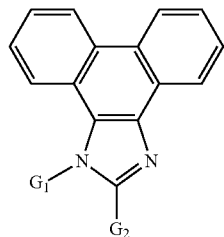

| Compound Number | G¹ | G² |
|---|---|---|
| 8878. | $A^{114}$ | $D^{166}$ |
| 8879. | $A^{115}$ | $D^{166}$ |
| 8880. | $A^{116}$ | $D^{166}$ |
| 8881. | $A^{117}$ | $D^{166}$ |
| 8882. | $A^{118}$ | $D^{166}$ |
| 8883. | $A^{119}$ | $D^{166}$ |
| 8884. | $A^{120}$ | $D^{166}$ |
| 8885. | $A^{121}$ | $D^{166}$ |
| 8886. | $A^{122}$ | $D^{166}$ |
| 8887. | $A^{123}$ | $D^{166}$ |
| 8888. | $A^{124}$ | $D^{166}$ |
| 8889. | $A^{125}$ | $D^{166}$ |
| 8890. | $A^{126}$ | $D^{166}$ |
| 8891. | $A^{127}$ | $D^{166}$ |
| 8892. | $A^{128}$ | $D^{166}$ |
| 8893. | $A^{129}$ | $D^{166}$ |
| 8894. | $A^{130}$ | $D^{166}$ |
| 8895. | $A^{131}$ | $D^{166}$ |
| 8896. | $A^{132}$ | $D^{166}$ |
| 8897. | $A^{101}$ | $D^{167}$ |
| 8898. | $A^{102}$ | $D^{167}$ |
| 8899. | $A^{103}$ | $D^{167}$ |
| 8900. | $A^{104}$ | $D^{167}$ |
| 8901. | $A^{105}$ | $D^{167}$ |
| 8902. | $A^{106}$ | $D^{167}$ |
| 8903. | $A^{107}$ | $D^{167}$ |
| 8904. | $A^{108}$ | $D^{167}$ |
| 8905. | $A^{109}$ | $D^{167}$ |
| 8906. | $A^{110}$ | $D^{167}$ |
| 8907. | $A^{111}$ | $D^{167}$ |
| 8908. | $A^{112}$ | $D^{167}$ |
| 8909. | $A^{113}$ | $D^{167}$ |
| 8910. | $A^{114}$ | $D^{167}$ |
| 8911. | $A^{115}$ | $D^{167}$ |
| 8912. | $A^{116}$ | $D^{167}$ |
| 8913. | $A^{117}$ | $D^{167}$ |
| 8914. | $A^{118}$ | $D^{167}$ |
| 8915. | $A^{119}$ | $D^{167}$ |
| 8916. | $A^{120}$ | $D^{167}$ |
| 8917. | $A^{121}$ | $D^{167}$ |
| 8918. | $A^{122}$ | $D^{167}$ |
| 8919. | $A^{123}$ | $D^{167}$ |
| 8920. | $A^{124}$ | $D^{167}$ |
| 8921. | $A^{125}$ | $D^{167}$ |
| 8922. | $A^{126}$ | $D^{167}$ |
| 8923. | $A^{127}$ | $D^{167}$ |
| 8924. | $A^{128}$ | $D^{167}$ |
| 8925. | $A^{129}$ | $D^{167}$ |
| 8926. | $A^{130}$ | $D^{167}$ |
| 8927. | $A^{131}$ | $D^{167}$ |
| 8928. | $A^{132}$ | $D^{167}$ |
| 8929. | $A^{101}$ | $D^{168}$ |
| 8930. | $A^{102}$ | $D^{168}$ |
| 8931. | $A^{103}$ | $D^{168}$ |
| 8932. | $A^{104}$ | $D^{168}$ |
| 8933. | $A^{105}$ | $D^{168}$ |
| 8934. | $A^{106}$ | $D^{168}$ |
| 8935. | $A^{107}$ | $D^{168}$ |
| 8936. | $A^{108}$ | $D^{168}$ |
| 8937. | $A^{109}$ | $D^{168}$ |
| 8938. | $A^{110}$ | $D^{168}$ |
| 8939. | $A^{111}$ | $D^{168}$ |
| 8940. | $A^{112}$ | $D^{168}$ |

-continued

Formula IV

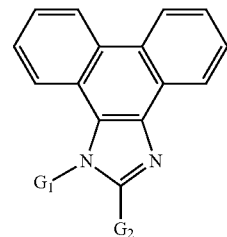

| Compound Number | G¹ | G² |
|---|---|---|
| 8941. | $A^{113}$ | $D^{168}$ |
| 8942. | $A^{114}$ | $D^{168}$ |
| 8943. | $A^{115}$ | $D^{168}$ |
| 8944. | $A^{116}$ | $D^{168}$ |
| 8945. | $A^{117}$ | $D^{168}$ |
| 8946. | $A^{118}$ | $D^{168}$ |
| 8947. | $A^{119}$ | $D^{168}$ |
| 8948. | $A^{120}$ | $D^{168}$ |
| 8949. | $A^{121}$ | $D^{168}$ |
| 8950. | $A^{122}$ | $D^{168}$ |
| 8951. | $A^{123}$ | $D^{168}$ |
| 8952. | $A^{124}$ | $D^{168}$ |
| 8953. | $A^{125}$ | $D^{168}$ |
| 8954. | $A^{126}$ | $D^{168}$ |
| 8955. | $A^{127}$ | $D^{168}$ |
| 8956. | $A^{128}$ | $D^{168}$ |
| 8957. | $A^{129}$ | $D^{168}$ |
| 8958. | $A^{130}$ | $D^{168}$ |
| 8959. | $A^{131}$ | $D^{168}$ |
| 8960. | $A^{132}$ | $D^{168}$ |
| 8961. | $D^{121}$ | $A^{101}$ |
| 8962. | $D^{121}$ | $A^{102}$ |
| 8963. | $D^{121}$ | $A^{103}$ |
| 8964. | $D^{121}$ | $A^{104}$ |
| 8965. | $D^{121}$ | $A^{105}$ |
| 8966. | $D^{121}$ | $A^{106}$ |
| 8967. | $D^{121}$ | $A^{107}$ |
| 8968. | $D^{121}$ | $A^{108}$ |
| 8969. | $D^{121}$ | $A^{109}$ |
| 8970. | $D^{121}$ | $A^{110}$ |
| 8971. | $D^{121}$ | $A^{111}$ |
| 8972. | $D^{121}$ | $A^{112}$ |
| 8973. | $D^{121}$ | $A^{113}$ |
| 8974. | $D^{121}$ | $A^{114}$ |
| 8975. | $D^{121}$ | $A^{115}$ |
| 8976. | $D^{121}$ | $A^{116}$ |
| 8977. | $D^{121}$ | $A^{117}$ |
| 8978. | $D^{121}$ | $A^{118}$ |
| 8979. | $D^{121}$ | $A^{119}$ |
| 8980. | $D^{121}$ | $A^{120}$ |
| 8981. | $D^{121}$ | $A^{121}$ |
| 8982. | $D^{121}$ | $A^{122}$ |
| 8983. | $D^{121}$ | $A^{123}$ |
| 8984. | $D^{121}$ | $A^{124}$ |
| 8985. | $D^{121}$ | $A^{125}$ |
| 8986. | $D^{121}$ | $A^{126}$ |
| 8987. | $D^{121}$ | $A^{127}$ |
| 8988. | $D^{121}$ | $A^{128}$ |
| 8989. | $D^{121}$ | $A^{129}$ |
| 8990. | $D^{121}$ | $A^{130}$ |
| 8991. | $D^{121}$ | $A^{131}$ |
| 8992. | $D^{121}$ | $A^{132}$ |
| 8993. | $D^{122}$ | $A^{101}$ |
| 8994. | $D^{122}$ | $A^{102}$ |
| 8995. | $D^{122}$ | $A^{103}$ |
| 8996. | $D^{122}$ | $A^{104}$ |
| 8997. | $D^{122}$ | $A^{105}$ |
| 8998. | $D^{122}$ | $A^{106}$ |
| 8999. | $D^{122}$ | $A^{107}$ |
| 9000. | $D^{122}$ | $A^{108}$ |
| 9001. | $D^{122}$ | $A^{109}$ |
| 9002. | $D^{122}$ | $A^{110}$ |
| 9003. | $D^{122}$ | $A^{111}$ |

221

-continued

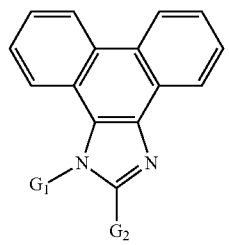

Formula IV

| Compound Number | $G^1$ | $G^2$ |
|---|---|---|
| 9004. | $D^{122}$ | $A^{112}$ |
| 9005. | $D^{122}$ | $A^{113}$ |
| 9006. | $D^{122}$ | $A^{114}$ |
| 9007. | $D^{122}$ | $A^{115}$ |
| 9008. | $D^{122}$ | $A^{116}$ |
| 9009. | $D^{122}$ | $A^{117}$ |
| 9010. | $D^{122}$ | $A^{118}$ |
| 9011. | $D^{122}$ | $A^{119}$ |
| 9012. | $D^{122}$ | $A^{120}$ |
| 9013. | $D^{122}$ | $A^{121}$ |
| 9014. | $D^{122}$ | $A^{122}$ |
| 9015. | $D^{122}$ | $A^{123}$ |
| 9016. | $D^{122}$ | $A^{124}$ |
| 9017. | $D^{122}$ | $A^{125}$ |
| 9018. | $D^{122}$ | $A^{126}$ |
| 9019. | $D^{122}$ | $A^{127}$ |
| 9020. | $D^{122}$ | $A^{128}$ |
| 9021. | $D^{122}$ | $A^{129}$ |
| 9022. | $D^{122}$ | $A^{130}$ |
| 9023. | $D^{122}$ | $A^{131}$ |
| 9024. | $D^{122}$ | $A^{132}$ |
| 9025. | $D^{123}$ | $A^{101}$ |
| 9026. | $D^{123}$ | $A^{102}$ |
| 9027. | $D^{123}$ | $A^{103}$ |
| 9028. | $D^{123}$ | $A^{104}$ |
| 9029. | $D^{123}$ | $A^{105}$ |
| 9030. | $D^{123}$ | $A^{106}$ |
| 9031. | $D^{123}$ | $A^{107}$ |
| 9032. | $D^{123}$ | $A^{108}$ |
| 9033. | $D^{123}$ | $A^{109}$ |
| 9034. | $D^{123}$ | $A^{110}$ |
| 9035. | $D^{123}$ | $A^{111}$ |
| 9036. | $D^{123}$ | $A^{112}$ |
| 9037. | $D^{123}$ | $A^{113}$ |
| 9038. | $D^{123}$ | $A^{114}$ |
| 9039. | $D^{123}$ | $A^{115}$ |
| 9040. | $D^{123}$ | $A^{116}$ |
| 9041. | $D^{123}$ | $A^{117}$ |
| 9042. | $D^{123}$ | $A^{118}$ |
| 9043. | $D^{123}$ | $A^{119}$ |
| 9044. | $D^{123}$ | $A^{120}$ |
| 9045. | $D^{123}$ | $A^{121}$ |
| 9046. | $D^{123}$ | $A^{122}$ |
| 9047. | $D^{123}$ | $A^{123}$ |
| 9048. | $D^{123}$ | $A^{124}$ |
| 9049. | $D^{123}$ | $A^{125}$ |
| 9050. | $D^{123}$ | $A^{126}$ |
| 9051. | $D^{123}$ | $A^{127}$ |
| 9052. | $D^{123}$ | $A^{128}$ |
| 9053. | $D^{123}$ | $A^{129}$ |
| 9054. | $D^{123}$ | $A^{130}$ |
| 9055. | $D^{123}$ | $A^{131}$ |
| 9056. | $D^{123}$ | $A^{132}$ |
| 9057. | $D^{124}$ | $A^{101}$ |
| 9058. | $D^{124}$ | $A^{102}$ |
| 9059. | $D^{124}$ | $A^{103}$ |
| 9060. | $D^{124}$ | $A^{104}$ |
| 9061. | $D^{124}$ | $A^{105}$ |
| 9062. | $D^{124}$ | $A^{106}$ |
| 9063. | $D^{124}$ | $A^{107}$ |
| 9064. | $D^{124}$ | $A^{108}$ |
| 9065. | $D^{124}$ | $A^{109}$ |
| 9066. | $D^{124}$ | $A^{110}$ |

222

-continued

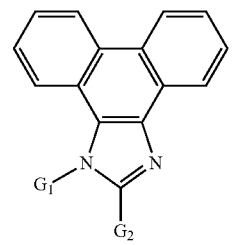

Formula IV

| Compound Number | $G^1$ | $G^2$ |
|---|---|---|
| 9067. | $D^{124}$ | $A^{111}$ |
| 9068. | $D^{124}$ | $A^{112}$ |
| 9069. | $D^{124}$ | $A^{113}$ |
| 9070. | $D^{124}$ | $A^{114}$ |
| 9071. | $D^{124}$ | $A^{115}$ |
| 9072. | $D^{124}$ | $A^{116}$ |
| 9073. | $D^{124}$ | $A^{117}$ |
| 9074. | $D^{124}$ | $A^{118}$ |
| 9075. | $D^{124}$ | $A^{119}$ |
| 9076. | $D^{124}$ | $A^{120}$ |
| 9077. | $D^{124}$ | $A^{121}$ |
| 9078. | $D^{124}$ | $A^{122}$ |
| 9079. | $D^{124}$ | $A^{123}$ |
| 9080. | $D^{124}$ | $A^{124}$ |
| 9081. | $D^{124}$ | $A^{125}$ |
| 9082. | $D^{124}$ | $A^{126}$ |
| 9083. | $D^{124}$ | $A^{127}$ |
| 9084. | $D^{124}$ | $A^{128}$ |
| 9085. | $D^{124}$ | $A^{129}$ |
| 9086. | $D^{124}$ | $A^{130}$ |
| 9087. | $D^{124}$ | $A^{131}$ |
| 9088. | $D^{124}$ | $A^{132}$ |
| 9089. | $D^{125}$ | $A^{101}$ |
| 9090. | $D^{125}$ | $A^{102}$ |
| 9091. | $D^{125}$ | $A^{103}$ |
| 9092. | $D^{125}$ | $A^{104}$ |
| 9093. | $D^{125}$ | $A^{105}$ |
| 9094. | $D^{125}$ | $A^{106}$ |
| 9095. | $D^{125}$ | $A^{107}$ |
| 9096. | $D^{125}$ | $A^{108}$ |
| 9097. | $D^{125}$ | $A^{109}$ |
| 9098. | $D^{125}$ | $A^{110}$ |
| 9099. | $D^{125}$ | $A^{111}$ |
| 9100. | $D^{125}$ | $A^{112}$ |
| 9101. | $D^{125}$ | $A^{113}$ |
| 9102. | $D^{125}$ | $A^{114}$ |
| 9103. | $D^{125}$ | $A^{115}$ |
| 9104. | $D^{125}$ | $A^{116}$ |
| 9105. | $D^{125}$ | $A^{117}$ |
| 9106. | $D^{125}$ | $A^{118}$ |
| 9107. | $D^{125}$ | $A^{119}$ |
| 9108. | $D^{125}$ | $A^{120}$ |
| 9109. | $D^{125}$ | $A^{121}$ |
| 9110. | $D^{125}$ | $A^{122}$ |
| 9111. | $D^{125}$ | $A^{123}$ |
| 9112. | $D^{125}$ | $A^{124}$ |
| 9113. | $D^{125}$ | $A^{125}$ |
| 9114. | $D^{125}$ | $A^{126}$ |
| 9115. | $D^{125}$ | $A^{127}$ |
| 9116. | $D^{125}$ | $A^{128}$ |
| 9117. | $D^{125}$ | $A^{129}$ |
| 9118. | $D^{125}$ | $A^{130}$ |
| 9119. | $D^{125}$ | $A^{131}$ |
| 9120. | $D^{125}$ | $A^{132}$ |
| 9121. | $D^{126}$ | $A^{101}$ |
| 9122. | $D^{126}$ | $A^{102}$ |
| 9123. | $D^{126}$ | $A^{103}$ |
| 9124. | $D^{126}$ | $A^{104}$ |
| 9125. | $D^{126}$ | $A^{105}$ |
| 9126. | $D^{126}$ | $A^{106}$ |
| 9127. | $D^{126}$ | $A^{107}$ |
| 9128. | $D^{126}$ | $A^{108}$ |
| 9129. | $D^{126}$ | $A^{109}$ |

Formula IV

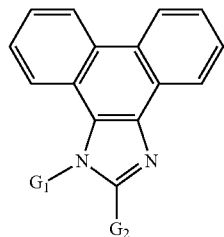

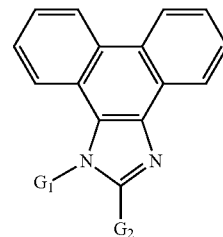

| Compound Number | $G^1$ | $G^2$ |
|---|---|---|
| 9130. | $D^{126}$ | $A^{110}$ |
| 9131. | $D^{126}$ | $A^{111}$ |
| 9132. | $D^{126}$ | $A^{112}$ |
| 9133. | $D^{126}$ | $A^{113}$ |
| 9134. | $D^{126}$ | $A^{114}$ |
| 9135. | $D^{126}$ | $A^{115}$ |
| 9136. | $D^{126}$ | $A^{116}$ |
| 9137. | $D^{126}$ | $A^{117}$ |
| 9138. | $D^{126}$ | $A^{118}$ |
| 9139. | $D^{126}$ | $A^{119}$ |
| 9140. | $D^{126}$ | $A^{120}$ |
| 9141. | $D^{126}$ | $A^{121}$ |
| 9142. | $D^{126}$ | $A^{122}$ |
| 9143. | $D^{126}$ | $A^{123}$ |
| 9144. | $D^{126}$ | $A^{124}$ |
| 9145. | $D^{126}$ | $A^{125}$ |
| 9146. | $D^{126}$ | $A^{126}$ |
| 9147. | $D^{126}$ | $A^{127}$ |
| 9148. | $D^{126}$ | $A^{128}$ |
| 9149. | $D^{126}$ | $A^{129}$ |
| 9150. | $D^{126}$ | $A^{130}$ |
| 9151. | $D^{126}$ | $A^{131}$ |
| 9152. | $D^{126}$ | $A^{132}$ |
| 9153. | $D^{127}$ | $A^{101}$ |
| 9154. | $D^{127}$ | $A^{102}$ |
| 9155. | $D^{127}$ | $A^{103}$ |
| 9156. | $D^{127}$ | $A^{104}$ |
| 9157. | $D^{127}$ | $A^{105}$ |
| 9158. | $D^{127}$ | $A^{106}$ |
| 9159. | $D^{127}$ | $A^{107}$ |
| 9160. | $D^{127}$ | $A^{108}$ |
| 9161. | $D^{127}$ | $A^{109}$ |
| 9162. | $D^{127}$ | $A^{110}$ |
| 9163. | $D^{127}$ | $A^{111}$ |
| 9164. | $D^{127}$ | $A^{112}$ |
| 9165. | $D^{127}$ | $A^{113}$ |
| 9166. | $D^{127}$ | $A^{114}$ |
| 9167. | $D^{127}$ | $A^{115}$ |
| 9168. | $D^{127}$ | $A^{116}$ |
| 9169. | $D^{127}$ | $A^{117}$ |
| 9170. | $D^{127}$ | $A^{118}$ |
| 9171. | $D^{127}$ | $A^{119}$ |
| 9172. | $D^{127}$ | $A^{120}$ |
| 9173. | $D^{127}$ | $A^{121}$ |
| 9174. | $D^{127}$ | $A^{122}$ |
| 9175. | $D^{127}$ | $A^{123}$ |
| 9176. | $D^{127}$ | $A^{124}$ |
| 9177. | $D^{127}$ | $A^{125}$ |
| 9178. | $D^{127}$ | $A^{126}$ |
| 9179. | $D^{127}$ | $A^{127}$ |
| 9180. | $D^{127}$ | $A^{128}$ |
| 9181. | $D^{127}$ | $A^{129}$ |
| 9182. | $D^{127}$ | $A^{130}$ |
| 9183. | $D^{127}$ | $A^{131}$ |
| 9184. | $D^{127}$ | $A^{132}$ |
| 9185. | $D^{128}$ | $A^{101}$ |
| 9186. | $D^{128}$ | $A^{102}$ |
| 9187. | $D^{128}$ | $A^{103}$ |
| 9188. | $D^{128}$ | $A^{104}$ |
| 9189. | $D^{128}$ | $A^{105}$ |
| 9190. | $D^{128}$ | $A^{106}$ |
| 9191. | $D^{128}$ | $A^{107}$ |
| 9192. | $D^{128}$ | $A^{108}$ |
| 9193. | $D^{128}$ | $A^{109}$ |
| 9194. | $D^{128}$ | $A^{110}$ |
| 9195. | $D^{128}$ | $A^{111}$ |
| 9196. | $D^{128}$ | $A^{112}$ |
| 9197. | $D^{128}$ | $A^{113}$ |
| 9198. | $D^{128}$ | $A^{114}$ |
| 9199. | $D^{128}$ | $A^{115}$ |
| 9200. | $D^{128}$ | $A^{116}$ |
| 9201. | $D^{128}$ | $A^{117}$ |
| 9202. | $D^{128}$ | $A^{118}$ |
| 9203. | $D^{128}$ | $A^{119}$ |
| 9204. | $D^{128}$ | $A^{120}$ |
| 9205. | $D^{128}$ | $A^{121}$ |
| 9206. | $D^{128}$ | $A^{122}$ |
| 9207. | $D^{128}$ | $A^{123}$ |
| 9208. | $D^{128}$ | $A^{124}$ |
| 9209. | $D^{128}$ | $A^{125}$ |
| 9210. | $D^{128}$ | $A^{126}$ |
| 9211. | $D^{128}$ | $A^{127}$ |
| 9212. | $D^{128}$ | $A^{128}$ |
| 9213. | $D^{128}$ | $A^{129}$ |
| 9214. | $D^{128}$ | $A^{130}$ |
| 9215. | $D^{128}$ | $A^{131}$ |
| 9216. | $D^{128}$ | $A^{132}$ |
| 9217. | $D^{129}$ | $A^{101}$ |
| 9218. | $D^{129}$ | $A^{102}$ |
| 9219. | $D^{129}$ | $A^{103}$ |
| 9220. | $D^{129}$ | $A^{104}$ |
| 9221. | $D^{129}$ | $A^{105}$ |
| 9222. | $D^{129}$ | $A^{106}$ |
| 9223. | $D^{129}$ | $A^{107}$ |
| 9224. | $D^{129}$ | $A^{108}$ |
| 9225. | $D^{129}$ | $A^{109}$ |
| 9226. | $D^{129}$ | $A^{110}$ |
| 9227. | $D^{129}$ | $A^{111}$ |
| 9228. | $D^{129}$ | $A^{112}$ |
| 9229. | $D^{129}$ | $A^{113}$ |
| 9230. | $D^{129}$ | $A^{114}$ |
| 9231. | $D^{129}$ | $A^{115}$ |
| 9232. | $D^{129}$ | $A^{116}$ |
| 9233. | $D^{129}$ | $A^{117}$ |
| 9234. | $D^{129}$ | $A^{118}$ |
| 9235. | $D^{129}$ | $A^{119}$ |
| 9236. | $D^{129}$ | $A^{120}$ |
| 9237. | $D^{129}$ | $A^{121}$ |
| 9238. | $D^{129}$ | $A^{122}$ |
| 9239. | $D^{129}$ | $A^{123}$ |
| 9240. | $D^{129}$ | $A^{124}$ |
| 9241. | $D^{129}$ | $A^{125}$ |
| 9242. | $D^{129}$ | $A^{126}$ |
| 9243. | $D^{129}$ | $A^{127}$ |
| 9244. | $D^{129}$ | $A^{128}$ |
| 9245. | $D^{129}$ | $A^{129}$ |
| 9246. | $D^{129}$ | $A^{130}$ |
| 9247. | $D^{129}$ | $A^{131}$ |
| 9248. | $D^{129}$ | $A^{132}$ |
| 9249. | $D^{130}$ | $A^{101}$ |
| 9250. | $D^{130}$ | $A^{102}$ |
| 9251. | $D^{130}$ | $A^{103}$ |
| 9252. | $D^{130}$ | $A^{104}$ |
| 9253. | $D^{130}$ | $A^{105}$ |
| 9254. | $D^{130}$ | $A^{106}$ |
| 9255. | $D^{130}$ | $A^{107}$ |

Formula IV

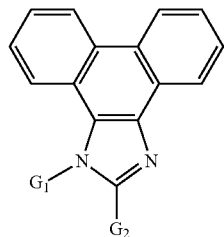

| Compound Number | $G^1$ | $G^2$ |
|---|---|---|
| 9256. | $D^{130}$ | $A^{108}$ |
| 9257. | $D^{130}$ | $A^{109}$ |
| 9258. | $D^{130}$ | $A^{110}$ |
| 9259. | $D^{130}$ | $A^{111}$ |
| 9260. | $D^{130}$ | $A^{112}$ |
| 9261. | $D^{130}$ | $A^{113}$ |
| 9262. | $D^{130}$ | $A^{114}$ |
| 9263. | $D^{130}$ | $A^{115}$ |
| 9264. | $D^{130}$ | $A^{116}$ |
| 9265. | $D^{130}$ | $A^{117}$ |
| 9266. | $D^{130}$ | $A^{118}$ |
| 9267. | $D^{130}$ | $A^{119}$ |
| 9268. | $D^{130}$ | $A^{120}$ |
| 9269. | $D^{130}$ | $A^{121}$ |
| 9270. | $D^{130}$ | $A^{122}$ |
| 9271. | $D^{130}$ | $A^{123}$ |
| 9272. | $D^{130}$ | $A^{124}$ |
| 9273. | $D^{130}$ | $A^{125}$ |
| 9274. | $D^{130}$ | $A^{126}$ |
| 9275. | $D^{130}$ | $A^{127}$ |
| 9276. | $D^{130}$ | $A^{128}$ |
| 9277. | $D^{130}$ | $A^{129}$ |
| 9278. | $D^{130}$ | $A^{130}$ |
| 9279. | $D^{130}$ | $A^{131}$ |
| 9280. | $D^{130}$ | $A^{132}$ |
| 9281. | $D^{131}$ | $A^{101}$ |
| 9282. | $D^{131}$ | $A^{102}$ |
| 9283. | $D^{131}$ | $A^{103}$ |
| 9284. | $D^{131}$ | $A^{104}$ |
| 9285. | $D^{131}$ | $A^{105}$ |
| 9286. | $D^{131}$ | $A^{106}$ |
| 9287. | $D^{131}$ | $A^{107}$ |
| 9288. | $D^{131}$ | $A^{108}$ |
| 9289. | $D^{131}$ | $A^{109}$ |
| 9290. | $D^{131}$ | $A^{110}$ |
| 9291. | $D^{131}$ | $A^{111}$ |
| 9292. | $D^{131}$ | $A^{112}$ |
| 9293. | $D^{131}$ | $A^{113}$ |
| 9294. | $D^{131}$ | $A^{114}$ |
| 9295. | $D^{131}$ | $A^{115}$ |
| 9296. | $D^{131}$ | $A^{116}$ |
| 9297. | $D^{131}$ | $A^{117}$ |
| 9298. | $D^{131}$ | $A^{118}$ |
| 9299. | $D^{131}$ | $A^{119}$ |
| 9300. | $D^{131}$ | $A^{120}$ |
| 9301. | $D^{131}$ | $A^{121}$ |
| 9302. | $D^{131}$ | $A^{122}$ |
| 9303. | $D^{131}$ | $A^{123}$ |
| 9304. | $D^{131}$ | $A^{124}$ |
| 9305. | $D^{131}$ | $A^{125}$ |
| 9306. | $D^{131}$ | $A^{126}$ |
| 9307. | $D^{131}$ | $A^{127}$ |
| 9308. | $D^{131}$ | $A^{128}$ |
| 9309. | $D^{131}$ | $A^{129}$ |
| 9310. | $D^{131}$ | $A^{130}$ |
| 9311. | $D^{131}$ | $A^{131}$ |
| 9312. | $D^{131}$ | $A^{132}$ |
| 9313. | $D^{132}$ | $A^{101}$ |
| 9314. | $D^{132}$ | $A^{102}$ |
| 9315. | $D^{132}$ | $A^{103}$ |
| 9316. | $D^{132}$ | $A^{104}$ |
| 9317. | $D^{132}$ | $A^{105}$ |
| 9318. | $D^{132}$ | $A^{106}$ |

Formula IV

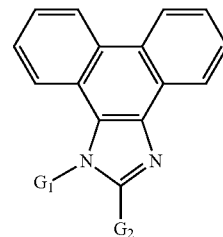

| Compound Number | $G^1$ | $G^2$ |
|---|---|---|
| 9319. | $D^{132}$ | $A^{107}$ |
| 9320. | $D^{132}$ | $A^{108}$ |
| 9321. | $D^{132}$ | $A^{109}$ |
| 9322. | $D^{132}$ | $A^{110}$ |
| 9323. | $D^{132}$ | $A^{111}$ |
| 9324. | $D^{132}$ | $A^{112}$ |
| 9325. | $D^{132}$ | $A^{113}$ |
| 9326. | $D^{132}$ | $A^{114}$ |
| 9327. | $D^{132}$ | $A^{115}$ |
| 9328. | $D^{132}$ | $A^{116}$ |
| 9329. | $D^{132}$ | $A^{117}$ |
| 9330. | $D^{132}$ | $A^{118}$ |
| 9331. | $D^{132}$ | $A^{119}$ |
| 9332. | $D^{132}$ | $A^{120}$ |
| 9333. | $D^{132}$ | $A^{121}$ |
| 9334. | $D^{132}$ | $A^{122}$ |
| 9335. | $D^{132}$ | $A^{123}$ |
| 9336. | $D^{132}$ | $A^{124}$ |
| 9337. | $D^{132}$ | $A^{125}$ |
| 9338. | $D^{132}$ | $A^{126}$ |
| 9339. | $D^{132}$ | $A^{127}$ |
| 9340. | $D^{132}$ | $A^{128}$ |
| 9341. | $D^{132}$ | $A^{129}$ |
| 9342. | $D^{132}$ | $A^{130}$ |
| 9343. | $D^{132}$ | $A^{131}$ |
| 9344. | $D^{132}$ | $A^{132}$ |
| 9345. | $D^{133}$ | $A^{101}$ |
| 9346. | $D^{133}$ | $A^{102}$ |
| 9347. | $D^{133}$ | $A^{103}$ |
| 9348. | $D^{133}$ | $A^{104}$ |
| 9349. | $D^{133}$ | $A^{105}$ |
| 9350. | $D^{133}$ | $A^{106}$ |
| 9351. | $D^{133}$ | $A^{107}$ |
| 9352. | $D^{133}$ | $A^{108}$ |
| 9353. | $D^{133}$ | $A^{109}$ |
| 9354. | $D^{133}$ | $A^{110}$ |
| 9355. | $D^{133}$ | $A^{111}$ |
| 9356. | $D^{133}$ | $A^{112}$ |
| 9357. | $D^{133}$ | $A^{113}$ |
| 9358. | $D^{133}$ | $A^{114}$ |
| 9359. | $D^{133}$ | $A^{115}$ |
| 9360. | $D^{133}$ | $A^{116}$ |
| 9361. | $D^{133}$ | $A^{117}$ |
| 9362. | $D^{133}$ | $A^{118}$ |
| 9363. | $D^{133}$ | $A^{119}$ |
| 9364. | $D^{133}$ | $A^{120}$ |
| 9365. | $D^{133}$ | $A^{121}$ |
| 9366. | $D^{133}$ | $A^{122}$ |
| 9367. | $D^{133}$ | $A^{123}$ |
| 9368. | $D^{133}$ | $A^{124}$ |
| 9369. | $D^{133}$ | $A^{125}$ |
| 9370. | $D^{133}$ | $A^{126}$ |
| 9371. | $D^{133}$ | $A^{127}$ |
| 9372. | $D^{133}$ | $A^{128}$ |
| 9373. | $D^{133}$ | $A^{129}$ |
| 9374. | $D^{133}$ | $A^{130}$ |
| 9375. | $D^{133}$ | $A^{131}$ |
| 9376. | $D^{133}$ | $A^{132}$ |
| 9377. | $D^{134}$ | $A^{101}$ |
| 9378. | $D^{134}$ | $A^{102}$ |
| 9379. | $D^{134}$ | $A^{103}$ |
| 9380. | $D^{134}$ | $A^{104}$ |
| 9381. | $D^{134}$ | $A^{105}$ |

227

-continued

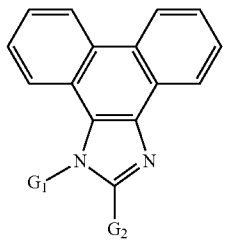

Formula IV

| Compound Number | G¹ | G² |
|---|---|---|
| 9382. | $D^{134}$ | $A^{106}$ |
| 9383. | $D^{134}$ | $A^{107}$ |
| 9384. | $D^{134}$ | $A^{108}$ |
| 9385. | $D^{134}$ | $A^{109}$ |
| 9386. | $D^{134}$ | $A^{110}$ |
| 9387. | $D^{134}$ | $A^{111}$ |
| 9388. | $D^{134}$ | $A^{112}$ |
| 9389. | $D^{134}$ | $A^{113}$ |
| 9390. | $D^{134}$ | $A^{114}$ |
| 9391. | $D^{134}$ | $A^{115}$ |
| 9392. | $D^{134}$ | $A^{116}$ |
| 9393. | $D^{134}$ | $A^{117}$ |
| 9394. | $D^{134}$ | $A^{118}$ |
| 9395. | $D^{134}$ | $A^{119}$ |
| 9396. | $D^{134}$ | $A^{120}$ |
| 9397. | $D^{134}$ | $A^{121}$ |
| 9398. | $D^{134}$ | $A^{122}$ |
| 9399. | $D^{134}$ | $A^{123}$ |
| 9400. | $D^{134}$ | $A^{124}$ |
| 9401. | $D^{134}$ | $A^{125}$ |
| 9402. | $D^{134}$ | $A^{126}$ |
| 9403. | $D^{134}$ | $A^{127}$ |
| 9404. | $D^{134}$ | $A^{128}$ |
| 9405. | $D^{134}$ | $A^{129}$ |
| 9406. | $D^{134}$ | $A^{130}$ |
| 9407. | $D^{134}$ | $A^{131}$ |
| 9408. | $D^{134}$ | $A^{132}$ |
| 9409. | $D^{135}$ | $A^{101}$ |
| 9410. | $D^{135}$ | $A^{102}$ |
| 9411. | $D^{135}$ | $A^{103}$ |
| 9412. | $D^{135}$ | $A^{104}$ |
| 9413. | $D^{135}$ | $A^{105}$ |
| 9414. | $D^{135}$ | $A^{106}$ |
| 9415. | $D^{135}$ | $A^{107}$ |
| 9416. | $D^{135}$ | $A^{108}$ |
| 9417. | $D^{135}$ | $A^{109}$ |
| 9418. | $D^{135}$ | $A^{110}$ |
| 9419. | $D^{135}$ | $A^{111}$ |
| 9420. | $D^{135}$ | $A^{112}$ |
| 9421. | $D^{135}$ | $A^{113}$ |
| 9422. | $D^{135}$ | $A^{114}$ |
| 9423. | $D^{135}$ | $A^{115}$ |
| 9424. | $D^{135}$ | $A^{116}$ |
| 9425. | $D^{135}$ | $A^{117}$ |
| 9426. | $D^{135}$ | $A^{118}$ |
| 9427. | $D^{135}$ | $A^{119}$ |
| 9428. | $D^{135}$ | $A^{120}$ |
| 9429. | $D^{135}$ | $A^{121}$ |
| 9430. | $D^{135}$ | $A^{122}$ |
| 9431. | $D^{135}$ | $A^{123}$ |
| 9432. | $D^{135}$ | $A^{124}$ |
| 9433. | $D^{135}$ | $A^{125}$ |
| 9434. | $D^{135}$ | $A^{126}$ |
| 9435. | $D^{135}$ | $A^{127}$ |
| 9436. | $D^{135}$ | $A^{128}$ |
| 9437. | $D^{135}$ | $A^{129}$ |
| 9438. | $D^{135}$ | $A^{130}$ |
| 9439. | $D^{135}$ | $A^{131}$ |
| 9440. | $D^{135}$ | $A^{132}$ |
| 9441. | $D^{136}$ | $A^{101}$ |
| 9442. | $D^{136}$ | $A^{102}$ |
| 9443. | $D^{136}$ | $A^{103}$ |
| 9444. | $D^{136}$ | $A^{104}$ |

228

-continued

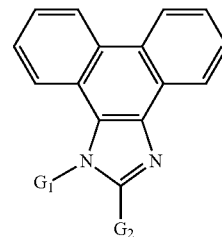

Formula IV

| Compound Number | G¹ | G² |
|---|---|---|
| 9445. | $D^{136}$ | $A^{105}$ |
| 9446. | $D^{136}$ | $A^{106}$ |
| 9447. | $D^{136}$ | $A^{107}$ |
| 9448. | $D^{136}$ | $A^{108}$ |
| 9449. | $D^{136}$ | $A^{109}$ |
| 9450. | $D^{136}$ | $A^{110}$ |
| 9451. | $D^{136}$ | $A^{111}$ |
| 9452. | $D^{136}$ | $A^{112}$ |
| 9453. | $D^{136}$ | $A^{113}$ |
| 9454. | $D^{136}$ | $A^{114}$ |
| 9455. | $D^{136}$ | $A^{115}$ |
| 9456. | $D^{136}$ | $A^{116}$ |
| 9457. | $D^{136}$ | $A^{117}$ |
| 9458. | $D^{136}$ | $A^{118}$ |
| 9459. | $D^{136}$ | $A^{119}$ |
| 9460. | $D^{136}$ | $A^{120}$ |
| 9461. | $D^{136}$ | $A^{121}$ |
| 9462. | $D^{136}$ | $A^{122}$ |
| 9463. | $D^{136}$ | $A^{123}$ |
| 9464. | $D^{136}$ | $A^{124}$ |
| 9465. | $D^{136}$ | $A^{125}$ |
| 9466. | $D^{136}$ | $A^{126}$ |
| 9467. | $D^{136}$ | $A^{127}$ |
| 9468. | $D^{136}$ | $A^{128}$ |
| 9469. | $D^{136}$ | $A^{129}$ |
| 9470. | $D^{136}$ | $A^{130}$ |
| 9471. | $D^{136}$ | $A^{131}$ |
| 9472. | $D^{136}$ | $A^{132}$ |
| 9473. | $D^{137}$ | $A^{101}$ |
| 9474. | $D^{137}$ | $A^{102}$ |
| 9475. | $D^{137}$ | $A^{103}$ |
| 9476. | $D^{137}$ | $A^{104}$ |
| 9477. | $D^{137}$ | $A^{105}$ |
| 9478. | $D^{137}$ | $A^{106}$ |
| 9479. | $D^{137}$ | $A^{107}$ |
| 9480. | $D^{137}$ | $A^{108}$ |
| 9481. | $D^{137}$ | $A^{109}$ |
| 9482. | $D^{137}$ | $A^{110}$ |
| 9483. | $D^{137}$ | $A^{111}$ |
| 9484. | $D^{137}$ | $A^{112}$ |
| 9485. | $D^{137}$ | $A^{113}$ |
| 9486. | $D^{137}$ | $A^{114}$ |
| 9487. | $D^{137}$ | $A^{115}$ |
| 9488. | $D^{137}$ | $A^{116}$ |
| 9489. | $D^{137}$ | $A^{117}$ |
| 9490. | $D^{137}$ | $A^{118}$ |
| 9491. | $D^{137}$ | $A^{119}$ |
| 9492. | $D^{137}$ | $A^{120}$ |
| 9493. | $D^{137}$ | $A^{121}$ |
| 9494. | $D^{137}$ | $A^{122}$ |
| 9495. | $D^{137}$ | $A^{123}$ |
| 9496. | $D^{137}$ | $A^{124}$ |
| 9497. | $D^{137}$ | $A^{125}$ |
| 9498. | $D^{137}$ | $A^{126}$ |
| 9499. | $D^{137}$ | $A^{127}$ |
| 9500. | $D^{137}$ | $A^{128}$ |
| 9501. | $D^{137}$ | $A^{129}$ |
| 9502. | $D^{137}$ | $A^{130}$ |
| 9503. | $D^{137}$ | $A^{131}$ |
| 9504. | $D^{137}$ | $A^{132}$ |
| 9505. | $D^{138}$ | $A^{101}$ |
| 9506. | $D^{138}$ | $A^{102}$ |
| 9507. | $D^{138}$ | $A^{103}$ |

229
-continued

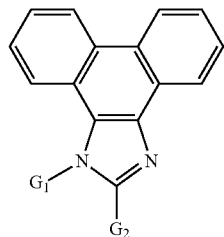

Formula IV

| Compound Number | $G^1$ | $G^2$ |
|---|---|---|
| 9508. | $D^{138}$ | $A^{104}$ |
| 9509. | $D^{138}$ | $A^{105}$ |
| 9510. | $D^{138}$ | $A^{106}$ |
| 9511. | $D^{138}$ | $A^{107}$ |
| 9512. | $D^{138}$ | $A^{108}$ |
| 9513. | $D^{138}$ | $A^{109}$ |
| 9514. | $D^{138}$ | $A^{110}$ |
| 9515. | $D^{138}$ | $A^{111}$ |
| 9516. | $D^{138}$ | $A^{112}$ |
| 9517. | $D^{138}$ | $A^{113}$ |
| 9518. | $D^{138}$ | $A^{114}$ |
| 9519. | $D^{138}$ | $A^{115}$ |
| 9520. | $D^{138}$ | $A^{116}$ |
| 9521. | $D^{138}$ | $A^{117}$ |
| 9522. | $D^{138}$ | $A^{118}$ |
| 9523. | $D^{138}$ | $A^{119}$ |
| 9524. | $D^{138}$ | $A^{120}$ |
| 9525. | $D^{138}$ | $A^{121}$ |
| 9526. | $D^{138}$ | $A^{122}$ |
| 9527. | $D^{138}$ | $A^{123}$ |
| 9528. | $D^{138}$ | $A^{124}$ |
| 9529. | $D^{138}$ | $A^{125}$ |
| 9530. | $D^{138}$ | $A^{126}$ |
| 9531. | $D^{138}$ | $A^{127}$ |
| 9532. | $D^{138}$ | $A^{128}$ |
| 9533. | $D^{138}$ | $A^{129}$ |
| 9534. | $D^{138}$ | $A^{130}$ |
| 9535. | $D^{138}$ | $A^{131}$ |
| 9536. | $D^{138}$ | $A^{132}$ |
| 9537. | $D^{139}$ | $A^{101}$ |
| 9538. | $D^{139}$ | $A^{102}$ |
| 9539. | $D^{139}$ | $A^{103}$ |
| 9540. | $D^{139}$ | $A^{104}$ |
| 9541. | $D^{139}$ | $A^{105}$ |
| 9542. | $D^{139}$ | $A^{106}$ |
| 9543. | $D^{139}$ | $A^{107}$ |
| 9544. | $D^{139}$ | $A^{108}$ |
| 9545. | $D^{139}$ | $A^{109}$ |
| 9546. | $D^{139}$ | $A^{110}$ |
| 9547. | $D^{139}$ | $A^{111}$ |
| 9548. | $D^{139}$ | $A^{112}$ |
| 9549. | $D^{139}$ | $A^{113}$ |
| 9550. | $D^{139}$ | $A^{114}$ |
| 9551. | $D^{139}$ | $A^{115}$ |
| 9552. | $D^{139}$ | $A^{116}$ |
| 9553. | $D^{139}$ | $A^{117}$ |
| 9554. | $D^{139}$ | $A^{118}$ |
| 9555. | $D^{139}$ | $A^{119}$ |
| 9556. | $D^{139}$ | $A^{120}$ |
| 9557. | $D^{139}$ | $A^{121}$ |
| 9558. | $D^{139}$ | $A^{122}$ |
| 9559. | $D^{139}$ | $A^{123}$ |
| 9560. | $D^{139}$ | $A^{124}$ |
| 9561. | $D^{139}$ | $A^{125}$ |
| 9562. | $D^{139}$ | $A^{126}$ |
| 9563. | $D^{139}$ | $A^{127}$ |
| 9564. | $D^{139}$ | $A^{128}$ |
| 9565. | $D^{139}$ | $A^{129}$ |
| 9566. | $D^{139}$ | $A^{130}$ |
| 9567. | $D^{139}$ | $A^{131}$ |
| 9568. | $D^{139}$ | $A^{132}$ |
| 9569. | $D^{140}$ | $A^{101}$ |
| 9570. | $D^{140}$ | $A^{102}$ |

230
-continued

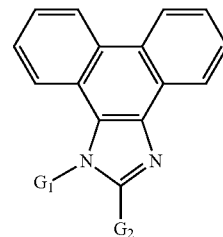

Formula IV

| Compound Number | $G^1$ | $G^2$ |
|---|---|---|
| 9571. | $D^{140}$ | $A^{103}$ |
| 9572. | $D^{140}$ | $A^{104}$ |
| 9573. | $D^{140}$ | $A^{105}$ |
| 9574. | $D^{140}$ | $A^{106}$ |
| 9575. | $D^{140}$ | $A^{107}$ |
| 9576. | $D^{140}$ | $A^{108}$ |
| 9577. | $D^{140}$ | $A^{109}$ |
| 9578. | $D^{140}$ | $A^{110}$ |
| 9579. | $D^{140}$ | $A^{111}$ |
| 9580. | $D^{140}$ | $A^{112}$ |
| 9581. | $D^{140}$ | $A^{113}$ |
| 9582. | $D^{140}$ | $A^{114}$ |
| 9583. | $D^{140}$ | $A^{115}$ |
| 9584. | $D^{140}$ | $A^{116}$ |
| 9585. | $D^{140}$ | $A^{117}$ |
| 9586. | $D^{140}$ | $A^{118}$ |
| 9587. | $D^{140}$ | $A^{119}$ |
| 9588. | $D^{140}$ | $A^{120}$ |
| 9589. | $D^{140}$ | $A^{121}$ |
| 9590. | $D^{140}$ | $A^{122}$ |
| 9591. | $D^{140}$ | $A^{123}$ |
| 9592. | $D^{140}$ | $A^{124}$ |
| 9593. | $D^{140}$ | $A^{125}$ |
| 9594. | $D^{140}$ | $A^{126}$ |
| 9595. | $D^{140}$ | $A^{127}$ |
| 9596. | $D^{140}$ | $A^{128}$ |
| 9597. | $D^{140}$ | $A^{129}$ |
| 9598. | $D^{140}$ | $A^{130}$ |
| 9599. | $D^{140}$ | $A^{131}$ |
| 9600. | $D^{140}$ | $A^{132}$ |
| 9601. | $D^{141}$ | $A^{101}$ |
| 9602. | $D^{141}$ | $A^{102}$ |
| 9603. | $D^{141}$ | $A^{103}$ |
| 9604. | $D^{141}$ | $A^{104}$ |
| 9605. | $D^{141}$ | $A^{105}$ |
| 9606. | $D^{141}$ | $A^{106}$ |
| 9607. | $D^{141}$ | $A^{107}$ |
| 9608. | $D^{141}$ | $A^{108}$ |
| 9609. | $D^{141}$ | $A^{109}$ |
| 9610. | $D^{141}$ | $A^{110}$ |
| 9611. | $D^{141}$ | $A^{111}$ |
| 9612. | $D^{141}$ | $A^{112}$ |
| 9613. | $D^{141}$ | $A^{113}$ |
| 9614. | $D^{141}$ | $A^{114}$ |
| 9615. | $D^{141}$ | $A^{115}$ |
| 9616. | $D^{141}$ | $A^{116}$ |
| 9617. | $D^{141}$ | $A^{117}$ |
| 9618. | $D^{141}$ | $A^{118}$ |
| 9619. | $D^{141}$ | $A^{119}$ |
| 9620. | $D^{141}$ | $A^{120}$ |
| 9621. | $D^{141}$ | $A^{121}$ |
| 9622. | $D^{141}$ | $A^{122}$ |
| 9623. | $D^{141}$ | $A^{123}$ |
| 9624. | $D^{141}$ | $A^{124}$ |
| 9625. | $D^{141}$ | $A^{125}$ |
| 9626. | $D^{141}$ | $A^{126}$ |
| 9627. | $D^{141}$ | $A^{127}$ |
| 9628. | $D^{141}$ | $A^{128}$ |
| 9629. | $D^{141}$ | $A^{129}$ |
| 9630. | $D^{141}$ | $A^{130}$ |
| 9631. | $D^{141}$ | $A^{131}$ |
| 9632. | $D^{141}$ | $A^{132}$ |
| 9633. | $D^{142}$ | $A^{101}$ |

Formula IV

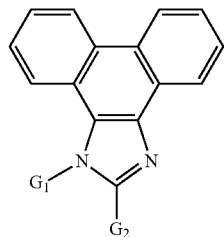

| Compound Number | G¹ | G² |
|---|---|---|
| 9634. | $D^{142}$ | $A^{102}$ |
| 9635. | $D^{142}$ | $A^{103}$ |
| 9636. | $D^{142}$ | $A^{104}$ |
| 9637. | $D^{142}$ | $A^{105}$ |
| 9638. | $D^{142}$ | $A^{106}$ |
| 9639. | $D^{142}$ | $A^{107}$ |
| 9640. | $D^{142}$ | $A^{108}$ |
| 9641. | $D^{142}$ | $A^{109}$ |
| 9642. | $D^{142}$ | $A^{110}$ |
| 9643. | $D^{142}$ | $A^{111}$ |
| 9644. | $D^{142}$ | $A^{112}$ |
| 9645. | $D^{142}$ | $A^{113}$ |
| 9646. | $D^{142}$ | $A^{114}$ |
| 9647. | $D^{142}$ | $A^{115}$ |
| 9648. | $D^{142}$ | $A^{116}$ |
| 9649. | $D^{142}$ | $A^{117}$ |
| 9650. | $D^{142}$ | $A^{118}$ |
| 9651. | $D^{142}$ | $A^{119}$ |
| 9652. | $D^{142}$ | $A^{120}$ |
| 9653. | $D^{142}$ | $A^{121}$ |
| 9654. | $D^{142}$ | $A^{122}$ |
| 9655. | $D^{142}$ | $A^{123}$ |
| 9656. | $D^{142}$ | $A^{124}$ |
| 9657. | $D^{142}$ | $A^{125}$ |
| 9658. | $D^{142}$ | $A^{126}$ |
| 9659. | $D^{142}$ | $A^{127}$ |
| 9660. | $D^{142}$ | $A^{128}$ |
| 9661. | $D^{142}$ | $A^{129}$ |
| 9662. | $D^{142}$ | $A^{130}$ |
| 9663. | $D^{142}$ | $A^{131}$ |
| 9664. | $D^{142}$ | $A^{132}$ |
| 9665. | $D^{143}$ | $A^{101}$ |
| 9666. | $D^{143}$ | $A^{102}$ |
| 9667. | $D^{143}$ | $A^{103}$ |
| 9668. | $D^{143}$ | $A^{104}$ |
| 9669. | $D^{143}$ | $A^{105}$ |
| 9670. | $D^{143}$ | $A^{106}$ |
| 9671. | $D^{143}$ | $A^{107}$ |
| 9672. | $D^{143}$ | $A^{108}$ |
| 9673. | $D^{143}$ | $A^{109}$ |
| 9674. | $D^{143}$ | $A^{110}$ |
| 9675. | $D^{143}$ | $A^{111}$ |
| 9676. | $D^{143}$ | $A^{112}$ |
| 9677. | $D^{143}$ | $A^{113}$ |
| 9678. | $D^{143}$ | $A^{114}$ |
| 9679. | $D^{143}$ | $A^{115}$ |
| 9680. | $D^{143}$ | $A^{116}$ |
| 9681. | $D^{143}$ | $A^{117}$ |
| 9682. | $D^{143}$ | $A^{118}$ |
| 9683. | $D^{143}$ | $A^{119}$ |
| 9684. | $D^{143}$ | $A^{120}$ |
| 9685. | $D^{143}$ | $A^{121}$ |
| 9686. | $D^{143}$ | $A^{122}$ |
| 9687. | $D^{143}$ | $A^{123}$ |
| 9688. | $D^{143}$ | $A^{124}$ |
| 9689. | $D^{143}$ | $A^{125}$ |
| 9690. | $D^{143}$ | $A^{126}$ |
| 9691. | $D^{143}$ | $A^{127}$ |
| 9692. | $D^{143}$ | $A^{128}$ |
| 9693. | $D^{143}$ | $A^{129}$ |
| 9694. | $D^{143}$ | $A^{130}$ |
| 9695. | $D^{143}$ | $A^{131}$ |
| 9696. | $D^{143}$ | $A^{132}$ |

Formula IV

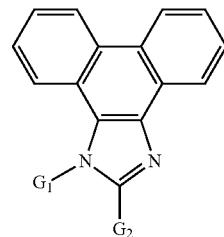

| Compound Number | G¹ | G² |
|---|---|---|
| 9697. | $D^{144}$ | $A^{101}$ |
| 9698. | $D^{144}$ | $A^{102}$ |
| 9699. | $D^{144}$ | $A^{103}$ |
| 9700. | $D^{144}$ | $A^{104}$ |
| 9701. | $D^{144}$ | $A^{105}$ |
| 9702. | $D^{144}$ | $A^{106}$ |
| 9703. | $D^{144}$ | $A^{107}$ |
| 9704. | $D^{144}$ | $A^{108}$ |
| 9705. | $D^{144}$ | $A^{109}$ |
| 9706. | $D^{144}$ | $A^{110}$ |
| 9707. | $D^{144}$ | $A^{111}$ |
| 9708. | $D^{144}$ | $A^{112}$ |
| 9709. | $D^{144}$ | $A^{113}$ |
| 9710. | $D^{144}$ | $A^{114}$ |
| 9711. | $D^{144}$ | $A^{115}$ |
| 9712. | $D^{144}$ | $A^{116}$ |
| 9713. | $D^{144}$ | $A^{117}$ |
| 9714. | $D^{144}$ | $A^{118}$ |
| 9715. | $D^{144}$ | $A^{119}$ |
| 9716. | $D^{144}$ | $A^{120}$ |
| 9717. | $D^{144}$ | $A^{121}$ |
| 9718. | $D^{144}$ | $A^{122}$ |
| 9719. | $D^{144}$ | $A^{123}$ |
| 9720. | $D^{144}$ | $A^{124}$ |
| 9721. | $D^{144}$ | $A^{125}$ |
| 9722. | $D^{144}$ | $A^{126}$ |
| 9723. | $D^{144}$ | $A^{127}$ |
| 9724. | $D^{144}$ | $A^{128}$ |
| 9725. | $D^{144}$ | $A^{129}$ |
| 9726. | $D^{144}$ | $A^{130}$ |
| 9727. | $D^{144}$ | $A^{131}$ |
| 9728. | $D^{144}$ | $A^{132}$ |
| 9729. | $D^{155}$ | $A^{101}$ |
| 9730. | $D^{155}$ | $A^{102}$ |
| 9731. | $D^{155}$ | $A^{103}$ |
| 9732. | $D^{155}$ | $A^{104}$ |
| 9733. | $D^{155}$ | $A^{105}$ |
| 9734. | $D^{155}$ | $A^{106}$ |
| 9735. | $D^{155}$ | $A^{107}$ |
| 9736. | $D^{155}$ | $A^{108}$ |
| 9737. | $D^{155}$ | $A^{109}$ |
| 9738. | $D^{155}$ | $A^{110}$ |
| 9739. | $D^{155}$ | $A^{111}$ |
| 9740. | $D^{155}$ | $A^{112}$ |
| 9741. | $D^{155}$ | $A^{113}$ |
| 9742. | $D^{155}$ | $A^{114}$ |
| 9743. | $D^{155}$ | $A^{115}$ |
| 9744. | $D^{155}$ | $A^{116}$ |
| 9745. | $D^{155}$ | $A^{117}$ |
| 9746. | $D^{155}$ | $A^{118}$ |
| 9747. | $D^{155}$ | $A^{119}$ |
| 9748. | $D^{155}$ | $A^{120}$ |
| 9749. | $D^{155}$ | $A^{121}$ |
| 9750. | $D^{155}$ | $A^{122}$ |
| 9751. | $D^{155}$ | $A^{123}$ |
| 9752. | $D^{155}$ | $A^{124}$ |
| 9753. | $D^{155}$ | $A^{125}$ |
| 9754. | $D^{155}$ | $A^{126}$ |
| 9755. | $D^{155}$ | $A^{127}$ |
| 9756. | $D^{155}$ | $A^{128}$ |
| 9757. | $D^{155}$ | $A^{129}$ |
| 9758. | $D^{155}$ | $A^{130}$ |
| 9759. | $D^{155}$ | $A^{131}$ |

Formula IV

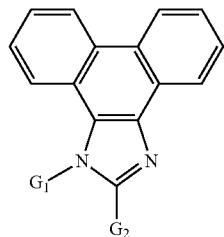

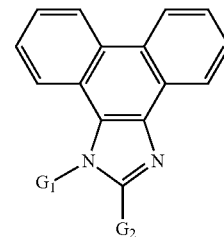

| Compound Number | G¹ | G² |
|---|---|---|
| 9760. | $D^{155}$ | $A^{132}$ |
| 9761. | $D^{156}$ | $A^{101}$ |
| 9762. | $D^{156}$ | $A^{102}$ |
| 9763. | $D^{156}$ | $A^{103}$ |
| 9764. | $D^{156}$ | $A^{104}$ |
| 9765. | $D^{156}$ | $A^{105}$ |
| 9766. | $D^{156}$ | $A^{106}$ |
| 9767. | $D^{156}$ | $A^{107}$ |
| 9768. | $D^{156}$ | $A^{108}$ |
| 9769. | $D^{156}$ | $A^{109}$ |
| 9770. | $D^{156}$ | $A^{110}$ |
| 9771. | $D^{156}$ | $A^{111}$ |
| 9772. | $D^{156}$ | $A^{112}$ |
| 9773. | $D^{156}$ | $A^{113}$ |
| 9774. | $D^{156}$ | $A^{114}$ |
| 9775. | $D^{156}$ | $A^{115}$ |
| 9776. | $D^{156}$ | $A^{116}$ |
| 9777. | $D^{156}$ | $A^{117}$ |
| 9778. | $D^{156}$ | $A^{118}$ |
| 9779. | $D^{156}$ | $A^{119}$ |
| 9780. | $D^{156}$ | $A^{120}$ |
| 9781. | $D^{156}$ | $A^{121}$ |
| 9782. | $D^{156}$ | $A^{122}$ |
| 9783. | $D^{156}$ | $A^{123}$ |
| 9784. | $D^{156}$ | $A^{124}$ |
| 9785. | $D^{156}$ | $A^{125}$ |
| 9786. | $D^{156}$ | $A^{126}$ |
| 9787. | $D^{156}$ | $A^{127}$ |
| 9788. | $D^{156}$ | $A^{128}$ |
| 9789. | $D^{156}$ | $A^{129}$ |
| 9790. | $D^{156}$ | $A^{130}$ |
| 9791. | $D^{156}$ | $A^{131}$ |
| 9792. | $D^{156}$ | $A^{132}$ |
| 9793. | $D^{157}$ | $A^{101}$ |
| 9794. | $D^{157}$ | $A^{102}$ |
| 9795. | $D^{157}$ | $A^{103}$ |
| 9796. | $D^{157}$ | $A^{104}$ |
| 9797. | $D^{157}$ | $A^{105}$ |
| 9798. | $D^{157}$ | $A^{106}$ |
| 9799. | $D^{157}$ | $A^{107}$ |
| 9800. | $D^{157}$ | $A^{108}$ |
| 9801. | $D^{157}$ | $A^{109}$ |
| 9802. | $D^{157}$ | $A^{110}$ |
| 9803. | $D^{157}$ | $A^{111}$ |
| 9804. | $D^{157}$ | $A^{112}$ |
| 9805. | $D^{157}$ | $A^{113}$ |
| 9806. | $D^{157}$ | $A^{114}$ |
| 9807. | $D^{157}$ | $A^{115}$ |
| 9808. | $D^{157}$ | $A^{116}$ |
| 9809. | $D^{157}$ | $A^{117}$ |
| 9810. | $D^{157}$ | $A^{118}$ |
| 9811. | $D^{157}$ | $A^{119}$ |
| 9812. | $D^{157}$ | $A^{120}$ |
| 9813. | $D^{157}$ | $A^{121}$ |
| 9814. | $D^{157}$ | $A^{122}$ |
| 9815. | $D^{157}$ | $A^{123}$ |
| 9816. | $D^{157}$ | $A^{124}$ |
| 9817. | $D^{157}$ | $A^{125}$ |
| 9818. | $D^{157}$ | $A^{126}$ |
| 9819. | $D^{157}$ | $A^{127}$ |
| 9820. | $D^{157}$ | $A^{128}$ |
| 9821. | $D^{157}$ | $A^{129}$ |
| 9822. | $D^{157}$ | $A^{130}$ |
| 9823. | $D^{157}$ | $A^{131}$ |
| 9824. | $D^{157}$ | $A^{132}$ |
| 9825. | $D^{158}$ | $A^{101}$ |
| 9826. | $D^{158}$ | $A^{102}$ |
| 9827. | $D^{158}$ | $A^{103}$ |
| 9828. | $D^{158}$ | $A^{104}$ |
| 9829. | $D^{158}$ | $A^{105}$ |
| 9830. | $D^{158}$ | $A^{106}$ |
| 9831. | $D^{158}$ | $A^{107}$ |
| 9832. | $D^{158}$ | $A^{108}$ |
| 9833. | $D^{158}$ | $A^{109}$ |
| 9834. | $D^{158}$ | $A^{110}$ |
| 9835. | $D^{158}$ | $A^{111}$ |
| 9836. | $D^{158}$ | $A^{112}$ |
| 9837. | $D^{158}$ | $A^{113}$ |
| 9838. | $D^{158}$ | $A^{114}$ |
| 9839. | $D^{158}$ | $A^{115}$ |
| 9840. | $D^{158}$ | $A^{116}$ |
| 9841. | $D^{158}$ | $A^{117}$ |
| 9842. | $D^{158}$ | $A^{118}$ |
| 9843. | $D^{158}$ | $A^{119}$ |
| 9844. | $D^{158}$ | $A^{120}$ |
| 9845. | $D^{158}$ | $A^{121}$ |
| 9846. | $D^{158}$ | $A^{122}$ |
| 9847. | $D^{158}$ | $A^{123}$ |
| 9848. | $D^{158}$ | $A^{124}$ |
| 9849. | $D^{158}$ | $A^{125}$ |
| 9850. | $D^{158}$ | $A^{126}$ |
| 9851. | $D^{158}$ | $A^{127}$ |
| 9852. | $D^{158}$ | $A^{128}$ |
| 9853. | $D^{158}$ | $A^{129}$ |
| 9854. | $D^{158}$ | $A^{130}$ |
| 9855. | $D^{158}$ | $A^{131}$ |
| 9856. | $D^{158}$ | $A^{132}$ |
| 9857. | $D^{159}$ | $A^{101}$ |
| 9858. | $D^{159}$ | $A^{102}$ |
| 9859. | $D^{159}$ | $A^{103}$ |
| 9860. | $D^{159}$ | $A^{104}$ |
| 9861. | $D^{159}$ | $A^{105}$ |
| 9862. | $D^{159}$ | $A^{106}$ |
| 9863. | $D^{159}$ | $A^{107}$ |
| 9864. | $D^{159}$ | $A^{108}$ |
| 9865. | $D^{159}$ | $A^{109}$ |
| 9866. | $D^{159}$ | $A^{110}$ |
| 9867. | $D^{159}$ | $A^{111}$ |
| 9868. | $D^{159}$ | $A^{112}$ |
| 9869. | $D^{159}$ | $A^{113}$ |
| 9870. | $D^{159}$ | $A^{114}$ |
| 9871. | $D^{159}$ | $A^{115}$ |
| 9872. | $D^{159}$ | $A^{116}$ |
| 9873. | $D^{159}$ | $A^{117}$ |
| 9874. | $D^{159}$ | $A^{118}$ |
| 9875. | $D^{159}$ | $A^{119}$ |
| 9876. | $D^{159}$ | $A^{120}$ |
| 9877. | $D^{159}$ | $A^{121}$ |
| 9878. | $D^{159}$ | $A^{122}$ |
| 9879. | $D^{159}$ | $A^{123}$ |
| 9880. | $D^{159}$ | $A^{124}$ |
| 9881. | $D^{159}$ | $A^{125}$ |
| 9882. | $D^{159}$ | $A^{126}$ |
| 9883. | $D^{159}$ | $A^{127}$ |
| 9884. | $D^{159}$ | $A^{128}$ |
| 9885. | $D^{159}$ | $A^{129}$ |

Formula IV

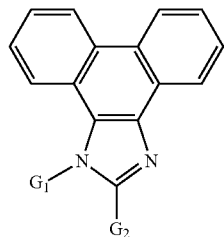

| Compound Number | G¹ | G² |
|---|---|---|
| 9886. | $D^{159}$ | $A^{130}$ |
| 9887. | $D^{159}$ | $A^{131}$ |
| 9888. | $D^{159}$ | $A^{132}$ |
| 9889. | $D^{160}$ | $A^{101}$ |
| 9890. | $D^{160}$ | $A^{102}$ |
| 9891. | $D^{160}$ | $A^{103}$ |
| 9892. | $D^{160}$ | $A^{104}$ |
| 9893. | $D^{160}$ | $A^{105}$ |
| 9894. | $D^{160}$ | $A^{106}$ |
| 9895. | $D^{160}$ | $A^{107}$ |
| 9896. | $D^{160}$ | $A^{108}$ |
| 9897. | $D^{160}$ | $A^{109}$ |
| 9898. | $D^{160}$ | $A^{110}$ |
| 9899. | $D^{160}$ | $A^{111}$ |
| 9900. | $D^{160}$ | $A^{112}$ |
| 9901. | $D^{160}$ | $A^{113}$ |
| 9902. | $D^{160}$ | $A^{114}$ |
| 9903. | $D^{160}$ | $A^{115}$ |
| 9904. | $D^{160}$ | $A^{116}$ |
| 9905. | $D^{160}$ | $A^{117}$ |
| 9906. | $D^{160}$ | $A^{118}$ |
| 9907. | $D^{160}$ | $A^{119}$ |
| 9908. | $D^{160}$ | $A^{120}$ |
| 9909. | $D^{160}$ | $A^{121}$ |
| 9910. | $D^{160}$ | $A^{122}$ |
| 9911. | $D^{160}$ | $A^{123}$ |
| 9912. | $D^{160}$ | $A^{124}$ |
| 9913. | $D^{160}$ | $A^{125}$ |
| 9914. | $D^{160}$ | $A^{126}$ |
| 9915. | $D^{160}$ | $A^{127}$ |
| 9916. | $D^{160}$ | $A^{128}$ |
| 9917. | $D^{160}$ | $A^{129}$ |
| 9918. | $D^{160}$ | $A^{130}$ |
| 9919. | $D^{160}$ | $A^{131}$ |
| 9920. | $D^{160}$ | $A^{132}$ |
| 9921. | $D^{161}$ | $A^{101}$ |
| 9922. | $D^{161}$ | $A^{102}$ |
| 9923. | $D^{161}$ | $A^{103}$ |
| 9924. | $D^{161}$ | $A^{104}$ |
| 9925. | $D^{161}$ | $A^{105}$ |
| 9926. | $D^{161}$ | $A^{106}$ |
| 9927. | $D^{161}$ | $A^{107}$ |
| 9928. | $D^{161}$ | $A^{108}$ |
| 9929. | $D^{161}$ | $A^{109}$ |
| 9930. | $D^{161}$ | $A^{110}$ |
| 9931. | $D^{161}$ | $A^{111}$ |
| 9932. | $D^{161}$ | $A^{112}$ |
| 9933. | $D^{161}$ | $A^{113}$ |
| 9934. | $D^{161}$ | $A^{114}$ |
| 9935. | $D^{161}$ | $A^{115}$ |
| 9936. | $D^{161}$ | $A^{116}$ |
| 9937. | $D^{161}$ | $A^{117}$ |
| 9938. | $D^{161}$ | $A^{118}$ |
| 9939. | $D^{161}$ | $A^{119}$ |
| 9940. | $D^{161}$ | $A^{120}$ |
| 9941. | $D^{161}$ | $A^{121}$ |
| 9942. | $D^{161}$ | $A^{122}$ |
| 9943. | $D^{161}$ | $A^{123}$ |
| 9944. | $D^{161}$ | $A^{124}$ |
| 9945. | $D^{161}$ | $A^{125}$ |
| 9946. | $D^{161}$ | $A^{126}$ |
| 9947. | $D^{161}$ | $A^{127}$ |
| 9948. | $D^{161}$ | $A^{128}$ |

Formula IV

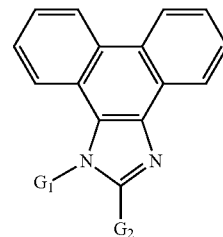

| Compound Number | G¹ | G² |
|---|---|---|
| 9949. | $D^{161}$ | $A^{129}$ |
| 9950. | $D^{161}$ | $A^{130}$ |
| 9951. | $D^{161}$ | $A^{131}$ |
| 9952. | $D^{161}$ | $A^{132}$ |
| 9953. | $D^{162}$ | $A^{101}$ |
| 9954. | $D^{162}$ | $A^{102}$ |
| 9955. | $D^{162}$ | $A^{103}$ |
| 9956. | $D^{162}$ | $A^{104}$ |
| 9957. | $D^{162}$ | $A^{105}$ |
| 9958. | $D^{162}$ | $A^{106}$ |
| 9959. | $D^{162}$ | $A^{107}$ |
| 9960. | $D^{162}$ | $A^{108}$ |
| 9961. | $D^{162}$ | $A^{109}$ |
| 9962. | $D^{162}$ | $A^{110}$ |
| 9963. | $D^{162}$ | $A^{111}$ |
| 9964. | $D^{162}$ | $A^{112}$ |
| 9965. | $D^{162}$ | $A^{113}$ |
| 9966. | $D^{162}$ | $A^{114}$ |
| 9967. | $D^{162}$ | $A^{115}$ |
| 9968. | $D^{162}$ | $A^{116}$ |
| 9969. | $D^{162}$ | $A^{117}$ |
| 9970. | $D^{162}$ | $A^{118}$ |
| 9971. | $D^{162}$ | $A^{119}$ |
| 9972. | $D^{162}$ | $A^{120}$ |
| 9973. | $D^{162}$ | $A^{121}$ |
| 9974. | $D^{162}$ | $A^{122}$ |
| 9975. | $D^{162}$ | $A^{123}$ |
| 9976. | $D^{162}$ | $A^{124}$ |
| 9977. | $D^{162}$ | $A^{125}$ |
| 9978. | $D^{162}$ | $A^{126}$ |
| 9979. | $D^{162}$ | $A^{127}$ |
| 9980. | $D^{162}$ | $A^{128}$ |
| 9981. | $D^{162}$ | $A^{129}$ |
| 9982. | $D^{162}$ | $A^{130}$ |
| 9983. | $D^{162}$ | $A^{131}$ |
| 9984. | $D^{162}$ | $A^{132}$ |
| 9985. | $D^{163}$ | $A^{101}$ |
| 9986. | $D^{163}$ | $A^{102}$ |
| 9987. | $D^{163}$ | $A^{103}$ |
| 9988. | $D^{163}$ | $A^{104}$ |
| 9989. | $D^{163}$ | $A^{105}$ |
| 9990. | $D^{163}$ | $A^{106}$ |
| 9991. | $D^{163}$ | $A^{107}$ |
| 9992. | $D^{163}$ | $A^{108}$ |
| 9993. | $D^{163}$ | $A^{109}$ |
| 9994. | $D^{163}$ | $A^{110}$ |
| 9995. | $D^{163}$ | $A^{111}$ |
| 9996. | $D^{163}$ | $A^{112}$ |
| 9997. | $D^{163}$ | $A^{113}$ |
| 9998. | $D^{163}$ | $A^{114}$ |
| 9999. | $D^{163}$ | $A^{115}$ |
| 10000. | $D^{163}$ | $A^{116}$ |
| 10001. | $D^{163}$ | $A^{117}$ |
| 10002. | $D^{163}$ | $A^{118}$ |
| 10003. | $D^{163}$ | $A^{119}$ |
| 10004. | $D^{163}$ | $A^{120}$ |
| 10005. | $D^{163}$ | $A^{121}$ |
| 10006. | $D^{163}$ | $A^{122}$ |
| 10007. | $D^{163}$ | $A^{123}$ |
| 10008. | $D^{163}$ | $A^{124}$ |
| 10009. | $D^{163}$ | $A^{125}$ |
| 10010. | $D^{163}$ | $A^{126}$ |
| 10011. | $D^{163}$ | $A^{127}$ |

237
-continued

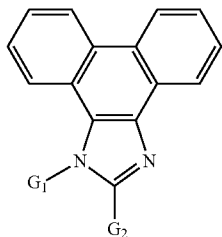

Formula IV

| Compound Number | G¹ | G² |
|---|---|---|
| 10012. | $D^{163}$ | $A^{128}$ |
| 10013. | $D^{163}$ | $A^{129}$ |
| 10014. | $D^{163}$ | $A^{130}$ |
| 10015. | $D^{163}$ | $A^{131}$ |
| 10016. | $D^{163}$ | $A^{132}$ |
| 10017. | $D^{164}$ | $A^{101}$ |
| 10018. | $D^{164}$ | $A^{102}$ |
| 10019. | $D^{164}$ | $A^{103}$ |
| 10020. | $D^{164}$ | $A^{104}$ |
| 10021. | $D^{164}$ | $A^{105}$ |
| 10022. | $D^{164}$ | $A^{106}$ |
| 10023. | $D^{164}$ | $A^{107}$ |
| 10024. | $D^{164}$ | $A^{108}$ |
| 10025. | $D^{164}$ | $A^{109}$ |
| 10026. | $D^{164}$ | $A^{110}$ |
| 10027. | $D^{164}$ | $A^{111}$ |
| 10028. | $D^{164}$ | $A^{112}$ |
| 10029. | $D^{164}$ | $A^{113}$ |
| 10030. | $D^{164}$ | $A^{114}$ |
| 10031. | $D^{164}$ | $A^{115}$ |
| 10032. | $D^{164}$ | $A^{116}$ |
| 10033. | $D^{164}$ | $A^{117}$ |
| 10034. | $D^{164}$ | $A^{118}$ |
| 10035. | $D^{164}$ | $A^{119}$ |
| 10036. | $D^{164}$ | $A^{120}$ |
| 10037. | $D^{164}$ | $A^{121}$ |
| 10038. | $D^{164}$ | $A^{122}$ |
| 10039. | $D^{164}$ | $A^{123}$ |
| 10040. | $D^{164}$ | $A^{124}$ |
| 10041. | $D^{164}$ | $A^{125}$ |
| 10042. | $D^{164}$ | $A^{126}$ |
| 10043. | $D^{164}$ | $A^{127}$ |
| 10044. | $D^{164}$ | $A^{128}$ |
| 10045. | $D^{164}$ | $A^{129}$ |
| 10046. | $D^{164}$ | $A^{130}$ |
| 10047. | $D^{164}$ | $A^{131}$ |
| 10048. | $D^{164}$ | $A^{132}$ |
| 10049. | $D^{165}$ | $A^{101}$ |
| 10050. | $D^{165}$ | $A^{102}$ |
| 10051. | $D^{165}$ | $A^{103}$ |
| 10052. | $D^{165}$ | $A^{104}$ |
| 10053. | $D^{165}$ | $A^{105}$ |
| 10054. | $D^{165}$ | $A^{106}$ |
| 10055. | $D^{165}$ | $A^{107}$ |
| 10056. | $D^{165}$ | $A^{108}$ |
| 10057. | $D^{165}$ | $A^{109}$ |
| 10058. | $D^{165}$ | $A^{110}$ |
| 10059. | $D^{165}$ | $A^{111}$ |
| 10060. | $D^{165}$ | $A^{112}$ |
| 10061. | $D^{165}$ | $A^{113}$ |
| 10062. | $D^{165}$ | $A^{114}$ |
| 10063. | $D^{165}$ | $A^{115}$ |
| 10064. | $D^{165}$ | $A^{116}$ |
| 10065. | $D^{165}$ | $A^{117}$ |
| 10066. | $D^{165}$ | $A^{118}$ |
| 10067. | $D^{165}$ | $A^{119}$ |
| 10068. | $D^{165}$ | $A^{120}$ |
| 10069. | $D^{165}$ | $A^{121}$ |
| 10070. | $D^{165}$ | $A^{122}$ |
| 10071. | $D^{165}$ | $A^{123}$ |
| 10072. | $D^{165}$ | $A^{124}$ |
| 10073. | $D^{165}$ | $A^{125}$ |
| 10074. | $D^{165}$ | $A^{126}$ |

238
-continued

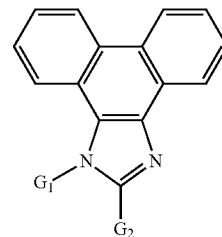

Formula IV

| Compound Number | G¹ | G² |
|---|---|---|
| 10075. | $D^{165}$ | $A^{127}$ |
| 10076. | $D^{165}$ | $A^{128}$ |
| 10077. | $D^{165}$ | $A^{129}$ |
| 10078. | $D^{165}$ | $A^{130}$ |
| 10079. | $D^{165}$ | $A^{131}$ |
| 10080. | $D^{165}$ | $A^{132}$ |
| 10081. | $D^{166}$ | $A^{101}$ |
| 10082. | $D^{166}$ | $A^{102}$ |
| 10083. | $D^{166}$ | $A^{103}$ |
| 10084. | $D^{166}$ | $A^{104}$ |
| 10085. | $D^{166}$ | $A^{105}$ |
| 10086. | $D^{166}$ | $A^{106}$ |
| 10087. | $D^{166}$ | $A^{107}$ |
| 10088. | $D^{166}$ | $A^{108}$ |
| 10089. | $D^{166}$ | $A^{109}$ |
| 10090. | $D^{166}$ | $A^{110}$ |
| 10091. | $D^{166}$ | $A^{111}$ |
| 10092. | $D^{166}$ | $A^{112}$ |
| 10093. | $D^{166}$ | $A^{113}$ |
| 10094. | $D^{166}$ | $A^{114}$ |
| 10095. | $D^{166}$ | $A^{115}$ |
| 10096. | $D^{166}$ | $A^{116}$ |
| 10097. | $D^{166}$ | $A^{117}$ |
| 10098. | $D^{166}$ | $A^{118}$ |
| 10099. | $D^{166}$ | $A^{119}$ |
| 10100. | $D^{166}$ | $A^{120}$ |
| 10101. | $D^{166}$ | $A^{121}$ |
| 10102. | $D^{166}$ | $A^{122}$ |
| 10103. | $D^{166}$ | $A^{123}$ |
| 10104. | $D^{166}$ | $A^{124}$ |
| 10105. | $D^{166}$ | $A^{125}$ |
| 10106. | $D^{166}$ | $A^{126}$ |
| 10107. | $D^{166}$ | $A^{127}$ |
| 10108. | $D^{166}$ | $A^{128}$ |
| 10109. | $D^{166}$ | $A^{129}$ |
| 10110. | $D^{166}$ | $A^{130}$ |
| 10111. | $D^{166}$ | $A^{131}$ |
| 10112. | $D^{166}$ | $A^{132}$ |
| 10113. | $D^{167}$ | $A^{101}$ |
| 10114. | $D^{167}$ | $A^{102}$ |
| 10115. | $D^{167}$ | $A^{103}$ |
| 10116. | $D^{167}$ | $A^{104}$ |
| 10117. | $D^{167}$ | $A^{105}$ |
| 10118. | $D^{167}$ | $A^{106}$ |
| 10119. | $D^{167}$ | $A^{107}$ |
| 10120. | $D^{167}$ | $A^{108}$ |
| 10121. | $D^{167}$ | $A^{109}$ |
| 10122. | $D^{167}$ | $A^{110}$ |
| 10123. | $D^{167}$ | $A^{111}$ |
| 10124. | $D^{167}$ | $A^{112}$ |
| 10125. | $D^{167}$ | $A^{113}$ |
| 10126. | $D^{167}$ | $A^{114}$ |
| 10127. | $D^{167}$ | $A^{115}$ |
| 10128. | $D^{167}$ | $A^{116}$ |
| 10129. | $D^{167}$ | $A^{117}$ |
| 10130. | $D^{167}$ | $A^{118}$ |
| 10131. | $D^{167}$ | $A^{119}$ |
| 10132. | $D^{167}$ | $A^{120}$ |
| 10133. | $D^{167}$ | $A^{121}$ |
| 10134. | $D^{167}$ | $A^{122}$ |
| 10135. | $D^{167}$ | $A^{123}$ |
| 10136. | $D^{167}$ | $A^{124}$ |
| 10137. | $D^{167}$ | $A^{125}$ |

-continued

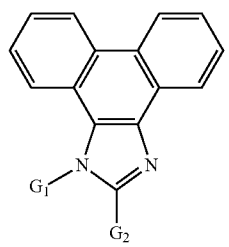

Formula IV

| Compound Number | $G^1$ | $G^2$ |
|---|---|---|
| 10138. | $D^{167}$ | $A^{126}$ |
| 10139. | $D^{167}$ | $A^{127}$ |
| 10140. | $D^{167}$ | $A^{128}$ |
| 10141. | $D^{167}$ | $A^{129}$ |
| 10142. | $D^{167}$ | $A^{130}$ |
| 10143. | $D^{167}$ | $A^{131}$ |
| 10144. | $D^{167}$ | $A^{132}$ |
| 10145. | $D^{168}$ | $A^{101}$ |
| 10146. | $D^{168}$ | $A^{102}$ |
| 10147. | $D^{168}$ | $A^{103}$ |
| 10148. | $D^{168}$ | $A^{104}$ |
| 10149. | $D^{168}$ | $A^{105}$ |
| 10150. | $D^{168}$ | $A^{106}$ |
| 10151. | $D^{168}$ | $A^{107}$ |
| 10152. | $D^{168}$ | $A^{108}$ |
| 10153. | $D^{168}$ | $A^{109}$ |
| 10154. | $D^{168}$ | $A^{110}$ |
| 10155. | $D^{168}$ | $A^{111}$ |
| 10156. | $D^{168}$ | $A^{112}$ |
| 10157. | $D^{168}$ | $A^{113}$ |
| 10158. | $D^{168}$ | $A^{114}$ |
| 10159. | $D^{168}$ | $A^{115}$ |
| 10160. | $D^{168}$ | $A^{116}$ |
| 10161. | $D^{168}$ | $A^{117}$ |
| 10162. | $D^{168}$ | $A^{118}$ |
| 10163. | $D^{168}$ | $A^{119}$ |
| 10164. | $D^{168}$ | $A^{120}$ |
| 10165. | $D^{168}$ | $A^{121}$ |
| 10166. | $D^{168}$ | $A^{122}$ |
| 10167. | $D^{168}$ | $A^{123}$ |
| 10168. | $D^{168}$ | $A^{124}$ |
| 10169. | $D^{168}$ | $A^{125}$ |
| 10170. | $D^{168}$ | $A^{126}$ |
| 10171. | $D^{168}$ | $A^{127}$ |
| 10172. | $D^{168}$ | $A^{128}$ |
| 10173. | $D^{168}$ | $A^{129}$ |
| 10174. | $D^{168}$ | $A^{130}$ |
| 10175. | $D^{168}$ | $A^{131}$ |
| 10176. | $D^{168}$ | $A^{132}$ |

In one embodiment, a first device is provided. The first device comprises a first organic light emitting device, further comprising an anode, a cathode; and an organic layer, disposed between the anode and the cathode, where the organic layer comprises a compound having the formula: a compound of formula

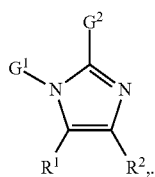

Formula I $G^1$ is an electron donor group or an electron acceptor group, and $G^2$ is also an electron donor group or an electron acceptor group. If $G^1$ is an electron donor group, then $G^2$ is an electron acceptor group, and if $G^1$ is an electron acceptor group, then $G^2$ is an electron donor group.

$R^1$ and $R^2$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R^1$ and $R^2$ are optionally joined to form a ring, which may be further substituted.

In one embodiment, the organic layer is an emissive layer.

In one embodiment, the electron acceptor group comprises at least one chemical group selected from the group consisting of a six-membered aromatic ring system having at least two nitrogen atoms and a 5-membered aromatic ring system containing at least one nitrogen atom, one oxygen atom, one sulfur atom, or one selenium atom.

In one embodiment, the first device emits a luminescent radiation at room temperature when a voltage is applied across the first organic light emitting device, wherein the luminescent radiation comprises a delayed fluorescence process.

In one embodiment, the emissive layer further comprises a first phosphorescent emitting material.

In one embodiment, the emissive layer further comprises a second phosphorescent emitting material.

In one embodiment, the emissive layer further comprises a host material.

In one embodiment, the compound is a host.

In one embodiment, the compound is an emissive dopant.

In one embodiment, the first device emits a white light at room temperature when a voltage is applied across the organic light emitting device.

In one embodiment, the compound emits a blue light having a peak wavelength between about 400 nm to about 500 nm.

In one embodiment, the compound emits a yellow light having a peak wavelength between about 530 nm to about 580 nm.

In one embodiment, the first device comprises a second organic light-emitting device, wherein the second organic light emitting device is stacked on the first organic light emitting device.

In one embodiment, the first device is a consumer product.

In one embodiment, the first device is an organic light-emitting device.

In one embodiment, the first device comprises a lighting panel.

In one embodiment, a method of making a first organic light emitting device is provided. The method comprises: depositing an anode on a substrate, depositing at least one organic layer comprising a compound of formula:

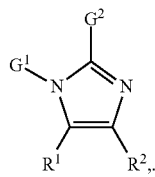

Formula I $G^1$ is an electron donor group or an electron acceptor group, and $G^2$ is also an electron donor group or an electron acceptor group. If $G^1$ is an electron donor group, then $G^2$ is an electron acceptor group, and if G¹ is an electron acceptor group, then G² is an electron donor group R¹ and R² are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. R¹ and R² are optionally joined to form a ring, which may be further substituted, and depositing a cathode, wherein the emissive layer is deposited between the anode and cathode.

In one embodiment, the at least one organic layer is deposited using a solution process.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as MoO$_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

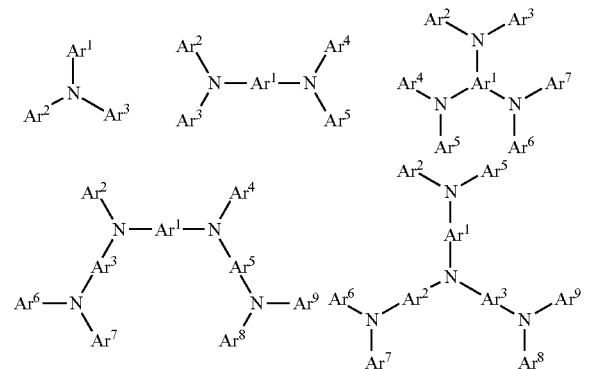

Each of Ar¹ to Ar⁹ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, Ar¹ to Ar⁹ is independently selected from the group consisting of:

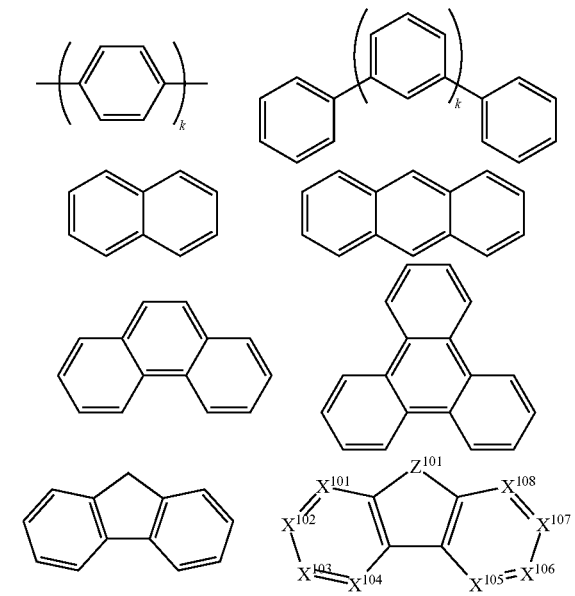

k is an integer from 1 to 20; X¹⁰¹ to X¹⁰⁸ is C (including CH) or N; Z¹⁰¹ is NAr¹, O, or S; Ar¹ has the same group defined above.

Examples of metal complexes used in HIL or HTL include, but not limit to the following general formula:

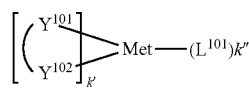

Met is a metal; (Y¹⁰¹-Y¹⁰²) is a bidentate ligand, Y¹⁰¹ and Y¹⁰² are independently selected from C, N, O, P, and S; L¹⁰¹ is another ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative.

In another aspect, $(Y^{101}\text{-}Y^{102})$ is a carbene ligand.

In another aspect, Met is selected from Ir, Pt, Os, and Zn.

In a further aspect, the metal complex has a smallest oxidation potential in solution vs. Fc$^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

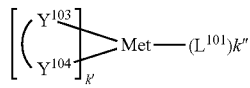

Met is a metal; $(Y^{103}\text{-}Y^{104})$ is a bidentate ligand, $Y^{103}$ and $Y^{104}$ are independently selected from C, N, O, P, and S; $L^{101}$ is another ligand; k' is an integer value from 1 to the maximum number of ligands that may be attached to the metal; and k'+k" is the maximum number of ligands that may be attached to the metal.

In one aspect, the metal complexes are:

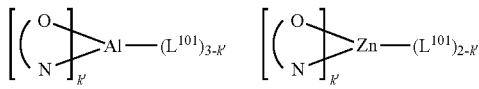

(O—N) is a bidentate ligand, having metal coordinated to atoms O and N.

In another aspect, Met is selected from Ir and Pt.

In a further aspect, $(Y^{103}\text{-}Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

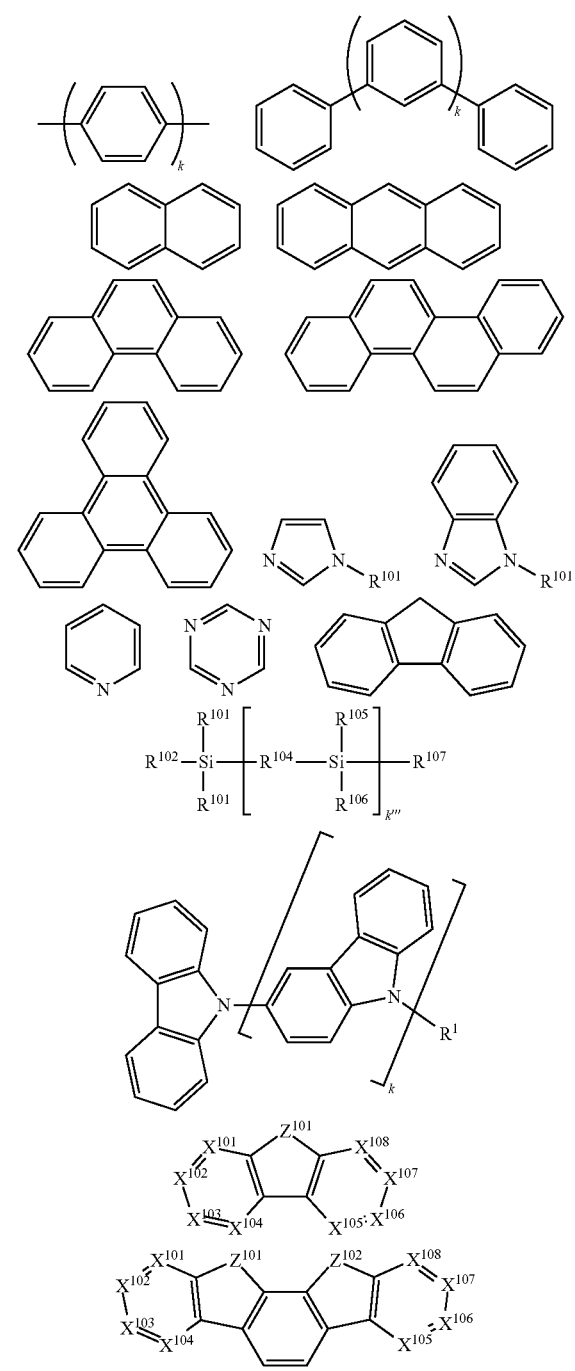

-continued

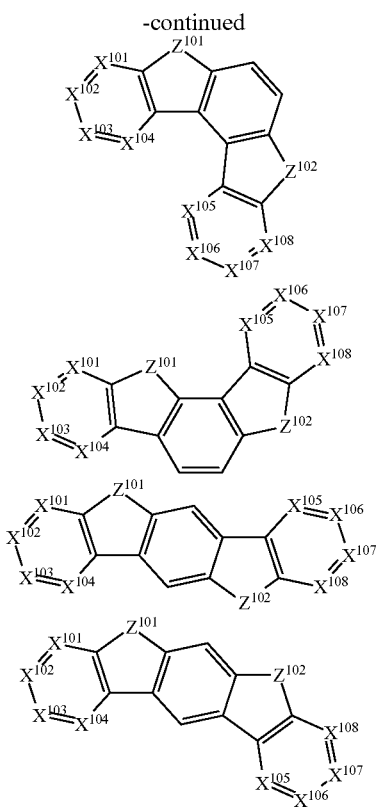

R$^{101}$ to R$^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 1 to 20; k''' is an integer from 0 to 20.

X$^{101}$ to X$^{108}$ is selected from C (including CH) or N.

Z$^{101}$ and Z$^{102}$ is selected from NR$^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

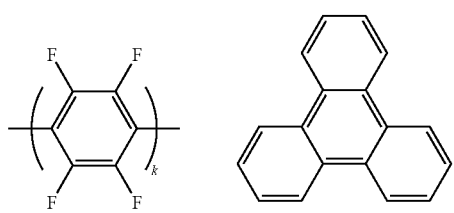

-continued

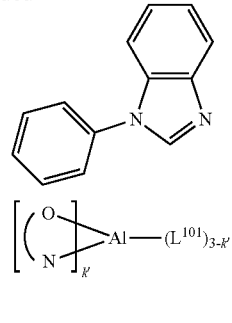

k is an integer from 1 to 20; L$^{101}$ is another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

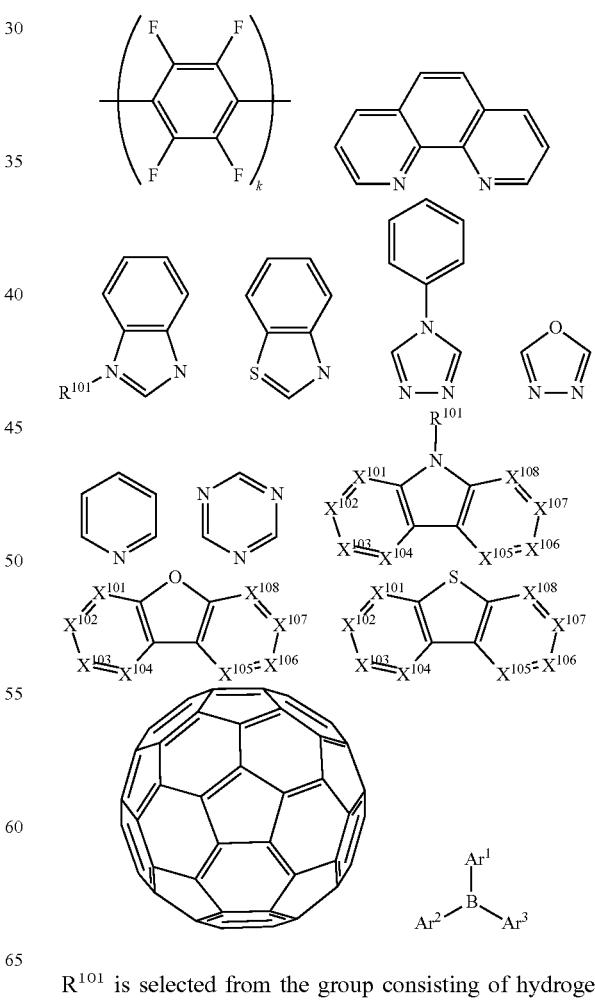

R$^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 1 to 20.

$X^{101}$ to $X^{108}$ is selected from C (including CH) or N.

In another aspect, the metal complexes used in ETL contains, but not limit to the following general formula:

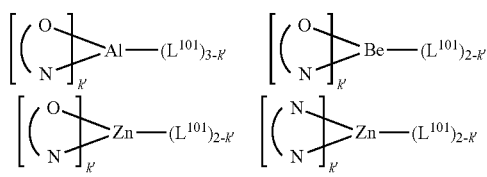

(O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exciton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phthalocyanine and porphryin compounds | 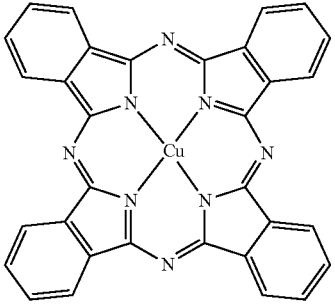 | Appl. Phys. Lett. 69, 2160 (1996) |
| Starburst triarylamines | 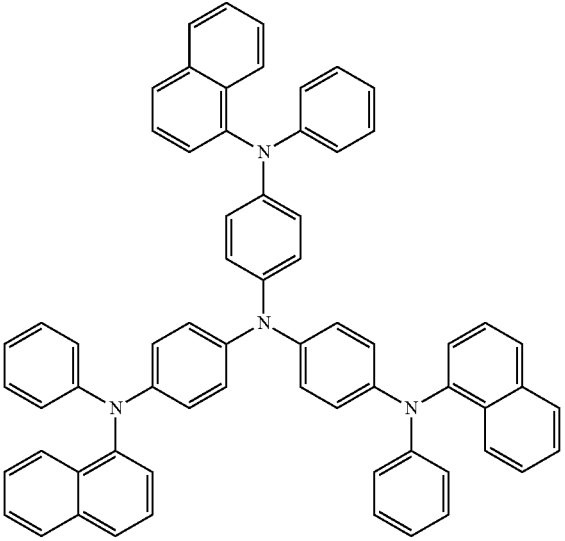 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-\!\!\left[CH_xF_y\right]_n\!\!-$ | Appl. Phys. Lett. 78, 673 (2001) |

TABLE 1-continued
| MATERIAL | EXAMPLES OF MATERIAL | PUBLICATIONS |
|---|---|---|
| Conducting polymers (e.g., PEDOT:PSS, polyaniline, polypthiophene) | 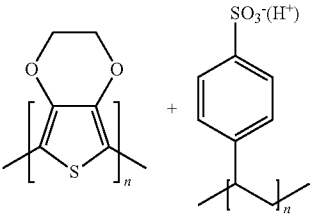 | Synth. Met. 87, 171 (1997) WO2007002683 |
| Phosphonic acid and sliane SAMs | 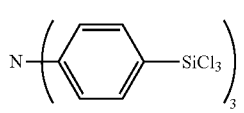 | US20030162053 |
| Triarylamine or polythiophene polymers with conductivity dopants | 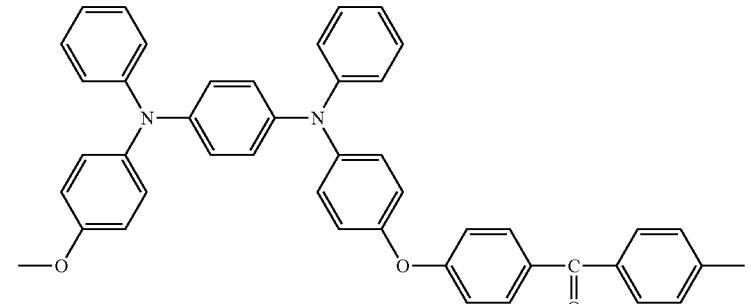 and 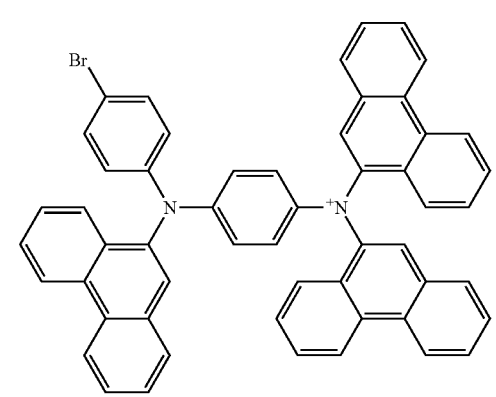 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 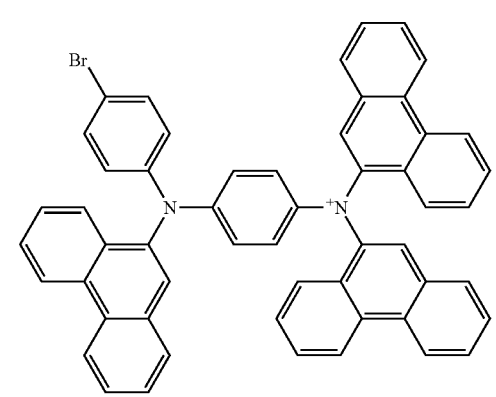 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 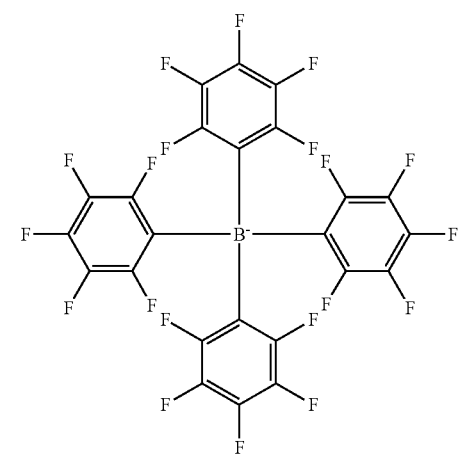 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |

TABLE 1-continued
| MATERIAL | EXAMPLES OF MATERIAL | PUBLICATIONS |
|---|---|---|
| Organic compounds with conductive inorganic compounds, such as molybdenum and tungsten oxides | 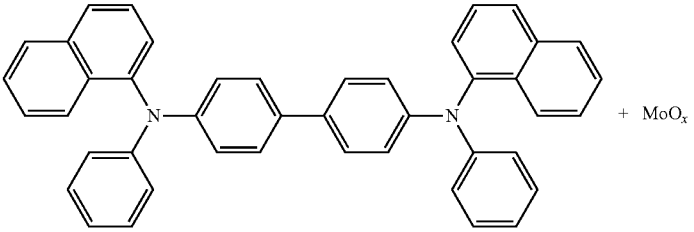 [SMILES: c1ccc(N(c2ccc(-c3ccc(N(c4ccccc4)c4cccc5ccccc45)cc3)cc2)c2cccc3ccccc23)cc1] + MoO$_x$ | US20050123751 SID Symposium Digest, 37, 923 (2006) WO2009018009 |
| n-type semiconducting organic complexes | 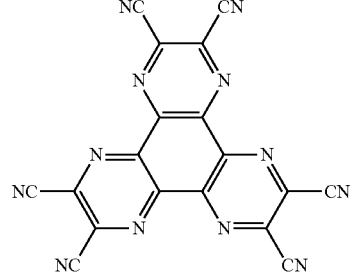 [SMILES: N#Cc1nc2c3nc(C#N)c(C#N)nc3c3nc(C#N)c(C#N)nc3c2nc1C#N] | US20020158242 |
| Metal organometallic complexes | 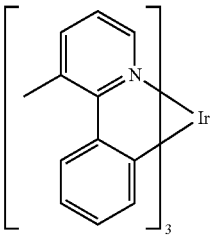 | US20060240279 |
| Cross-linkable compounds | 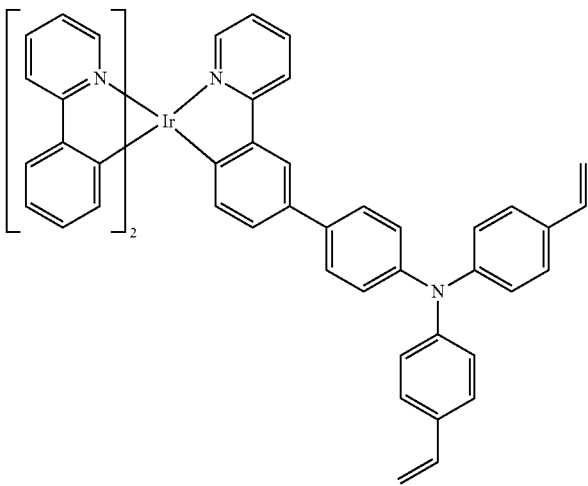 | US20080220265 |

TABLE 1-continued

| MATERIAL | EXAMPLES OF MATERIAL | PUBLICATIONS |
|---|---|---|
| Polythiophene based polymers and copolymers | | WO 2011075644 EP2350216 |

Hole transporting materials

| | | |
|---|---|---|
| Triarylamines e.g., TPD, α-NPD) | | Appl. Phys. Lett. 51, 913 (1987) |
| | | U.S. Pat. No. 5,061,569 |
| | | EP650955 |

TABLE 1-continued
| MATERIAL | EXAMPLES OF MATERIAL | PUBLICATIONS |
|---|---|---|
| | 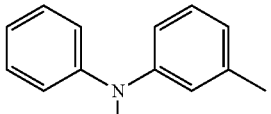 | J. Mater. Chem. 3, 319 (1993) |
| | 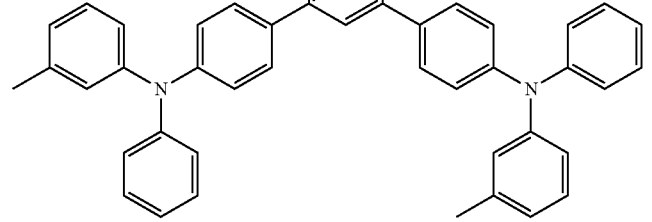 | Appl. Phys. Lett. 90, 183503 (2007) |
| | 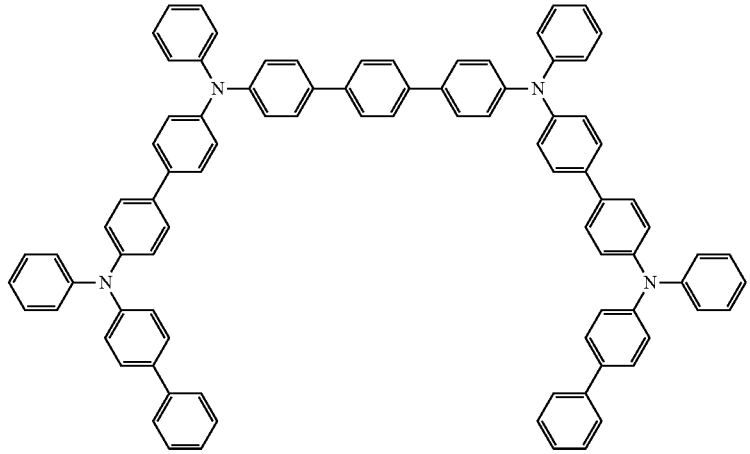 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 1-continued

| MATERIAL | EXAMPLES OF MATERIAL | PUBLICATIONS |
| --- | --- | --- |
| Triaylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 US20110163302 |
| Indolocarbazoles | | Synth. Met. 111, 421 (2000) |

TABLE 1-continued

| MATERIAL | EXAMPLES OF MATERIAL | PUBLICATIONS |
|---|---|---|
| Isoindole compounds | | Chem. Mater. 15, 3148 (2003) |
| Metal carbene complexes | | US20080018221 |

Phosphorescent OLED host materials
Red hosts

| | | |
|---|---|---|
| Arylcarbazoles | | Appl. Phys. Lett. 78, 1622 (2001) |
| Metal 8-hydroxy-quinolates (e.g., Alq$_3$, BAlq) | | Nature 395, 151 (1998) |
| | | US20060202194 |

TABLE 1-continued
| MATERIAL | EXAMPLES OF MATERIAL | PUBLICATIONS |
|---|---|---|
| | 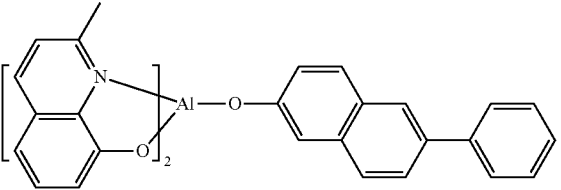 | WO2005014551 |
| | 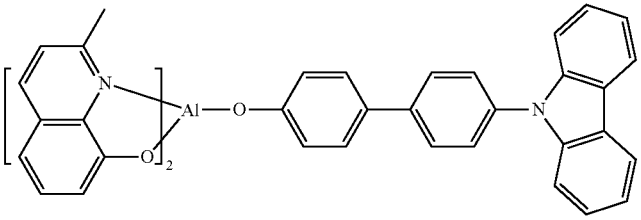 | WO2006072002 |
| Metal phenoxy-benzothiazole compounds | 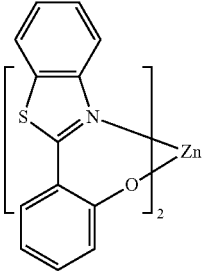 | Appl. Phys. Lett. 90, 123509 (2007) |
| Conjugated oligomers and polymers (e.g., polyfluorene) | 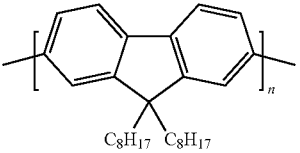 | Org. Electron. 1, 15 (2000) |
| Aromatic fused rings | 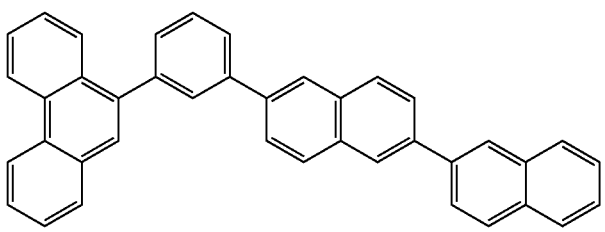 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 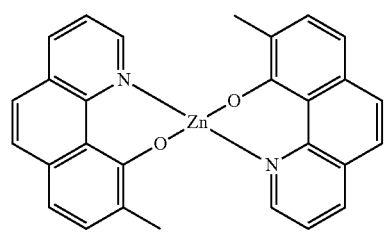 | WO2010056066 |

TABLE 1-continued
| MATERIAL | EXAMPLES OF MATERIAL | PUBLICATIONS |
|---|---|---|
| Chrysene based compounds | 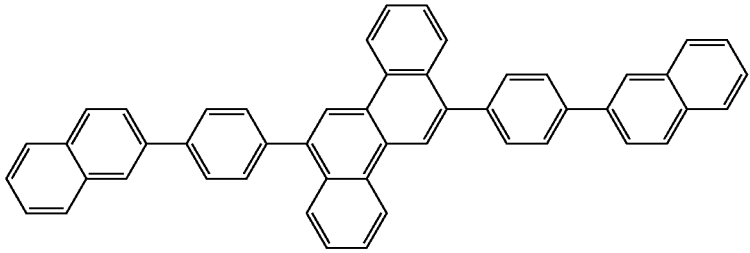 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
| Green hosts | | |
| Arylcarbazoles | 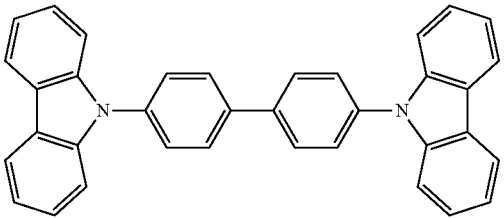 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 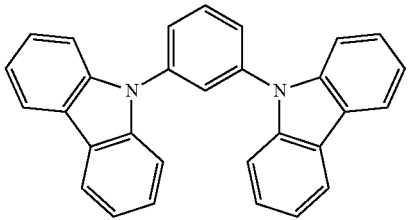 [SMILES: c1cc(-n2c3ccccc3c3ccccc32)cc(-n2c3ccccc3c3ccccc32)c1] | US20030175553 |
| | 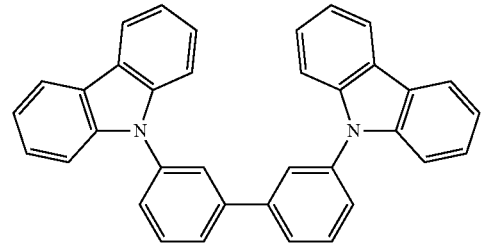 [SMILES: c1cc(-c2cccc(-n3c4ccccc4c4ccccc43)c2)cc(-n2c3ccccc3c3ccccc32)c1] | WO2001039234 |
| Aryltriphenylene compounds | 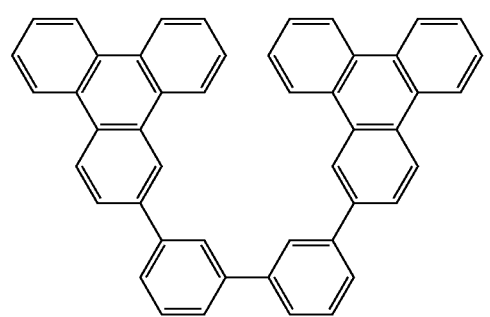 [SMILES: c1cc(-c2cccc(-c3ccc4c5ccccc5c5ccccc5c4c3)c2)cc(-c2ccc3c4ccccc4c4ccccc4c3c2)c1] | US20060280965 |

TABLE 1-continued
| MATERIAL | EXAMPLES OF MATERIAL | PUBLICATIONS |
|---|---|---|
| | 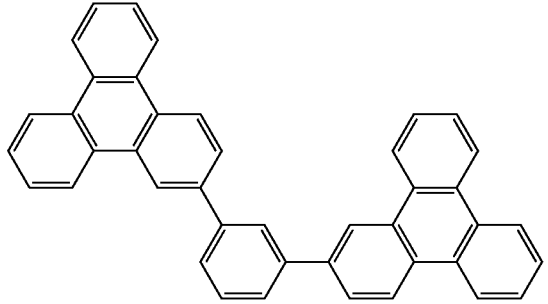 [SMILES: c1cc(-c2ccc3c4ccccc4c4ccccc4c3c2)cc(-c2ccc3c4ccccc4c4ccccc4c3c2)c1] | US20060280965 |
| | 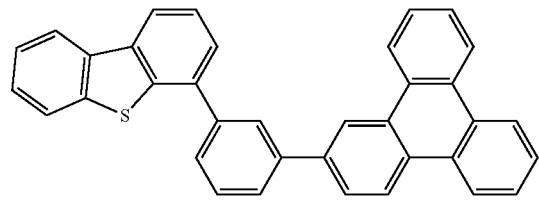 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 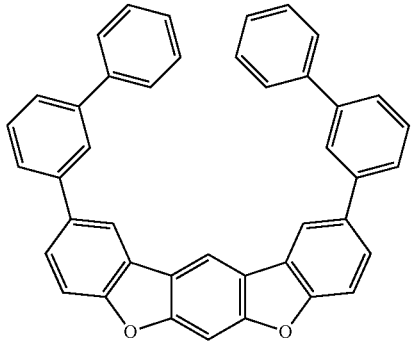 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 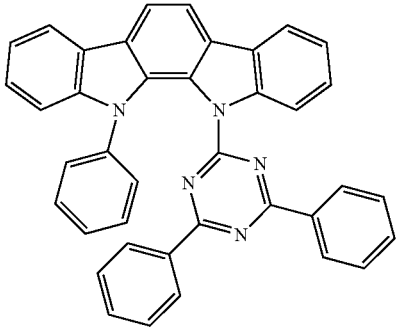 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 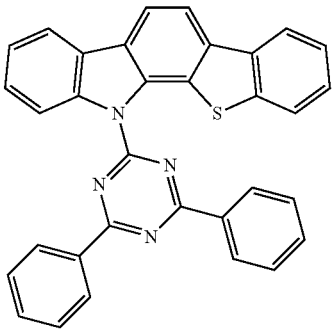 [SMILES: c1ccc(-c2nc(-c3ccccc3)nc(-n3c4ccccc4c4ccc5c6ccccc6sc5c43)n2)cc1] | WO2010107244 |

TABLE 1-continued
| MATERIAL | EXAMPLES OF MATERIAL | PUBLICATIONS |
|---|---|---|
| Aza-carbazole/ DBT/DBF | 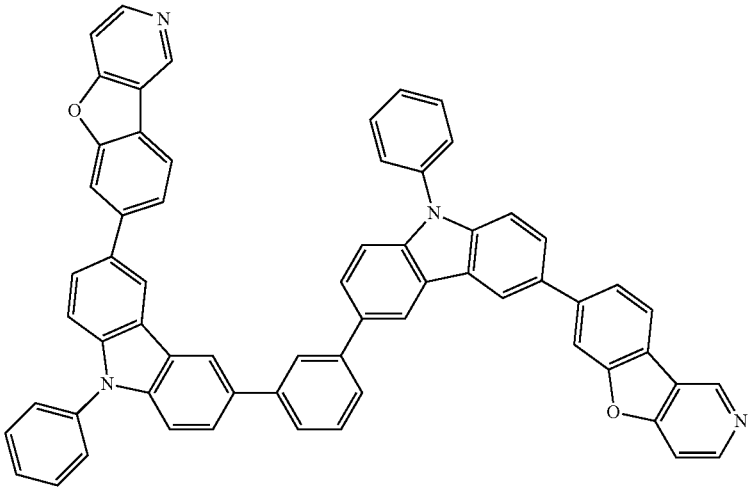 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 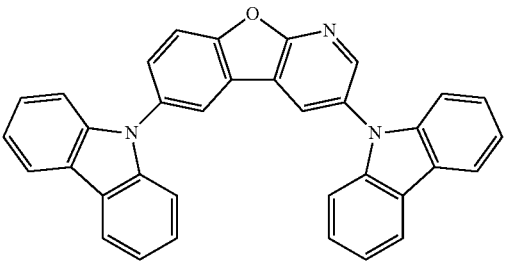 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 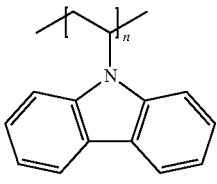 | Appl. Phys. Lett. 77, 2280 (2000) |
| Spirofluorene compounds | 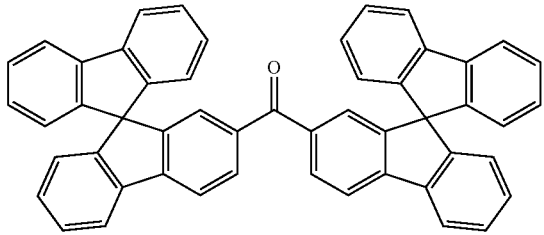 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 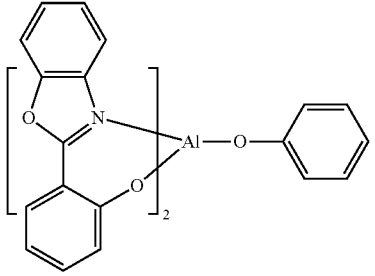 | WO2005089025 |

TABLE 1-continued
| MATERIAL | EXAMPLES OF MATERIAL | PUBLICATIONS |
|---|---|---|
| | 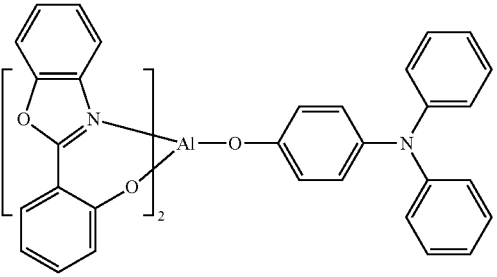 | WO2006132173 |
| | 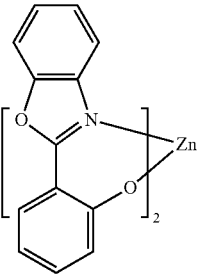 | JP200511610 |
| Spirofluorene-carbazole compounds | 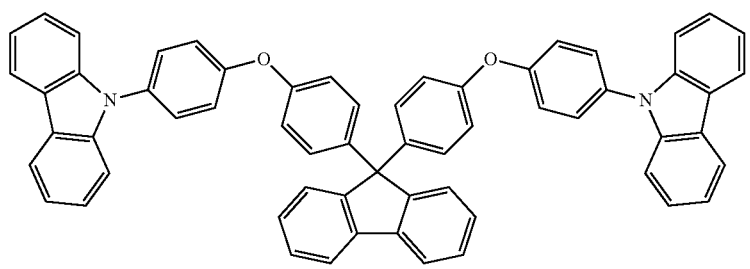 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
| | 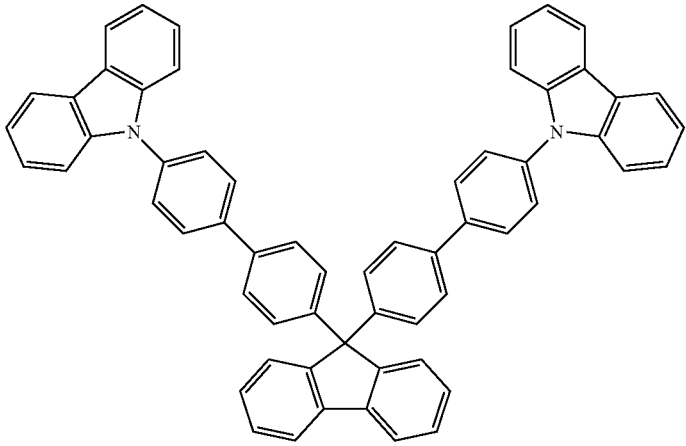 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 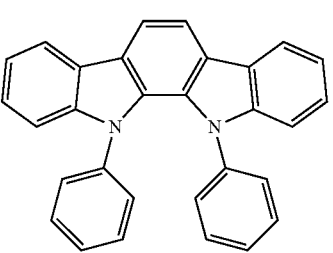 [SMILES: c1ccc(-n2c3ccccc3c3ccc4c5ccccc5n(-c5ccccc5)c4c32)cc1] | WO2007063796 |

TABLE 1-continued

| MATERIAL | EXAMPLES OF MATERIAL | PUBLICATIONS |
|---|---|---|
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |
| Metal phenoxy-pyridine compounds | | WO2005030900 |

TABLE 1-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |

Blue hosts

| | | |
|---|---|---|
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

TABLE 1-continued
| MATERIAL | EXAMPLES OF MATERIAL | PUBLICATIONS |
|---|---|---|
| | 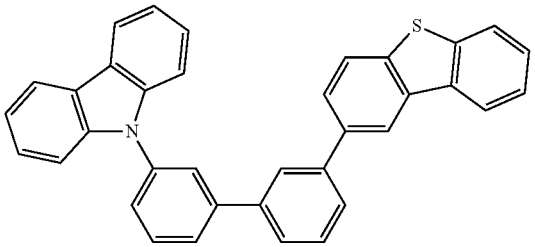 [SMILES: c1cc(-c2cccc(-n3c4ccccc4c4ccccc43)c2)cc(-c2ccc3sc4ccccc4c3c2)c1] | US20090030202, US20090017330 |
| | 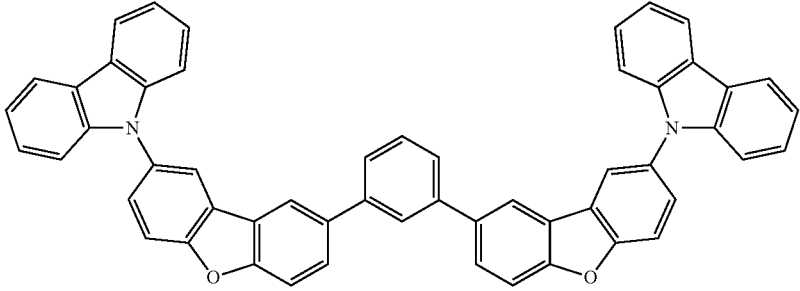 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 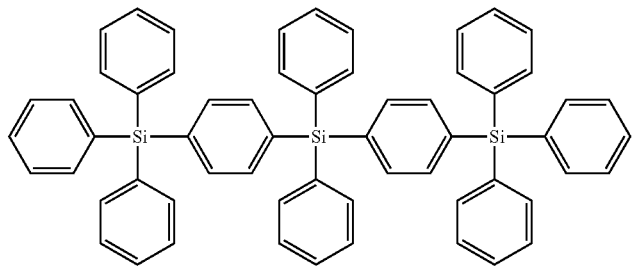 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 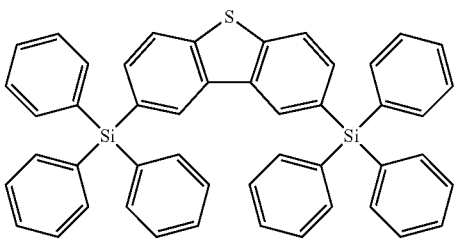 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 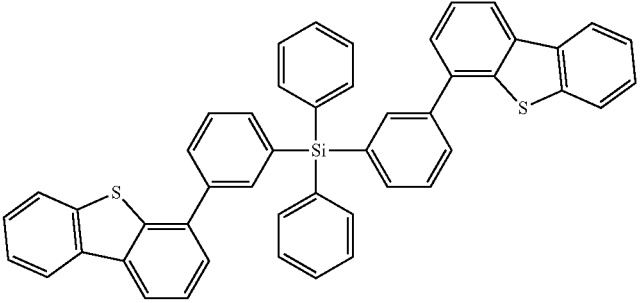 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 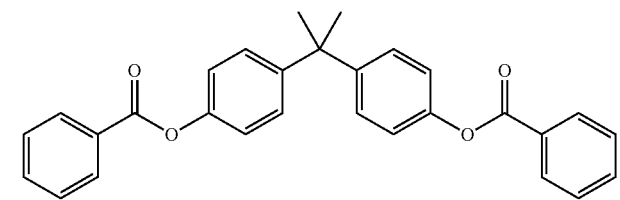 [SMILES: CC(C)(c1ccc(OC(=O)c2ccccc2)cc1)c1ccc(OC(=O)c2ccccc2)cc1] | WO2006100298 |

TABLE 1-continued

| MATERIAL | EXAMPLES OF MATERIAL | PUBLICATIONS |
|---|---|---|
| Carbazole linked by non-conjugated groups | | US20040115476 |
| Aza-carbazoles | | US20060121308 |
| High triplet metal organometallic complex | | U.S. Pat. No. 7,154,114 |

Phosphorescent dopants
Red dopants

| | | |
|---|---|---|
| Heavy metal porphyrins (e.g., PtOEP) | | Nature 395, 151 (1998) |
| Iridium (III) organometallic complexes | | Appl. Phys. Lett. 78, 1622 (2001) |

TABLE 1-continued
| MATERIAL | EXAMPLES OF MATERIAL | PUBLICATIONS |
|---|---|---|
|  | 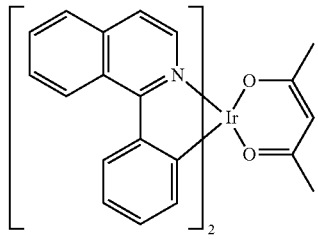 | US2006835469 |
|  | 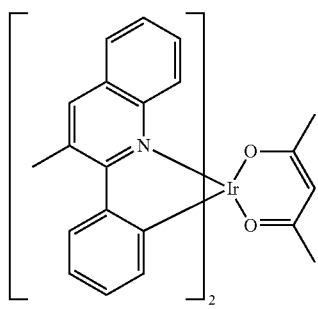 | US2006835469 |
|  | 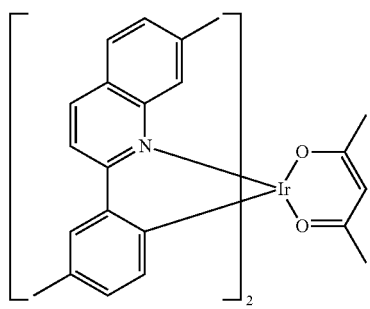 | US20060202194 |
|  | 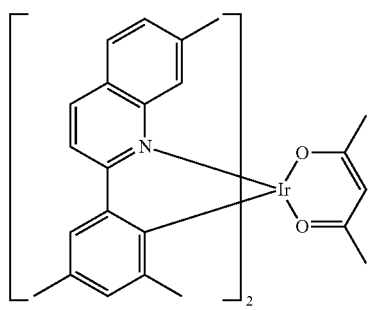 | US20060202194 |
|  | 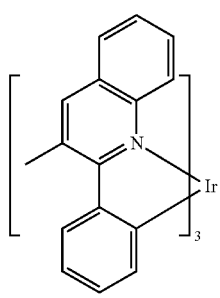 | US20070087321 |

TABLE 1-continued
| MATERIAL | EXAMPLES OF MATERIAL | PUBLICATIONS |
|---|---|---|
| | 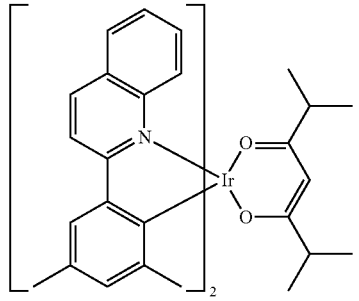 | US20080261076 US20100090591 |
| | 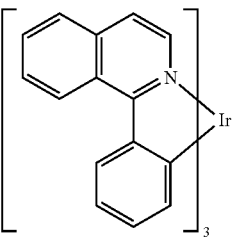 | US20070087321 |
| | 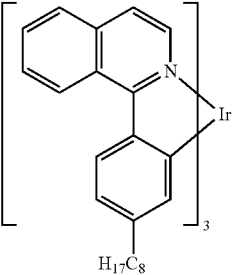 | Adv. Mater. 19, 739 (2007) |
| | 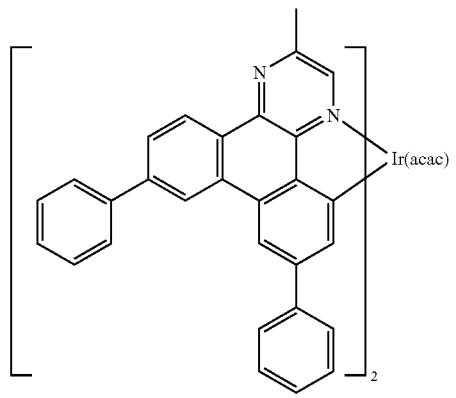 | WO2009100991 |
| | 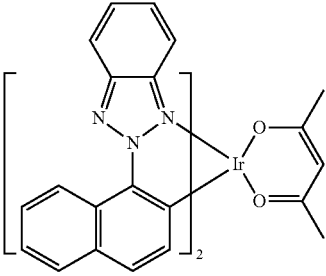 | WO2008101842 |

TABLE 1-continued
| MATERIAL | EXAMPLES OF MATERIAL | PUBLICATIONS |
|---|---|---|
| | 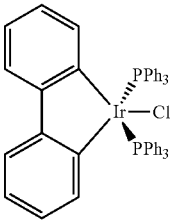 | U.S. Pat. No. 7,232,618 |
| Platinum (II) organometallic complexes | 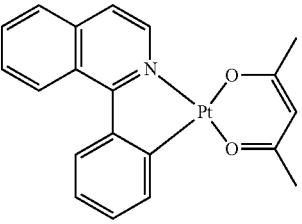 | WO2003040257 |
| | 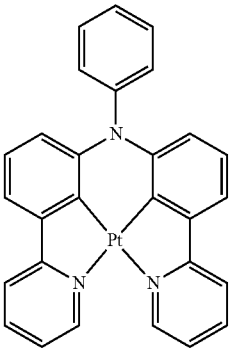 | US20070103060 |
| Osminum (III) complexes | 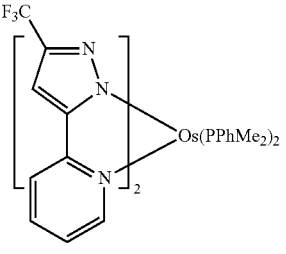 | Chem. Mater. 17, 3532 (2005) |
| Ruthenium (II) complexes | 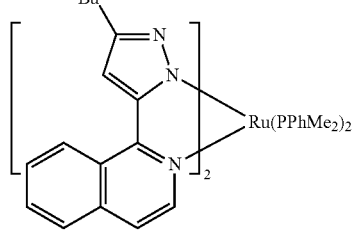 | Adv. Mater. 17, 1059 (2005) |
| Rhenium (I), (II), and (III) complexes | 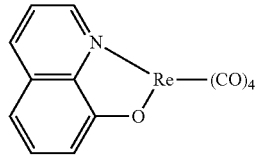 | US20050244673 |

TABLE 1-continued
| MATERIAL | EXAMPLES OF MATERIAL | PUBLICATIONS |
|---|---|---|
| | Green dopants | |
| Iridium (III) organometallic complexes | 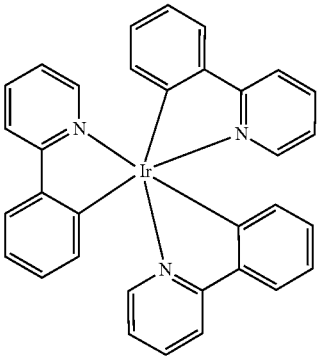<br>and its derivatives | Inorg. Chem. 40, 1704 (2001) |
| | 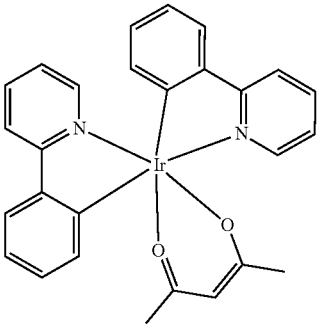 | US20020034656 |
| | 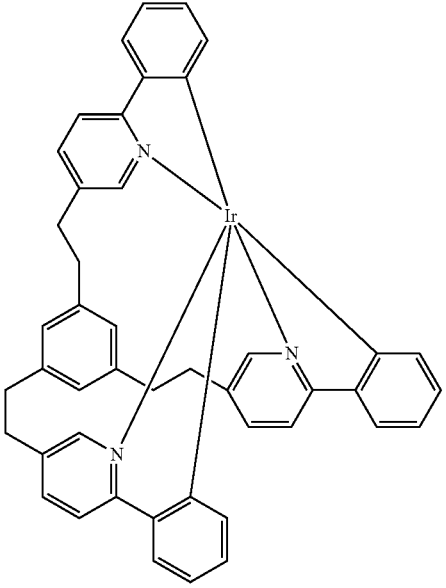 | U.S. Pat. No. 7,332,232 |

TABLE 1-continued

| MATERIAL | EXAMPLES OF MATERIAL | PUBLICATIONS |
|---|---|---|
| | | US20090108737 |
| | | WO2010028151 |
| | | EP1841834B |
| | | US20060127696 |
| | | US20090039776 |

TABLE 1-continued

| MATERIAL | EXAMPLES OF MATERIAL | PUBLICATIONS |
|---|---|---|
| | | U.S. Pat. No. 6,921,915 |
| | | US20100244004 |
| | | U.S. Pat. No. 6,687,266 |
| | | Chem. Mater. 16, 2480 (2004) |
| | | US20070190359 |

| MATERIAL | EXAMPLES OF MATERIAL | PUBLICATIONS |
|---|---|---|
| | 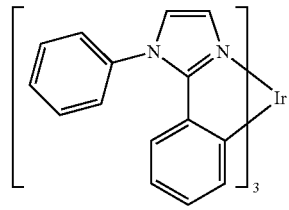 | US20060008670 JP2007123392 |
| | 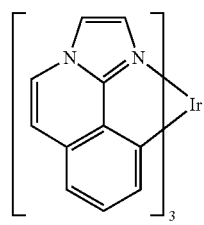 | WO2010086089, WO2011044988 |
| | 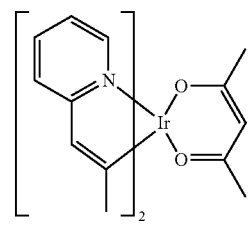 | Adv. Mater. 16, 2003 (2004) |
| | 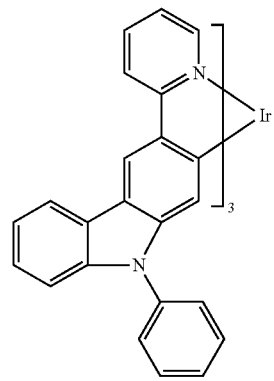 | Angew. Chem. Int. Ed. 2006, 45, 7800 |
| | 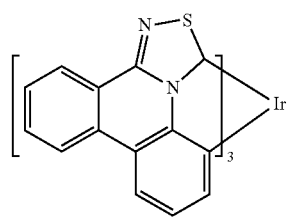 | WO2009050290 |
| | 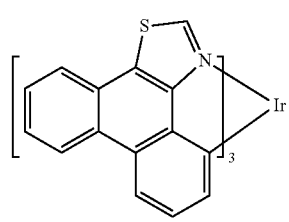 | US20090165846 |

| MATERIAL | EXAMPLES OF MATERIAL | PUBLI-CATIONS |
|---|---|---|
| | 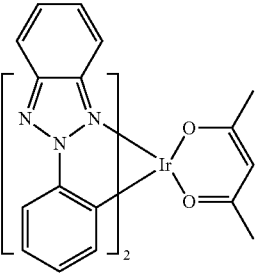 | US20080015355 |
| | 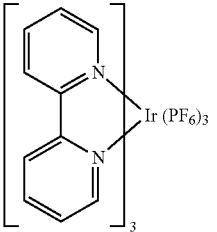 | US20010015432 |
| | 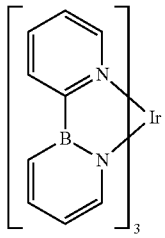 | US20100295032 |
| Monomer for polymeric metal organometallic compounds | 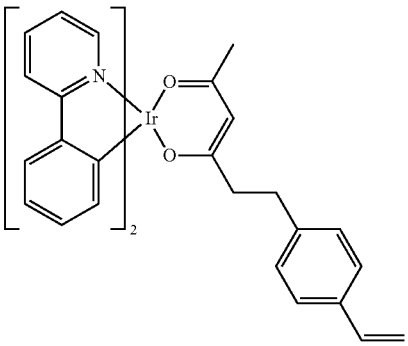 | U.S. Pat. No. 7,250,226, U.S. Pat. No. 7,396,598 |
| Pt (II) organometallic complexes, including polydentated ligands | 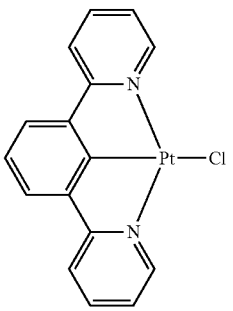 | Appl. Phys. Lett. 86, 153505 (2005) |

TABLE 1-continued
| MATERIAL | EXAMPLES OF MATERIAL | PUBLICATIONS |
|---|---|---|
| | 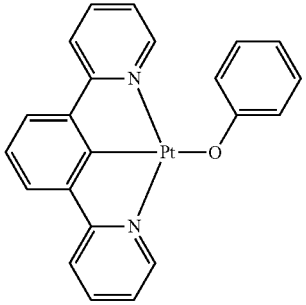 | Appl. Phys. Lett. 86, 153505 (2005) |
| | 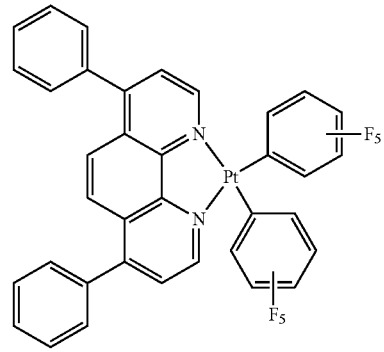 | Chem. Lett. 34, 592 (2005) |
| | 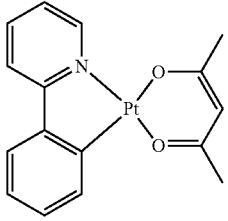 | WO2002015645 |
| | 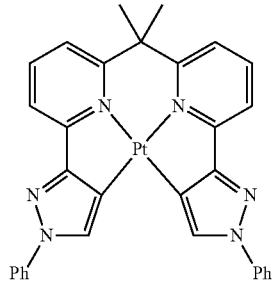 | US20060263635 |
| | 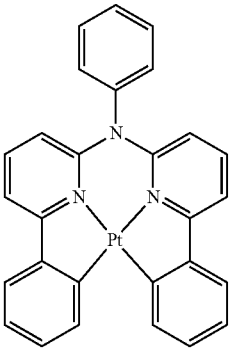 | US20060182992<br>US20070103060 |

TABLE 1-continued
| MATERIAL | EXAMPLES OF MATERIAL | PUBLICATIONS |
|---|---|---|
| Cu complexes | 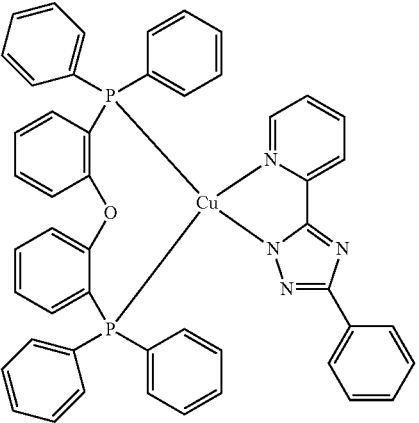 | WO2009000673 |
| | 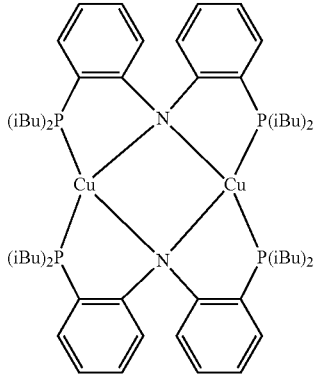 | US20070111026 |
| Gold complexes | 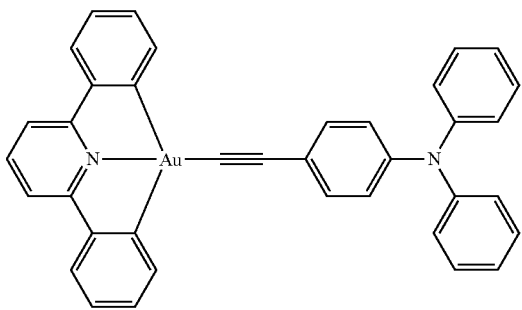 | Chem. Commun. 2906 (2005) |
| Rhenium (III) complexes | 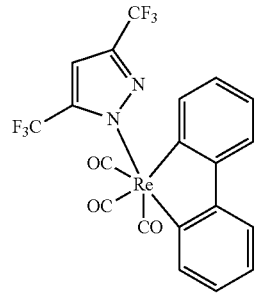 | Inorg. Chem. 42, 1248 (2003) |

TABLE 1-continued

| MATERIAL | EXAMPLES OF MATERIAL | PUBLICATIONS |
|---|---|---|
| Osmium (II) complexes | | U.S. Pat. No. 7,279,704 |
| Deuterated organometallic complexes | | US20030138657 |
| Organometallic complexes with two or more metal centers | | US20030152802 |
| | | U.S. Pat. No. 7,090,928 |

TABLE 1-continued
| MATERIAL | EXAMPLES OF MATERIAL | PUBLICATIONS |
|---|---|---|
| Blue dopants | | |
| Iridium (III) organometallic complexes | 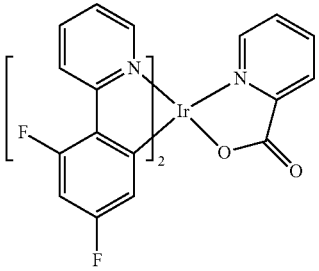 | WO2002002714 |
| | 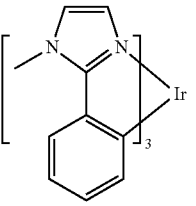 | WO2006009024 |
| | 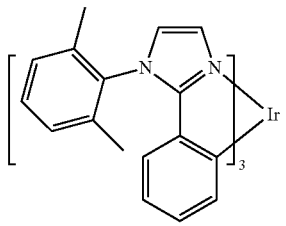 | US20060251923<br>US20110057559<br>US20110204333 |
| | 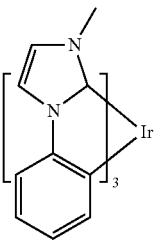 | U.S. Pat. No. 7,393,599,<br>WO2006056418,<br>US20050260441,<br>WO2005019373 |
| | 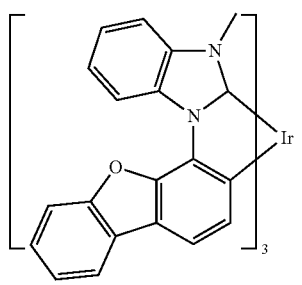 | U.S. Pat. No. 7,534,505 |

TABLE 1-continued

| MATERIAL | EXAMPLES OF MATERIAL | PUBLICATIONS |
|---|---|---|
| | [structure] | WO2011051404 |
| | [structure] | U.S. Pat. No. 7,445,855 |
| | [structure] | US20070190359, US20080297033, US20100148663 |
| | [structure] | U.S. Pat. No. 7,338,722 |
| | [structure] | US20020134984 |

TABLE 1-continued

| MATERIAL | EXAMPLES OF MATERIAL | PUBLICATIONS |
|---|---|---|
| | | Angew. Chem. Int. Ed. 47, 1 (2008) |
| | | Chem. Mater. 18, 5119 (2006) |
| | | Inorg. Chem. 46, 4308 (2007) |
| | | WO2005123873 |
| | | WO2005123873 |

| MATERIAL | EXAMPLES OF MATERIAL | PUBLICATIONS |
|---|---|---|
| | 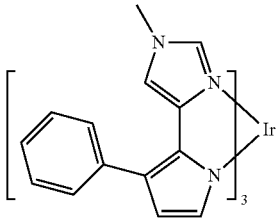 | WO2007004380 |
| | 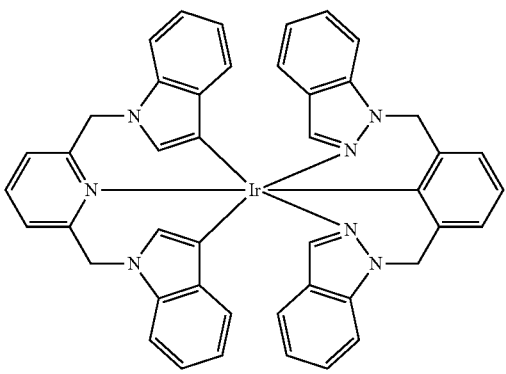 | WO2006082742 |
| Osmium (II) complexes | 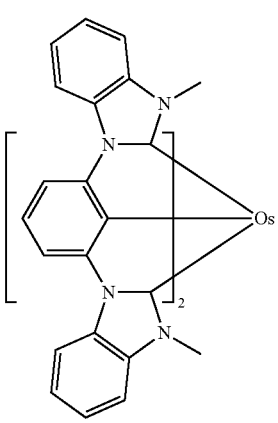 | U.S. Pat. No. 7,279,704 |
| | 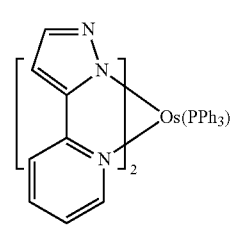 | Organometallics 23, 3745 (2004) |
| Gold complexes | 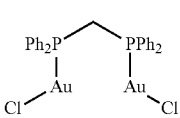 | Appl. Phys. Lett. 74, 1361 (1999) |
| Platinum (II) complexes | 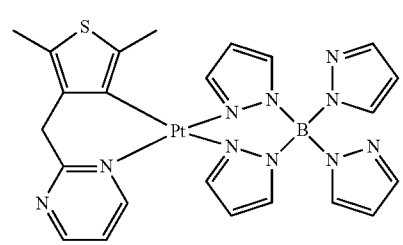 | WO2006098120, WO2006103874 |

TABLE 1-continued

| MATERIAL | EXAMPLES OF MATERIAL | PUBLICATIONS |
|---|---|---|
| Pt tetradentate complexes with at least one metal-carbene bond | 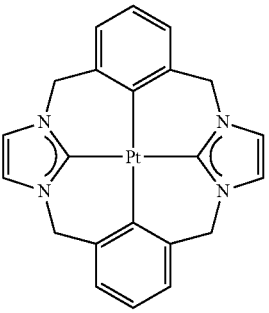 | U.S. Pat. No. 7,655,323 |
| Exciton/hole blocking layer materials | | |
| Bathocuprine compounds (e.g., BCP, BPhen) | 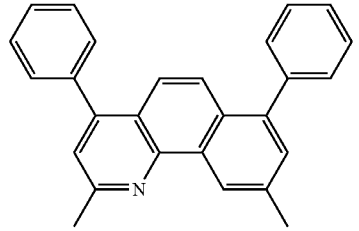 [SMILES: Cc1cc(-c2ccccc2)c2ccc3c(-c4ccccc4)cc(C)nc3c2c1] | Appl. Phys. Lett. 75, 4 (1999) |
| | 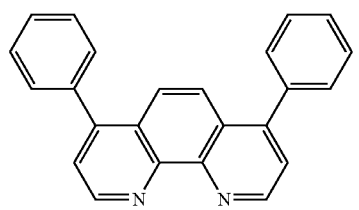 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 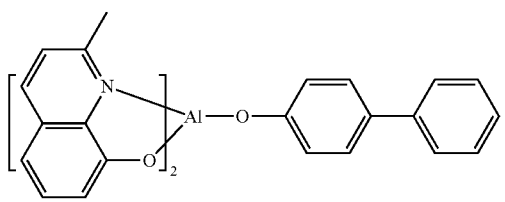 | Appl. Phys. Lett. 81, 162 (2002) |
| 5-member ring electron deficient heterocycles such as triazole, oxadiazole, imidazole, benzoimidazole | 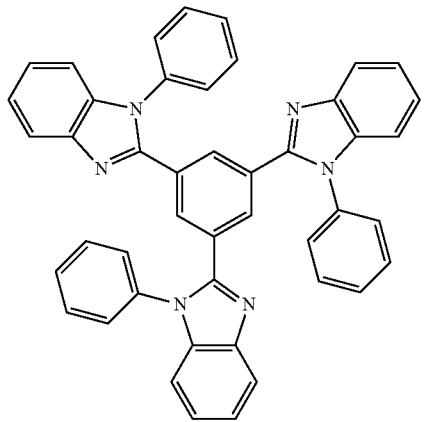 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 1-continued
| MATERIAL | EXAMPLES OF MATERIAL | PUBLICATIONS |
|---|---|---|
| Triphenylene compounds | 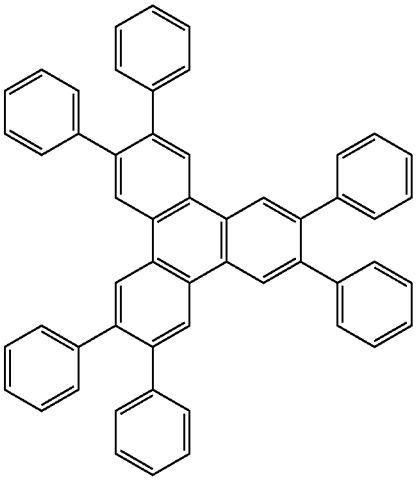 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 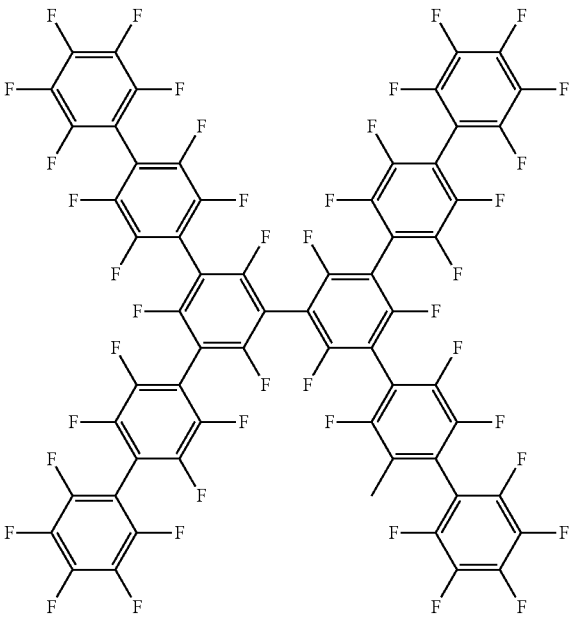 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 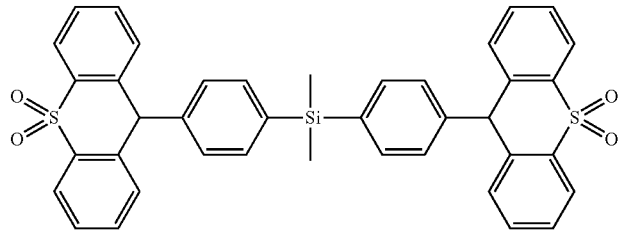 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 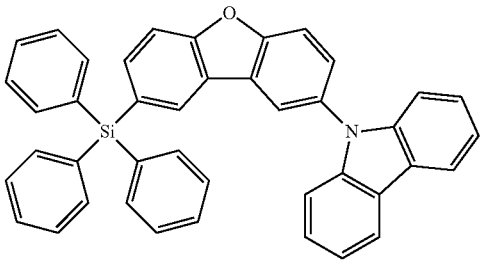 [SMILES: c1ccc([Si](c2ccccc2)(c2ccccc2)c2ccc3oc4ccc(-n5c6ccccc6c6ccccc65)cc4c3c2)cc1] | WO2010079051 |

| MATERIAL | EXAMPLES OF MATERIAL | PUBLICATIONS |
|---|---|---|
| Aza-carbazoles | 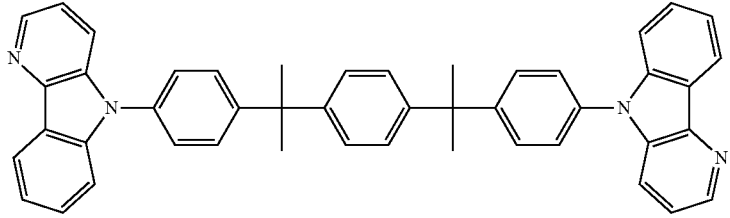 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 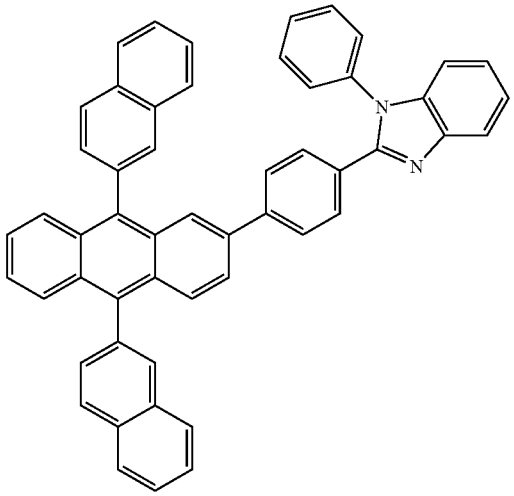 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 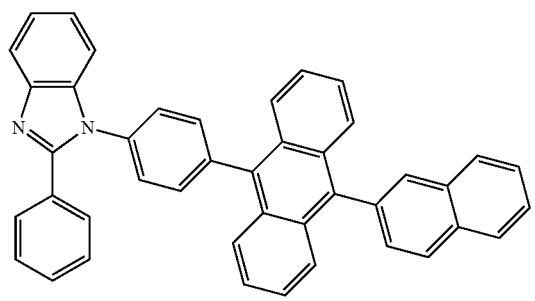 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 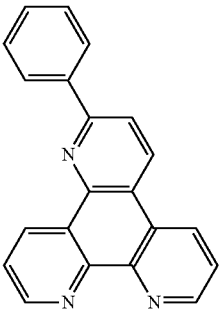 [SMILES: c1ccc(-c2ccc3c4cccnc4c4ncccc4c3n2)cc1] | US20090115316 |

TABLE 1-continued

| MATERIAL | EXAMPLES OF MATERIAL | PUBLICATIONS |
|---|---|---|
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |

TABLE 1-continued
| MATERIAL | EXAMPLES OF MATERIAL | PUBLICATIONS |
|---|---|---|
|  | 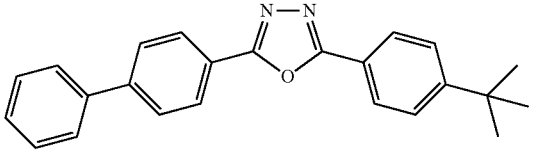 [SMILES: CC(C)(C)c1ccc(-c2nnc(-c3ccc(-c4ccccc4)cc3)o2)cc1] | Appl. Phys. Lett. 55, 1489 (1989) |
|  | 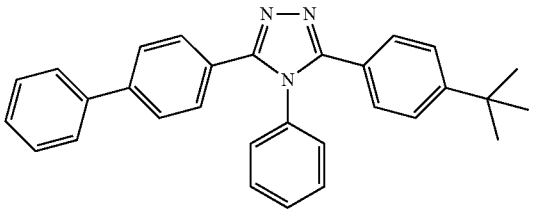 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 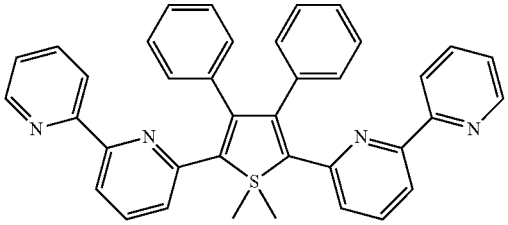 [SMILES: CS1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 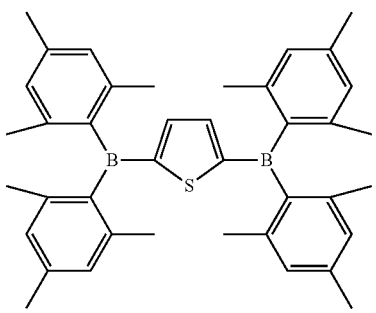 | J. Am. Chem. Soc. 120, 9714 (1998) |
| Fluorinated aromatic compounds | 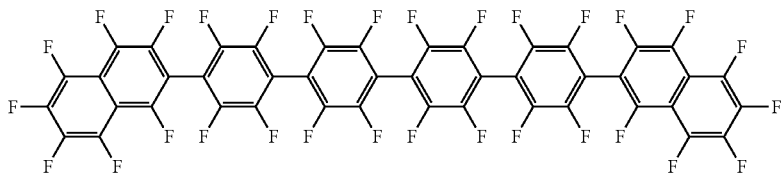 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 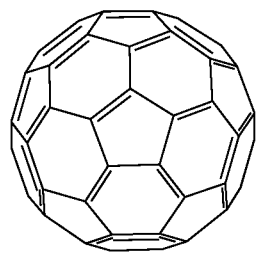 | US20090101870 |

TABLE 1-continued
| MATERIAL | EXAMPLES OF MATERIAL | PUBLICATIONS |
|---|---|---|
| Triazine complexes | 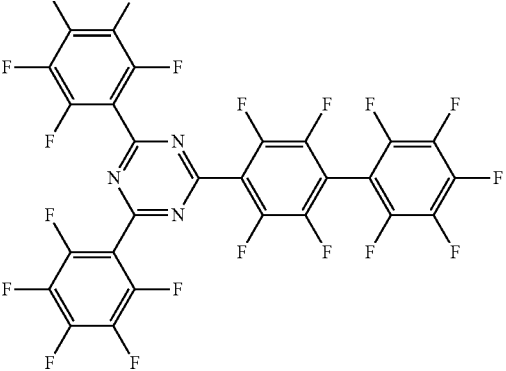 | US20040036077 |
| Zn (N^N) complexes | 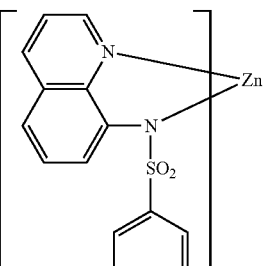 | U.S. Pat. No. 6,528,187 |
EXPERIMENTAL
TABLE 2
Calculated electronic properties of compounds of Formula I.
| Compound | HOMO (eV) | LUMO (eV) | Gap (eV) | Calc. T1 (nm) | Calc. T1 (eV) | Calc. S1 (nm) | Calc. S1 (eV) | $\Delta E_{S-T}$ (eV) |
|---|---|---|---|---|---|---|---|---|
| Compound 22 | −5.44 | −2.13 | −3.31 | 448 | 2.77 | 446 | 2.78 | 0.01 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | $\Delta E_{S-T}$ (eV) |
|---|---|---|---|---|---|---|---|---|
| Compound 662 | −5.22 | −2.25 | −2.97 | 476 | 2.61 | 475 | 2.61 | 0 |
| Compound 1430 | −5.10 | −2.08 | −3.02 | 504 | 2.46 | 500 | 2.48 | 0.02 |
| Compound 1750 | −4.85 | −2.14 | −2.71 | 540 | 2.30 | 538 | 2.30 | 0 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | $\Delta E_{S-T}$ (eV) |
|---|---|---|---|---|---|---|---|---|
| Compound 1654 | −5.04 | −2.18 | −2.87 | 511 | 2.43 | 509 | 2.44 | 0.01 |
| Compound 1974 | −4.93 | −2.19 | −2.74 | 524 | 2.37 | 522 | 2.38 | 0.01 |
| Compound 502 | −5.31 | −2.15 | −3.15 | 467 | 2.66 | 465 | 2.67 | 0.01 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | $\Delta E_{S-T}$ (eV) |
|---|---|---|---|---|---|---|---|---|
| Compound 470 | −4.91 | −2.10 | −2.81 | 532 | 2.33 | 531 | 2.34 | 0.01 |
| Compound 246 | −4.72 | −2.18 | −2.54 | 587 | 2.11 | 586 | 2.12 | 0.01 |
| Compound 694 | −5.14 | −2.23 | −2.91 | 492 | 2.52 | 491 | 2.53 | 0.01 |

TABLE 2-continued
Calculated electronic properties of compounds of Formula I.
| Compound | HOMO (eV) | LUMO (eV) | Gap (eV) | Calc. T1 (nm) | Calc. T1 (eV) | Calc. S1 (nm) | Calc. S1 (eV) | $\Delta E_{S-T}$ (eV) |
|---|---|---|---|---|---|---|---|---|
| 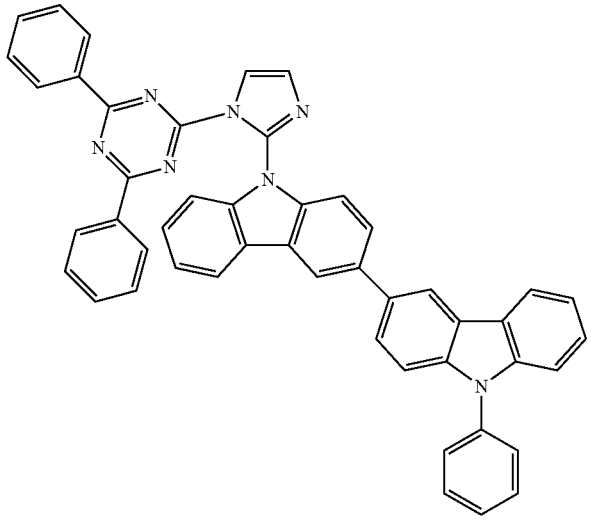 Compound 118 | −5.02 | −2.12 | −2.90 | 500 | 2.48 | 499 | 2.48 | 0 |
| 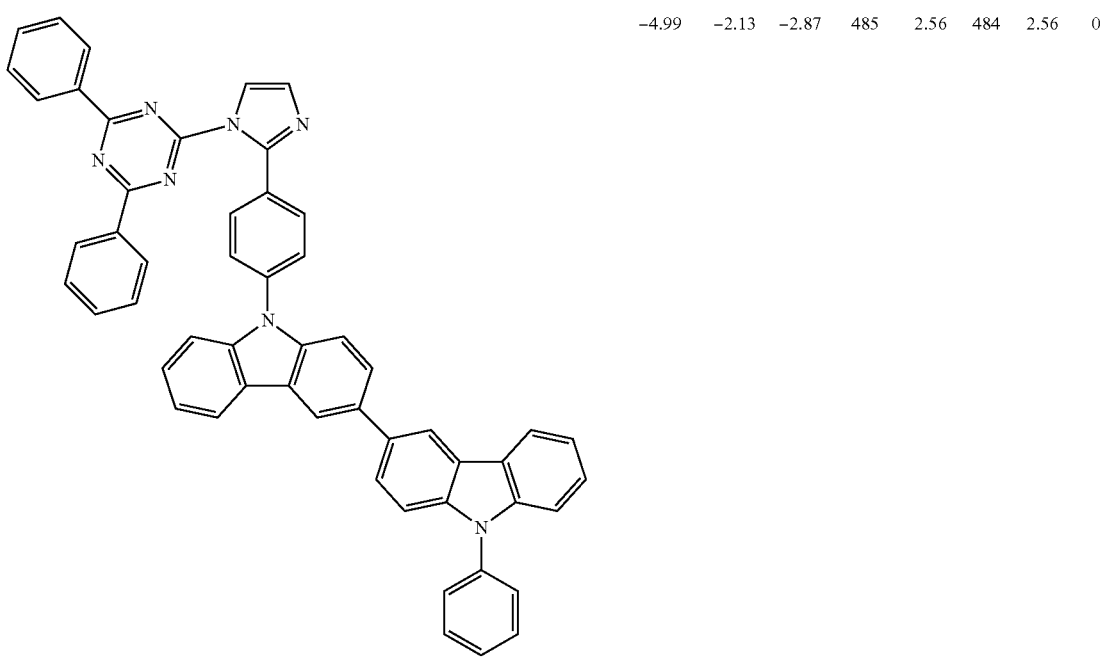 Compound 758 | −4.99 | −2.13 | −2.87 | 485 | 2.56 | 484 | 2.56 | 0 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | ΔE$_{S-T}$ (eV) |
|---|---|---|---|---|---|---|---|---|
| Compound 23 | −5.49 | −2.06 | −3.43 | 425 | 2.92 | 416 | 2.98 | 0.06 |
| Compound 663 | −5.25 | −2.12 | −3.13 | 458 | 2.71 | 444 | 2.79 | 0.08 |
| Compound 1431 | −5.15 | −2.00 | −3.15 | 472 | 2.63 | 460 | 2.70 | 0.07 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | $\Delta E_{S-T}$ (eV) |
|---|---|---|---|---|---|---|---|---|
| Compound 1655 | −5.11 | −2.06 | −3.06 | 475 | 2.61 | 468 | 2.65 | 0.04 |
| Compound 1975 | −4.92 | −2.08 | −2.84 | 506 | 2.45 | 495 | 2.51 | 0.06 |
| Compound 503 | −5.35 | −2.080 | −3.27 | 439 | 2.82 | 436 | 2.84 | 0.02 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | $\Delta E_{S-T}$ (eV) |
|---|---|---|---|---|---|---|---|---|
| Compound 471 | −4.94 | −2.02 | −2.92 | 497 | 2.49 | 495 | 2.51 | 0.02 |
| Compound 247 | −4.72 | −2.09 | −2.63 | 550 | 2.25 | 550 | 2.25 | 0 |
| Compound 55 | −5.14 | −2.13 | −3.01 | 468 | 2.65 | 467 | 2.66 | 0.01 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | ΔE$_{S-T}$ (eV) |
|---|---|---|---|---|---|---|---|---|
| Compound 119 | −5.03 | −2.04 | −2.99 | 474 | 2.62 | 473 | 2.62 | 0 |
| Compound 759 | −4.93 | −2.11 | −2.82 | 489 | 2.54 | 484 | 2.56 | 0.02 |
| Compound 3414 | −5.47 | −2.11 | −3.37 | 438 | 2.83 | 436 | 2.84 | 0.01 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | $\Delta E_{S-T}$ (eV) |
|---|---|---|---|---|---|---|---|---|
| Compound 4822 | −5.17 | −2.04 | −3.13 | 480 | 2.58 | 477 | 2.60 | 0.02 |
| Compound 5142 | −4.98 | −2.06 | −2.92 | 499 | 2.48 | 496 | 2.50 | 0.02 |
| Compound 5046 | −5.13 | −2.13 | −3.01 | 492 | 2.52 | 490 | 2.53 | 0.01 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | $\Delta E_{S-T}$ (eV) |
|---|---|---|---|---|---|---|---|---|
| Compound 5366 | −5.02 | −2.12 | −2.90 | 493 | 2.52 | 491 | 2.53 | 0.01 |
| Compound 3894 | −5.35 | −2.12 | −3.23 | 456 | 2.72 | 454 | 2.73 | 0.01 |
| Compound 3862 | −4.97 | −2.06 | −2.91 | 513 | 2.42 | 512 | 2.42 | 0 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | $\Delta E_{S-T}$ (eV) |
|---|---|---|---|---|---|---|---|---|
| Compound 3638 | −4.76 | −2.13 | −2.63 | 565 | 2.19 | 564 | 2.20 | 0.01 |
| Compound 3446 | −5.17 | −2.20 | −2.98 | 482 | 2.57 | 481 | 2.58 | 0.01 |
| Compound 3510 | −5.06 | −2.09 | −2.97 | 487 | 2.55 | 486 | 2.55 | 0 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | ΔE$_{S-T}$ (eV) |
|---|---|---|---|---|---|---|---|---|
| Compound 4150 | −5.01 | −2.10 | −2.91 | 473 | 2.62 | 472 | 2.63 | 0.01 |
| Compound 24 | −5.34 | −2.00 | −3.34 | 444 | 2.79 | 442 | 2.81 | 0.02 |
| Compound 664 | −5.28 | −2.01 | −3.27 | 435 | 2.85 | 432 | 2.87 | 0.02 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | ΔE$_{S-T}$ (eV) |
|---|---|---|---|---|---|---|---|---|
| Compound 1432 | −4.97 | −1.95 | −3.03 | 502 | 2.47 | 499 | 2.48 | 0.01 |
| Compound 1752 | −4.85 | −1.93 | −2.92 | 499 | 2.48 | 496 | 2.50 | 0.02 |
| Compound 5110 | −5.39 | −2.18 | −3.22 | 474 | 2.62 | 460 | 2.70 | 0.08 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | $\Delta E_{S-T}$ (eV) |
|---|---|---|---|---|---|---|---|---|
| Compound 8534 | −4.88 | −2.20 | −2.67 | 565 | 2.19 | 559 | 2.22 | 0.03 |
| Compound 5 | −5.32 | −2.19 | −3.13 | 486 | 2.55 | 478 | 2.59 | 0.04 |
| Compound 645 | −5.21 | −2.23 | −2.98 | 491 | 2.53 | 477 | 2.60 | 0.07 |
| Compound 3397 | −5.36 | −2.14 | −3.22 | 471 | 2.63 | 463 | 2.68 | 0.05 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | $\Delta E_{S-T}$ (eV) |
|---|---|---|---|---|---|---|---|---|
| Compound 4805 | −5.07 | −2.04 | −3.03 | 511 | 2.43 | 500 | 2.48 | 0.05 |
| Compound 5125 | −4.90 | −2.07 | −2.84 | 525 | 2.36 | 512 | 2.42 | 0.06 |
| Compound 2966 | −5.18 | −1.72 | −3.45 | 425 | 2.92 | 413 | 3.00 | 0.08 |
| Compound 6358 | −5.18 | −1.88 | −3.30 | 448 | 2.77 | 435 | 2.85 | 0.08 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | $\Delta E_{S-T}$ (eV) |
|---|---|---|---|---|---|---|---|---|
| Comparative Compound 1 | −5.50 | −1.15 | −4.35 | 396 | 3.13 | 329 | 3.77 | 0.64 |
| Comparative Compound 2 | −5.84 | −2.08 | −3.76 | 437 | 2.84 | 388 | 3.20 | 0.36 |
| Comparative Compound 3 | −5.62 | −1.21 | −4.41 | 417 | 2.97 | 356 | 3.48 | 0.51 |
| Comparative Compound 4 | −5.52 | −1.16 | −4.36 | 396 | 3.13 | 359 | 3.45 | 0.32 |

TABLE 2-continued

Calculated electronic properties of compounds of Formula I.

| Compound | HOMO (eV) | LUMO (eV) | Gap (eV) | Calc. T1 (nm) | Calc. T1 (eV) | Calc. S1 (nm) | Calc. S1 (eV) | $\Delta E_{S-T}$ (eV) |
|---|---|---|---|---|---|---|---|---|
| Comparative Compound 5 | −5.86 | −2.06 | −3.80 | 426 | 2.91 | 378 | 3.28 | 0.37 |
| Comparative Compound 6 | −6.35 | −2.11 | −4.23 | 420 | 2.95 | 375 | 3.31 | 0.36 |

Density Functional Theory (DFT) calculations were performed using the Gaussian 09 software package with the B3LYP functional and the 6-31 g(d) basis set. As reported in Table 2, compounds of Formula I with donor and acceptor groups connected through the imidazole group have very small singlet-triplet energy gap. On the other hand, the singlet-triplet gap of the comparative compounds that have no donor or acceptor, or donor only, or acceptor only groups connected to imidazole group was calculated to be significantly larger. All of the comparative compounds have calculated singlet-triplet gap greater than 0.32 eV. The small singlet-triplet gap exhibited by compounds of Formula I enables these compounds to be used for a variety of applications in OLEDs, including, but not limited to, host materials delayed fluorescent emitters.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound having the formula:

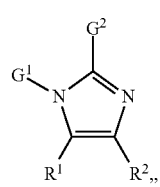

Formula I wherein:
(i) $G^1$ is an electron donor group and $G^2$ is an electron acceptor group, or
(ii) $G^1$ is an electron acceptor group and $G^2$ is an electron donor group;

wherein:
(A) the electron donor group comprises at least one chemical group selected from the group consisting of:

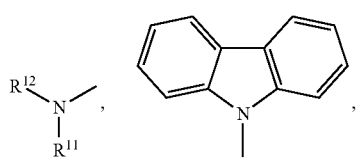

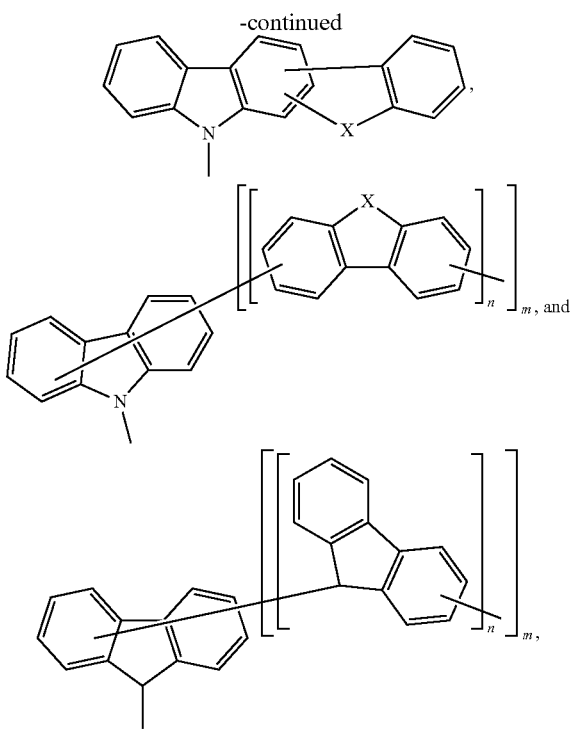

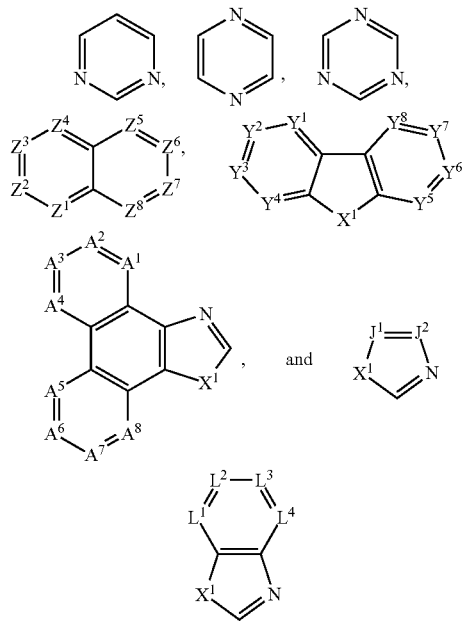

wherein n is an integer from 1 to 20,
wherein m is an integer from 1 to 20,
wherein X is selected from the group consisting of O, S, and $NR^{14}$, and
wherein $R^{11}$ and $R^{12}$ are selected from the group consisting of aryl and heteroaryl; and
(B) the electron acceptor group is selected from the group consisting of:

wherein $Z^1$ to $Z^8$ independently comprise C or N,
wherein at least two of $Z^1$ to $Z^8$ are N,
wherein $Y^1$ to $Y^8$ independently comprise C or N,
wherein at least one of $Y^1$ to $Y^8$ is N,
wherein $A^1$ to $A^8$ independently comprise C or N,
wherein $J^1$ and $J^2$ independently comprise C or N,
wherein $L^1$ to $L^4$ independently comprise C or N,
wherein $X^1$ is O, S, or $NR^{14}$, and
wherein $R^{14}$ is aryl or heteroaryl;
wherein the electron acceptor group is optionally substituted;
wherein $R^1$ and $R^2$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein $R^1$ and $R^2$ are optionally joined to form a ring, which may be further substituted.

2. The compound of claim 1, wherein the donor group is selected from the group consisting of:

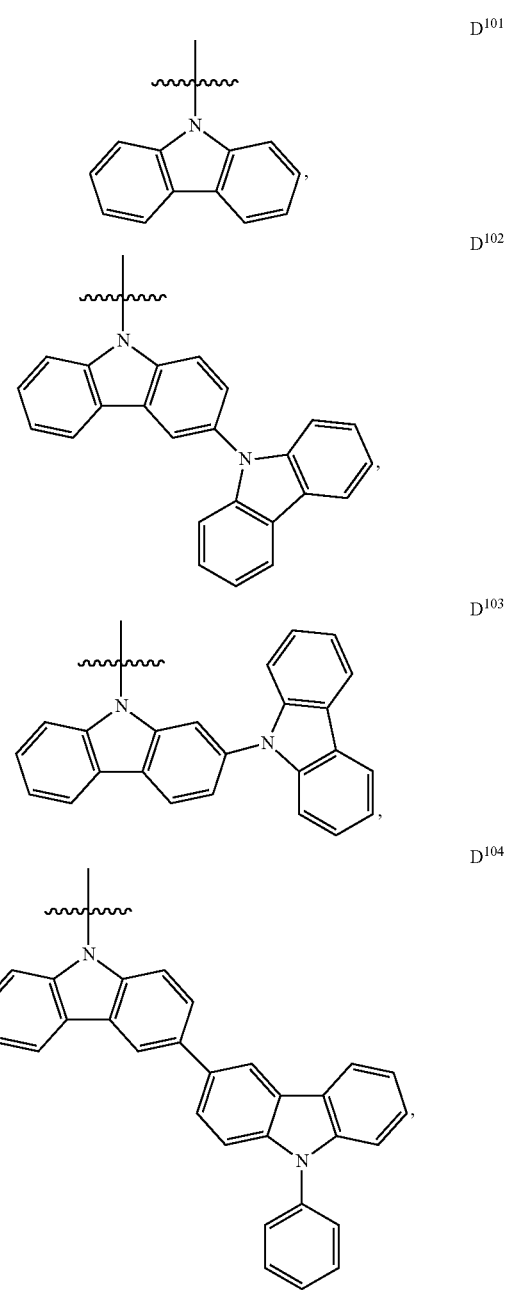

D¹⁰⁵
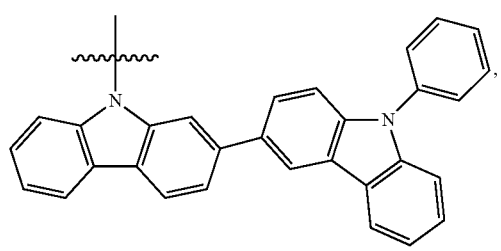
D¹⁰⁶
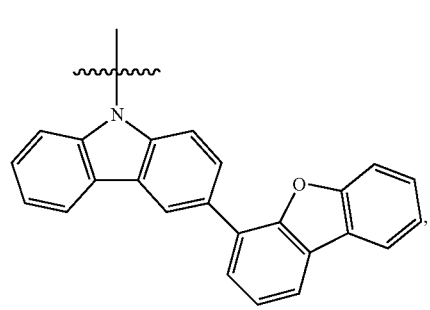
D¹⁰⁷
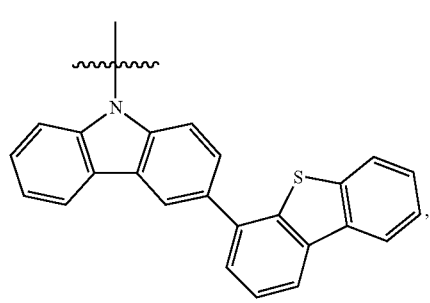
D¹⁰⁸
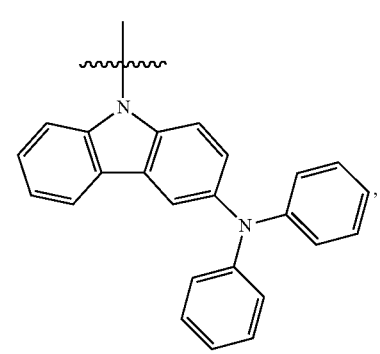
D¹⁰⁹
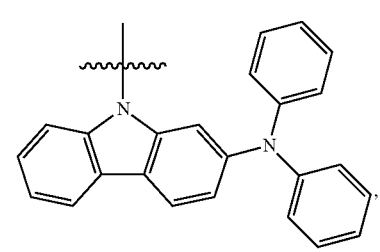
D¹¹⁰
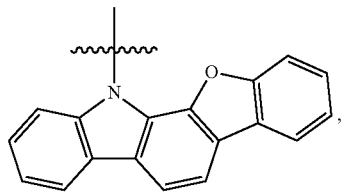
D¹¹¹
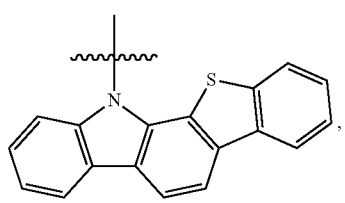
D¹¹²
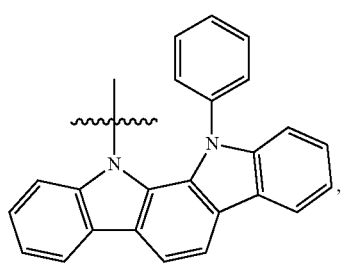
D¹¹³
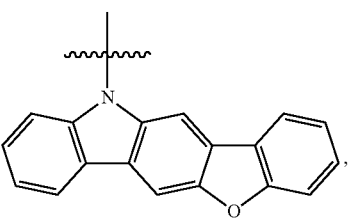
D¹¹⁴
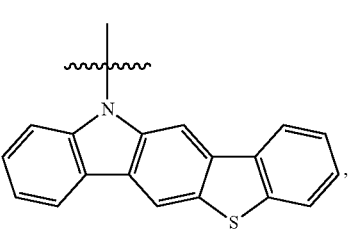
D¹¹⁵
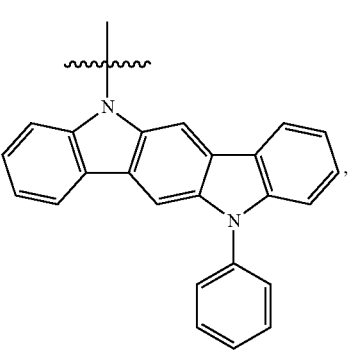

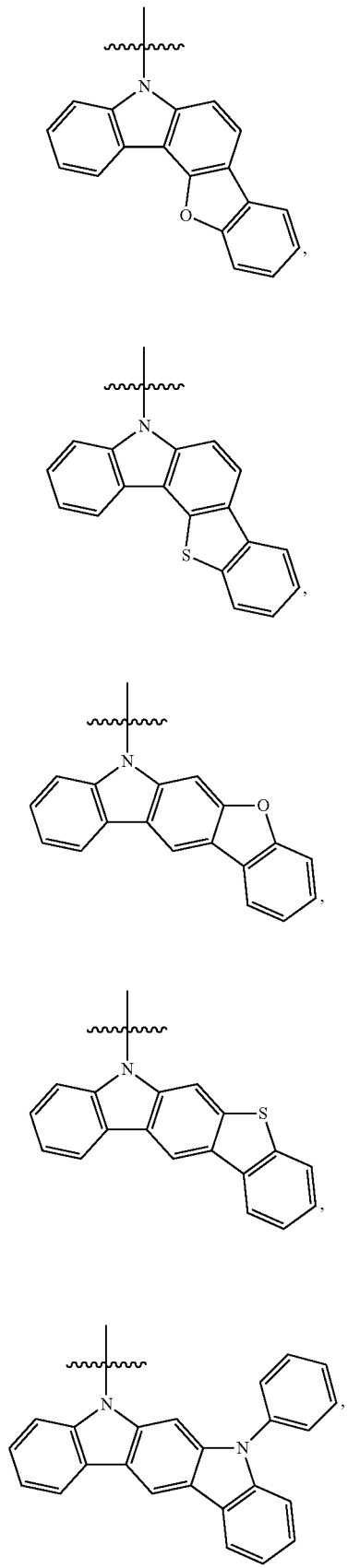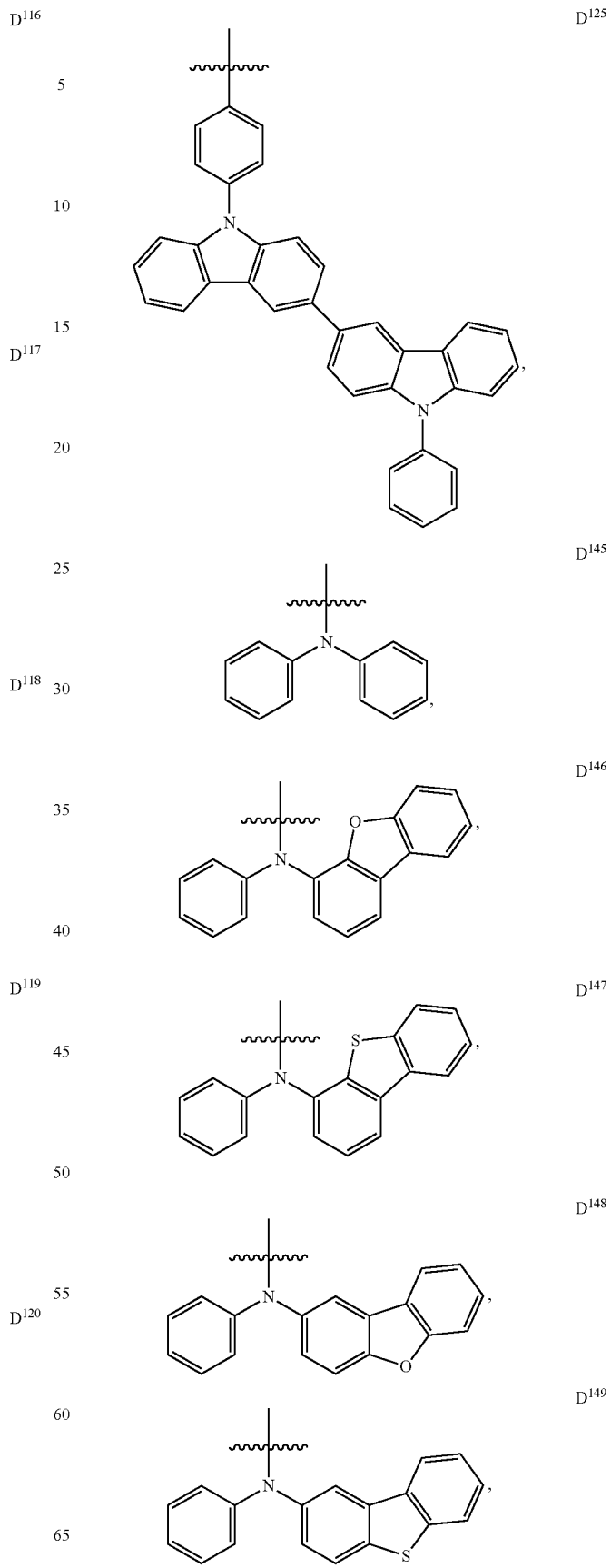

-continued
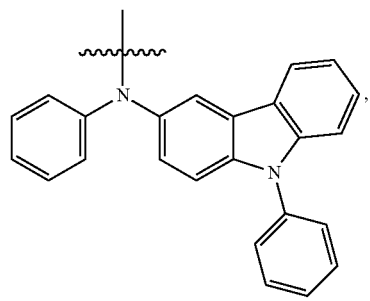 D¹⁵⁰
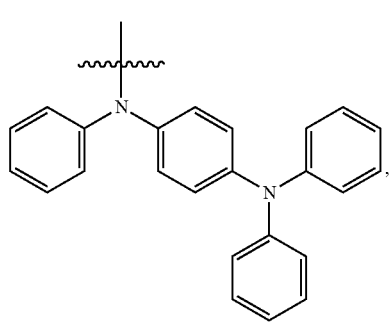 D¹⁵¹
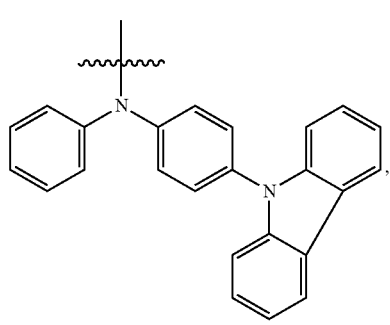 D¹⁵²
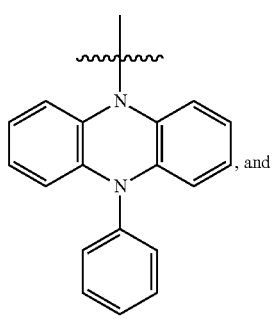, and D¹⁵³
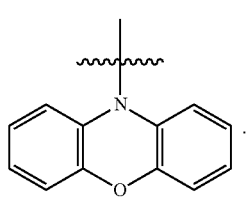. D¹⁵⁴
3. The compound of claim 1, wherein the acceptor group is selected from the group consisting of:
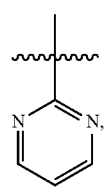 A¹⁰¹
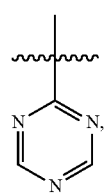 A¹⁰²
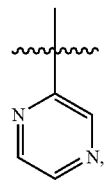 A¹⁰³
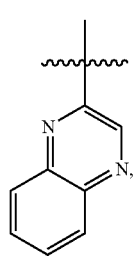 A¹⁰⁴
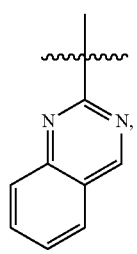 A¹⁰⁵
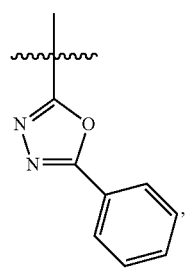 A¹⁰⁶

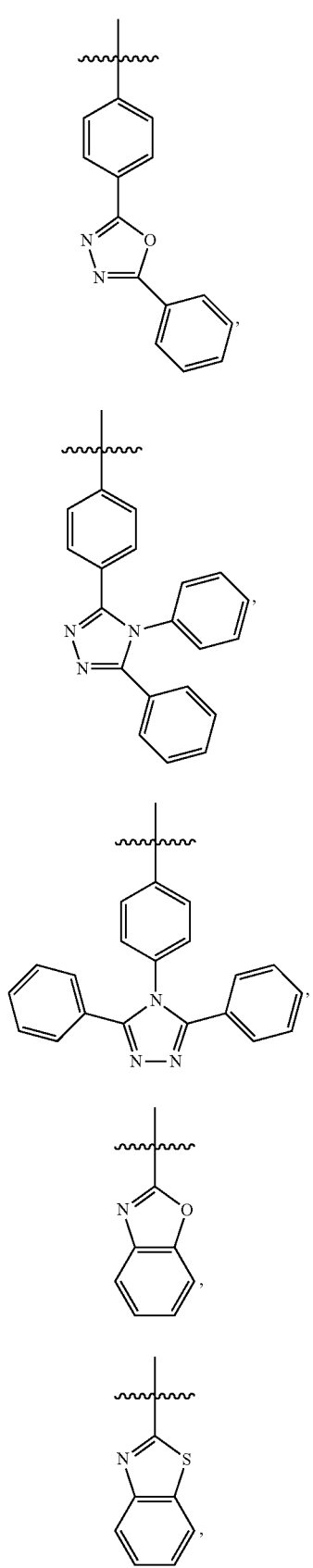
A[107]
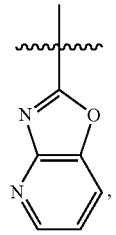
A[112]
A[108]
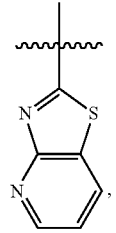
A[113]
A[109]
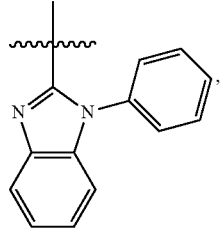
A[114]
A[110]
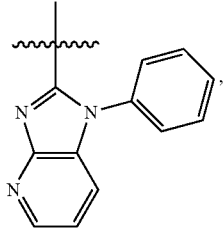
A[115]
A[111]
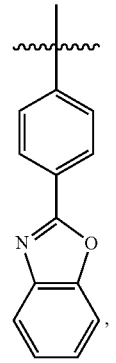
A[116]

A[117] 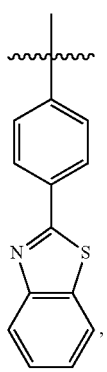
A[118] 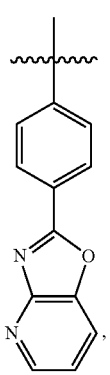
A[119] 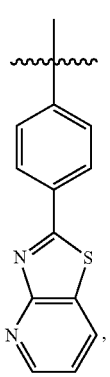
A[120] 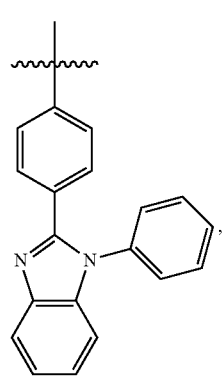
A[121] 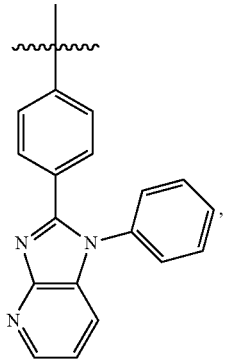
A[122] 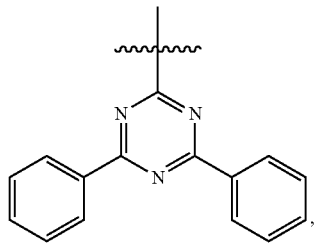
A[123] 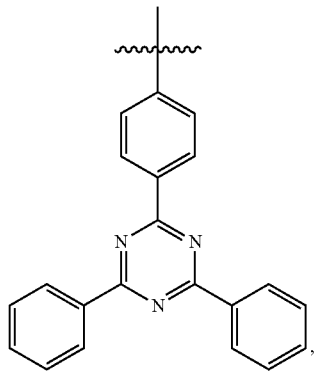
A[124] 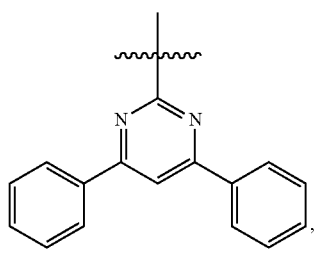
A[125] 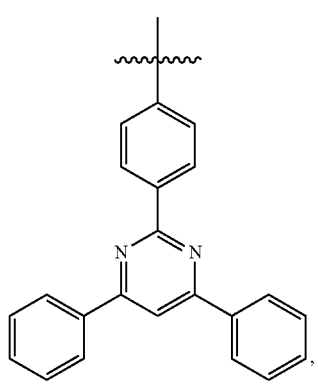

A¹²⁶ 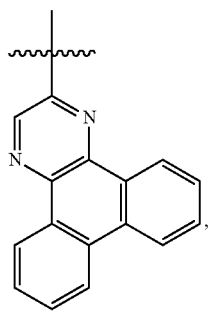
A¹²⁷ 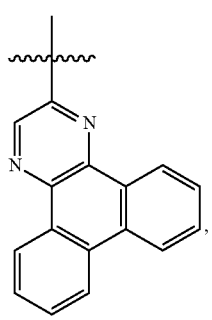
A¹²⁸ 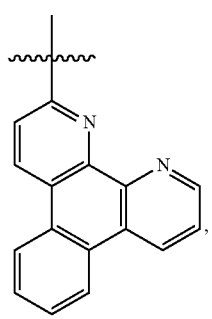
A¹²⁹ 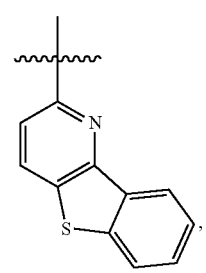
A¹³⁰ 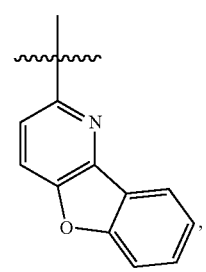
A¹³¹ 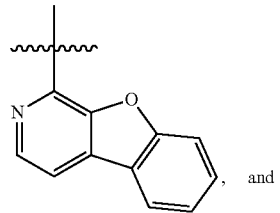, and
A¹³² 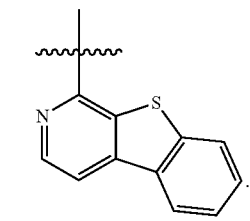.
4. The compound of claim 1, wherein the compound is selected from the group consisting of:
Compound 22
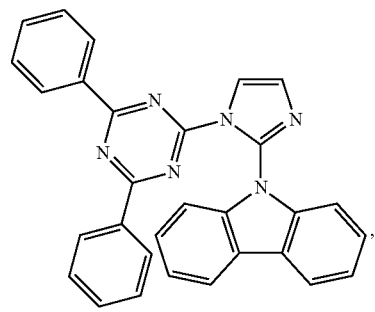
Compound 1430
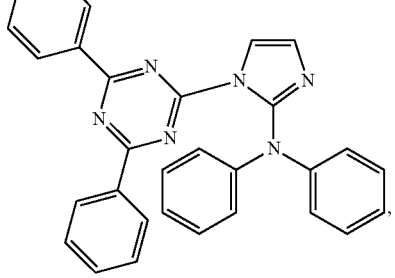
Compound 1654
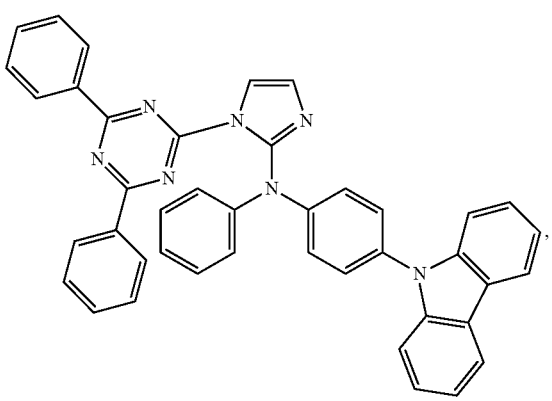

Compound 502
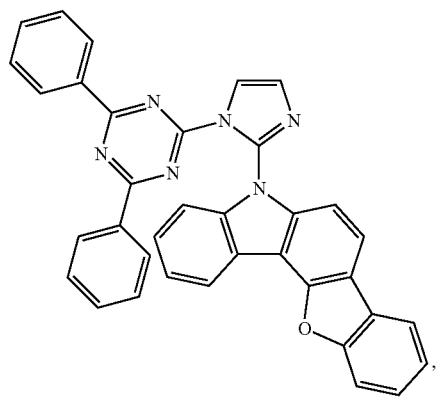
Compound 694
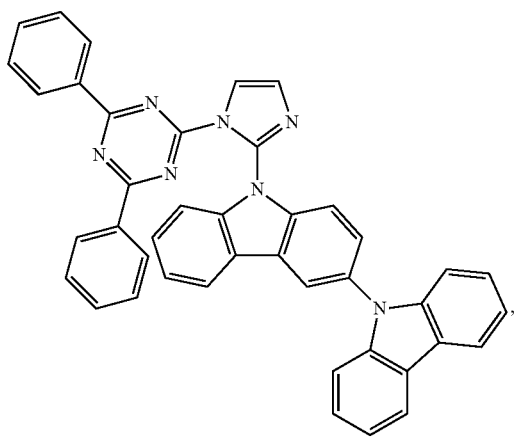
Compound 470
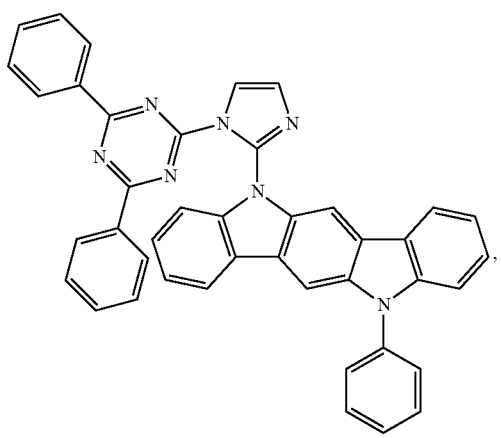
Compound 118
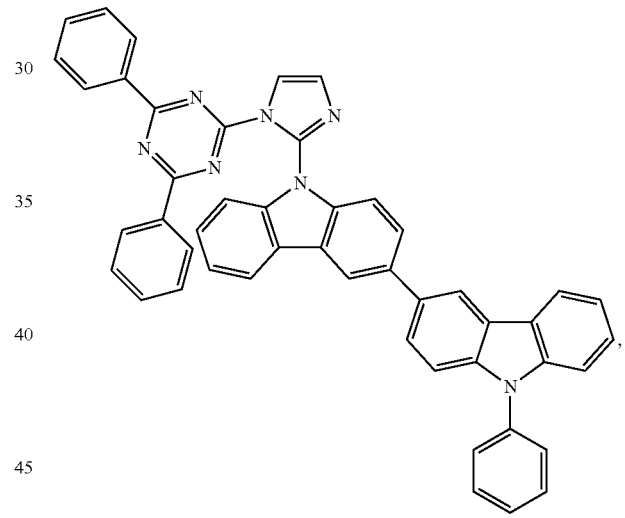
Compound 246
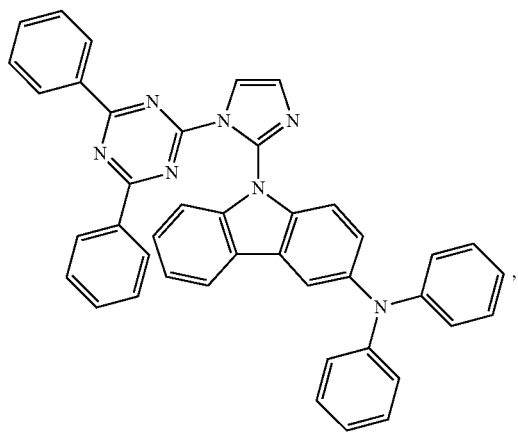
Compound 23
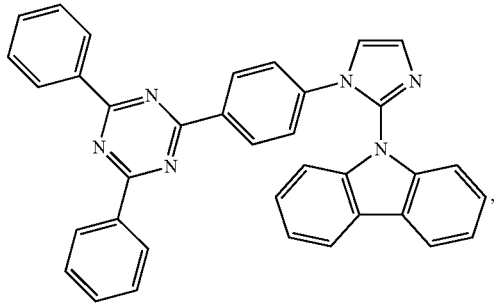

-continued
Compound 1431
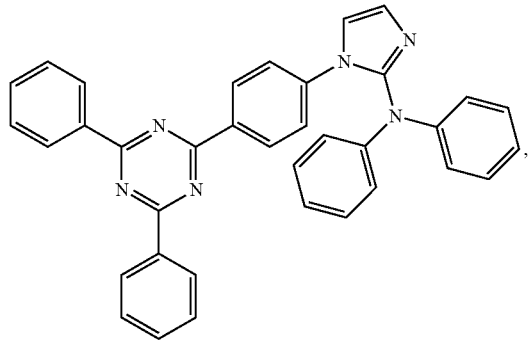
Compound 1655
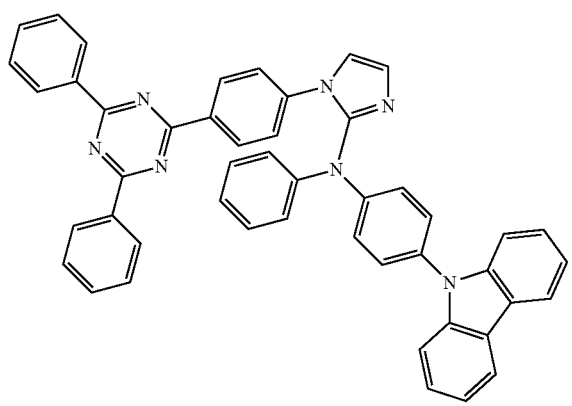
Compound 503
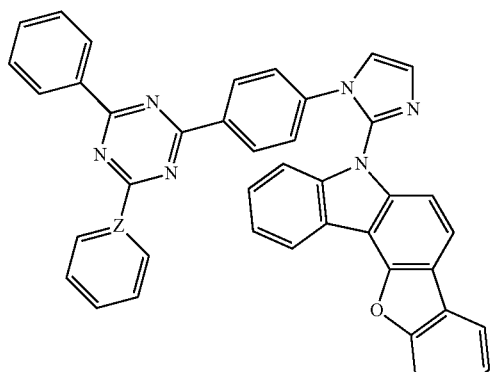
Compound 471
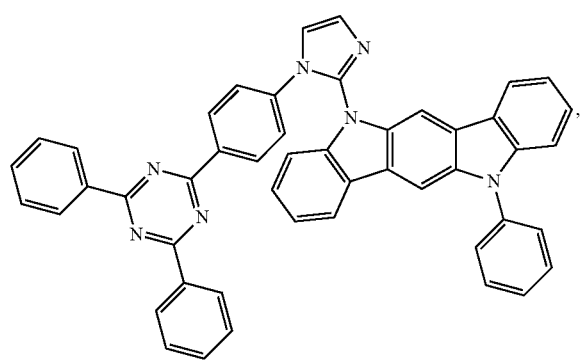
-continued
Compound 247
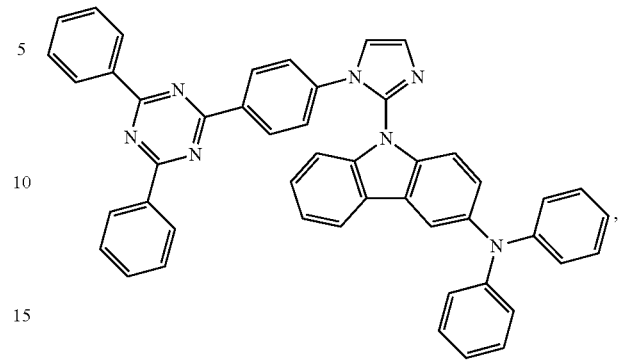
Compound 55
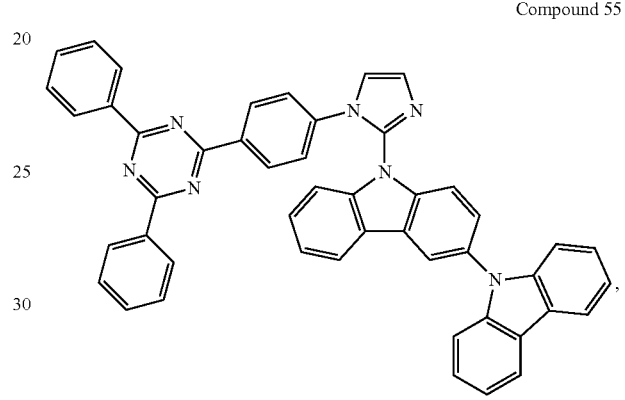
Compound 119
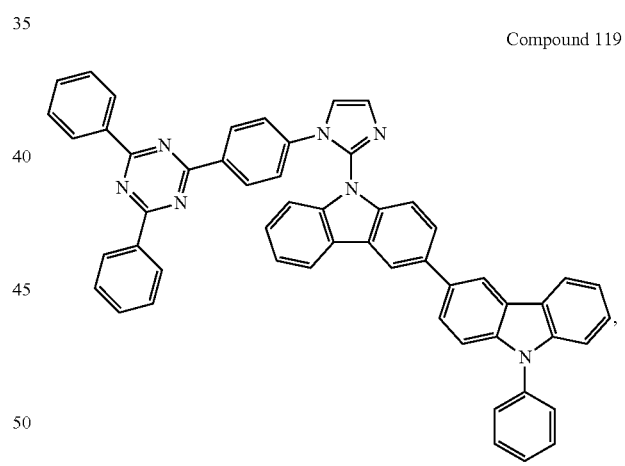
Compound 3414
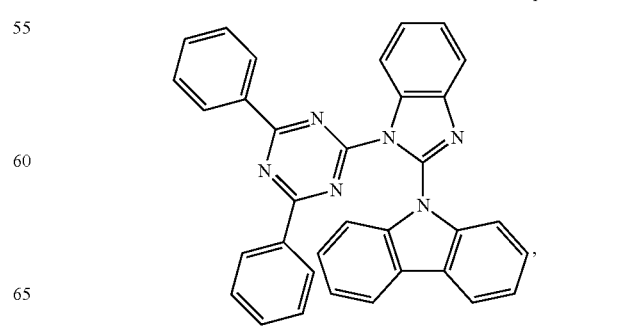

Compound 4822
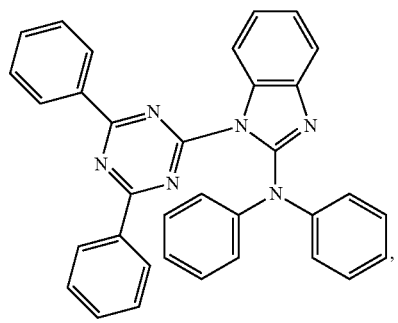
Compound 5046
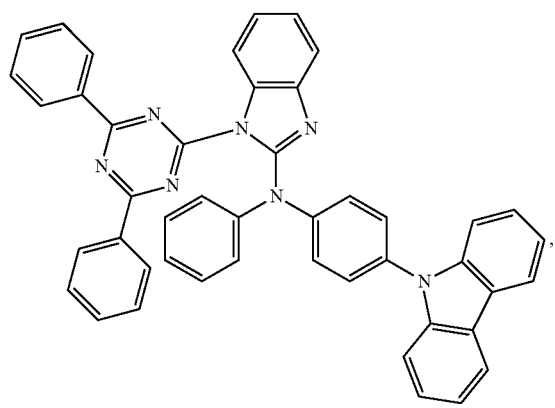
Compound 5046
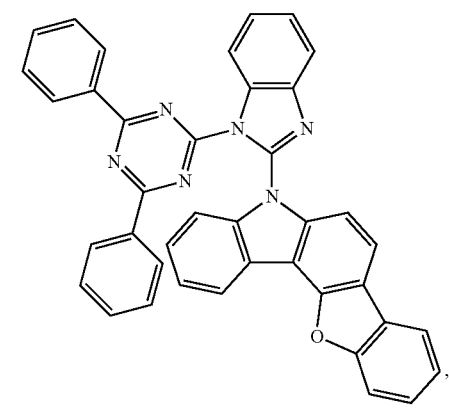
Compound 3894
Compound 3862
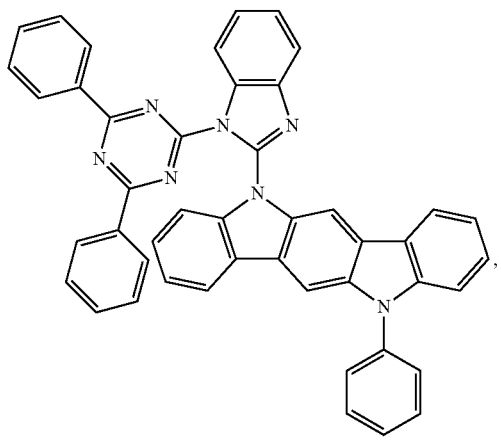
Compound 3638
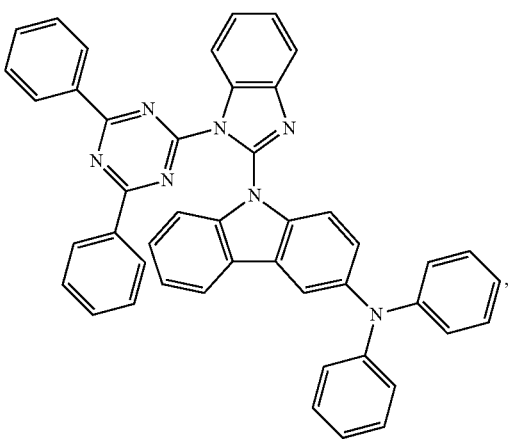
Compound 3446
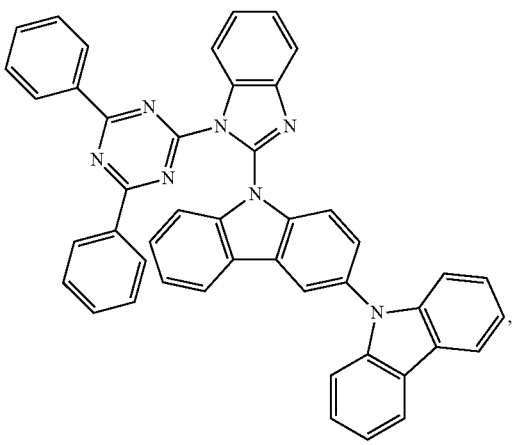

Compound 3510
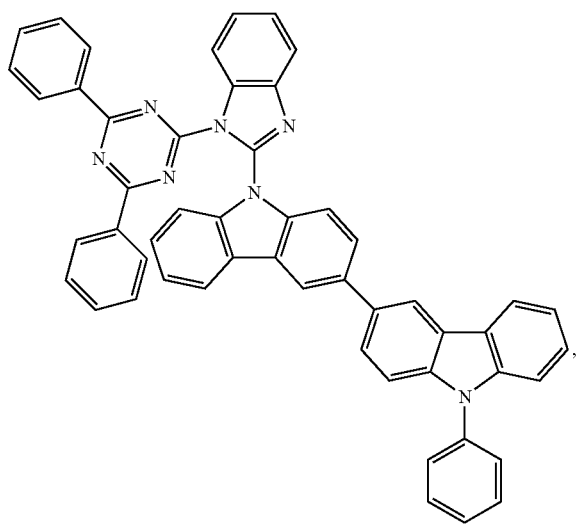
Compound 4150
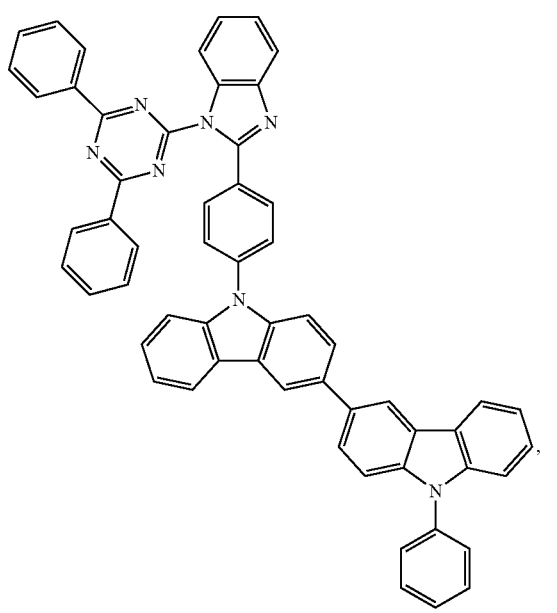
Compound 24
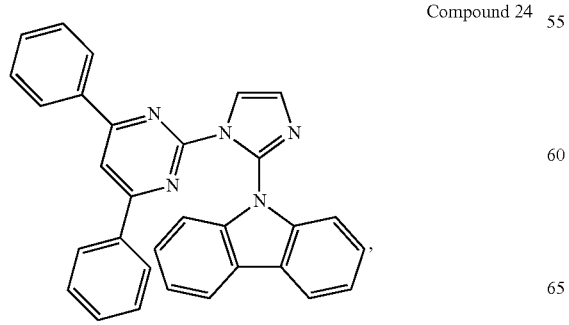
Compound 1432
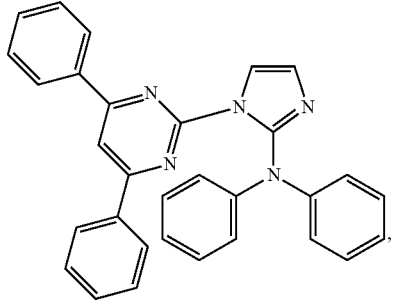
Compound 5110
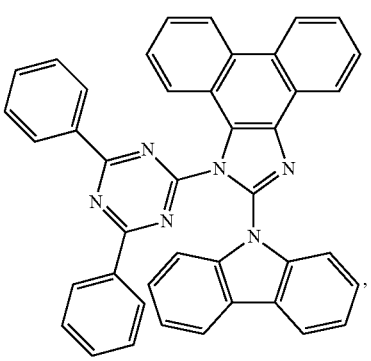
Compound 5
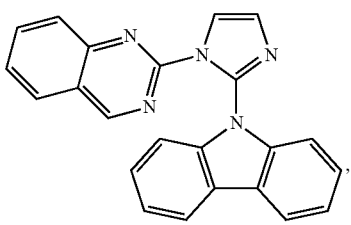
Compound 3397
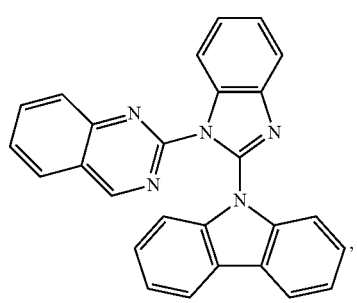
Compound 4805
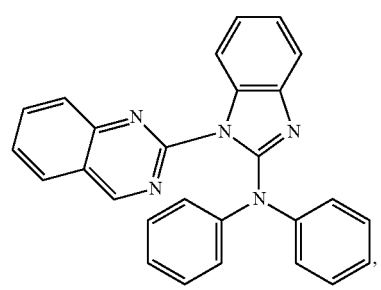

Compound 2966

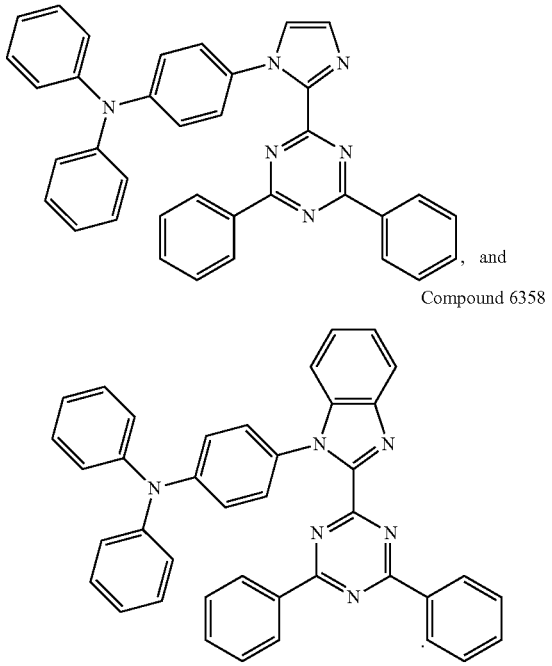

, and

Compound 6358

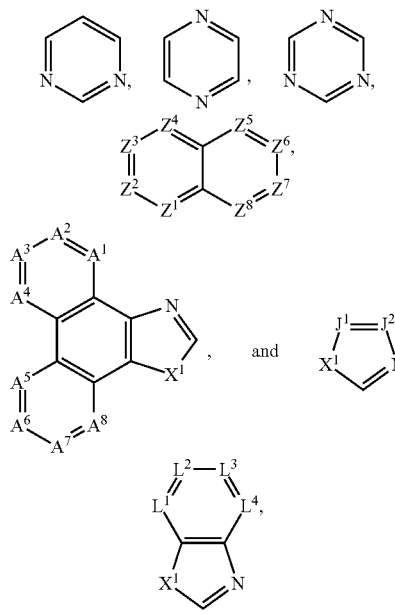

5. The compound of claim 1, wherein the electron accepting group is selected from the group consisting of:

[structures shown]

wherein the electron acceptor group is optionally substituted.

6. A first device comprising a first organic light emitting device, further comprising:
an anode;
a cathode; and
an organic layer, disposed between the anode and the cathode;
wherein the organic layer comprises a compound having the formula:

Formula I

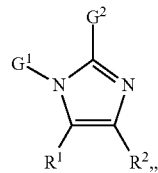

wherein:
(i) $G^1$ is an electron donor group and $G^2$ is an electron acceptor group, or
(ii) $G^1$ is an electron acceptor group and $G^2$ is an electron donor group;
wherein:
(A) the electron donor group comprises at least one chemical group selected from the group consisting of:

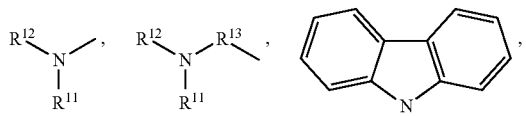

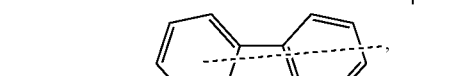

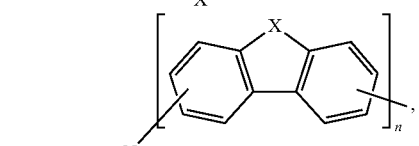

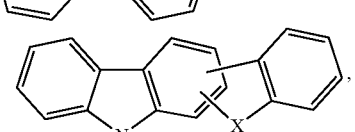

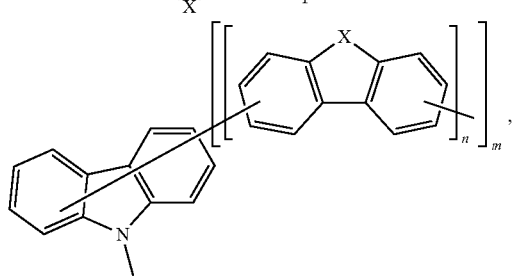

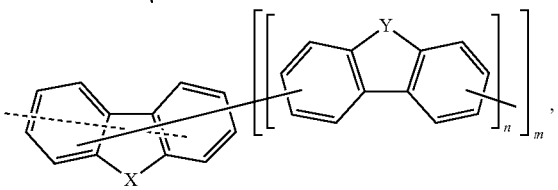

-continued

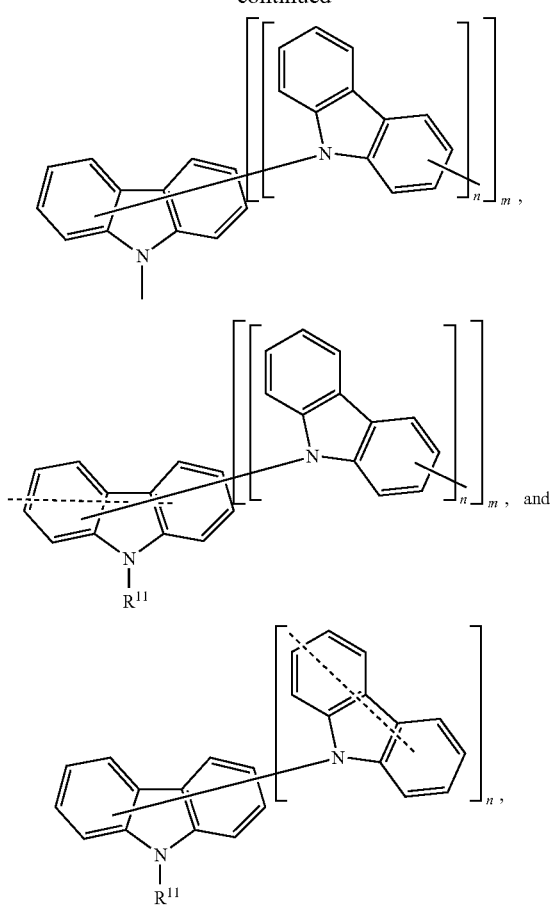

wherein n is an integer from 1 to 20, wherein m is an integer from 1 to 20, wherein X and Y are independently selected from the group consisting of O, S, and $NR^{14}$, and wherein $R^{11}$, $R^{12}$, $R^{13}$ and $R^{14}$ are selected from the group consisting of aryl and heteroaryl; and (B) the electron acceptor group is selected from the group consisting of:

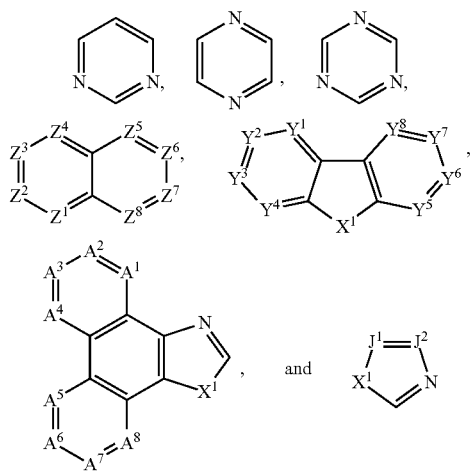

-continued

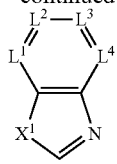

wherein $Z^1$ to $Z^8$ independently comprise C or N, wherein at least two of $Z^1$ to $Z^8$ are N, wherein $Y^1$ to $Y^8$ independently comprise C or N, wherein at least one of $Y^1$ to $Y^8$ is N, wherein $A^1$ to $A^8$ independently comprise C or N, wherein $J^1$ and $J^2$ independently comprise C or N, wherein $L^1$ to $L^4$ independently comprise C or N, wherein $X^1$ is O, S, or $NR^{14}$, and wherein $R^{14}$ is aryl or heteroaryl;

wherein the electron acceptor group is optionally substituted;

wherein $R^1$ and $R^2$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein $R^1$ and $R^2$ are optionally joined to form a ring, which may be further substituted; and wherein the compound is an emissive dopant.

7. The first device of claim 6, wherein the organic layer is an emissive layer.

8. The first device of claim 6, wherein the electron acceptor group comprises at least one chemical group selected from the group consisting of a six-membered aromatic ring system having at least two nitrogen atoms and a 5-membered aromatic ring system containing at least one nitrogen atom, one oxygen atom, one sulfur atom, or one selenium atom.

9. The first device of claim 6, wherein the first device emits a luminescent radiation at room temperature when a voltage is applied across the first organic light emitting device;

wherein the luminescent radiation comprises a delayed fluorescence process.

10. The first device of claim 6, wherein the emissive layer further comprises a first phosphorescent emitting material.

11. The first device of claim 10, wherein the first device emits a white light at room temperature when a voltage is applied across the organic light emitting device.

12. The first device of claim 11, wherein the compound emits a blue light having a peak wavelength between about 400 nm to about 500 nm.

13. The first device of claim 11, wherein the compound emits a yellow light having a peak wavelength between about 530 nm to about 580 nm.

14. The first device of claim 10, wherein the emissive layer further comprises a second phosphorescent emitting material.

15. The first device of claim 6, wherein the emissive layer further comprises a host material.

16. The first device of claim 6, wherein the compound is a host.

17. The first device of claim 6, wherein the first device comprises a second organic light-emitting device;

wherein the second organic light emitting device is stacked on the first organic light emitting device.

18. The first device of claim 6, wherein the first device is a consumer product.

19. The first device of claim 6, wherein the first device is an organic light-emitting device.

20. The first device of claim 6, wherein the first device comprises a lighting panel.

21. A method of making a first organic light emitting device, comprising:

depositing an anode on a substrate;

depositing at least one organic layer comprising a compound of formula:

Formula I

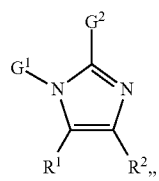

wherein:

(i) $G^1$ is an electron donor group and $G^2$ is an electron acceptor group, or (ii) $G^1$ is an electron acceptor group and $G^2$ is an electron donor group;

wherein:

(A) the electron donor group comprises at least one chemical group selected from the group consisting of:

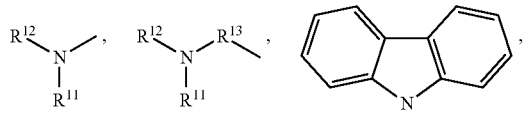

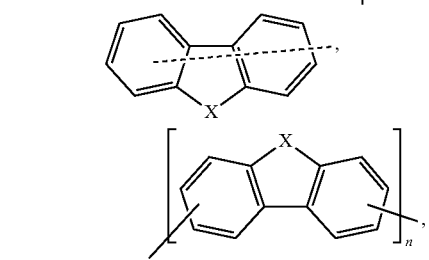

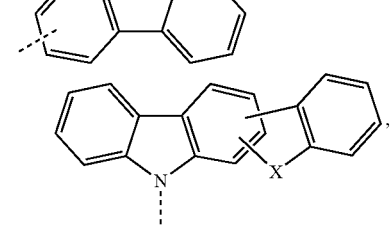

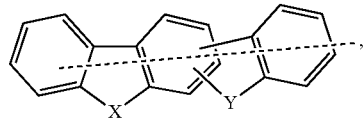

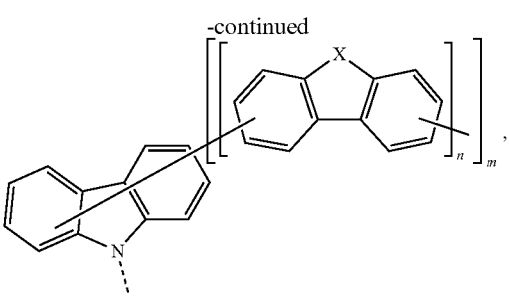

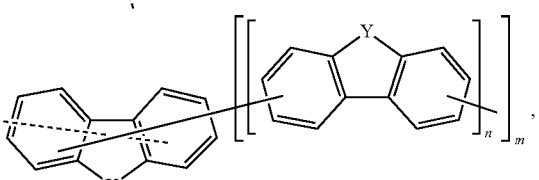

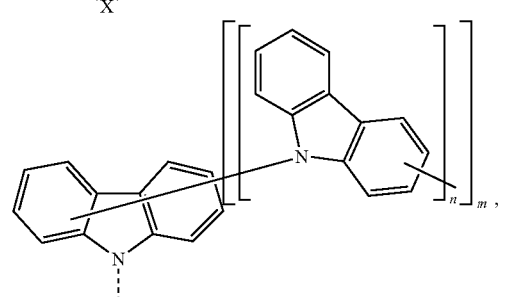

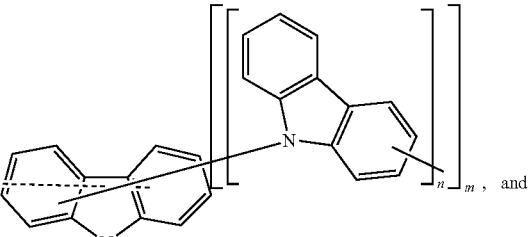

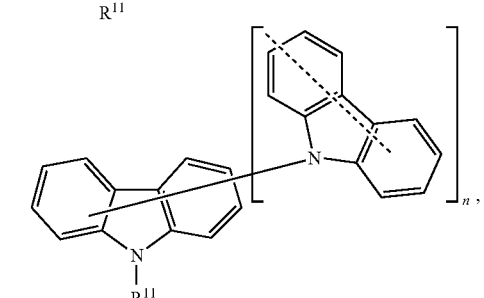

wherein n is an integer from 1 to 20,
wherein m is an integer from 1 to 20,
wherein X and Y are independently selected from the group consisting of O, S, and $NR^{14}$, and
wherein $R^{11}$, $R^{12}$, $R^{13}$ and $R^{14}$ are selected from the group consisting of aryl and heteroaryl; and (B) the electron acceptor group is selected from the group consisting of:

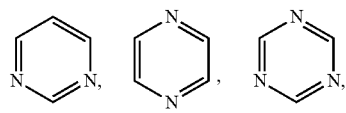

-continued

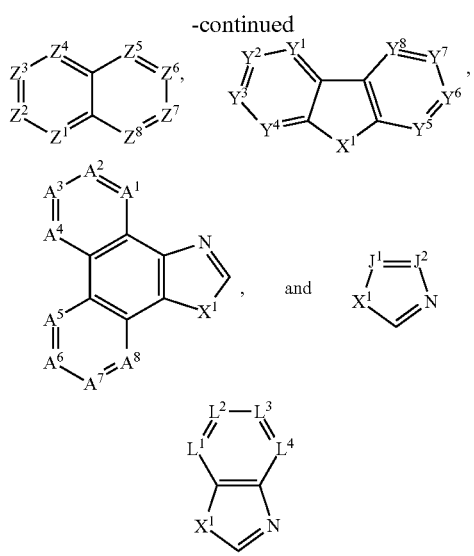

wherein $Z^1$ to $Z^8$ independently comprise C or N,
wherein at least two of $Z^1$ to $Z^8$ are N,
wherein $Y^1$ to $Y^8$ independently comprise C or N,
wherein at least one of $Y^1$ to $Y^8$ is N,
wherein $A^1$ to $A^8$ independently comprise C or N,
wherein $J^1$ and $J^2$ independently comprise C or N,
wherein $L^1$ to $L^4$ independently comprise C or N,
wherein $X^1$ is O, S, or $NR^{14}$, and
wherein $R^{14}$ is aryl or heteroaryl;
wherein the electron acceptor group is optionally substituted;
wherein $R^1$ and $R^2$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfonyl, sulfinyl, sulfonyl, phosphino, and combinations thereof;
wherein $R^1$ and $R^2$ are optionally joined to form a ring, which may be further substituted; and
wherein the compound is an emissive dopant
depositing a cathode;
wherein the emissive layer is deposited between the anode and cathode.
22. The method of claim 21, wherein the at least one organic layer is deposited using a solution process.

* * * * *

UNITED STATES PATENT AND TRADEMARK OFFICE
CERTIFICATE OF CORRECTION

PATENT NO. : 9,512,136 B2
APPLICATION NO. : 13/685458
DATED : December 6, 2016
INVENTOR(S) : Chun Lin, Chuanjun Xia and Raymond Kwong Page 1 of 4

It is certified that error appears in the above-identified patent and that said Letters Patent is hereby corrected as shown below:

In the Claims

Column 354, Lines 60-67, please delete

" 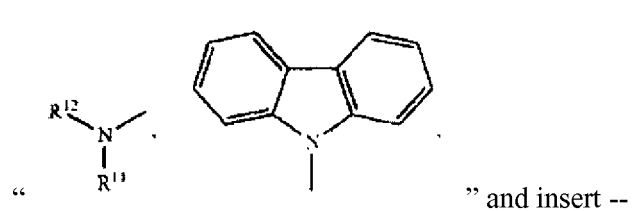 " and insert -- 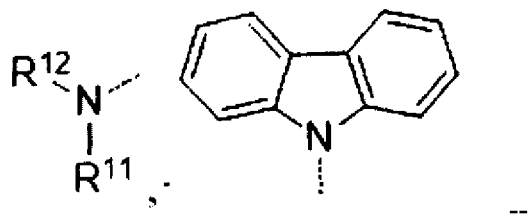 --

Column 355, Lines 1-7, please delete

" 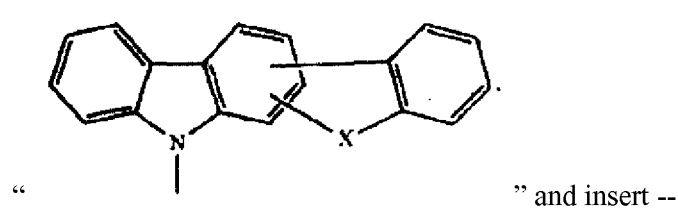 " and insert -- 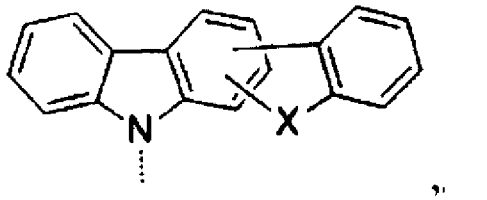 --

Signed and Sealed this
Twentieth Day of June, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,512,136 B2

Page 2 of 4

Column 355, Lines 8-17, please delete

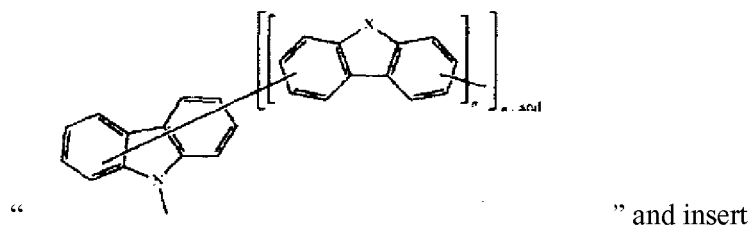

" and insert

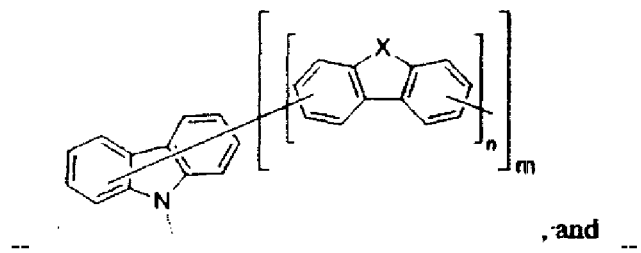

, and --

Column 355, Lines 17-27, please delete

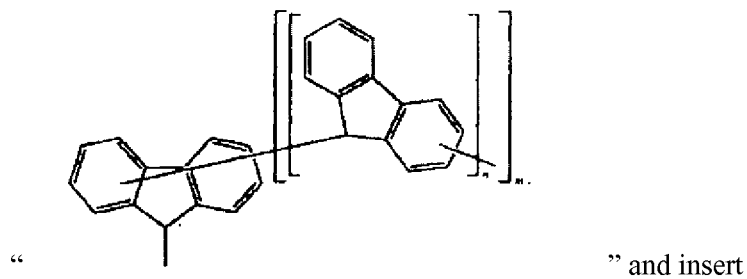

" and insert

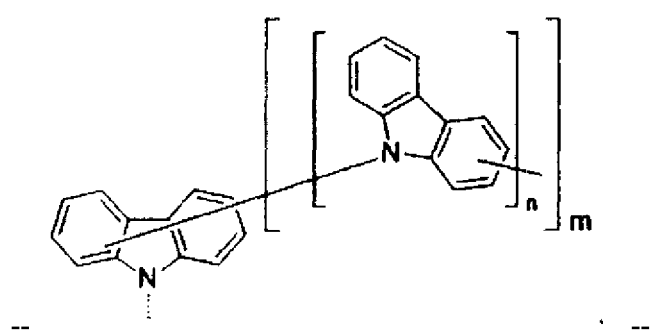

. --

Column 360, Lines 1-24, please delete

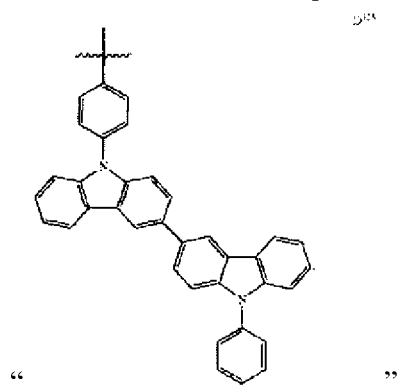

" "

CERTIFICATE OF CORRECTION (continued)   Page 3 of 4
U.S. Pat. No. 9,512,136 B2

Column 375, Lines 25-50, please delete

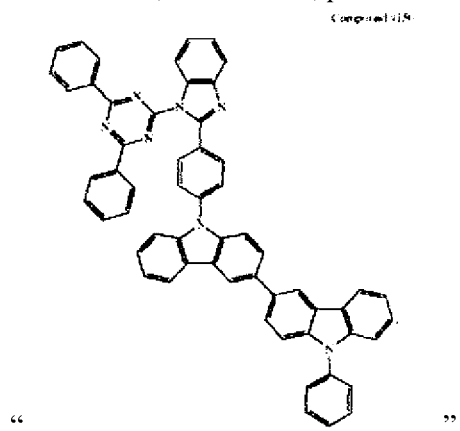

" "

Column 378, Lines 20-25, please delete

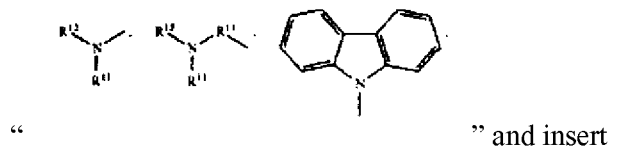

" " and insert

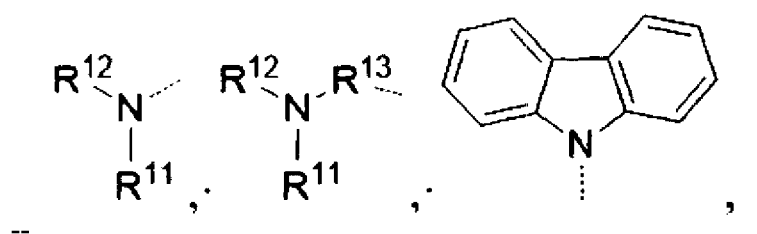

--

Column 378, Lines 50-59, please delete

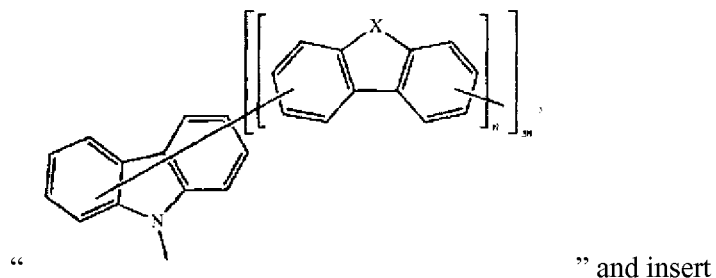

" " and insert

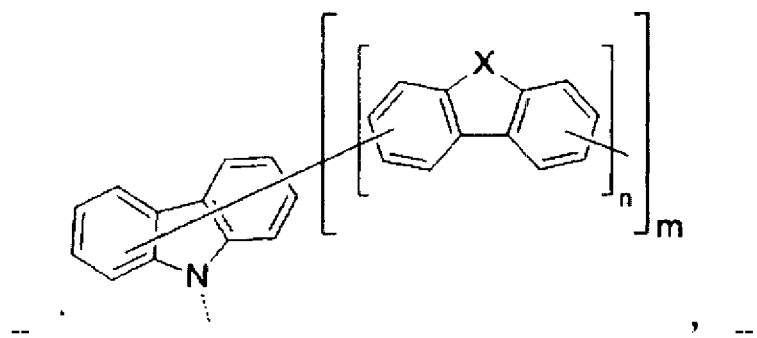

--

CERTIFICATE OF CORRECTION (continued)
U.S. Pat. No. 9,512,136 B2

Column 379, Lines 1-12, please delete

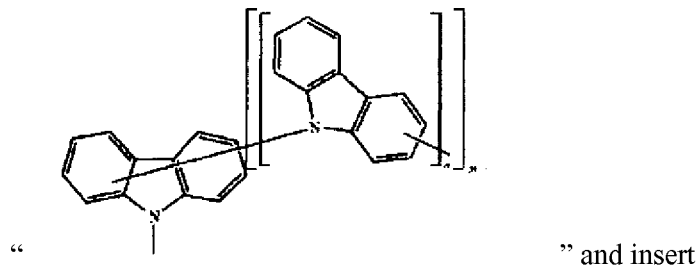

" and insert

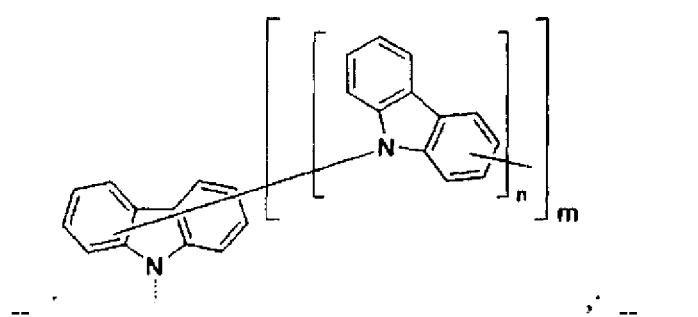

, --

Column 381, Lines 35-42, please delete

" and insert

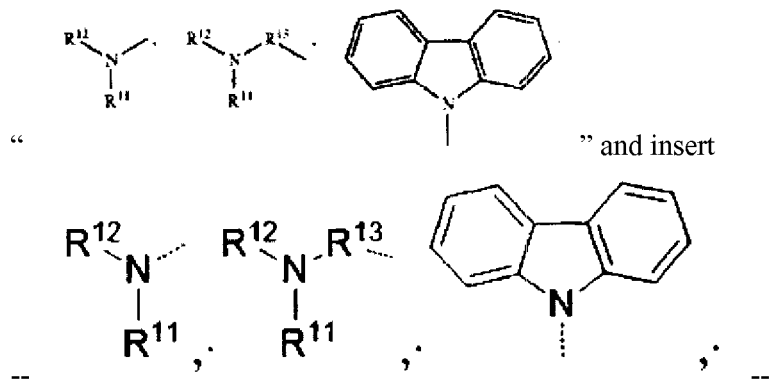

, --